(12) United States Patent
Hayama et al.

(10) Patent No.: US 10,797,244 B2
(45) Date of Patent: Oct. 6, 2020

(54) COMPOUND, MATERIAL FOR ORGANIC ELECTROLUMINESCENT ELEMENT, ORGANIC ELECTROLUMINESCENT ELEMENT, AND ELECTRONIC DEVICE

(71) Applicant: IDEMITSU KOSAN CO., LTD., Tokyo (JP)

(72) Inventors: Tomoharu Hayama, Sodegaura (JP); Tetsuya Masuda, Sodegaura (JP); Masahiro Kawamura, Sodegaura (JP); Hirokatsu Ito, Sodegaura (JP); Yumiko Mizuki, Sodegaura (JP); Tomoki Kato, Sodegaura (JP); Takushi Shiomi, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 297 days.

(21) Appl. No.: 15/328,747

(22) PCT Filed: Apr. 28, 2016

(86) PCT No.: PCT/JP2016/063387
§ 371 (c)(1),
(2) Date: Jan. 24, 2017

(87) PCT Pub. No.: WO2016/175292
PCT Pub. Date: Nov. 3, 2016

(65) Prior Publication Data
US 2017/0213982 A1 Jul. 27, 2017

(30) Foreign Application Priority Data

Apr. 28, 2015 (JP) .................. 2015-092319

(51) Int. Cl.
*H01L 51/00* (2006.01)
*C07D 401/10* (2006.01)
*H01L 51/50* (2006.01)

(52) U.S. Cl.
CPC ........ *H01L 51/0067* (2013.01); *C07D 401/10* (2013.01); *H01L 51/0054* (2013.01); *H01L 51/0055* (2013.01); *H01L 51/0072* (2013.01); *H01L 51/0077* (2013.01); *H01L 51/50* (2013.01); *H01L 51/5056* (2013.01); *H01L 51/5072* (2013.01); *H01L 51/5076* (2013.01)

(58) Field of Classification Search
CPC .............. C07D 401/10; H01L 51/0054; H01L 51/0055; H01L 51/0067; H01L 51/0072; H01L 51/0077; H01L 51/50; H01L 51/5056; H01L 51/5072; H01L 51/5076; C07C 11/06
See application file for complete search history.

(56) References Cited

U.S. PATENT DOCUMENTS

| | | | | |
|---|---|---|---|---|
| 8,679,647 B2 * | 3/2014 | Pflumm | ............... | H01L 51/002 428/690 |
| 2009/0009067 A1 * | 1/2009 | Nishimura | .......... | H01L 51/0052 313/504 |
| 2012/0104941 A1 * | 5/2012 | Jung | .................... | C07D 239/26 313/504 |
| 2015/0034938 A1 | 2/2015 | Kang et al. | | |
| 2015/0236264 A1 | 8/2015 | Kim et al. | | |
| 2015/0349268 A1 * | 12/2015 | Zeng | .................. | H01L 51/0067 257/40 |
| 2016/0308157 A1 * | 10/2016 | Cho | .................... | H01L 51/5004 |
| 2017/0077414 A1 * | 3/2017 | Kim | .................... | H01L 51/0067 |

FOREIGN PATENT DOCUMENTS

| | | |
|---|---|---|
| EP | 2 315 753 A2 | 5/2011 |
| EP | 2 452 997 A2 | 5/2012 |
| JP | 2012-501091 A | 1/2012 |
| JP | 5596687 B2 | 9/2014 |
| JP | 2016-006039 A | 1/2016 |
| KR | 10-1367254 B1 | 3/2014 |
| KR | 10-2014-0057687 A | 5/2014 |

(Continued)

OTHER PUBLICATIONS

English International Preliminary Report on Patentability dated Oct. 31, 2017 in corresponding application No. PCT/JP2016/063387.
International Search Report issued in International Patent Application No. PCT/JP2016/063387 dated Aug. 2, 2016.

*Primary Examiner* — Dawn L Garrett
(74) *Attorney, Agent, or Firm* — Foley & Lardner LLP

(57) ABSTRACT

A compound is represented by a formula (1). In the formula (1); Ar represents an aromatic hydrocarbon group or a heterocyclic group having 4 or more fused rings and 22 or less ring atoms; Ar optionally has a substituent; $R_{11}$ is a substituted or unsubstituted aromatic hydrocarbon group; when $R_{11}$ is an aromatic hydrocarbon group having a substituent, the substituent is not a heterocyclic group; $X_1$ represents a nitrogen atom or a carbon atom bonded with $R_{12}$ ($CR_{12}$); $R_{12}$ represents a hydrogen atom or a substituent; $L_1$ represents a single bond or a linking group; $X_2$ and $X_3$ each independently represent a nitrogen atom or a carbon atom bonded with $R_2$ ($CR_2$); $R_1$ and $R_2$ each independently represent a hydrogen atom or a substituent; and $L_2$ is a linking group.

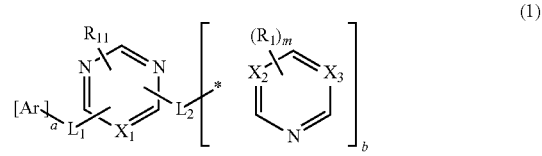

26 Claims, 1 Drawing Sheet

(56) References Cited

FOREIGN PATENT DOCUMENTS

| | | |
|---|---|---|
| KR | 10-2014-0094408 A | 7/2014 |
| KR | 10-2015-0027562 A | 3/2015 |
| KR | 10-2015-0120875 A | 10/2015 |
| KR | 10-2015-0131998 A | 11/2015 |
| WO | WO-2010/024572 A2 | 3/2010 |
| WO | WO-2011/021689 A1 | 2/2011 |
| WO | WO-2012/046839 A1 | 4/2012 |
| WO | 10-2013-0060157 A | 6/2013 |
| WO | WO-2013/162148 A1 | 10/2013 |
| WO | WO-2014/081168 A1 | 5/2014 |
| WO | WO-2014/098043 A1 | 6/2014 |
| WO | WO-2015/008866 A1 | 1/2015 |
| WO | WO-2016/003225 A2 | 1/2016 |

\* cited by examiner

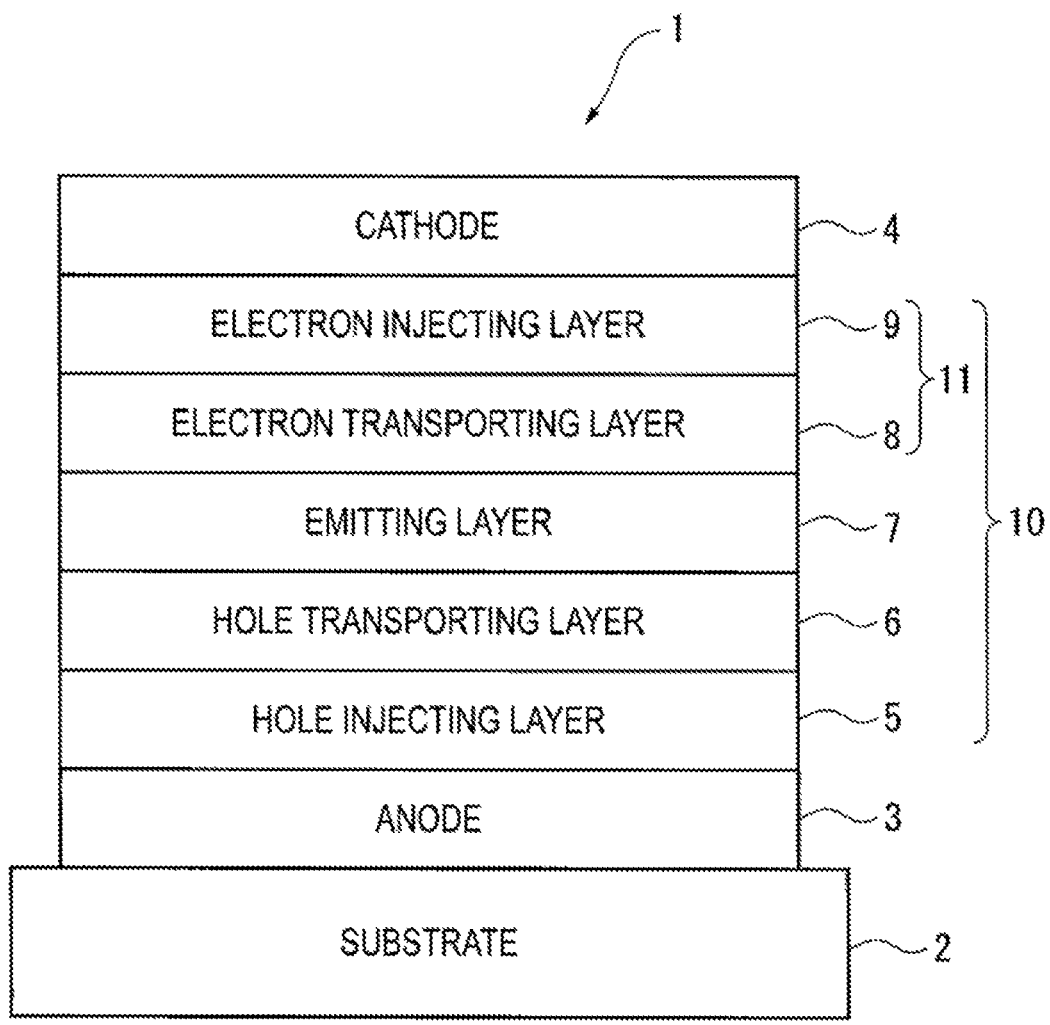

COMPOUND, MATERIAL FOR ORGANIC ELECTROLUMINESCENT ELEMENT, ORGANIC ELECTROLUMINESCENT ELEMENT, AND ELECTRONIC DEVICE

CROSS-REFERENCE TO RELATED APPLICATIONS

The present application is a U.S. national stage application claiming the benefit of International Patent Application No. PCT/JP2016/063387, filed Apr. 28, 2016, which claims the benefit of priority to Japanese Patent Application No. 2015-092319, filed Apr. 28, 2015, the entireties of which are hereby incorporated by reference.

TECHNICAL FIELD

The present invention relates to a compound, a material for an organic electroluminescence device, an organic electroluminescence device, and an electronic device.

BACKGROUND ART

An organic electroluminescence device (hereinafter, occasionally abbreviated as organic EL device) using an organic substance is highly expected to be used as an inexpensive solid-emitting full-color display device having a large area and has been variously developed. A typical organic EL device includes an emitting layer and a pair of opposing electrodes (i.e., an anode and a cathode) between which the emitting layer is interposed. When an electric field is applied on both electrodes, electrons are injected from the cathode while holes are injected from the anode. Recombination of the electrons and the holes in the emitting layer generates an excited state. Energy generated when the excited state is returned to the ground state is radiated as light.

A typical organic EL device exhibits a higher drive voltage and lower luminescence intensity and lower luminous efficiency than those of an inorganic light-emitting diode. In recent organic EL devices, an improvement in a compound used for forming an organic layer has been made (see, for instance, Patent Literatures 1 and 9).

CITATION LIST

Patent Literature(s)

Patent Literature 1: US Patent Application Publication No. 2015/0034938

Patent Literature 2: Japanese Patent No. 5596687

Patent Literature 3: International Publication No. WO2013/162148

Patent Literature 4: Korean Patent No. 1367254

Patent Literature 5: EP Patent Application Publication No. 2452997

Patent Literature 6: EP Patent Application Publication No. 2315753

Patent Literature 7: International Publication No. WO2011/021689

Patent Literature 8: International Publication No. WO2015/008866

Patent Literature 9: International Publication No. WO2014/098043

SUMMARY OF THE INVENTION

Problems to be Solved by the Invention

In order to further improve a performance of an organic EL device, a decrease in a drive voltage and an improvement of a luminous efficiency have been required.

An object of the invention is to provide an organic electroluminescence device capable of decreasing a drive voltage and improving a luminous efficiency, a compound usable in the organic electroluminescence device, a material for an organic electroluminescence device (hereinafter, also referred to as an organic-EL-device material) containing the compound, and an electronic device.

Means for Solving the Problems

According to an aspect of the invention, a compound is represented by a formula (1).

[Formula 1]

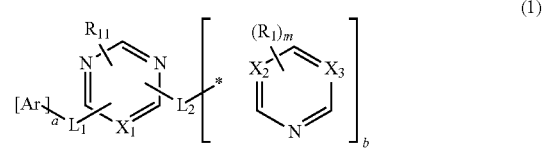

(1)

In the formula (1), Ar represents an aromatic hydrocarbon group having 4 or more fused rings and 22 or less ring atoms, or a heterocyclic group having 4 or more fused rings and 22 or less ring atoms; Ar optionally has a substituent; a is 1 or 2, a plurality of Ar are optionally the same or different; $R_{11}$ is a substituted or unsubstituted aromatic hydrocarbon group having 6 to 30 ring carbon atoms; when $R_{11}$ is an aromatic hydrocarbon group having a substituent and 6 to 30 ring carbon atoms, the substituent is not a heterocyclic group; $X_1$ represents a nitrogen atom or a carbon atom ($CR_{12}$) bonded with $R_{12}$; $R_{12}$ represents a hydrogen atom or a substituent; $L_1$ represents a single bond or a linking group; $L_1$ as the linking group is selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted and linear or branched hydrocarbon group having a carbon-carbon double bond and 2 to 30 carbon atoms, and a substituted or unsubstituted and linear or branched hydrocarbon group having a carbon-carbon triple bond and 2 to 30 carbon atoms; $X_2$ and $X_3$ each independently represent a nitrogen atom or a carbon atom ($CR_2$) bonded with $R_2$; $R_1$ and $R_2$ each independently represent a hydrogen atom or a substituent; $R_1$ as the substituent, $R_2$ as the substituent, and $R_{12}$ as the substituent are each independently selected from the group consisting of a substituted or unsubstituted alkyl group having 1 to 30 carbon atoms, a substituted or unsubstituted halogenated alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aromatic hydrocarbon group having 6 to 14 ring carbon atoms, a substituted or unsubstituted alkoxy group having 1 to 30 carbon atoms, a substituted or unsubstituted aryloxy group having 6 to 14 ring carbon atoms, a substituted or unsubstituted alkylthio group having 1 to 30 carbon atoms, a substituted or unsubstituted arylthio group having 6 to 14 ring carbon atoms, a substituted or unsubstituted silyl group, a nitro group, a cyano group, a halogen atom; when $R_{12}$ is an aromatic hydrocarbon group having a substituent and 6 to 14 ring carbon atoms, the substituent is not a heterocyclic group; m is an integer of 2 or more; a plurality of $R_1$ are optionally the same or different; a plurality of $R_2$ are optionally the same or different; $R_1$ and $R_2$ are optionally bonded to each other to form a ring structure; $L_2$ is a linking group and $L_2$ as the linking group is selected from the group consisting of a substituted or unsubstituted aromatic hydrocarbon group having 6 to 30 ring carbon atoms; b is an integer of 1 to 5; a structure parenthesized by b is optionally the same or different, and * indicates a bonding site to L2 in the structure parenthesized by b.

According to another aspect of the invention, an organic-electroluminescence-device material contains the compound according to the above aspect of the invention.

According to still another aspect of the invention, an organic EL device includes: an anode; a cathode; and one or more organic layers including an emitting layer, in which at least one of the organic layers contains the compound according to the above aspect of the invention.

According to a further aspect of the invention, an organic EL device includes: an anode; a cathode; and an organic layer including an emitting layer and an electron transporting zone, in which the emitting layer is interposed between the anode and the cathode, the electron transporting zone is interposed between the emitting layer and the cathode, and the electron transporting zone contains the compound according to the above aspect of the invention.

According to a still further aspect of the invention, an electronic device includes the organic electroluminescence device according to the above aspect of the invention.

According to the above aspects of the invention, an organic electroluminescence device capable of decreasing a drive voltage and improving a luminous efficiency, a compound usable in the organic electroluminescence device, a material for an organic electroluminescence device containing the compound and an electronic device can be provided.

BRIEF DESCRIPTION OF DRAWING

The FIGURE schematically shows an exemplary arrangement of an organic EL device according to an exemplary embodiment of the invention.

DESCRIPTION OF EMBODIMENT(S)

Compound

A compound according to an exemplary embodiment of the invention is represented by a formula (1).

[Formula 2]

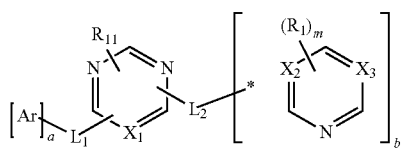

(1)

In the formula (1), Ar is an aromatic hydrocarbon group having 4 or more fused rings and 22 or less ring atoms or a heterocyclic group having 4 or more fused rings and 22 or less ring atoms. Ar preferably has 4 to 6 fused rings and 22 or less ring atoms. Ar may have a substituent.

Since Ar has a structure including 4 or more fused rings, it is inferred that a π conjugated molecular plane extends to improve mobility of carriers. Moreover, it is also inferred that, when the ring atoms of Ar exceeds 22, a molecular energy gap becomes narrow to decrease carrier injectability to the emitting layer.

In the exemplary embodiment, Ar is preferably an aromatic hydrocarbon group having 4 or more fused rings and 22 or less ring atoms and may have a substituent.

Herein, the "aromatic hydrocarbon group having 4 or more fused rings and 22 or less ring atoms" means an aromatic hydrocarbon group having 4 or more fused rings in total in which six-membered rings are fused or a six-membered ring(s) and a five-membered ring(s) are fused and the number of the atoms forming the fused rings is 22 or less. The "heterocyclic group having 4 or more fused rings and 22 or less ring atoms" is defined substantially the same as the aromatic hydrocarbon group and is different from the aromatic hydrocarbon group in that at least one of the atoms forming the fused ring is a hetero atom.

In the exemplary embodiment, Ar is preferably an aromatic hydrocarbon group derived from a ring represented by a formula (10) and may have a substituent.

[Formula 3]

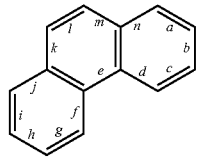

(10)

In the formula (10), a monocyclic ring or a fused ring is fused to at least one of positions a, b, c, d, e, f, g, h, i and l. The fused ring may be an aromatic ring or a hetero ring. In the formula (10), a fused ring formed by fusing the ring to at least one of the positions a to l has 22 or less ring atoms.

In the formula (10), for instance, when a six-membered ring (e.g., a benzene ring) is fused to the positions d, e and f, Ar has a fused ring structure represented by a formula (10A).

[Formula 4]

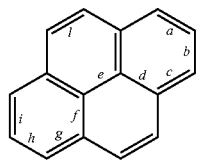

(10A)

Since a pyrene ring represented by the formula (10A) is structured to have four fused rings and 16 carbon atoms, the number of the ring atoms is 16, which satisfies the conditions of Ar in the formula (1).

In the exemplary embodiment, Ar is preferably an aromatic hydrocarbon group derived from any ring selected from the group consisting of rings represented by formulae (10a) to (10f). Ar is more preferably an aromatic hydrocarbon group derived from the ring represented by the formula (10a). Ar is also more preferably an aromatic hydrocarbon group derived from the ring represented by the formula (10c). Ar is also more preferably an aromatic hydrocarbon group derived from the ring represented by the formula (10e). Ar is more preferably an aromatic hydrocarbon group derived from the ring represented by the formula (10f). The aromatic hydrocarbon group may have a substituent.

[Formula 5]

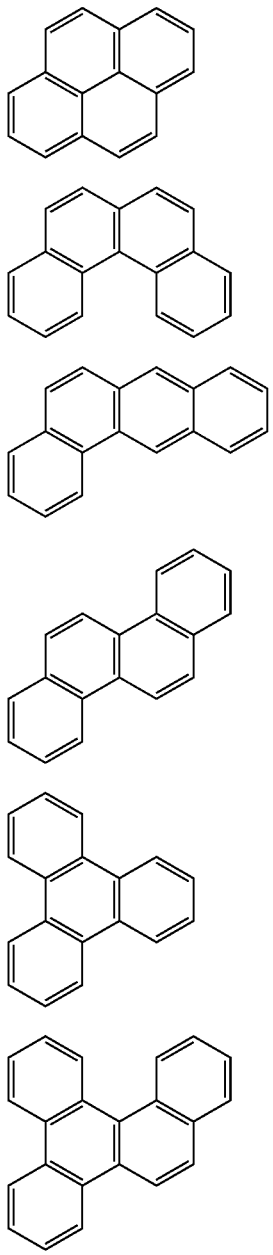

(10a)

(10b)

(10c)

(10d)

(10e)

(10f)

In the exemplary embodiment, Ar is preferably any group selected from the group consisting of groups represented by formulae (10g) to (10o). The groups represented by the formulae (10g) to (10o) are preferably unsubstituted, however, may further have a substituent.

[Formula 6]

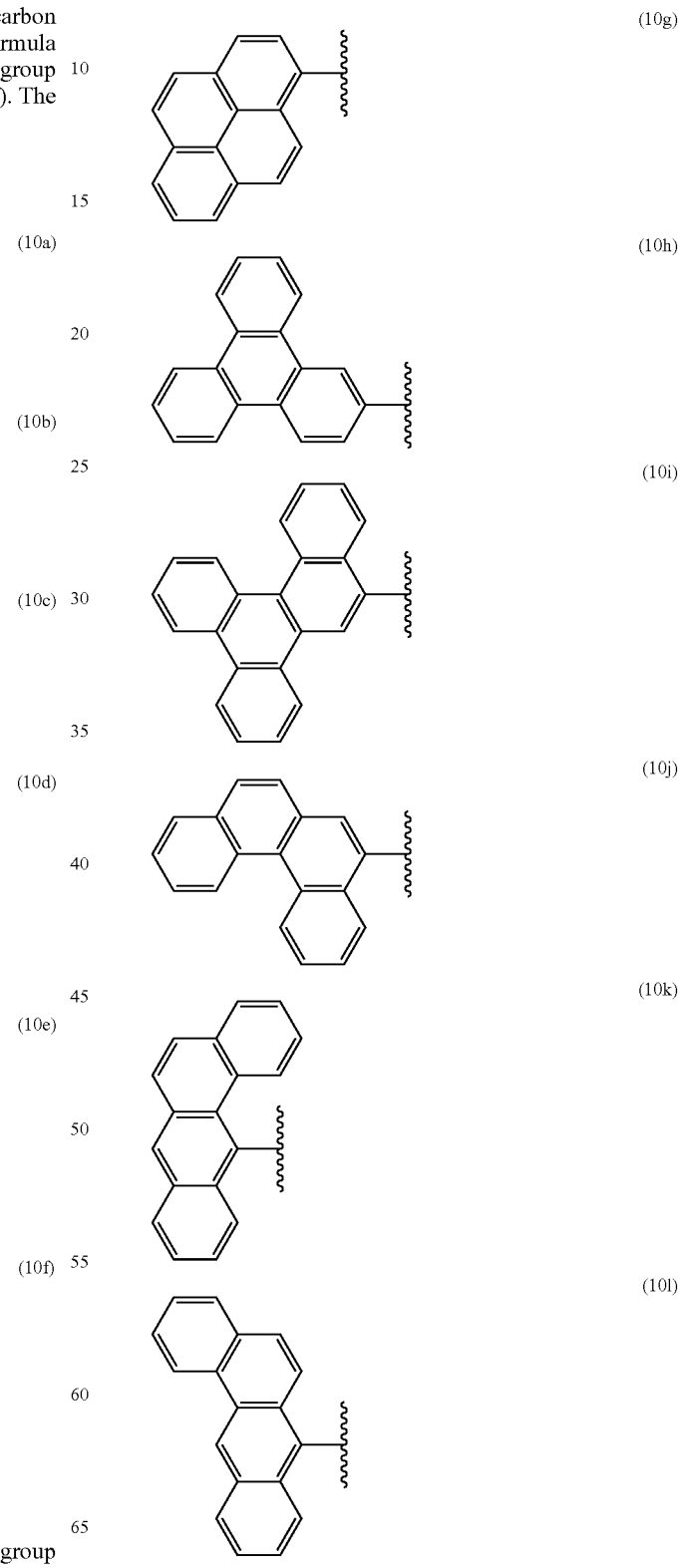

(10g)

(10h)

(10i)

(10j)

(10k)

(10l)

(10m)

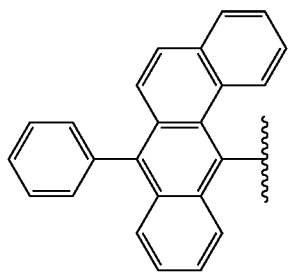

(10n)

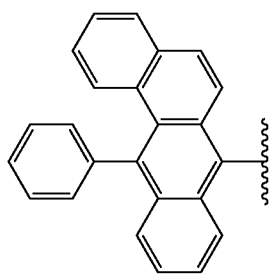

(10o)

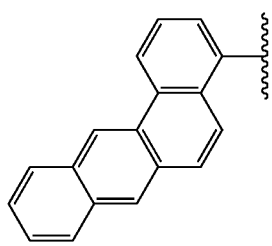

In the exemplary embodiment, Ar is preferably an aromatic hydrocarbon group derived from a ring represented by a formula (11) and may have a substituent.

[Formula 7]

(11)

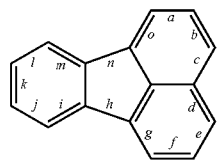

In the formula (11), a monocyclic ring or a fused ring is fused to at least one of positions a, b, e, f, j, k and l. The fused ring may be an aromatic ring or a hetero ring. In the formula (11), a fused ring formed by fusing the ring to at least one of the positions a, b, e, f, j, k and l has 22 or less ring atoms.

In the formula (11), for instance, when a six-membered ring (e.g., a benzene ring) is fused to the position k, Ar has a fused ring structure represented by a formula (11A).

[Formula 8]

(11A)

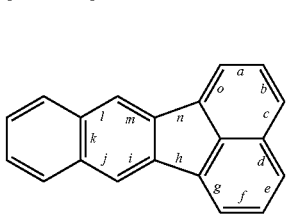

Since a benzo[k]fluoranthene ring represented by the formula (11A) is structured to have five fused rings and 20 carbon atoms, the number of the ring atoms is 20, which satisfies the conditions of Ar in the formula (1).

In the exemplary embodiment, Ar is also preferably an aromatic hydrocarbon group derived from any ring selected from the group consisting of rings represented by formulae (11a) to (11e). The aromatic hydrocarbon group may have a substituent.

[Formula 9]

(11a)

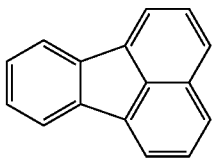

(11b)

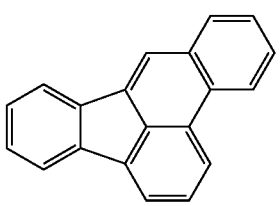

(11c)

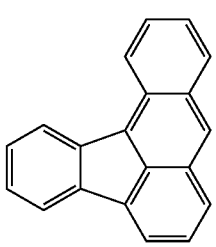

(11d)

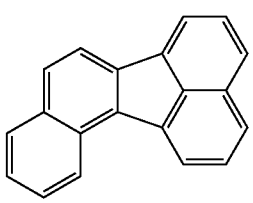

(11e)

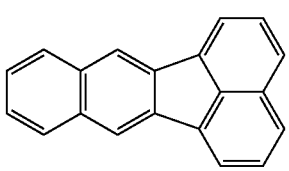

In the exemplary embodiment, Ar is also preferably any group selected from the group consisting of groups represented by formulae (11g) and (11h). The groups represented by the formulae (11g) and (11h) are preferably unsubstituted, however, may further have a substituent.

[Formula 10]

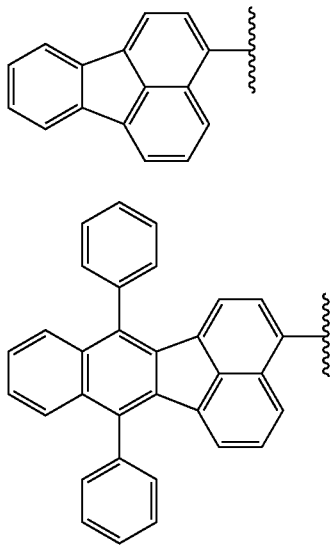

(11g)

(11h)

In the exemplary embodiment, when Ar is the heterocyclic group having 4 or more fused rings and 22 or less ring atoms, a structure of the heterocyclic group is exemplified by a structure in which at least one carbon atom is replaced by a hetero atom in the fused ring structure of the aromatic hydrocarbon group for Ar. The hetero atom included in the heterocyclic group for Ar is selected from the group consisting of a nitrogen atom, oxygen atom, sulfur atom and silicon atom. A plurality of hetero atoms contained in the fused ring structure may be mutually the same or different.

In the exemplary embodiment, Ar is also preferably a heterocyclic group derived from any ring selected from the group consisting of rings represented by formulae (12a) to (12f) and (13a) to (13d). The heterocyclic group may have a substituent.

[Formula 11]

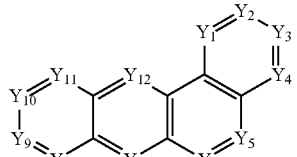

(12a)

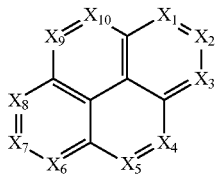

(12b)

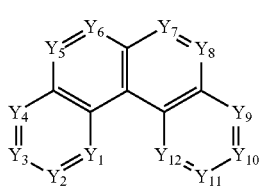

(12c)

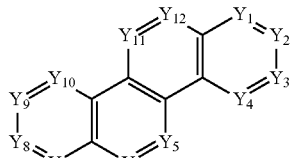

(12d)

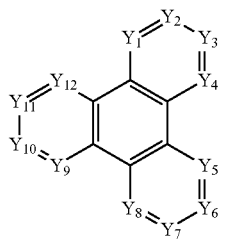

(12e)

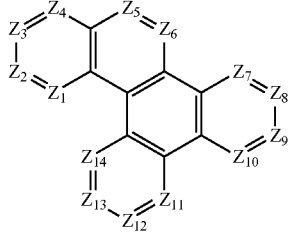

(12f)

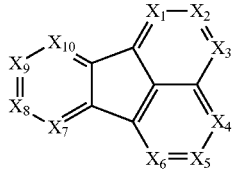

[Formula 12]

(13a)

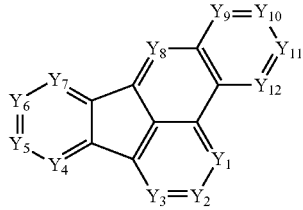

(13b)

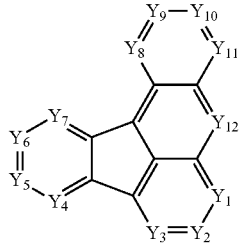

(13c)

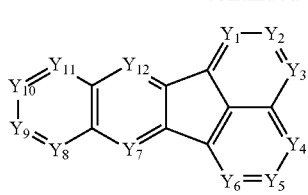

(13d)

In the formulae (12a) and (13a), $X_1$ to $X_{10}$ each independently represent a carbon atom or a nitrogen atom. At least one of $X_1$ to $X_{10}$ is a nitrogen atom.

In the formulae (12b) to (12e) and (13b) to (13d), $Y_1$ to $Y_{12}$ each independently represent a carbon atom or a nitrogen atom. At least one of $Y_1$ to $Y_{12}$ is a nitrogen atom.

In the formula (12f), $Z_1$ to $Z_{14}$ represent a carbon atom or a nitrogen atom. At least one of $Z_1$ to $Z_{14}$ is a nitrogen atom.

The carbon atoms in $X_1$ to $X_{10}$, $Y_1$ to $Y_{12}$ and $Z_1$ to $Z_{14}$ are respectively bonded to hydrogen atoms or substituents.

In the exemplary embodiment, when Ar has a substituent, the substituent is preferably selected from the group consisting of a substituted or unsubstituted alkyl group having 1 to 30 carbon atoms, a substituted or unsubstituted aromatic hydrocarbon group having 6 to 18 ring carbon atoms, a substituted or unsubstituted alkoxy having 1 to 30 carbon atoms, a substituted or unsubstituted aryloxy having 6 to 18 ring carbon atoms, and a halogen atom.

In the exemplary embodiment, Ar is also preferably unsubstituted.

In the formula (1), a is 1 or 2, preferably 1. A plurality of Ar may be the same or different.

In the formula (1), $R_{11}$ is a substituted or unsubstituted aromatic hydrocarbon group having 6 to 30 ring carbon atoms, more preferably a substituted or unsubstituted aromatic hydrocarbon group having 6 to 18 ring carbon atoms, further preferably a substituted or unsubstituted phenyl group. When $R_{11}$ is an aromatic hydrocarbon group having a substituent, the substituent is not a heterocyclic group. When $R_{11}$ has a substituent, the substituent is preferably selected from the group consisting of a substituted or unsubstituted alkyl group having 1 to 30 carbon atoms, a substituted or unsubstituted aromatic hydrocarbon group having 6 to 18 ring carbon atoms, a substituted or unsubstituted alkoxy having 1 to 30 carbon atoms, a substituted or unsubstituted aryloxy having 6 to 18 ring carbon atoms, a cyano group and a halogen atom.

In the formula (1), $X_1$ represents a nitrogen atom or a carbon atom bonded with $R_{12}$ ($CR_{12}$). $R_{12}$ represents a hydrogen atom or a substituent. $R_{12}$ as the substituent is selected from the group consisting of a substituted or unsubstituted alkyl having 1 to 30 carbon atoms, a substituted or unsubstituted halogenated alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aromatic hydrocarbon group having 6 to 14 ring carbon atoms, a substituted or unsubstituted alkoxy group having 1 to 30 carbon atoms, a substituted or unsubstituted aryloxy group having 6 to 14 ring carbon atoms, a substituted or unsubstituted alkylthio group having 1 to 30 carbon atoms, a substituted or unsubstituted arylthio group having 6 to 14 ring carbon atoms, a substituted or unsubstituted silyl group, a nitro group, a cyano group, and a halogen atom. When $R_{12}$ as the substituent is an aromatic hydrocarbon group having 6 to 14 ring carbon atoms and further having a substituent, the substituent is not a heterocyclic group.

$X_1$ is also preferably a nitrogen atom or $CR_{12}$ (in which $R_{12}$ is a hydrogen atom). $X_1$ is also preferably $CR_{12}$ (in which $R_{12}$ is a hydrogen atom).

In the exemplary embodiment, $R_{11}$ and $R_{12}$ are not bonded to each other. Accordingly, in the exemplary embodiment, the ring including $X_1$ and two nitrogen atoms in the formula (1) is not a fused ring.

In the formula (1), $L_1$ is a single bond or a linking group. $L_1$ as the linking group is selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted and linear or branched hydrocarbon group having a carbon-carbon double bond and 2 to 30 carbon atoms, and a substituted or unsubstituted and linear or branched hydrocarbon group having a carbon-carbon triple bond and 2 to 30 carbon atoms.

In the exemplary embodiment, $L_1$ is a single bond or a linking group. $L_1$ as the linking group is preferably a substituted or unsubstituted aromatic hydrocarbon group having 6 to 30 ring carbon atoms. $L_1$ as the linking group is preferably a substituted or unsubstituted aromatic hydrocarbon group having 6 to 18 ring carbon atoms. More preferably, $L_1$ as the linking group is selected from the group consisting of a substituted or unsubstituted phenylene group, a substituted or unsubstituted naphthalenediyl group, and a substituted or unsubstituted biphenyldiyl group. Further preferably, $L_1$ as the linking group is a substituted or unsubstituted phenylene group.

In the formula (1), $X_2$ and $X_3$ each independently represent a nitrogen atom or a carbon atom bonded with $R_2$ ($CR_2$).

In the exemplary embodiment, at least one of $X_2$ and $X_3$ is preferably a carbon atom bonded with $R_2$ ($CR_2$).

In the exemplary embodiment, it is also preferable that $X_2$ and $X_3$ are each a carbon atom bonded with $R_2$ ($CR_2$). It is more preferable that $X_2$ and $X_3$ are each a carbon atom bonded with $R_2$ ($CR_2$), and $R_1$ and $R_2$ are each a hydrogen atom.

In the formula (1), $R_1$ and $R_2$ are each independently a hydrogen atom or a substituent. m is an integer of 2 or more. A plurality of $R_1$ may be the same or different. A plurality of $R_2$ may be the same or different. $R_1$ and $R_2$ may be bonded to each other to form a ring structure.

$R_1$ as the substituent and $R_2$ as the substituent are each independently selected from the group consisting of a substituted or unsubstituted alkyl having 1 to 30 carbon atoms, a substituted or unsubstituted halogenated alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aromatic hydrocarbon group having 6 to 14 ring carbon atoms, a substituted or unsubstituted alkoxy group having 1 to 30 carbon atoms, a substituted or unsubstituted aryloxy group having 6 to 14 ring carbon atoms, a substituted or unsubstituted alkylthio group having 1 to 30 carbon atoms, a substituted or unsubstituted arylthio group having 6 to 14 ring carbon atoms, a substituted or unsubstituted silyl group, a nitro group, a cyano group, and a halogen atom.

In the exemplary embodiment, $R_1$ and $R_2$ are each independently preferably a hydrogen atom or a substituted or unsubstituted aromatic hydrocarbon group having 6 to 14 ring carbon atoms, more preferably a hydrogen atom or a substituted or unsubstituted aromatic hydrocarbon group having 6 to 10 ring carbon atoms, further preferably a hydrogen atom.

In the formula (1), $L_2$ is a linking group. $L_2$ as the linking group is selected from the group consisting of a substituted or unsubstituted aromatic hydrocarbon group having 6 to 30 ring carbon atoms, preferably selected from the group consisting of a substituted or unsubstituted aromatic hydrocarbon group having 6 to 18 ring carbon atoms.

In the exemplary embodiment, $L_2$ is preferably selected from the group consisting of a substituted or unsubstituted phenylene group, a substituted or unsubstituted naphthalenediyl group, and a substituted or unsubstituted biphenyldiyl group. More preferably, $L_2$ is a substituted or unsubstituted phenylene group.

Herein, a phenylene group having a substituent (i.e., a substituted phenylene group) means that the phenylene group has a bond for bonding to the substituent in addition to two bonds. The same applies to other divalent groups each having a substituent.

In the formula (1), b is an integer of 1 to 5. A structure parenthesized by b may be the same or different. * indicates a bonding site to $L_2$ in the structure parenthesized by b. b is preferably 1.

In the exemplary embodiment, preferably, a is 1 and b is 1. In this case, the compound according to the exemplary embodiment is represented by a formula (1X).

[Formula 13]

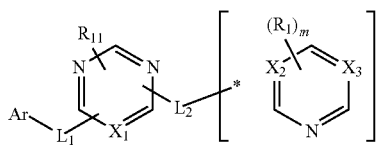

(1X)

When $X_1$ is $CR_{12}$, the compound according to the exemplary embodiment is represented by a formula (12), (13) or (14). When $X_1$ is a nitrogen atom, the compound according to the exemplary embodiment is represented by a formula (15).

[Formula 14]

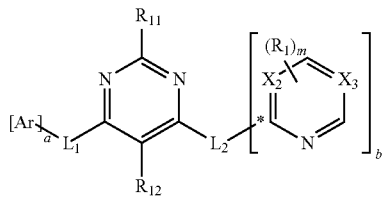

(12)

[Formula 15]

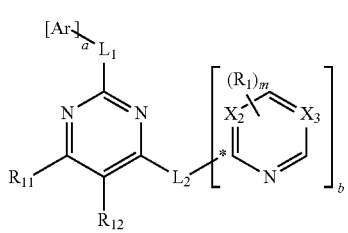

(13)

[Formula 16]

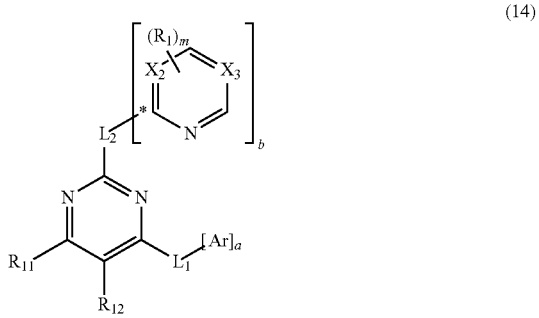

(14)

[Formula 17]

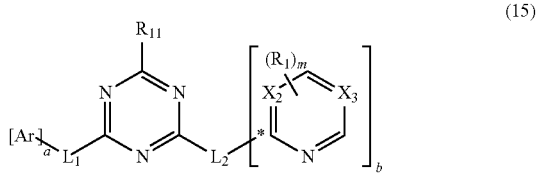

(15)

In the formulae (12) to (15), Ar, a, $R_{11}$, $R_{12}$, $L_1$, $X_2$, $X_3$, $R_1$, $R_2$, $L_2$, *, m and b represent the same as Ar, a, $R_{11}$, $R_{12}$, $L_1$, $X_2$, $X_3$, $R_1$, $R_2$, $L_2$, *, m and b in the formula (1).

In a molecule of the compound represented by the formula (1) in the exemplary embodiment, a first structure represented by a formula (1a) is preferably different from a second structure represented by a formula (1b). Signs in the formulae (1a) and (1b) represent the same as described above.

[Formula 18]

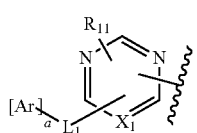

(1a)

[Formula 19]

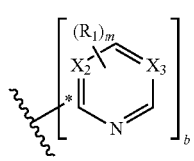

(1b)

In the compound according to the exemplary embodiment, the first structure is bonded to the second structure via $L_2$. $L_2$ is not a single bond but a linking group. Since a HOMO level or a LUMO level of the compound is positioned in a proper range by the bonding of the first structure and the second structure via the linking group, charges are advantageously injected, which is preferable for a low voltage-driven organic EL device.

The second structure represented by the formula (1b) is also preferably represented by a formula (1b-1) or a formula (1b-2).

[Formula 20]

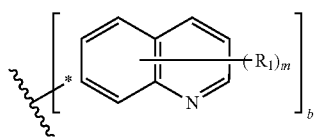
(1b-1)

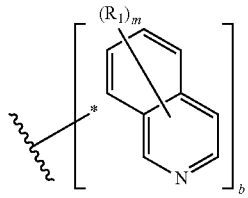
(1b-2)

In the formula (1b-1) and the formula (1b-2), $R_1$, *, m and b respectively represent the same as $R_1$, *, m and b in the formula (1). A plurality of $R_1$ may be bonded to each other to form a ring structure. In the formula (1b-1) and the formula (1b-2), m is preferably 6.

In the exemplary embodiment, $R_1$ is also preferably a hydrogen atom in the formula (1b-1) and the formula (1b-2).

The second structure represented by the formula (1b) is preferably any one structure selected from the group consisting of a monocyclic ring structure represented by each of formulae (1c) to (1i) and a fused ring structure represented by each of formulae (1j) to (1z), (1ba), (1bb) and (1bc).

[Formula 21]

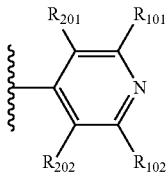
(1c)

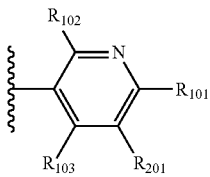
(1d)

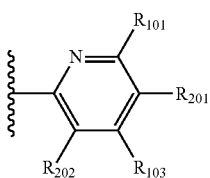
(1e)

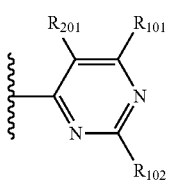
(1f)

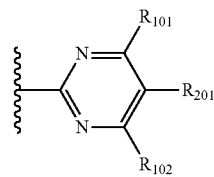
(1g)

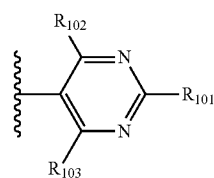
(1h)

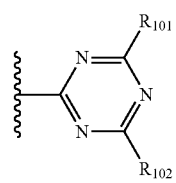
(1i)

[Formula 22]

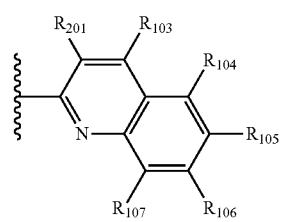
(1j)

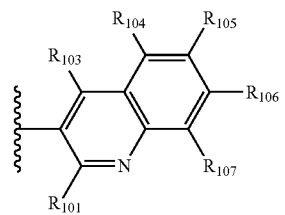
(1k)

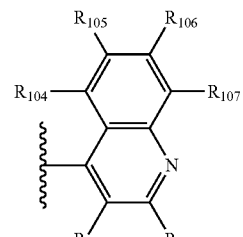
(1l)

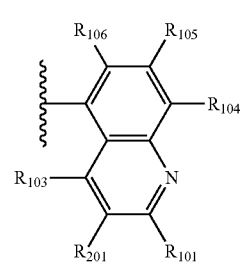
(1m)

(1n) 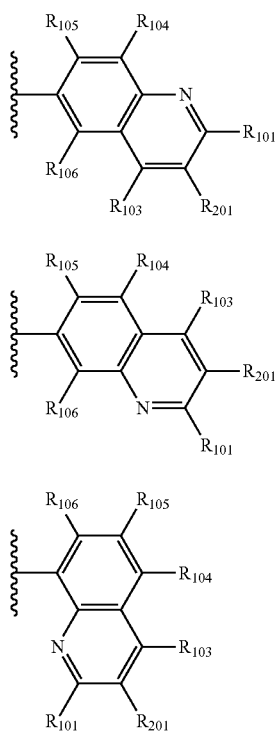
(1o)
(1p)
[Formula 23]
(1q) 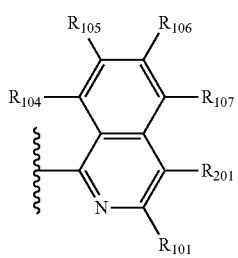
(1r) 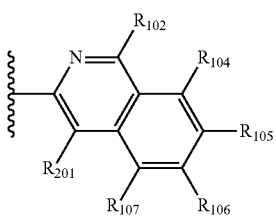
(1s) 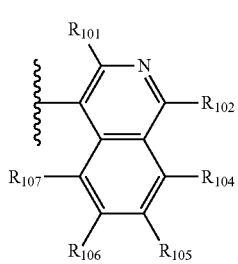
(1t) 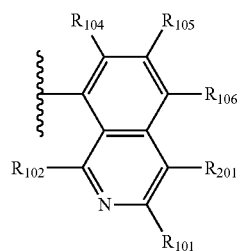
(1u) 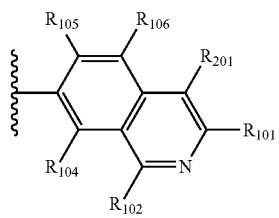
(1v) 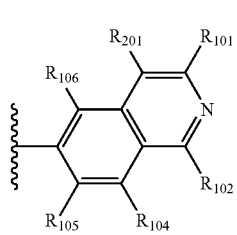
(1w) 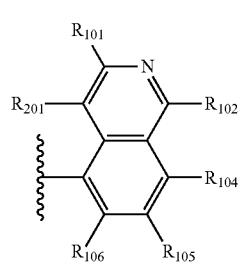
[Formula 24]
(1x) 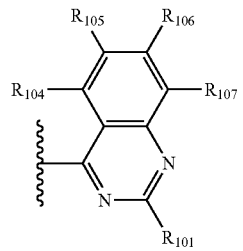
(1y) 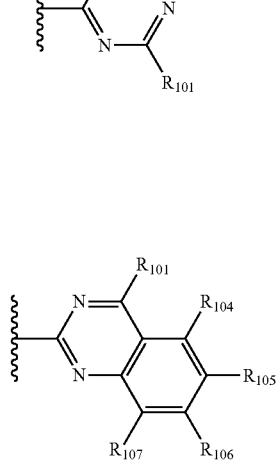

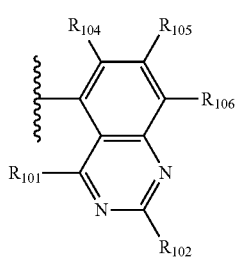
(1z)

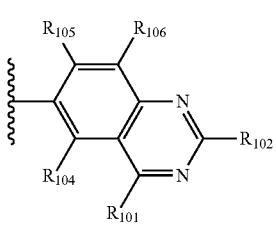
(1ba)

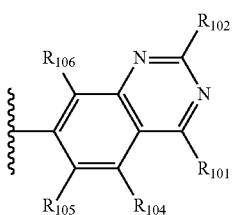
(1bb)

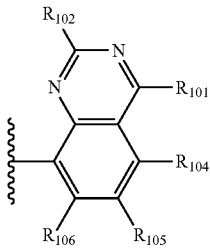
(1bc)

In the formulae (1c) to (1z), (1ba), (1bb) and (1bc), $R_{101}$ to $R_{107}$ and $R_{201}$ to $R_{202}$ each independently represent the same as $R_1$ and $R_2$ in the formula (1). Any two or more groups selected from $R_{101}$ to $R_{107}$ and $R_{201}$ to $R_{202}$ may be bonded to each other to form a ring structure.

In the exemplary embodiment, the second structure represented by the formula (1b) is more preferably any one structure selected from the group consisting of the structures represented by the formulae (1c), (1d), (1e) and (1j) to (1w), further preferably any one structure selected from the group consisting of the structures represented by the formulae (1c), (1d), (1e), (1j), (1k), (1l), (1q), (1r) and (1s). In the compound according to the exemplary embodiment in which the second structure represented by the formula (1b) is the structure represented by the formula (1c) or (1d), a lithium atom included in an electron-donating dopant and an organic metal complex is easily coordinated with a nitrogen atom of the second structure.

In the exemplary embodiment, $R_{101}$ to $R_{107}$ and $R_{201}$ to $R_{202}$ are each independently preferably a hydrogen atom or a substituted or unsubstituted aromatic hydrocarbon group having 6 to 14 ring carbon atoms, more preferably a hydrogen atom or a substituted or unsubstituted aromatic hydrocarbon group having 6 to 10 ring carbon atoms, further preferably a hydrogen atom.

Manufacturing Method of Compound According to Exemplary Embodiment

The compound according to the exemplary embodiment can be manufactured by, for instance, a method described in Examples described below. The compound according to the exemplary embodiment can be synthesized by application of known substitution reactions and/or materials depending on a target compound in accordance with the method described in the Examples.

Examples of the compound according to the exemplary embodiment are given below. It should be noted that the compound of the invention is not limited to the examples.

[Formula 25]

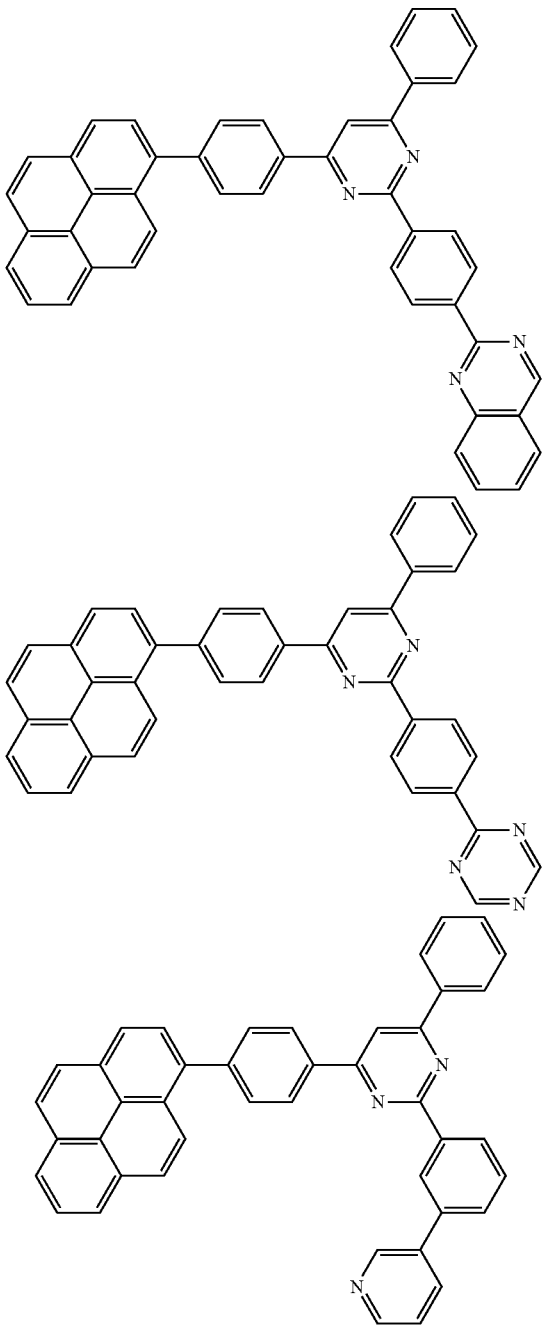

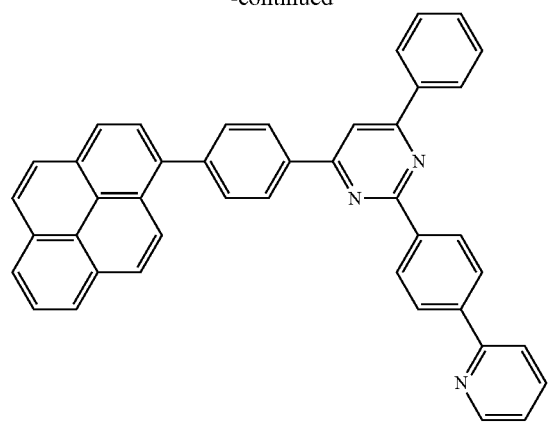
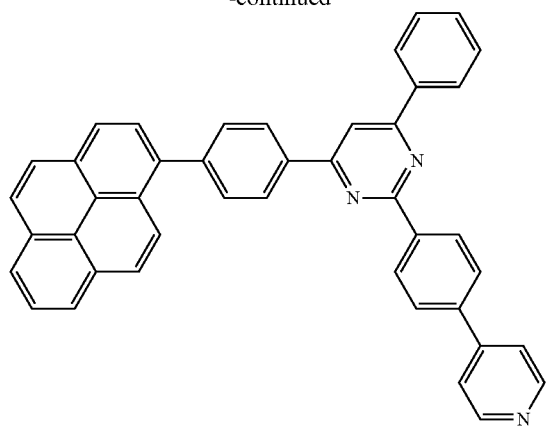
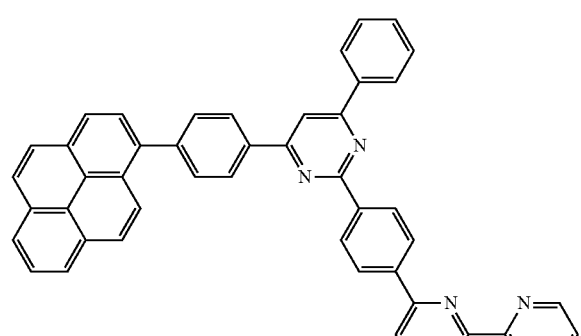
[Formula 26]
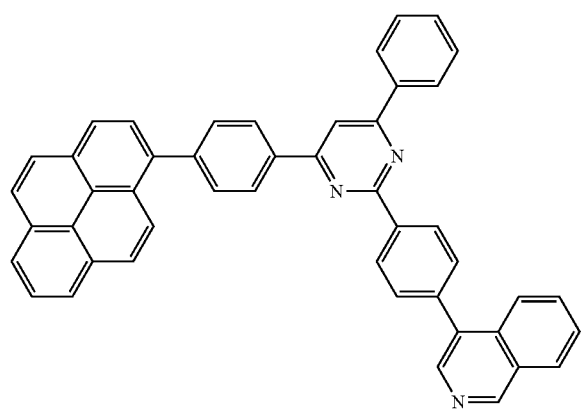
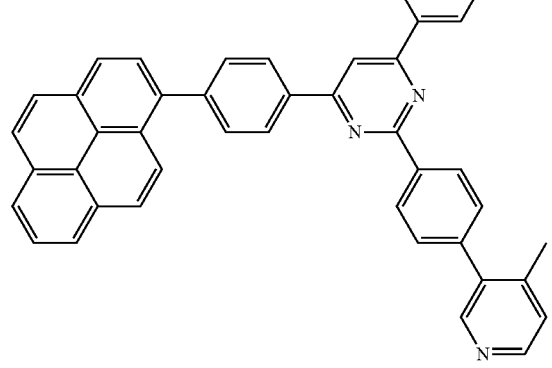
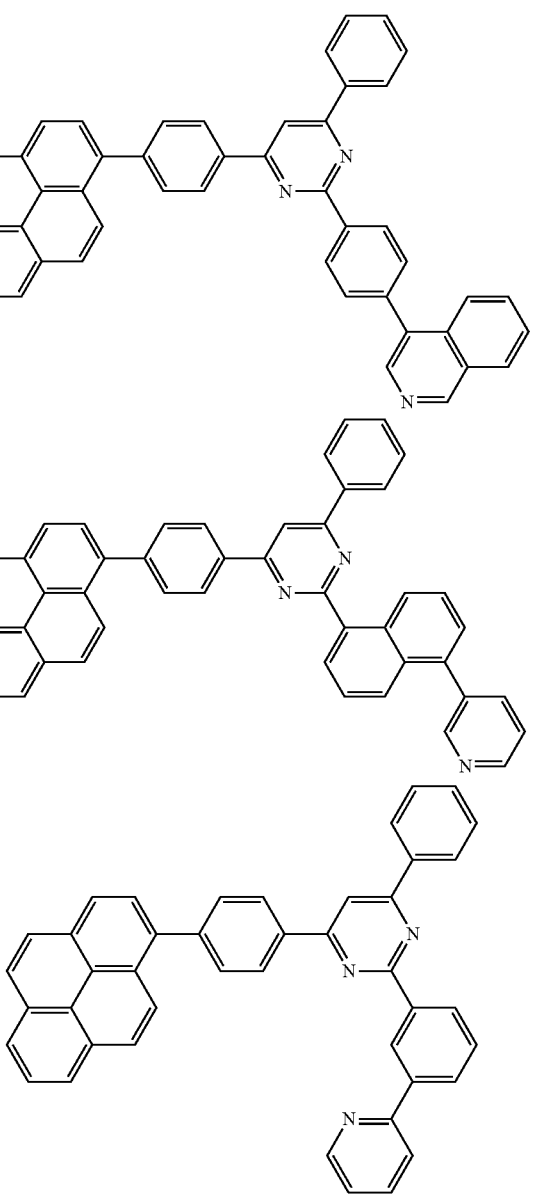

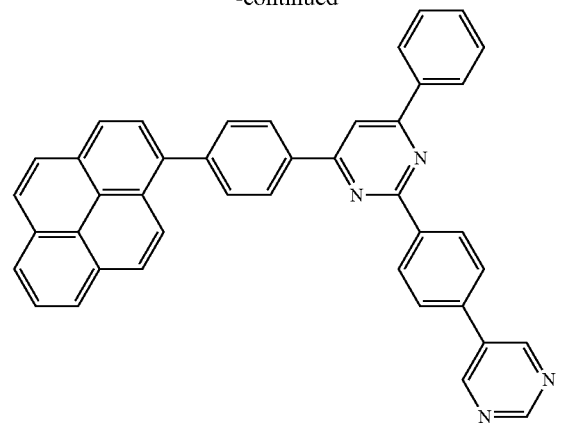
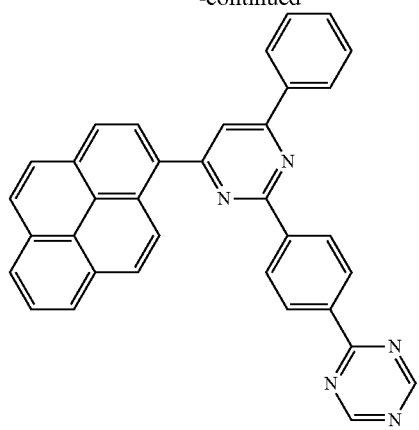
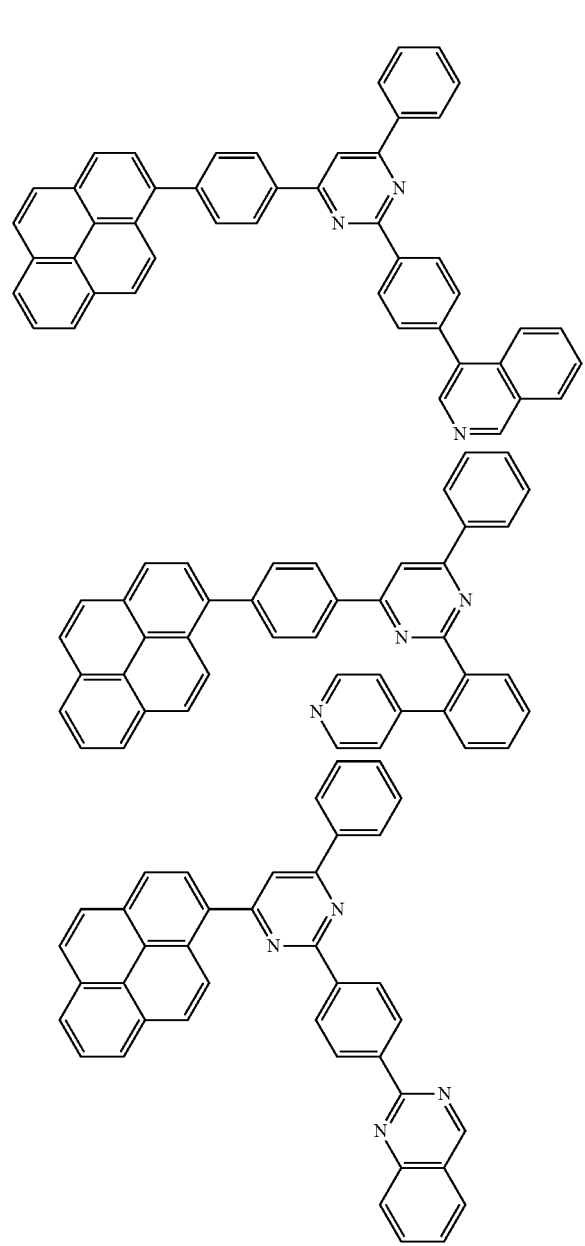
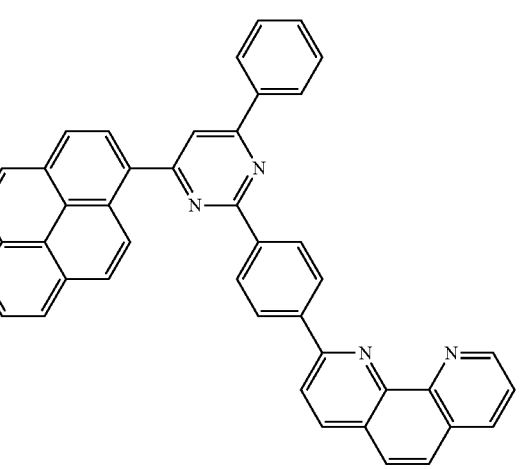
[Formula 27]
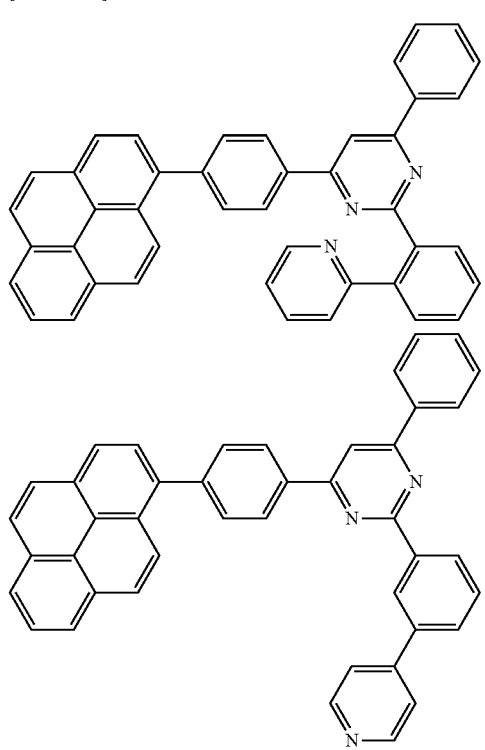

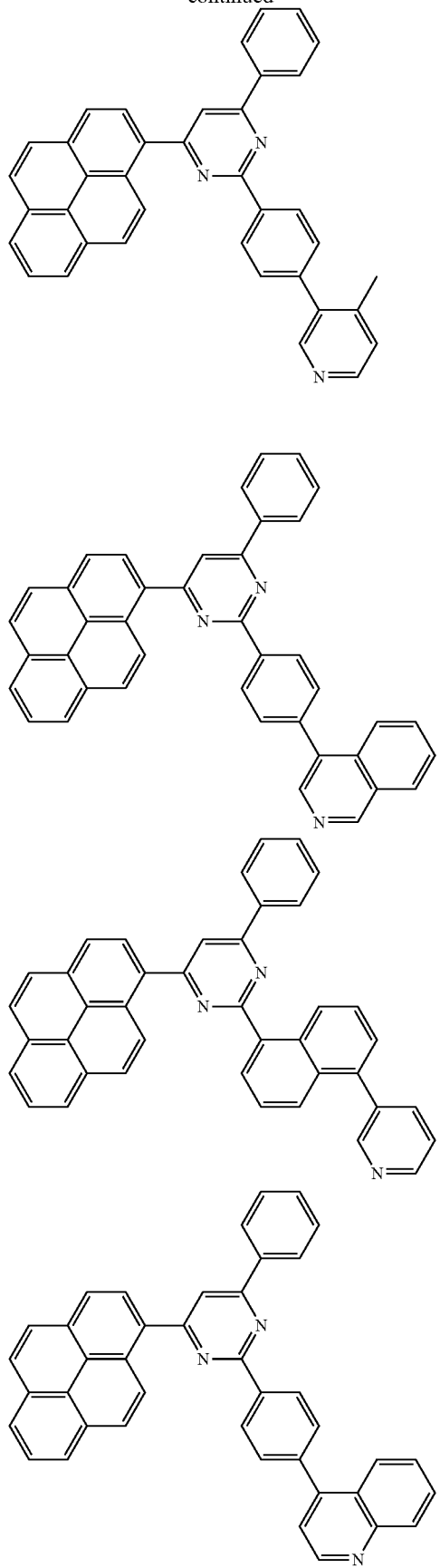
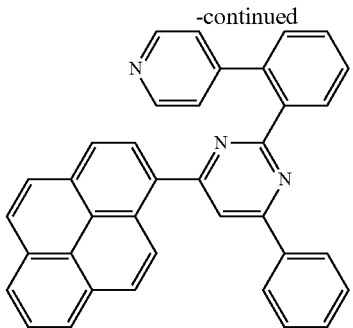
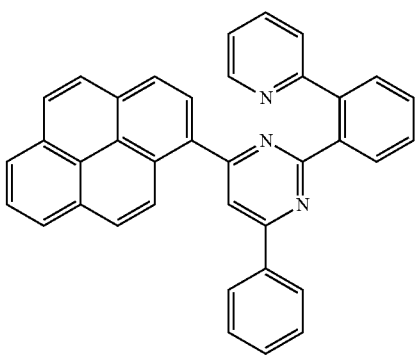
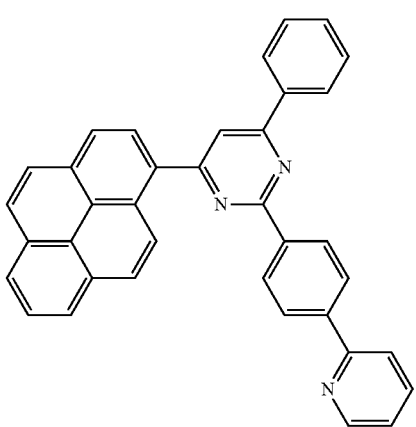
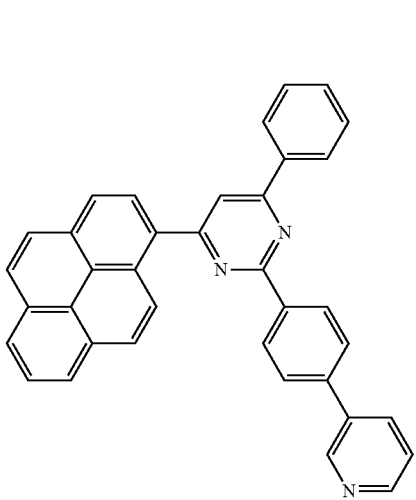

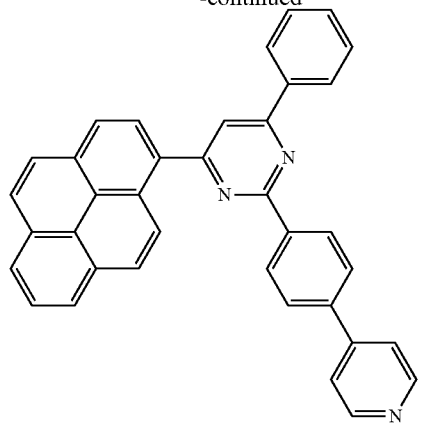
[Formula 28]
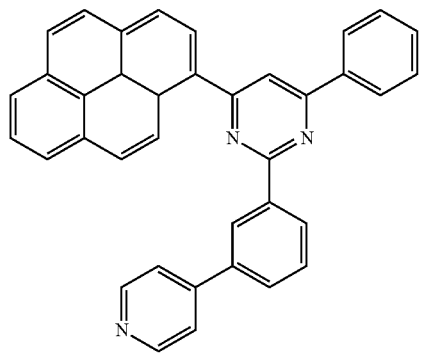
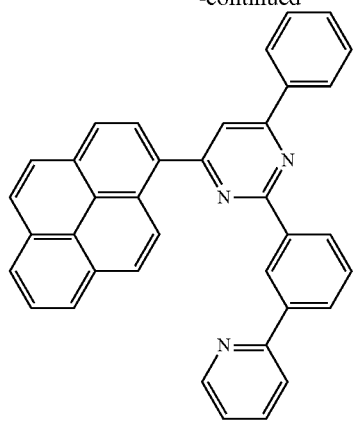
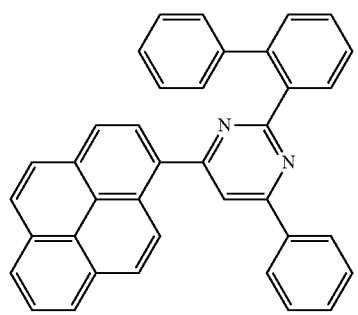
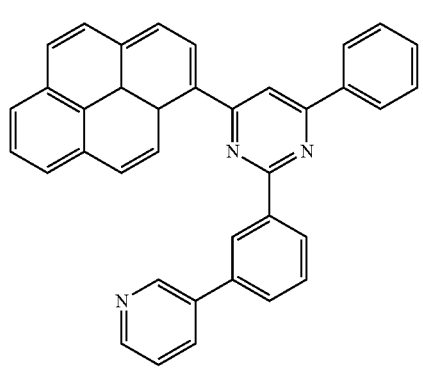
[Formula 29]
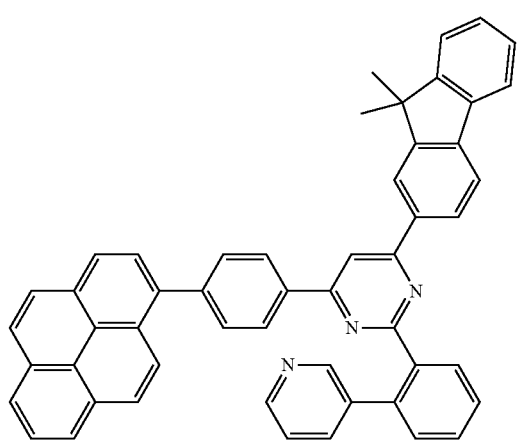

29
-continued
30
-continued
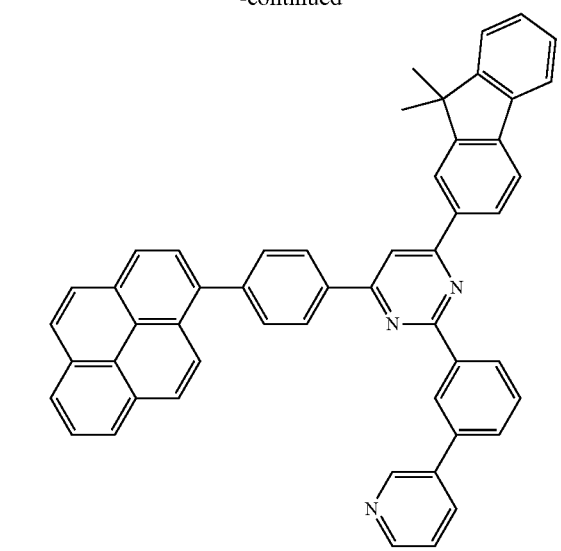
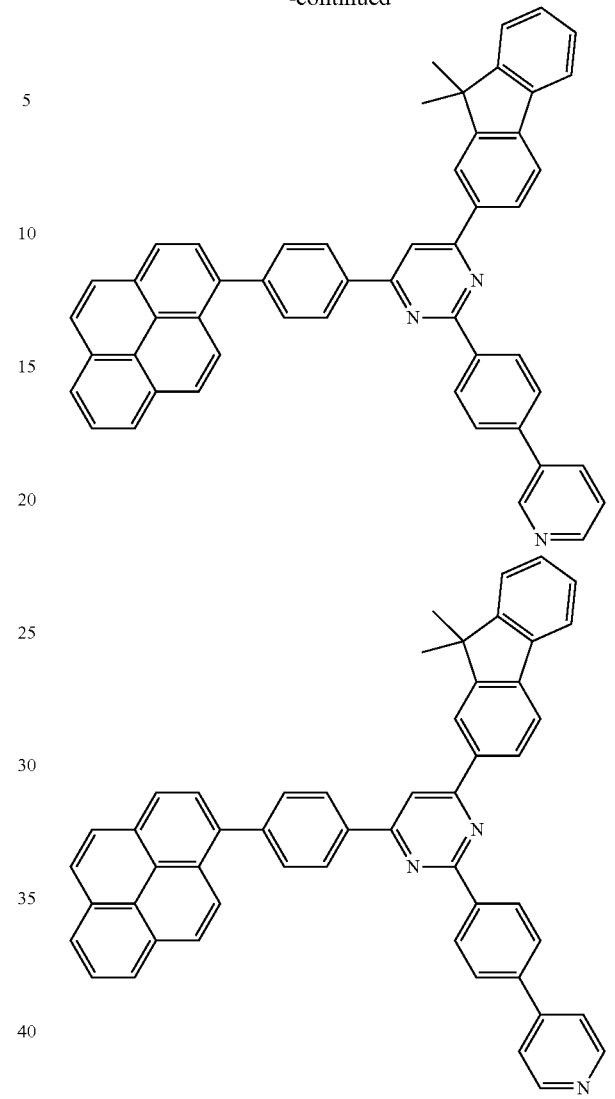
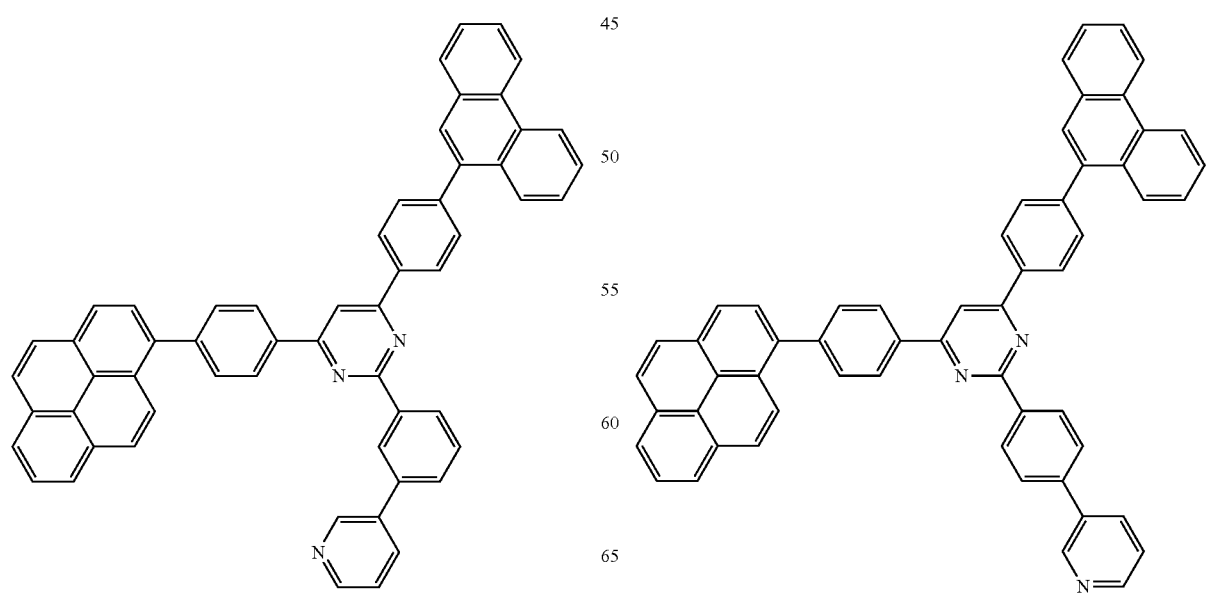

31
-continued
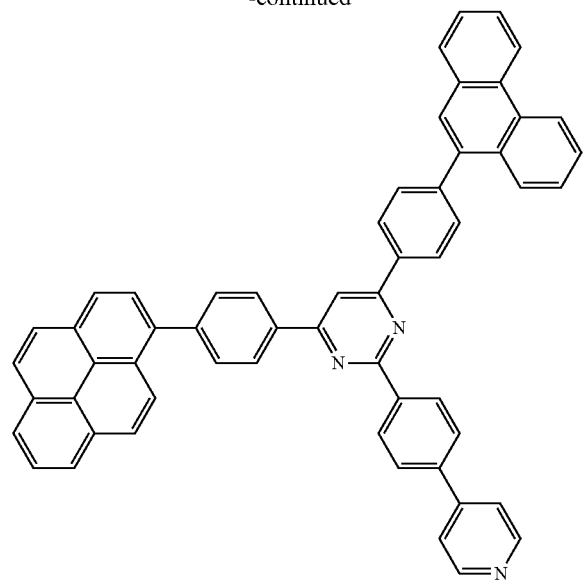
[Formula 30]
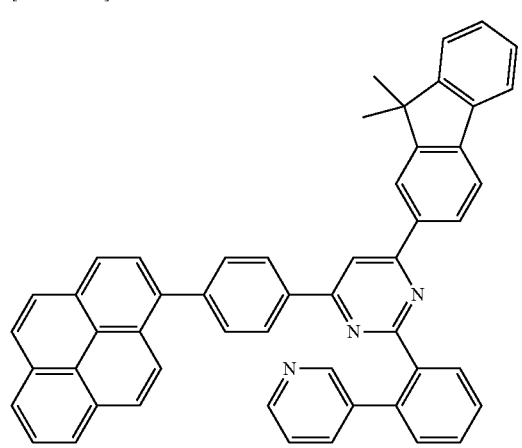
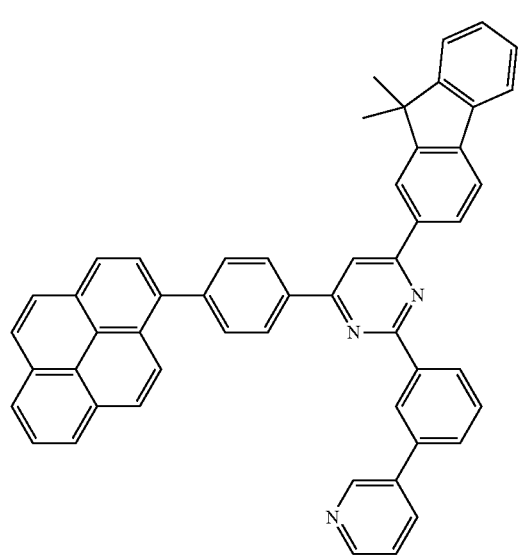
32
-continued
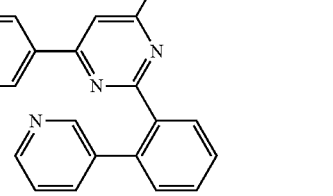
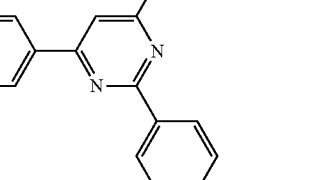
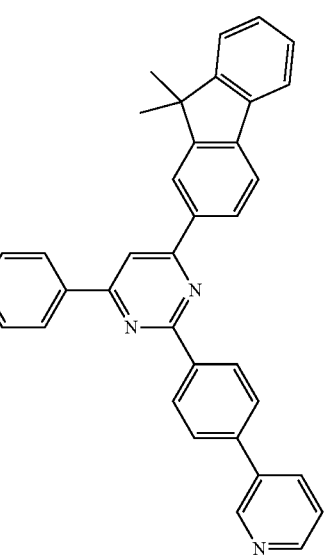

[Formula 31]
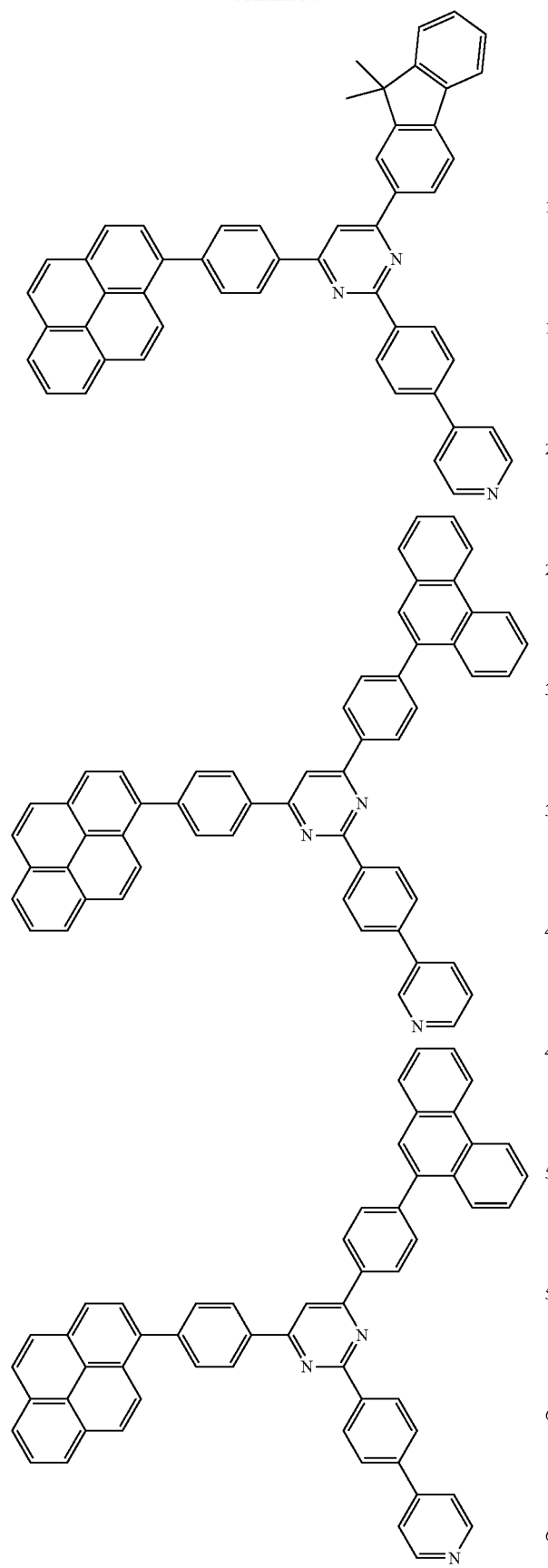
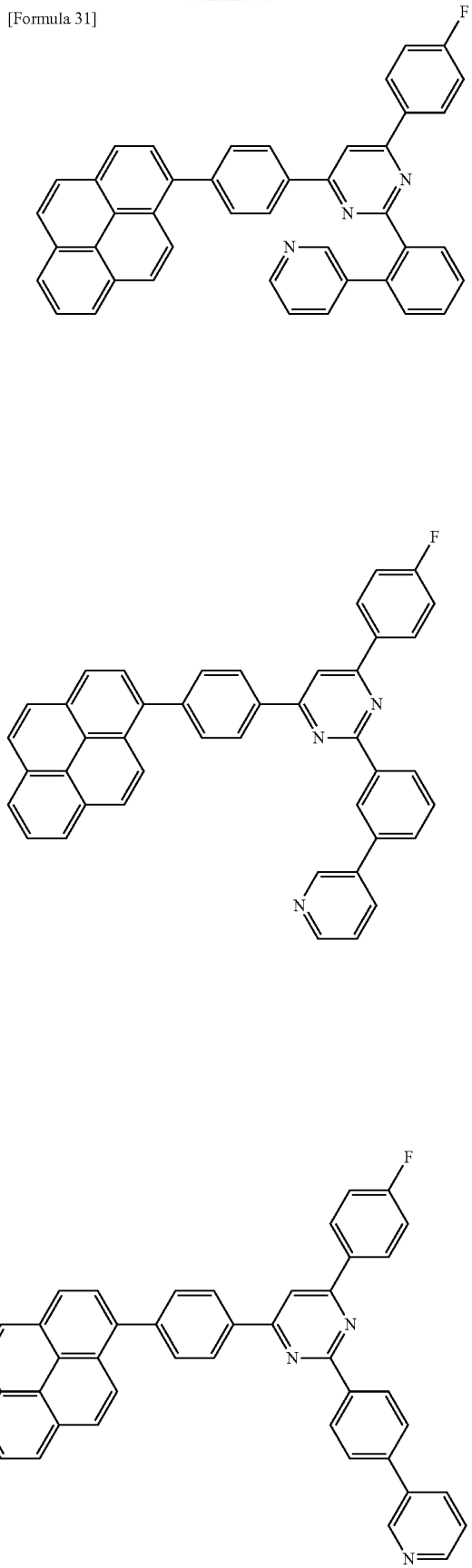

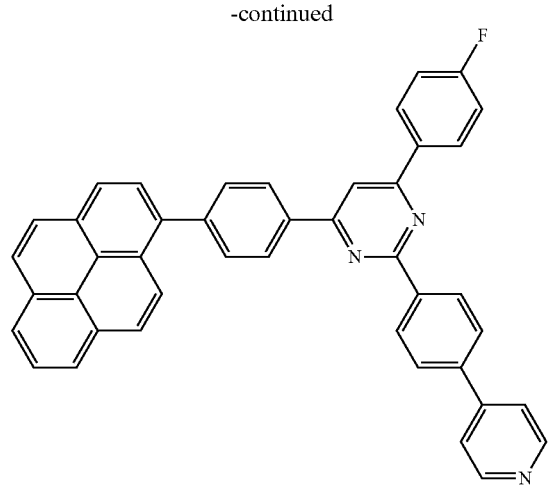
[Formula 32]
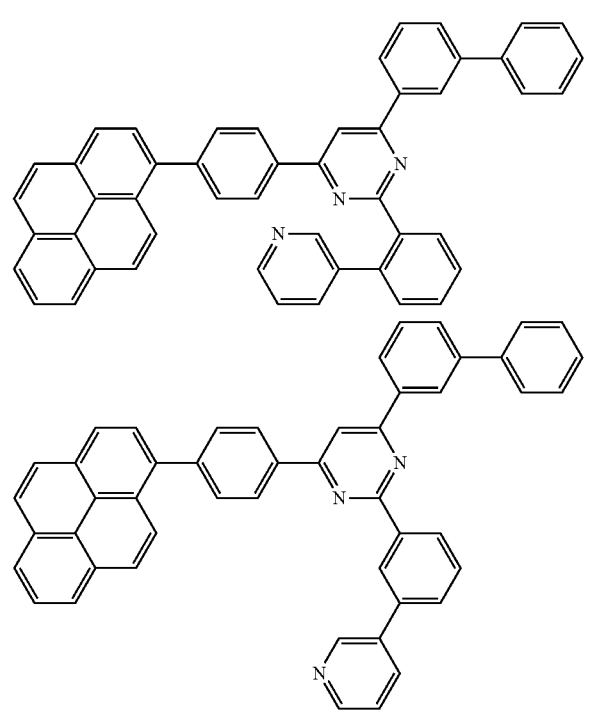
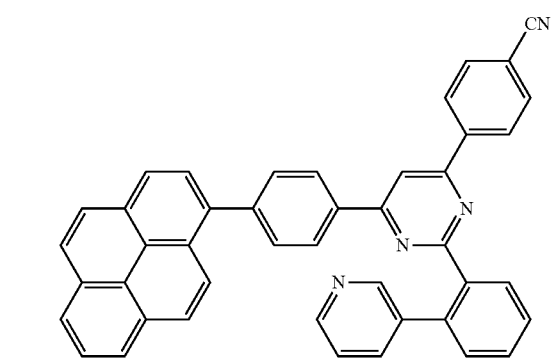
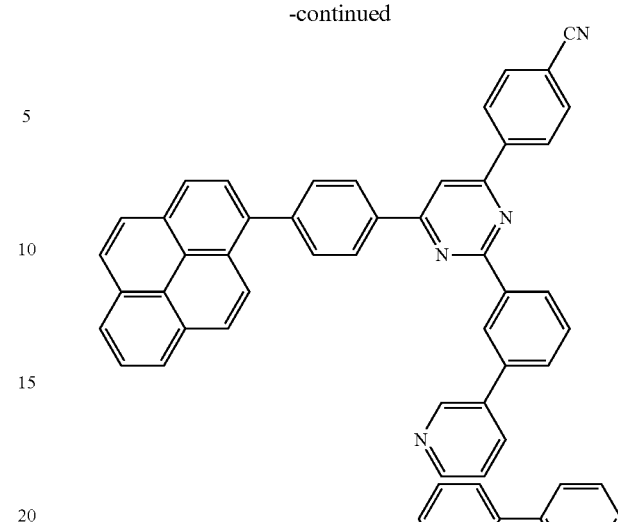
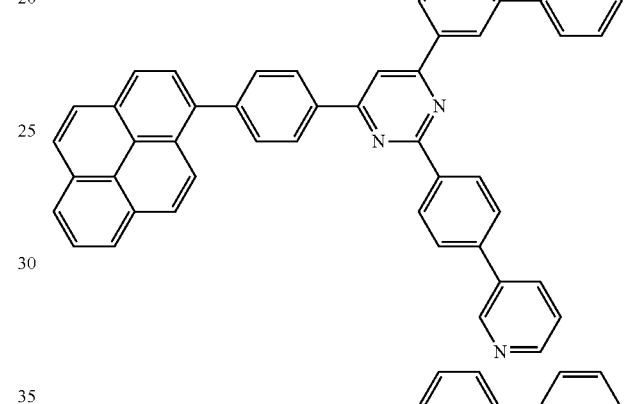
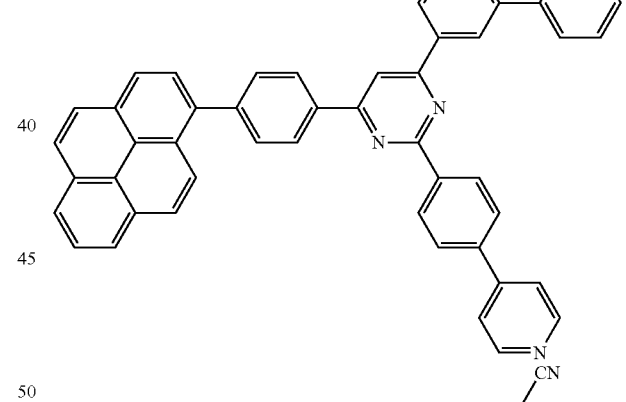
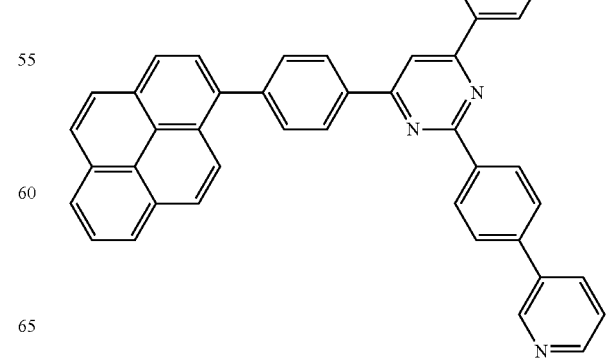

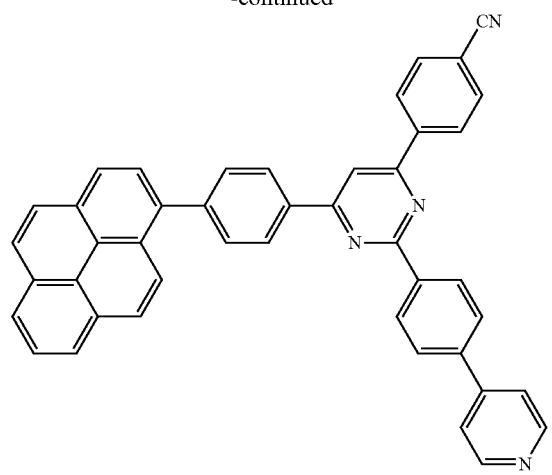
[Formula 33]
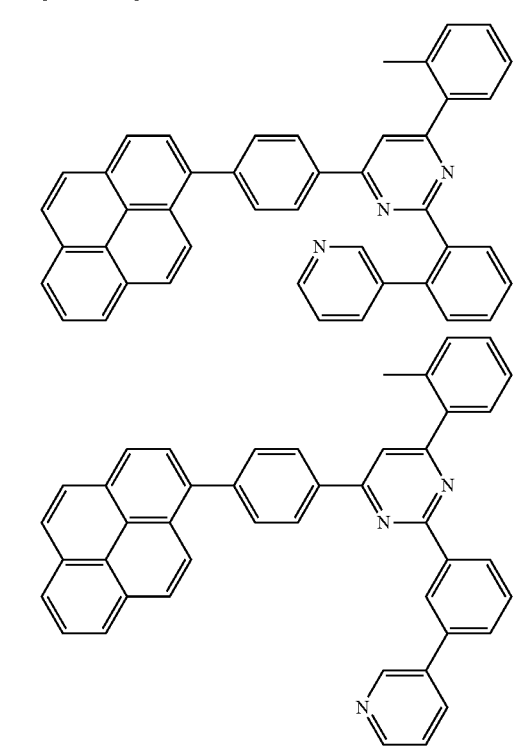
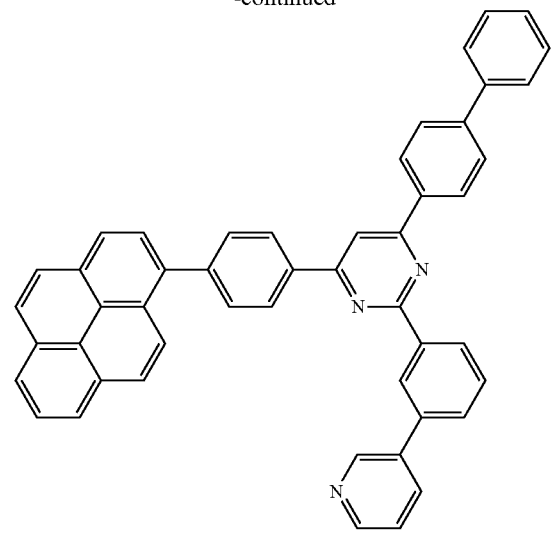

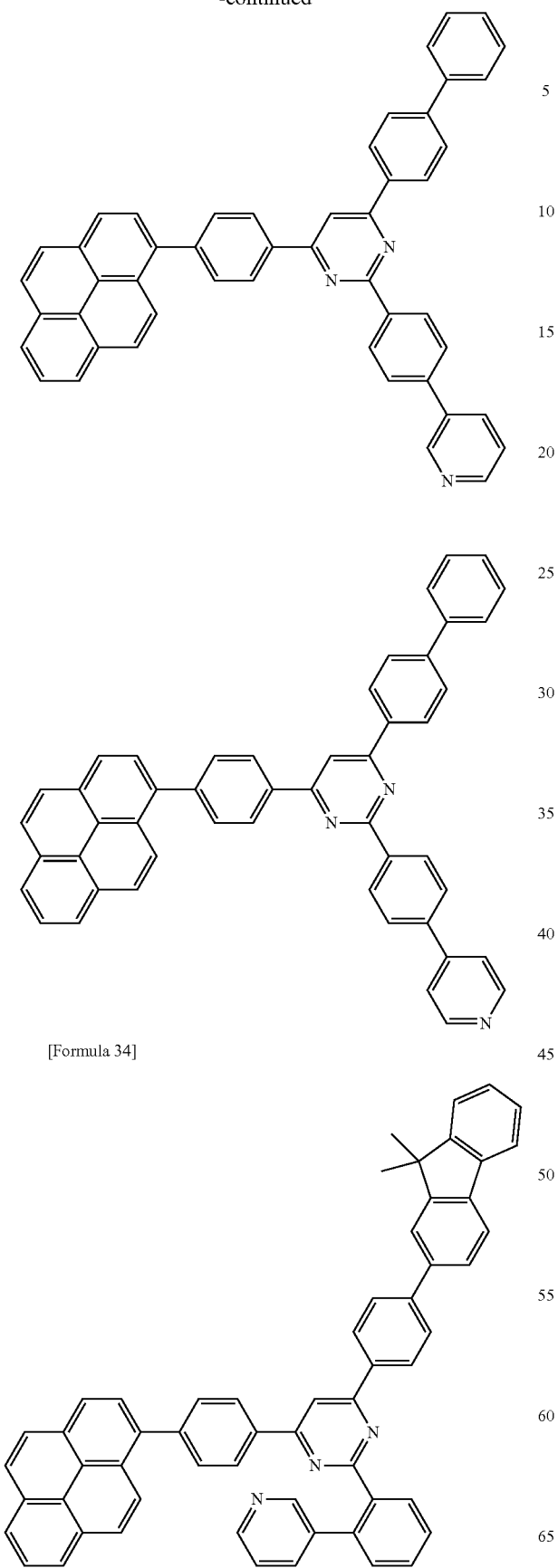
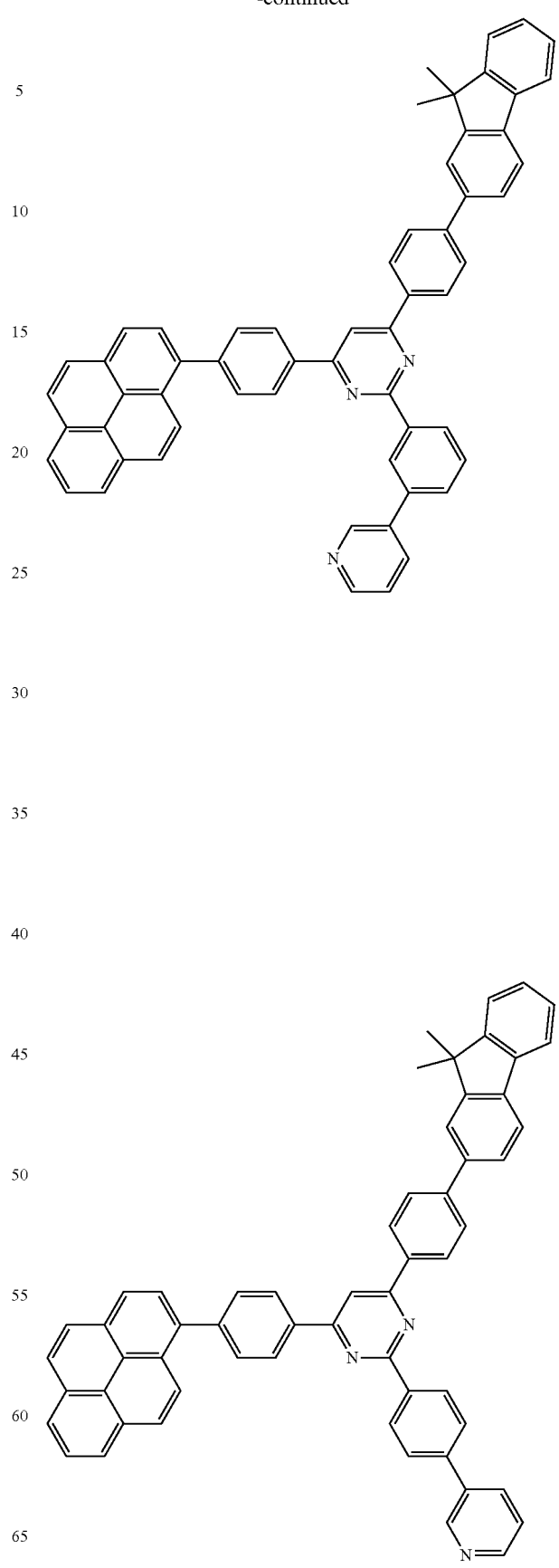

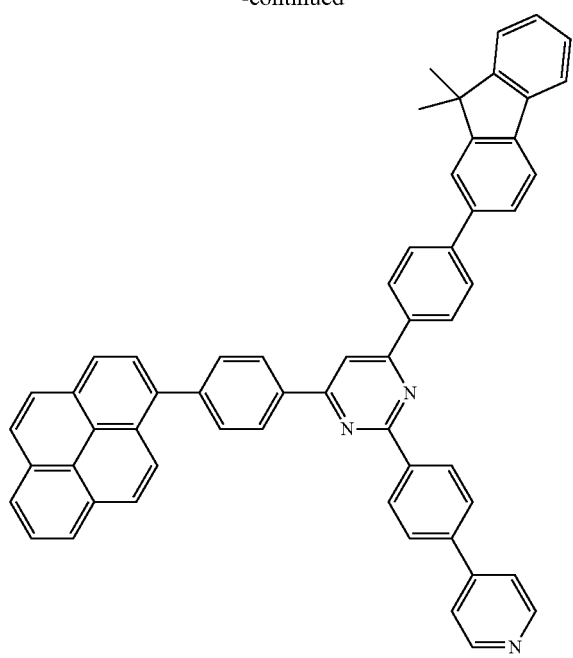
[Formula 35]
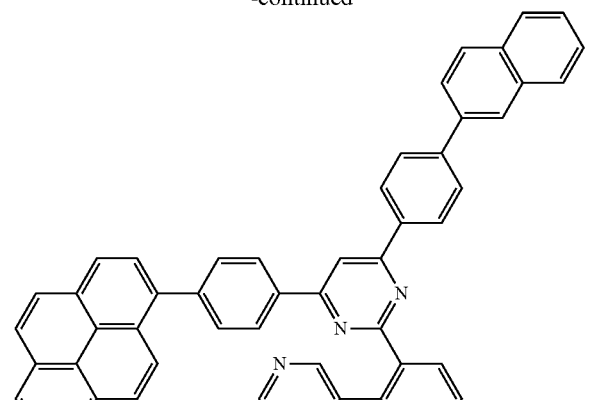
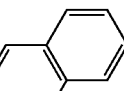
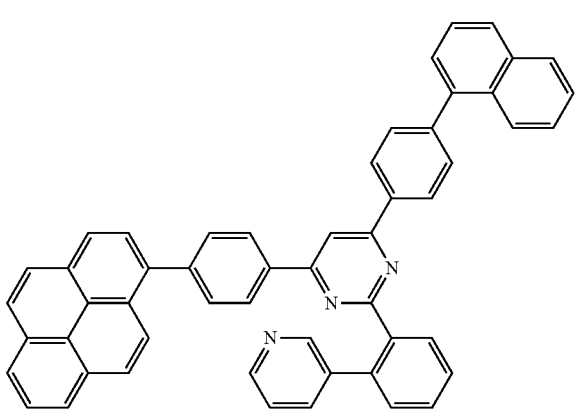
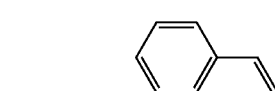
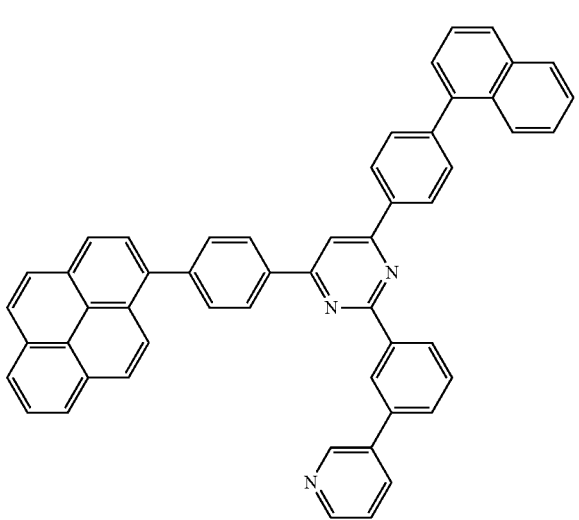
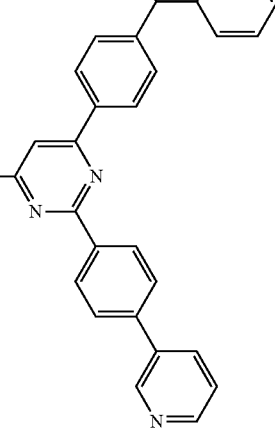

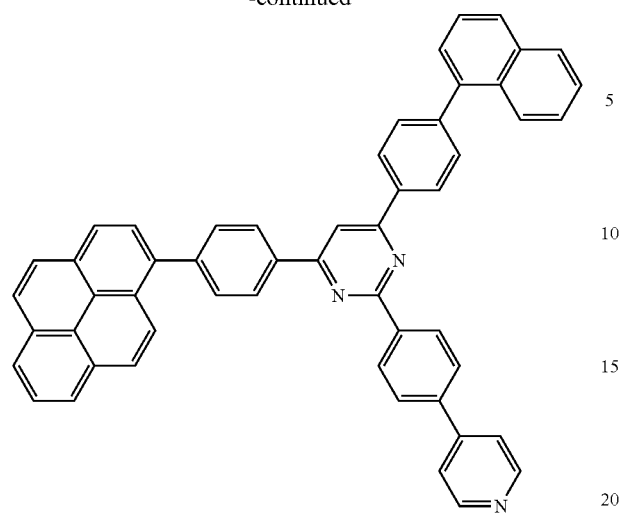
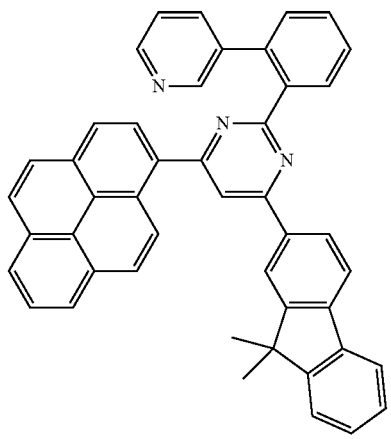
[Formula 36]
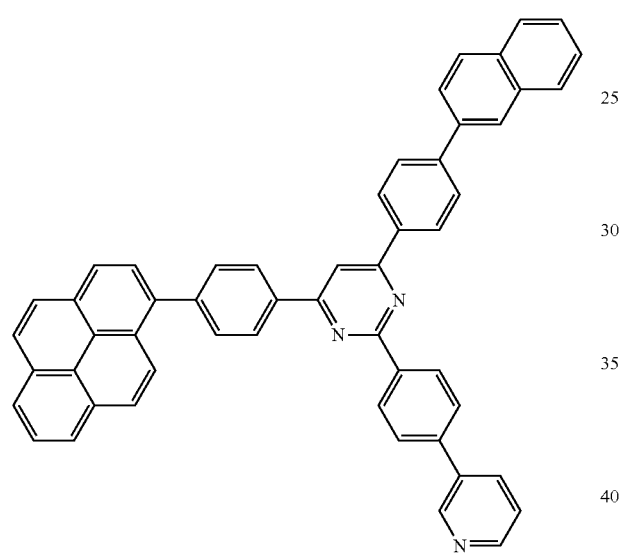
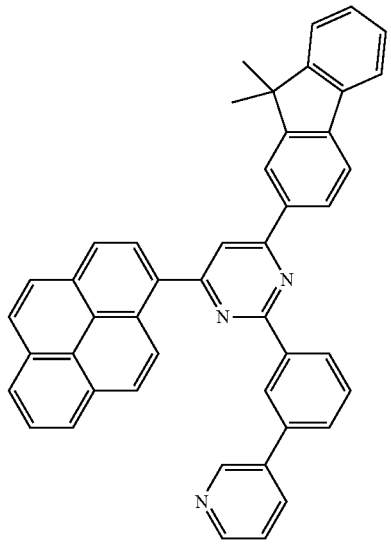
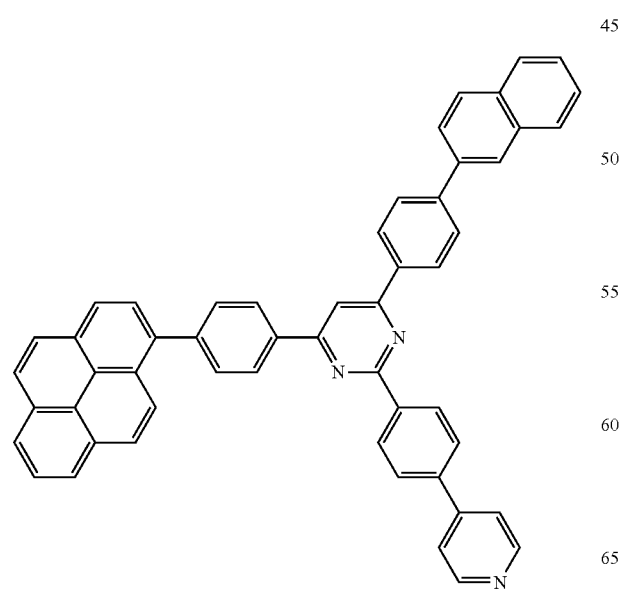
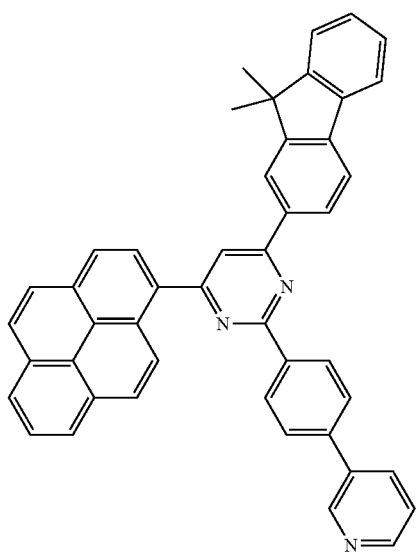

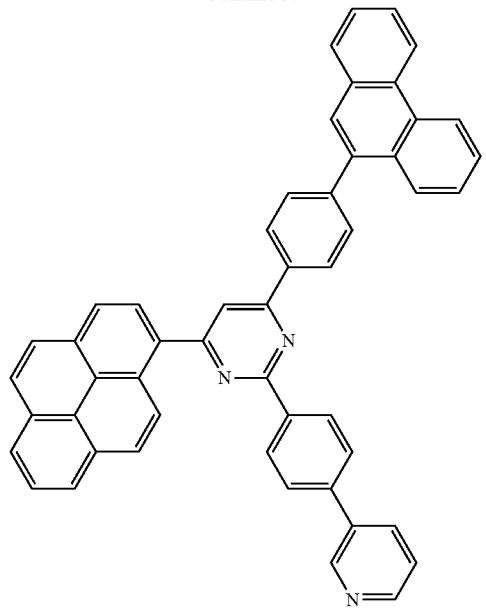
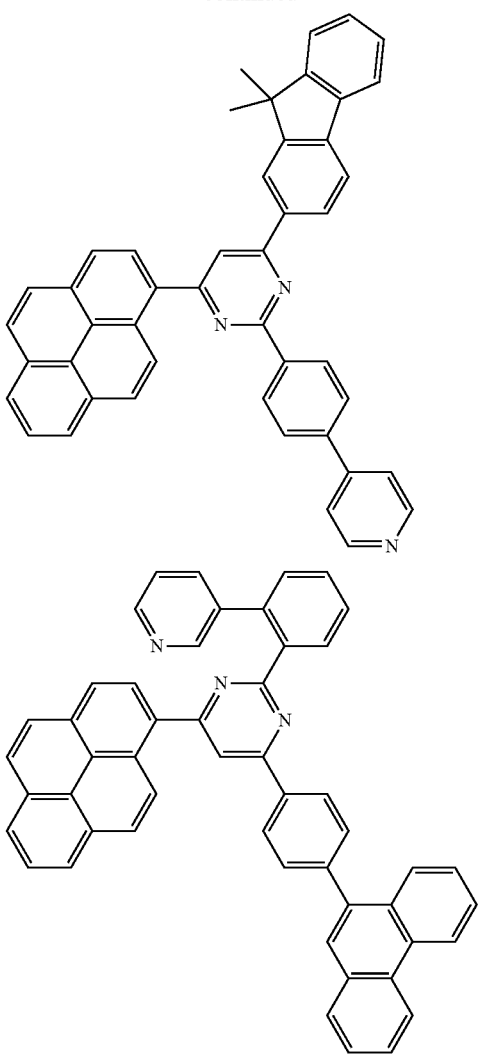
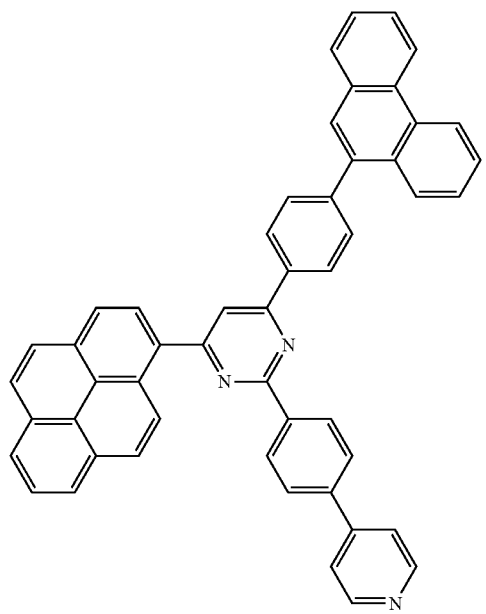
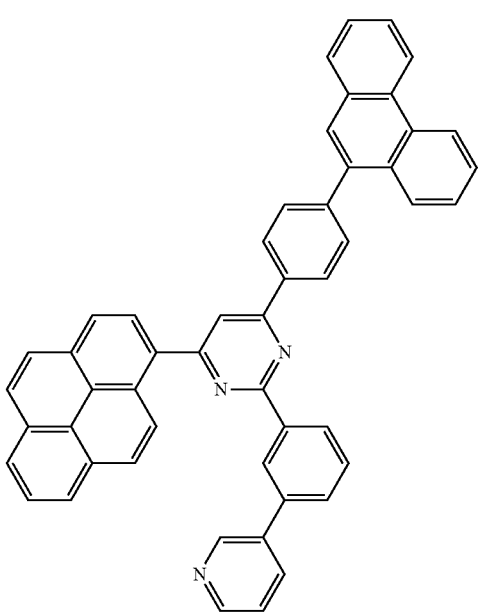

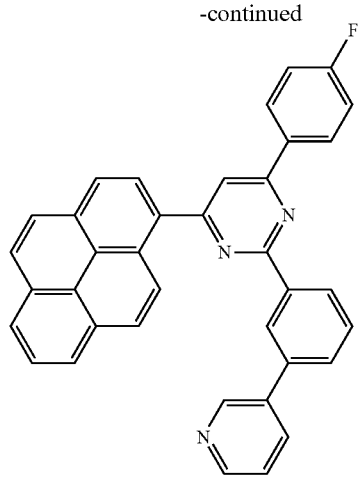
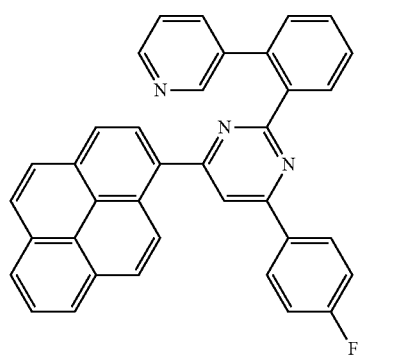
[Formula 37]
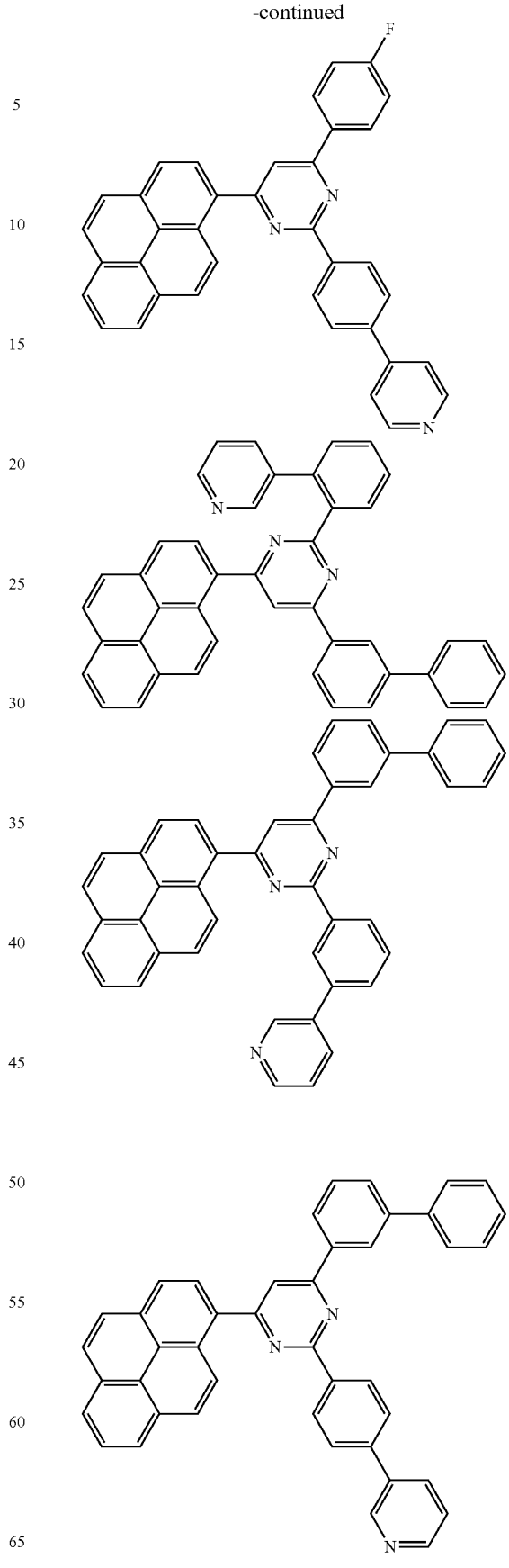

[Formula 38]
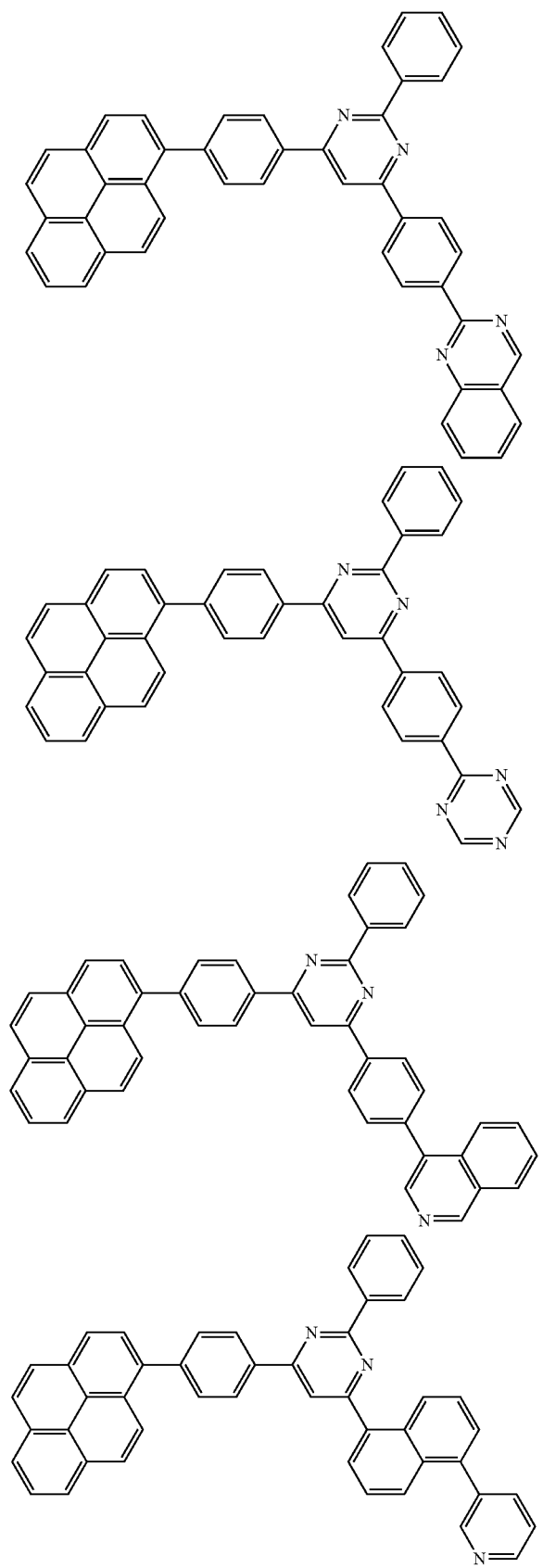
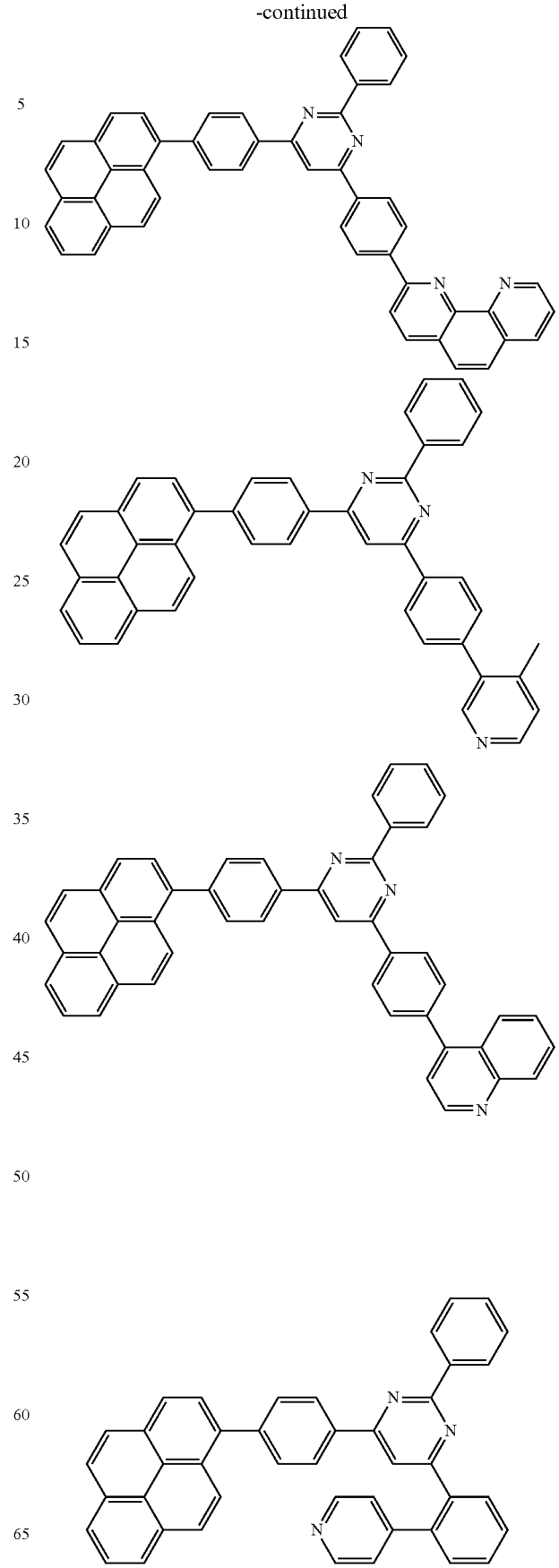

[Formula 39]
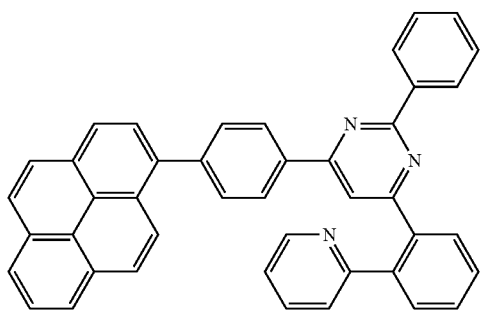
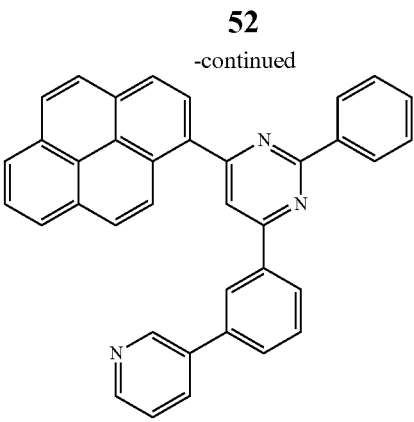
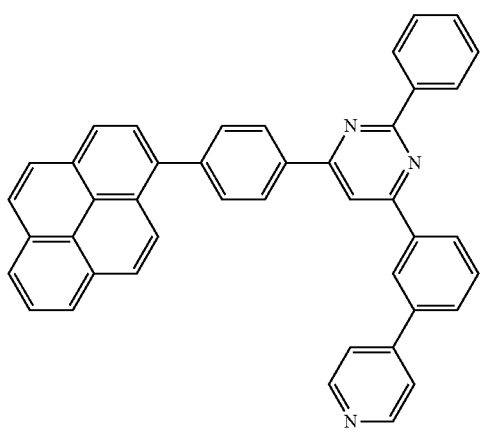
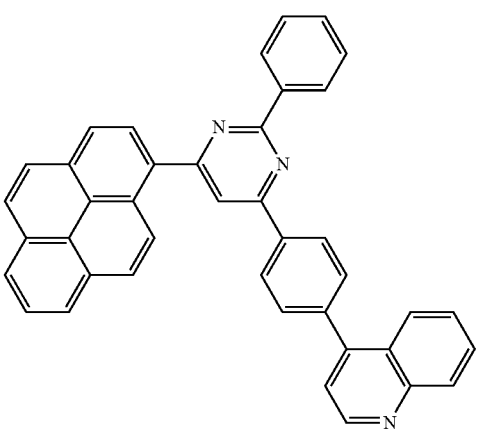
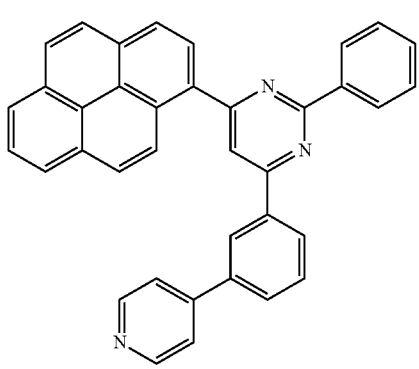
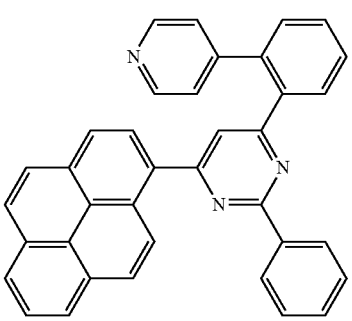
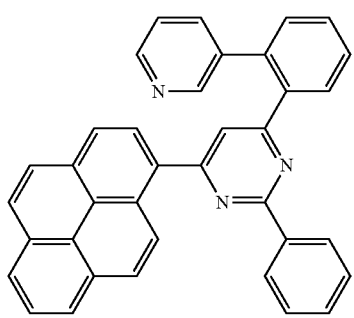
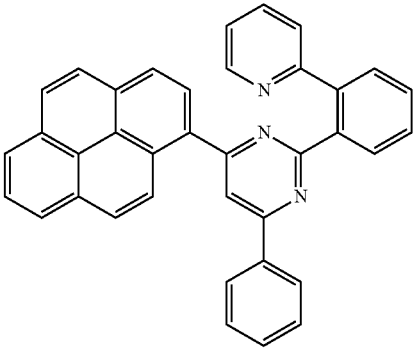

[Formula 40]
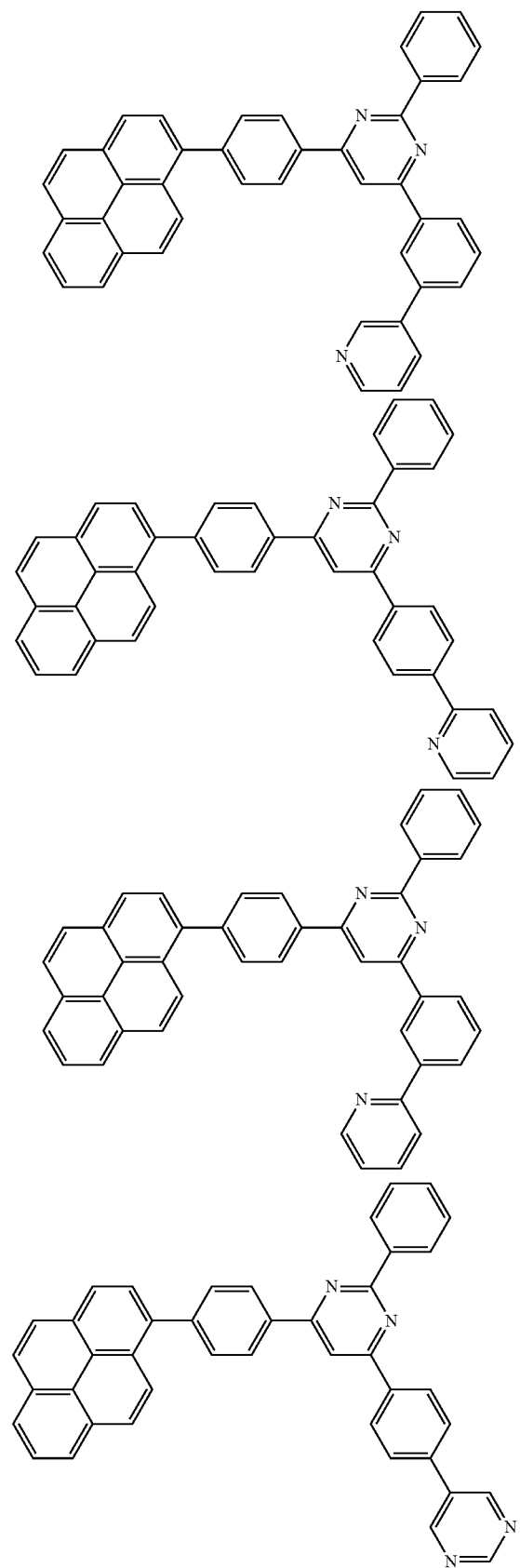
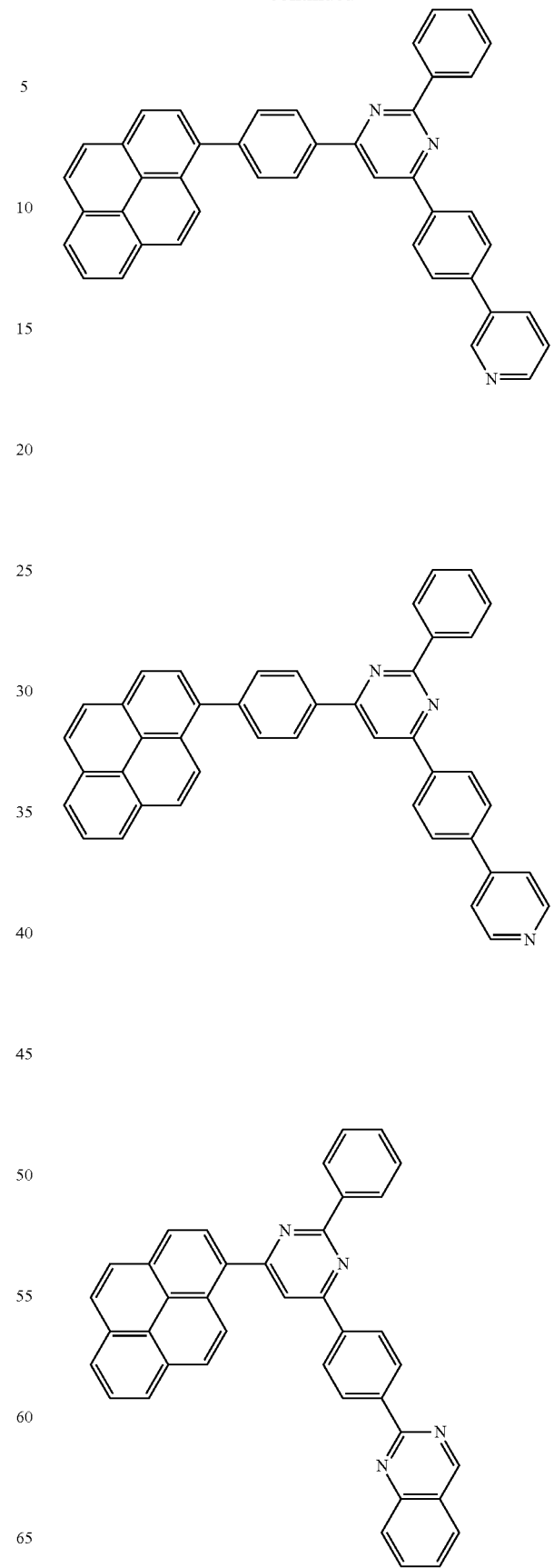

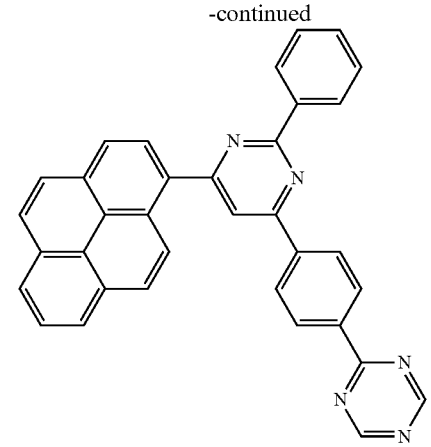
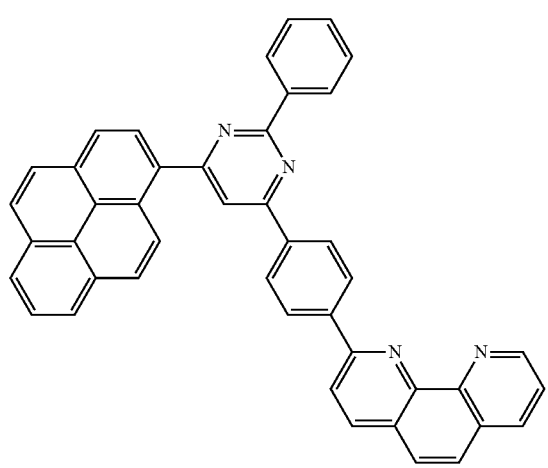
[Formula 41]
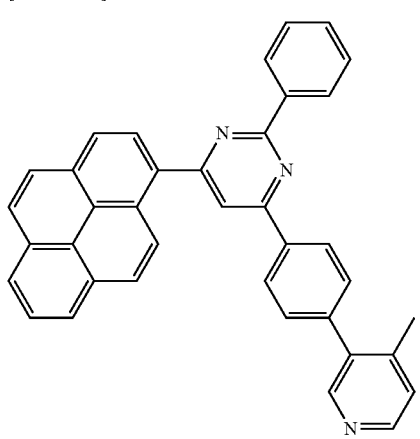
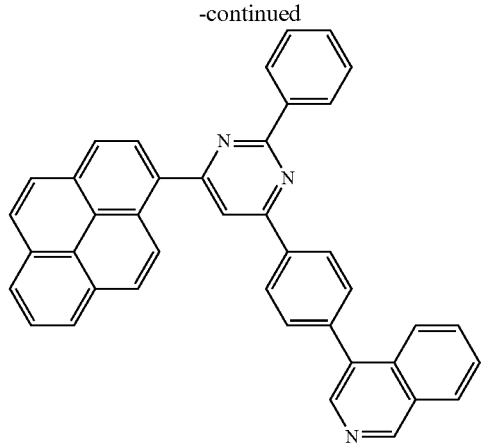
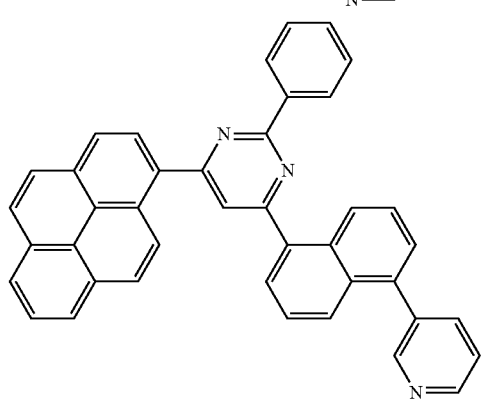
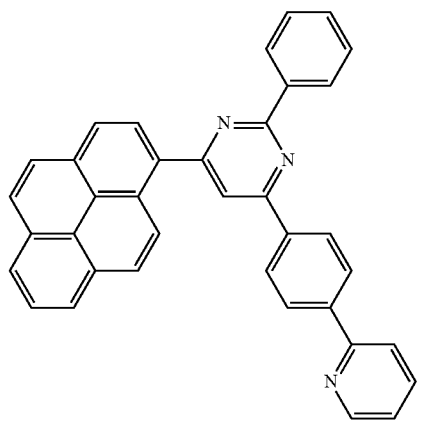
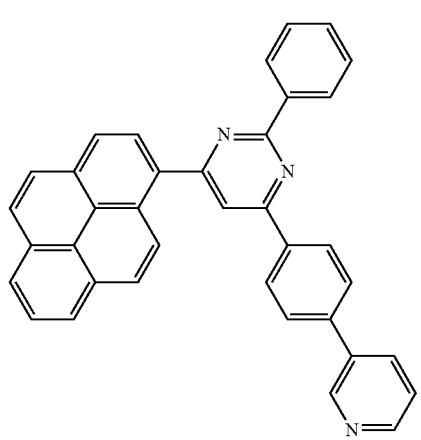

[Formula 42]
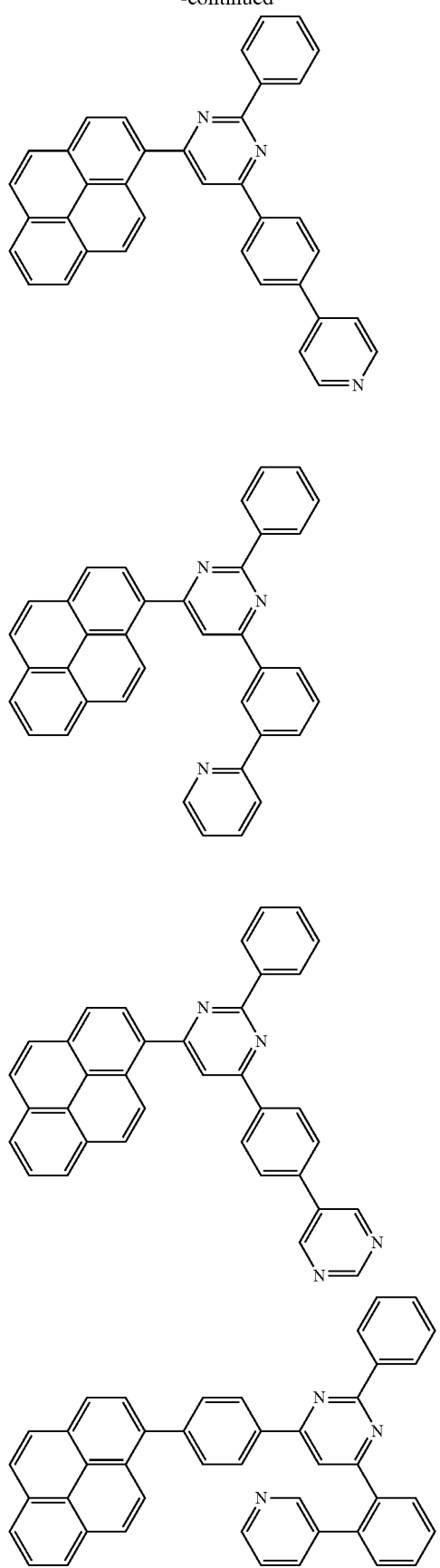
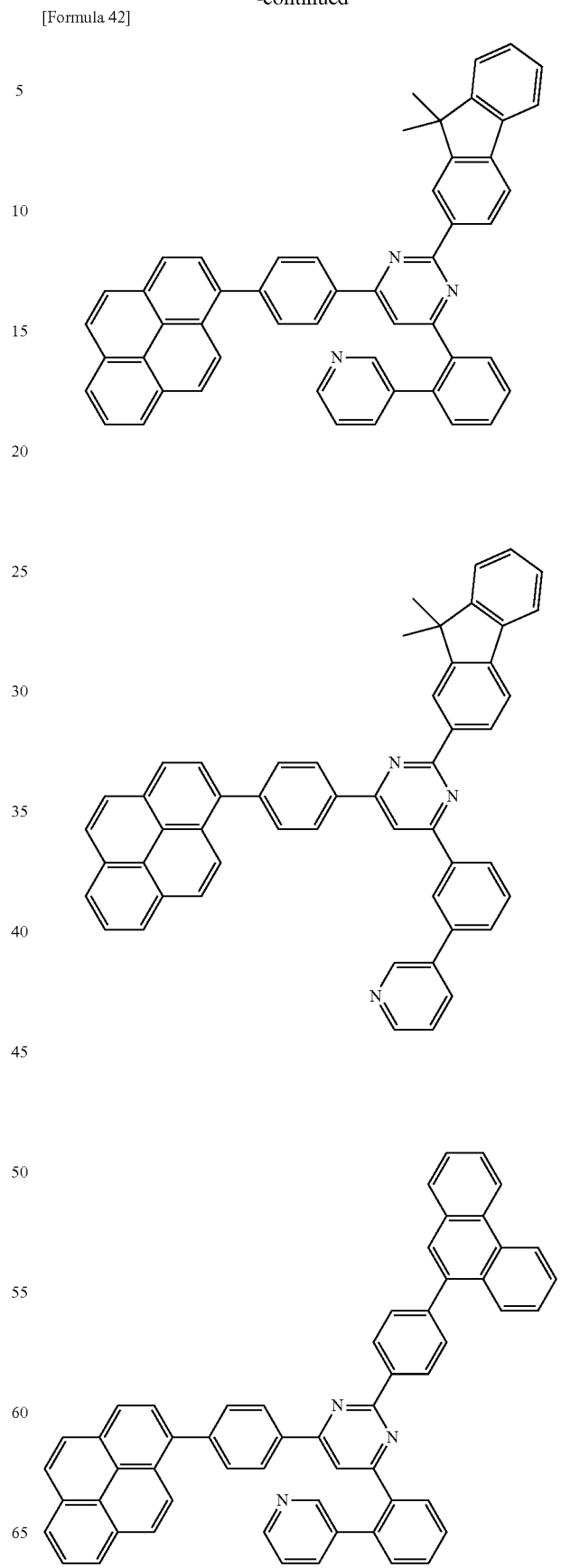

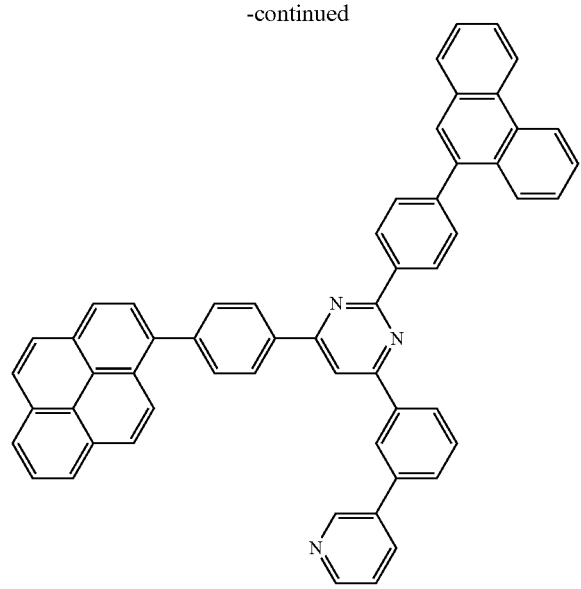
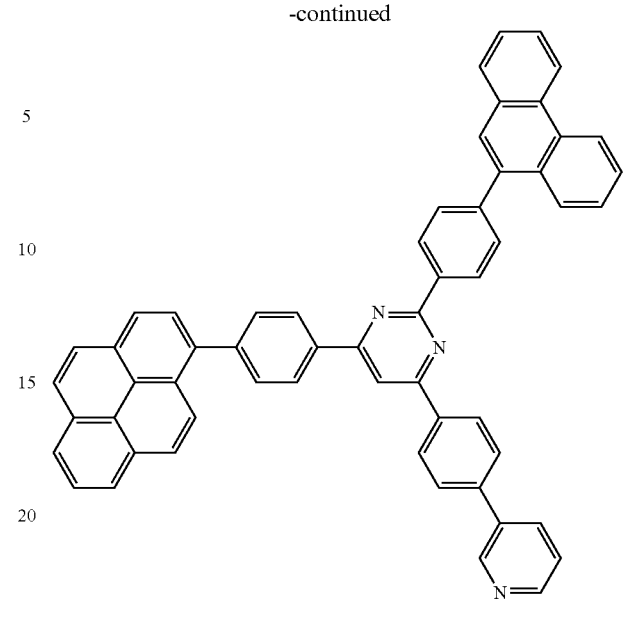
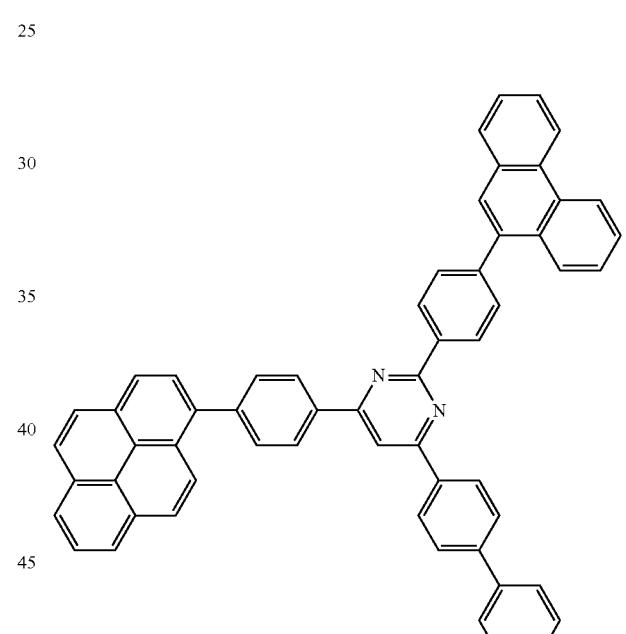
[Formula 43]
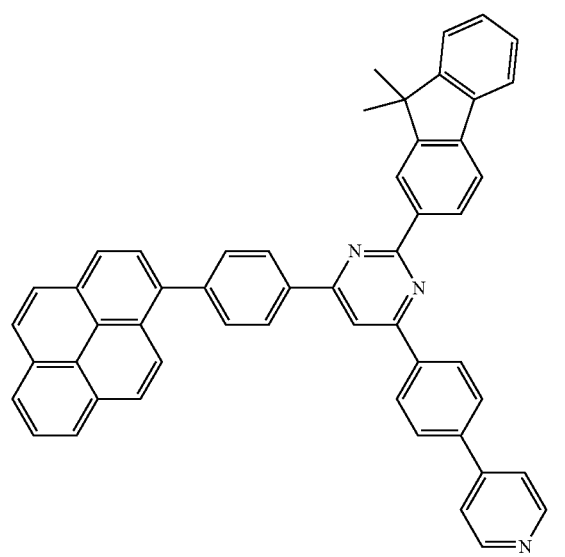
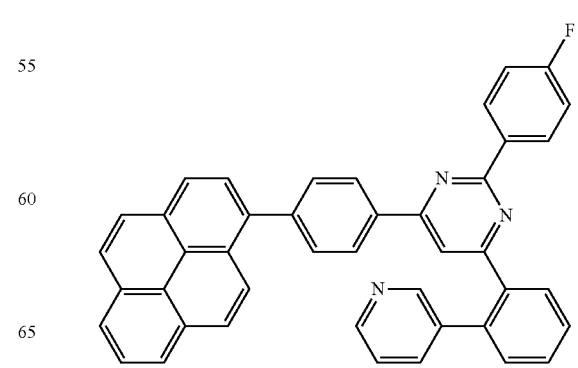

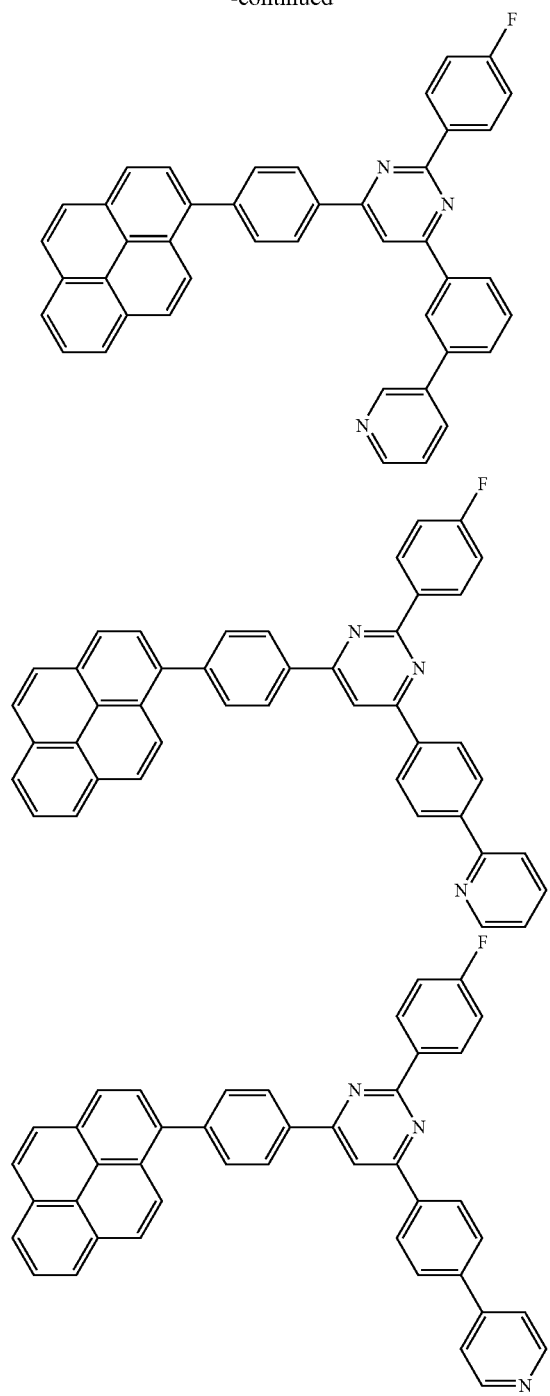
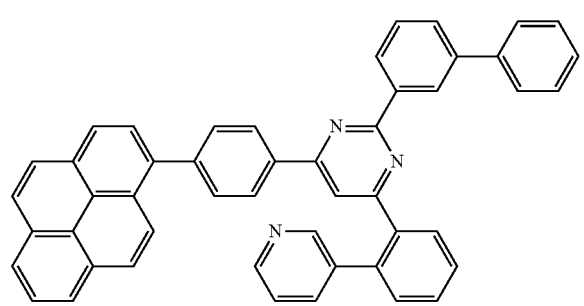
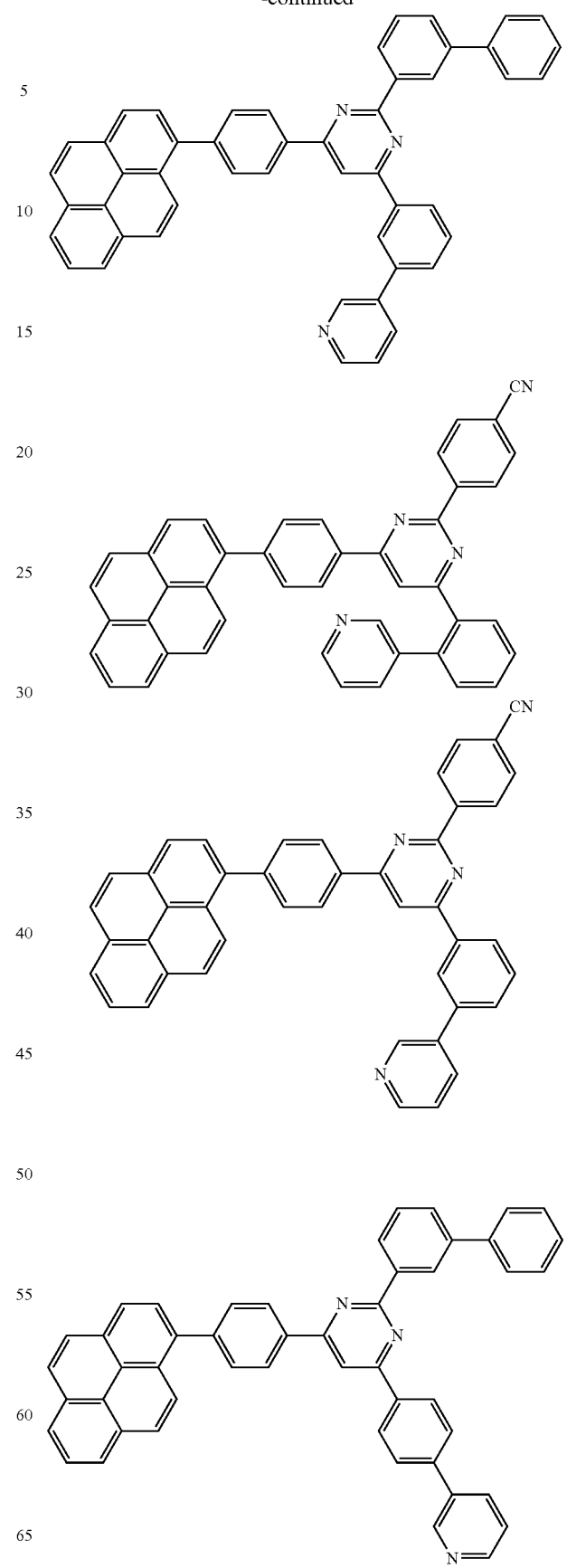
[Formula 44]

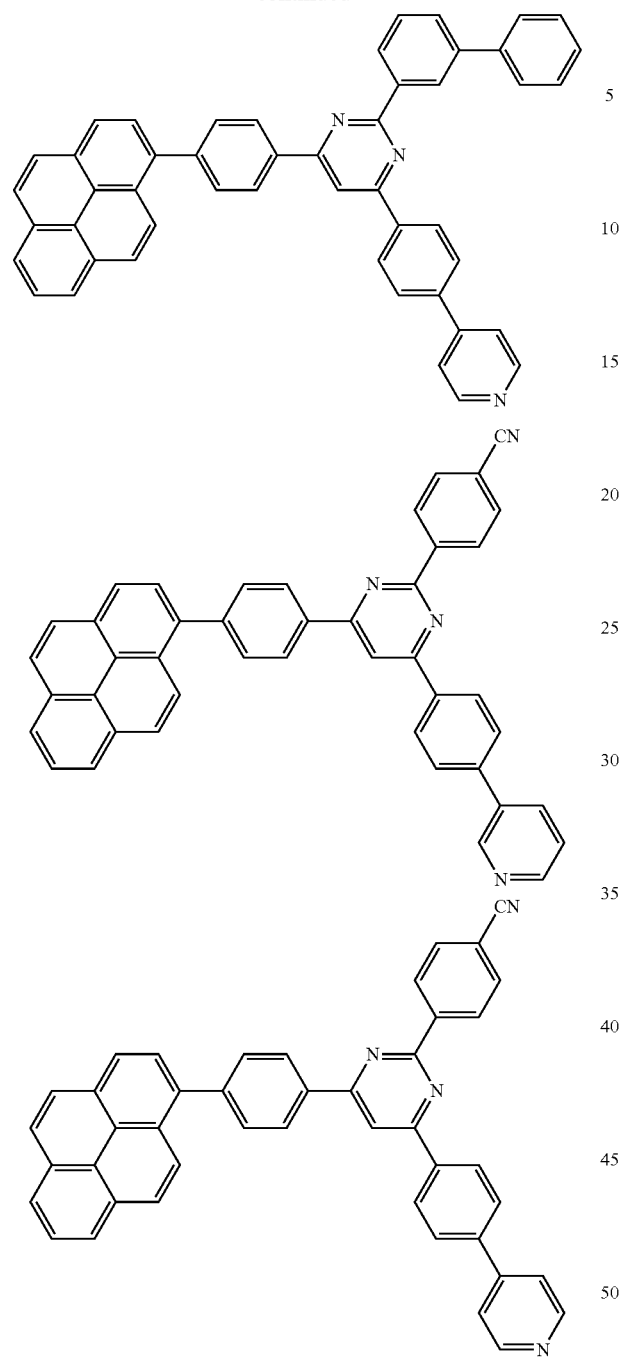
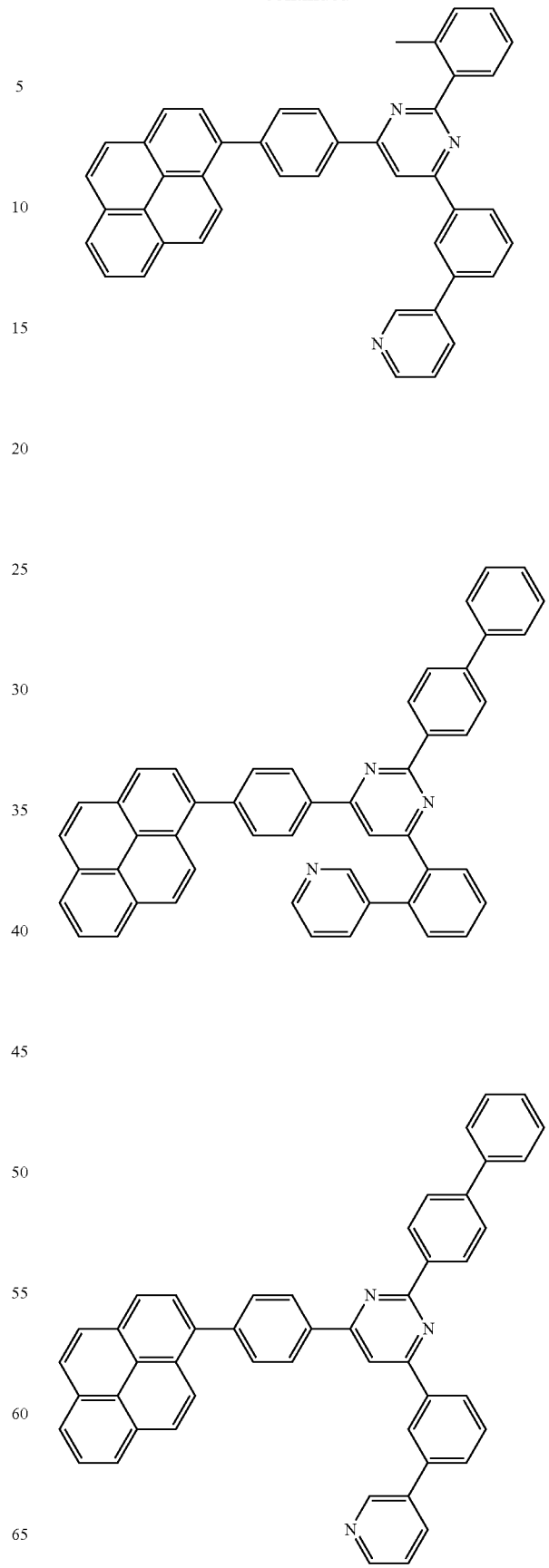
[Formula 45]
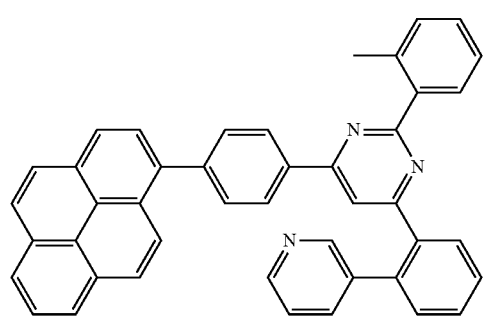

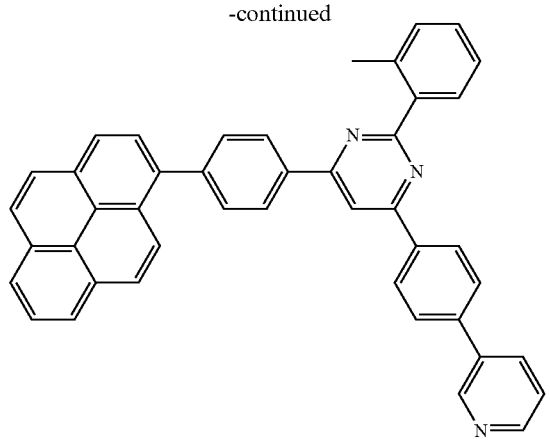
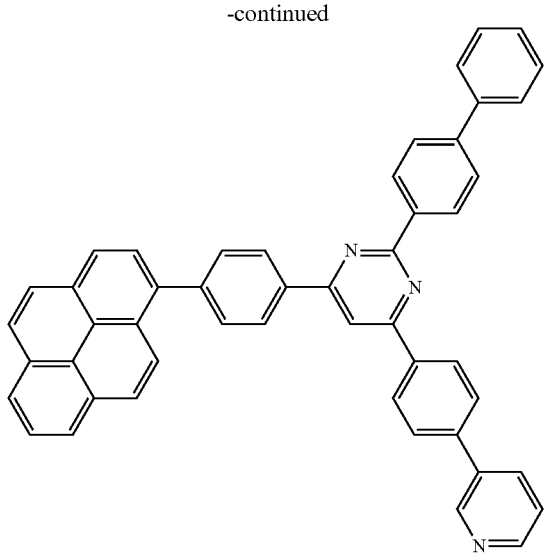
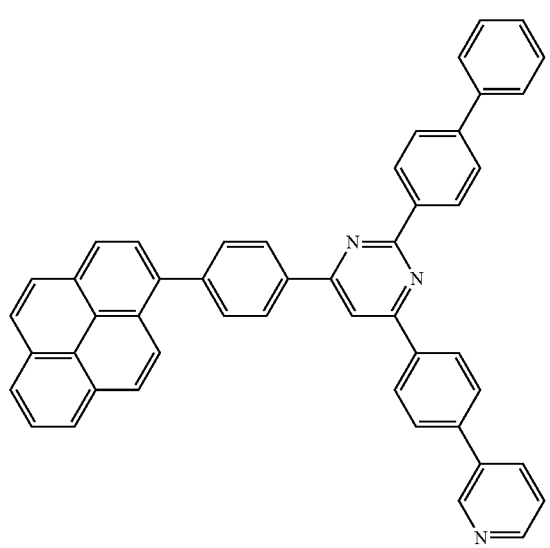
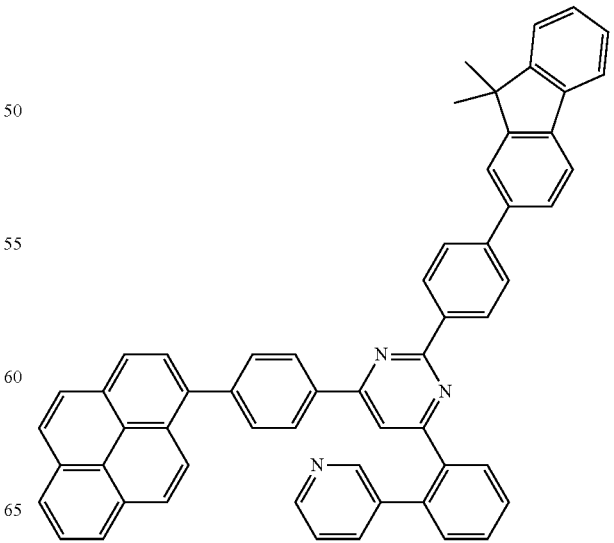
[Formula 46]

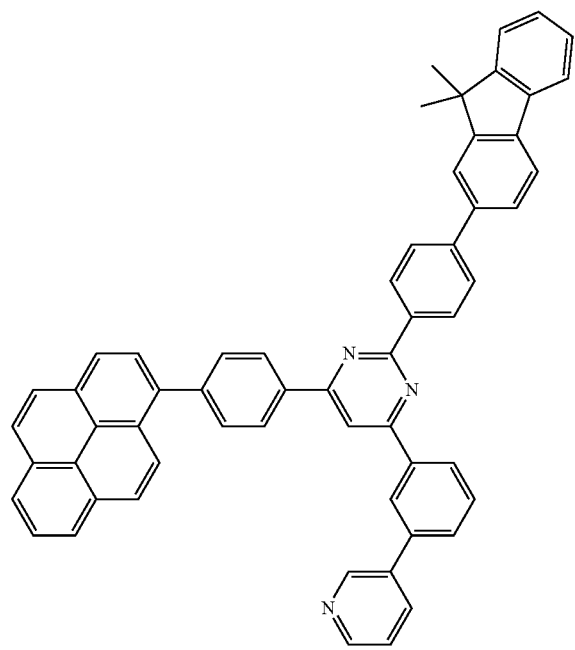
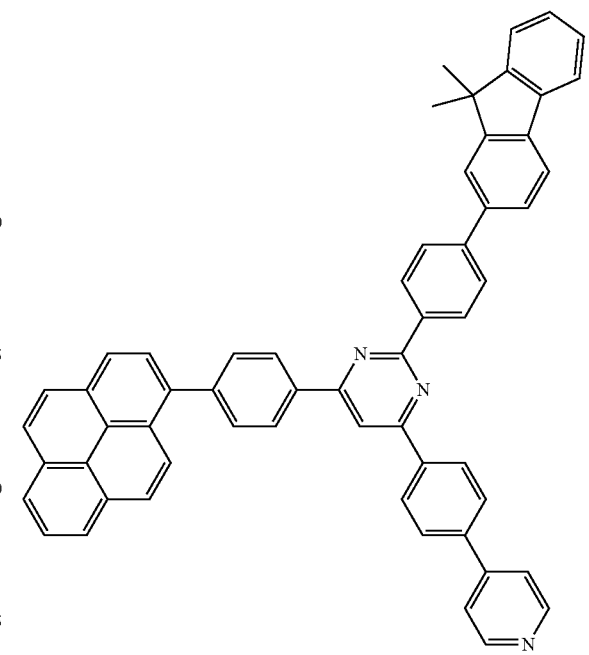
[Formula 47]
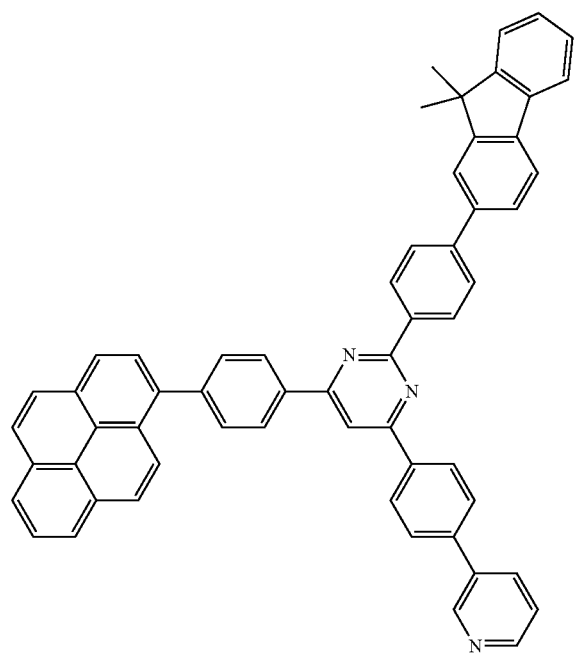
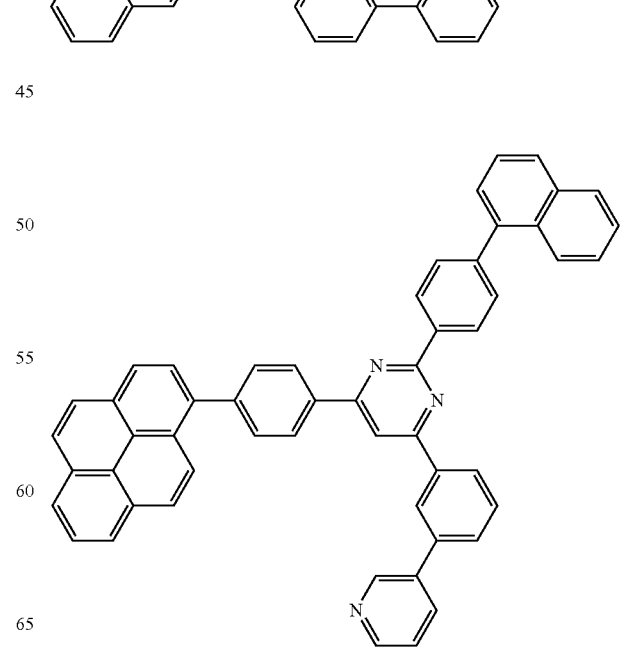

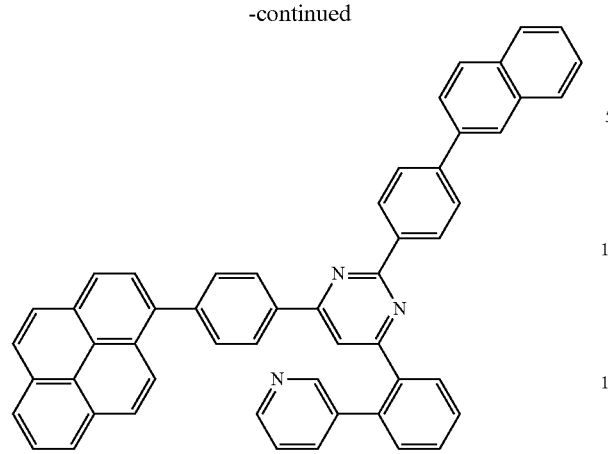
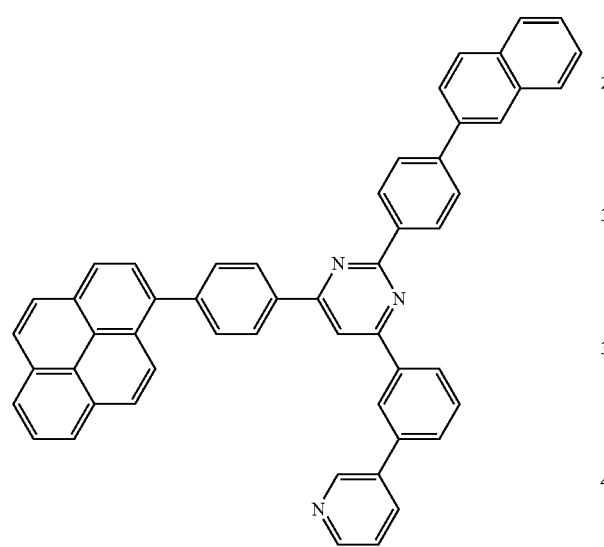
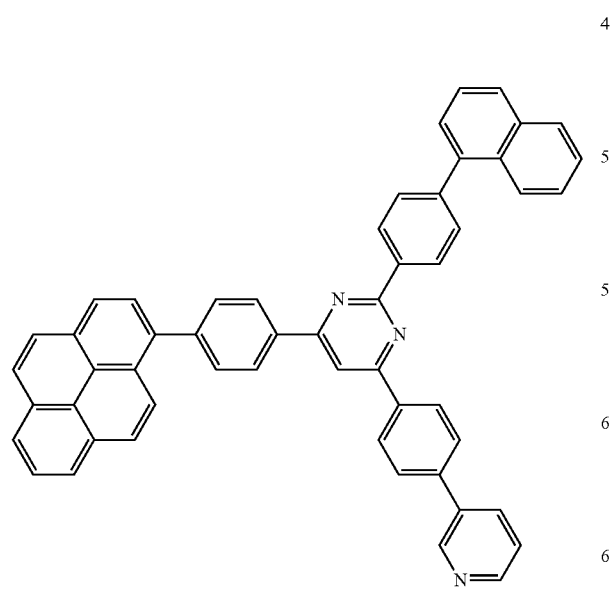
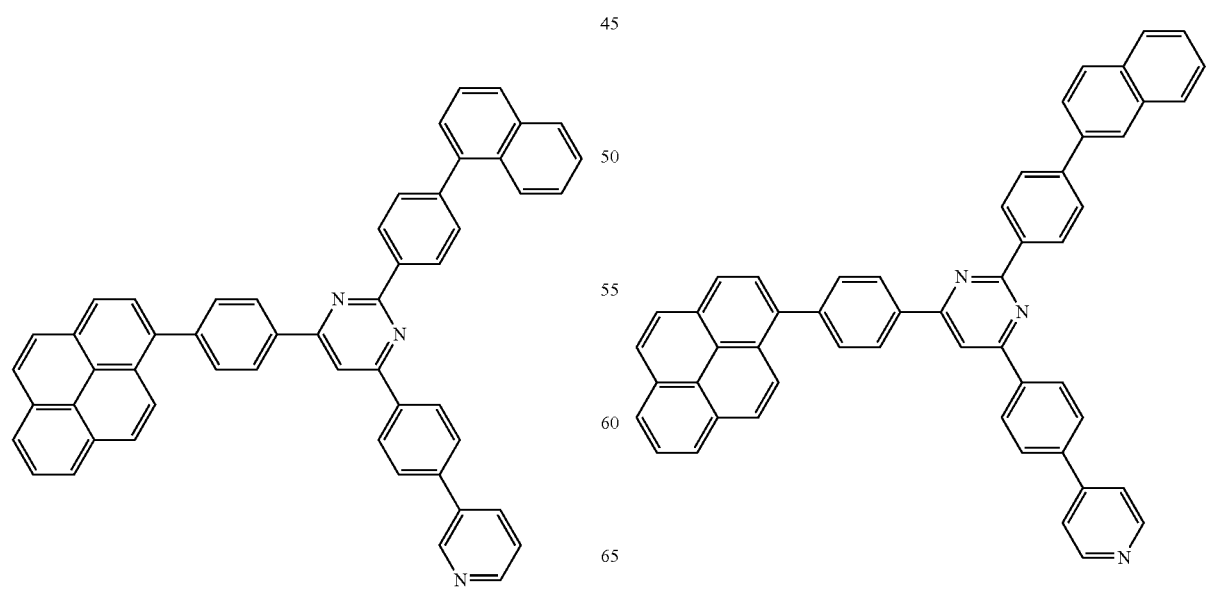

[Formula 47]
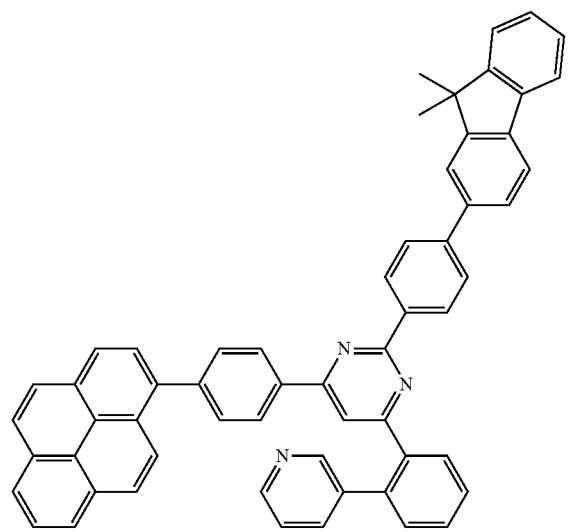
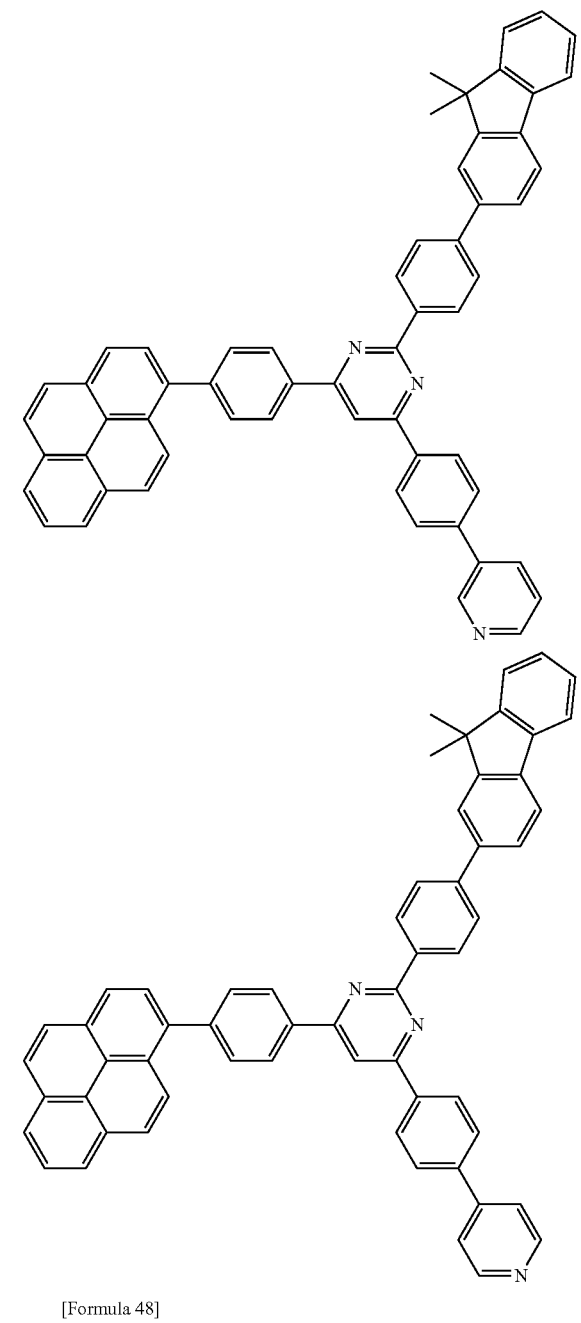
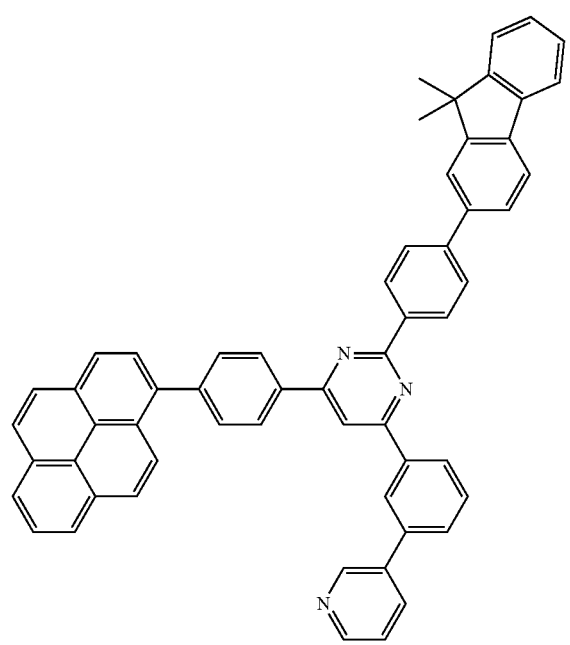
[Formula 48]
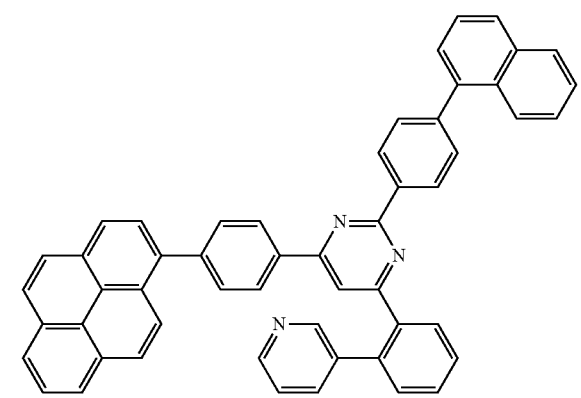

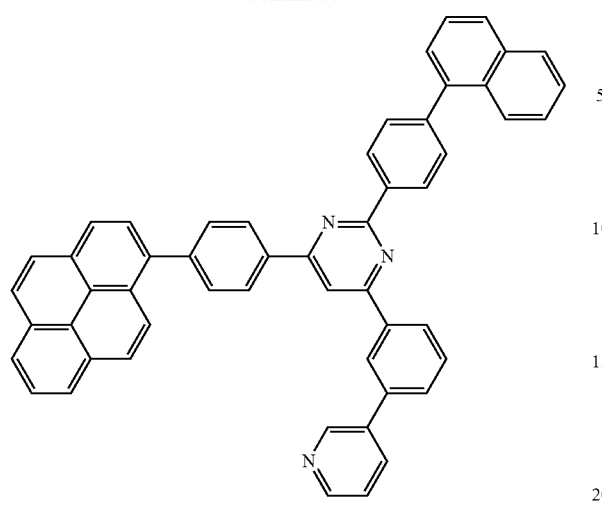
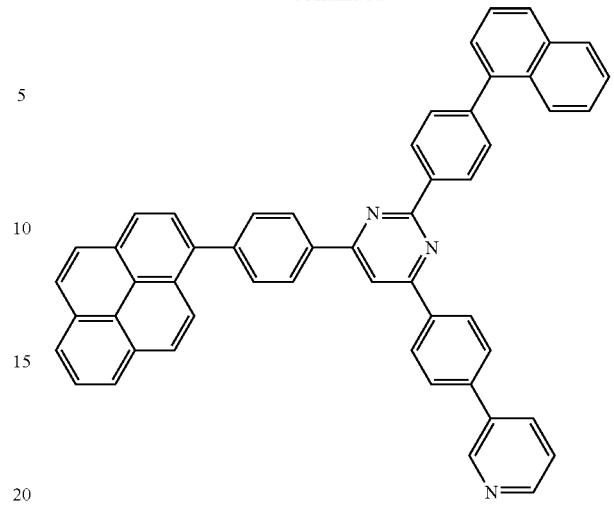
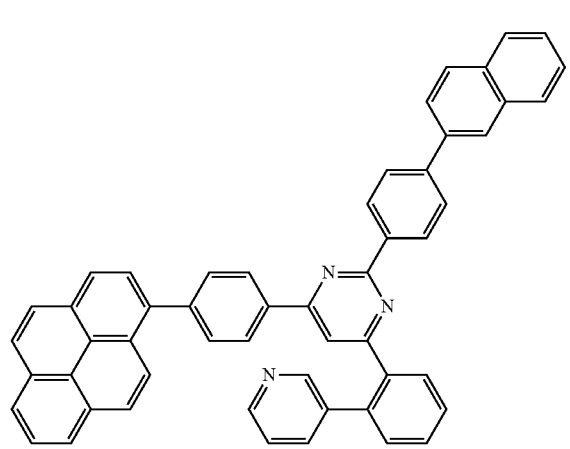
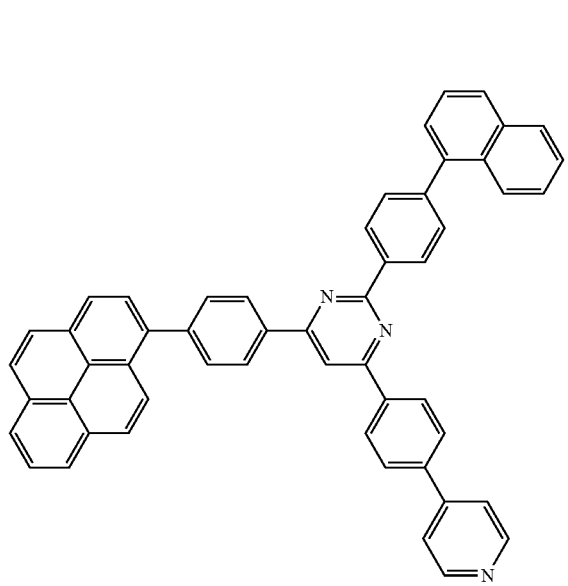
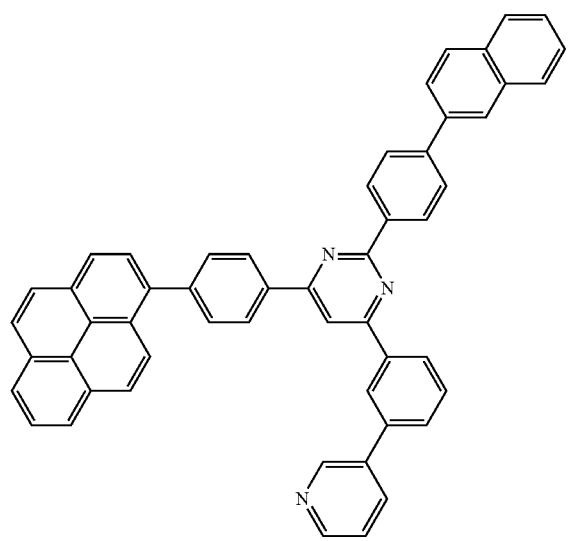
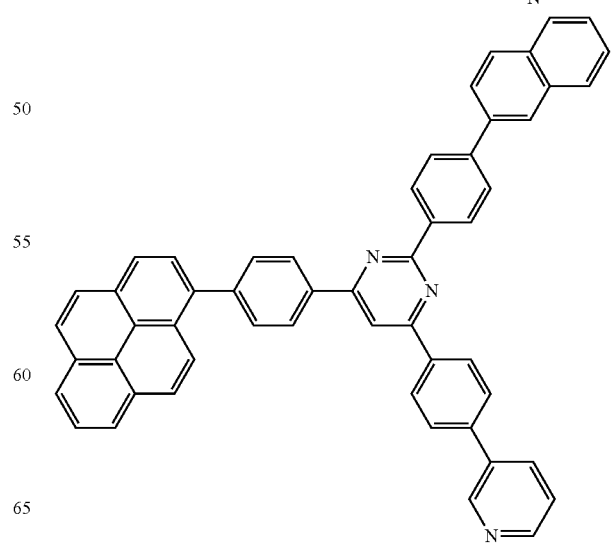

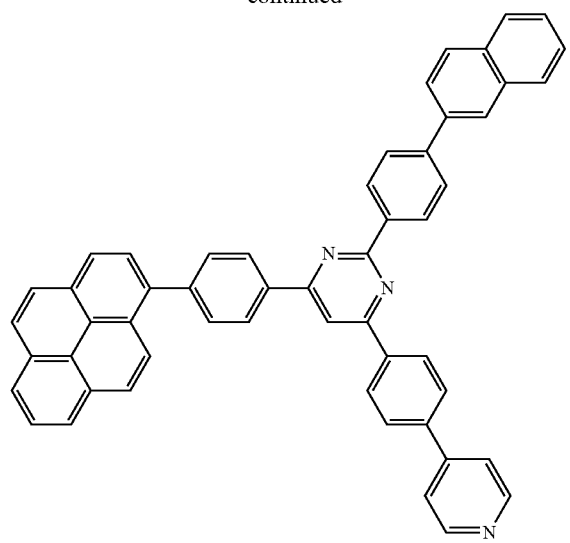
[Formula 49]
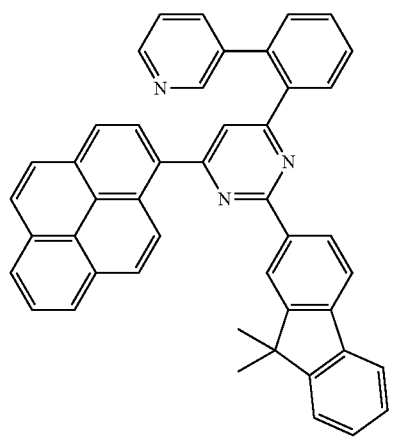
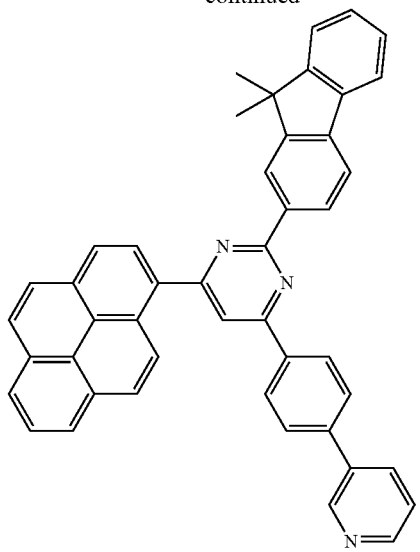
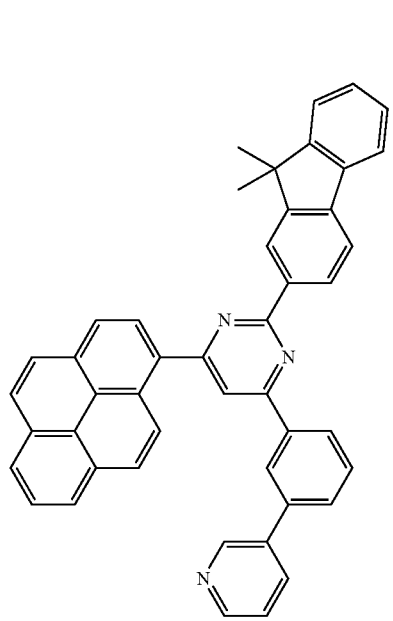
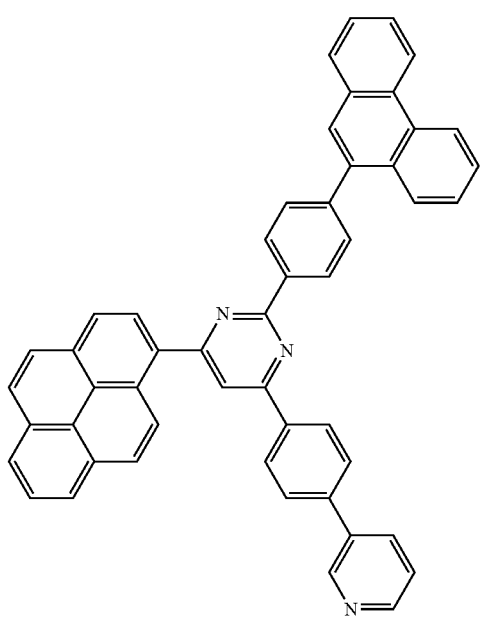

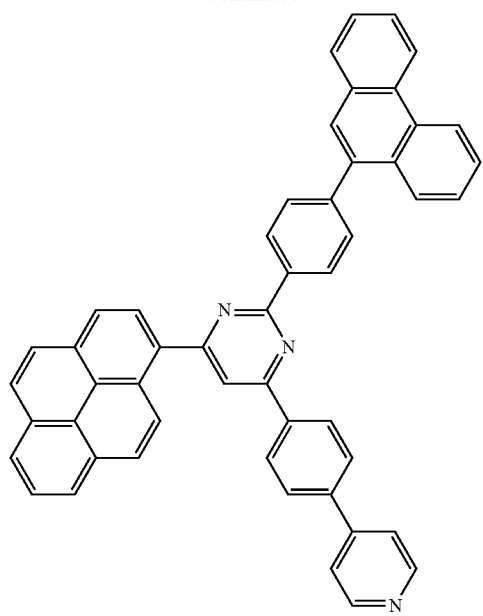
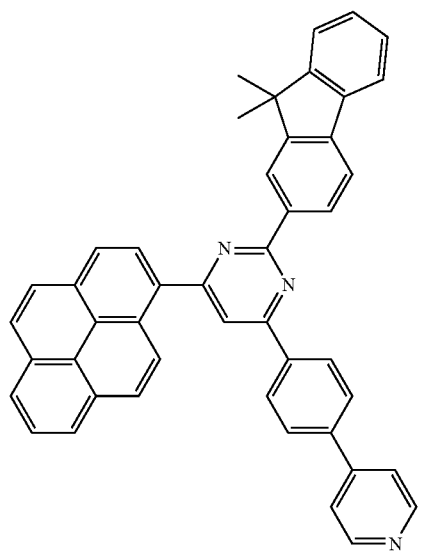
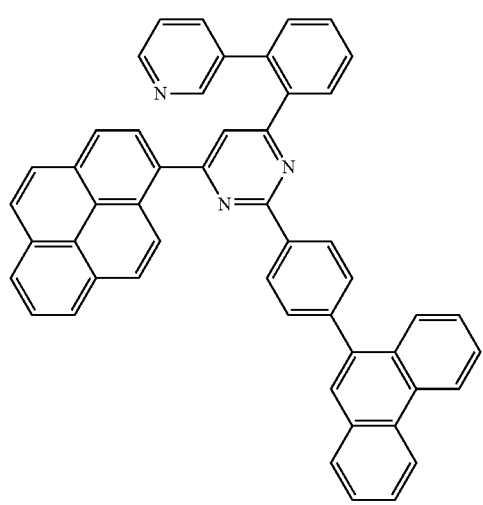
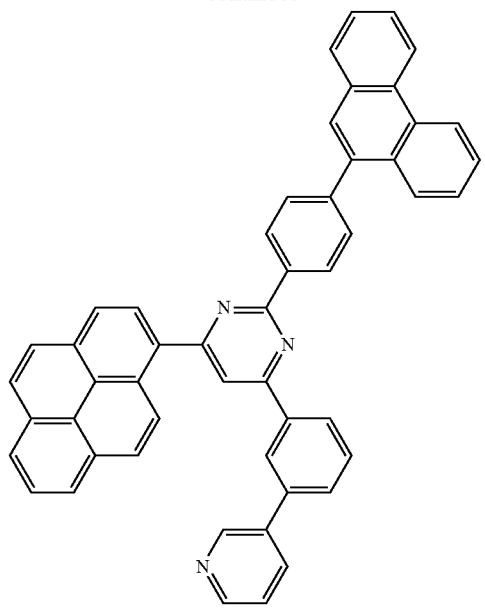
[Formula 50]
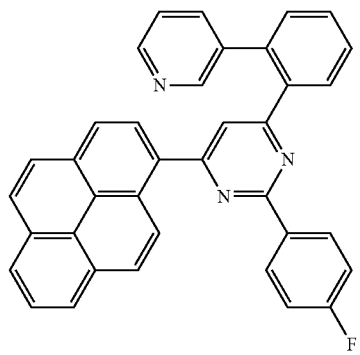

79
-continued
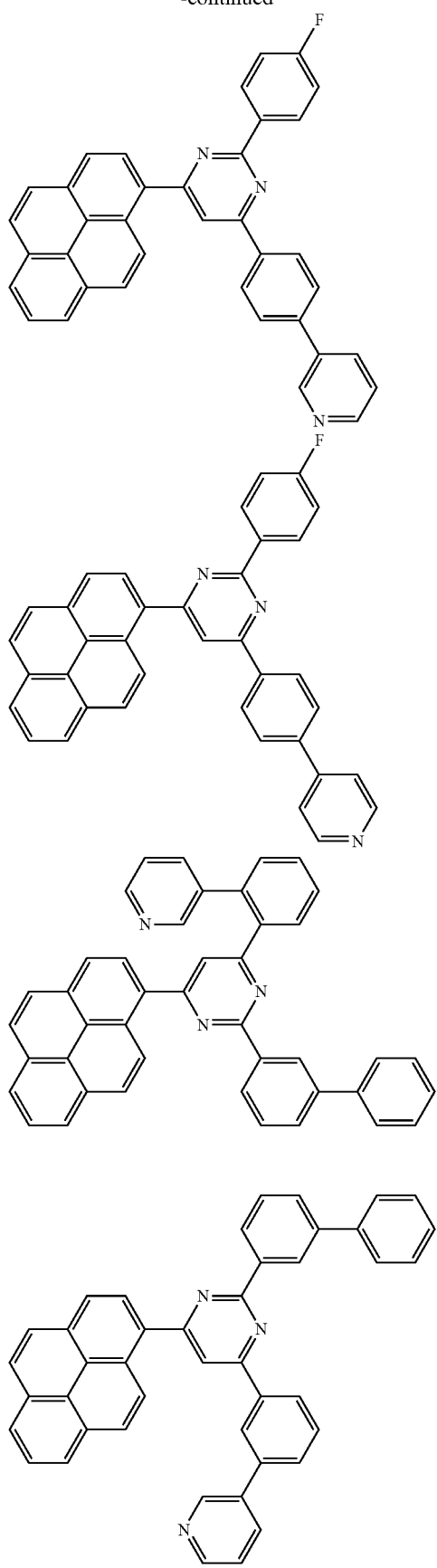
80
-continued
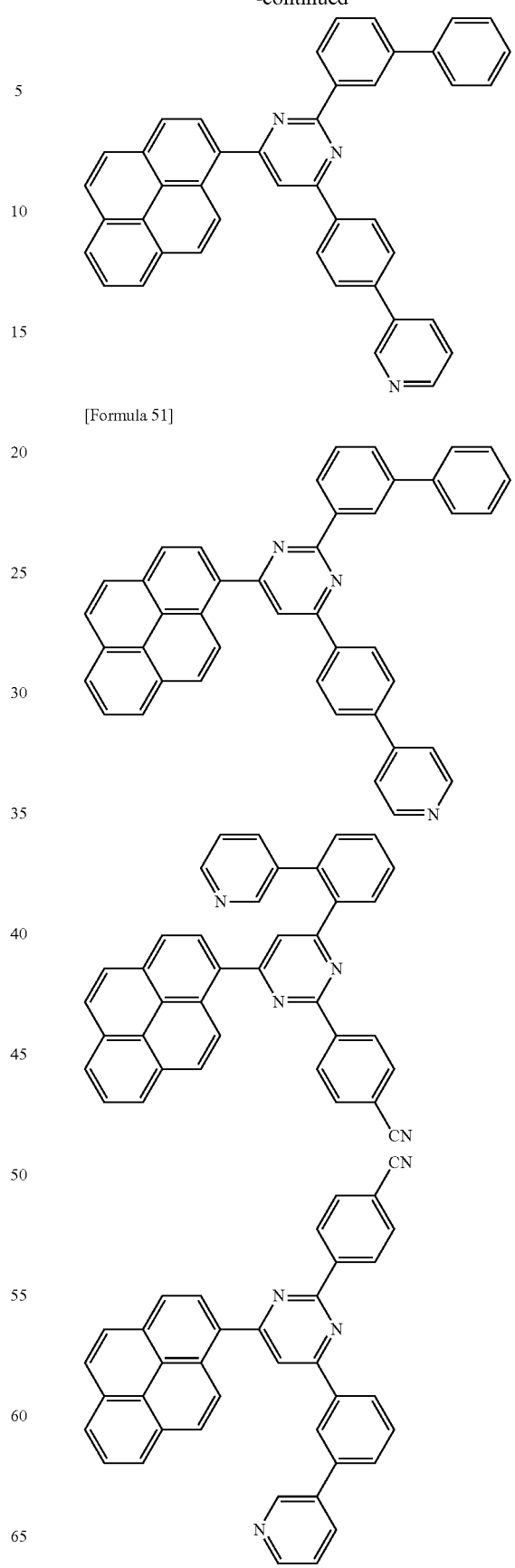
[Formula 51]

-continued
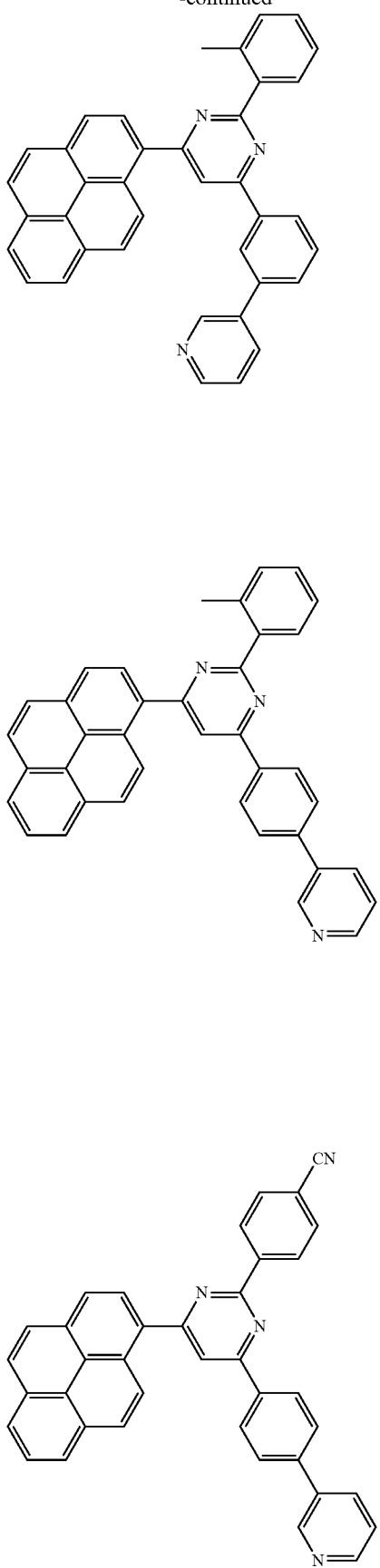
-continued
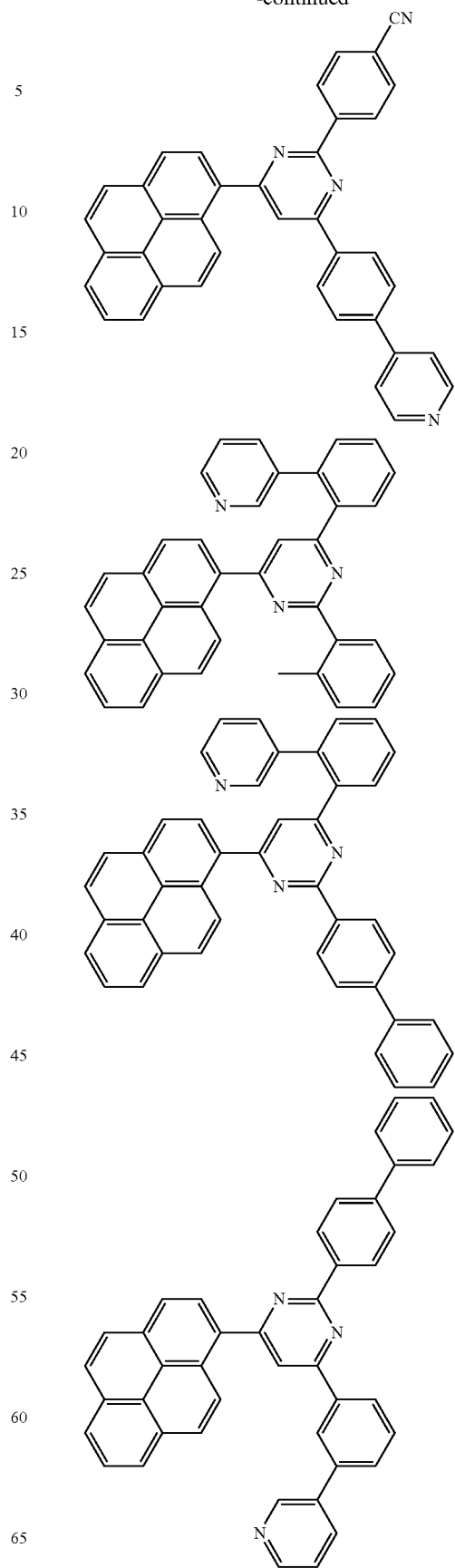

[Formula 52]
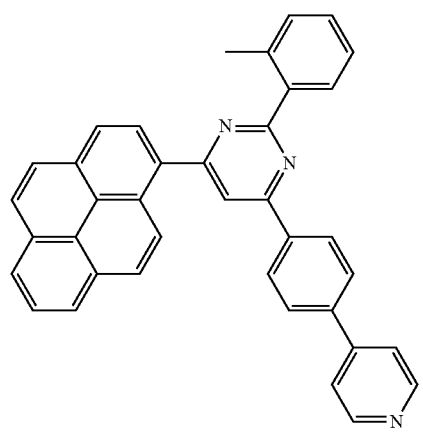
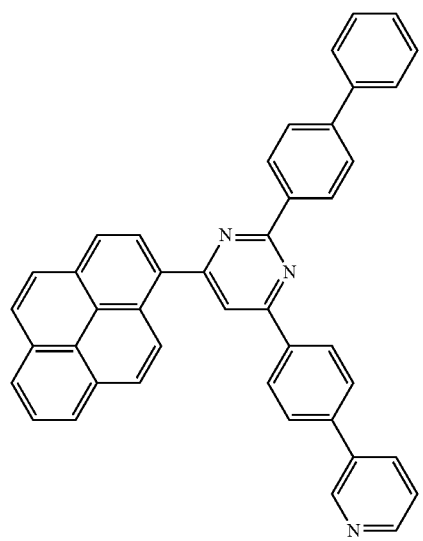
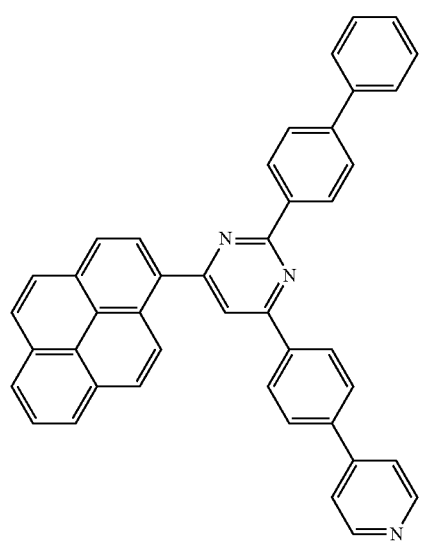
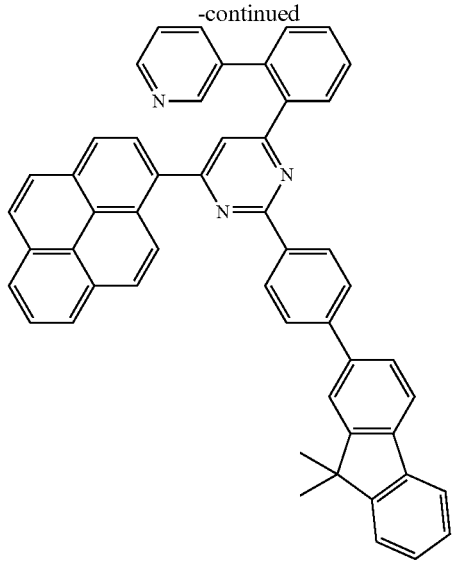
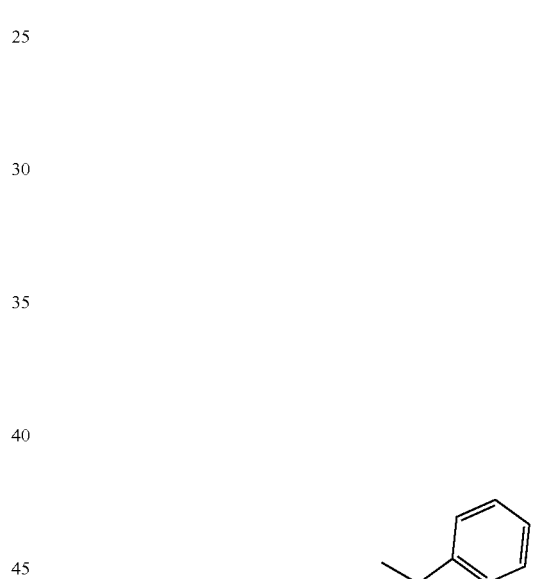
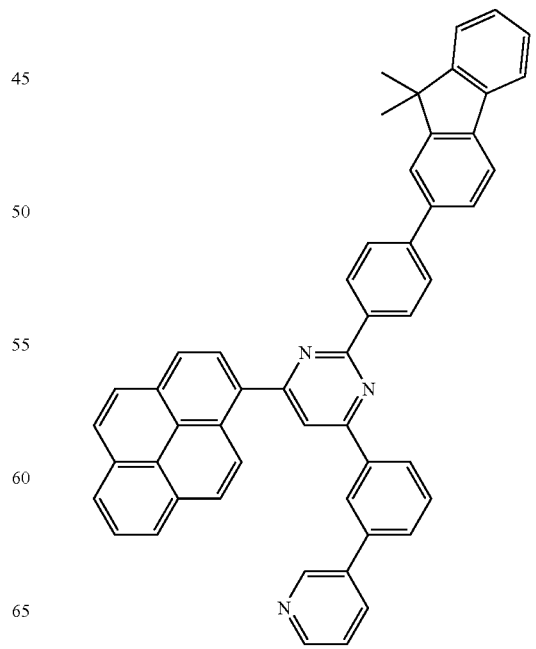

[Formula 53]
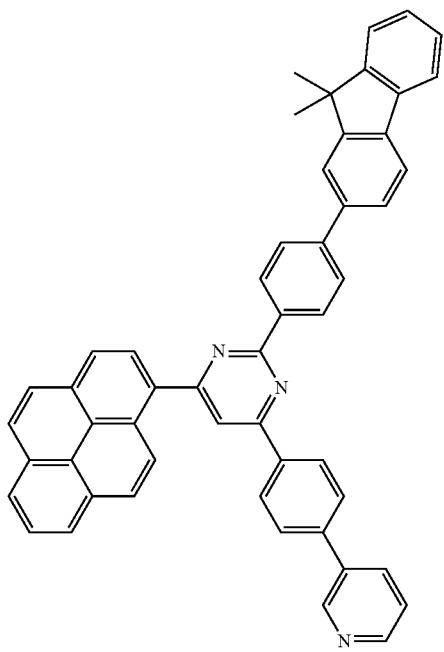
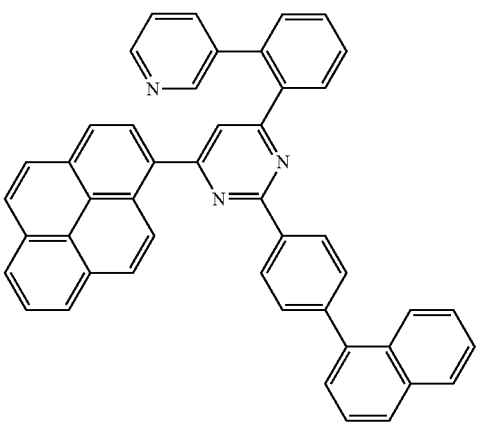
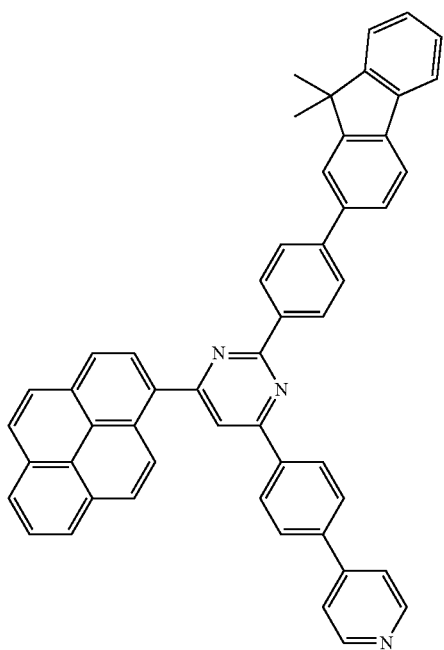
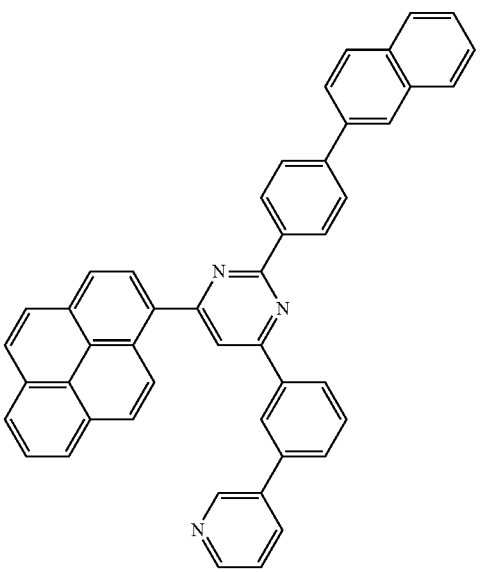

87
-continued
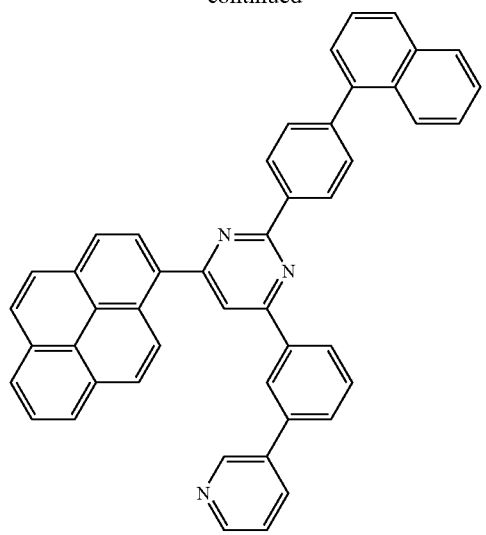
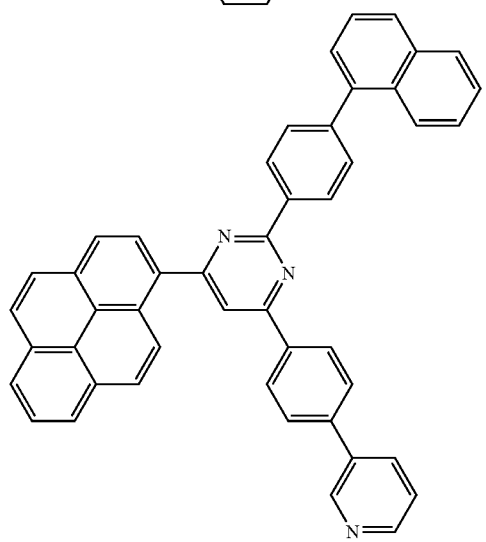
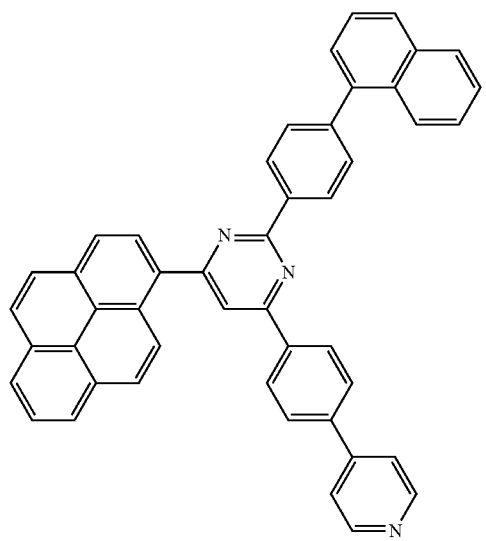
88
-continued
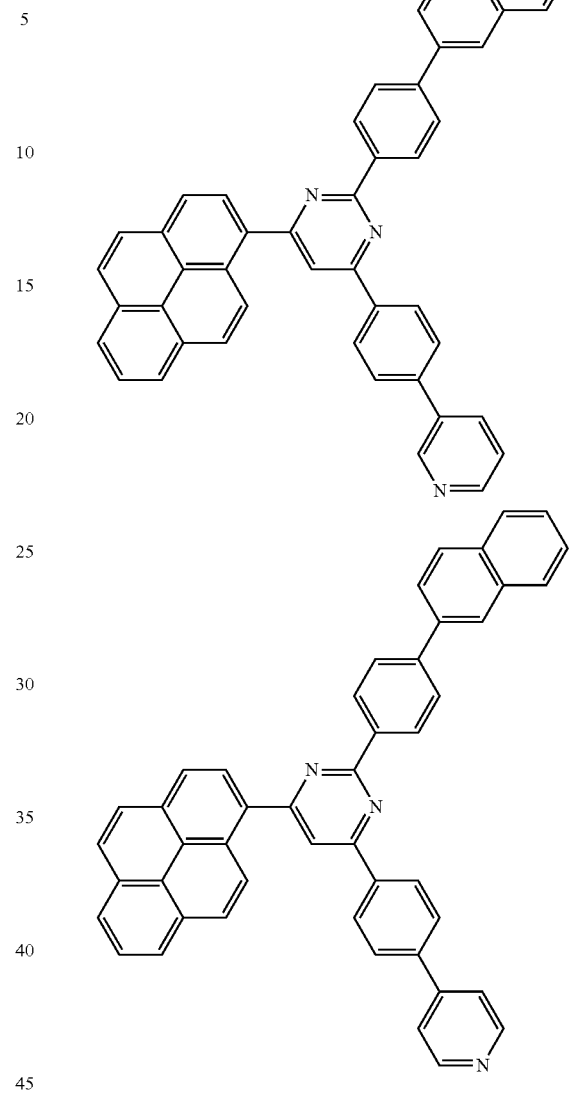
[Formula 54]
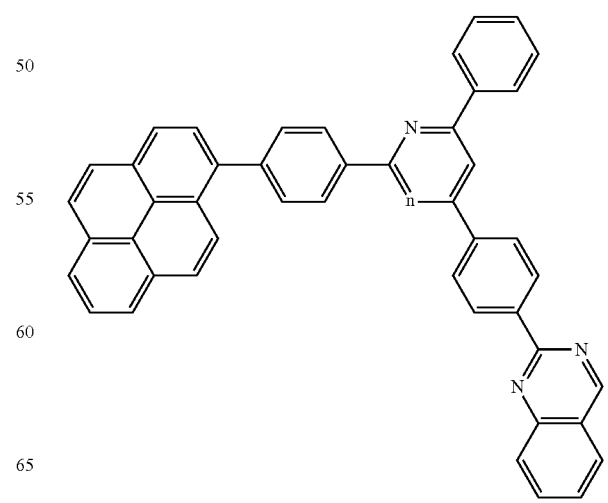

-continued
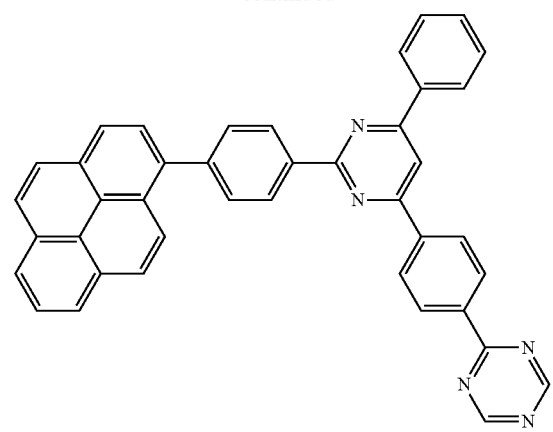
-continued
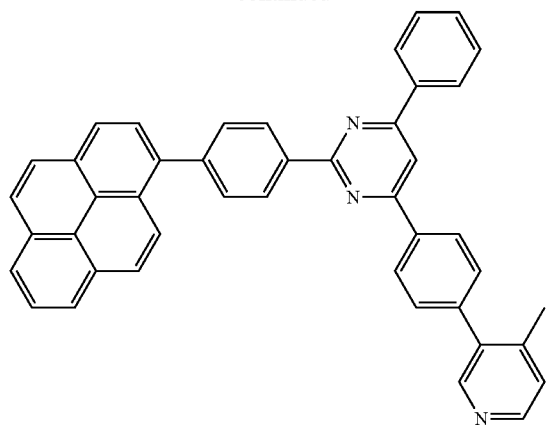
[Formula 55]
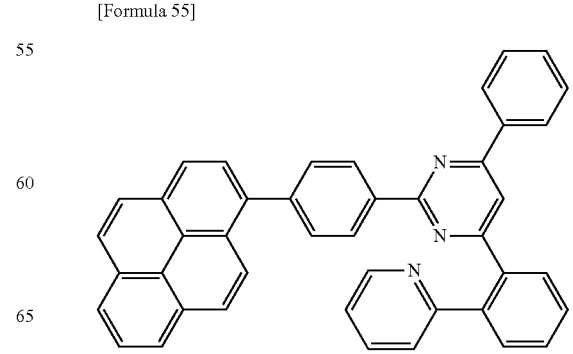

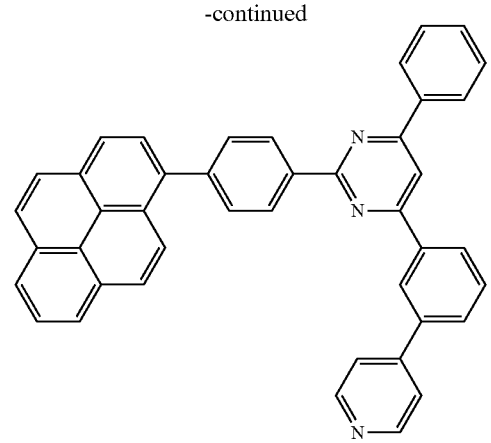
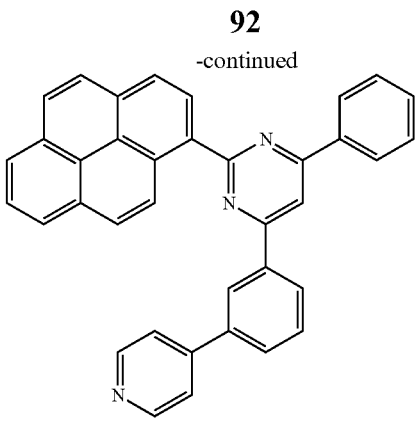
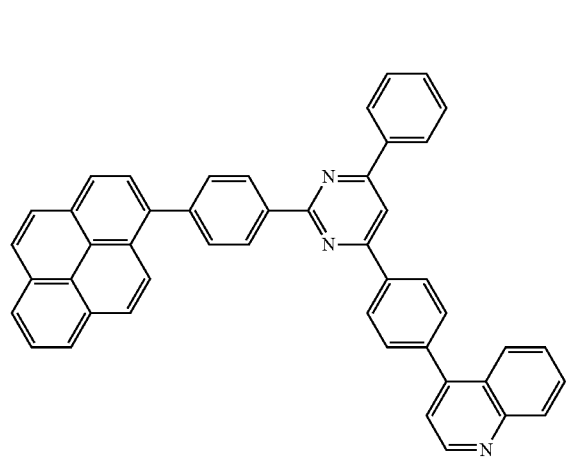
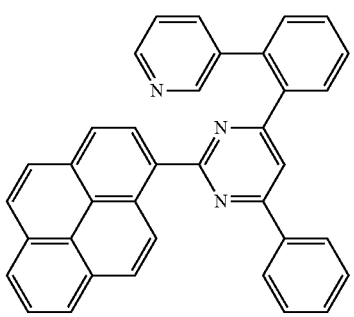
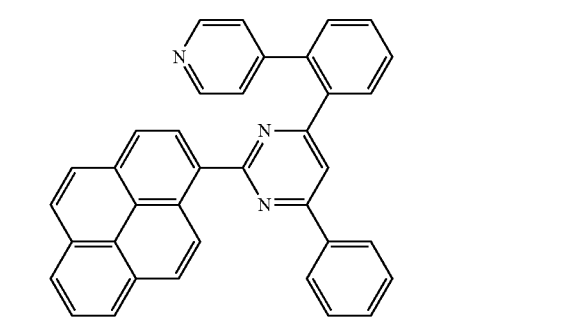
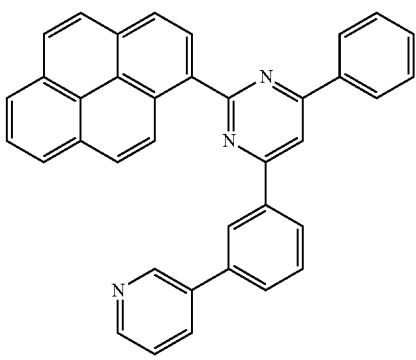
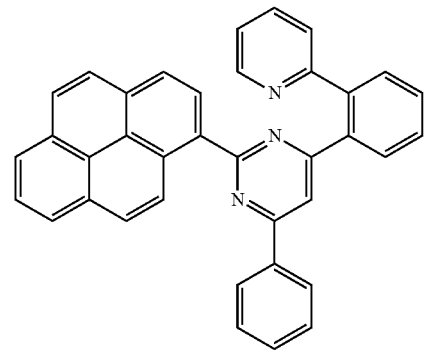
[Formula 56]
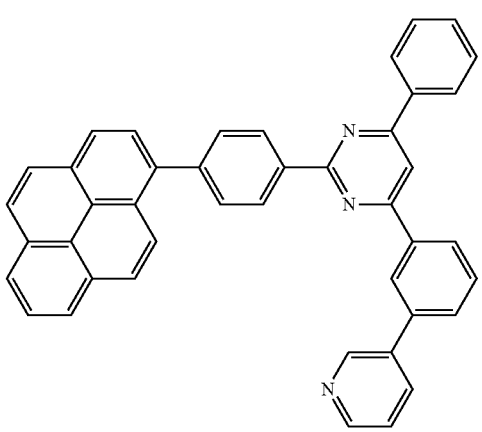

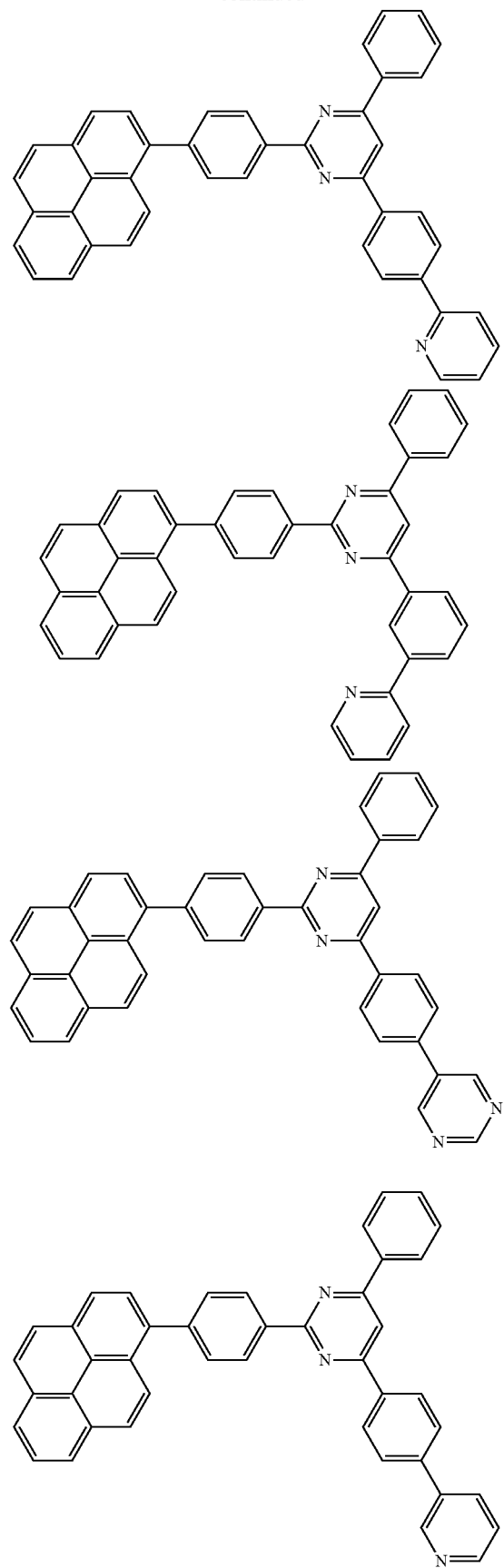
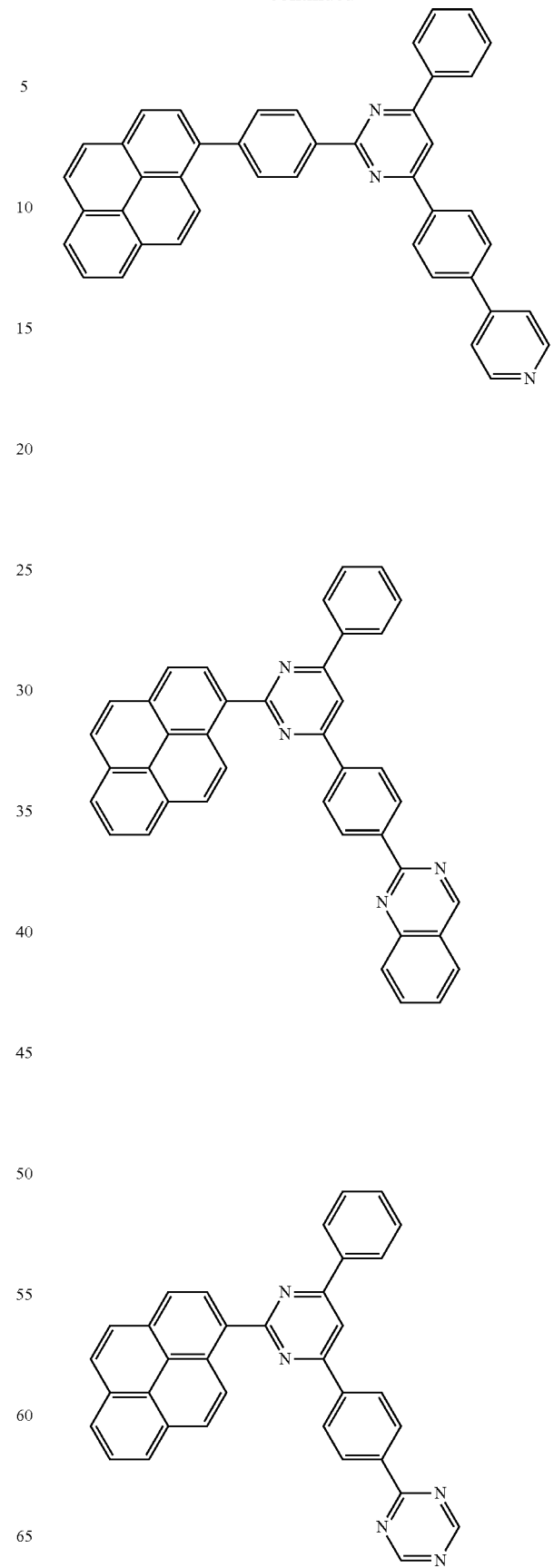

95
-continued
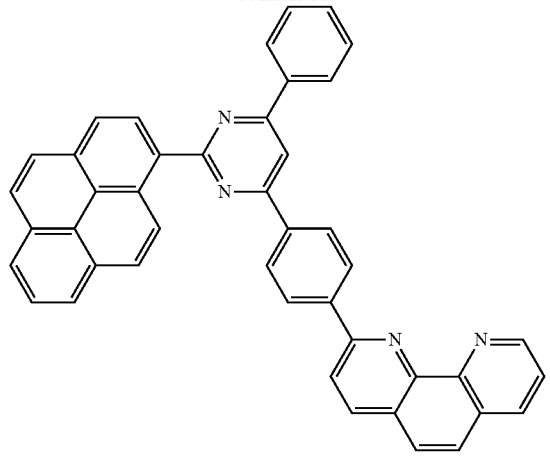
[Formula 57]
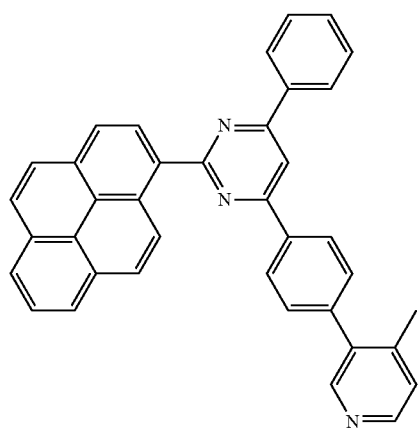
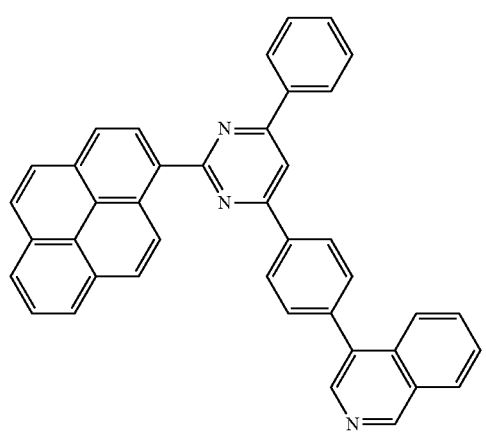
96
-continued
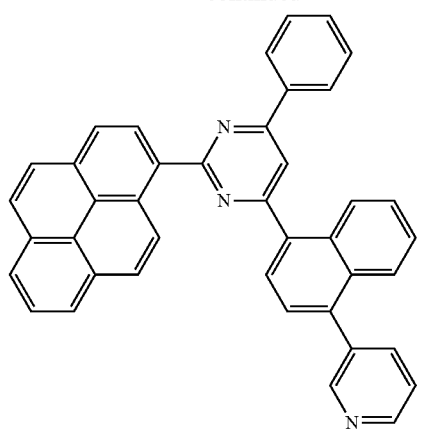
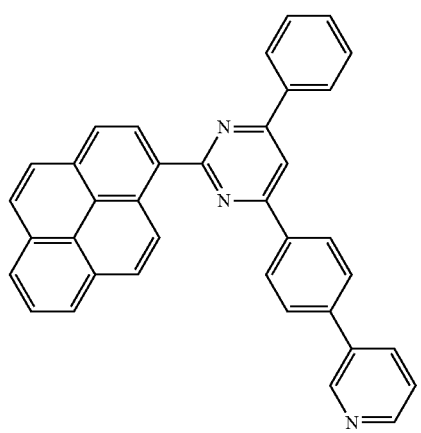

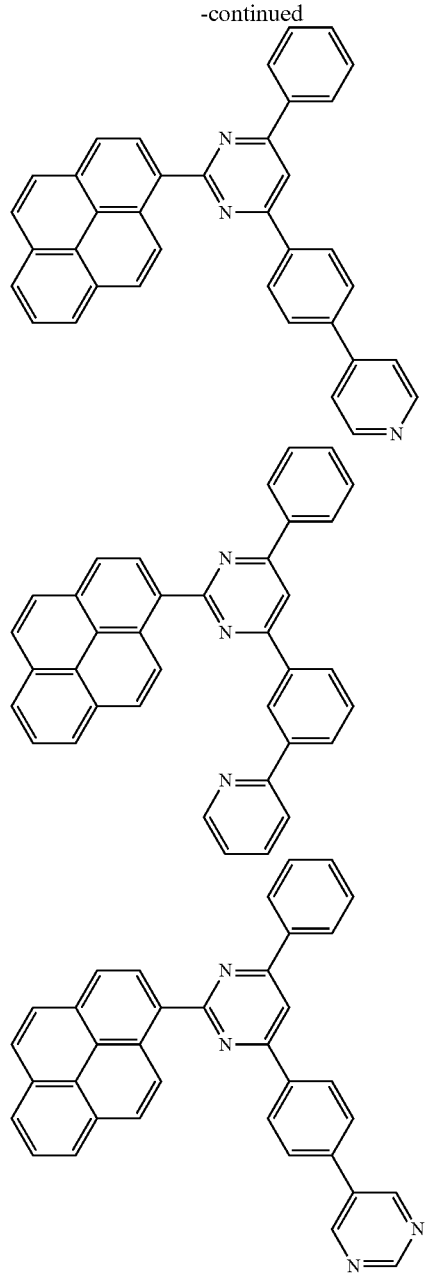
[Formula 58]
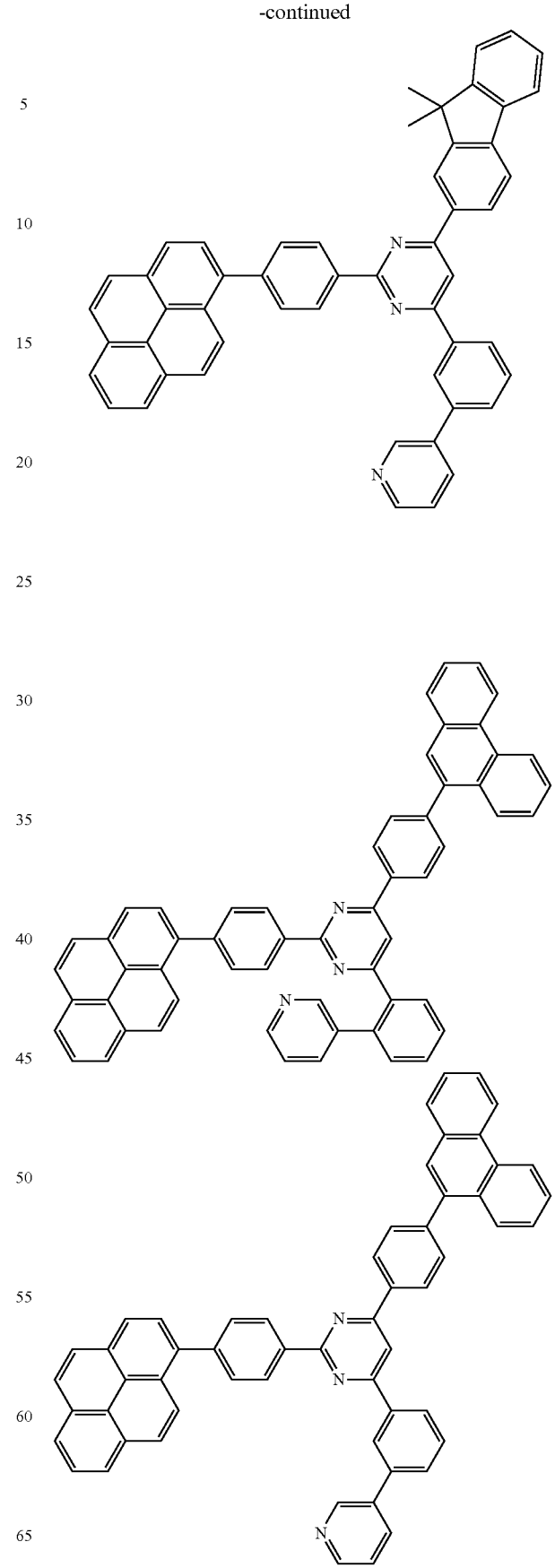

99
-continued
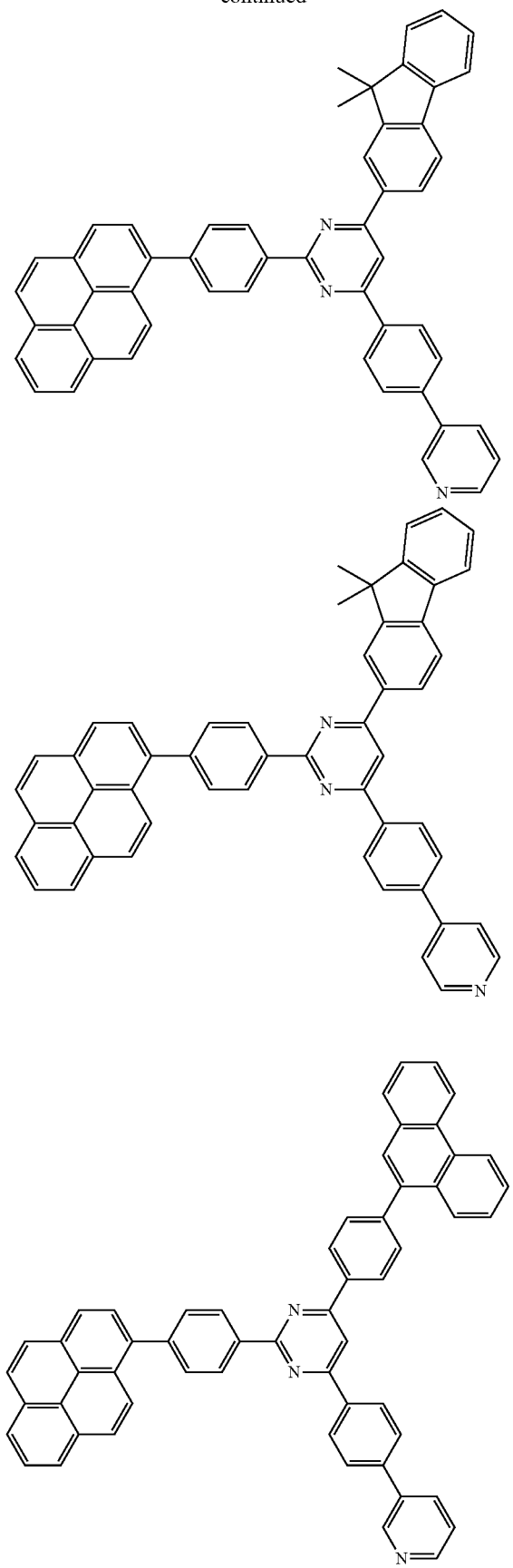
100
-continued
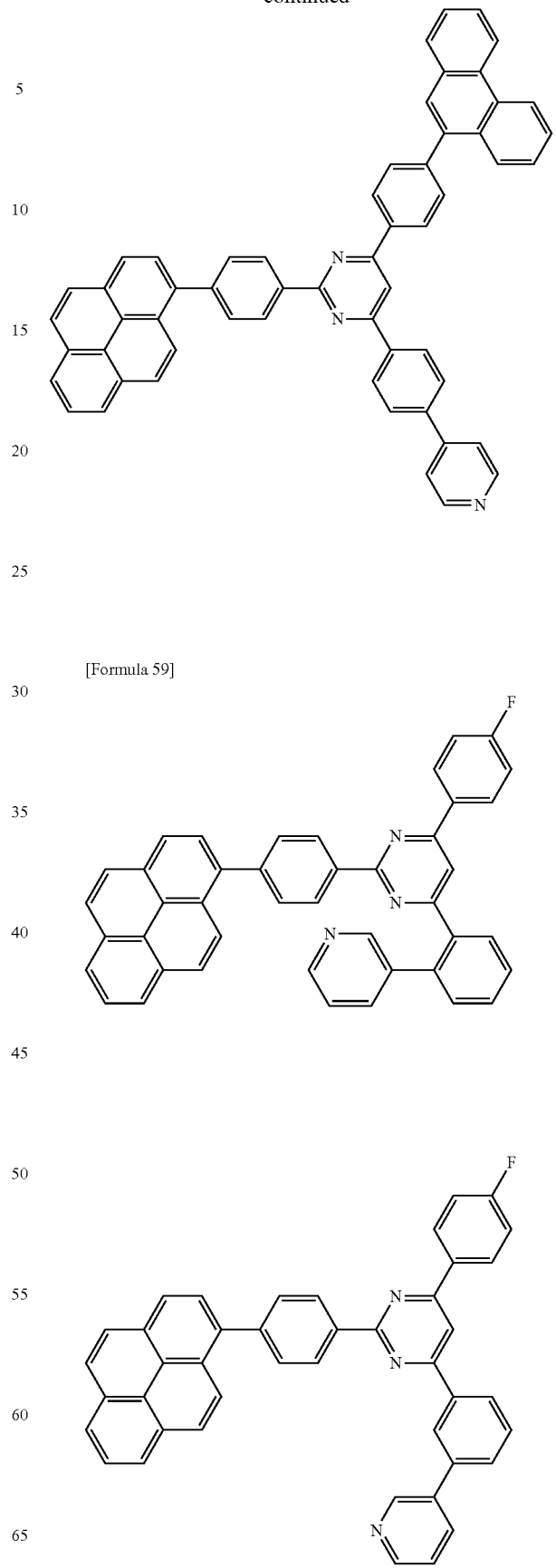
[Formula 59]

101
-continued
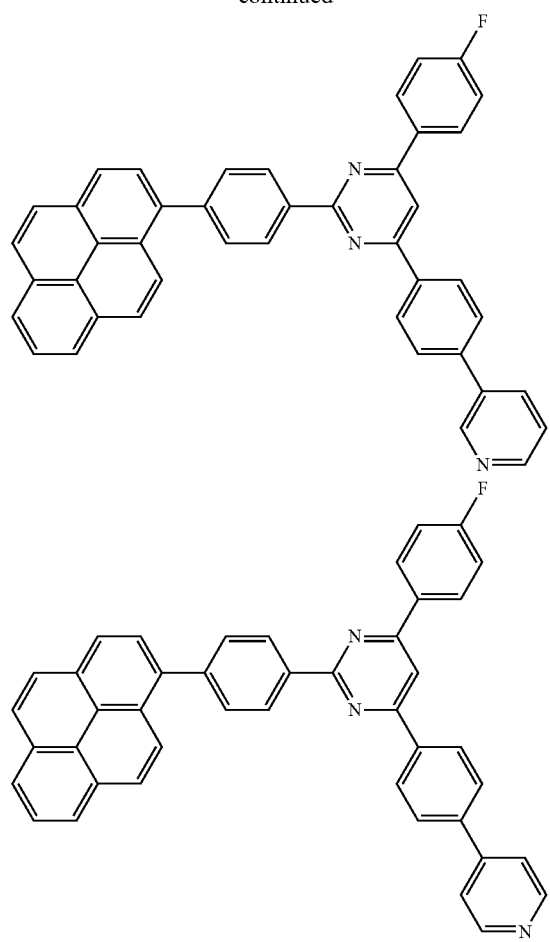
[Formula 60]
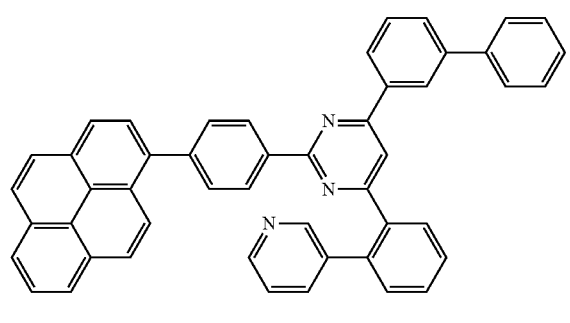
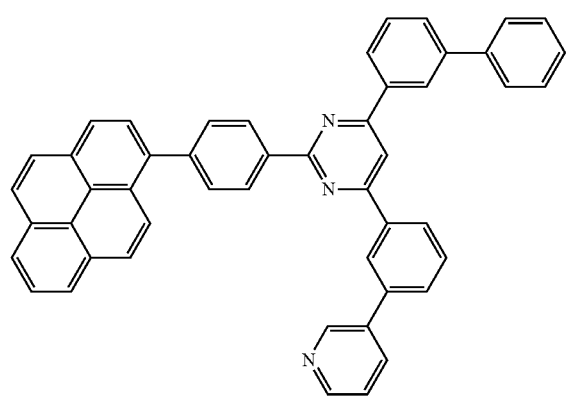
102
-continued
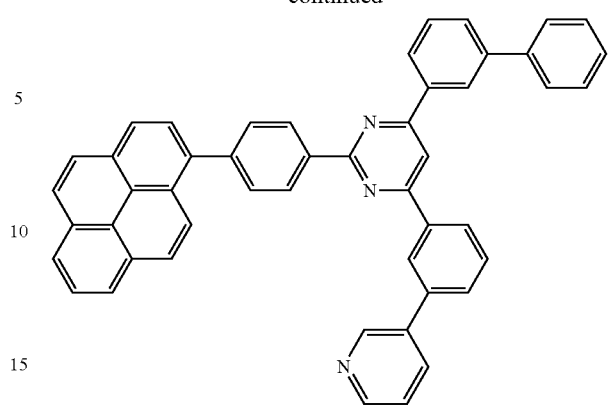
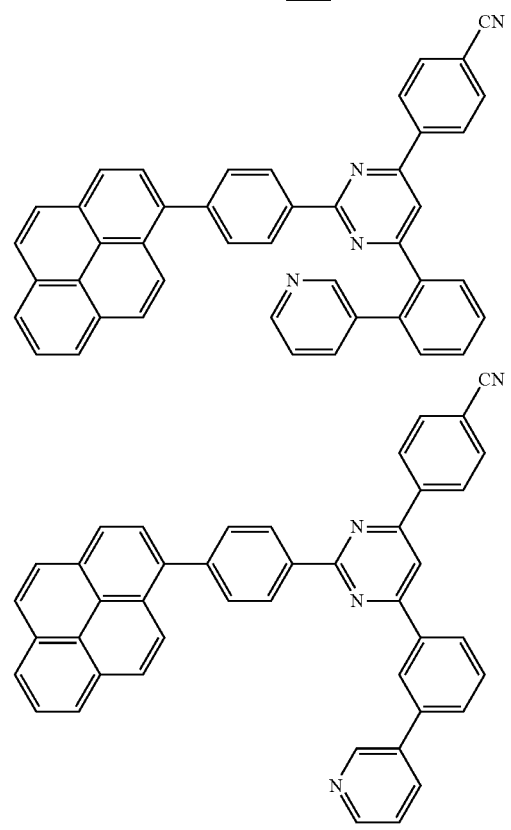
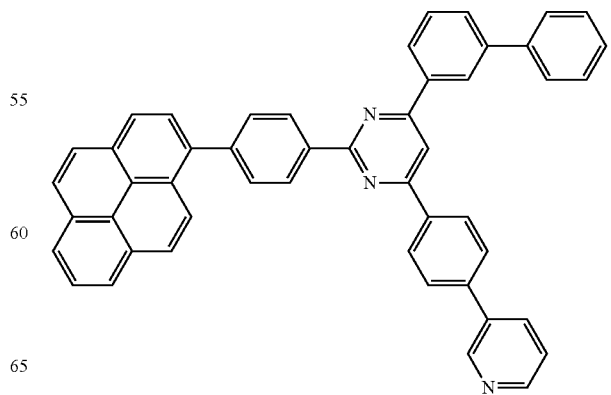

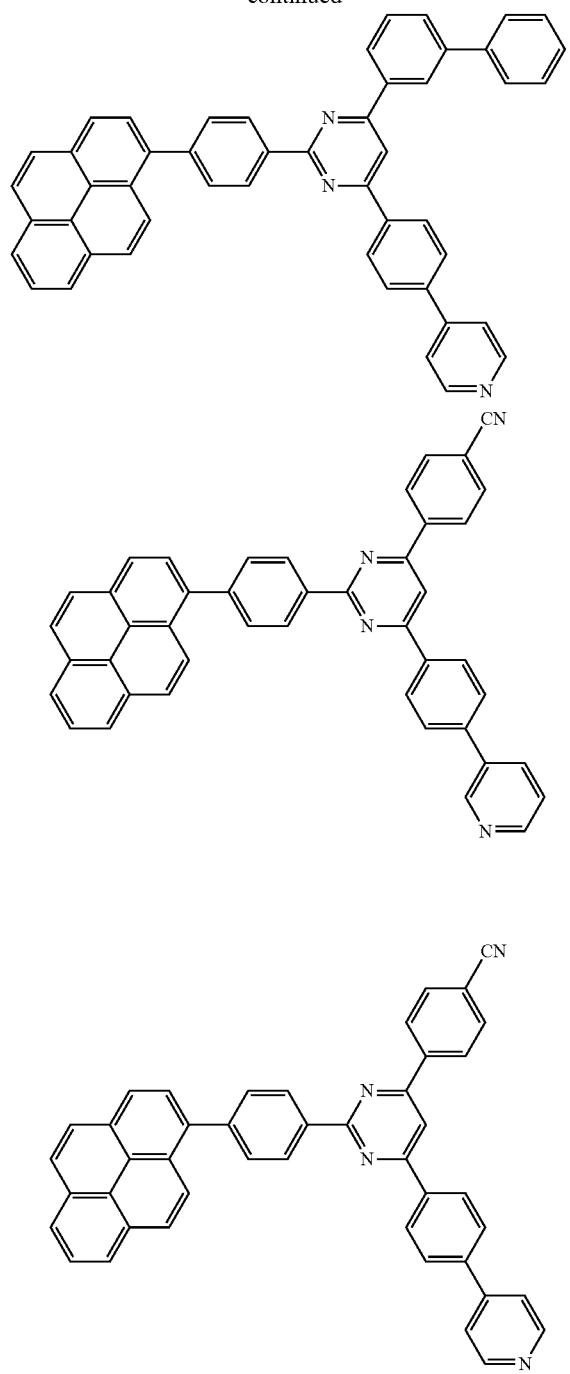
[Formula 61]
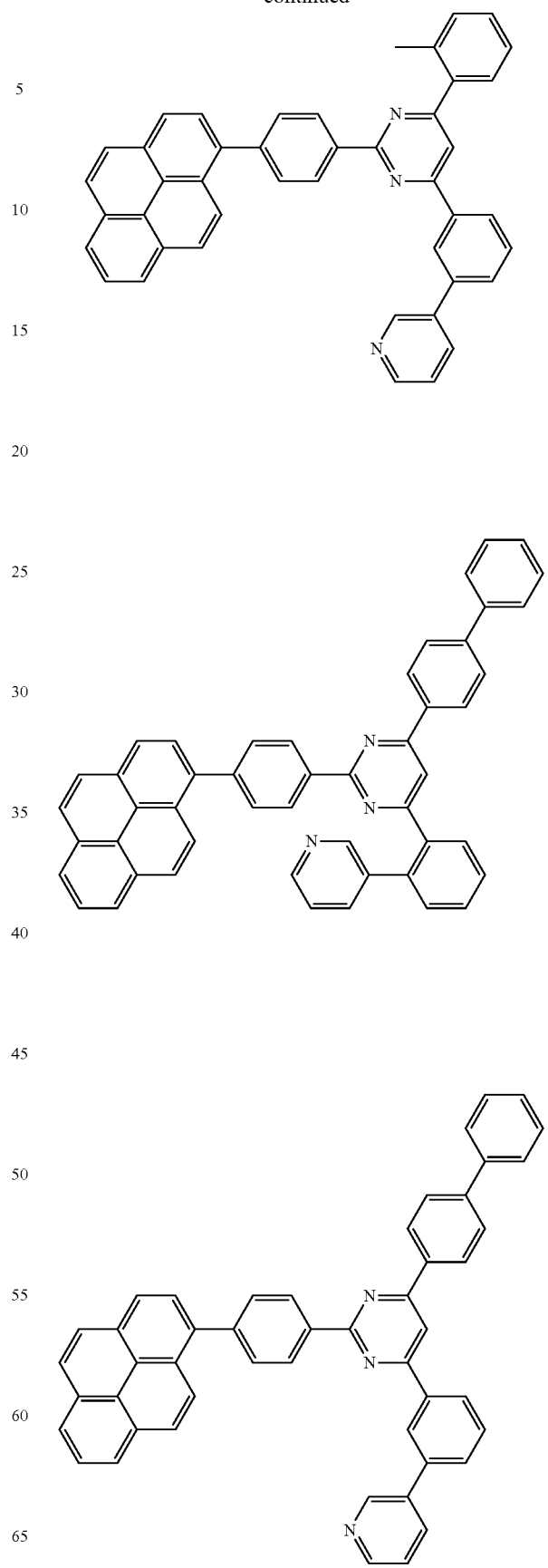

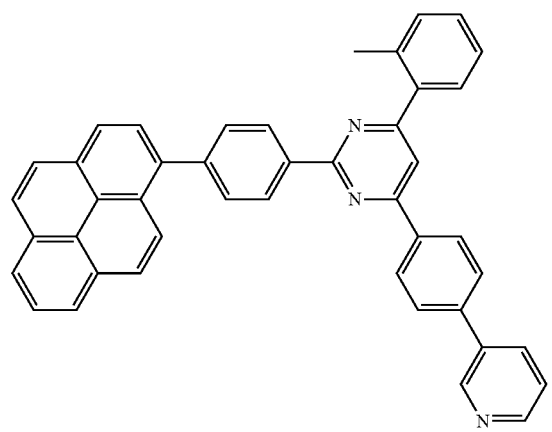
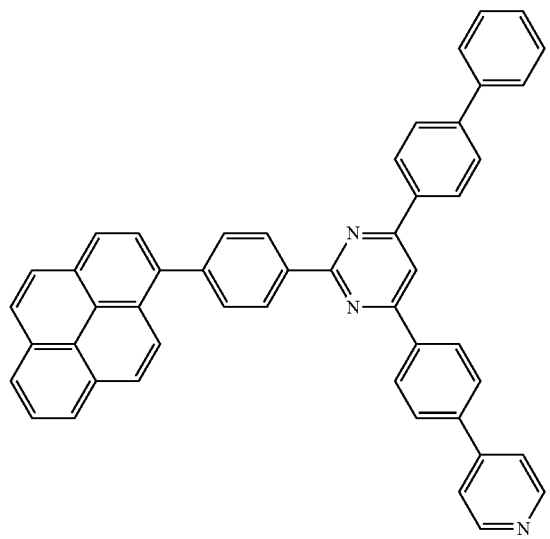
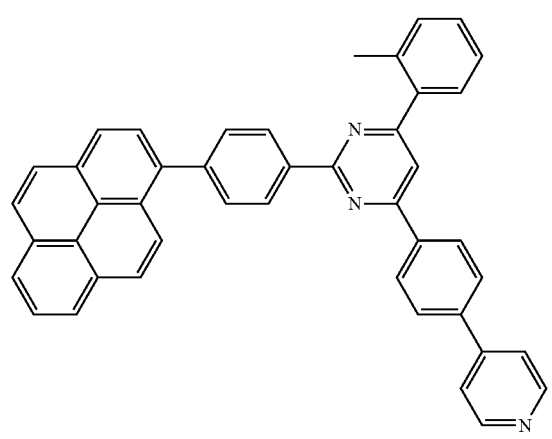
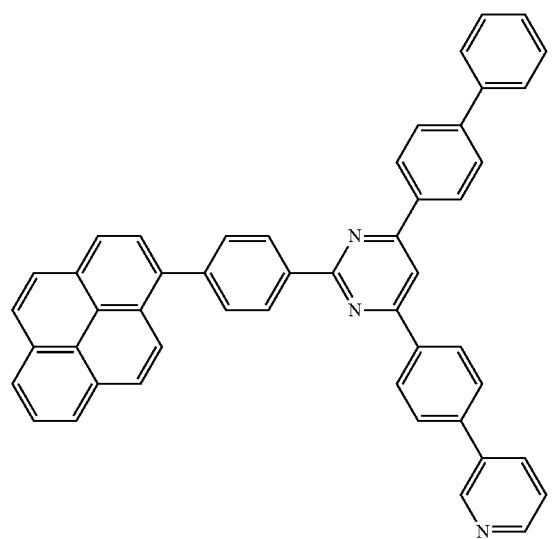
[Formula 62]
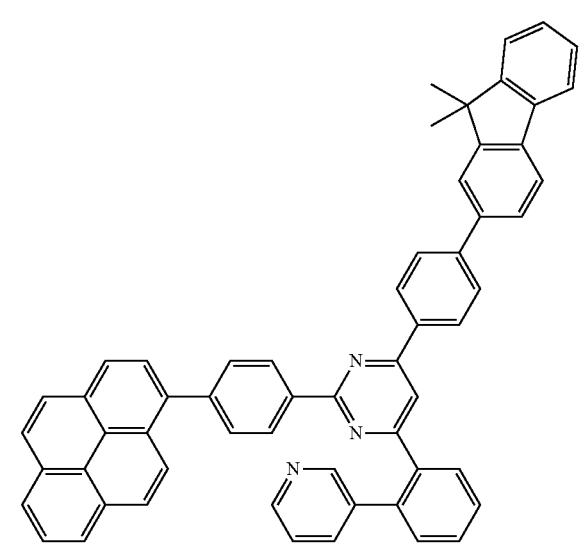

107
-continued
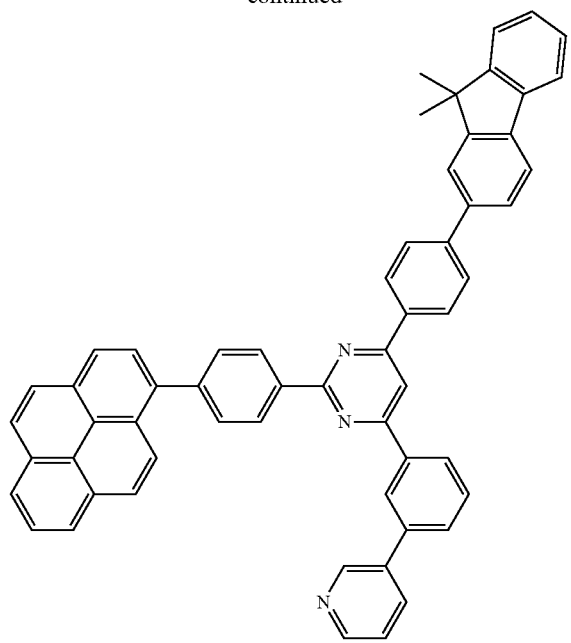
108
-continued
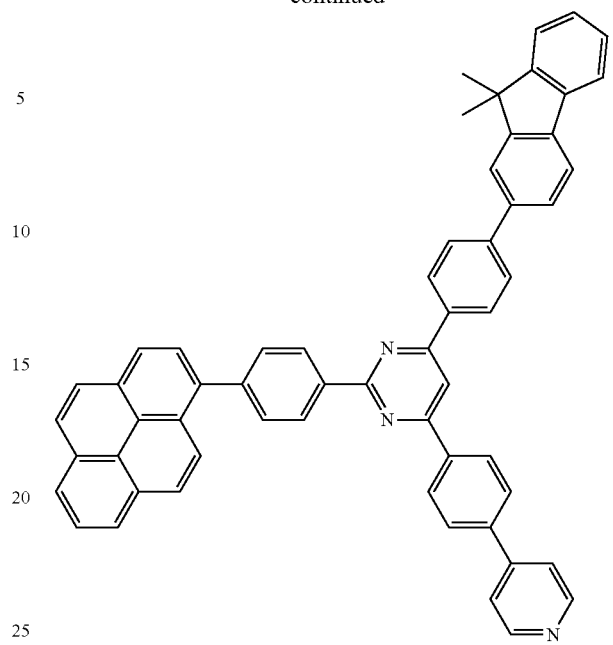
[Formula 63]
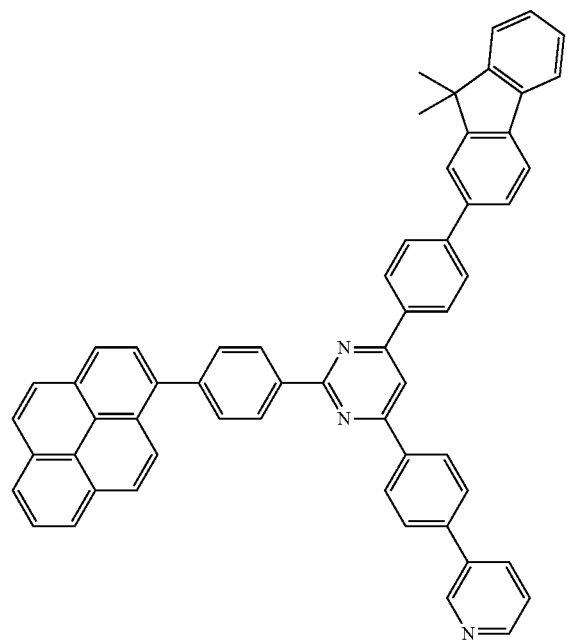
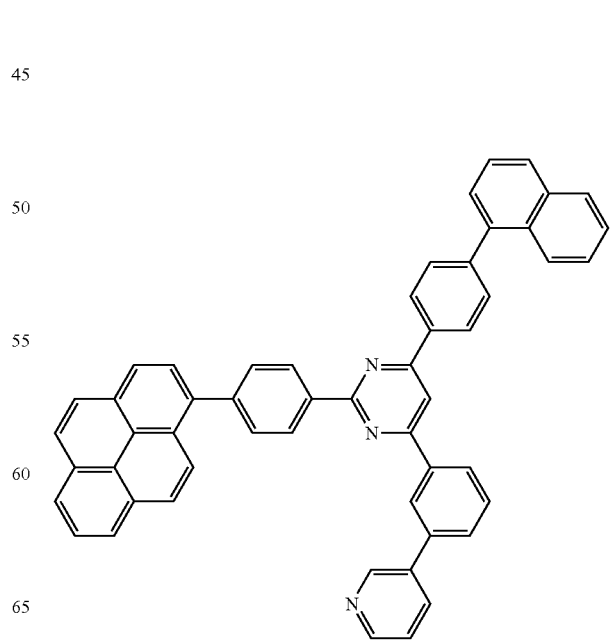

109
-continued
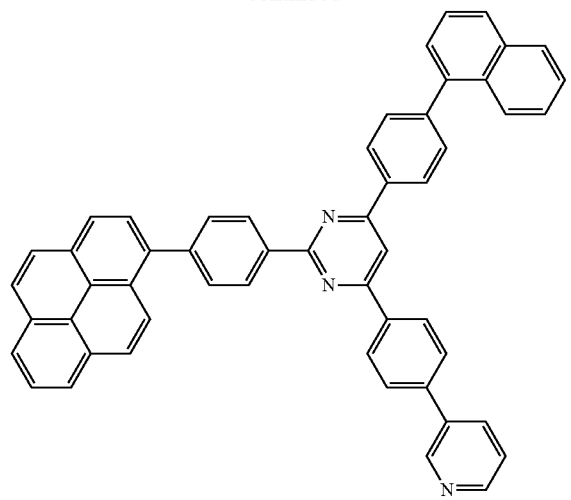
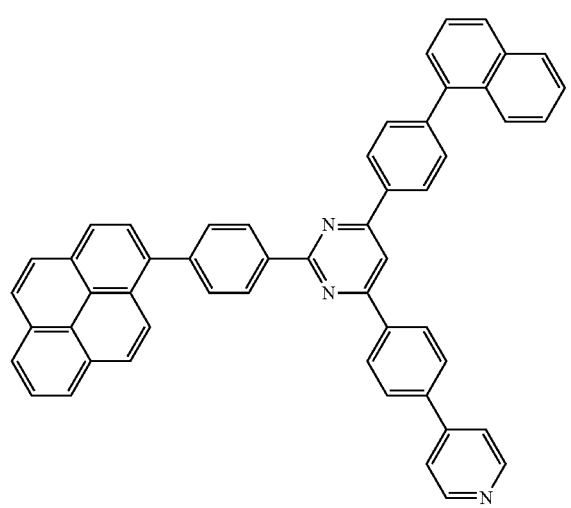
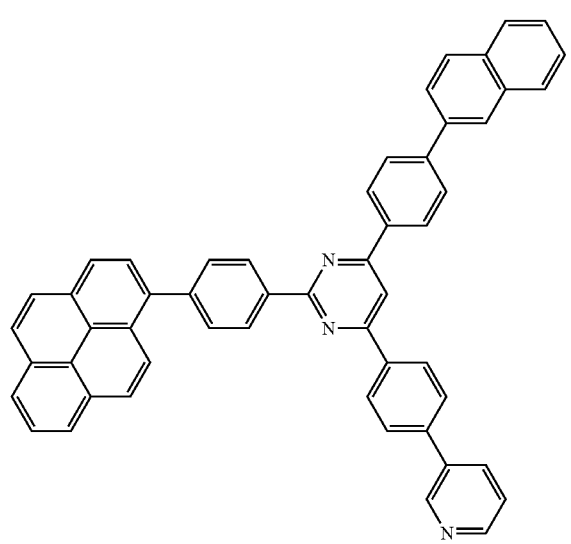
110
-continued
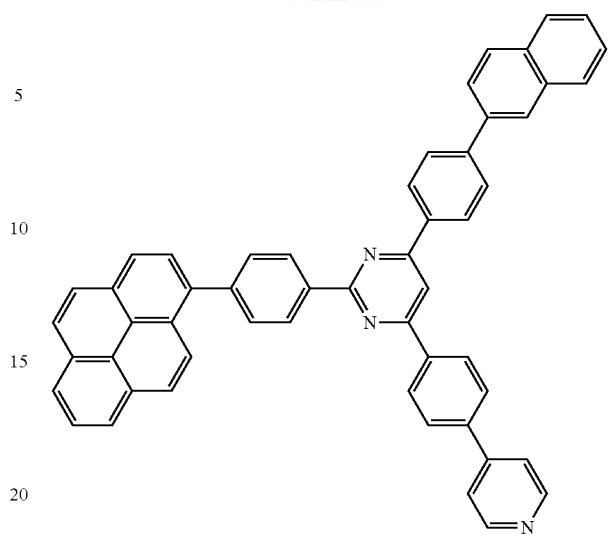
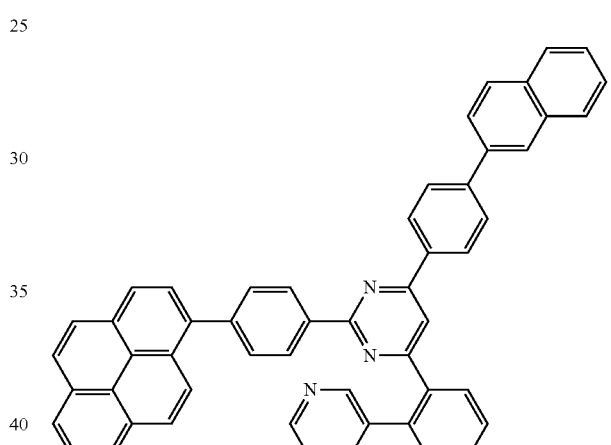
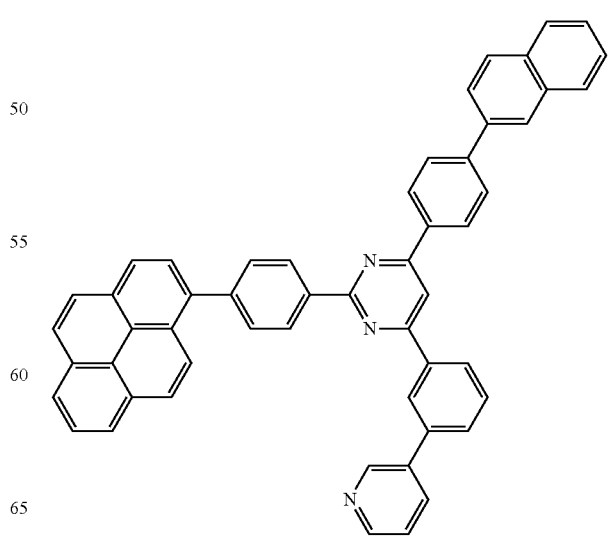

111
-continued
[Formula 64]
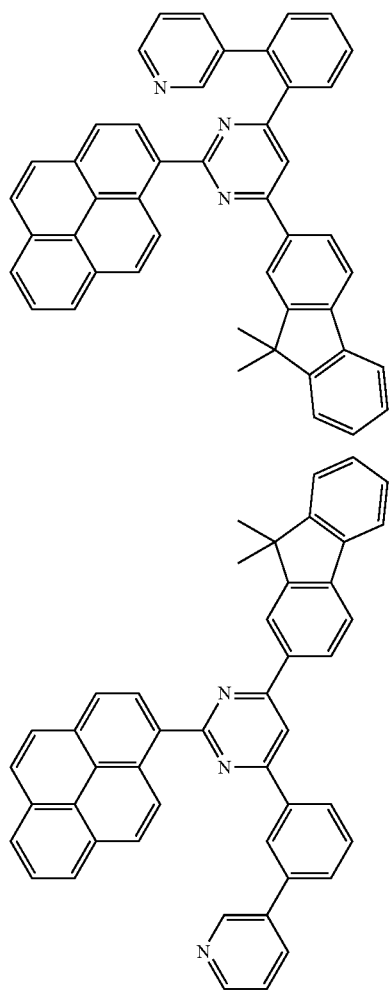
112
-continued

-continued
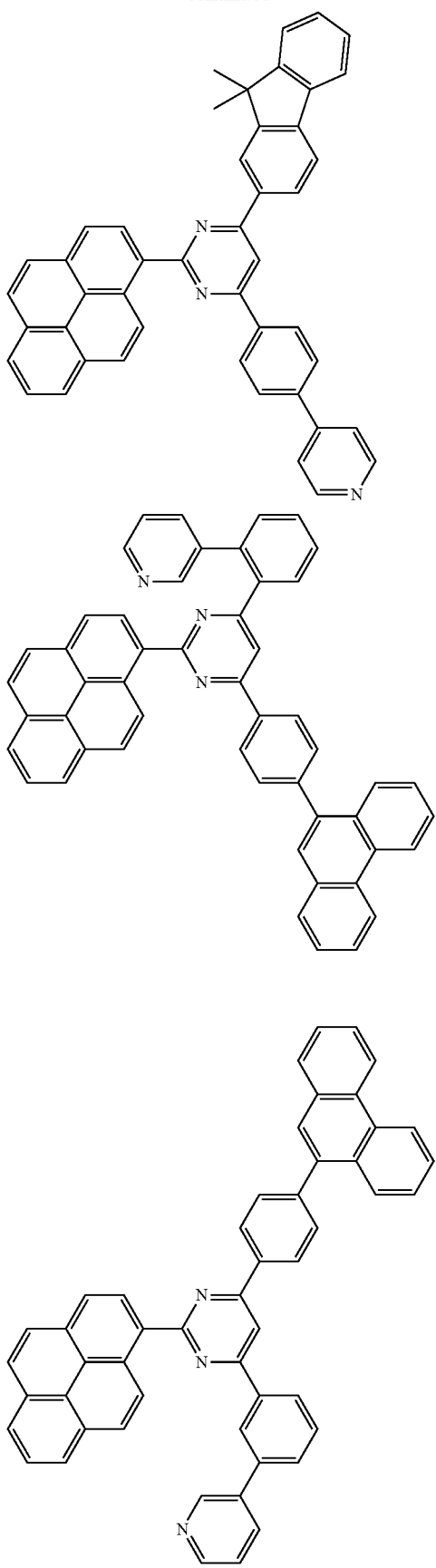
-continued
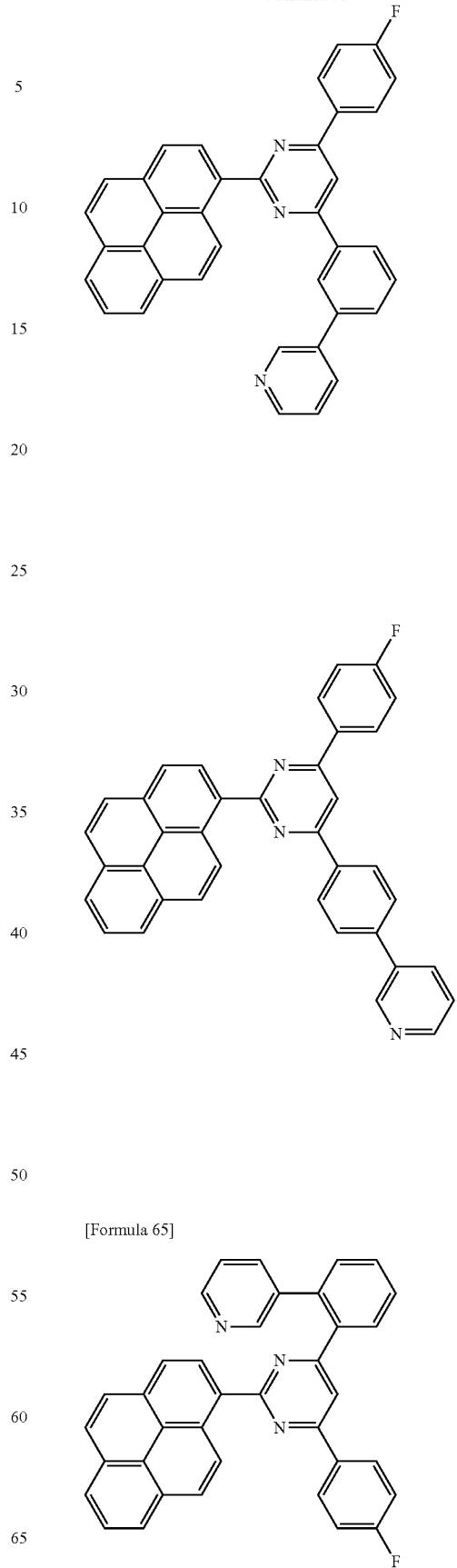
[Formula 65]

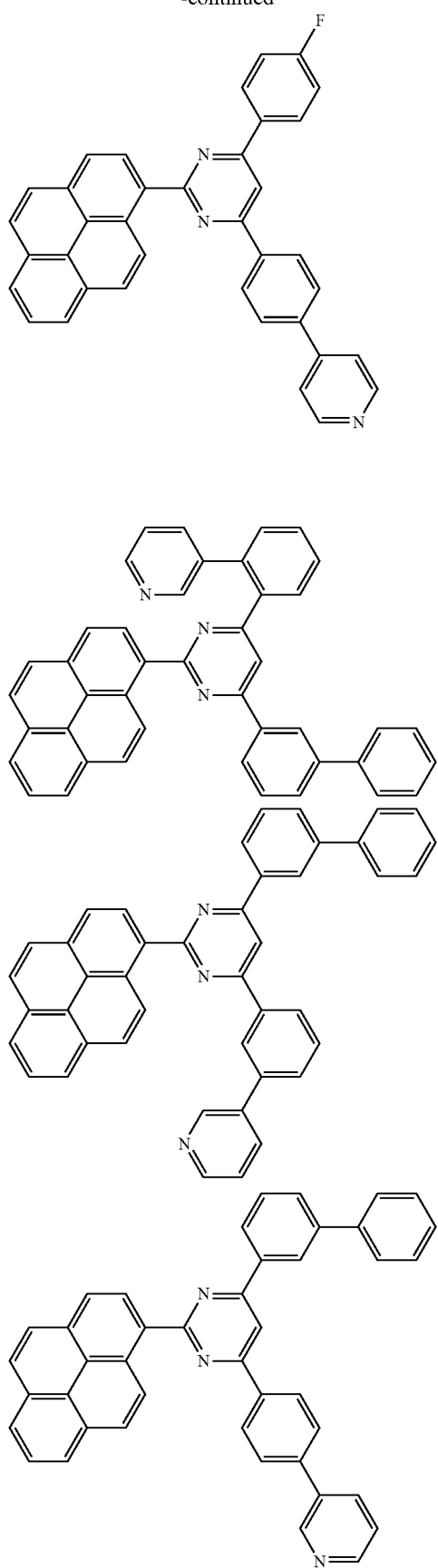
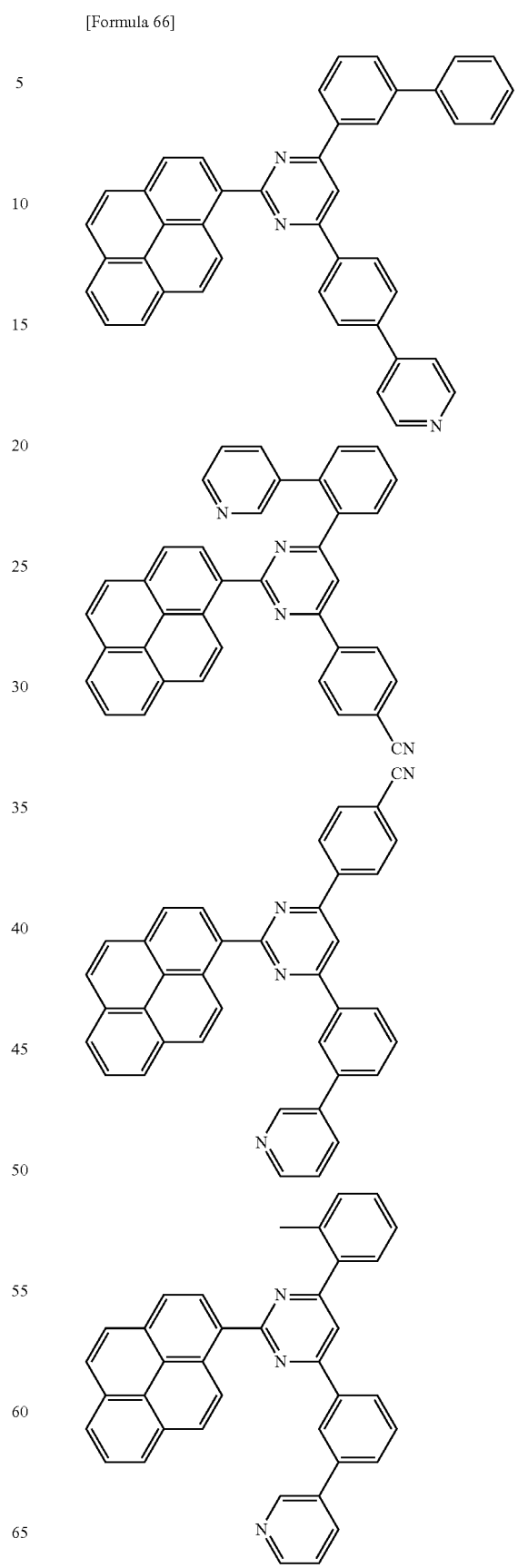
[Formula 66]

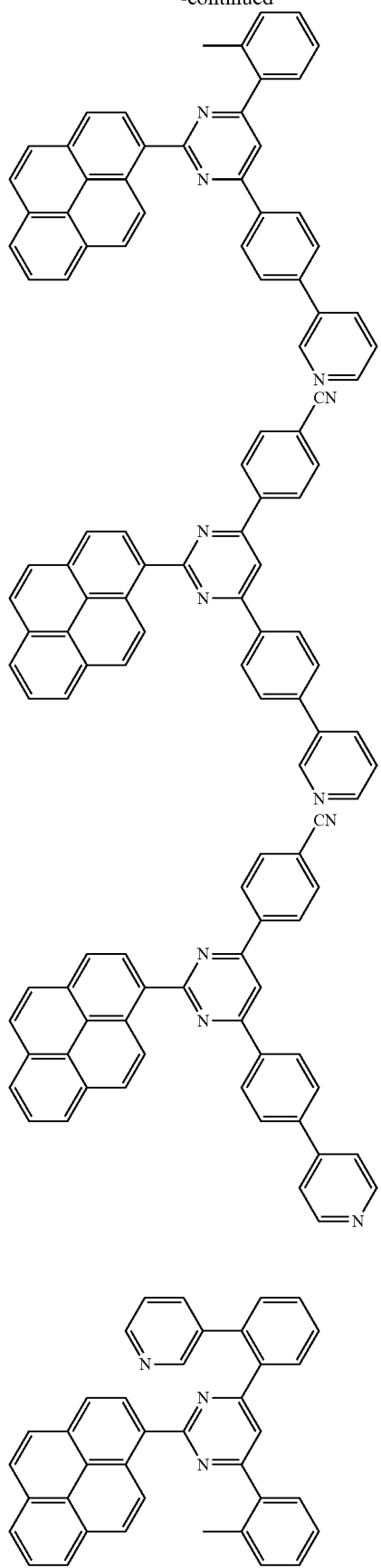
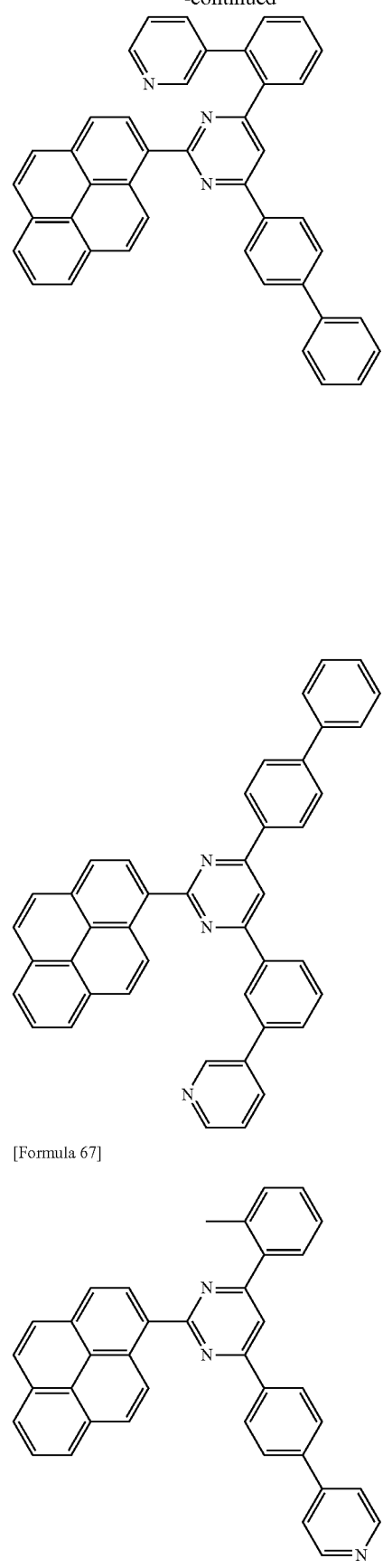

119
-continued
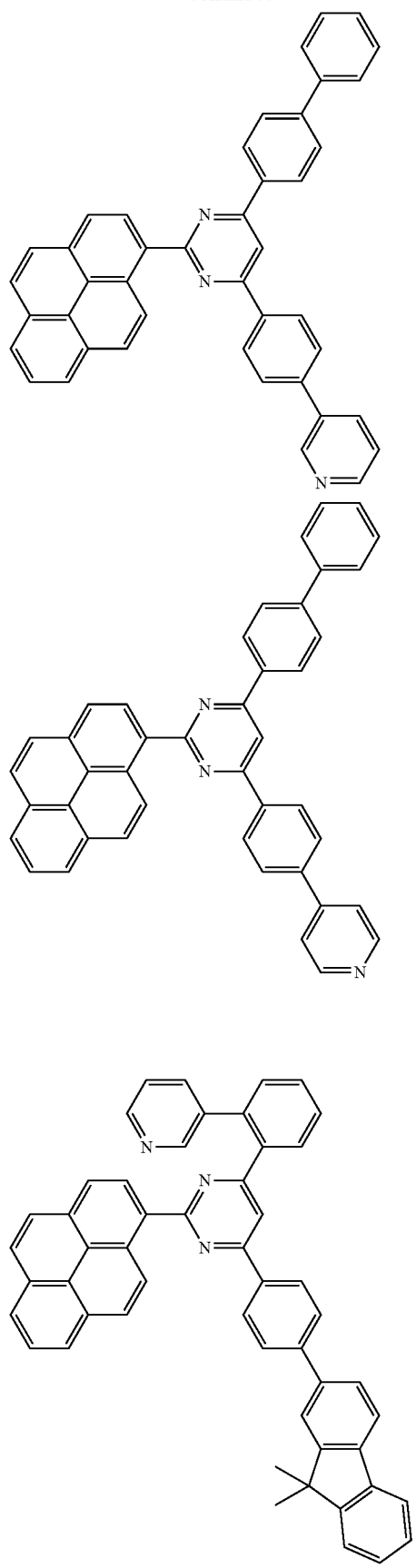
120
-continued
[Formula 68]
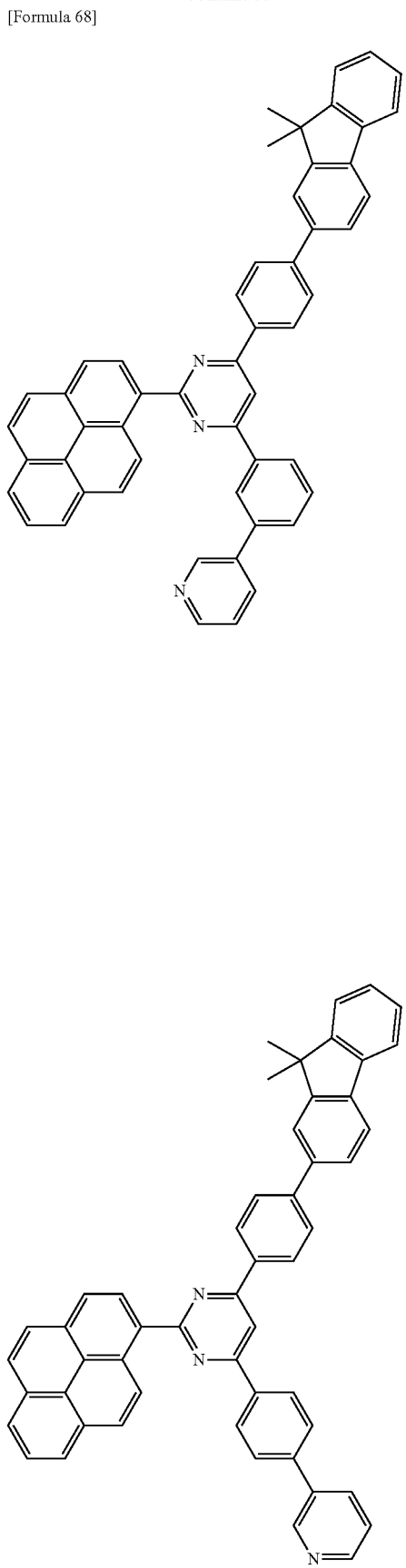

121
-continued
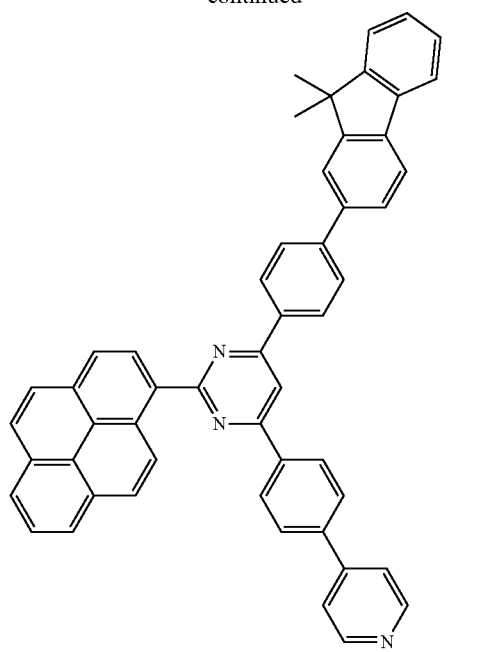
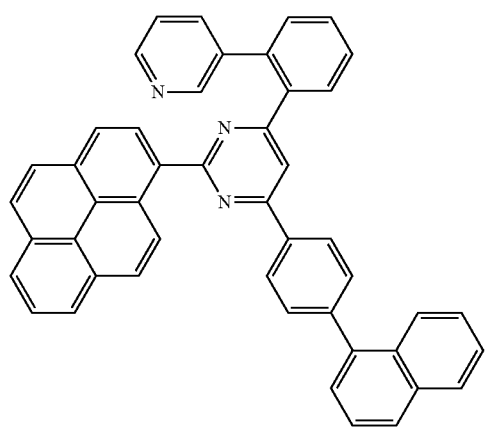
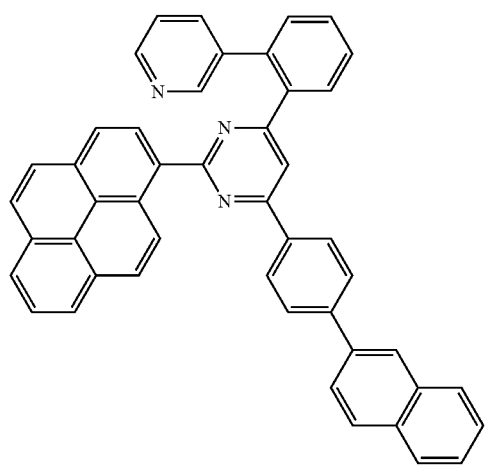
122
-continued
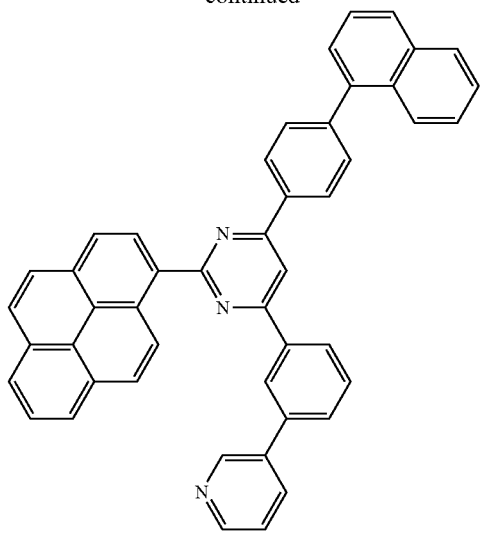
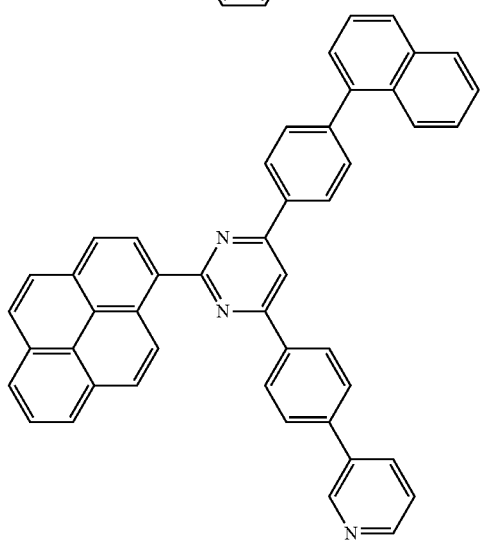
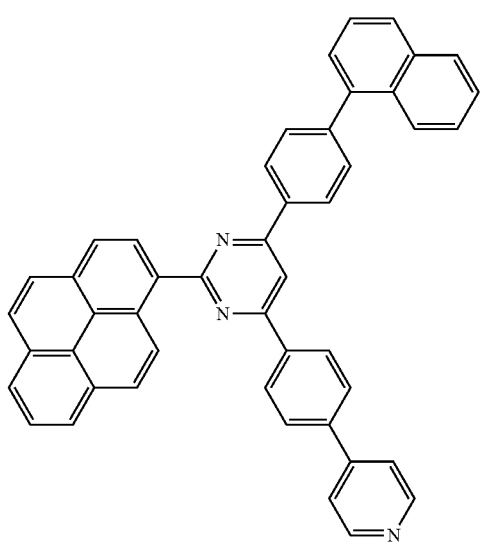

[Formula 69]
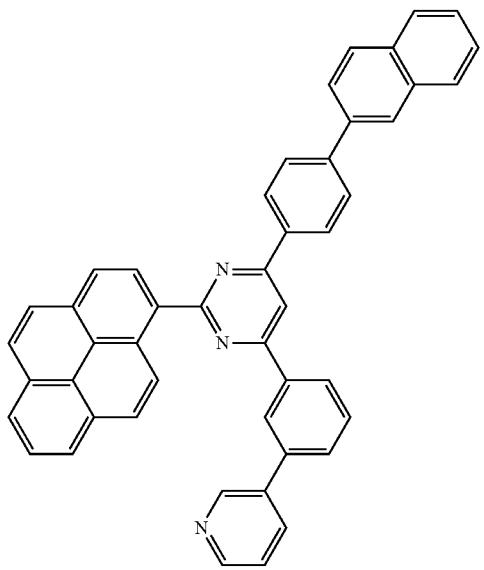
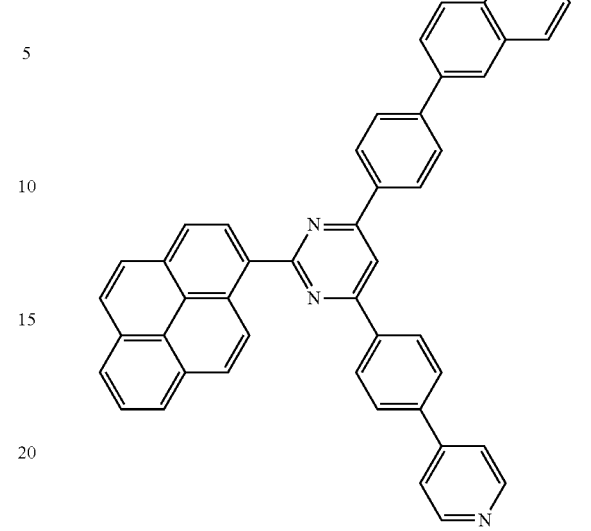
[Formula 70]
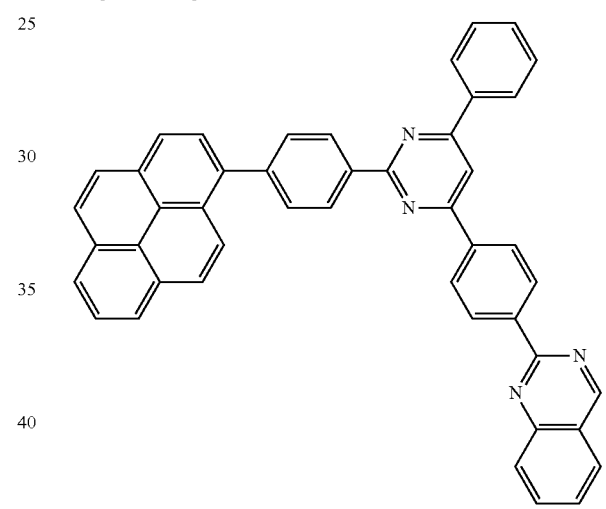
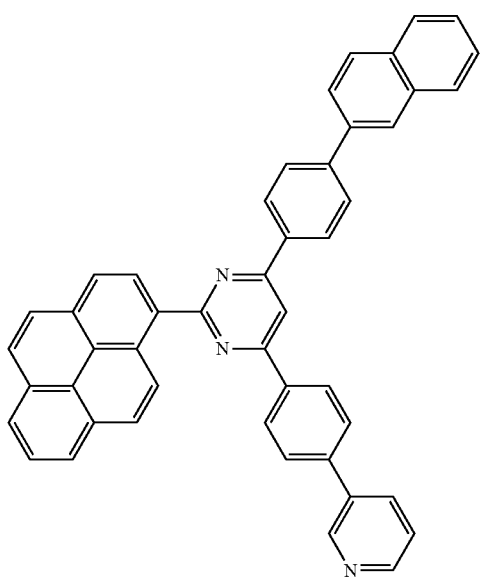

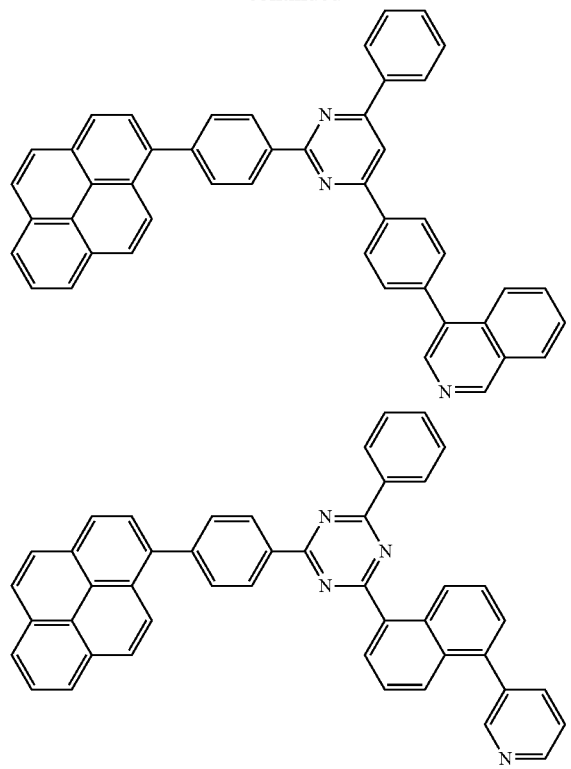
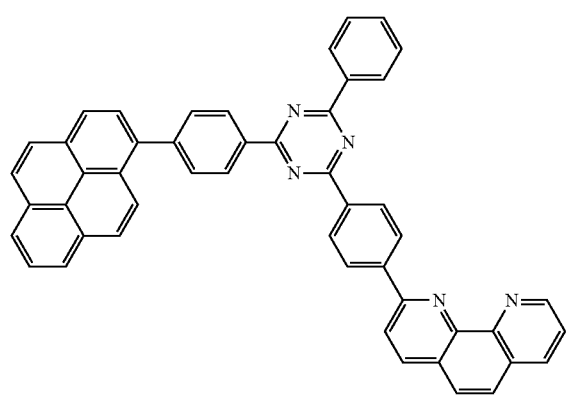
[Formula 71]
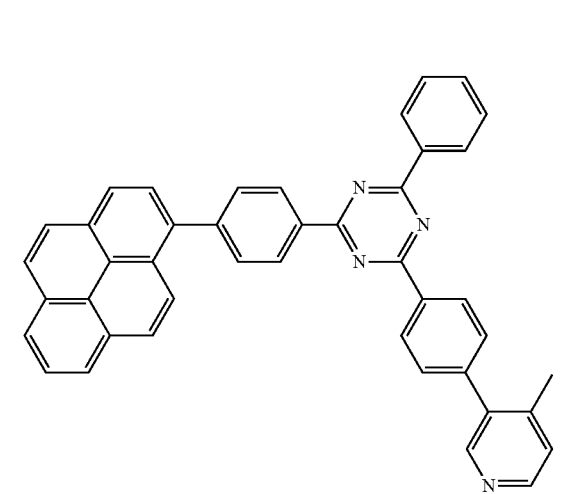
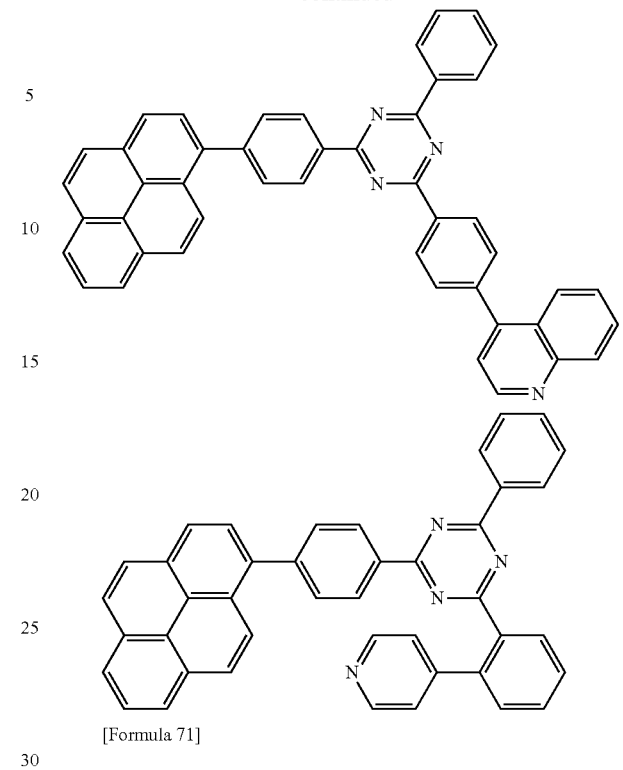
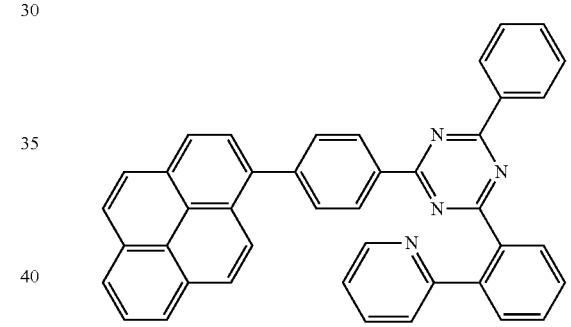
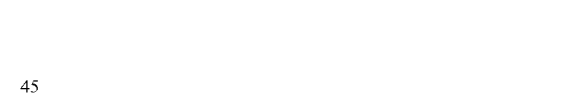
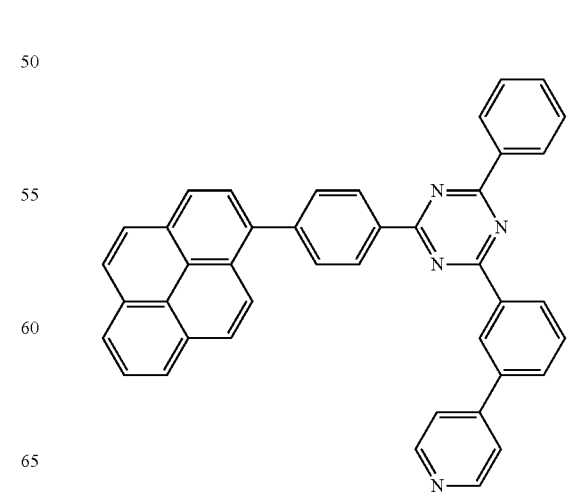

127
-continued
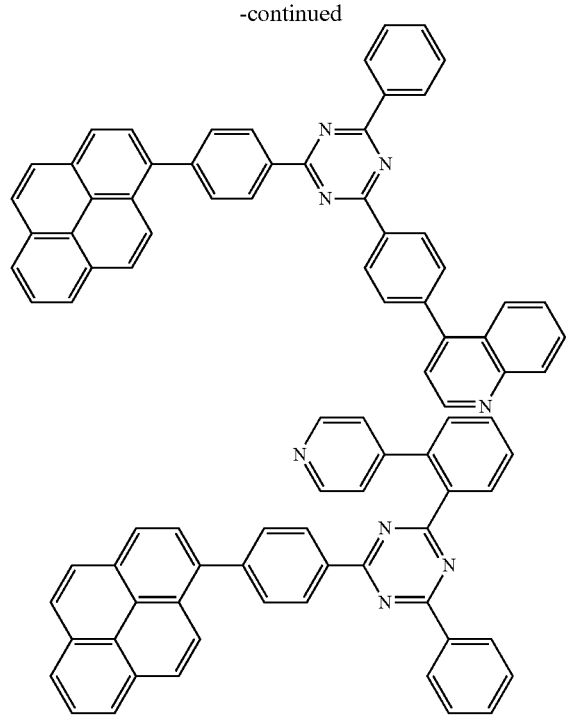
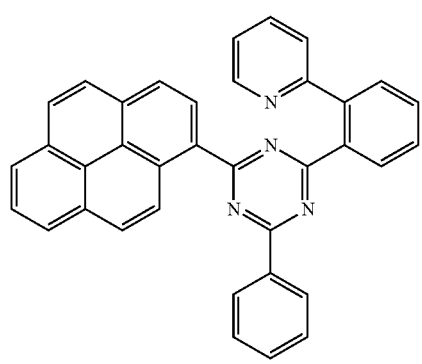
128
-continued
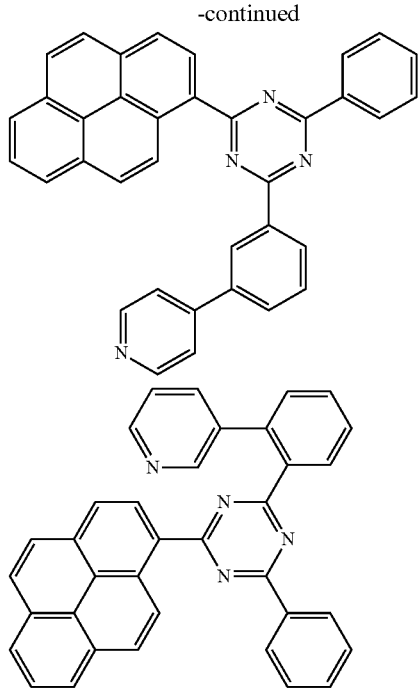
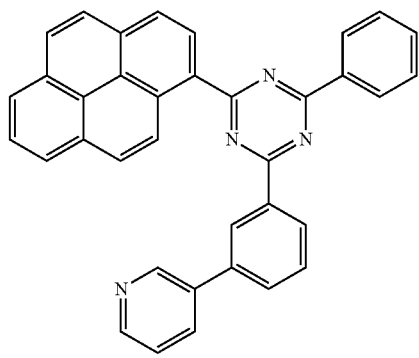
[Formula 71]
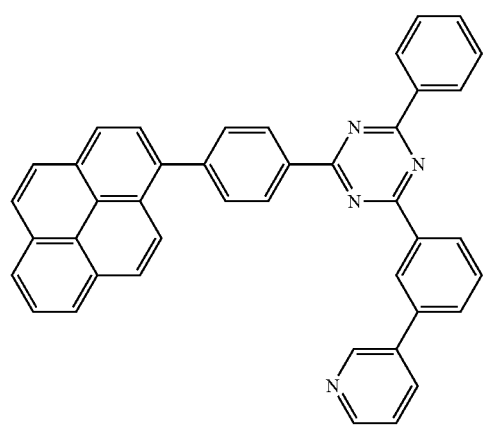
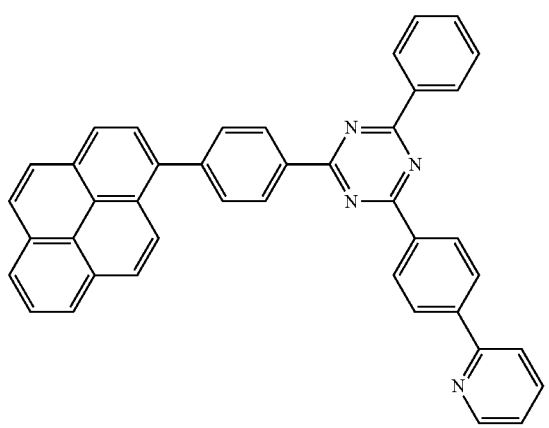

-continued
129
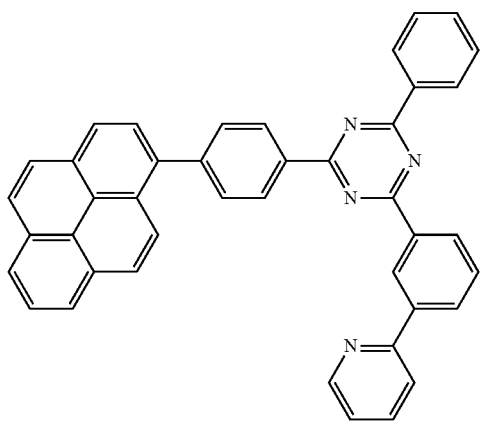
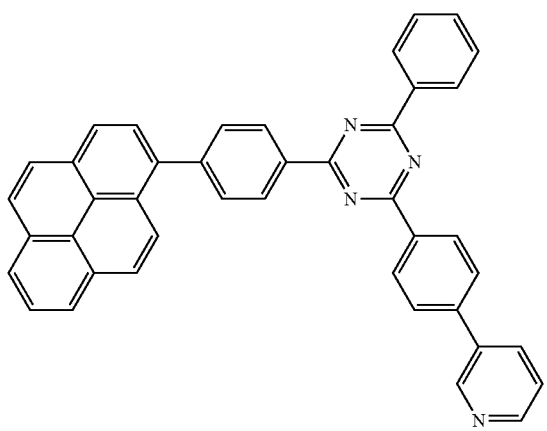
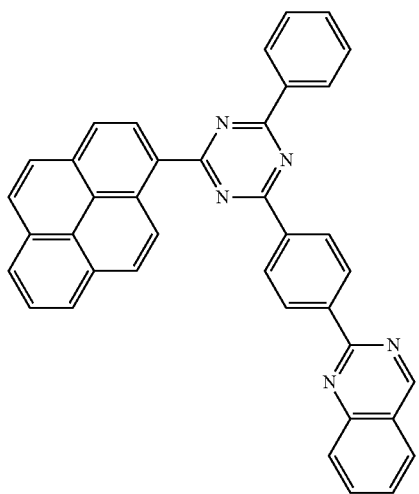
130
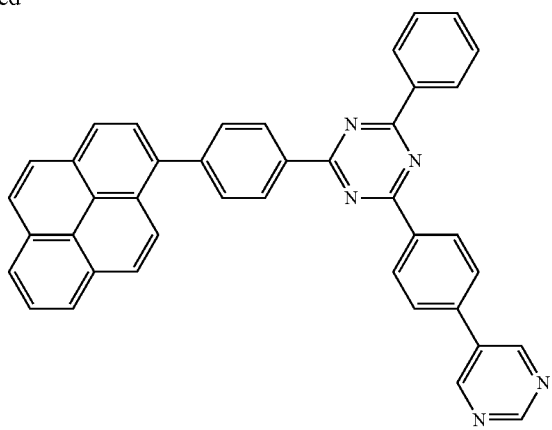
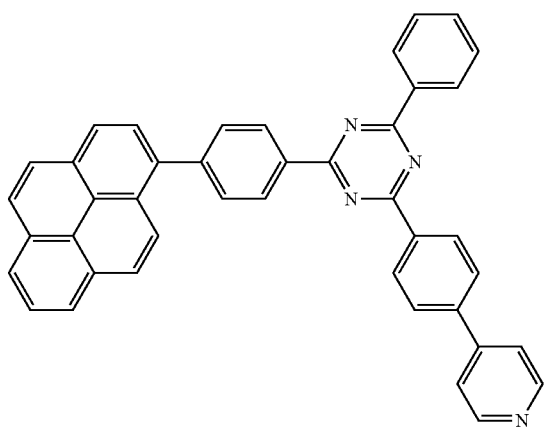
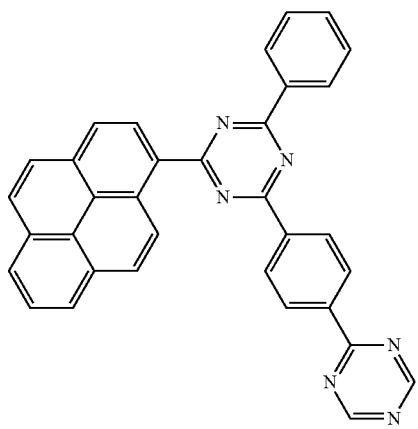

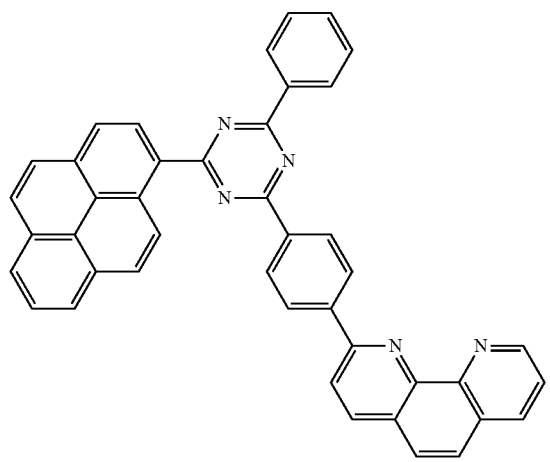
[Formula 72]
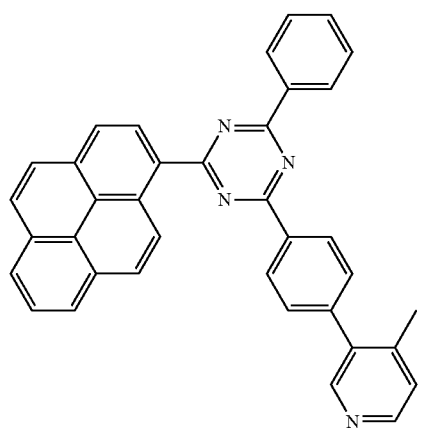
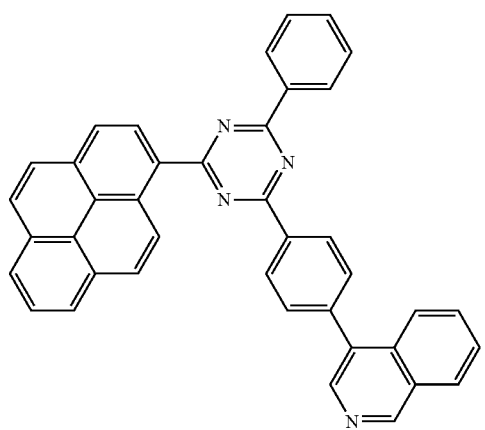
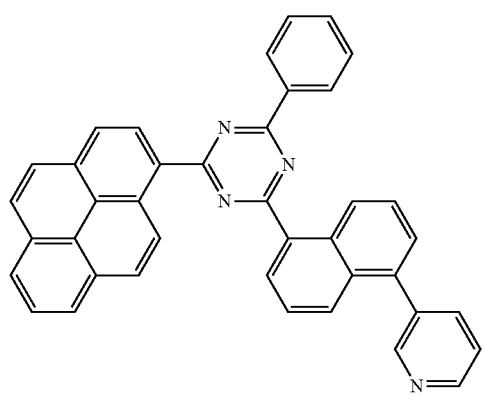
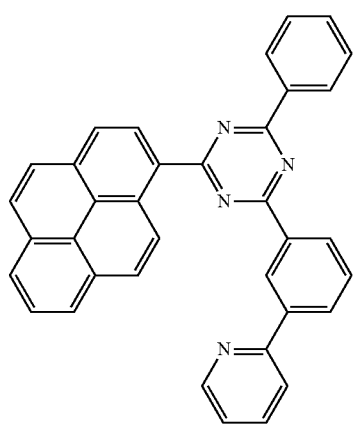

133
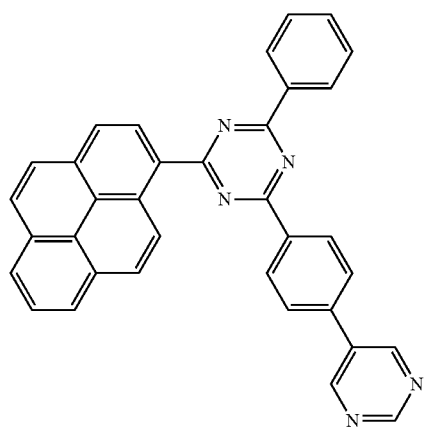
134
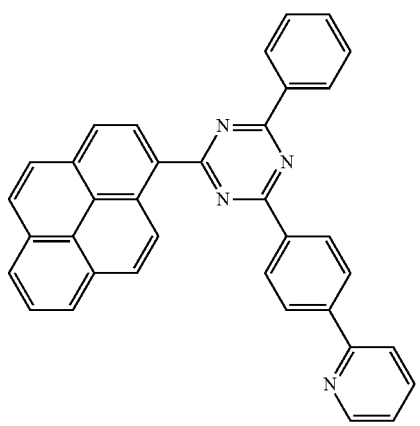
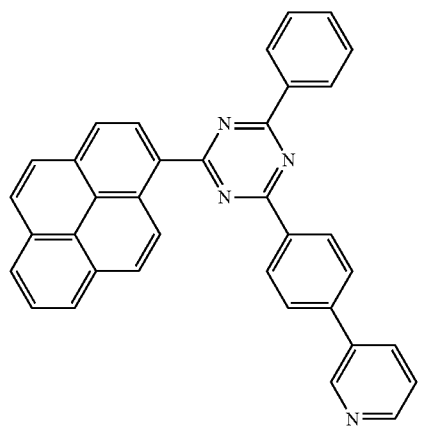
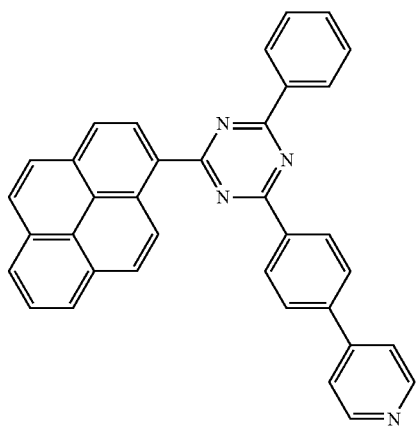
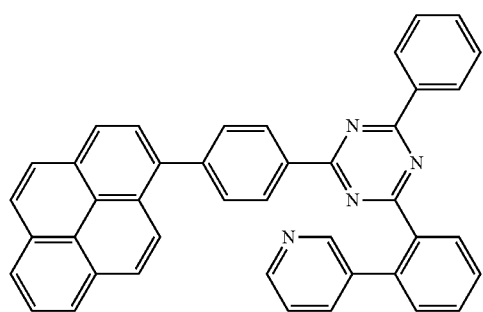 [SMILES: c1ccc(-c2nc(-c3ccc(-c4ccc5ccc6cccc7ccc4c5c67)cc3)nc(-c3ccccc3-c3cccnc3)n2)cc1]

-continued
[Formula 73]
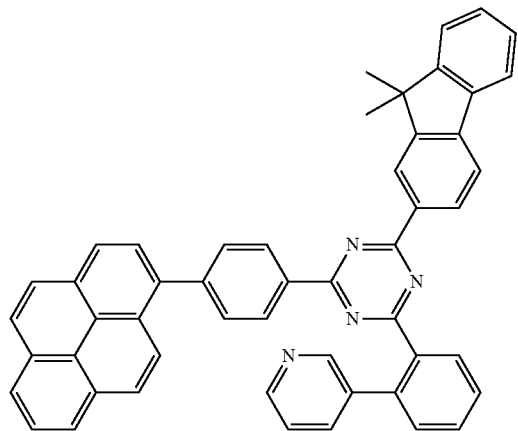
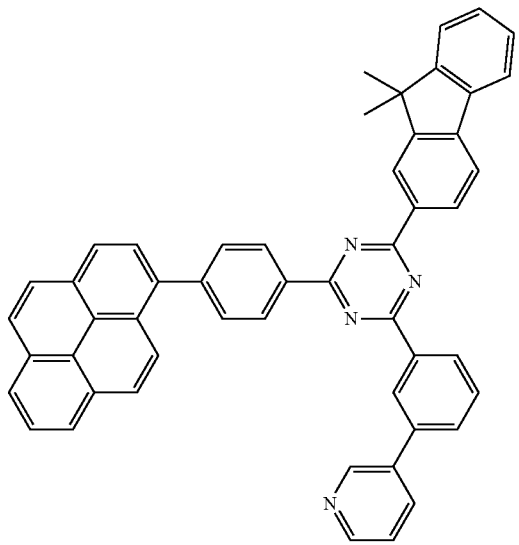
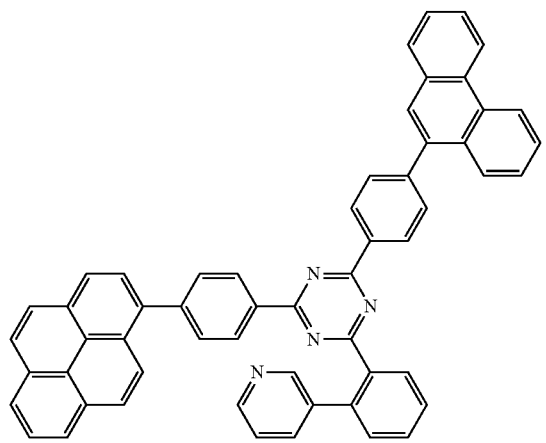
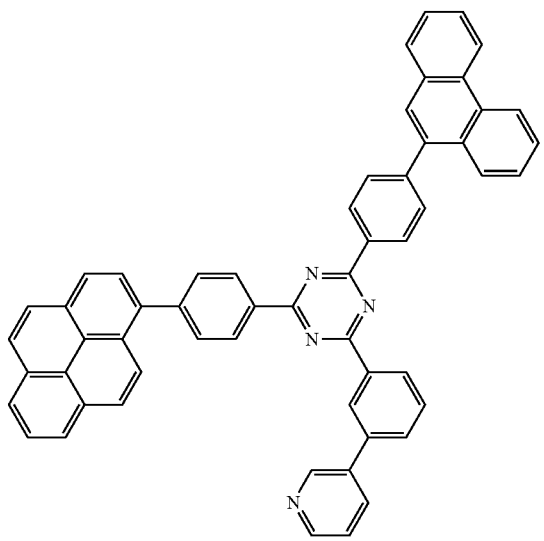
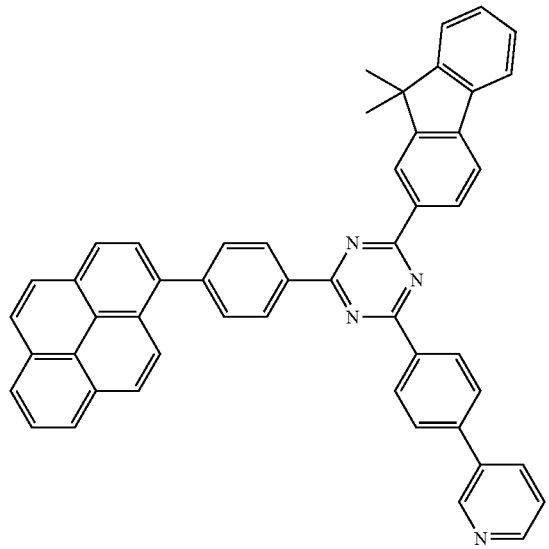
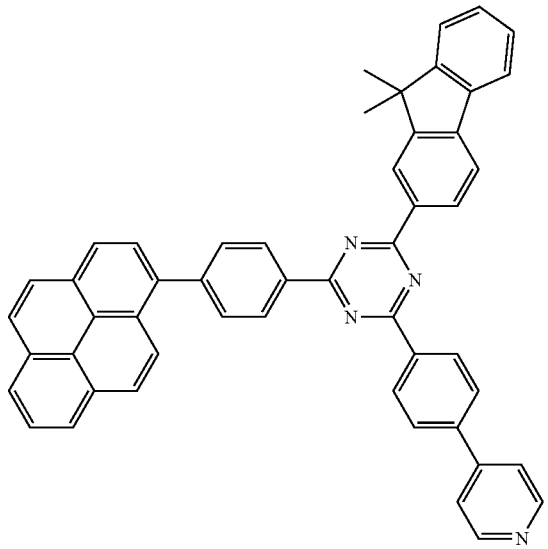

137 138
-continued
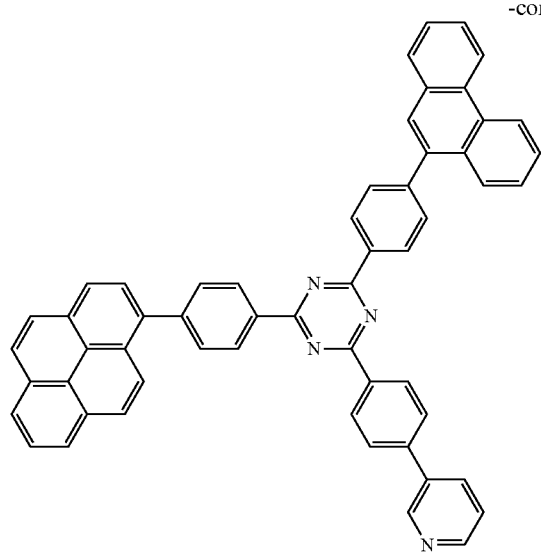
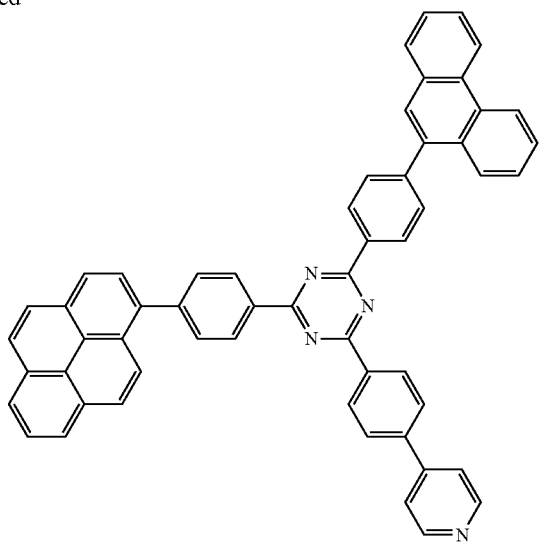
[Formula 74]
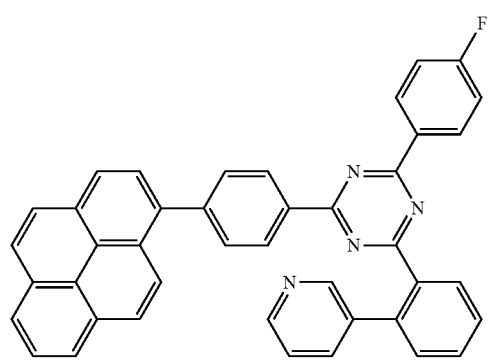
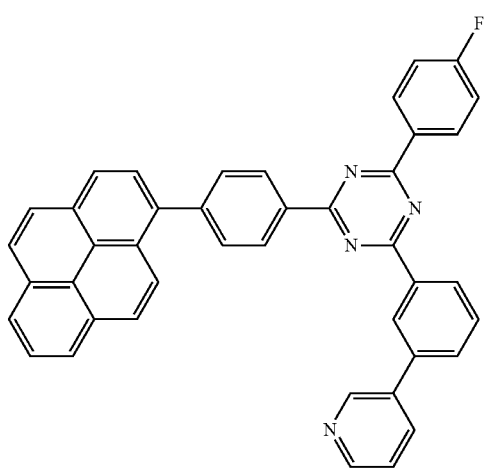
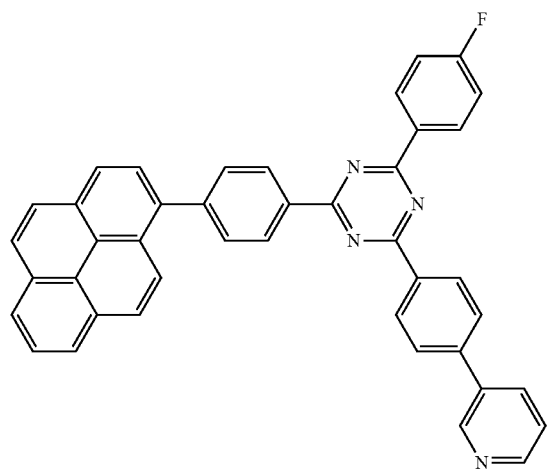
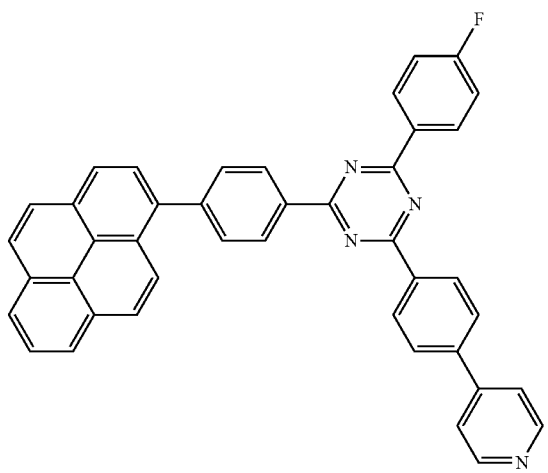

-continued
[Formula 75]
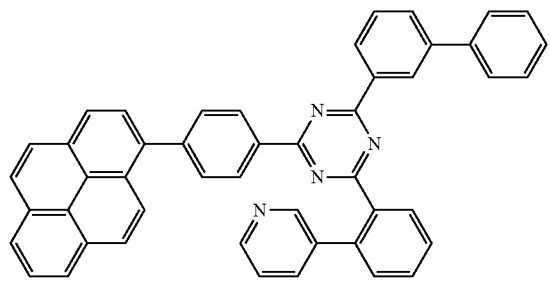
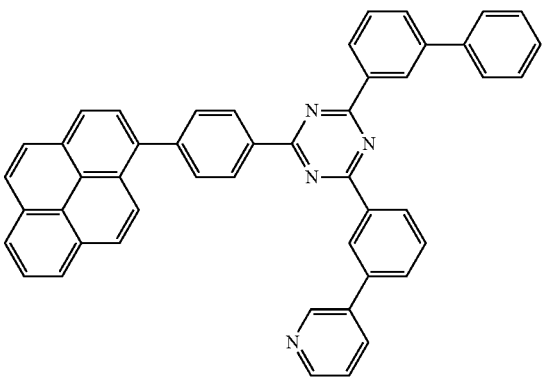
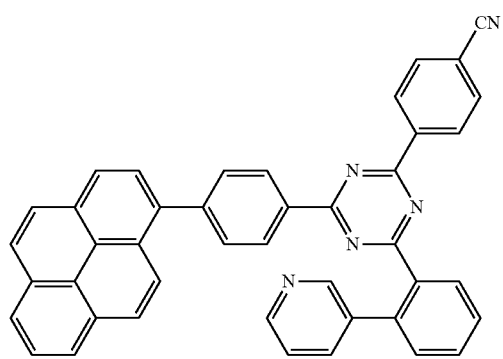
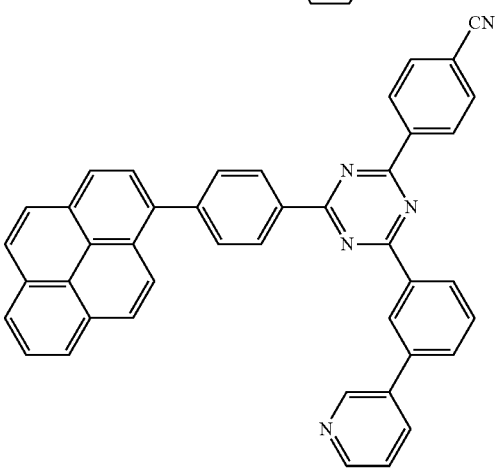
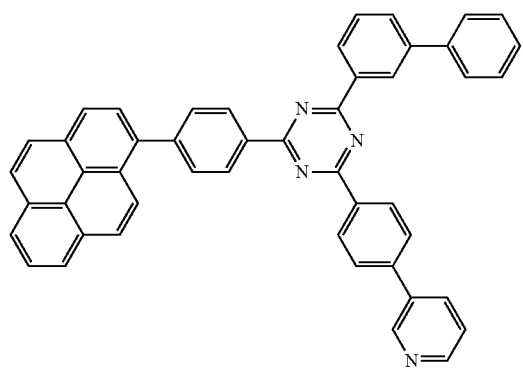
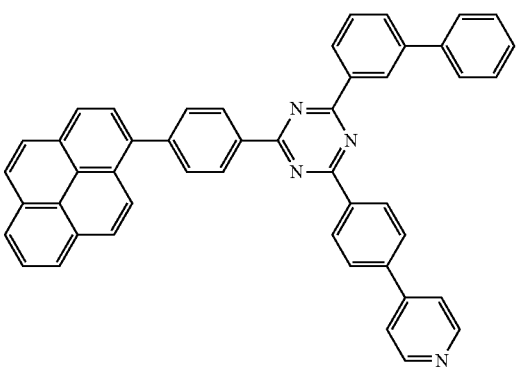
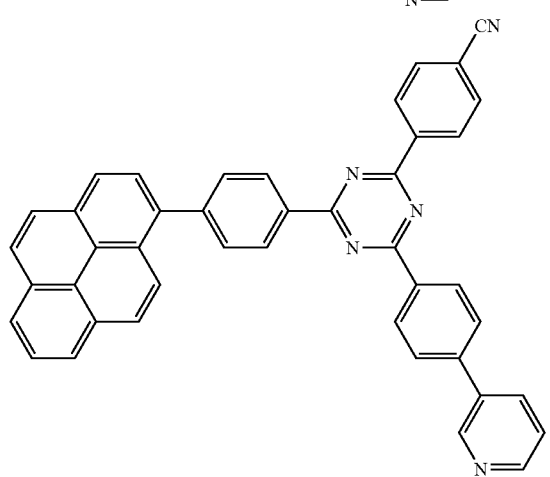
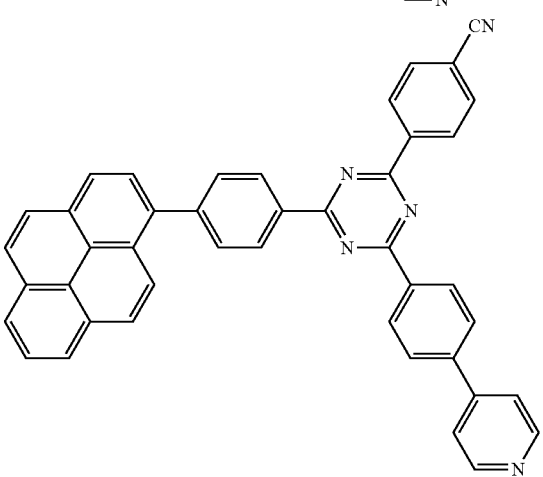

-continued
[Formula 76]
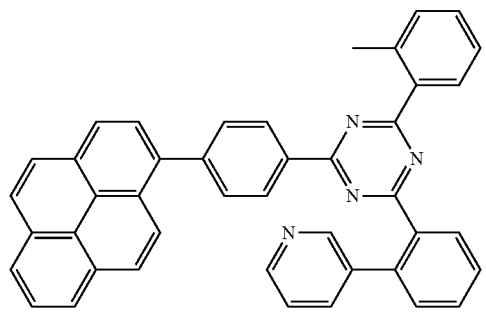
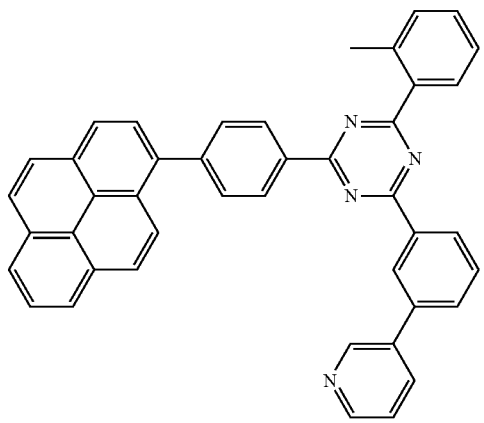
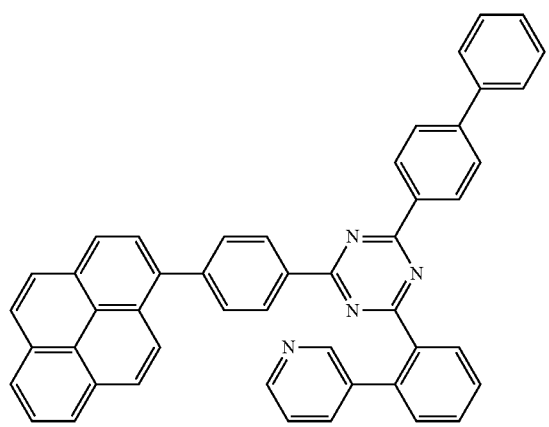
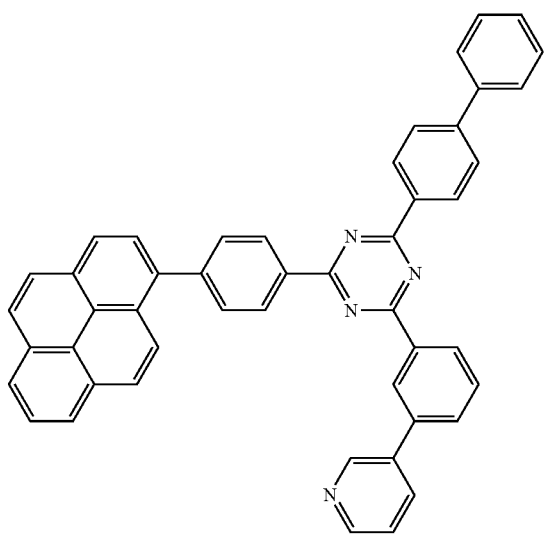
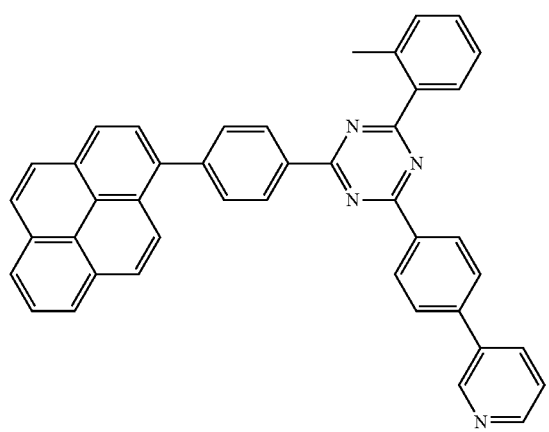
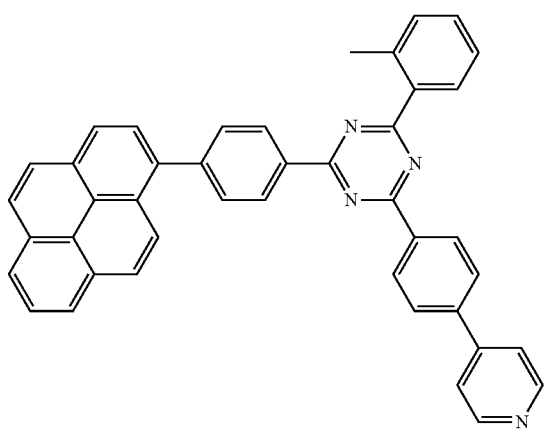

-continued
143
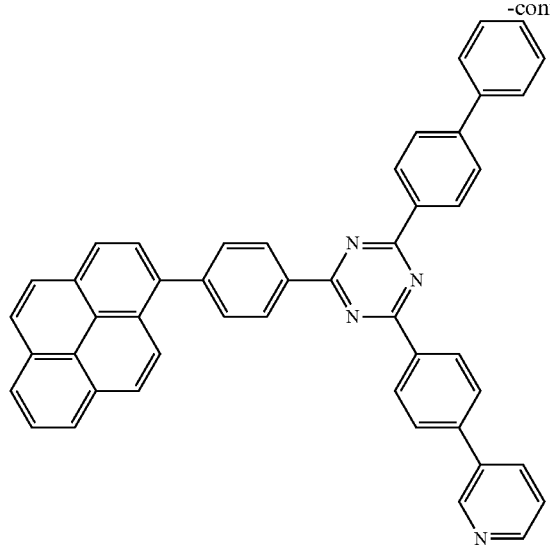
144
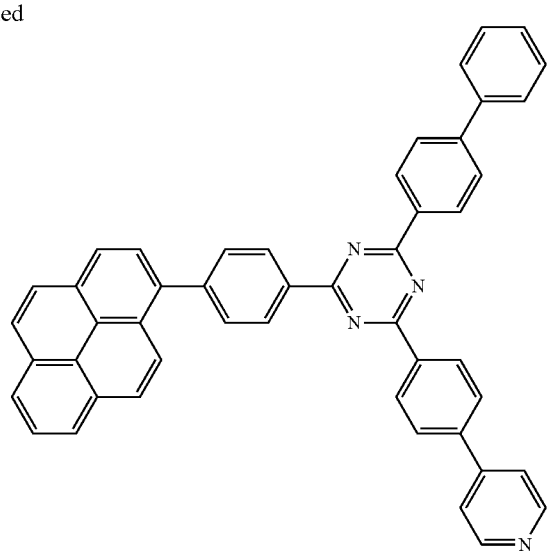
[Formula 77]
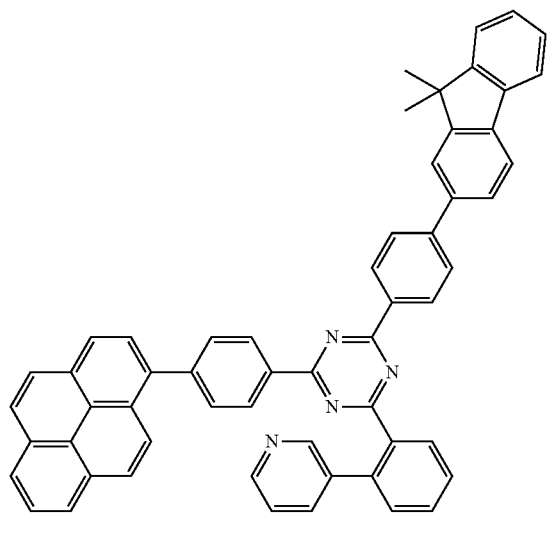
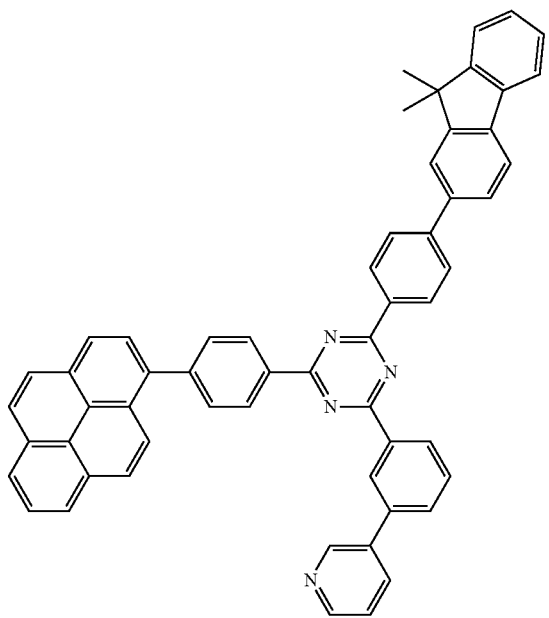

-continued
145
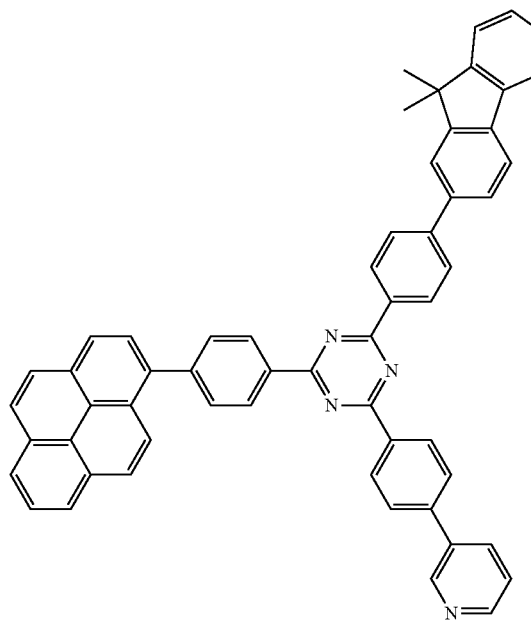
146
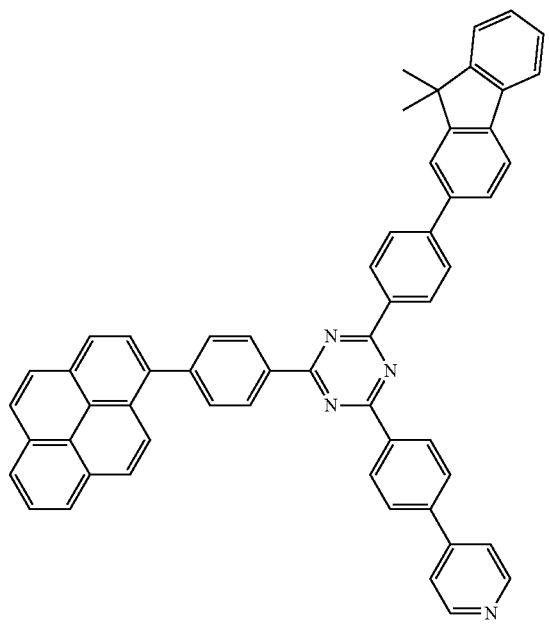
[Formula 78]
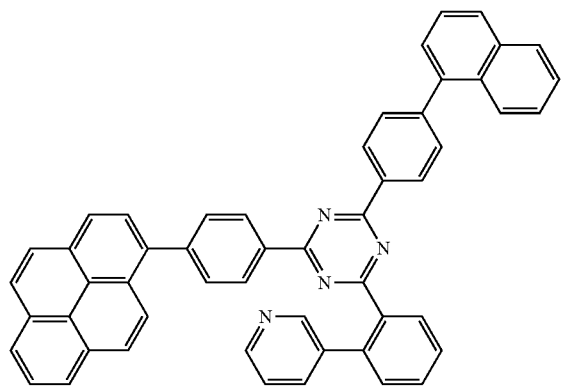
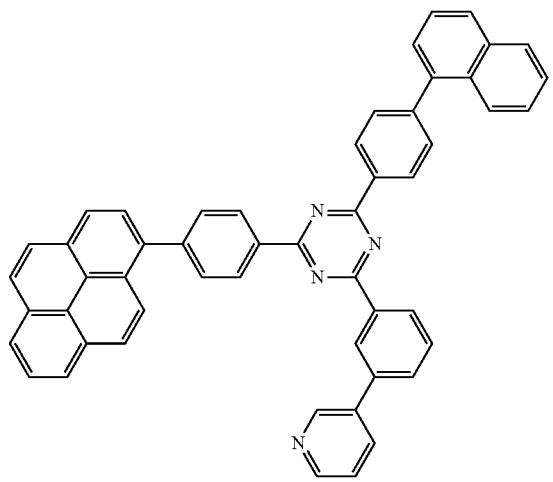
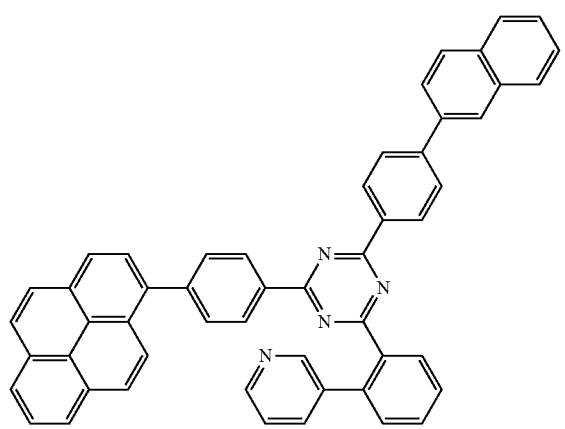
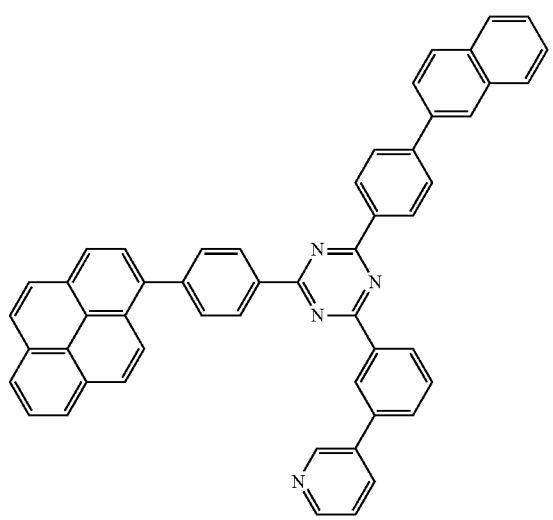

-continued
147
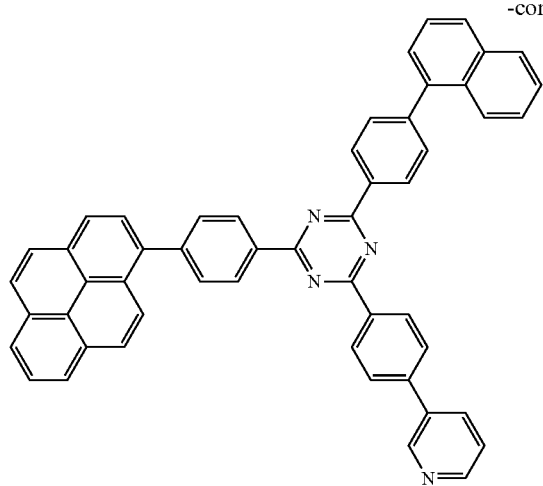
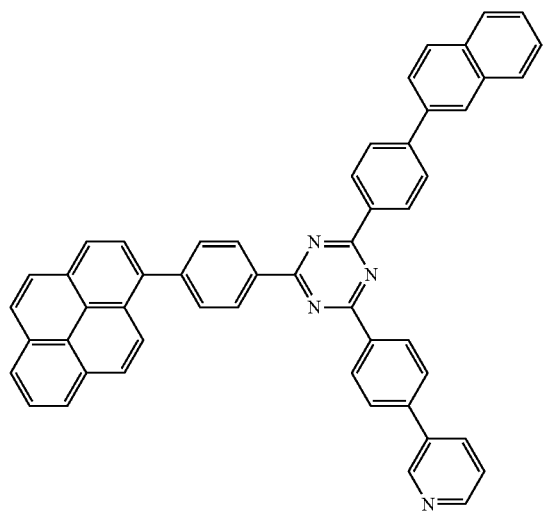
148
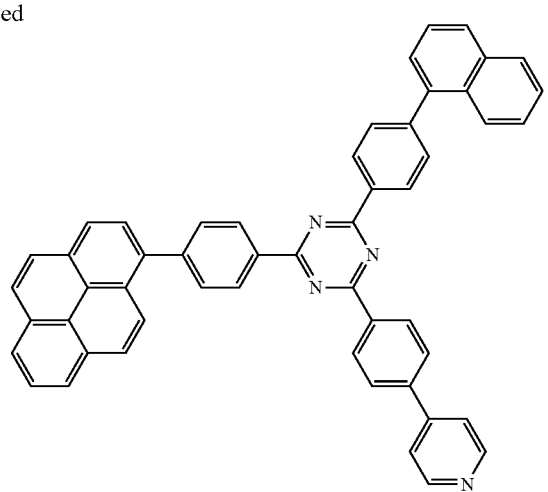
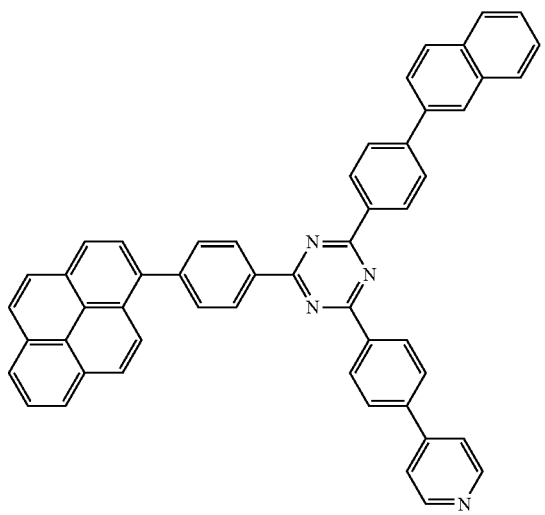
[Formula 79]
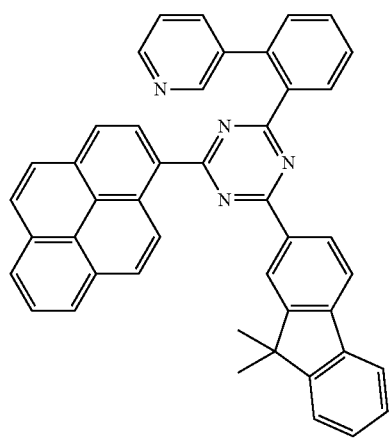
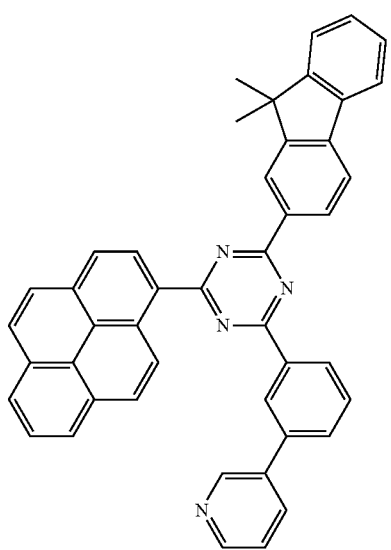

149
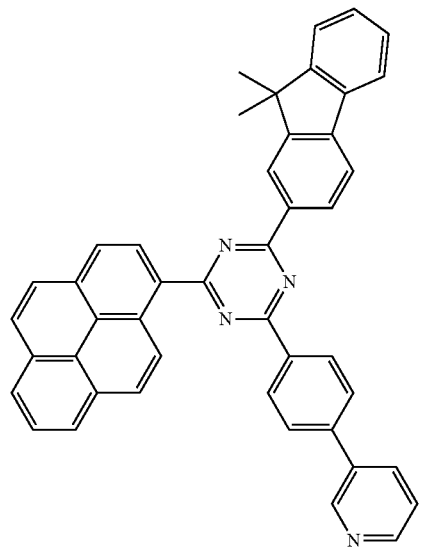
150
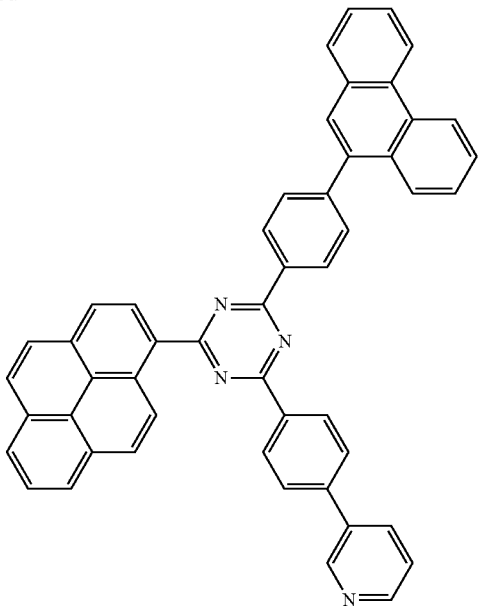
-continued
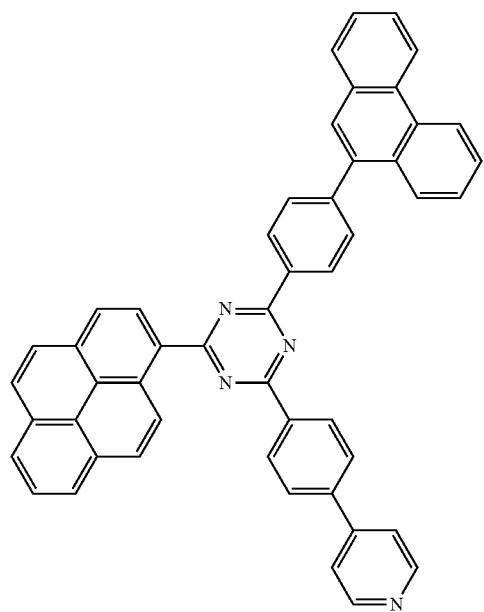

-continued
151
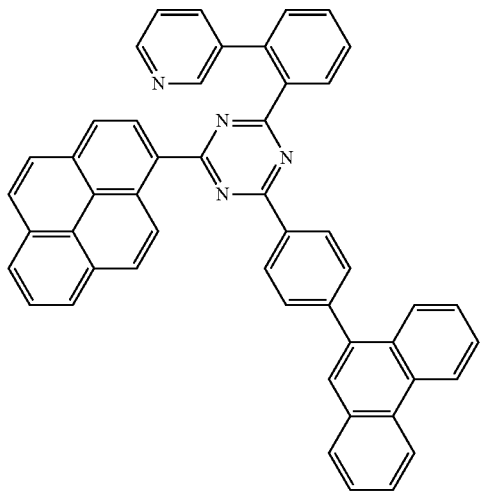
152
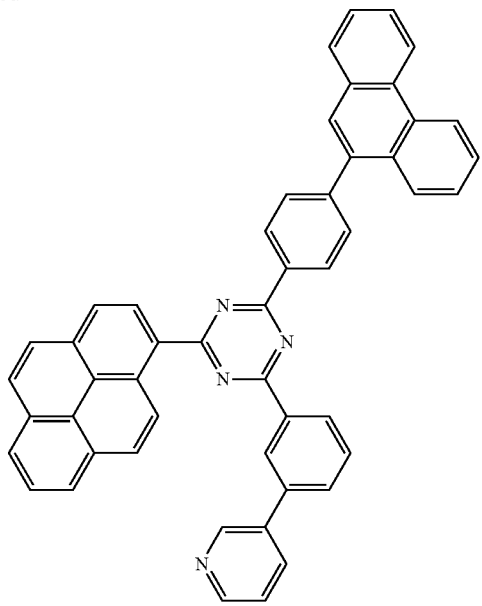
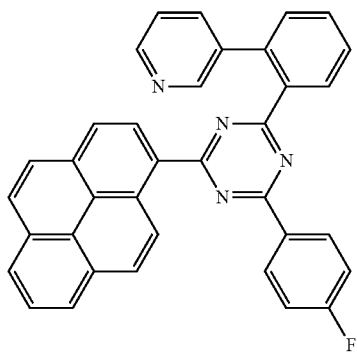
[Formula 80]
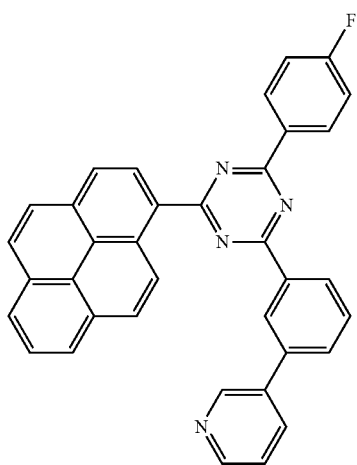
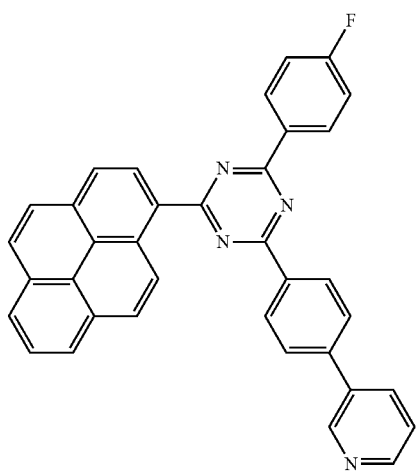

-continued
153
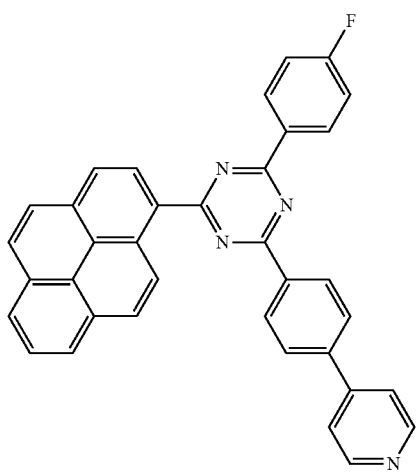
154
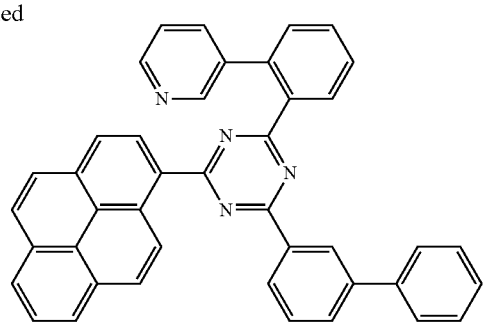
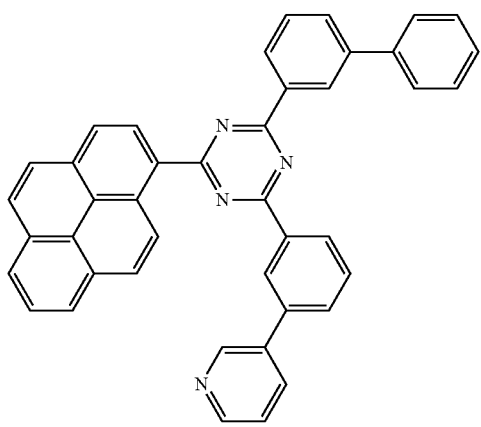
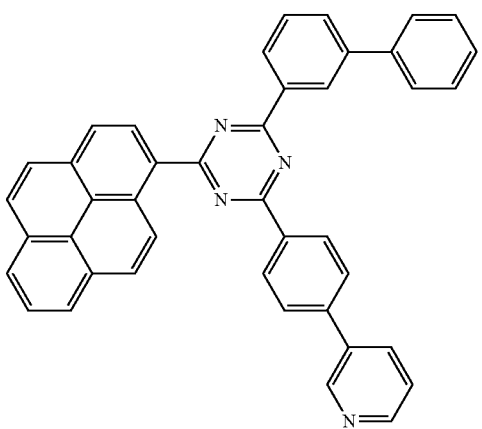
[Formula 81]
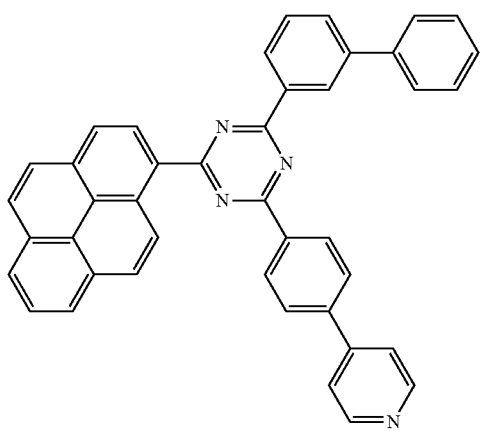
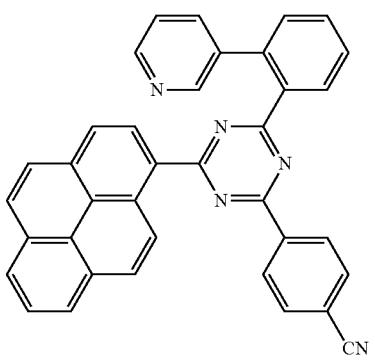

155
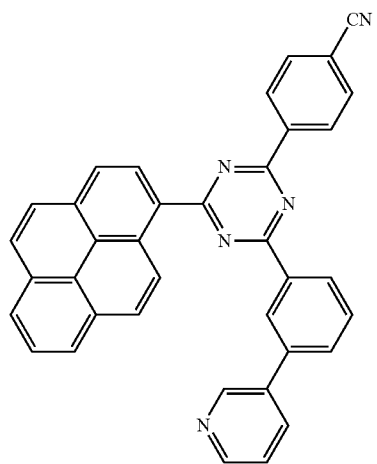
156
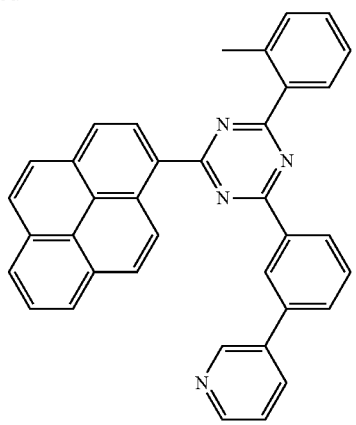
-continued
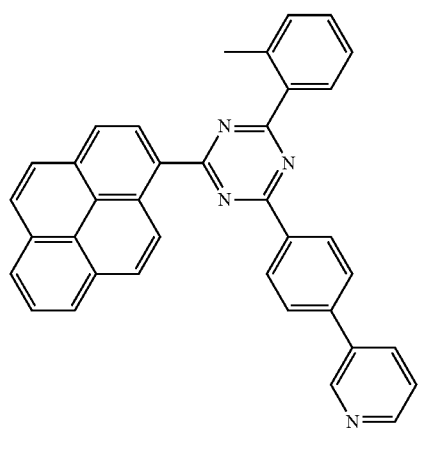
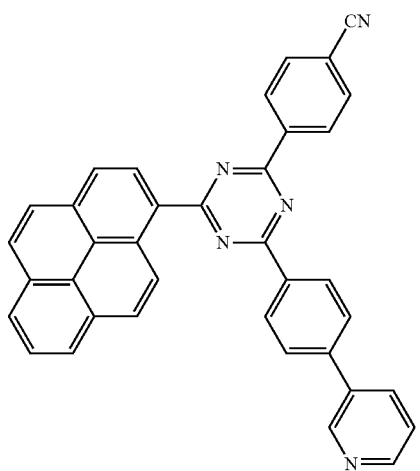
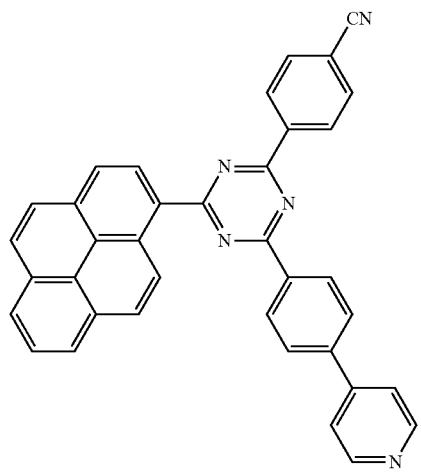
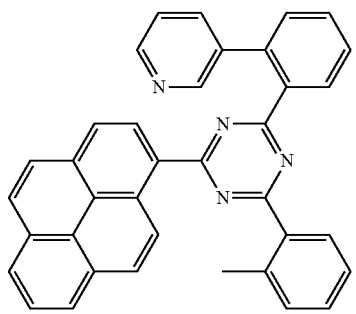

-continued
157
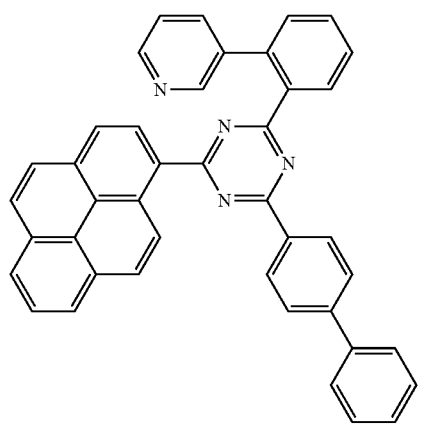
158
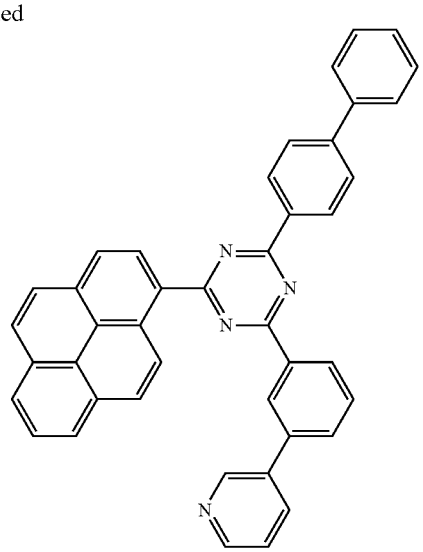
[Formula 82]
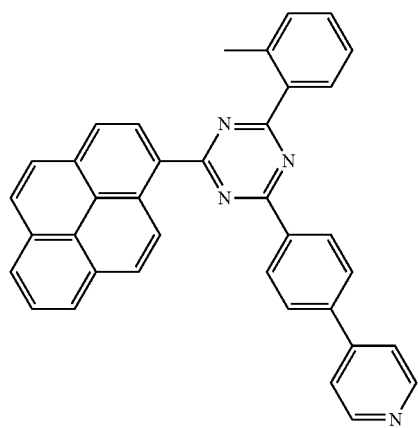
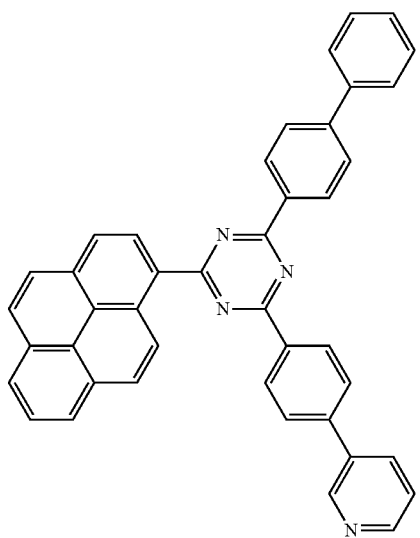
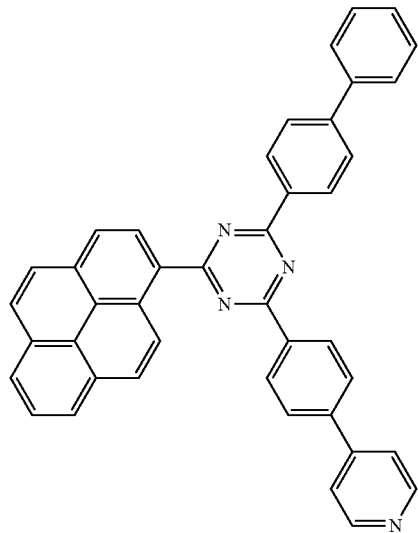
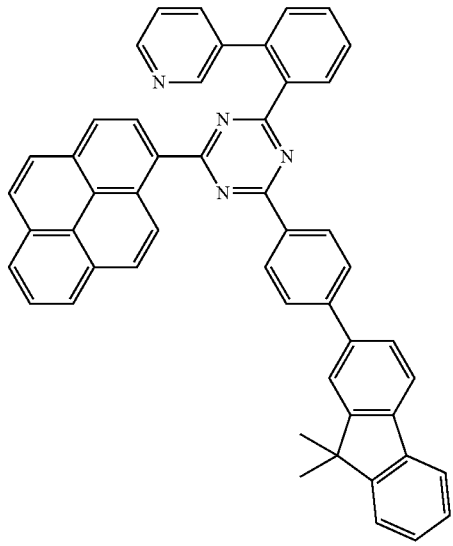

[Formula 83]
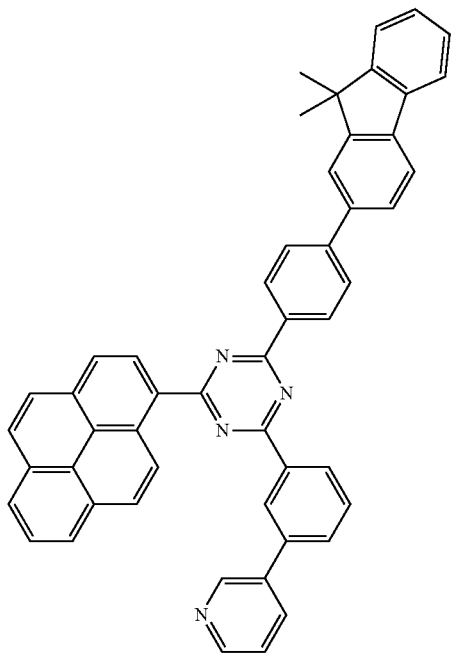
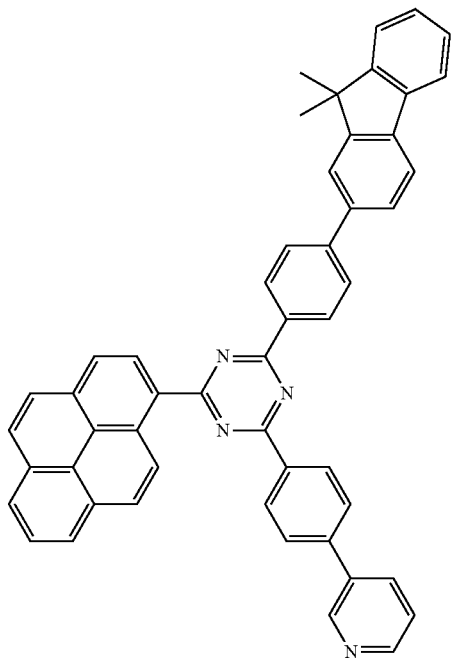
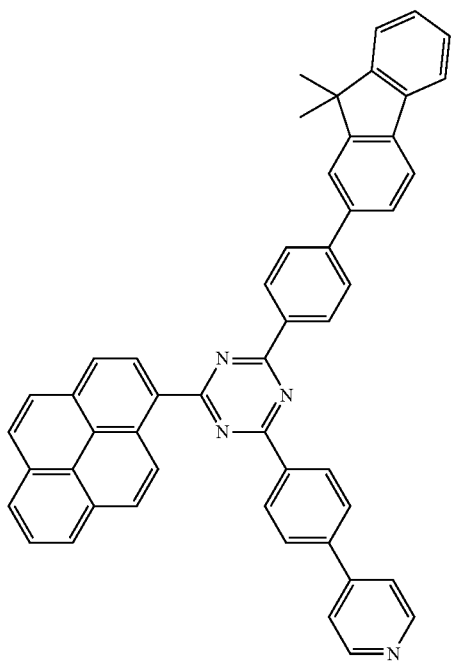

[Formula 84]
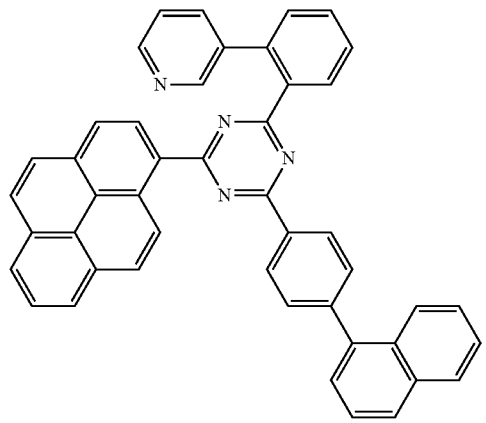
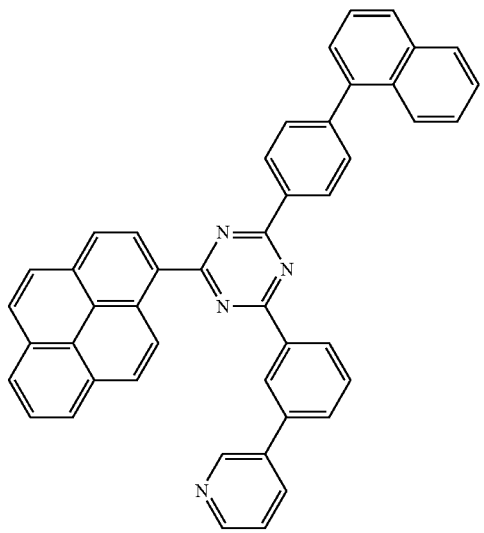
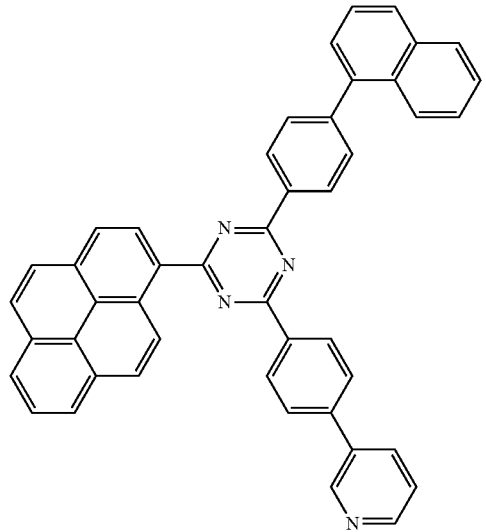
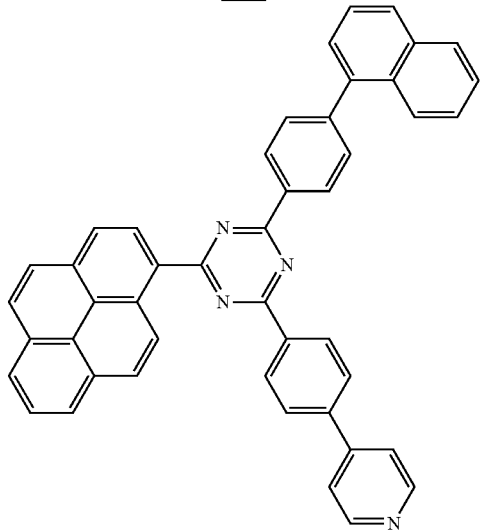
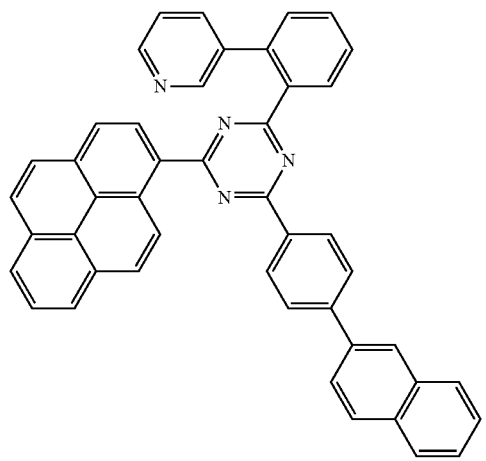
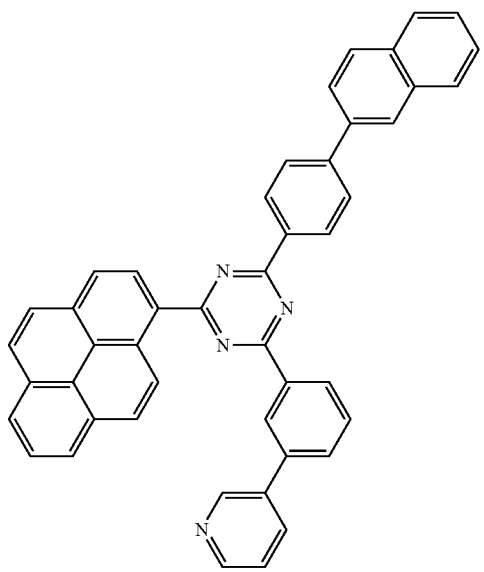

163
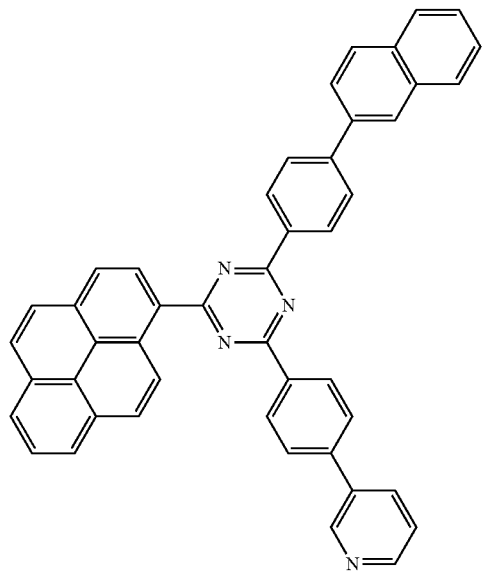
164
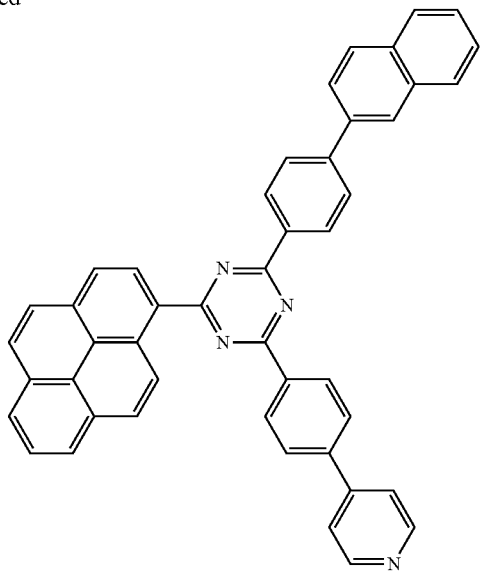
[Formula 85]
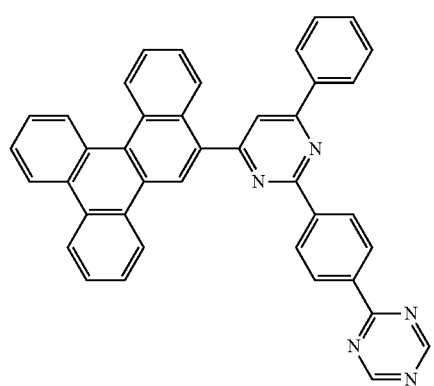
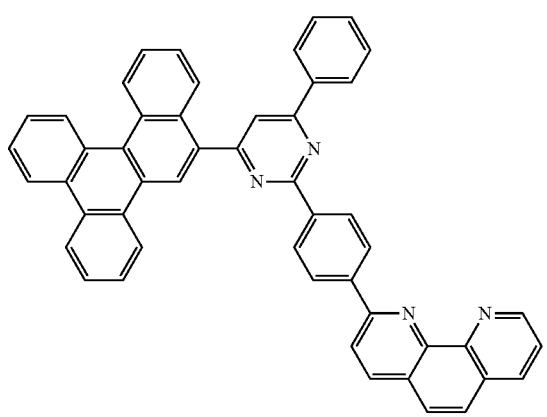
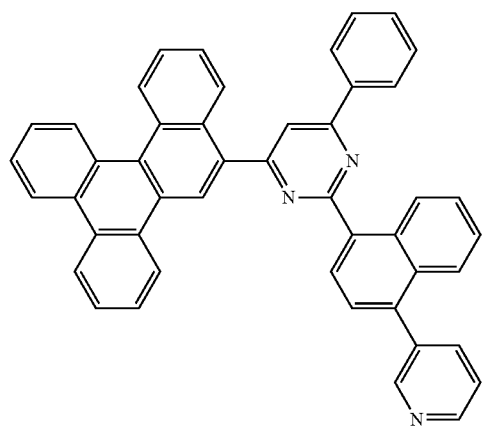
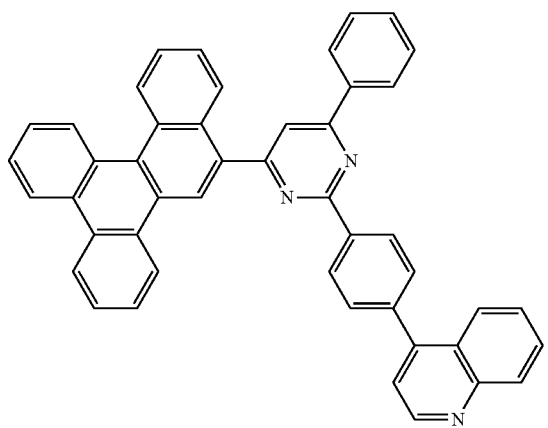

165
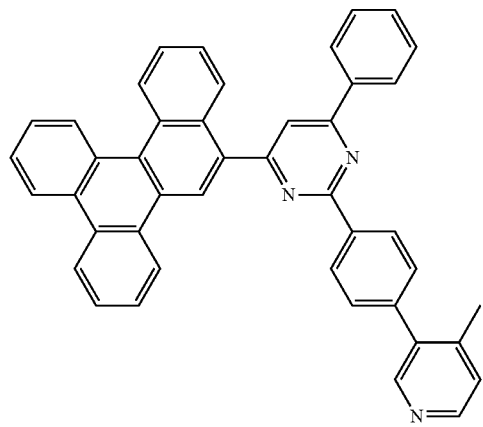
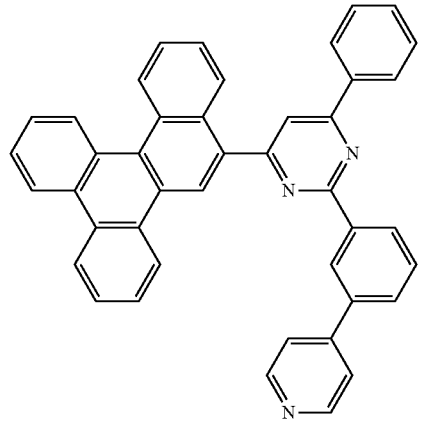
166
-continued
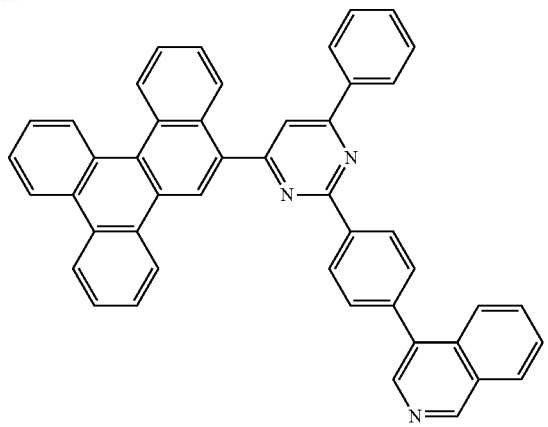
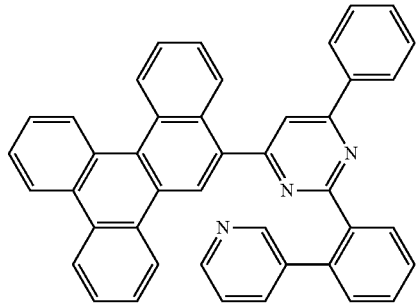
[Formula 86]
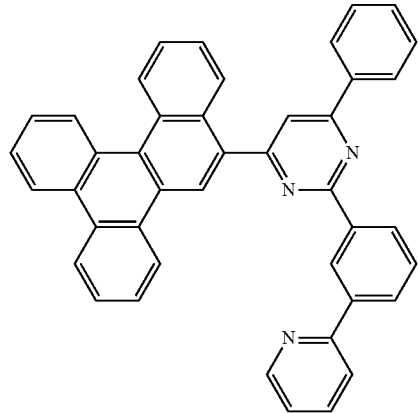
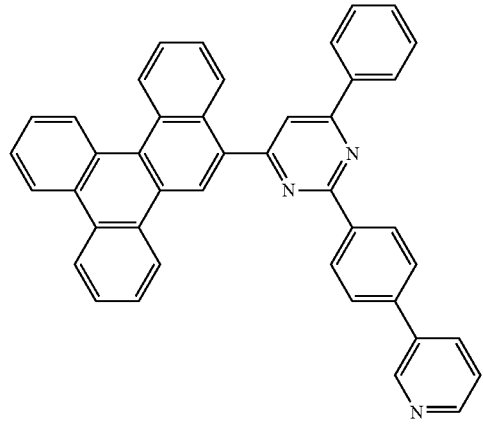
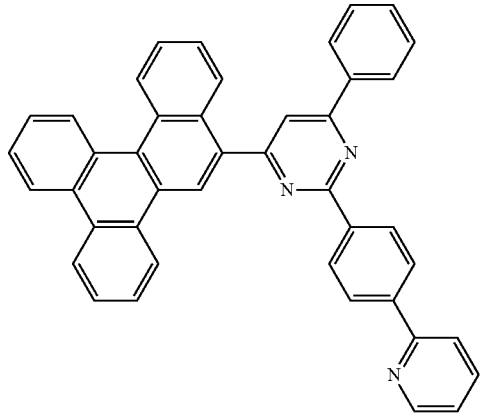
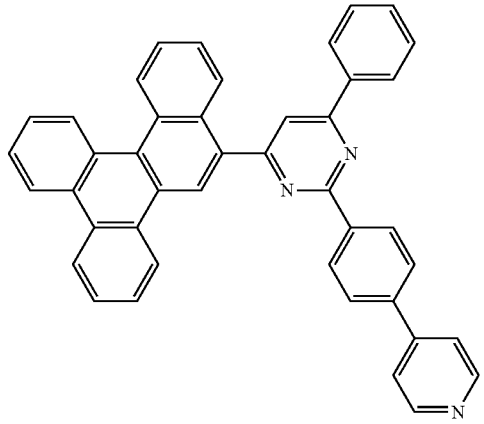

-continued
[Formula 87]
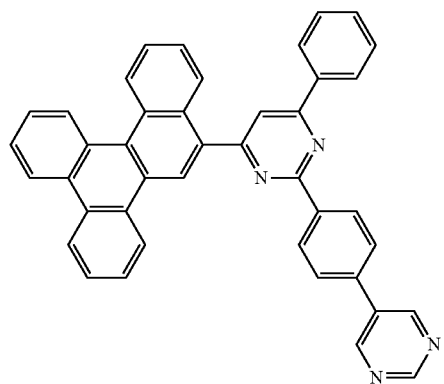 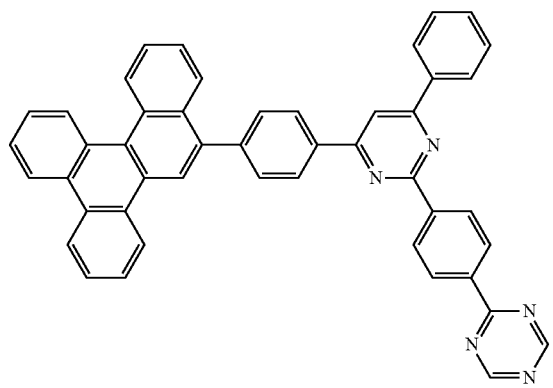
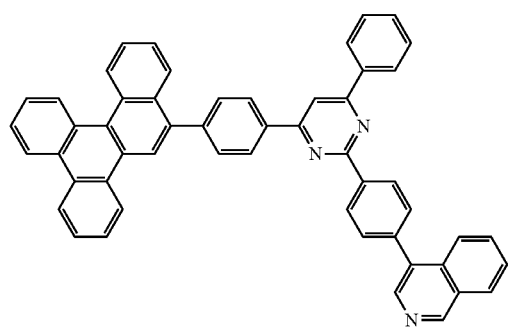 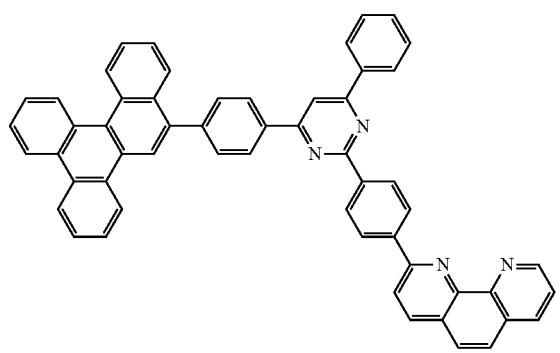
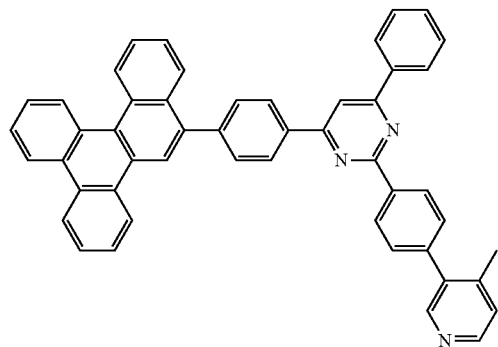 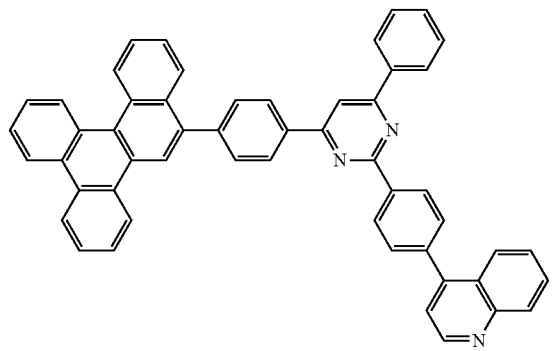
[Formula 88]
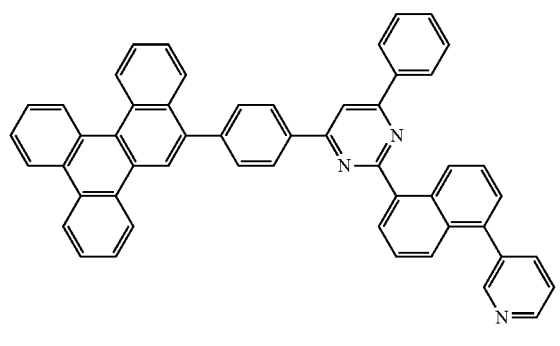 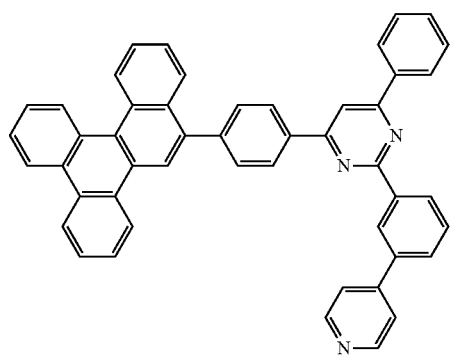

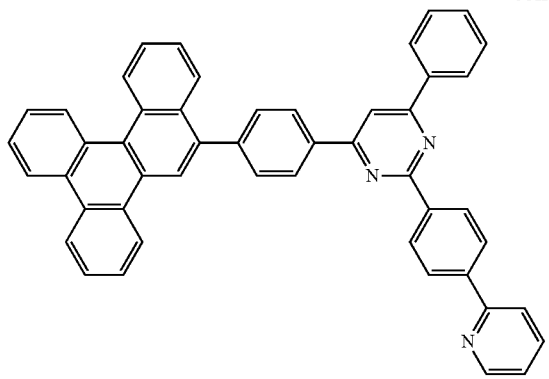
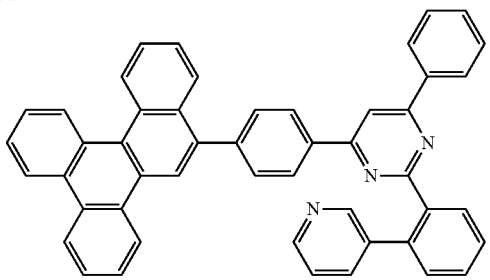
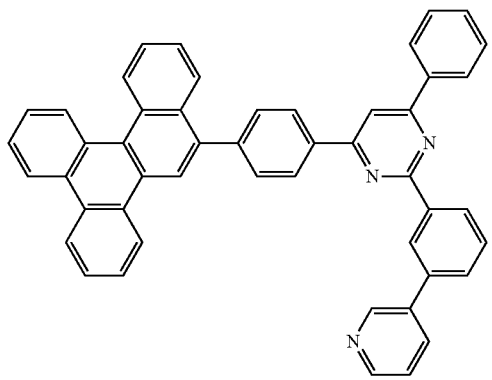
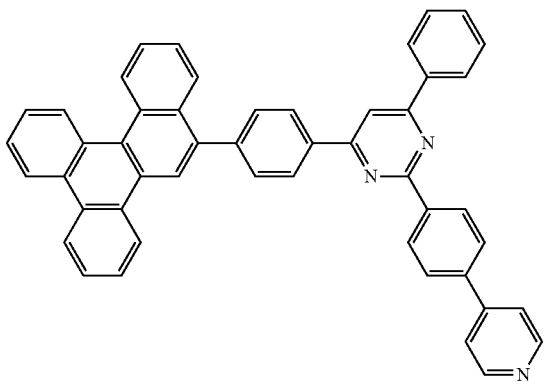
[Formula 89]
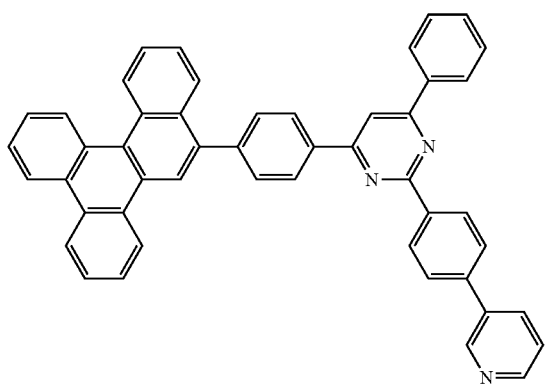
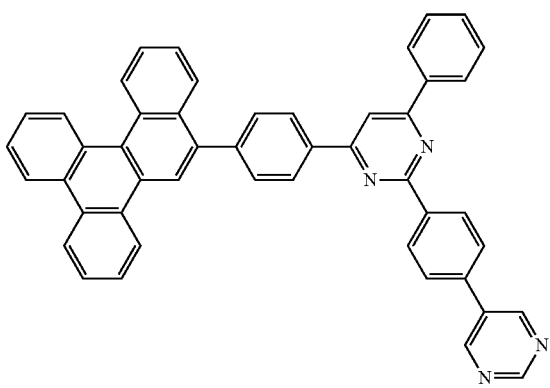
[Formula 90]
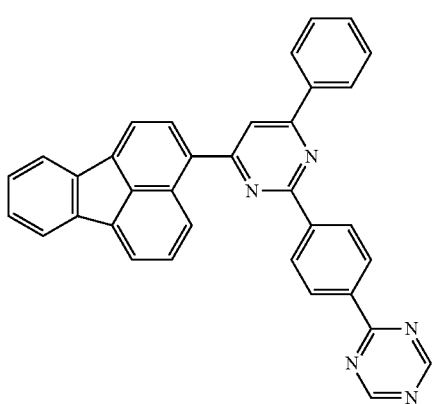
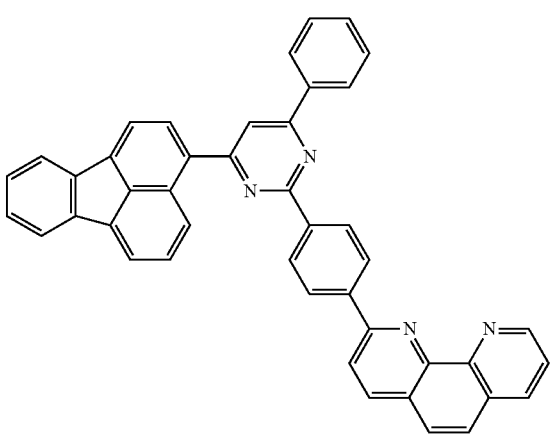

-continued
171
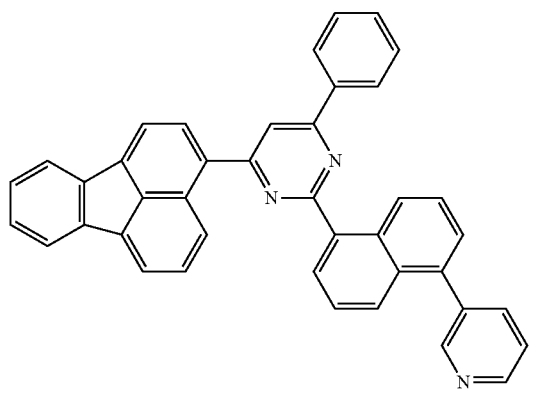
172
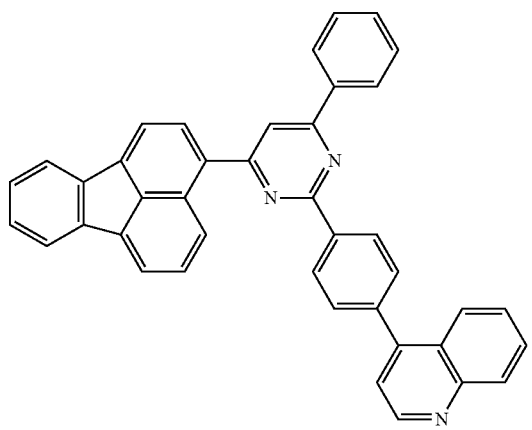
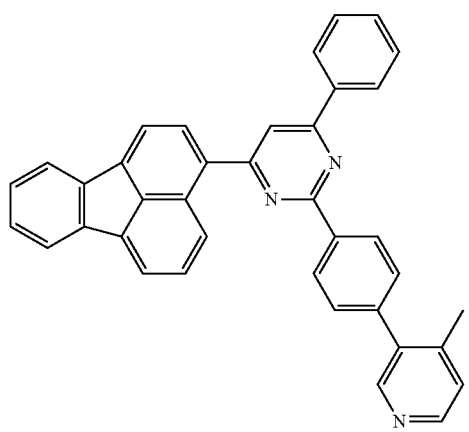
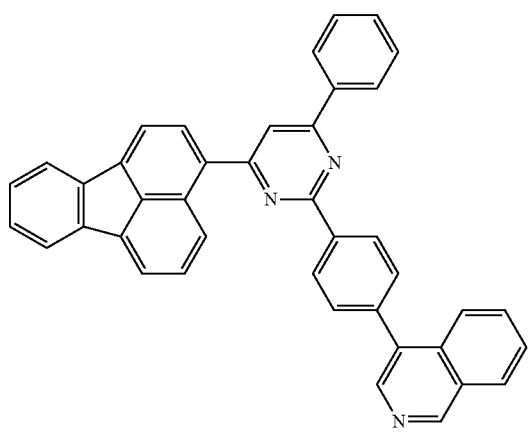
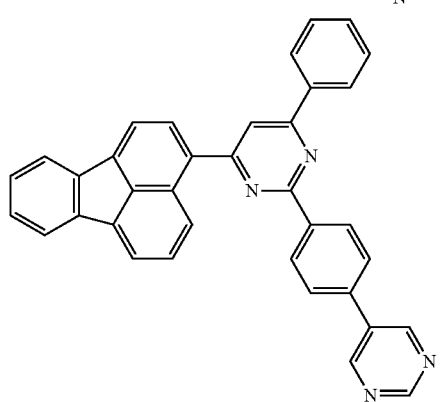
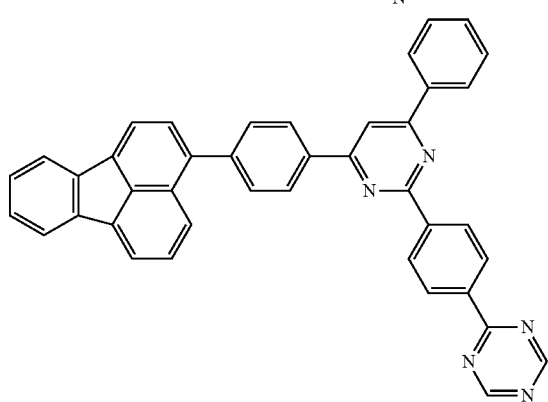
[Formula 91]
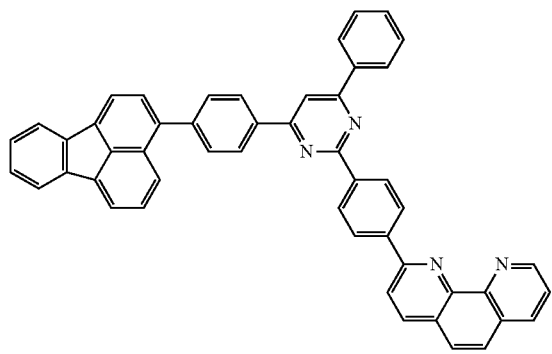
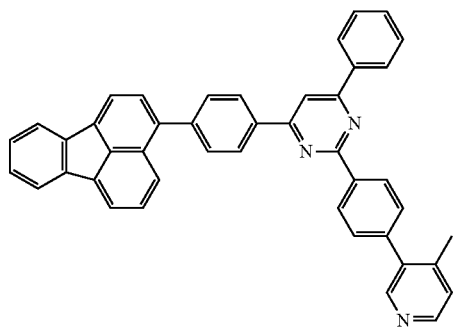

-continued
173
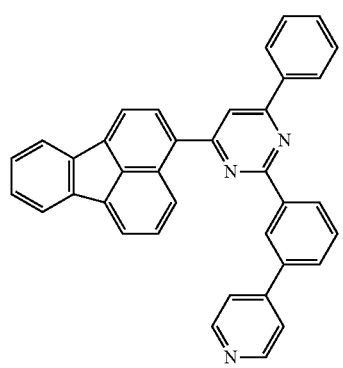
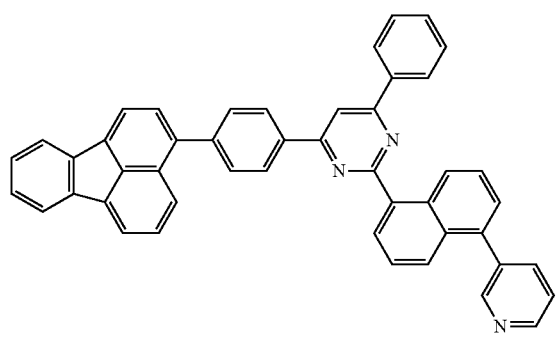
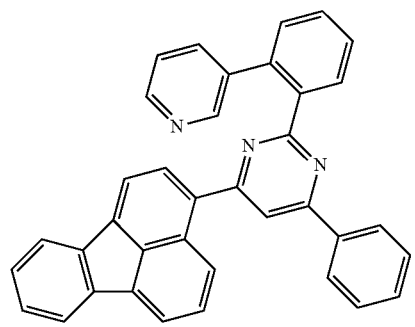
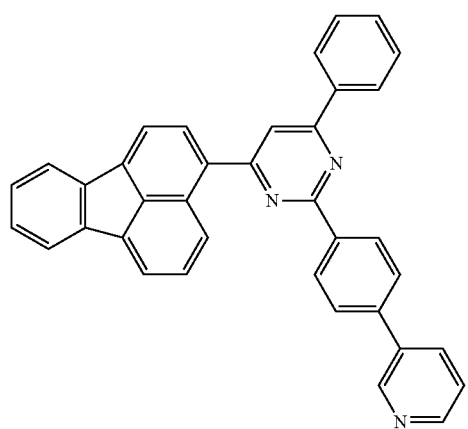
174
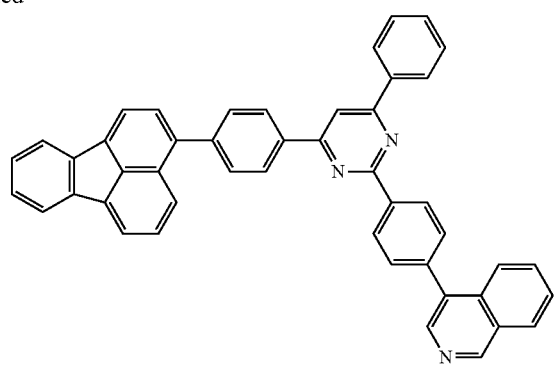
[Formula 92]
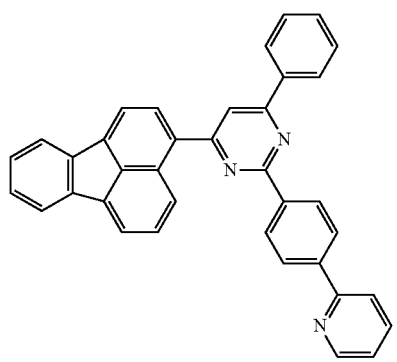
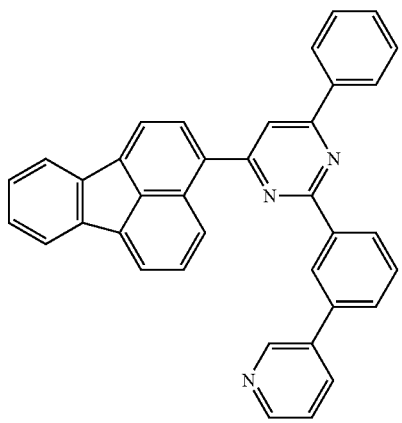
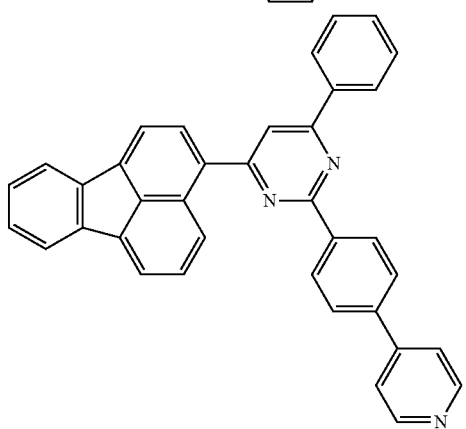

[Formula 93]
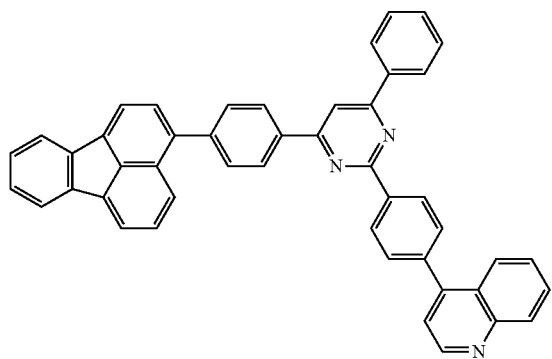 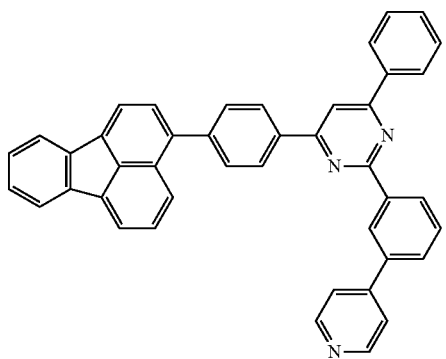
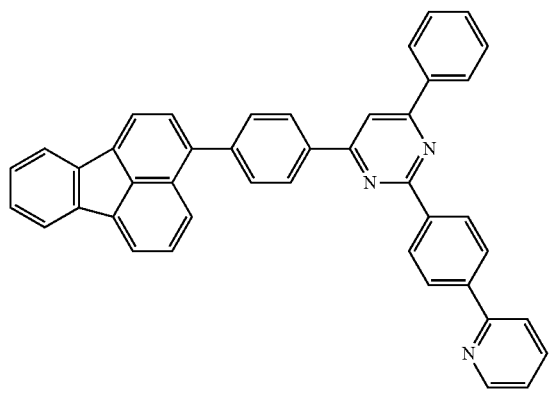 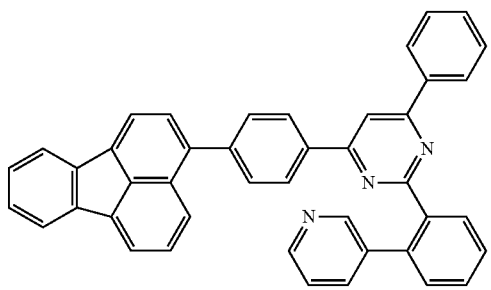
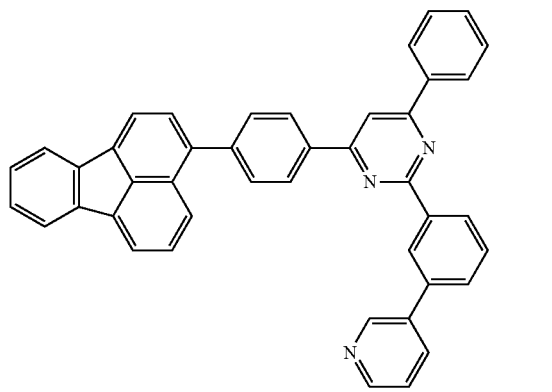 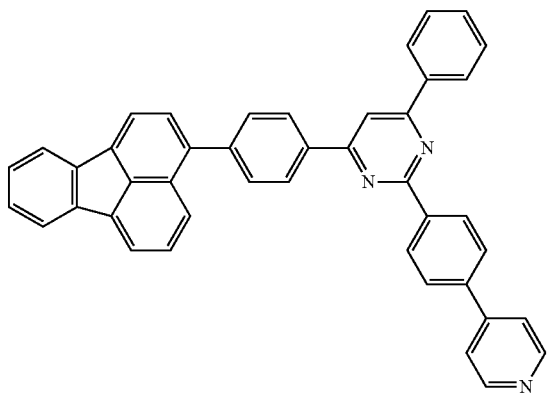
[Formula 94]
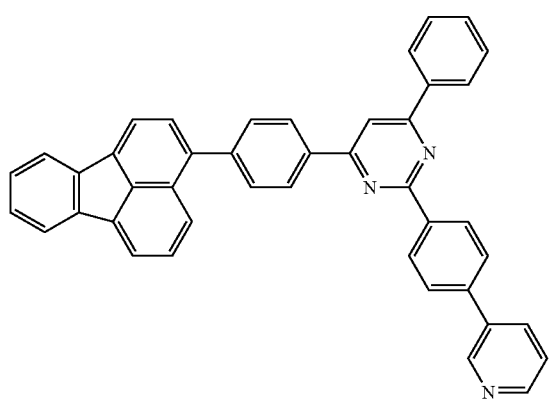 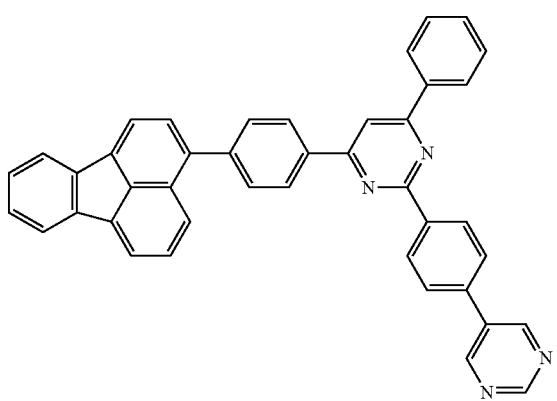

[Formula 95]
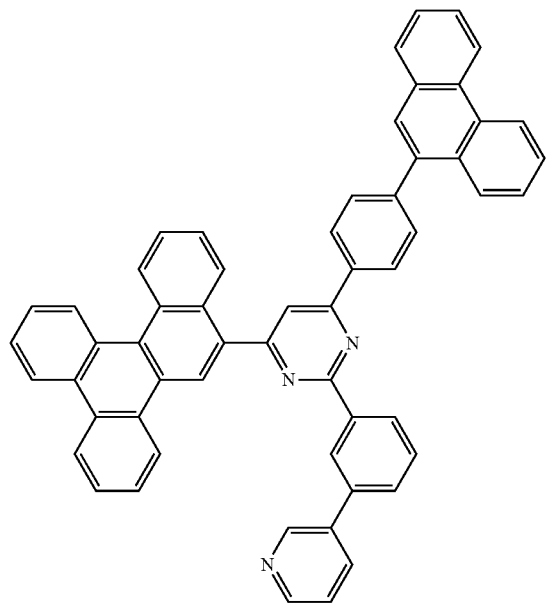
177
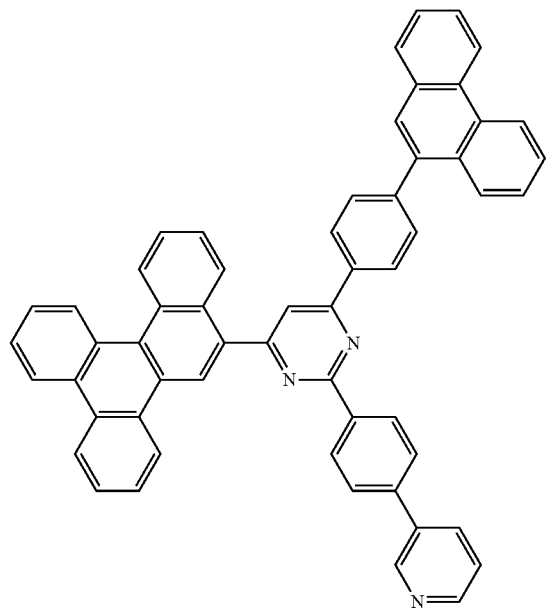
178
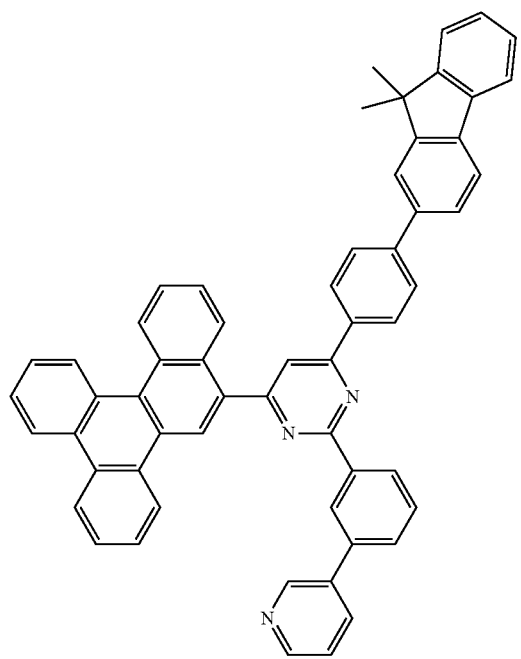
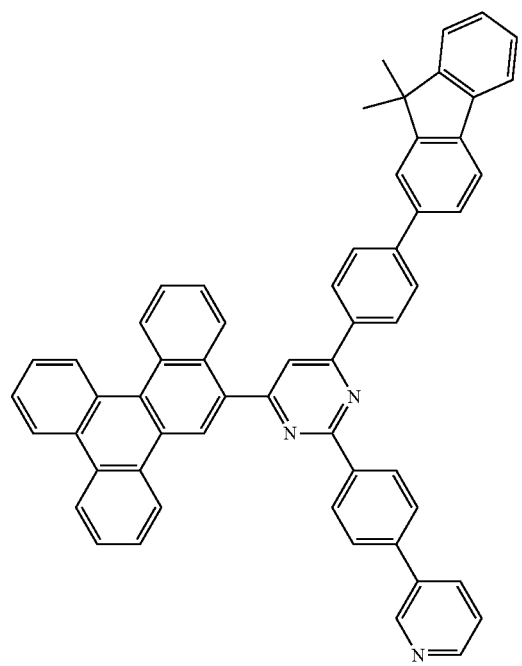

-continued
179
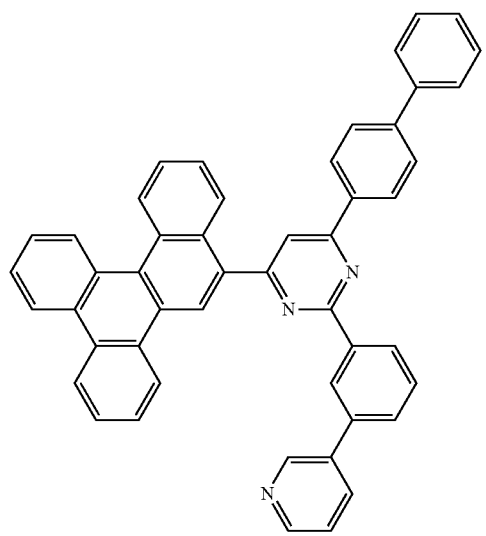
180
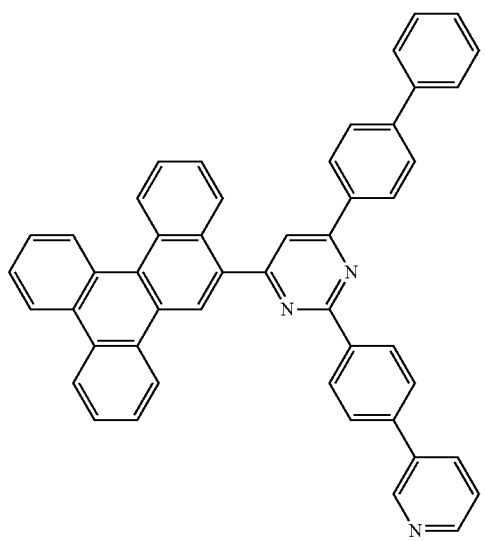
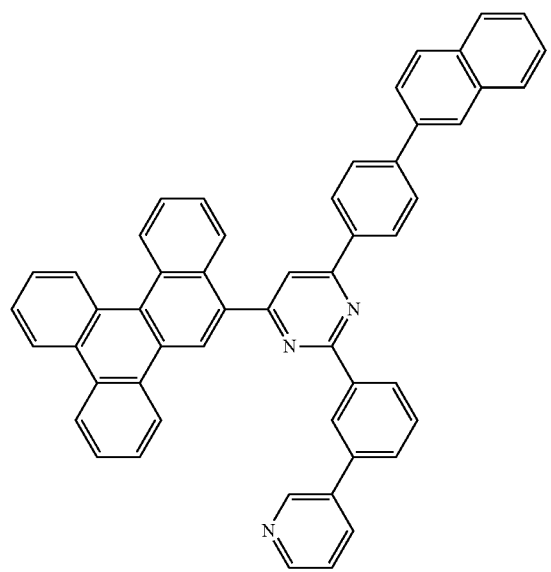
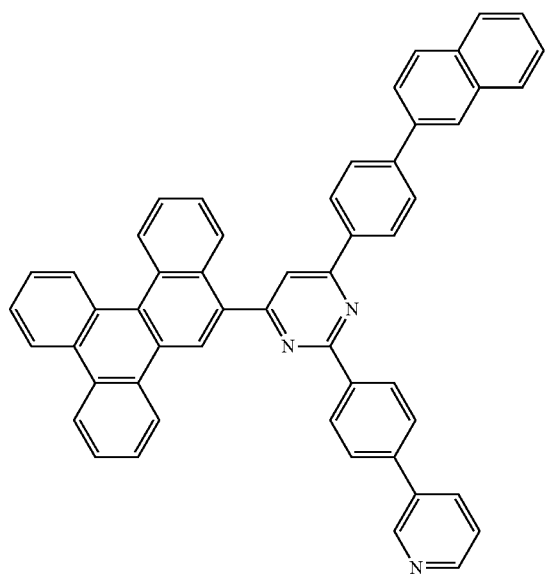

[Formula 96]
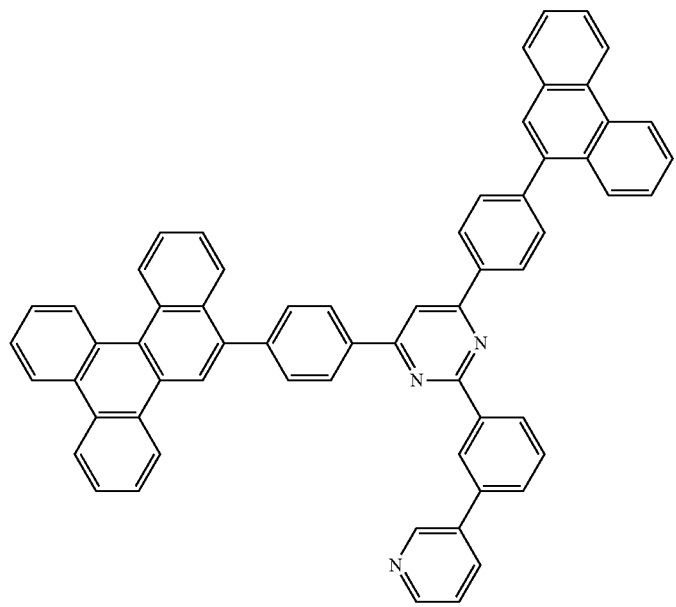
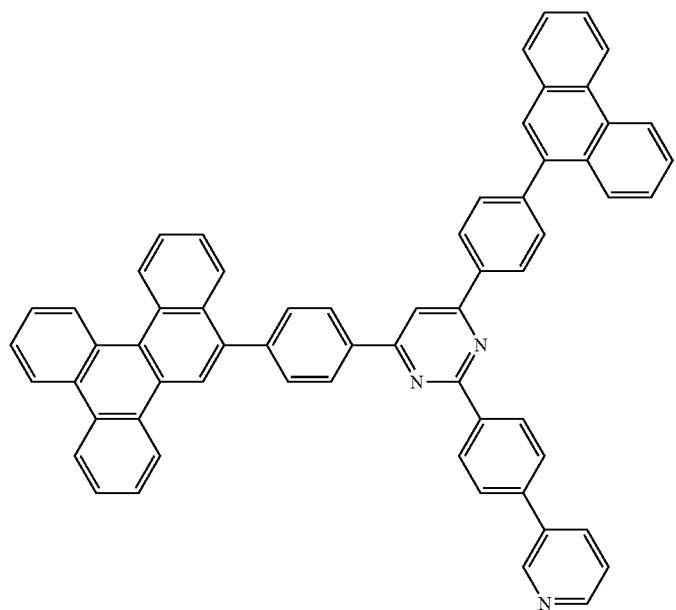

-continued
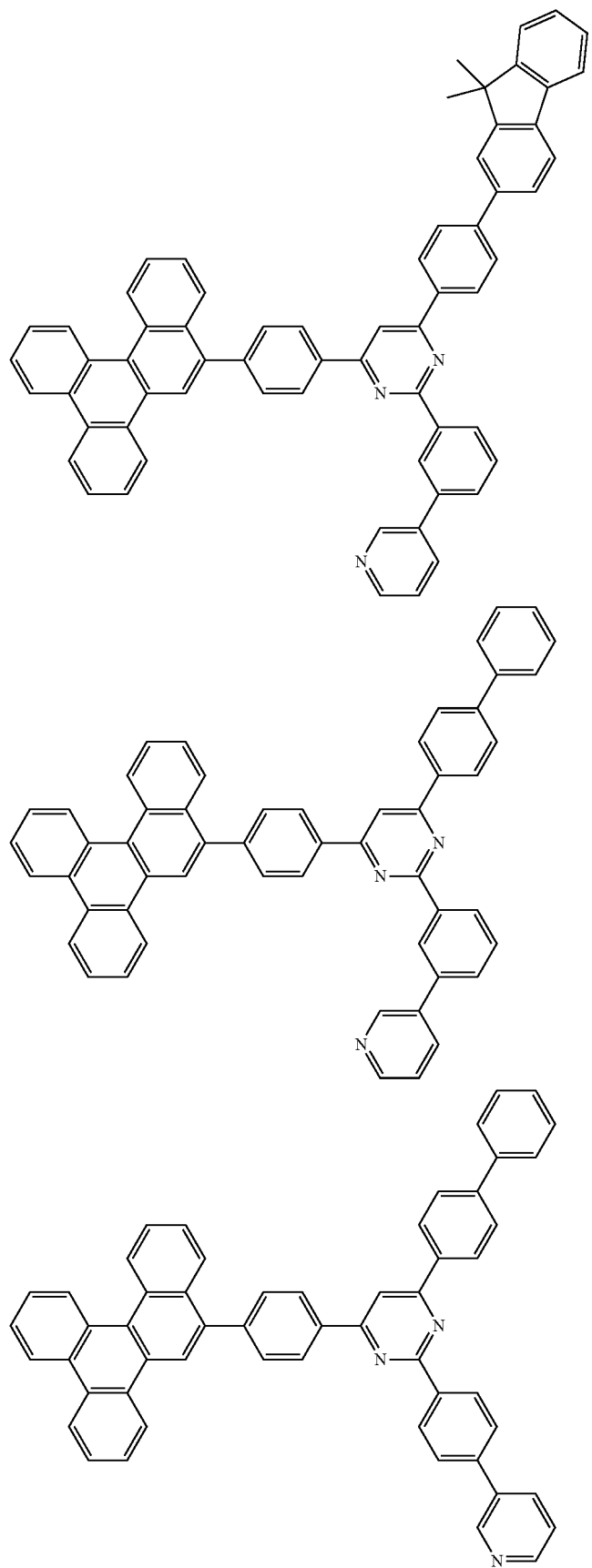

-continued
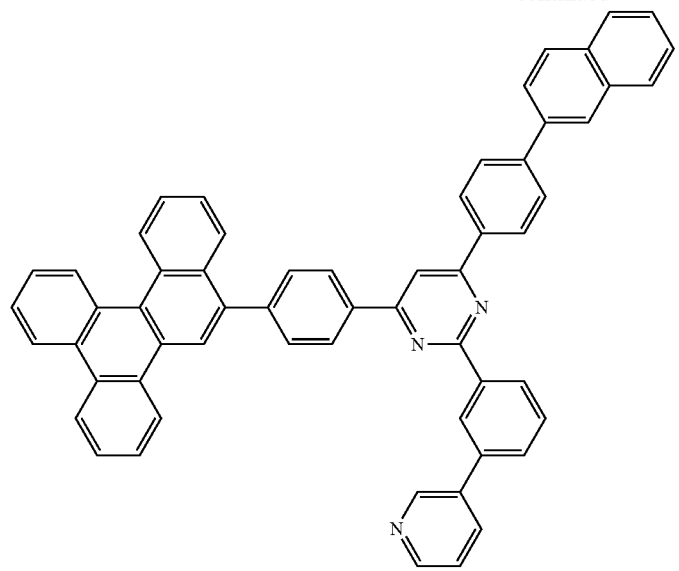
[Formula 97]
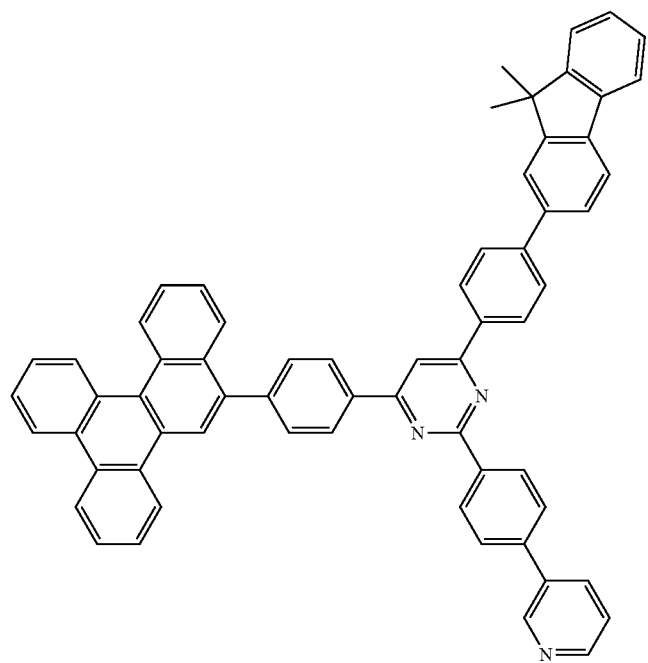

-continued
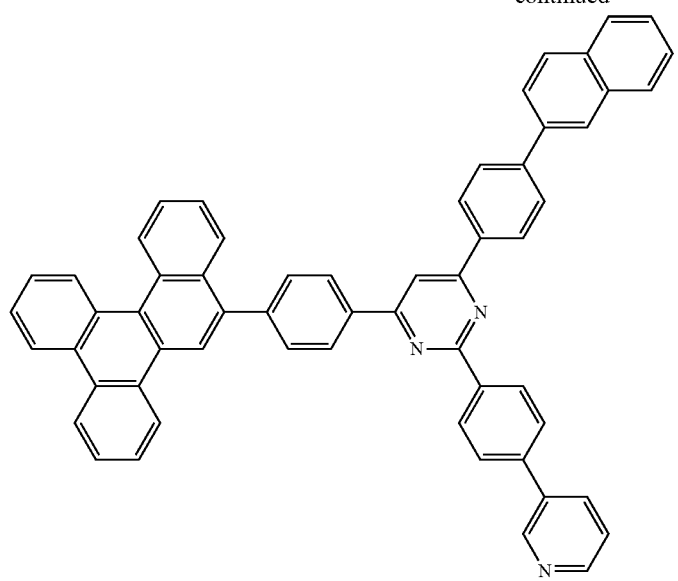
[Formula 98]
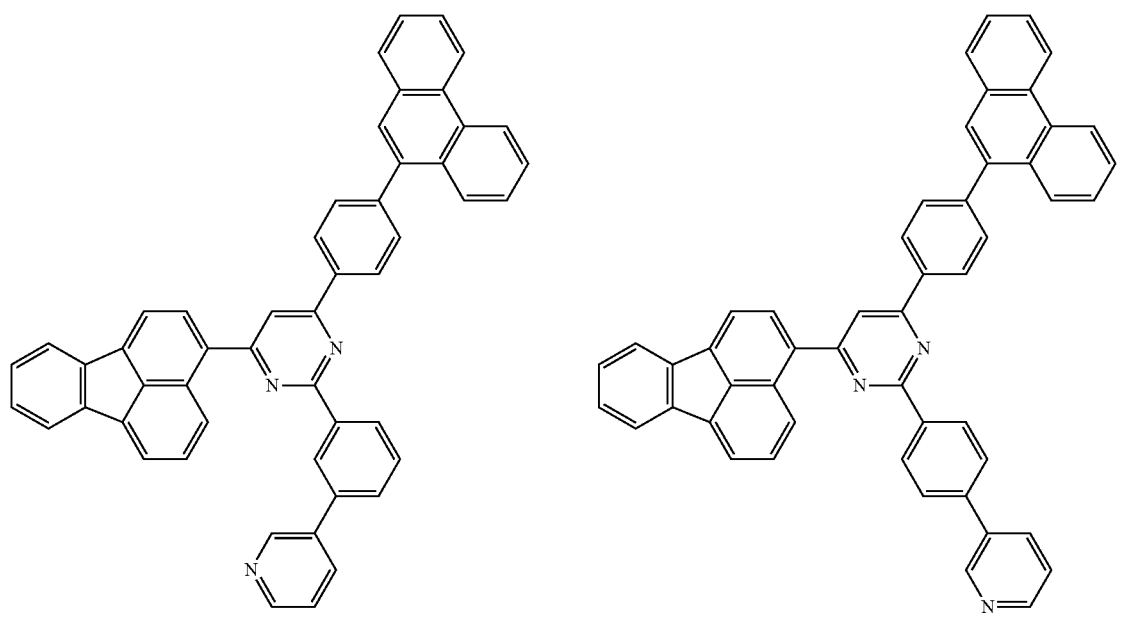

189 190
-continued
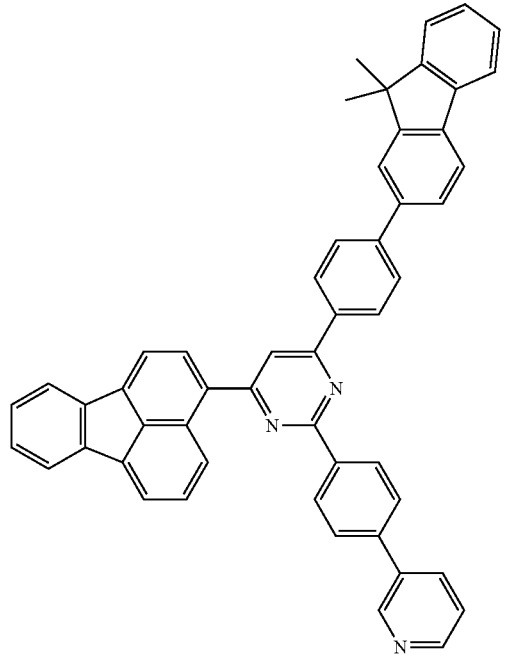
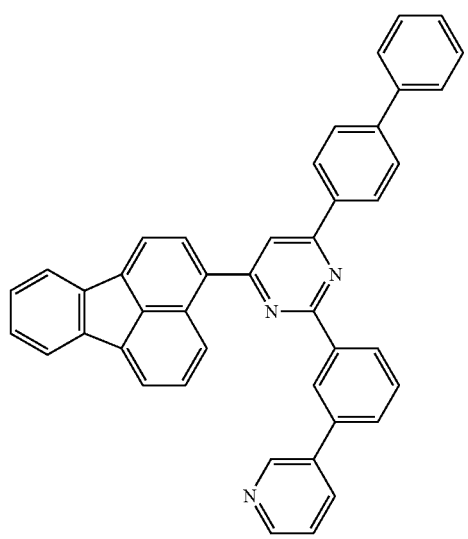
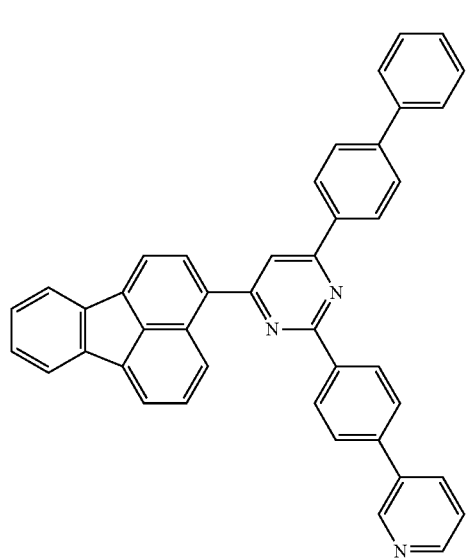
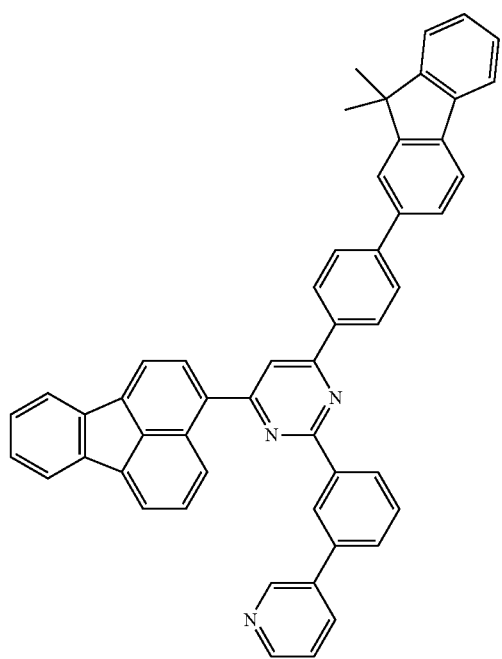

-continued
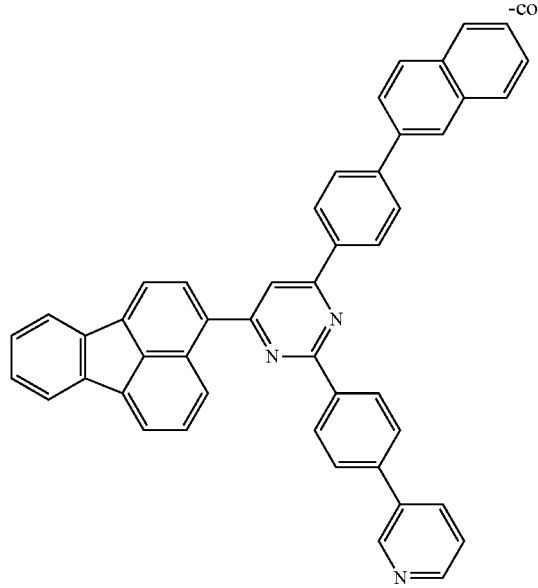
[Formula 99]
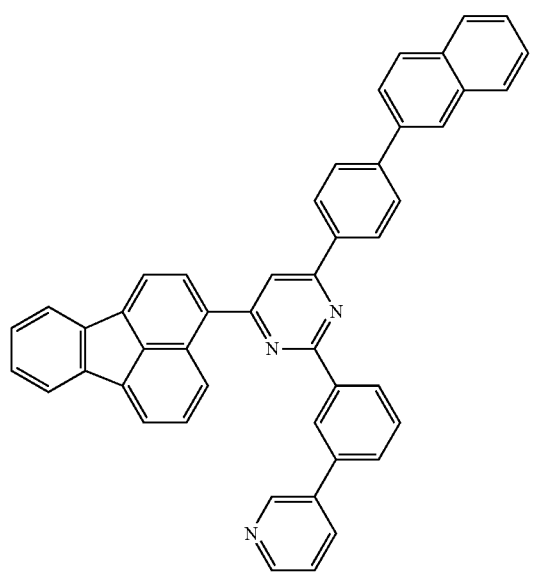

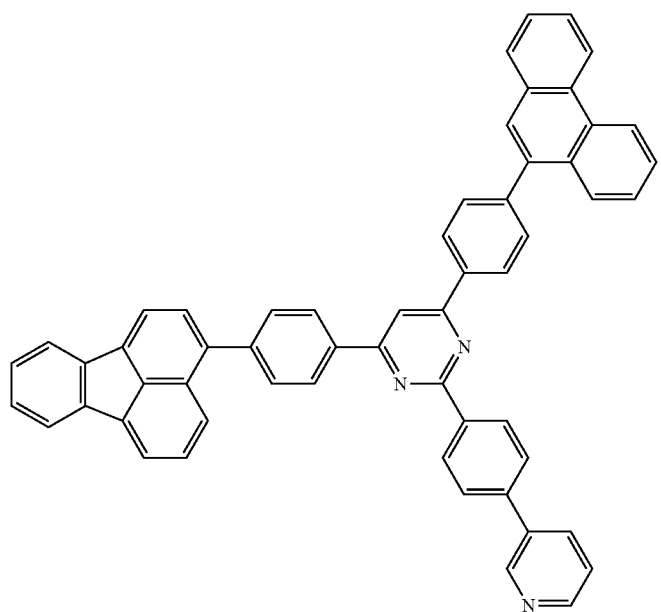
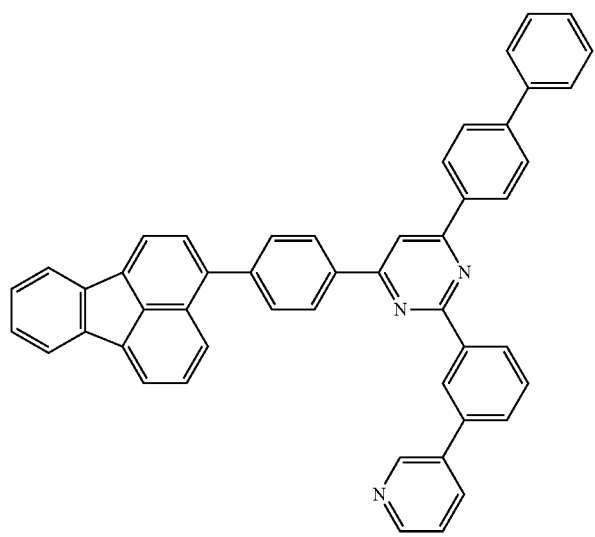

-continued
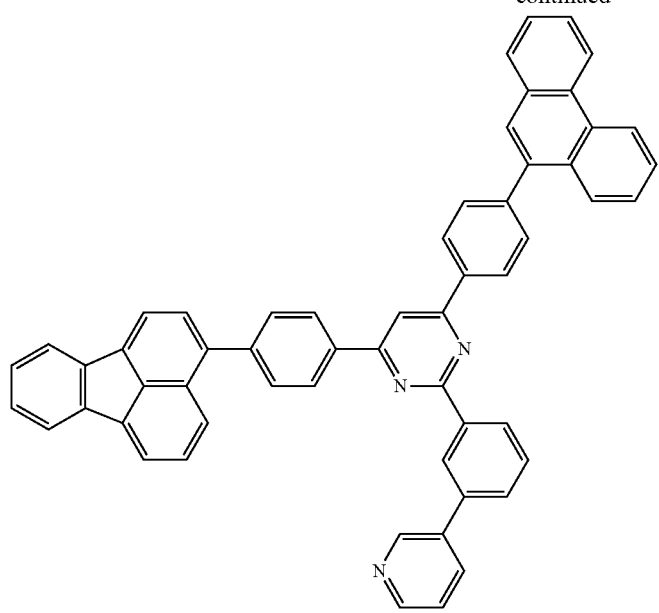
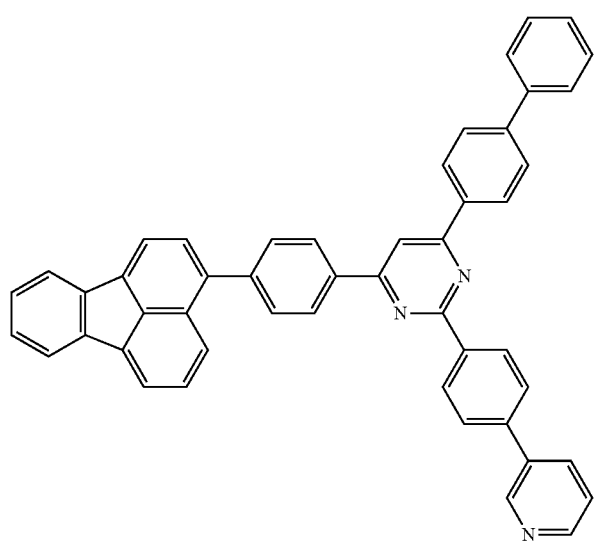

-continued
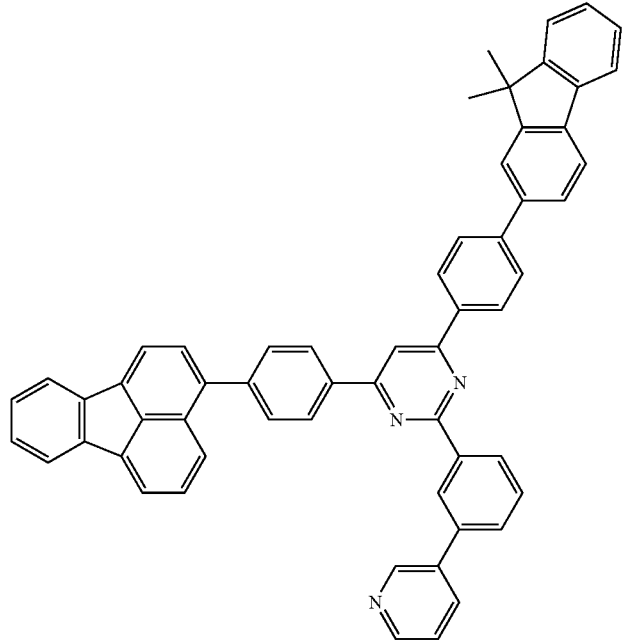
[Formula 100]
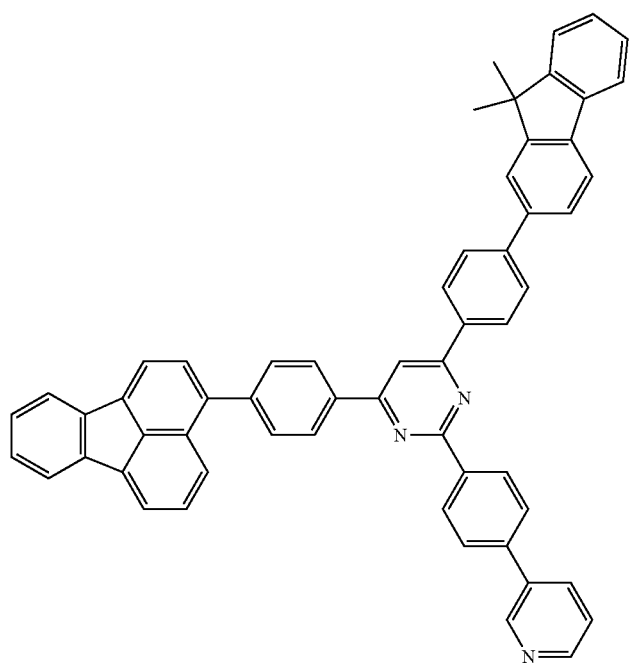

-continued
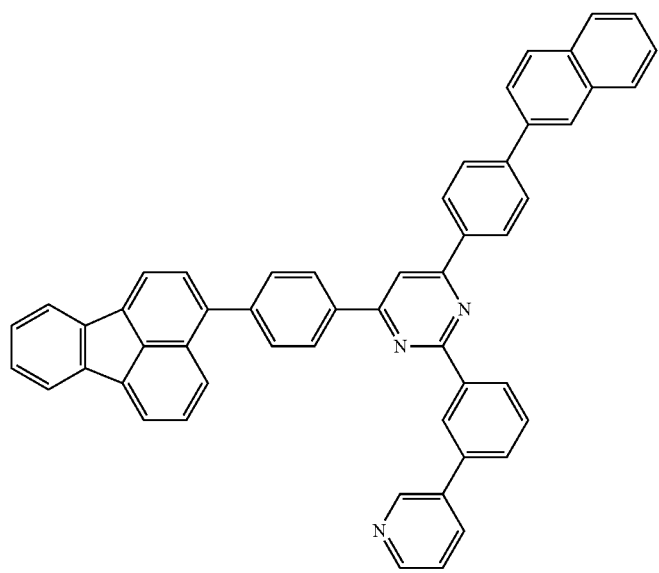
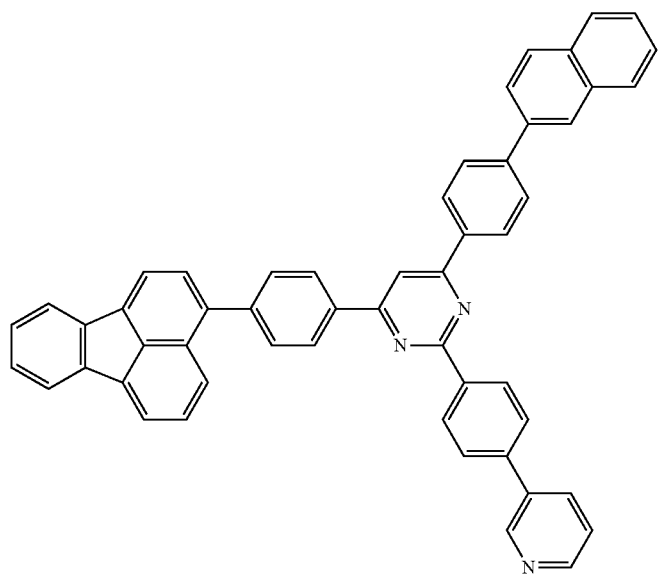
[Formula 101]
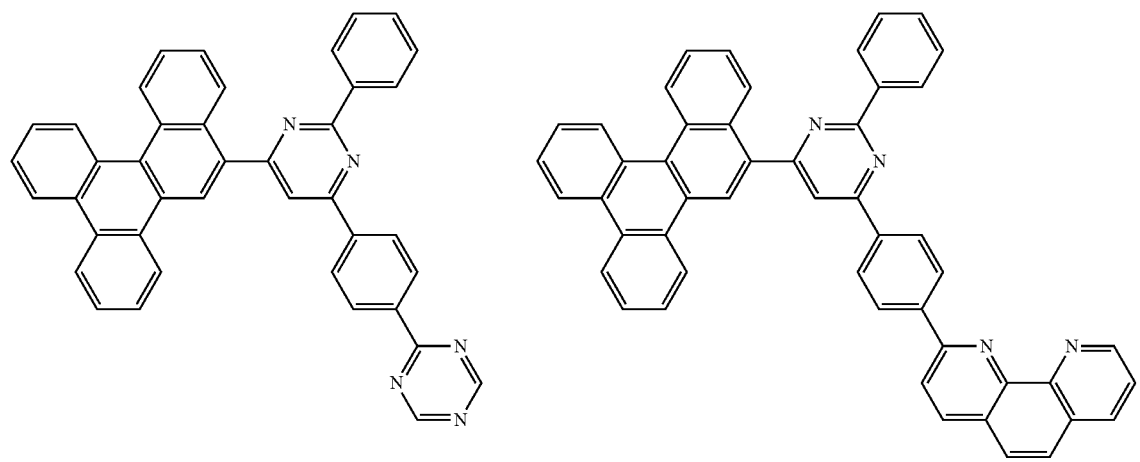

-continued
| 201 | 202 |
|---|---|
| 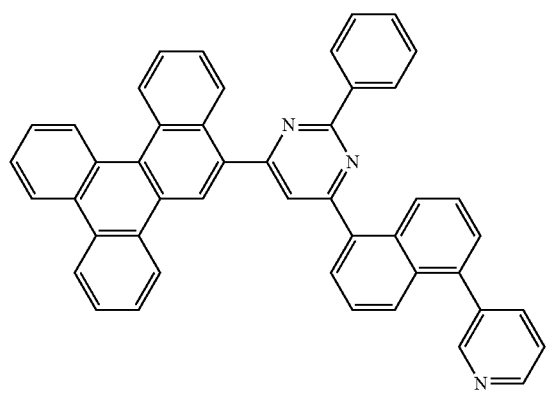 | 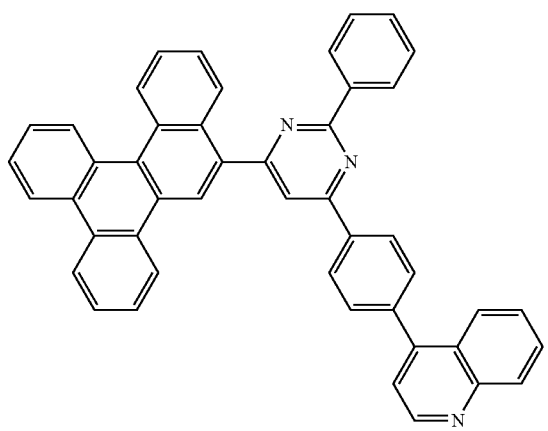 |
| 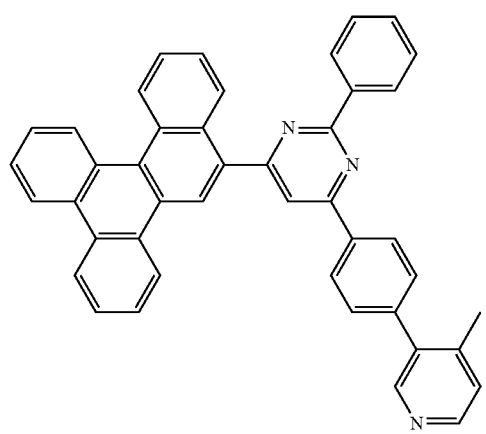 | 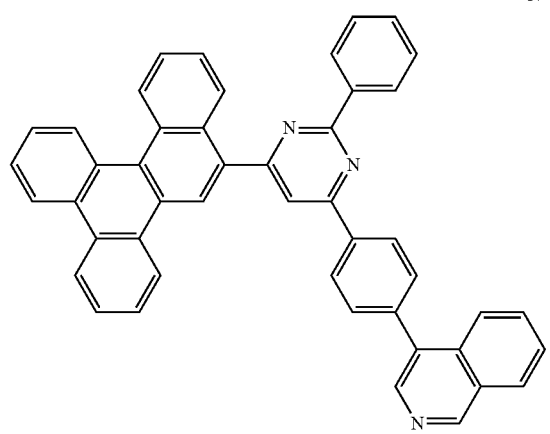 |
| 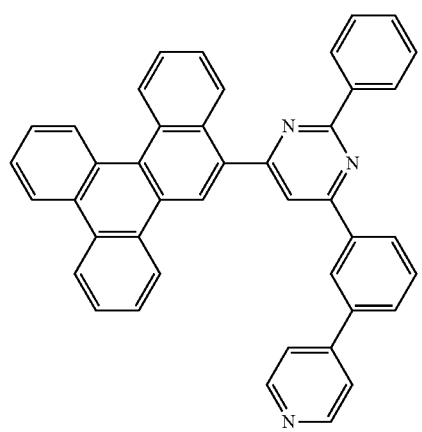 | 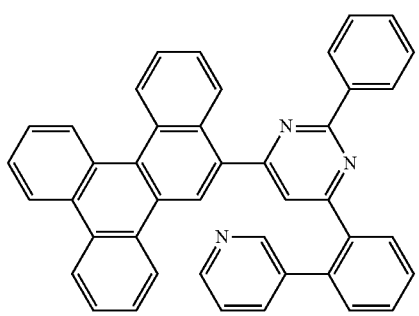 |
| 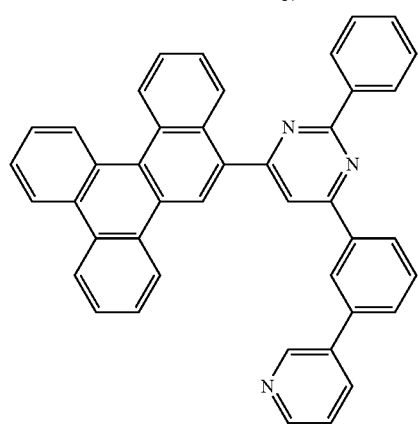 | |

[Formula 102]
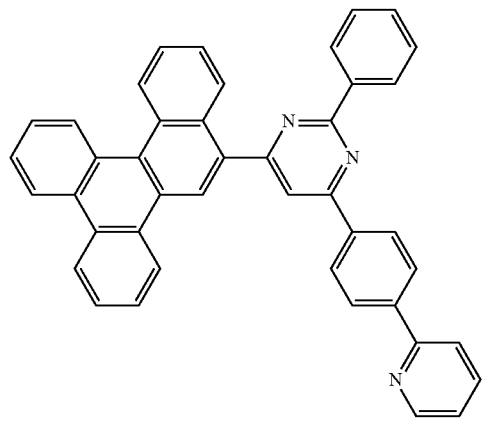
203
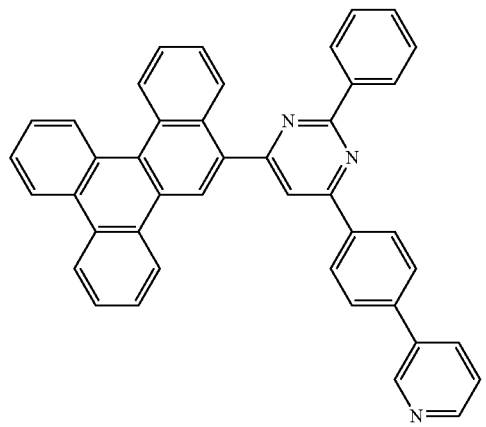
204
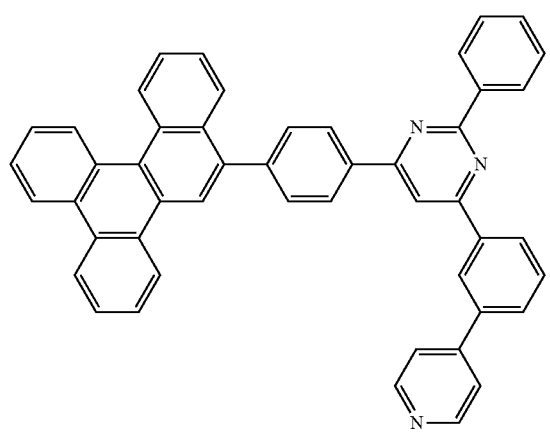
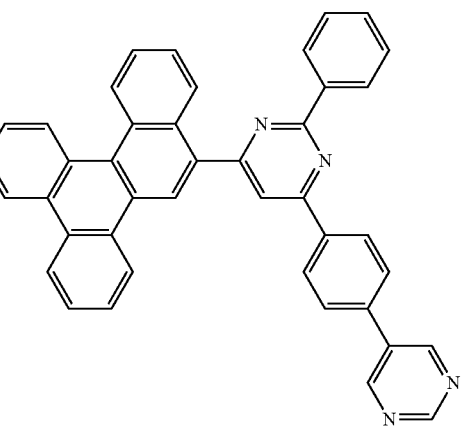
[Formula 103]
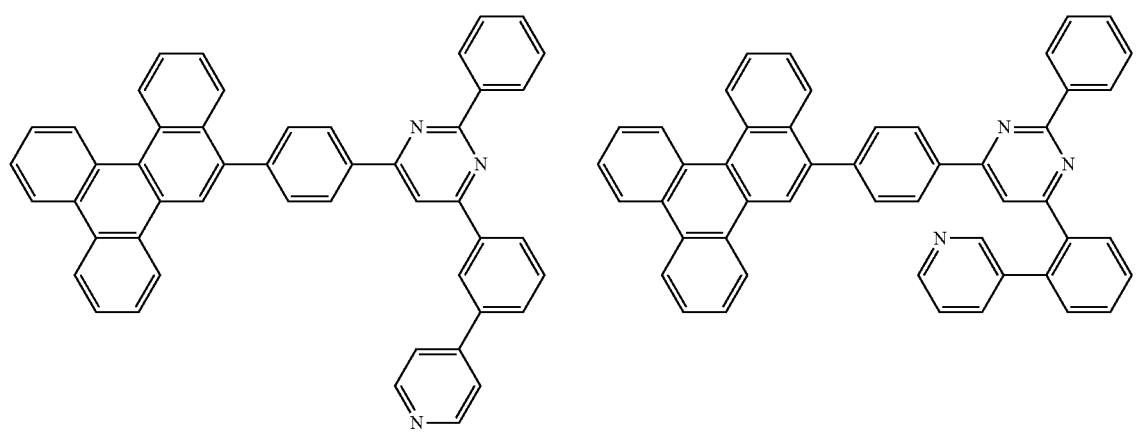

-continued
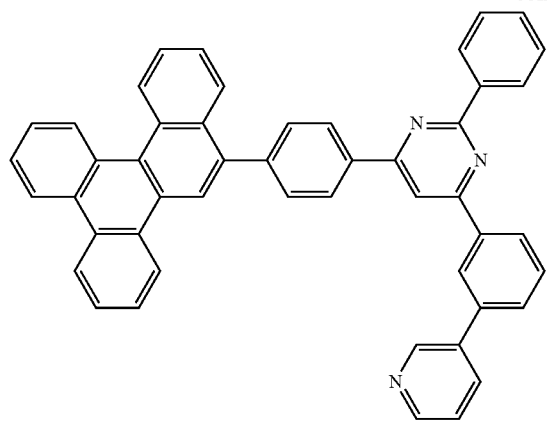
[Formula 104]
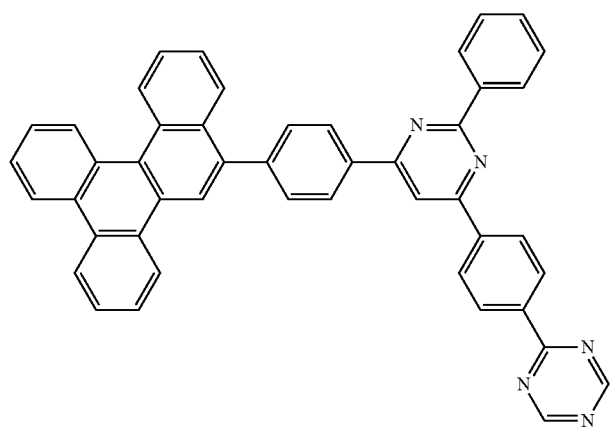
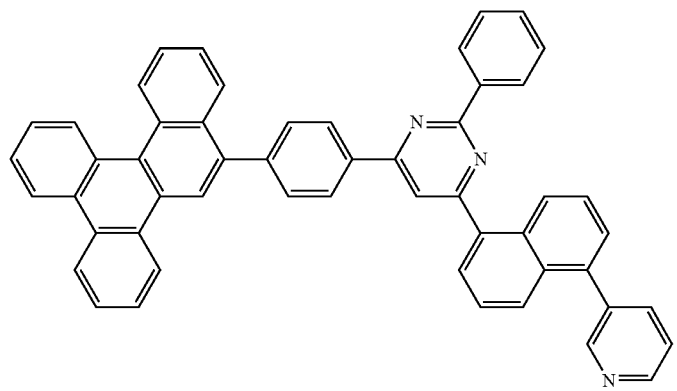
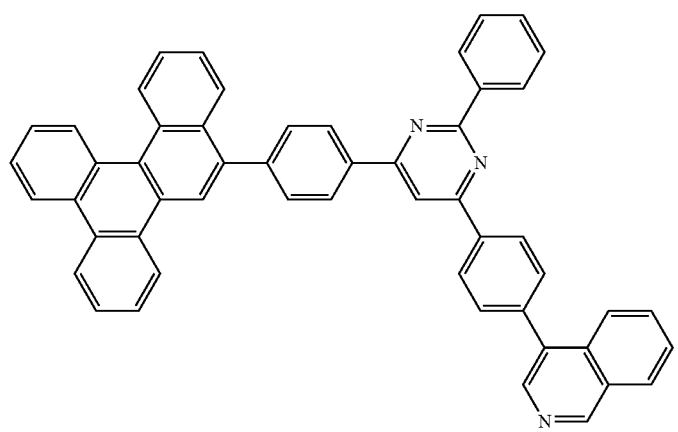

-continued
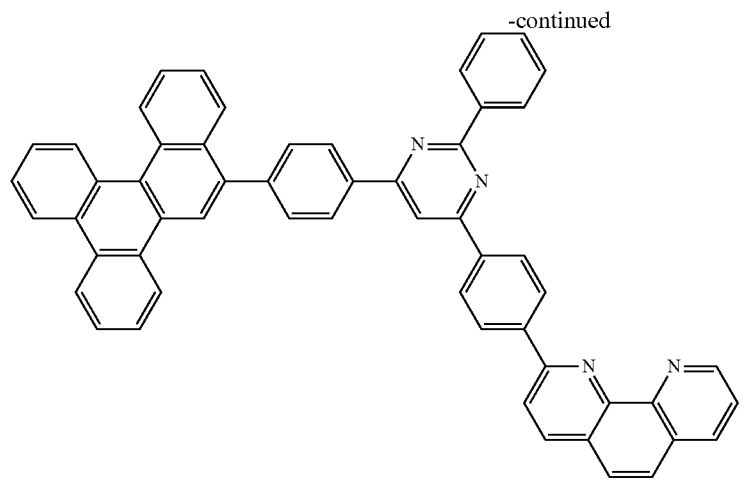
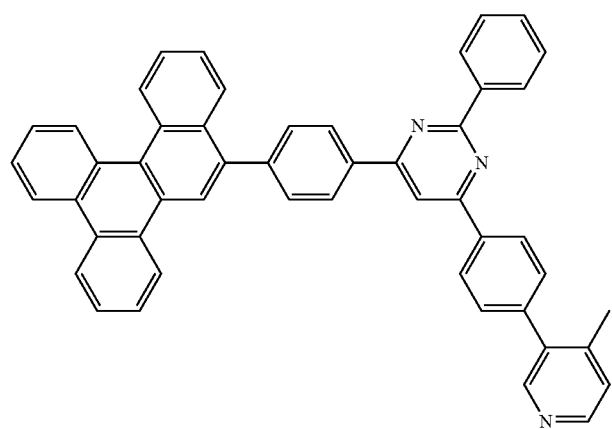
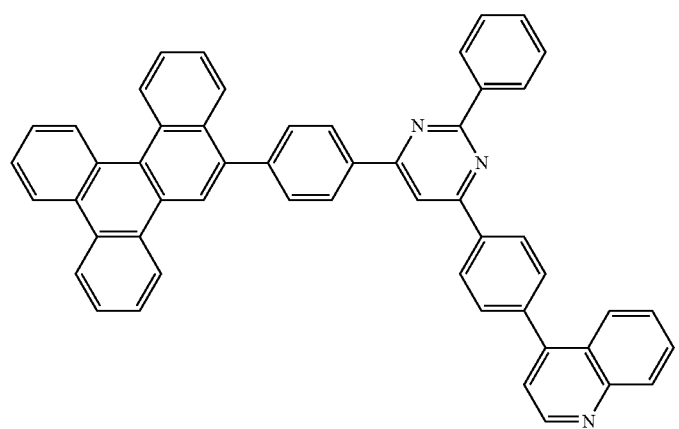

[Formula 105]
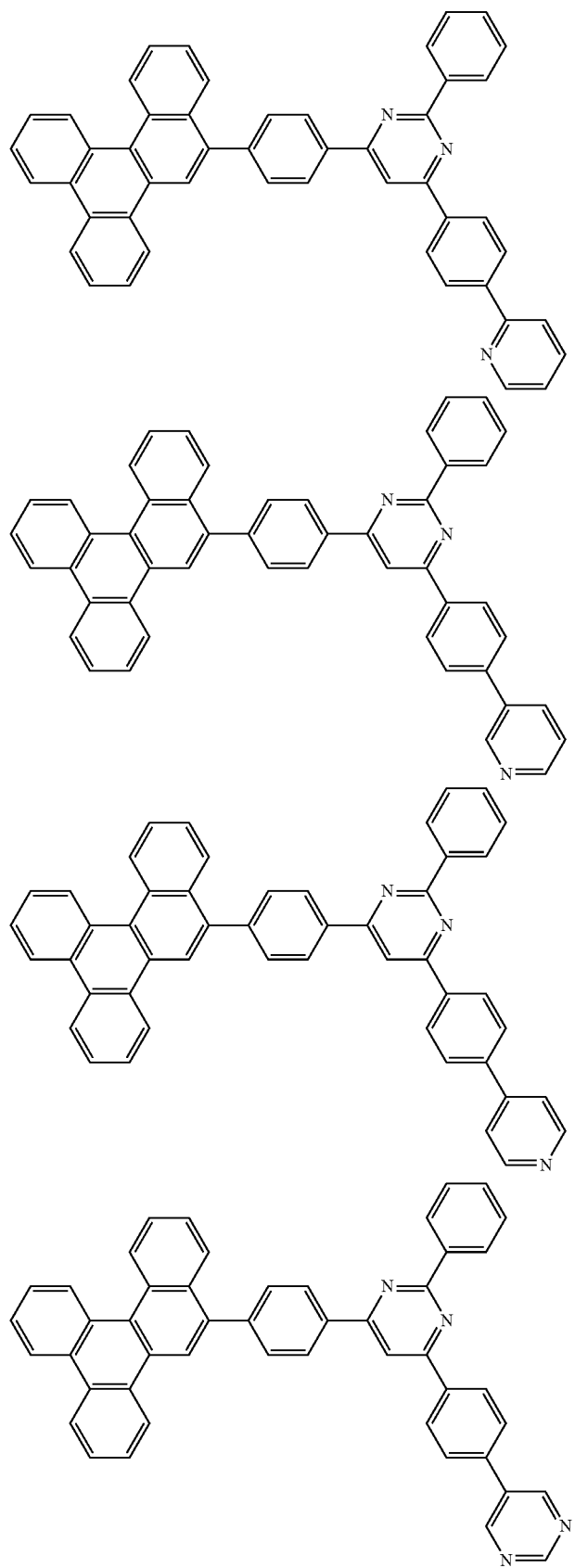

211 212
-continued
[Formula 106]
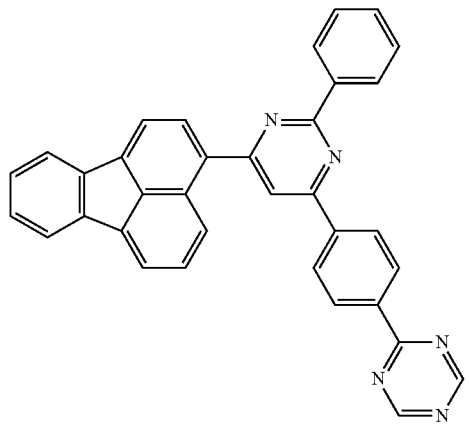
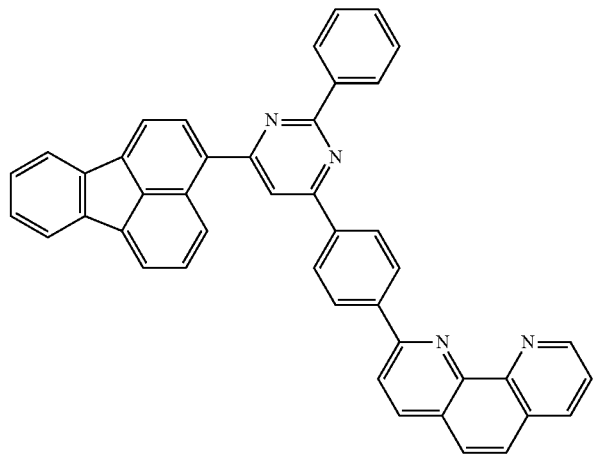
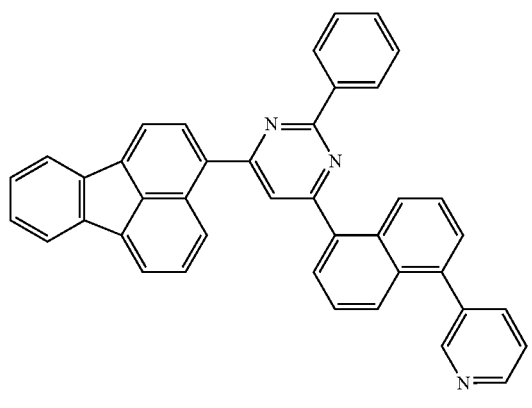
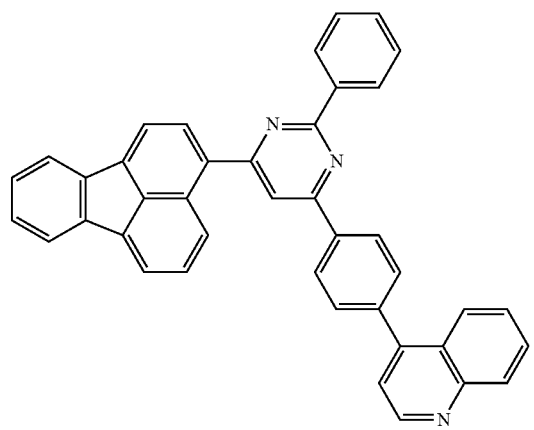
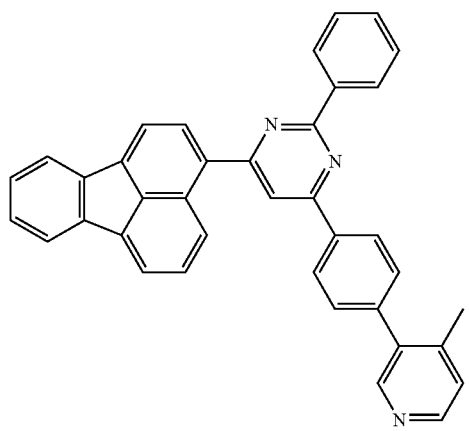
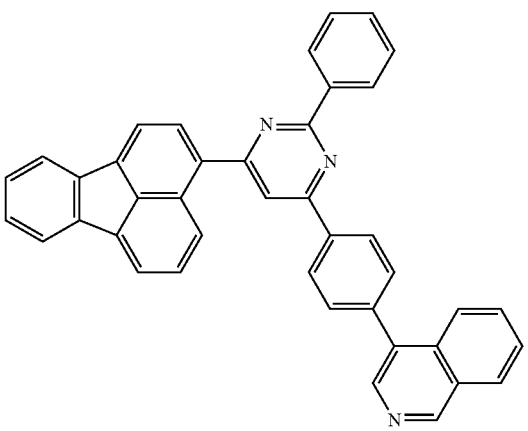

213 214
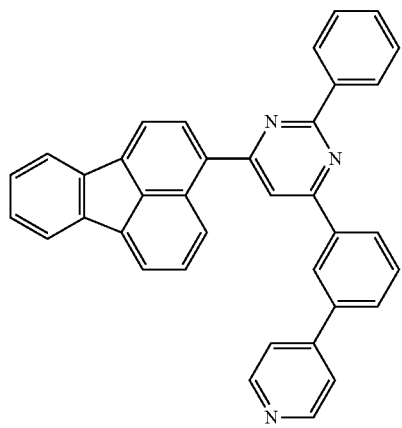 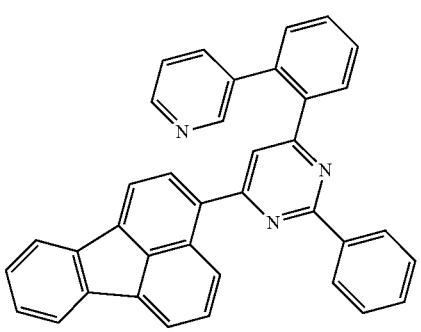
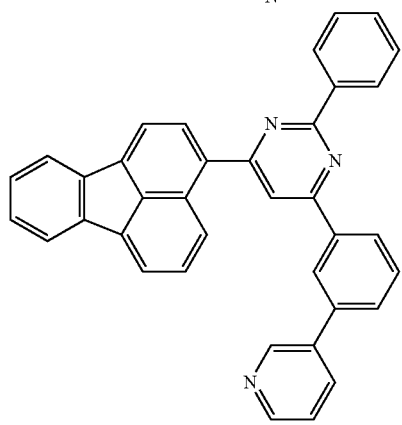
[Formula 107]
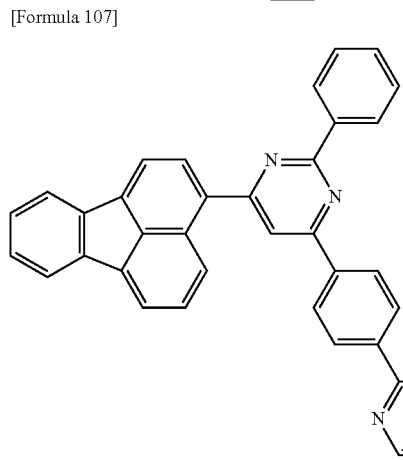 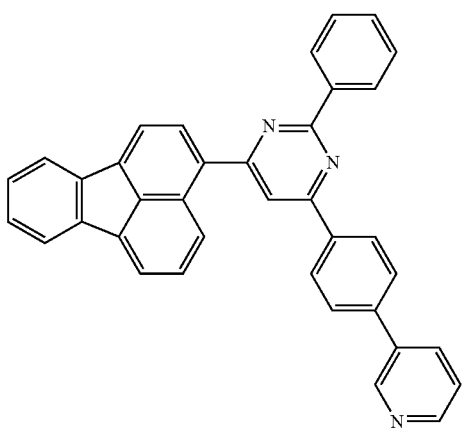
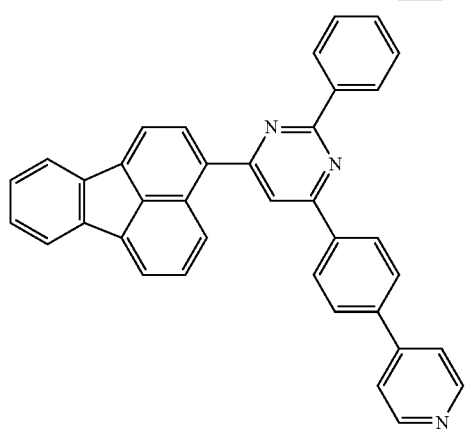 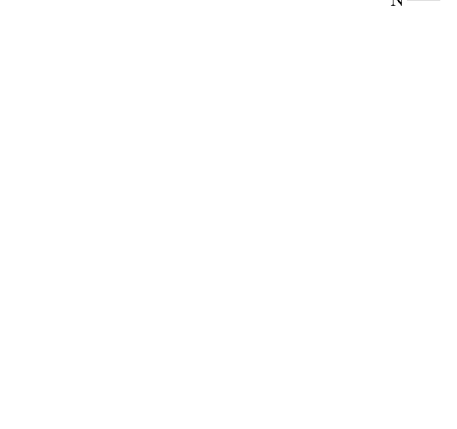

-continued
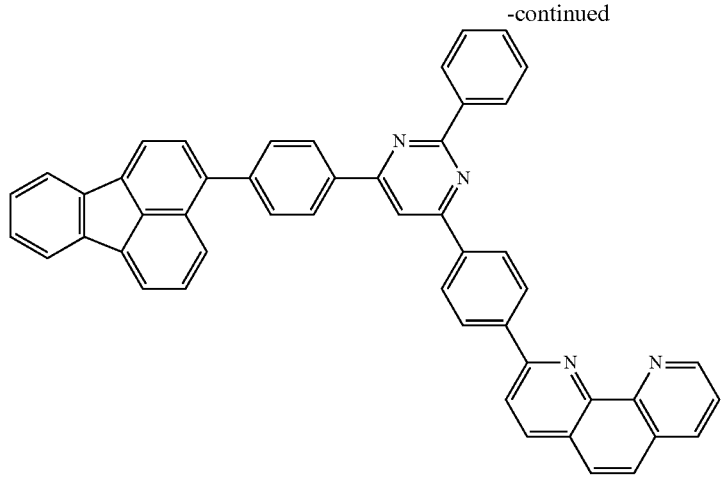
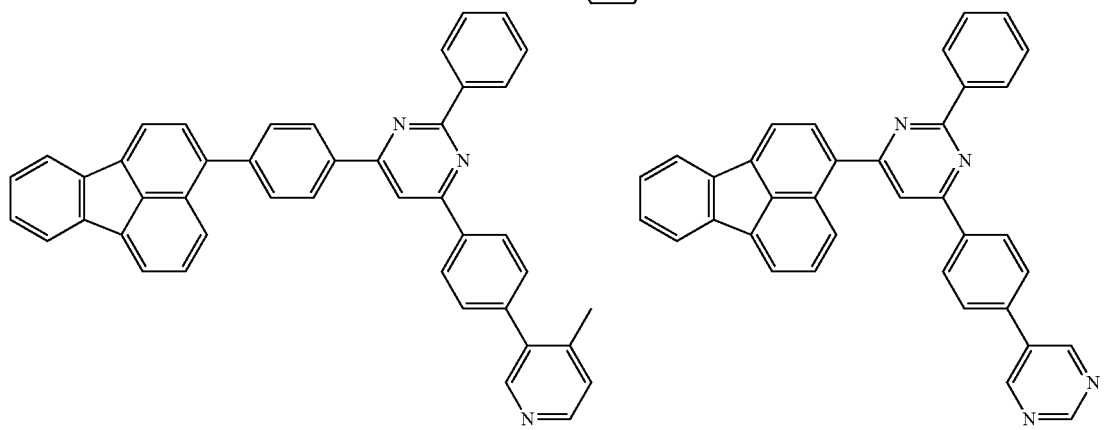
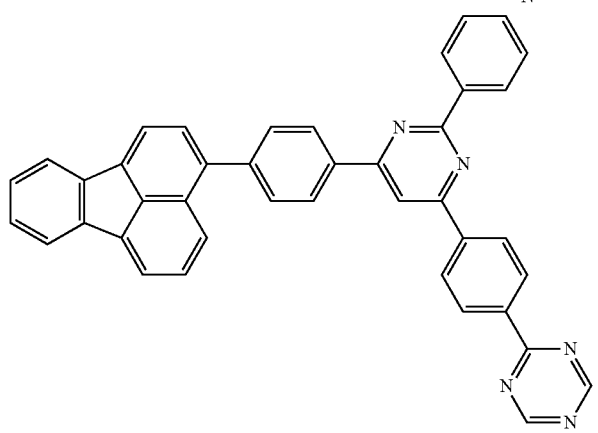
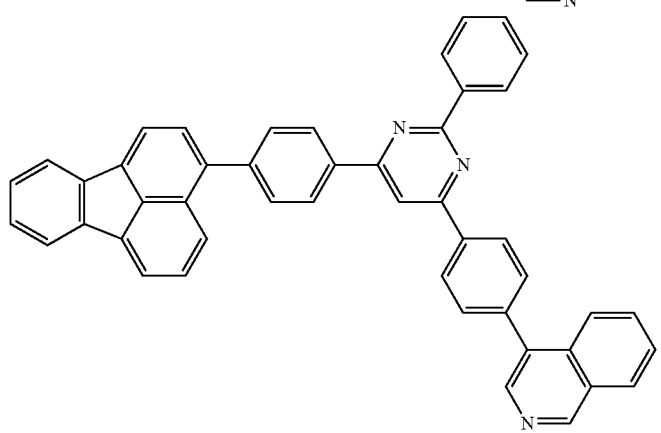

-continued
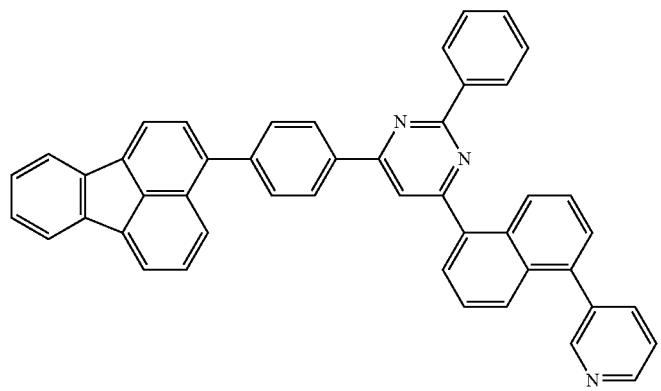
[Formula 108]
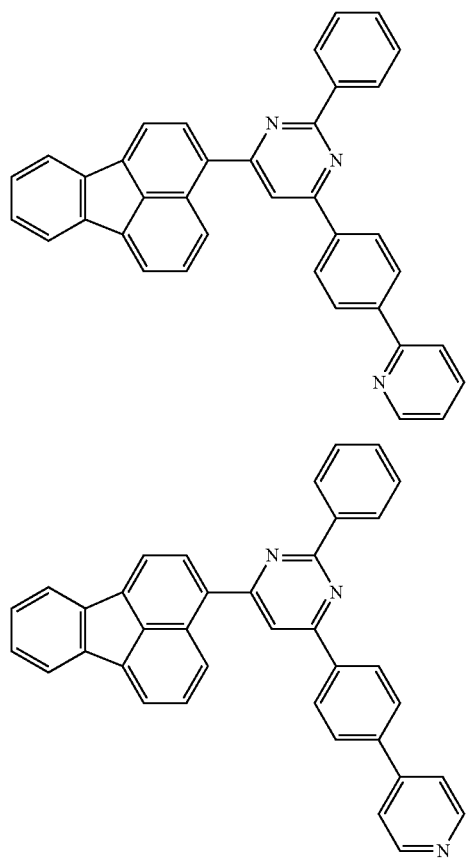
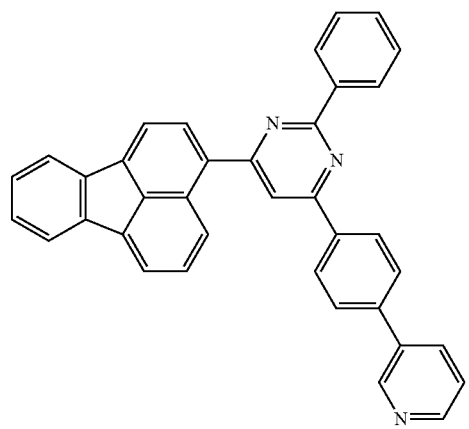
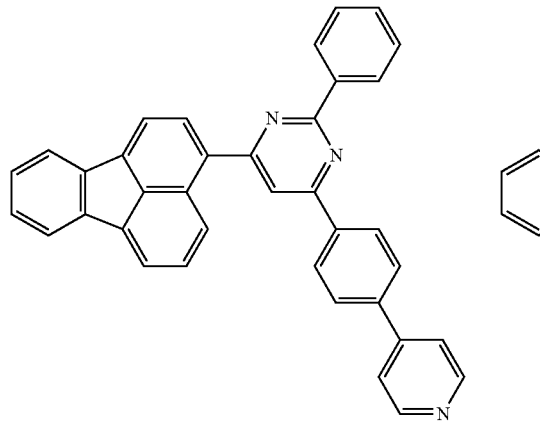
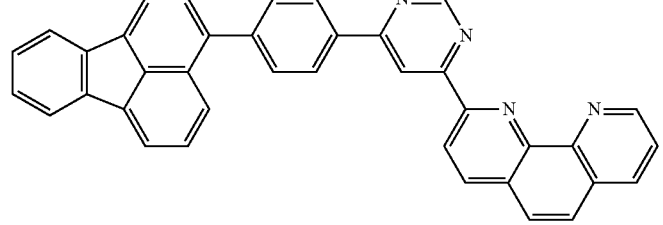
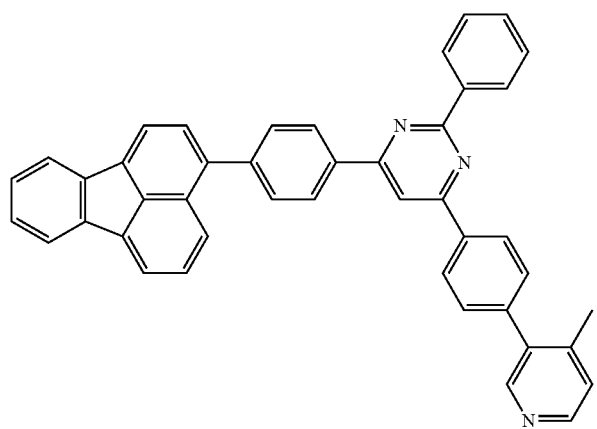
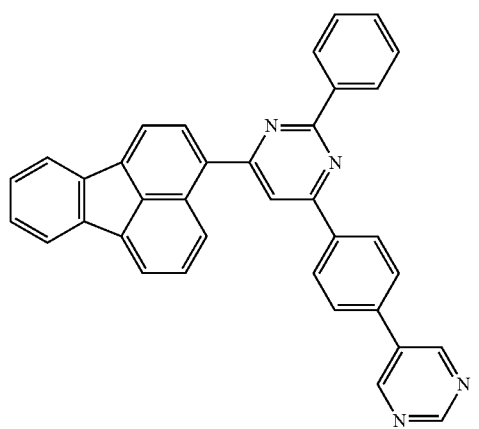

-continued
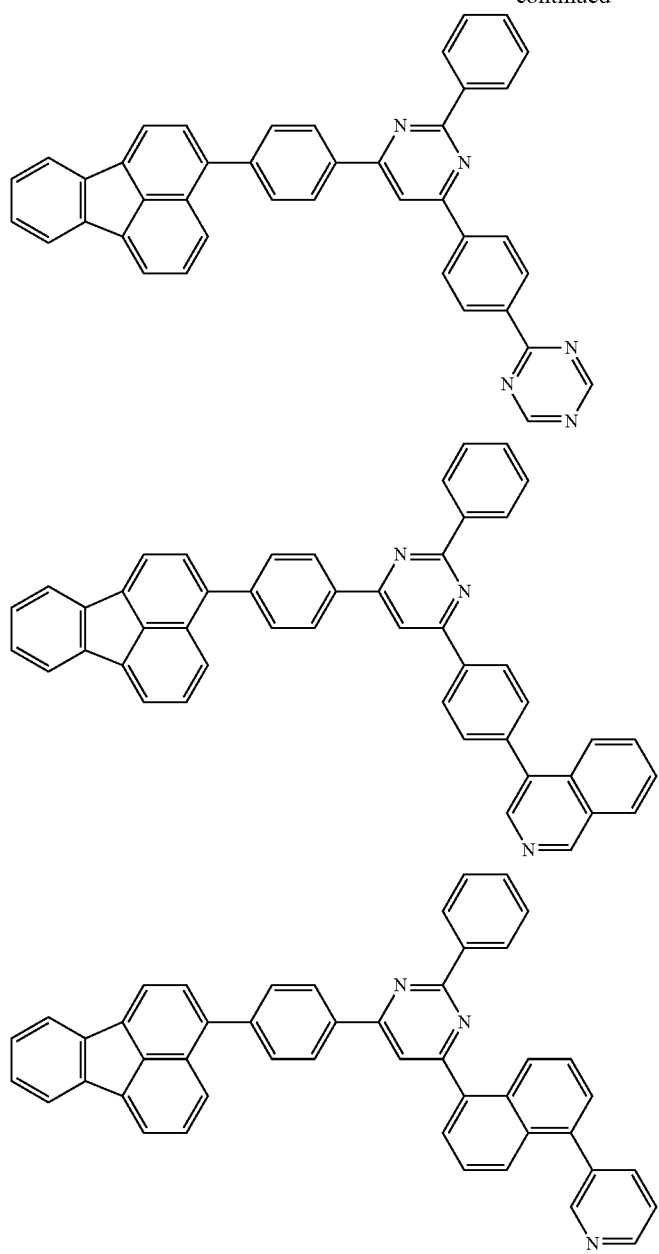
[Formula 109]
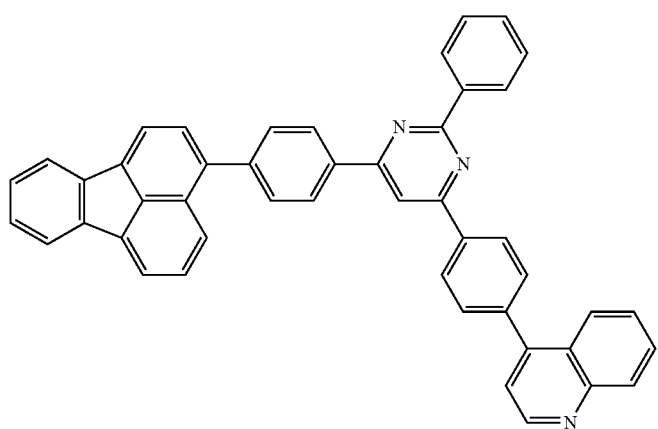

-continued
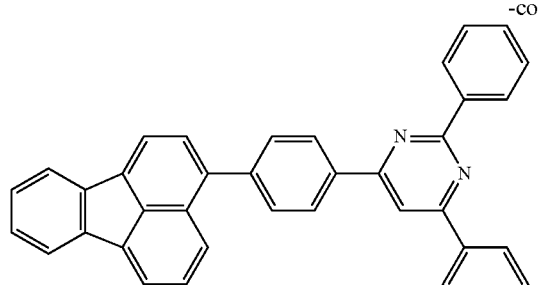
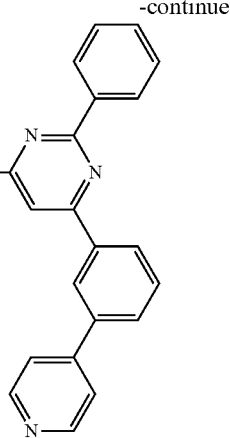
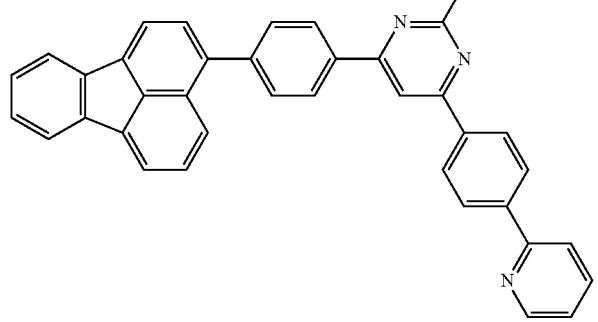
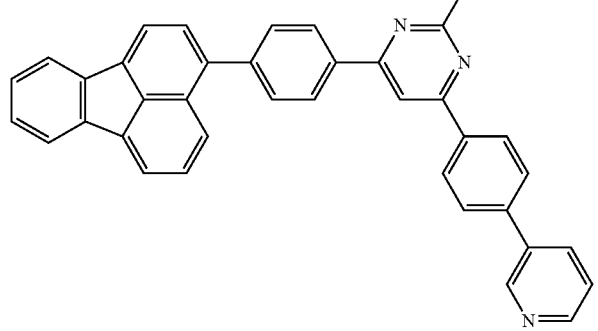
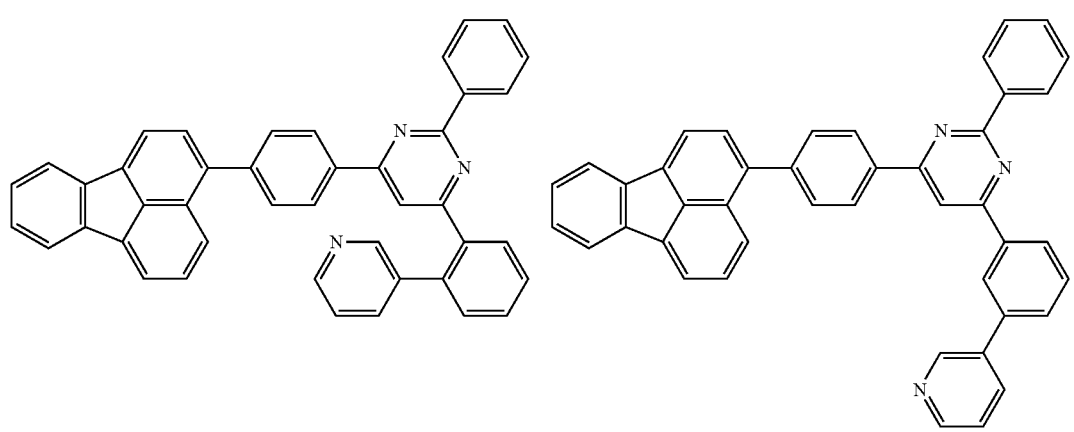

-continued
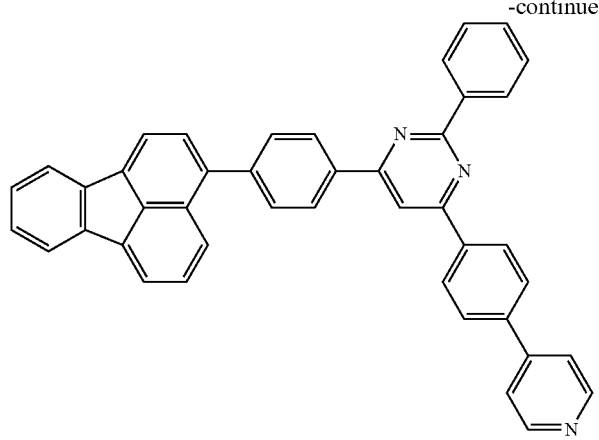
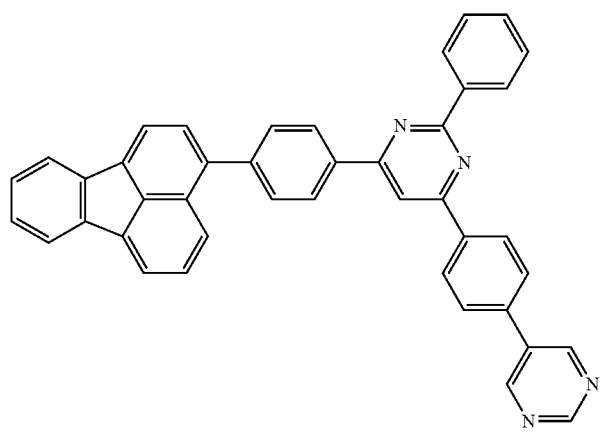
[Formula 110]
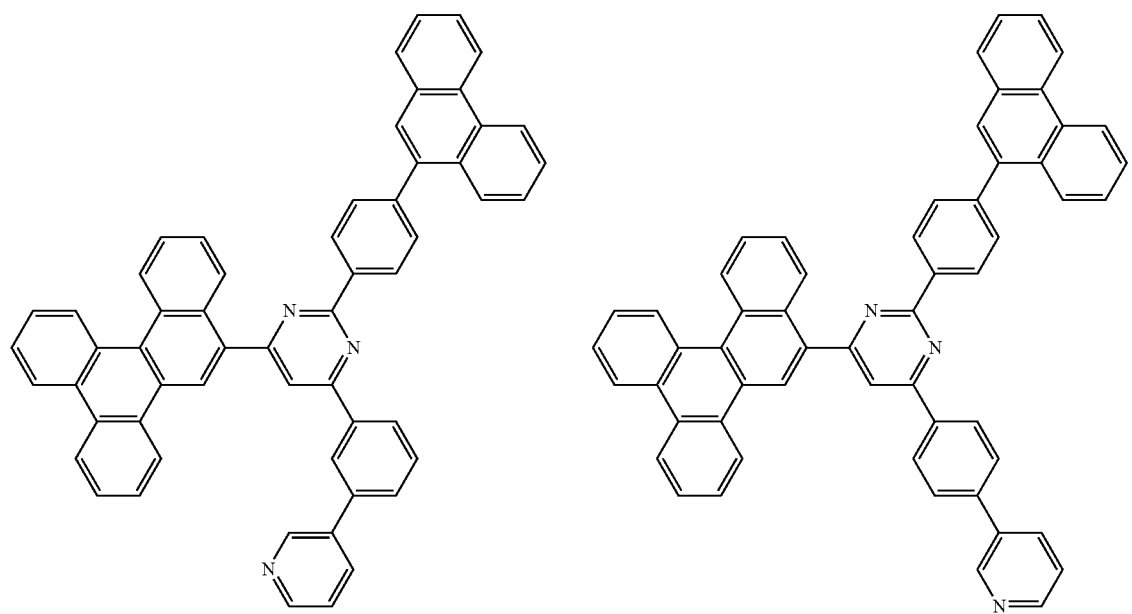

-continued
225
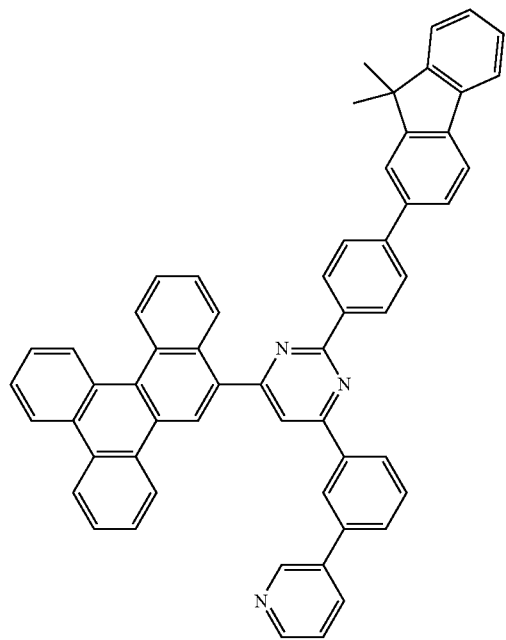
226
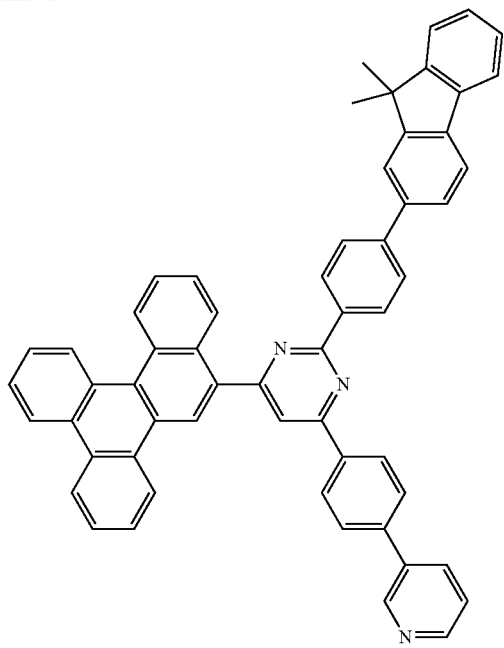
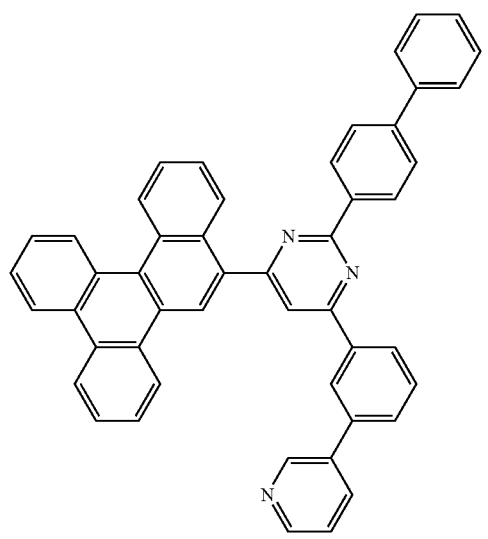
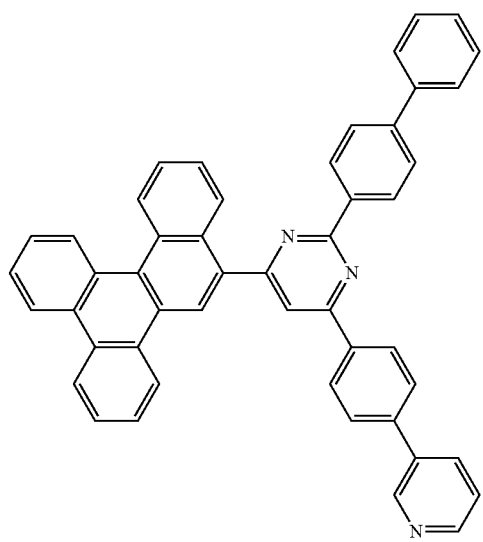

-continued
227
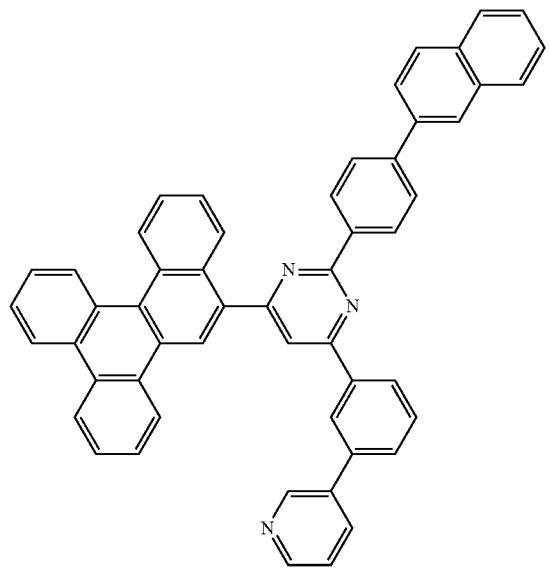
228
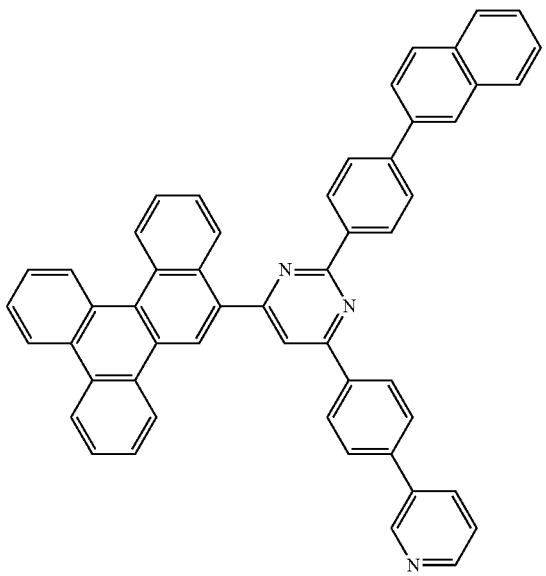
[Formula 111]
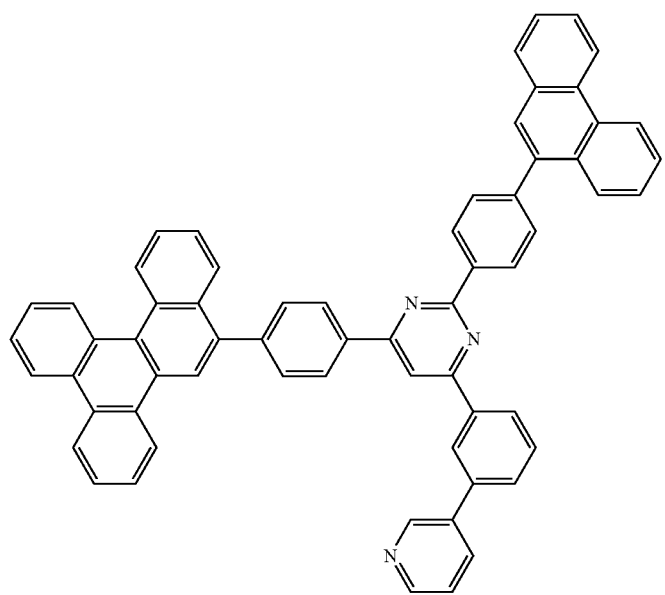

-continued
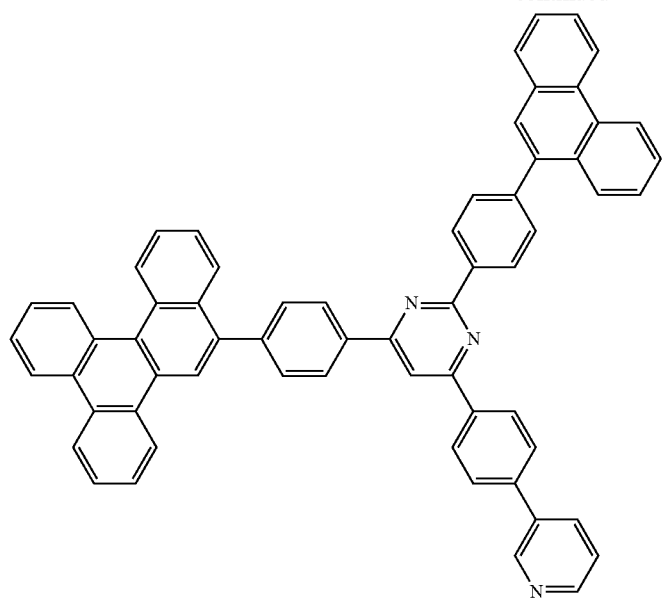
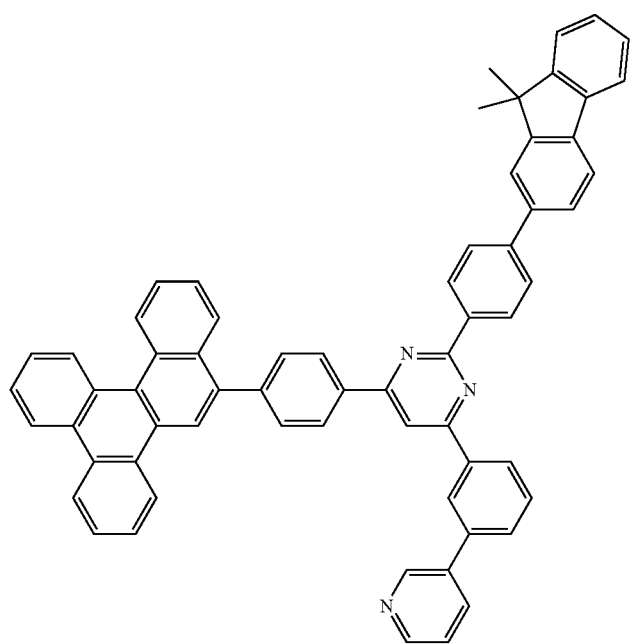

-continued
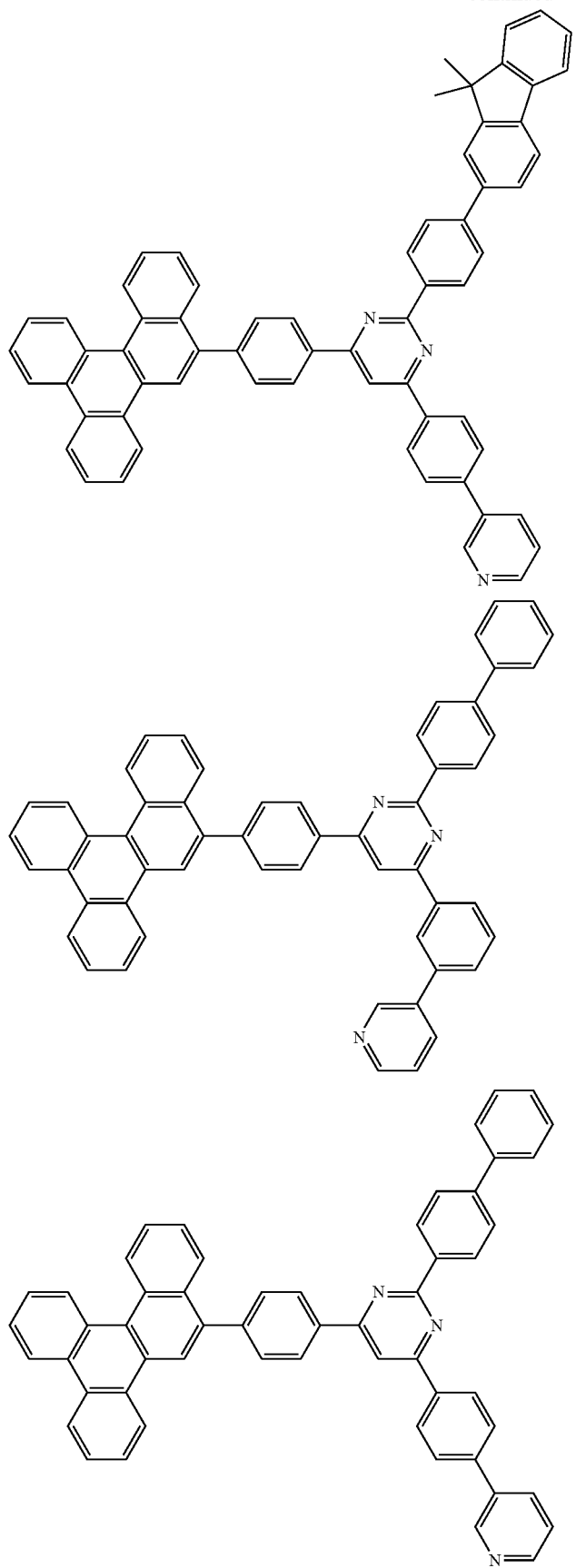

-continued
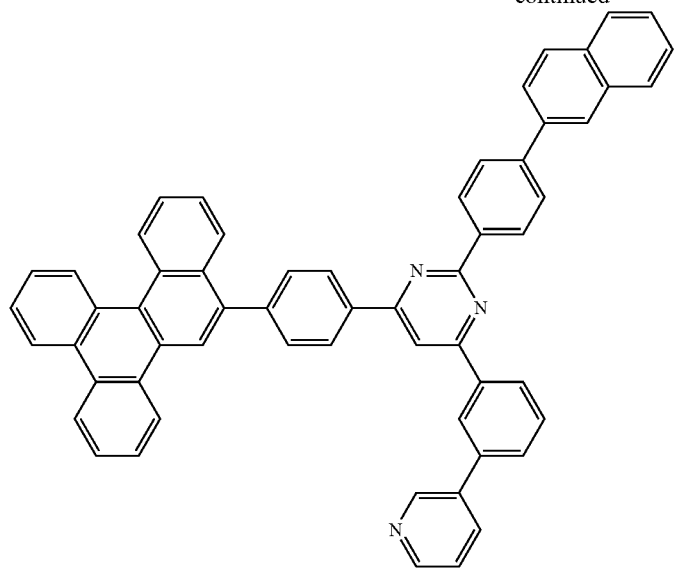
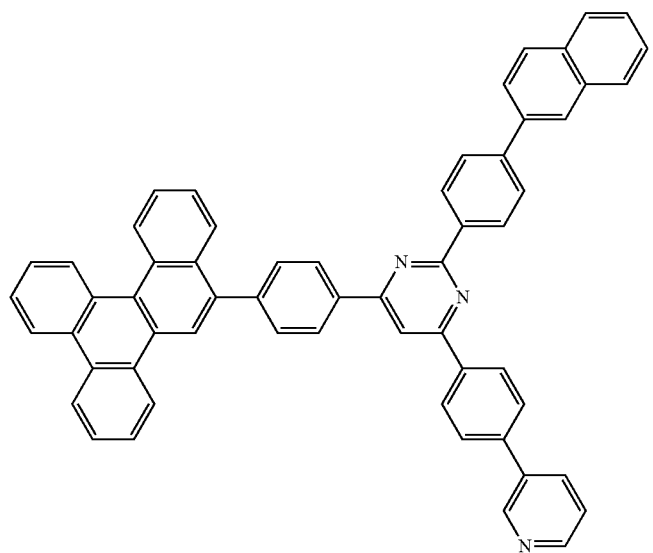

[Formula 112]
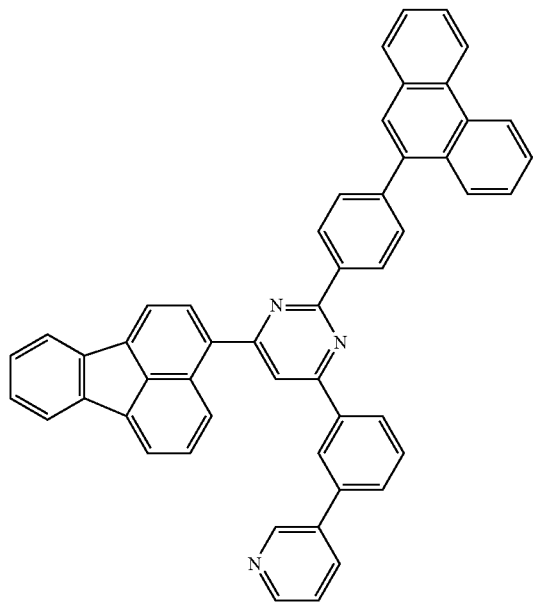
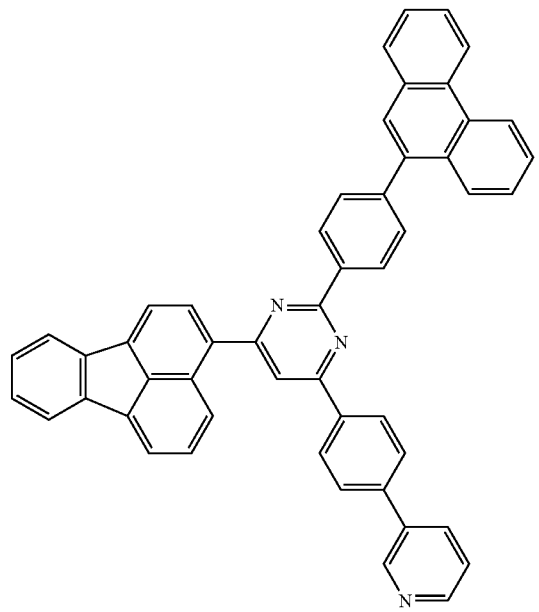
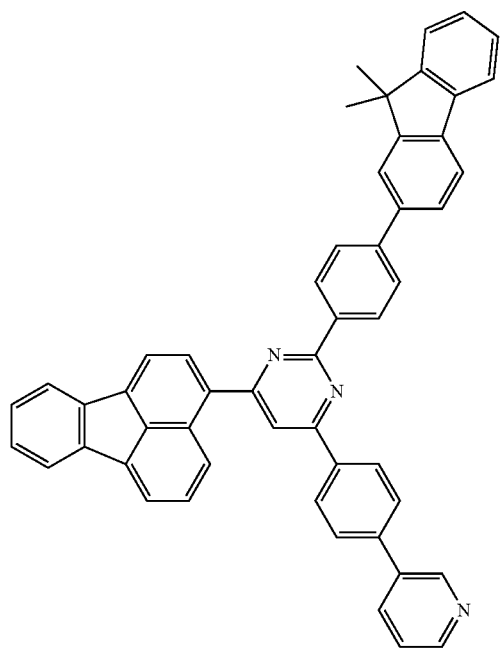
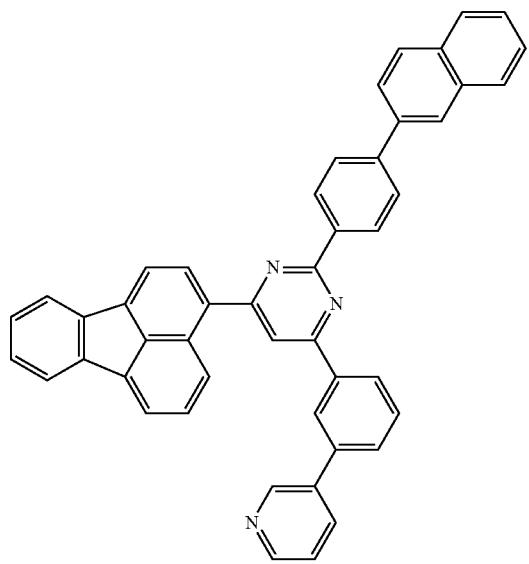

-continued
237 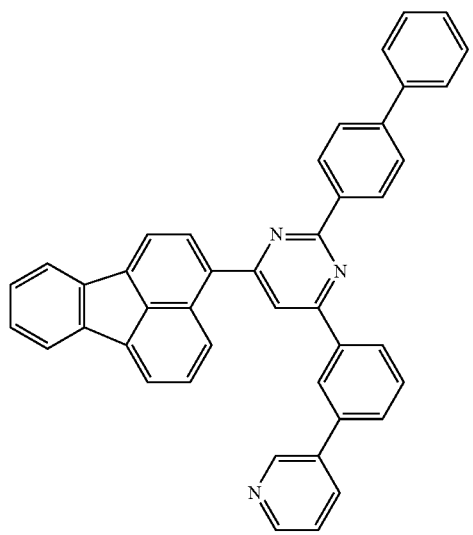
238 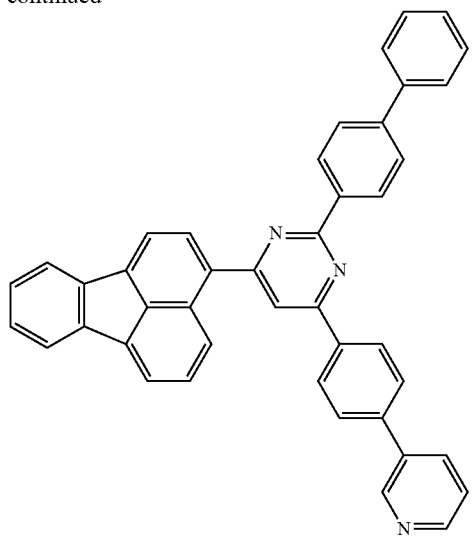
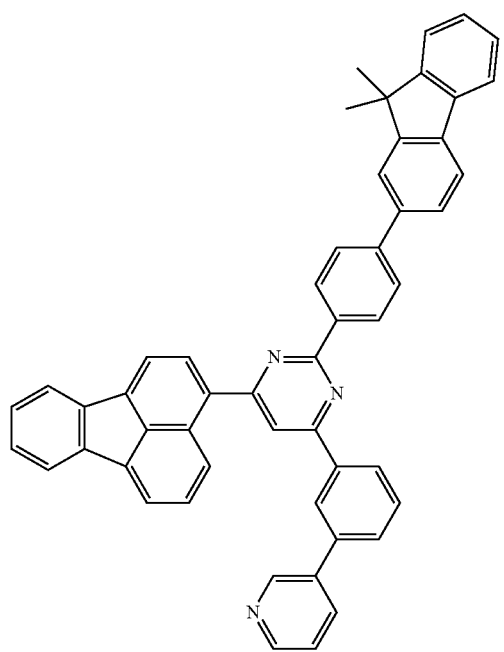
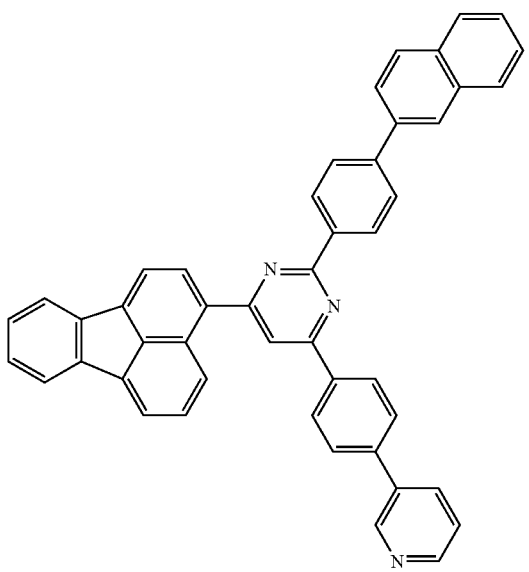

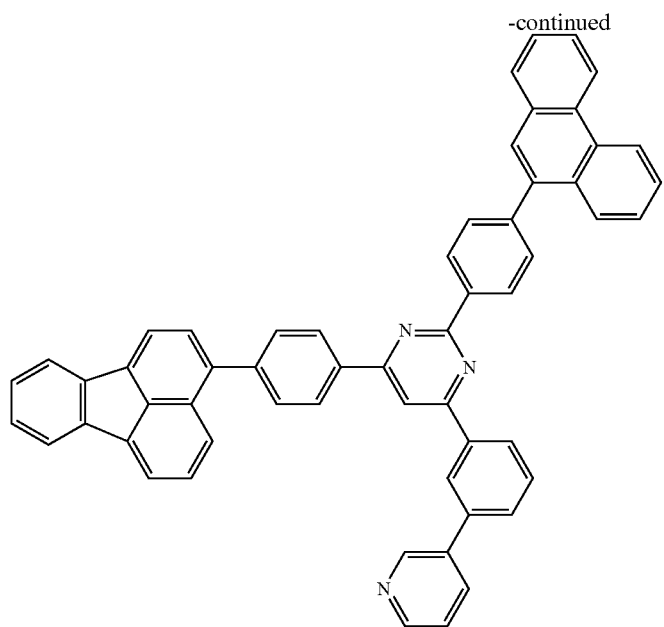
[Formula 113]
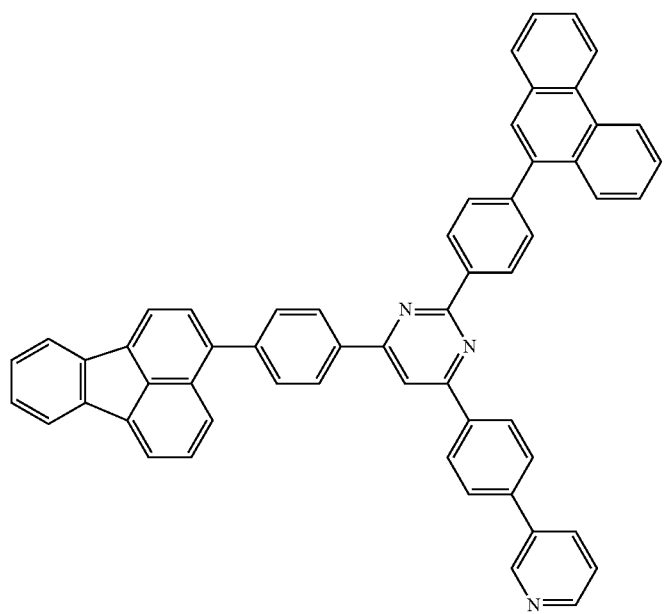

-continued
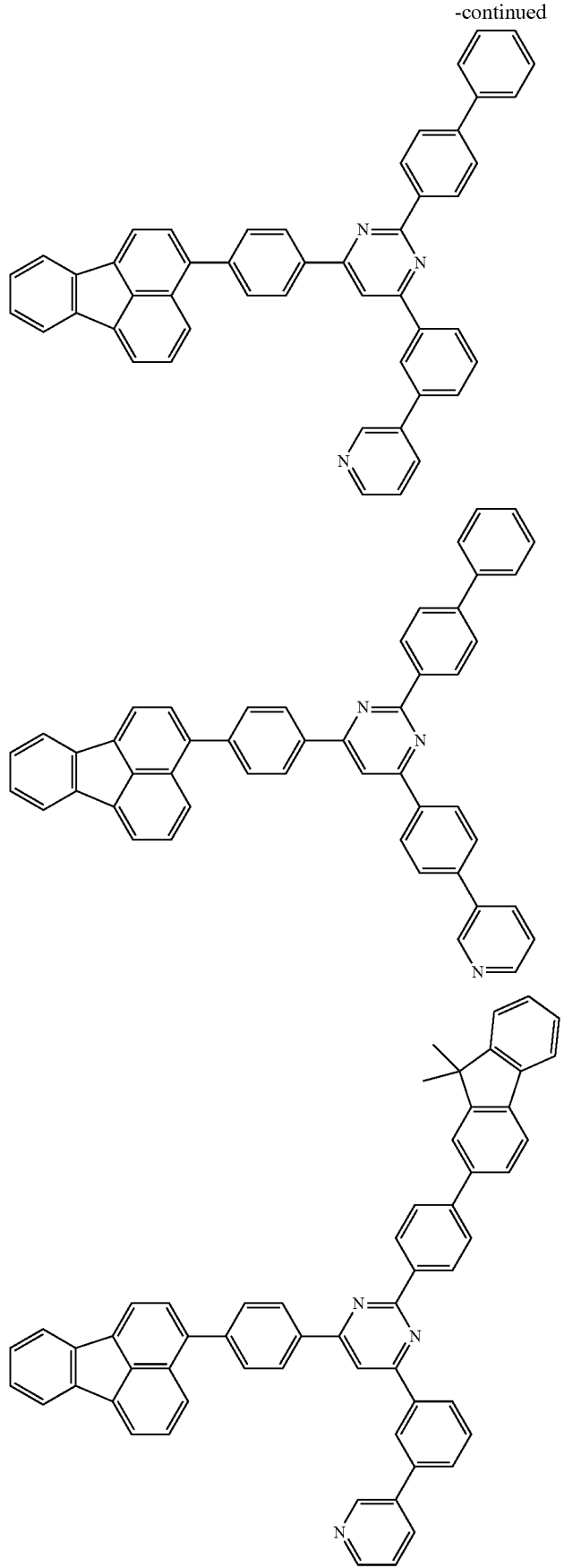

-continued
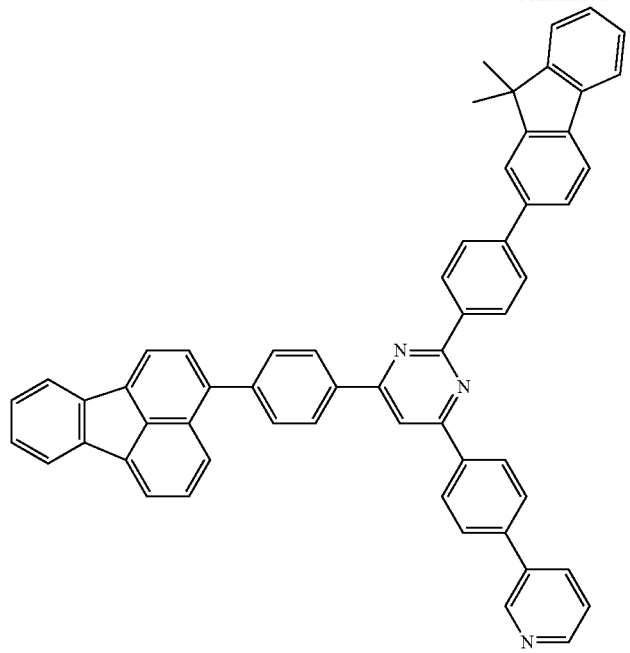
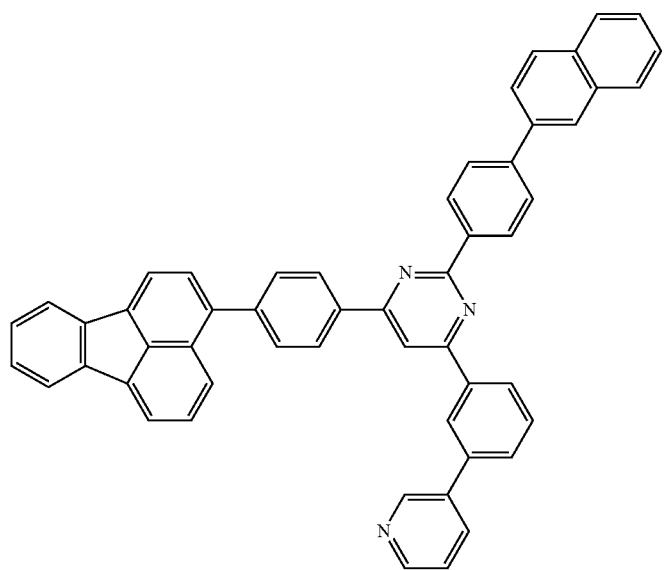

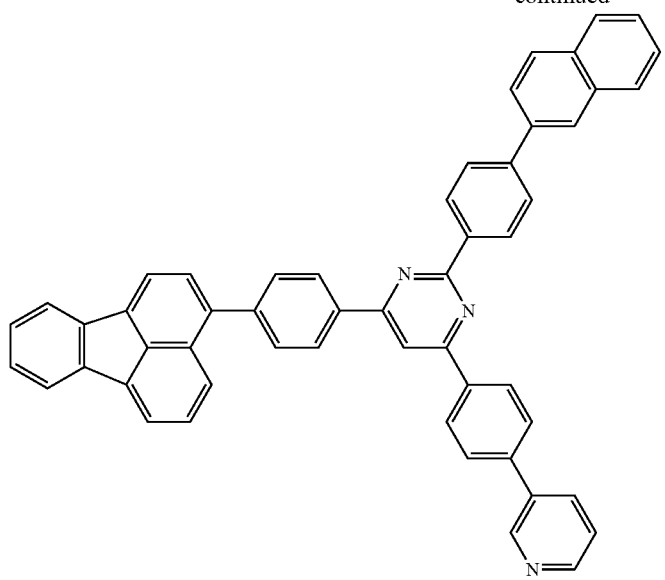
[Formula 114]
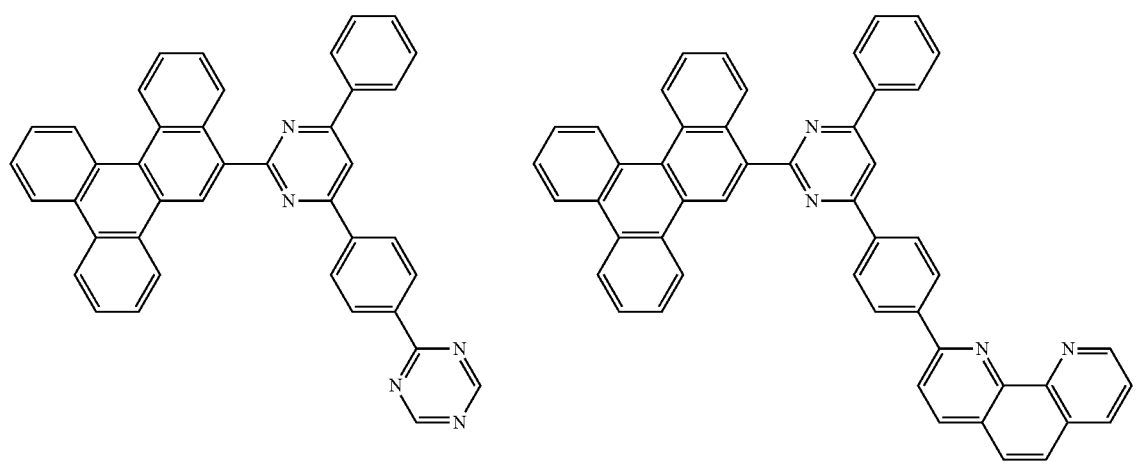
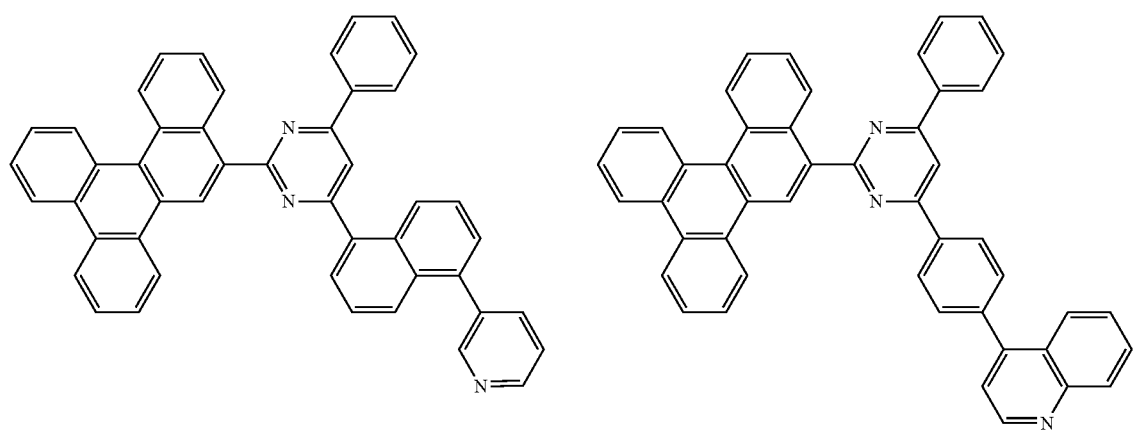

-continued
247
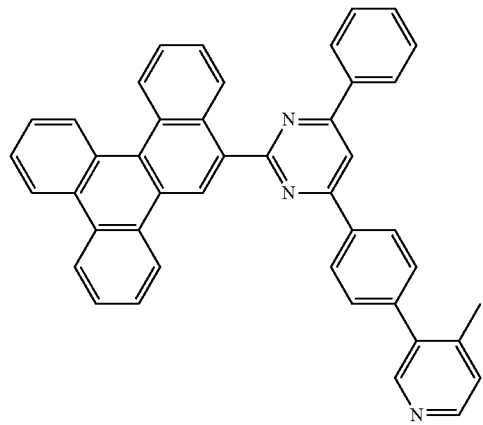
248
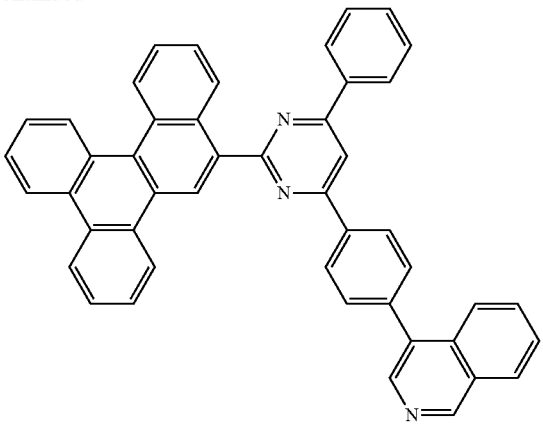
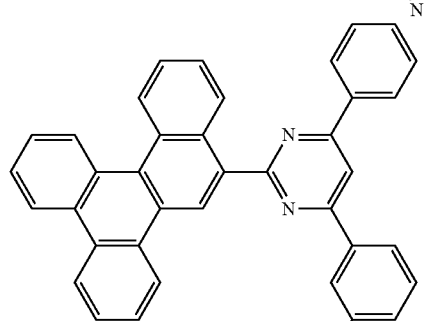
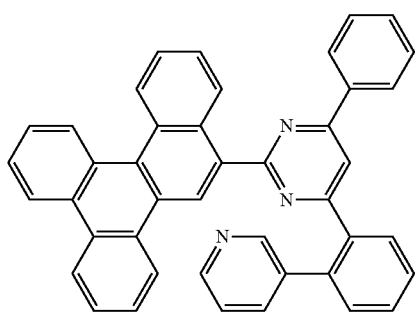
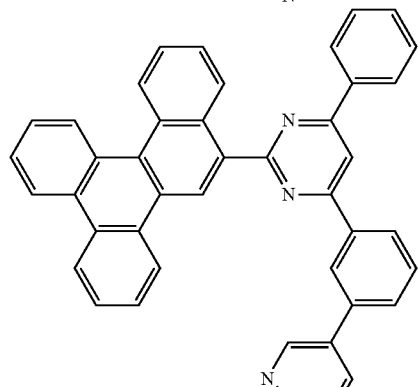
[Formula 115]
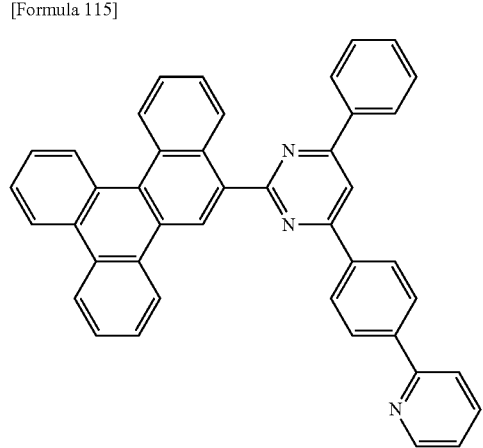
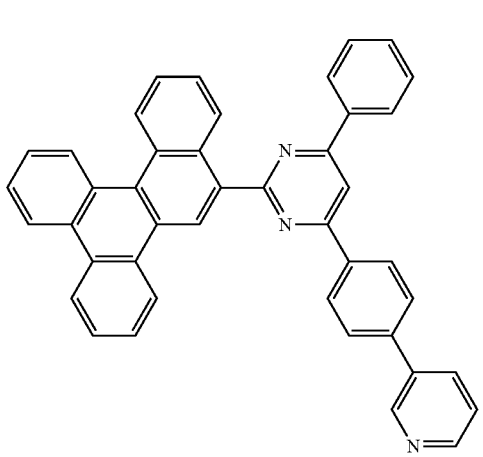

249
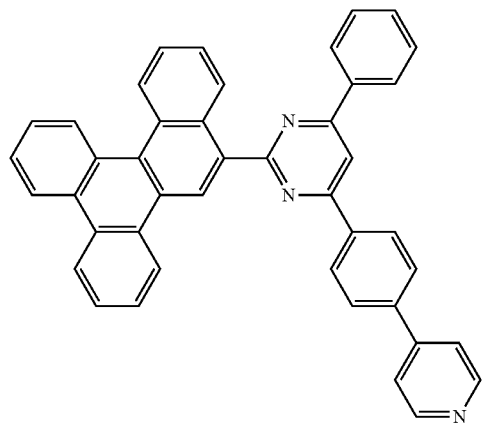
250
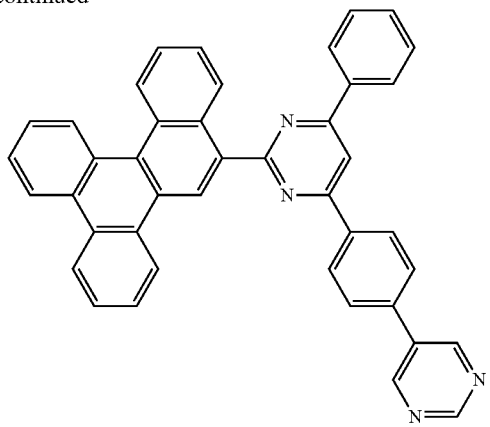
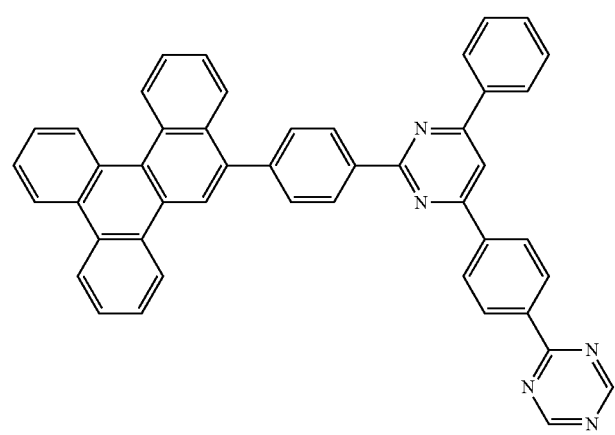
[Formula 116]
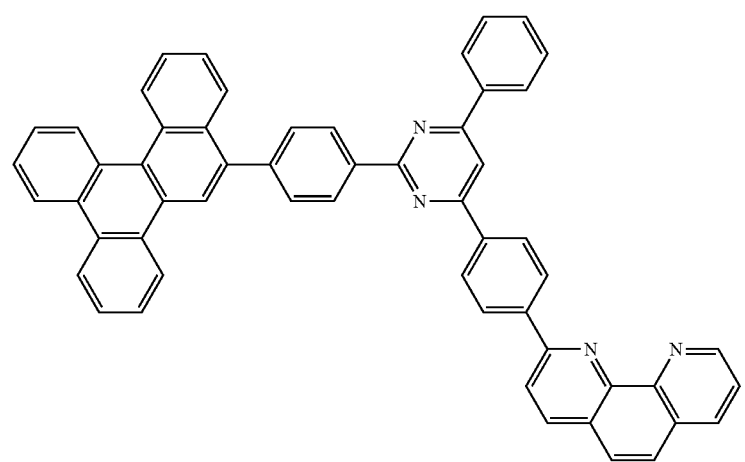

-continued
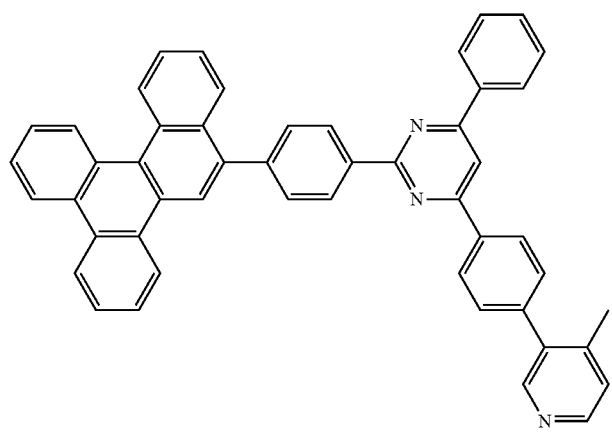
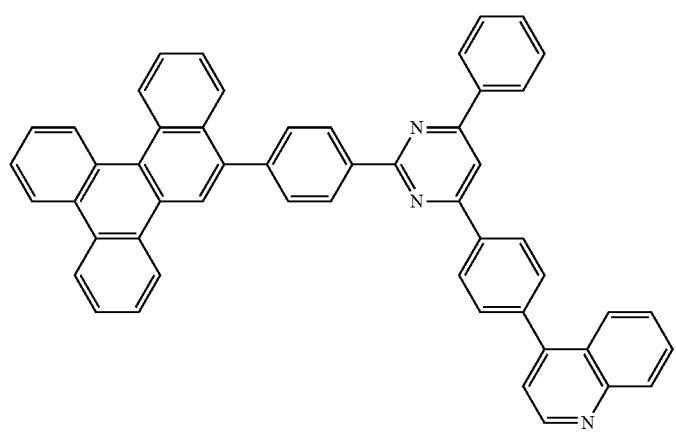
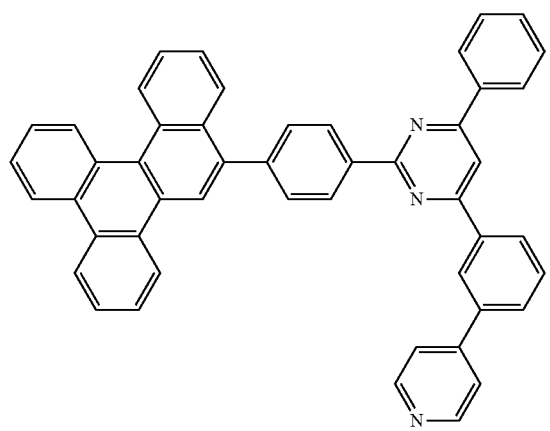
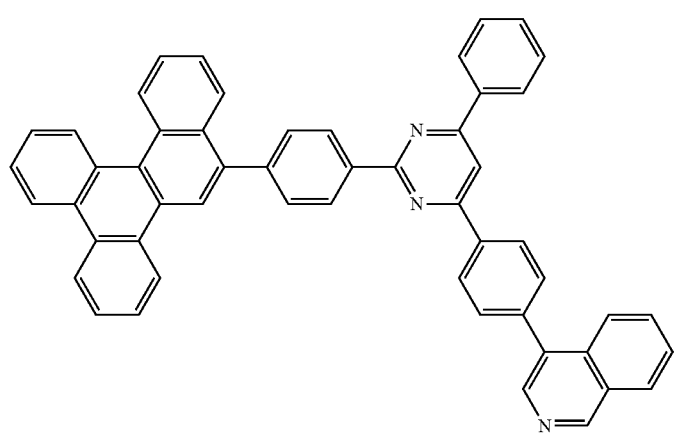

-continued
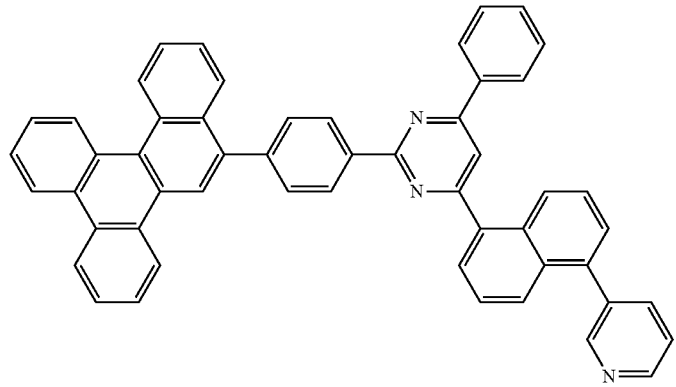
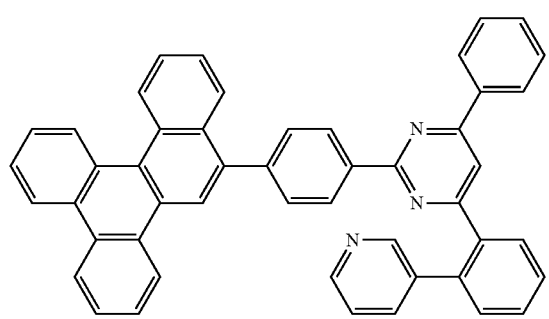
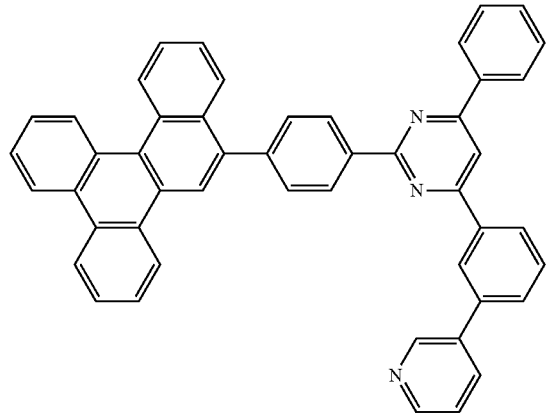
[Formula 117]
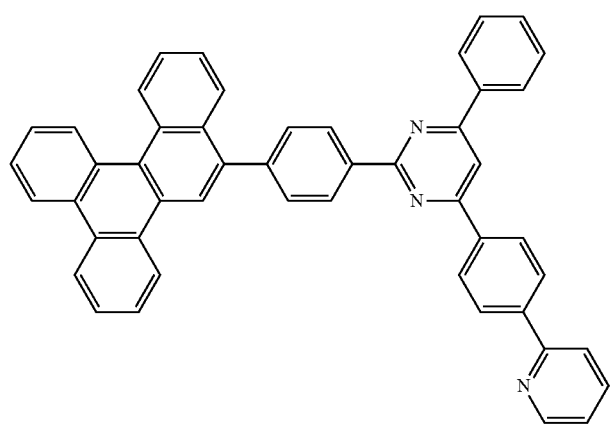

-continued
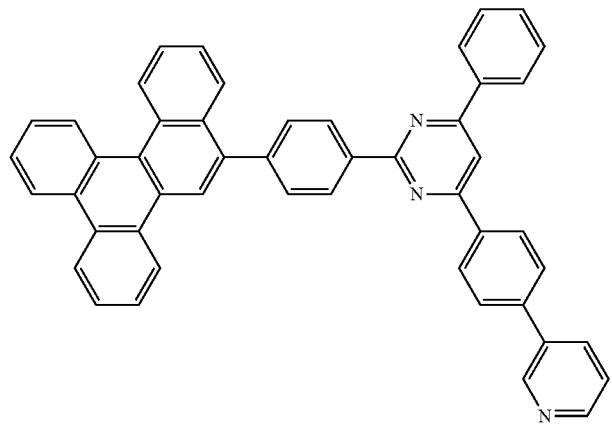
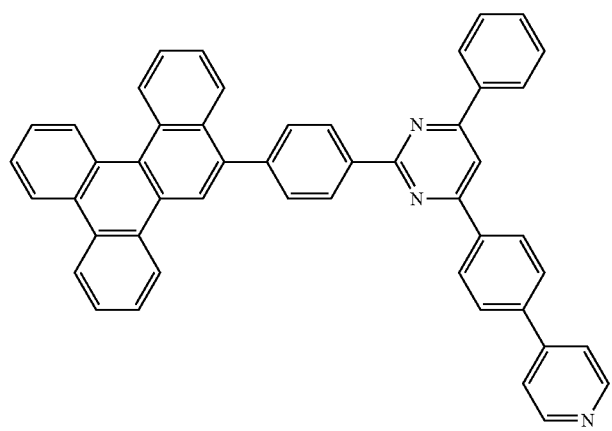
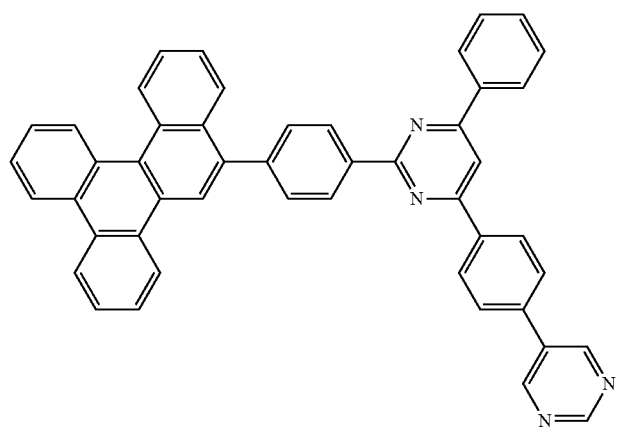

[Formula 118]
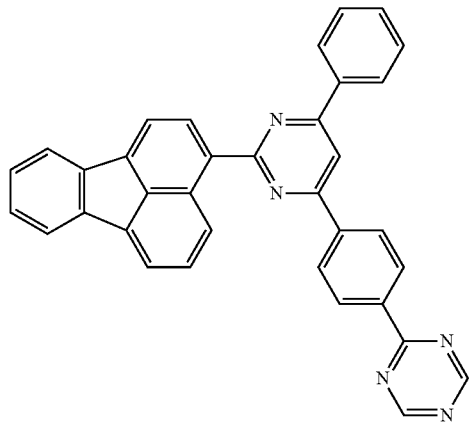
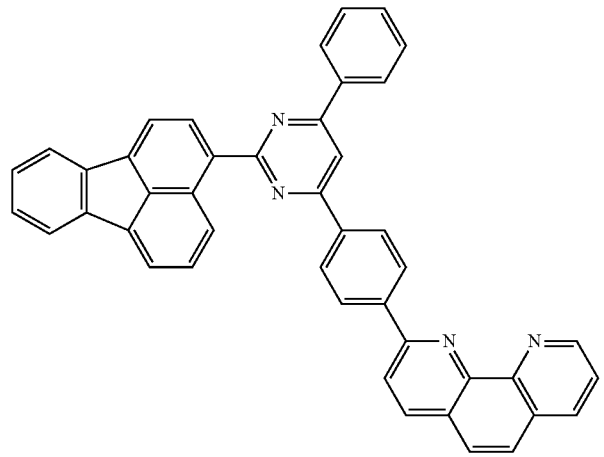
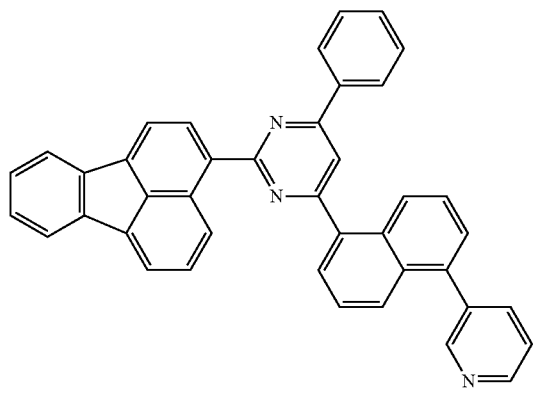
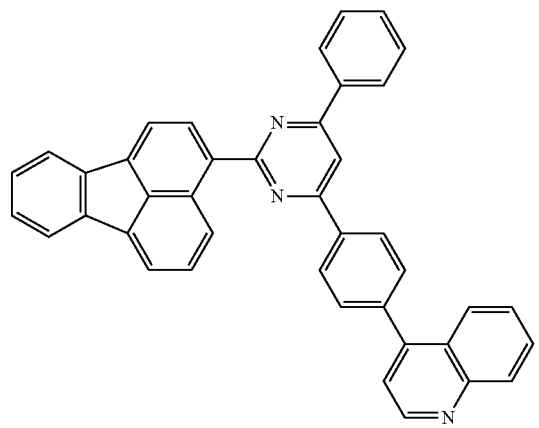
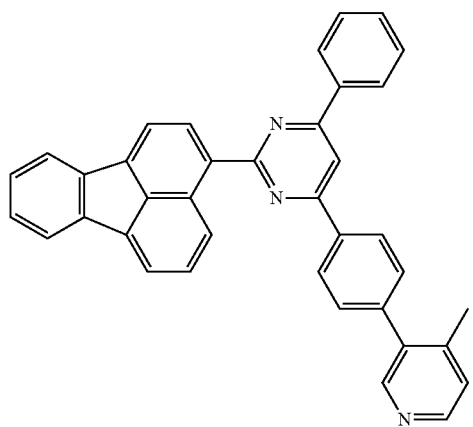
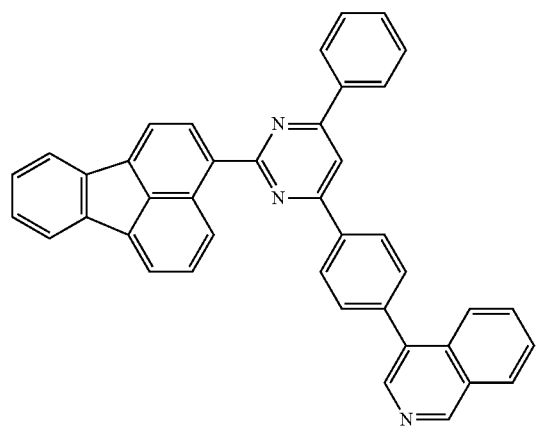

259
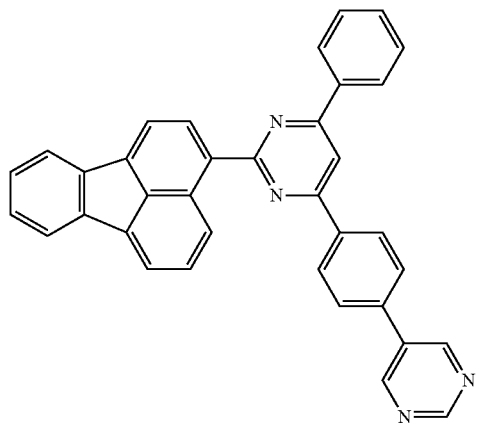
260
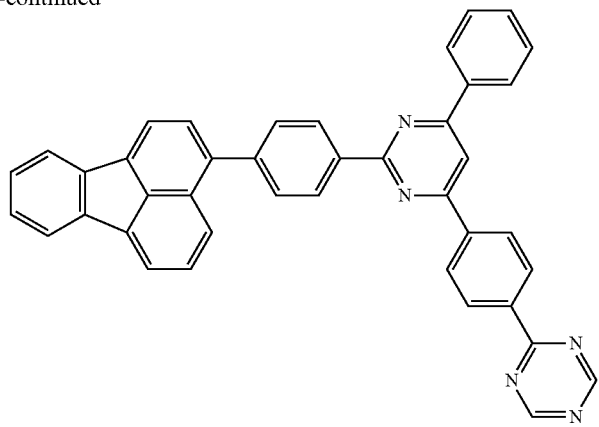
[Formula 119]
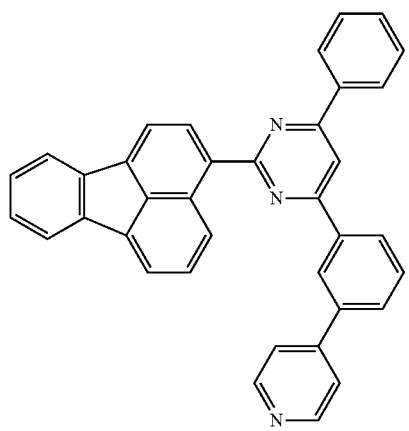
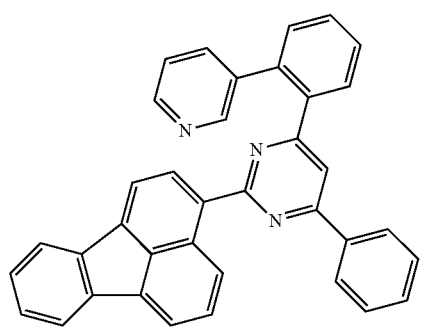
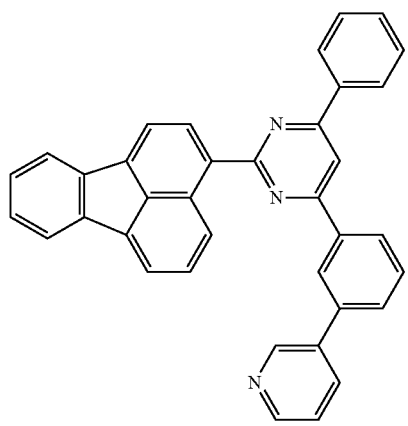
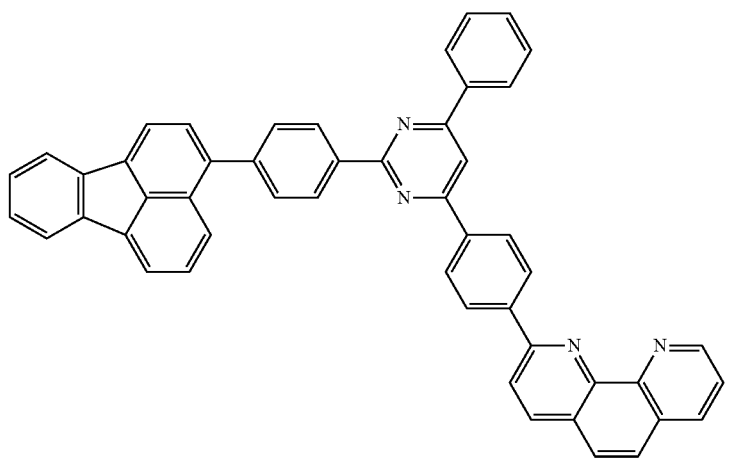

-continued
261
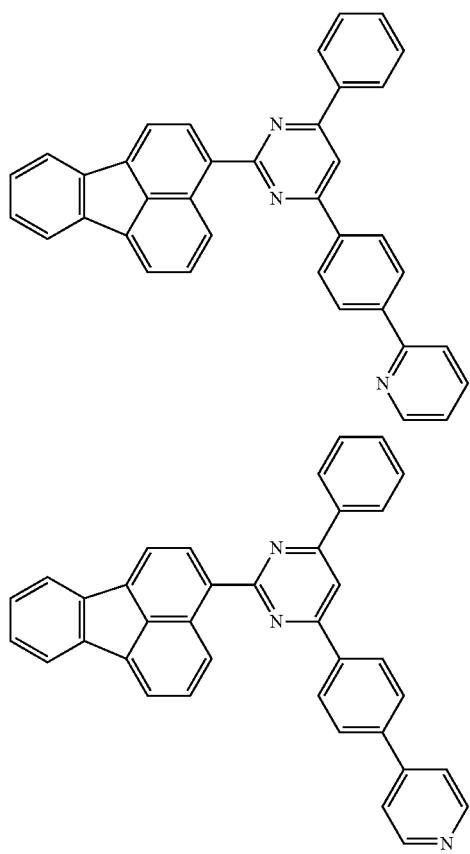
262
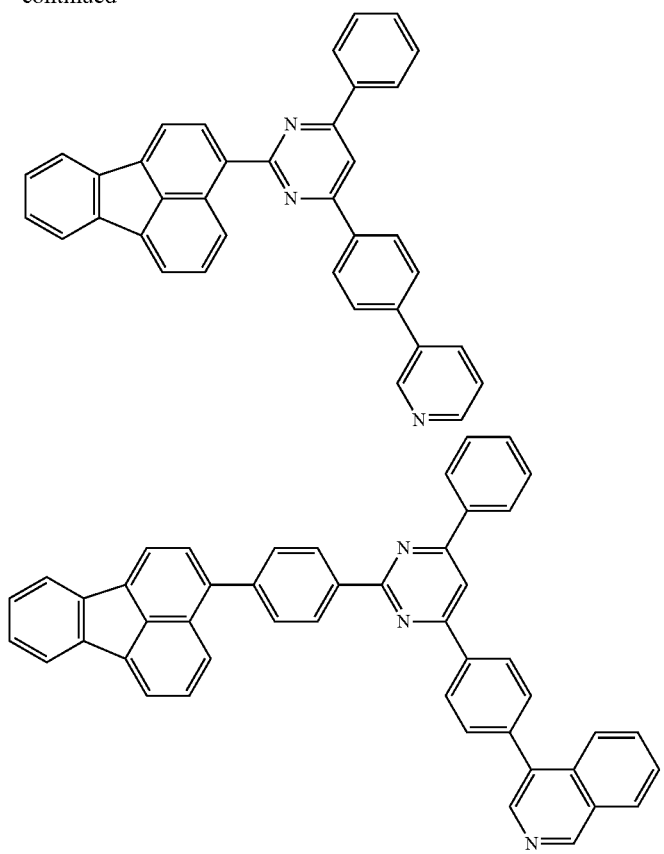
[Formula 120]
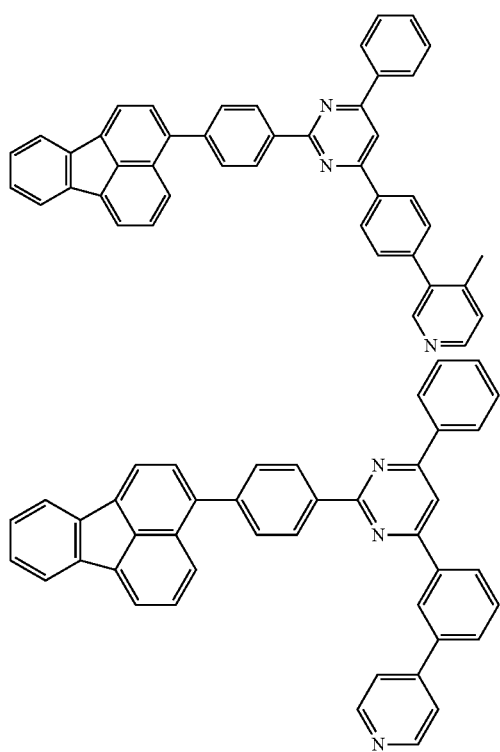
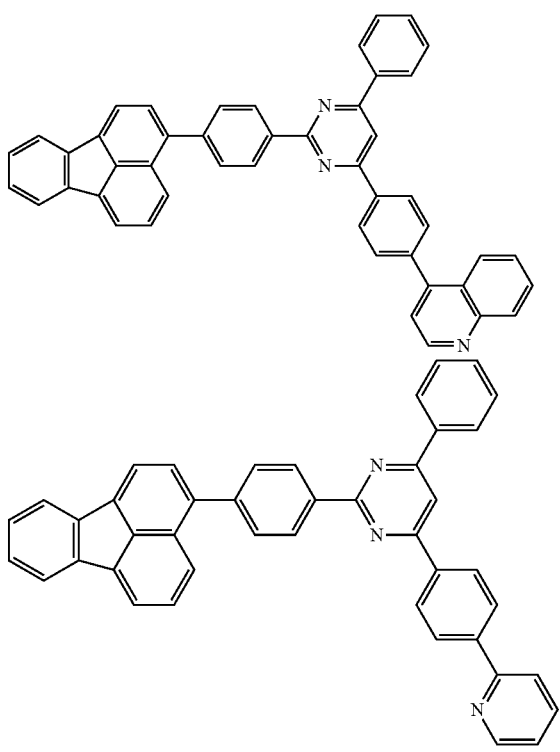

263
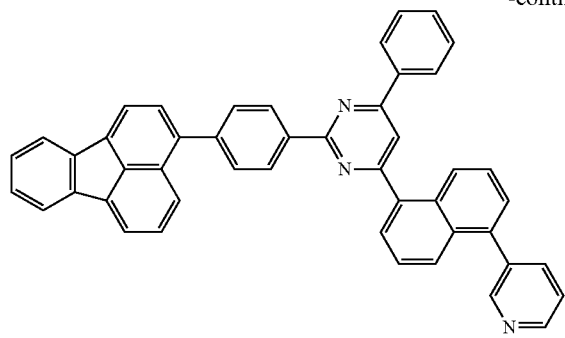
264
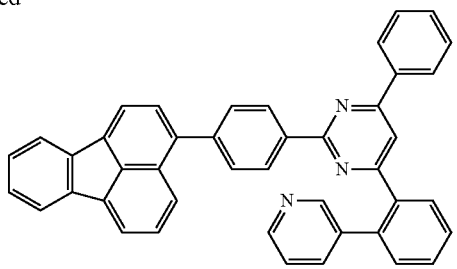
-continued
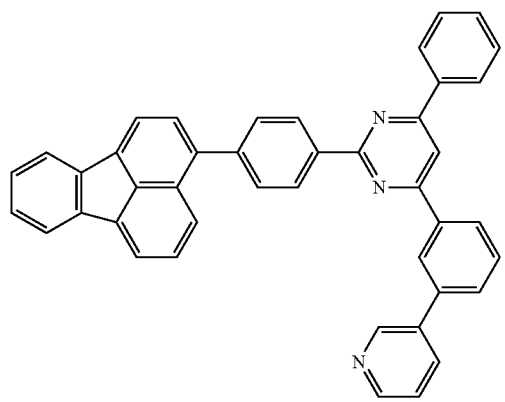
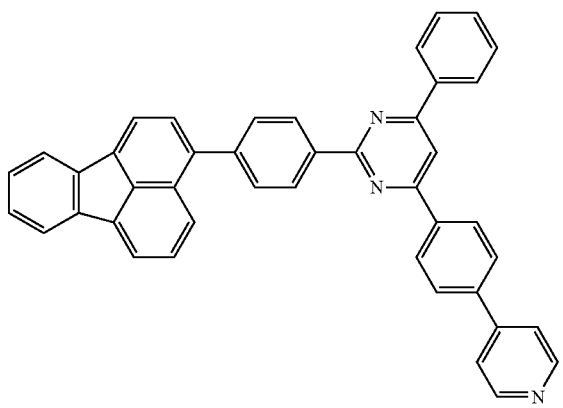
[Formula 121]
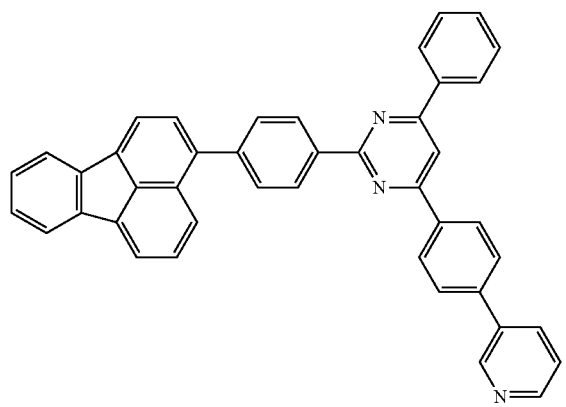
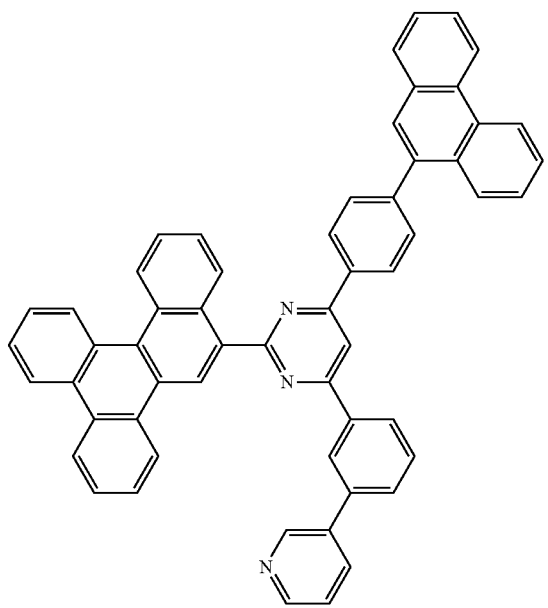

-continued
265
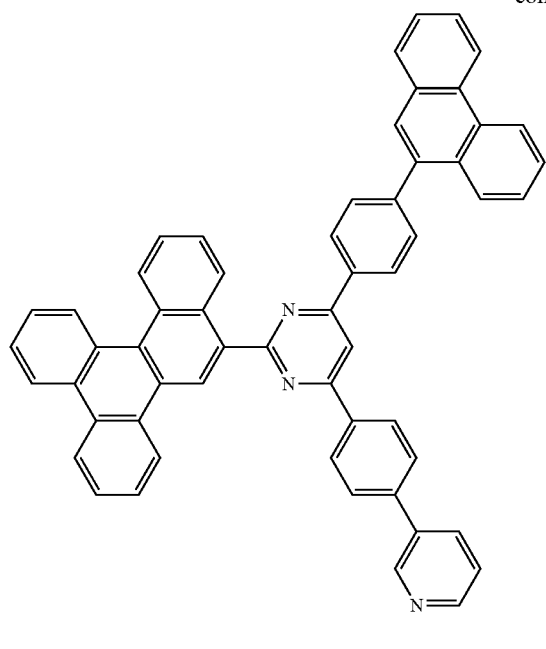
266
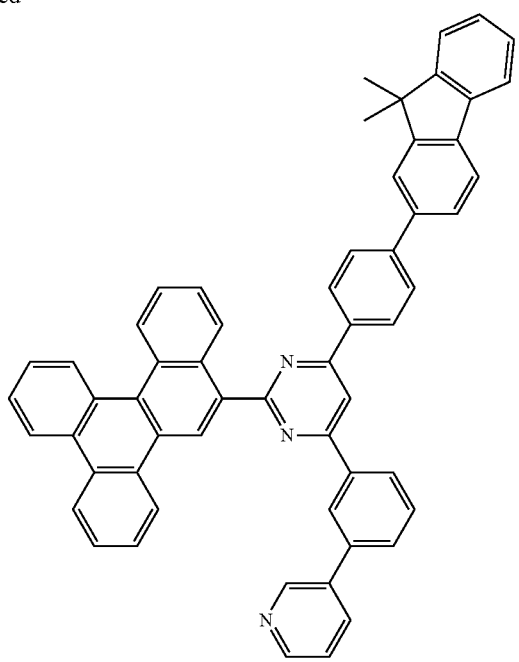
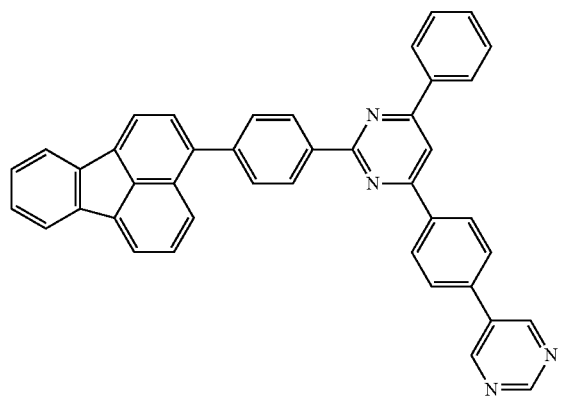
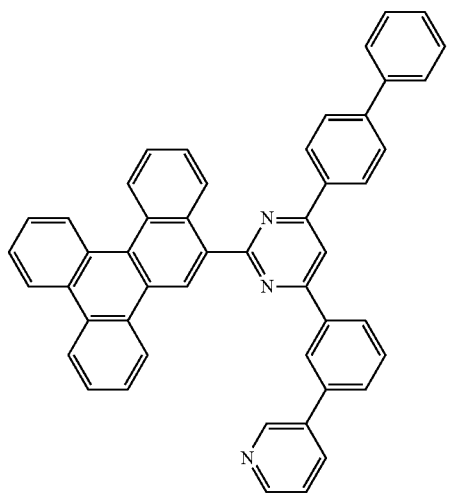
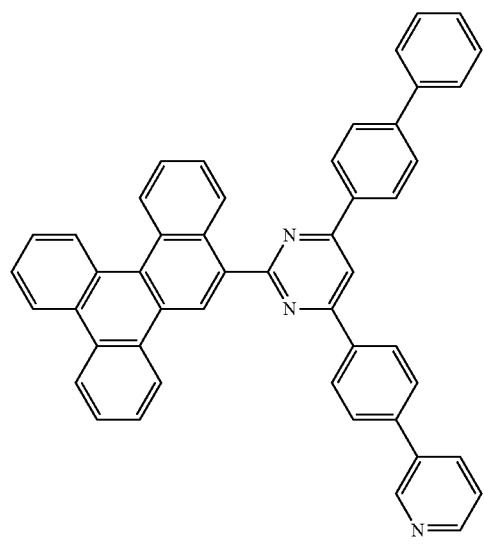

[Formula 122]
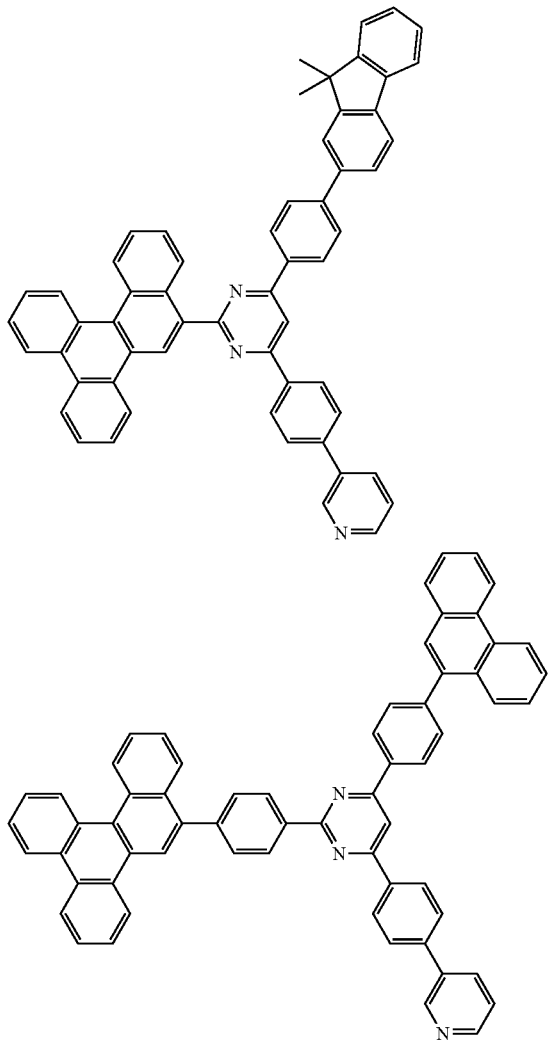
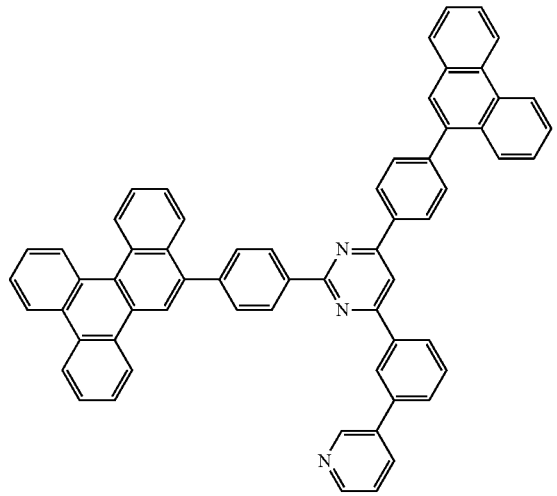
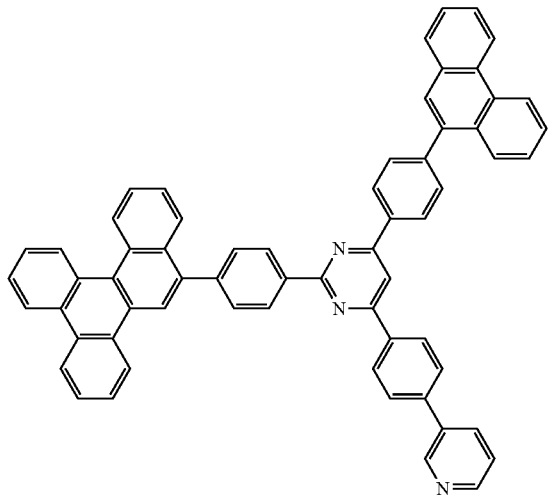
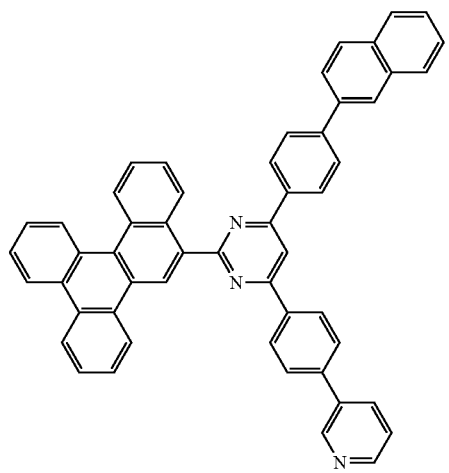
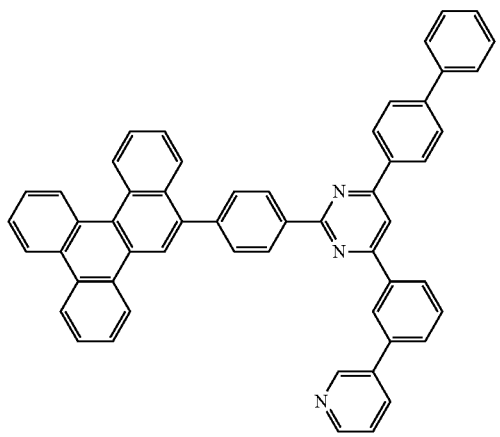
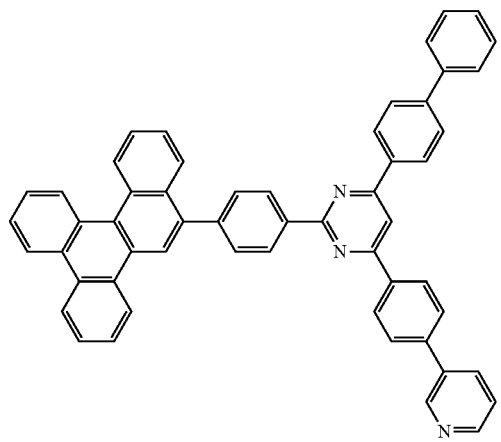

[Formula 123]
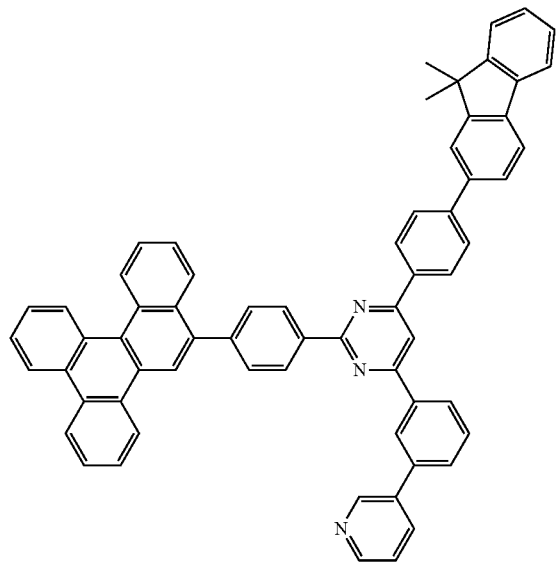
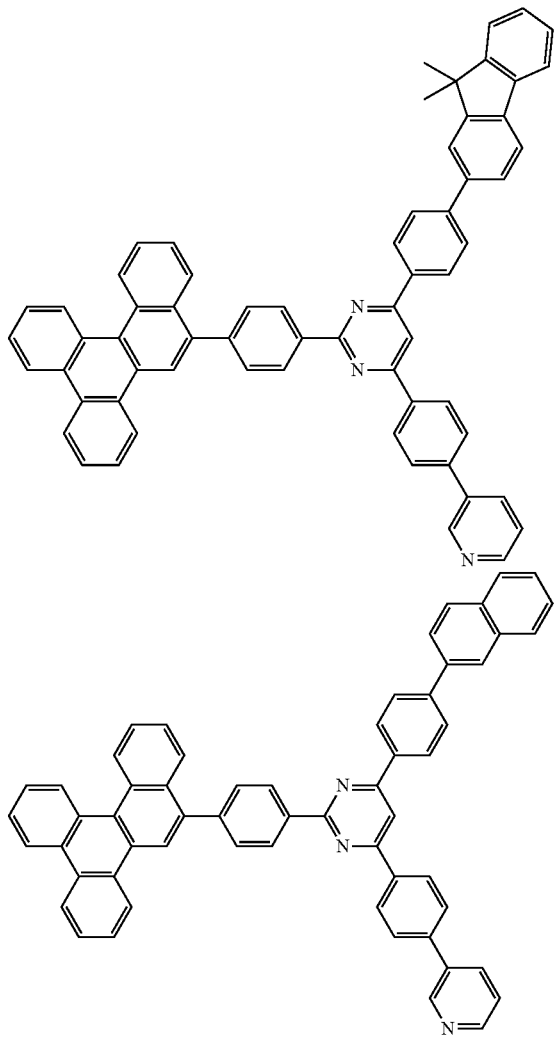
[Formula 124]
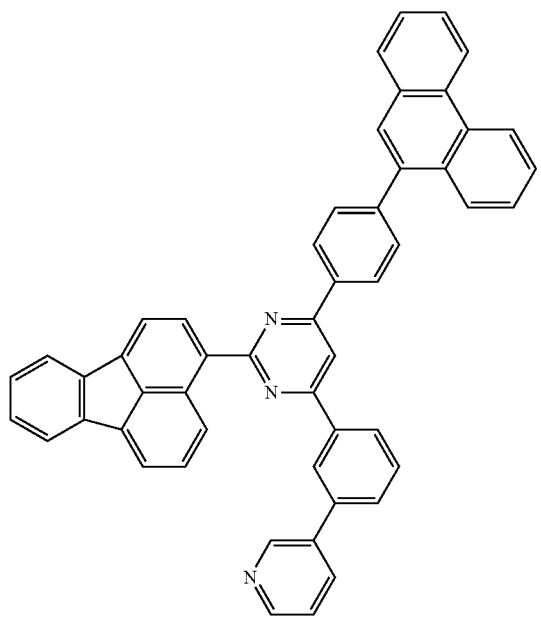
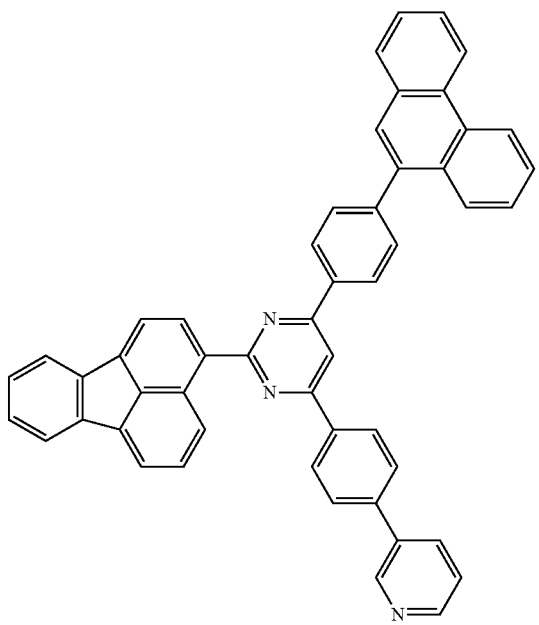

271
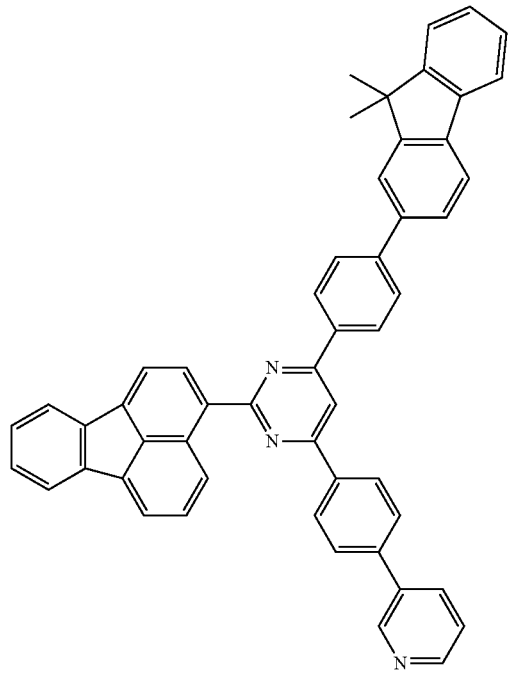
272
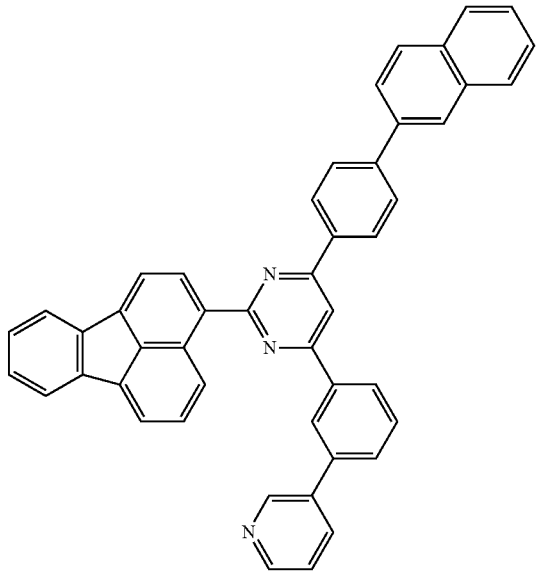
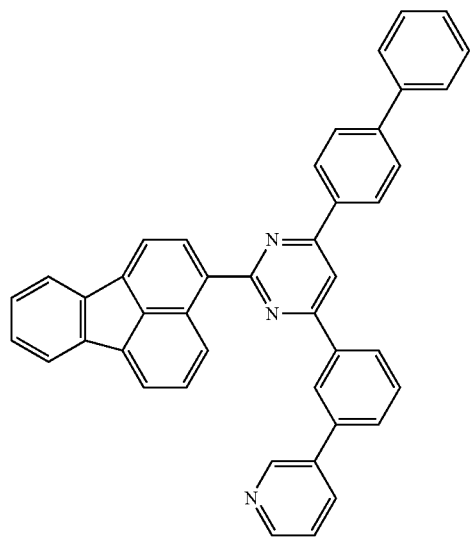
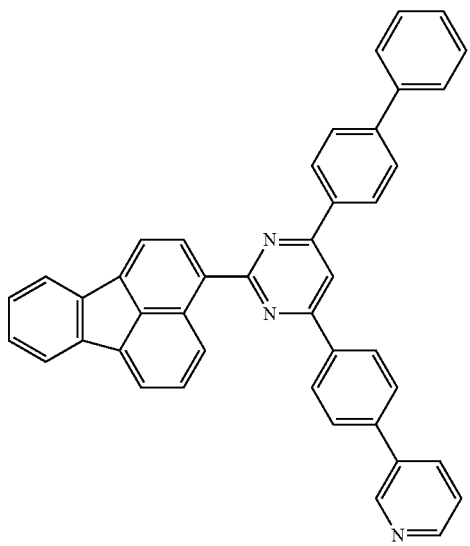

273
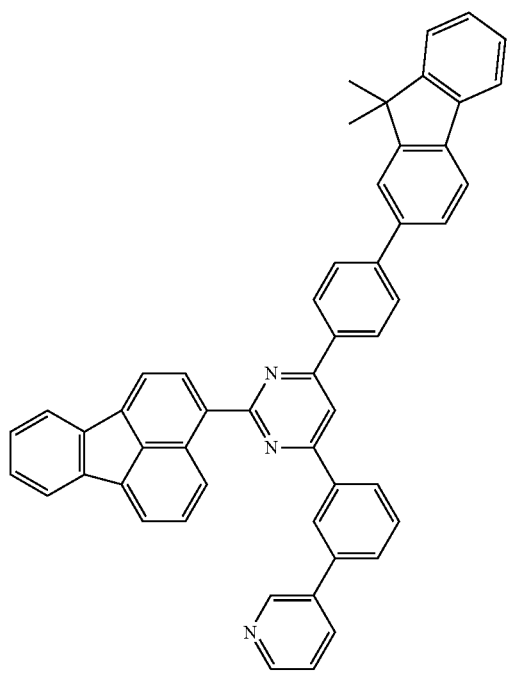
274
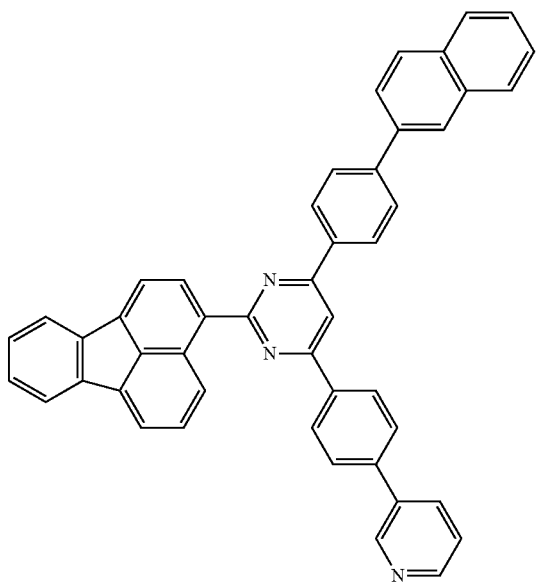
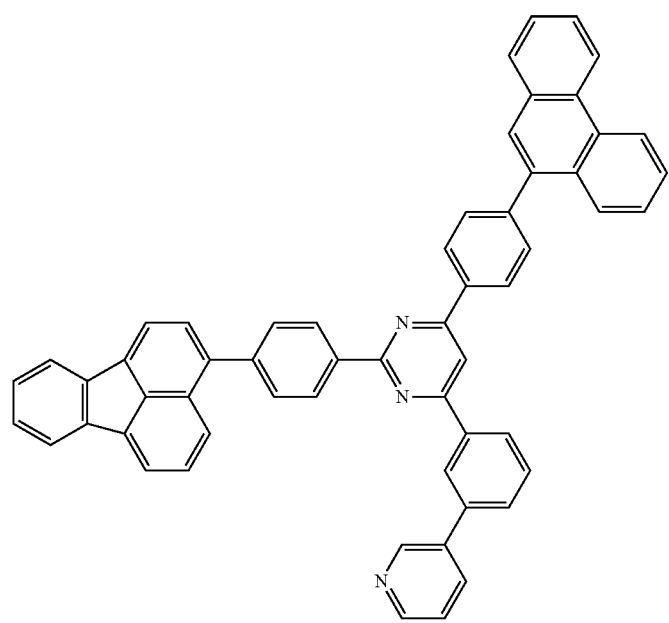

[Formula 125]
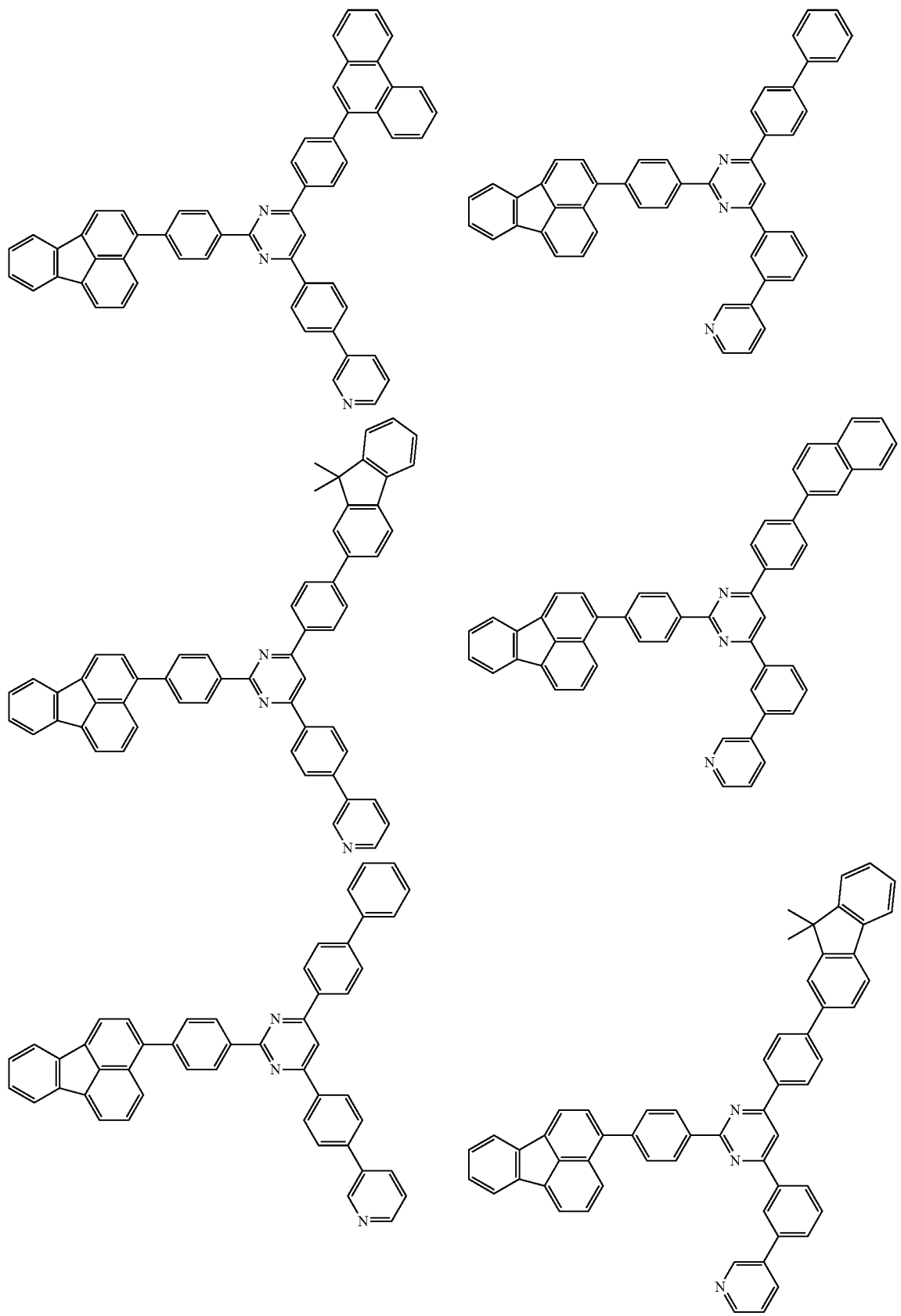

-continued
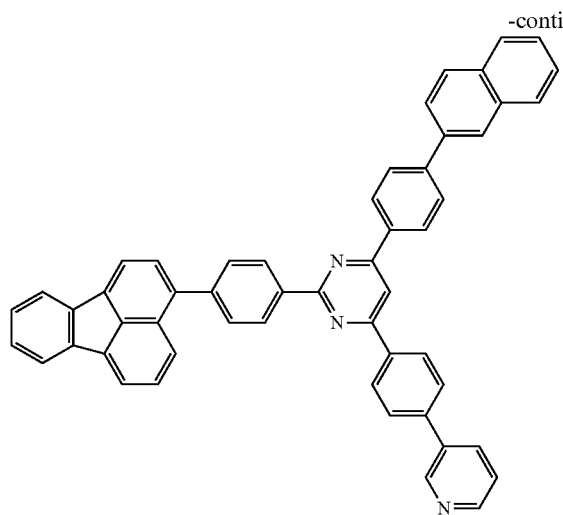
[Formula 126]
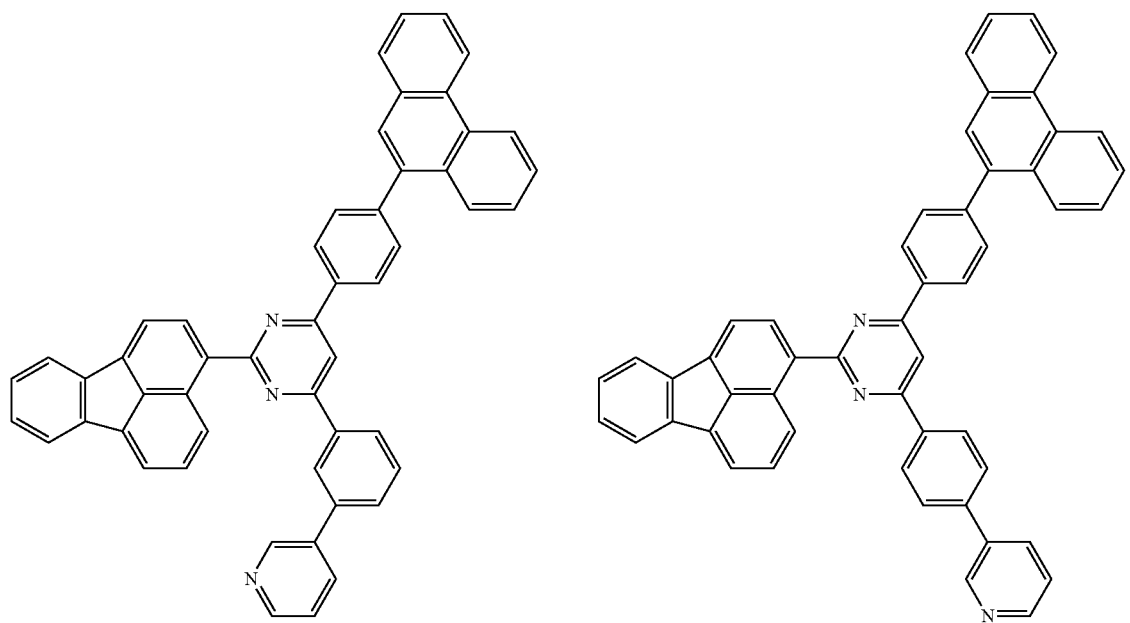

-continued
279
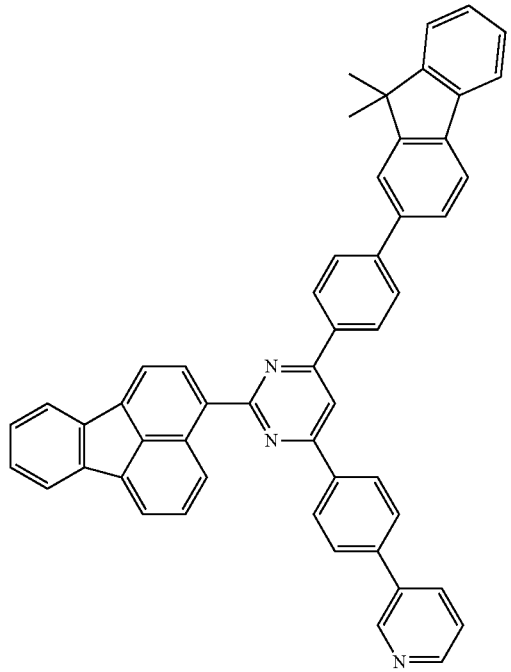
280
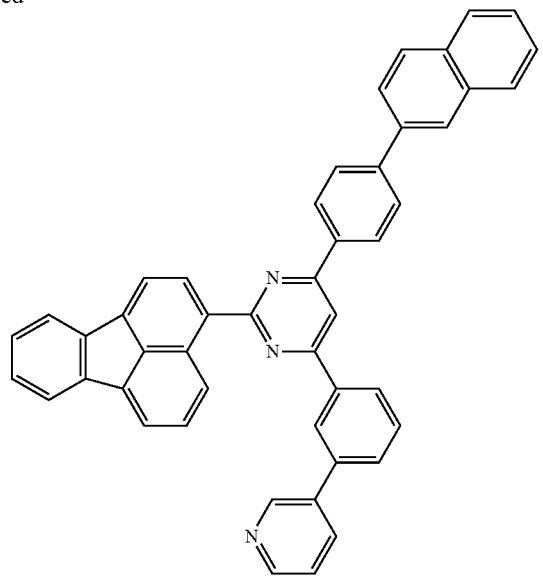
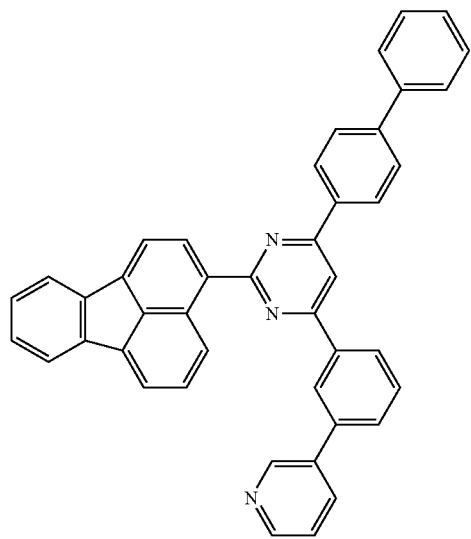
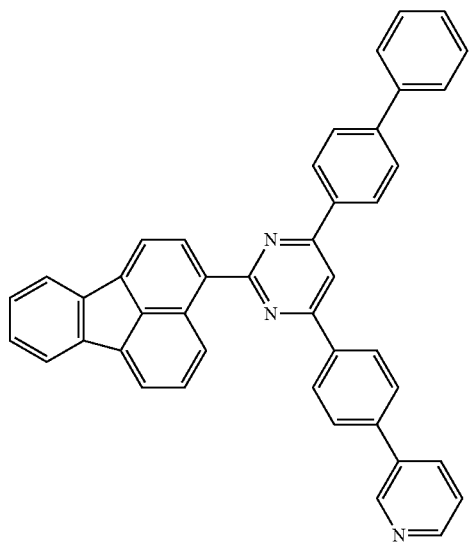

-continued
281
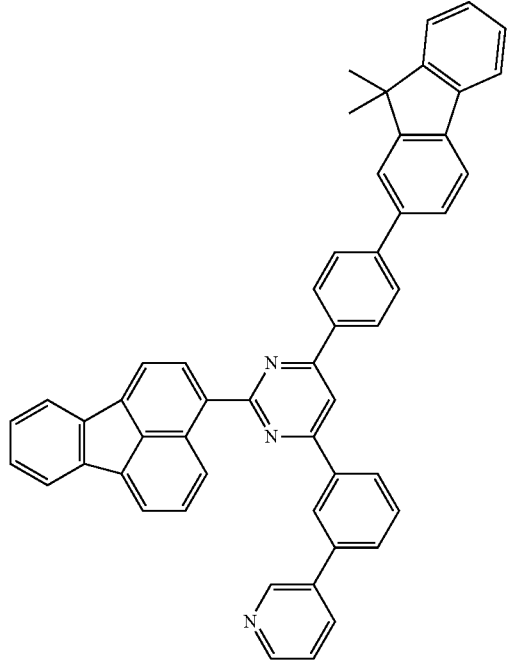
282
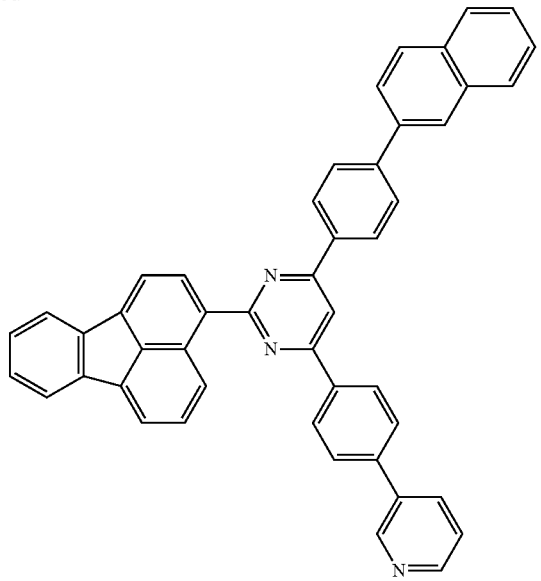
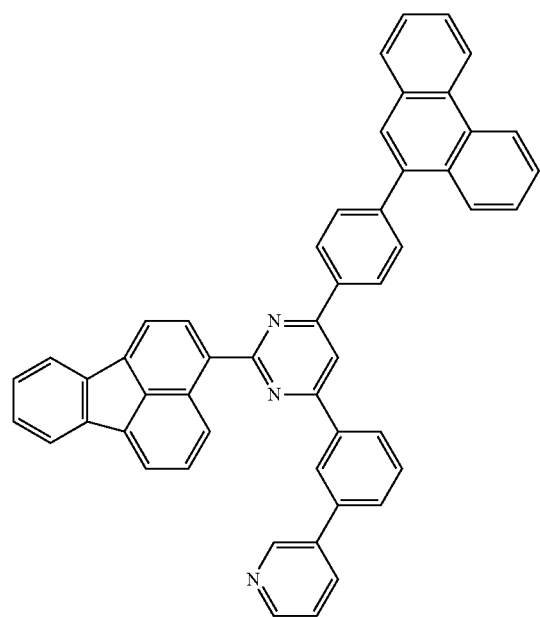

283
284
-continued
[Formula 127]
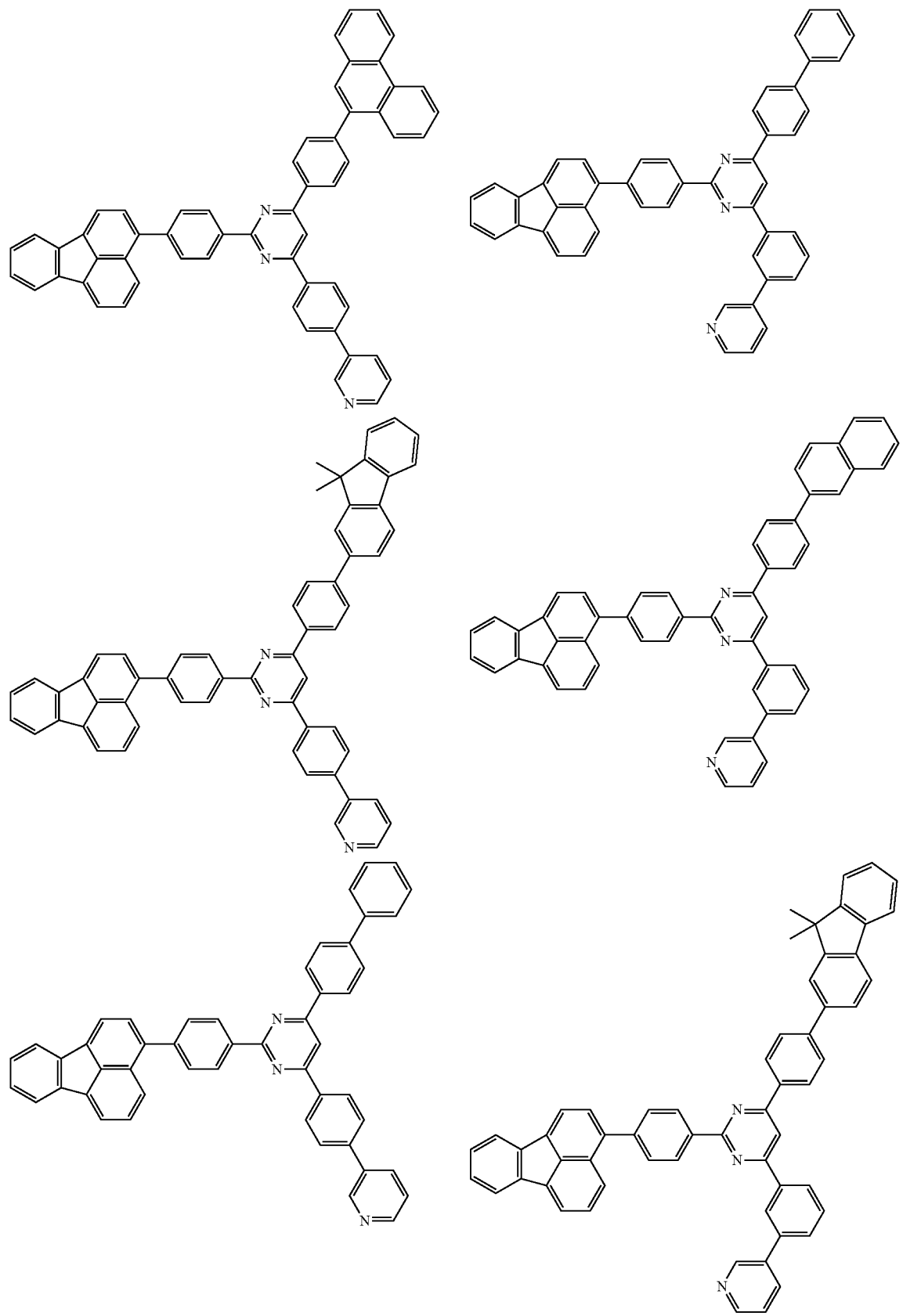

-continued
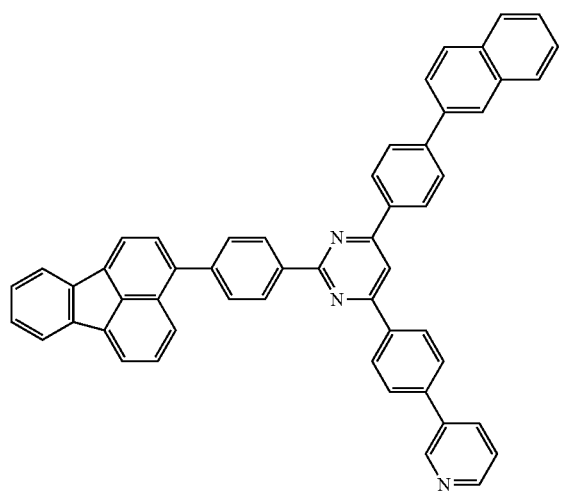 [SMILES: c1cncc(-c2ccc(-c3cc(-c4ccc(-c5ccc6ccccc6c5)cc4)nc(-c4ccc(-c5ccc6c7c(cccc57)-c5ccccc5-6)cc4)n3)cc2)c1]
[Formula 128]
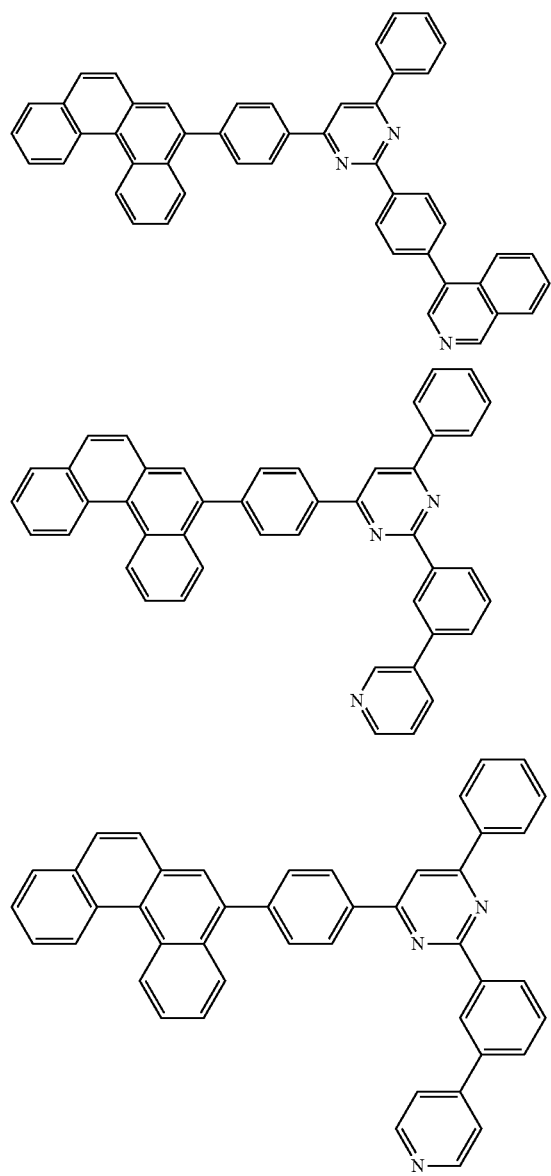
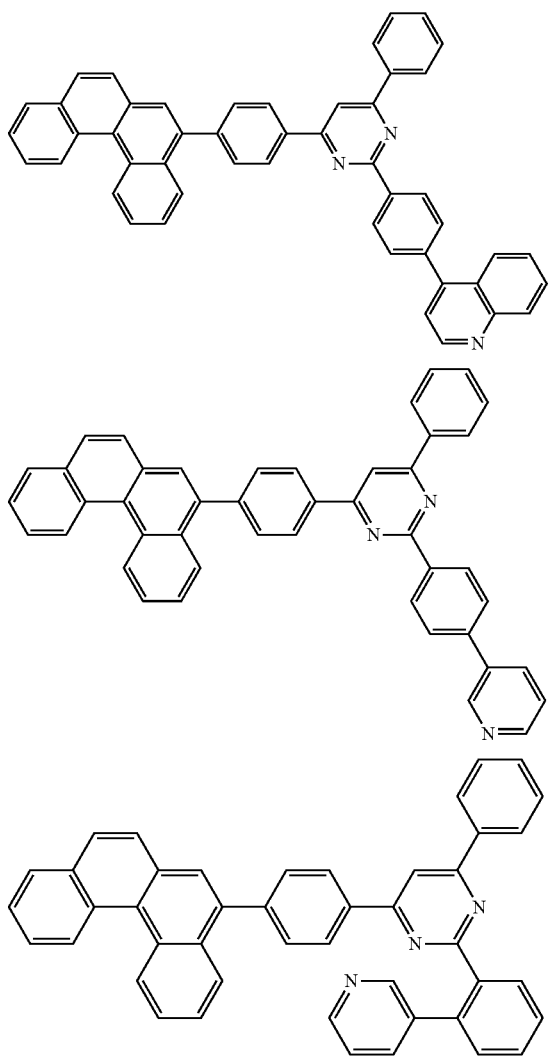

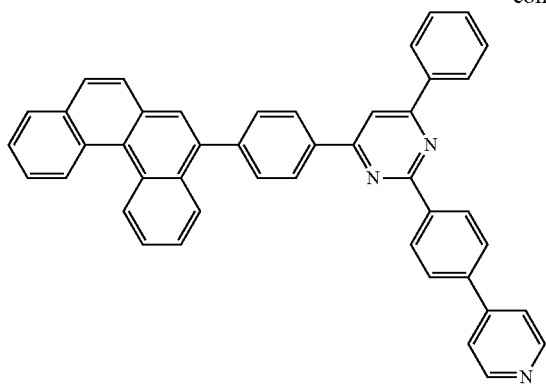
[Formula 129]
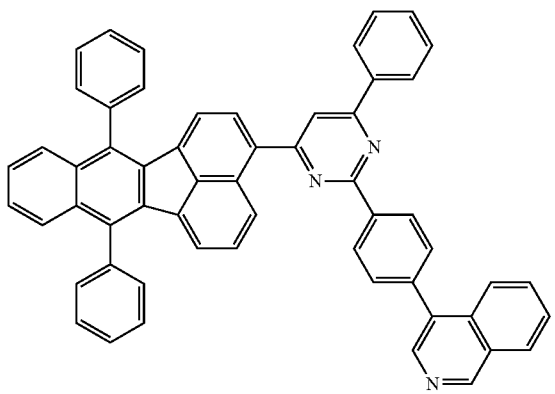
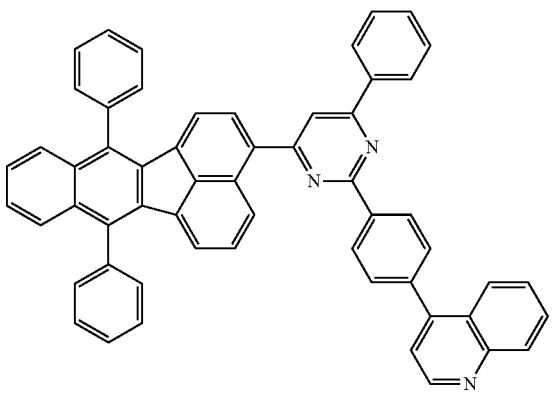
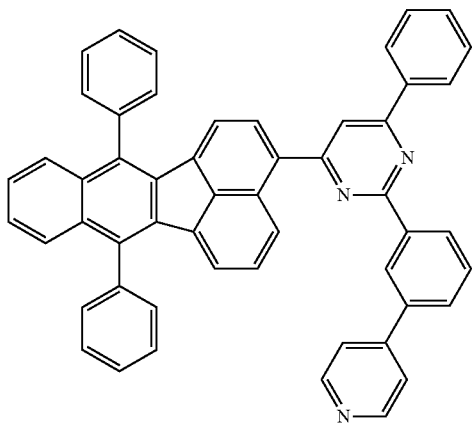
[Formula 130]
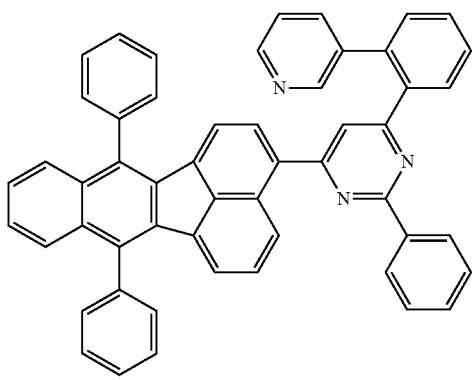
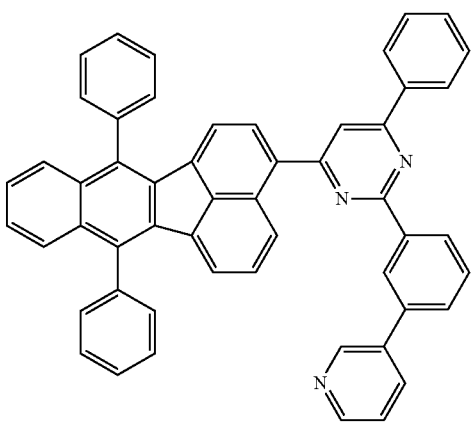

-continued
| 289 | 290 |
|---|---|
| 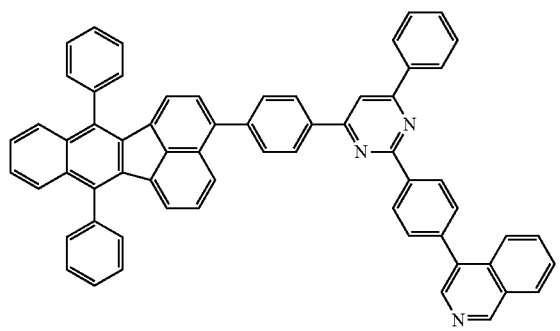 | 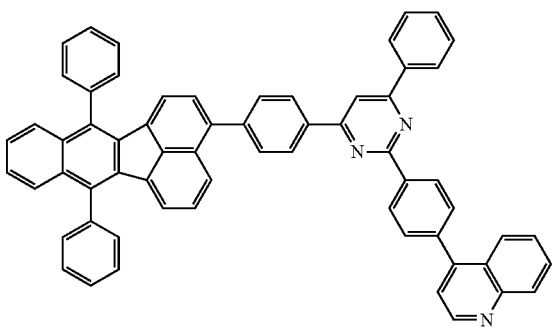 |
| 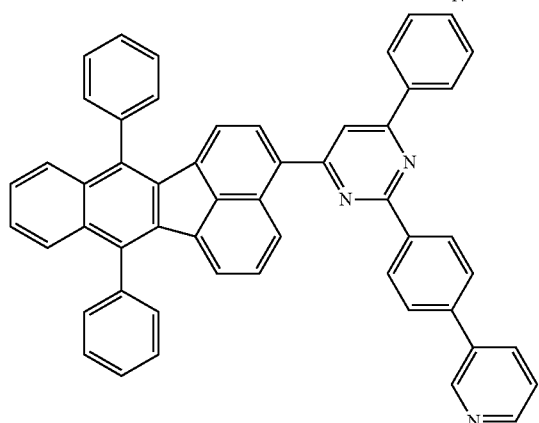 | 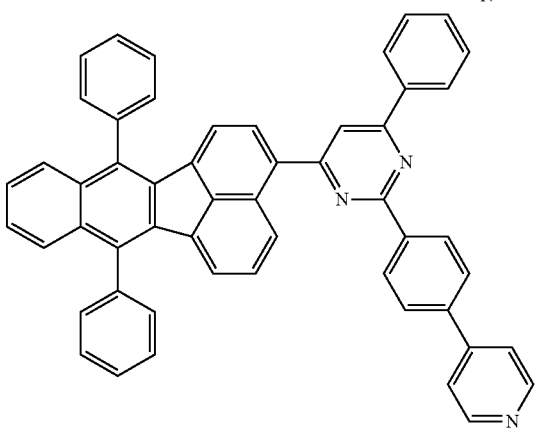 |
| 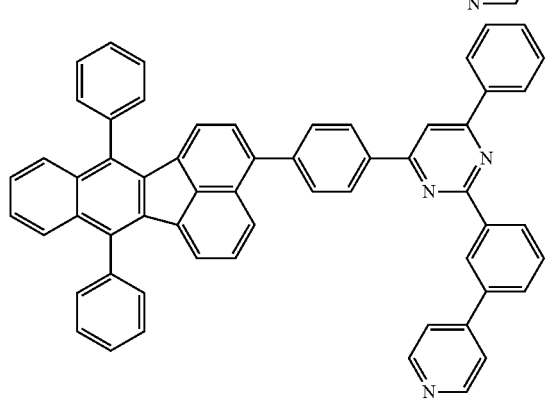 | 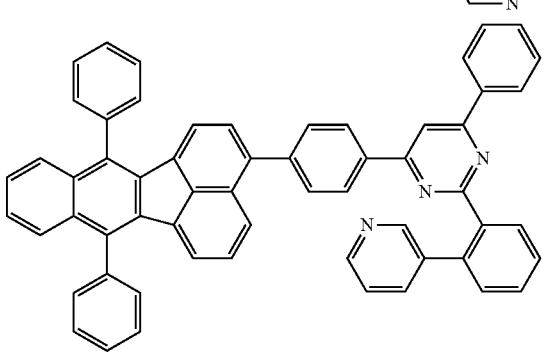 |
| 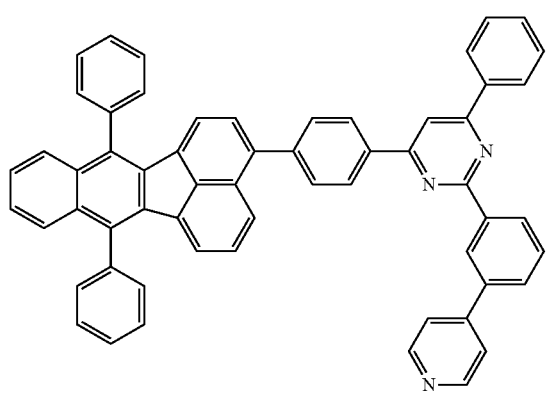 | 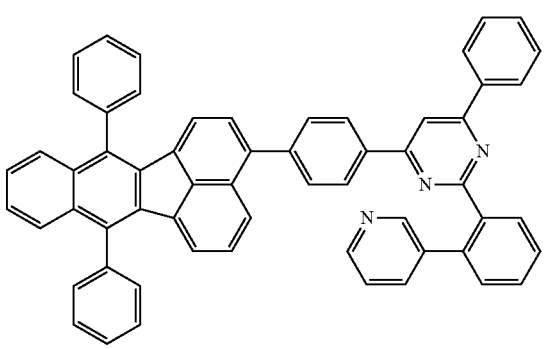 |

-continued
[Formula 131]
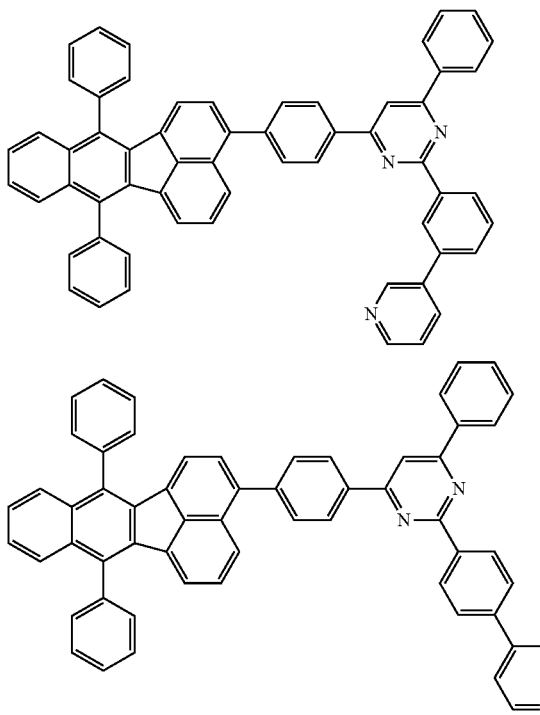
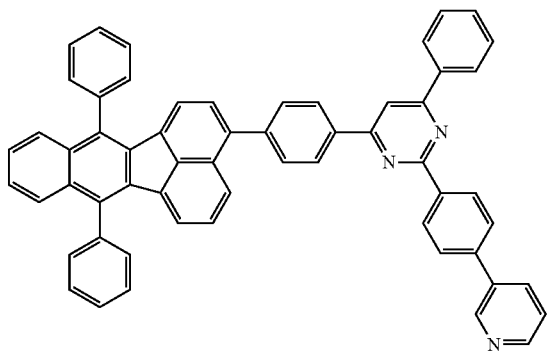
[Formula 132]
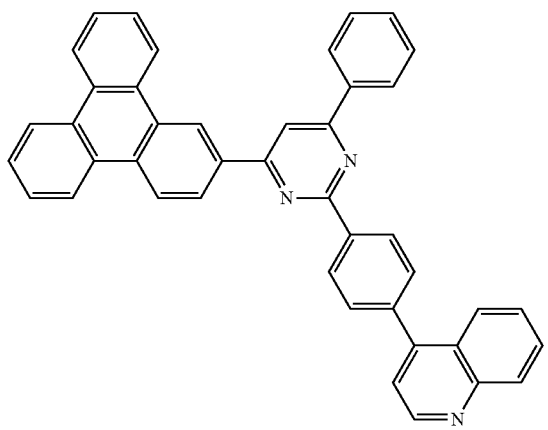
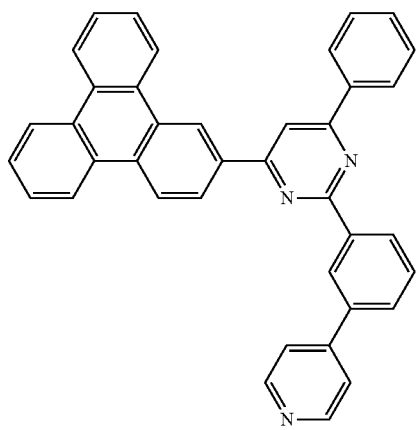
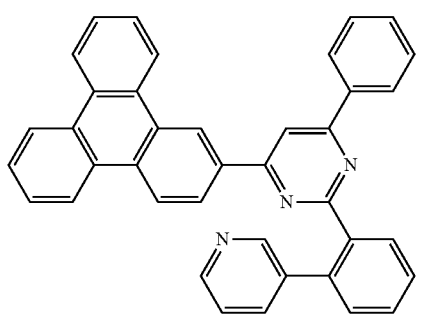
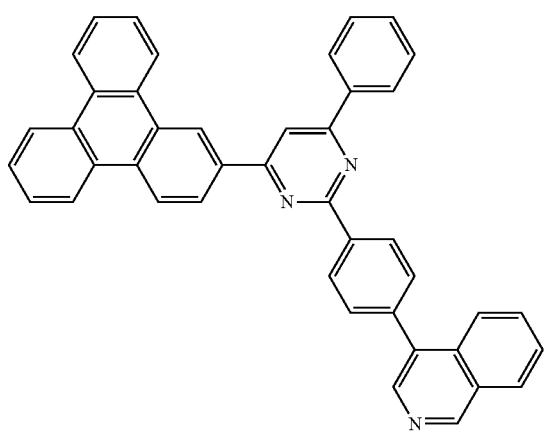

-continued
293
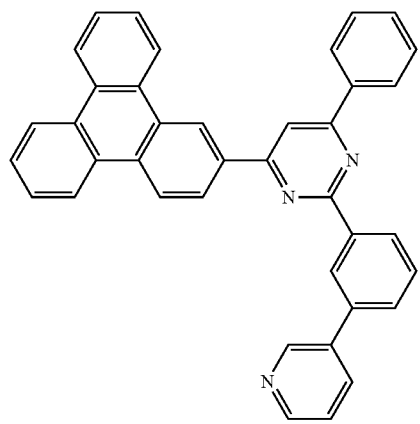
294
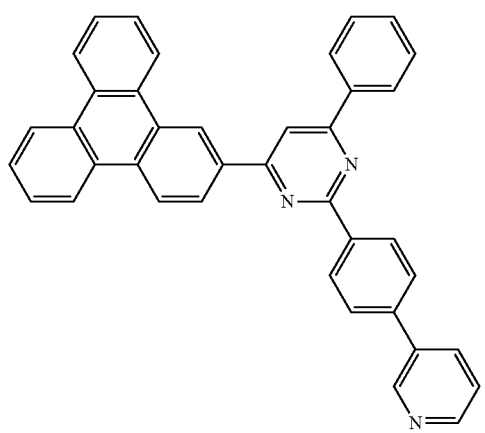
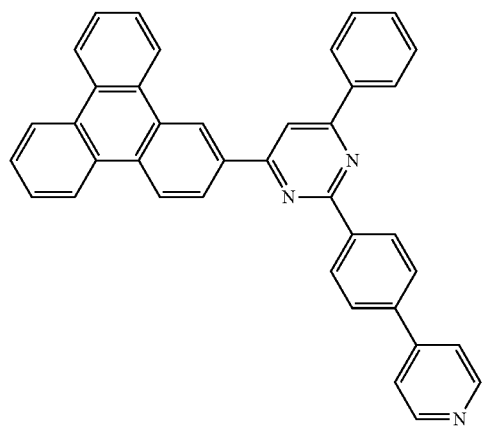
[Formula 133]
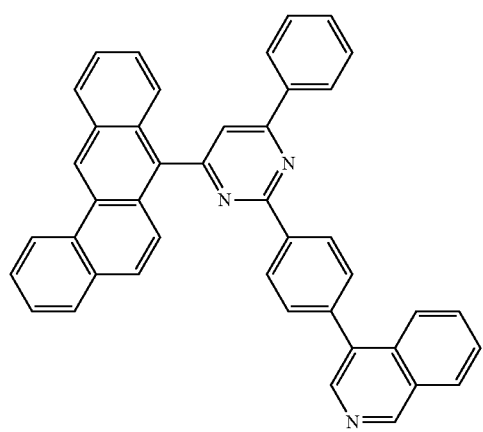
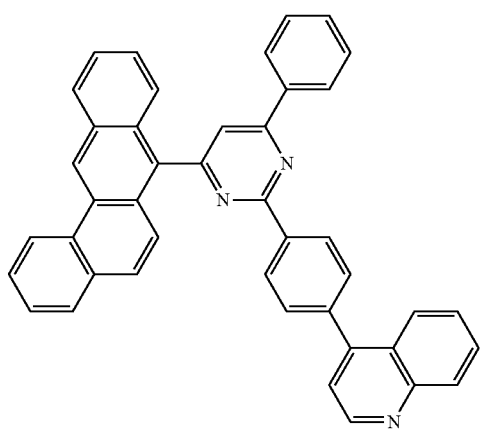

295
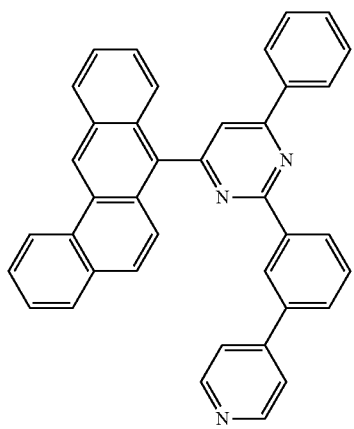
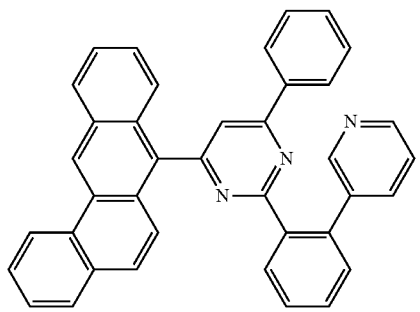
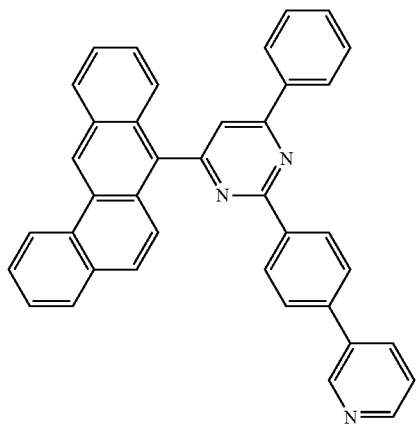
296
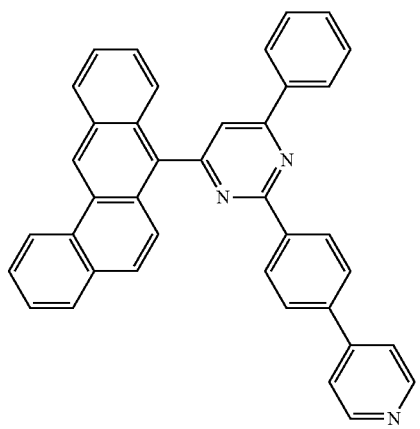
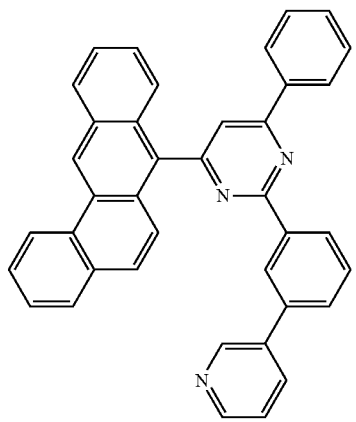
[Formula 134]
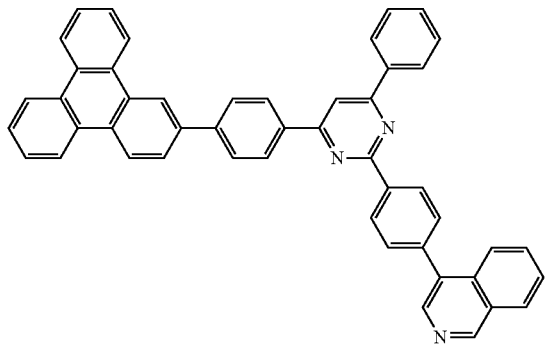
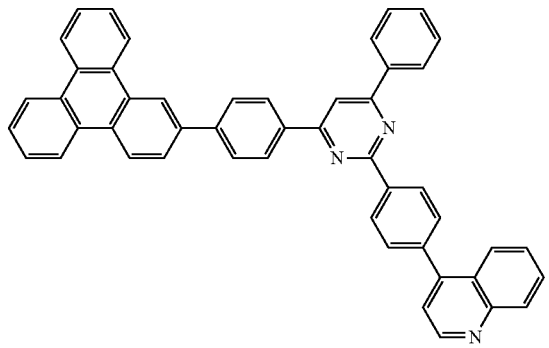

297
-continued
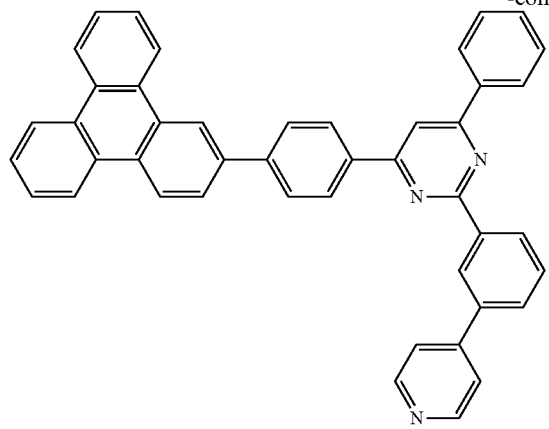
298
[Formula 135]
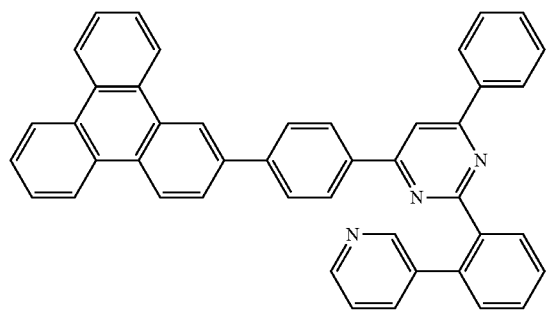
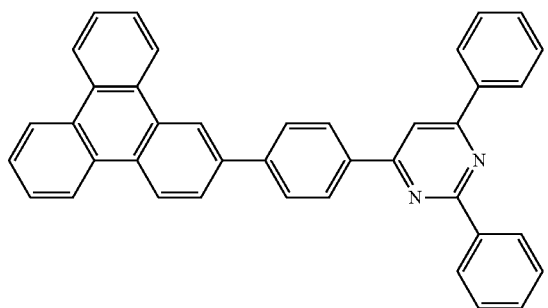
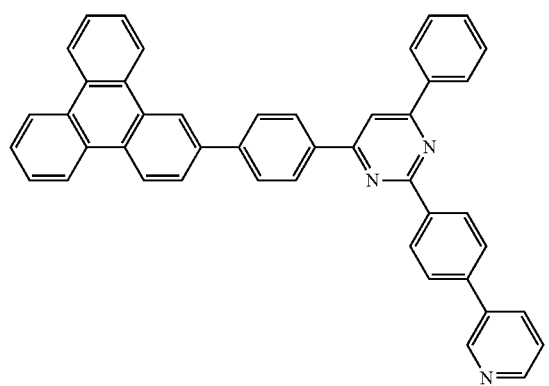
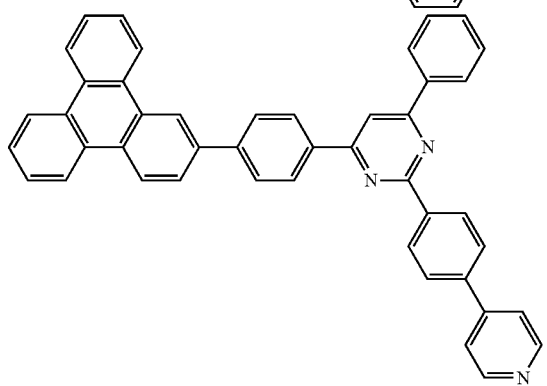
[Formula 136]
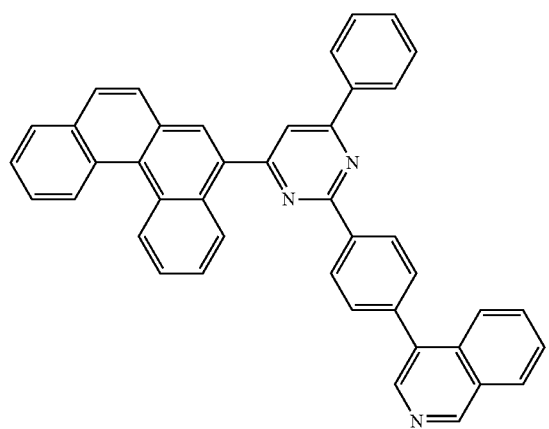
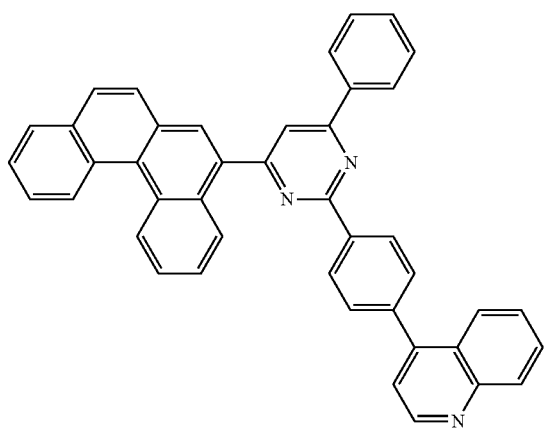

299 300
-continued
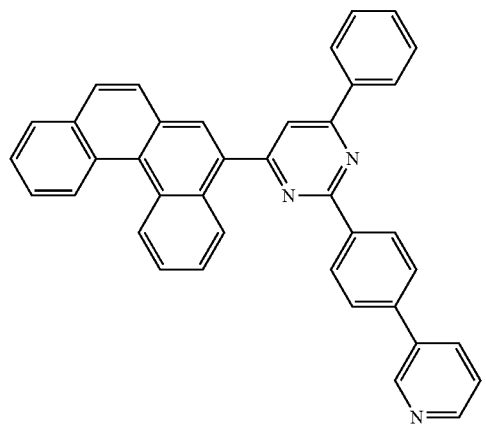
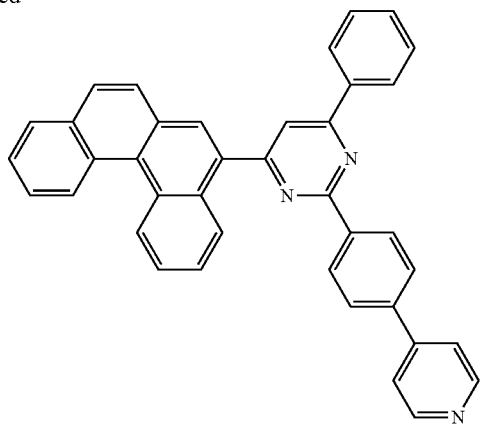
[Formula 137]
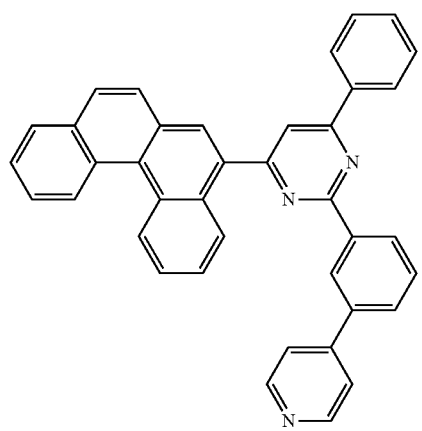
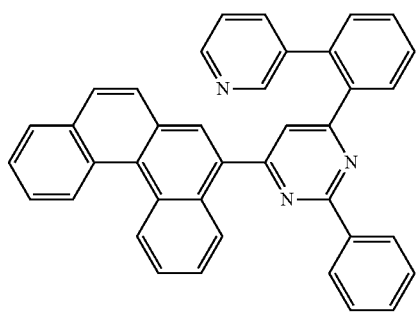
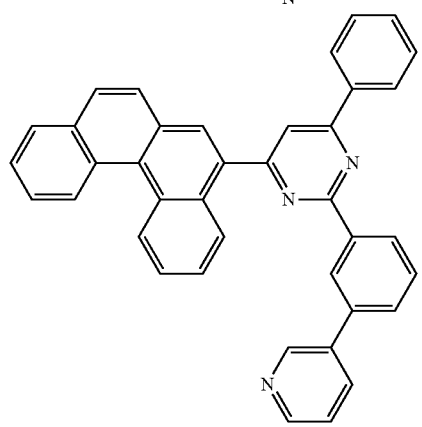
[Formula 138]
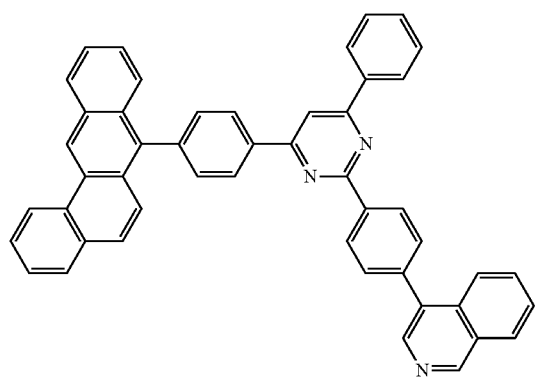
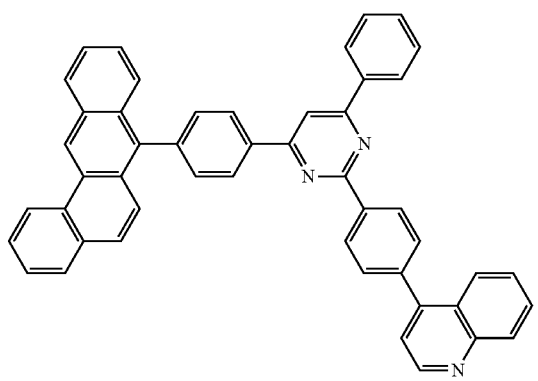

-continued
301  302
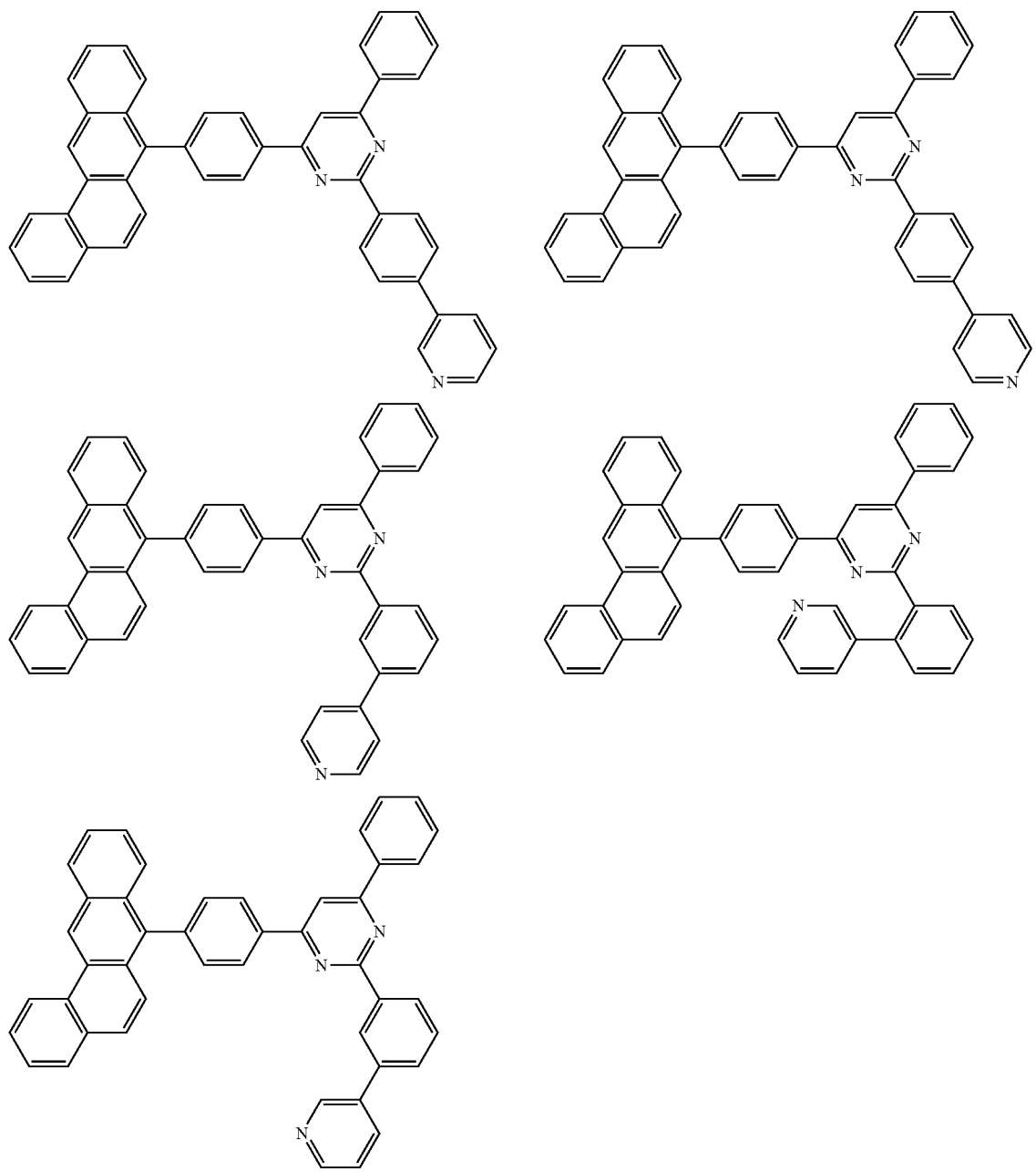
[Formula 139]
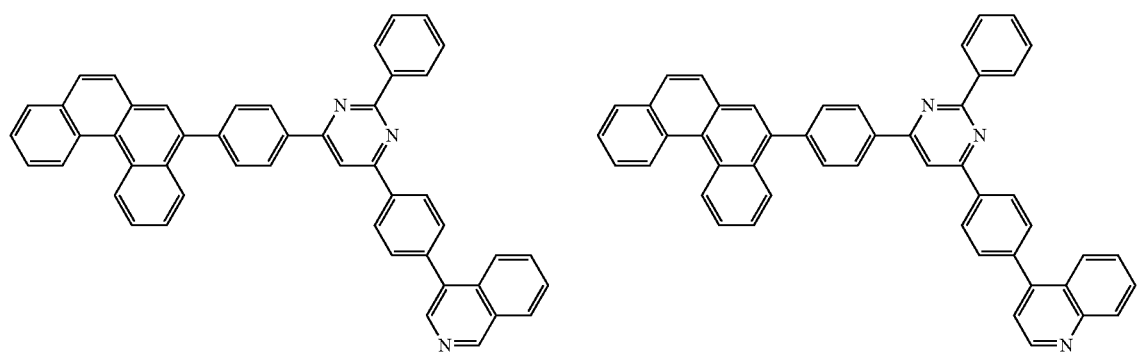

-continued
303
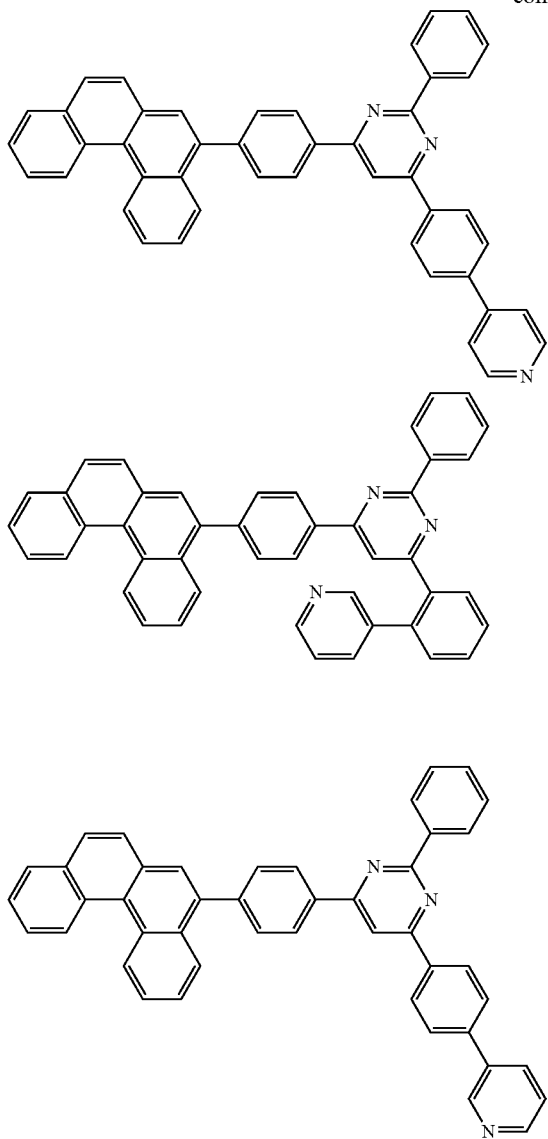
304
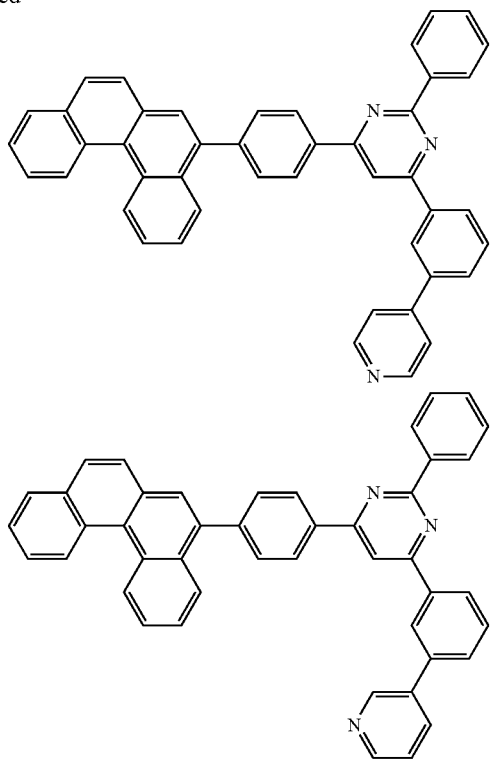
[Formula 140]
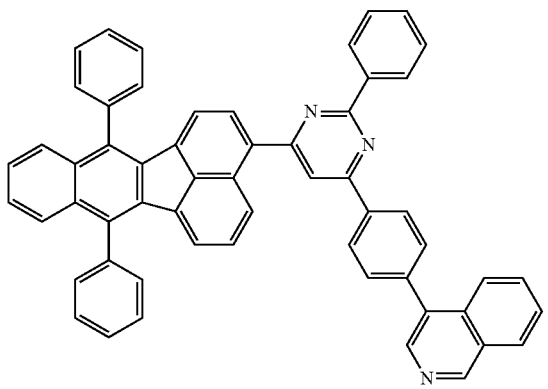 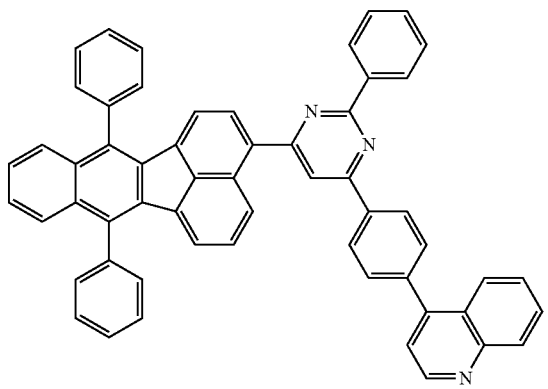

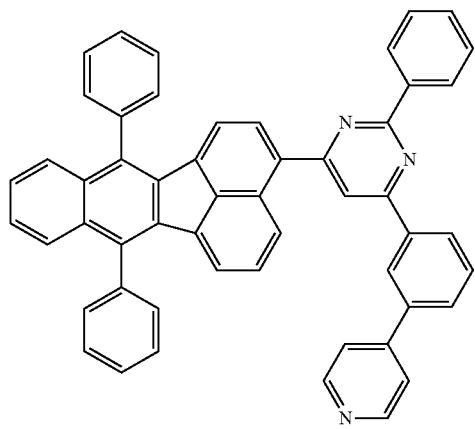
[Formula 141]
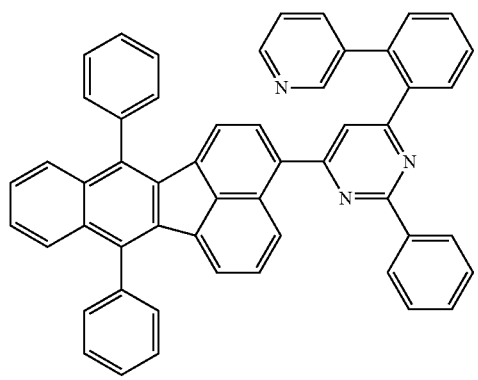
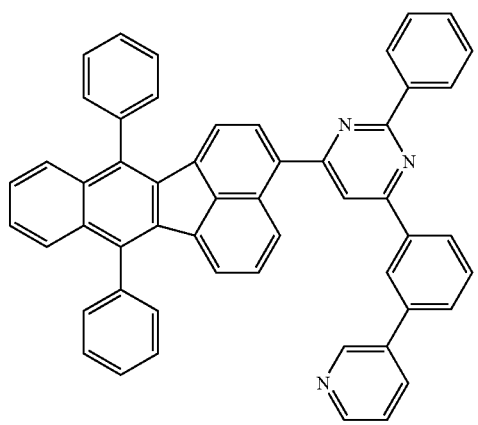
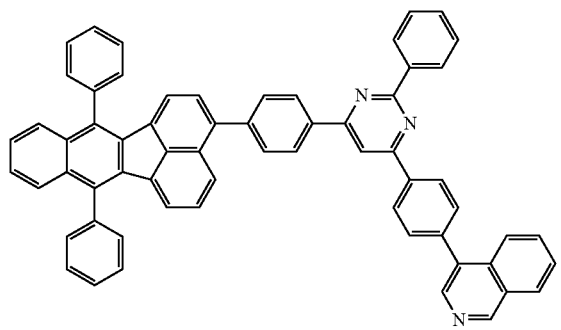
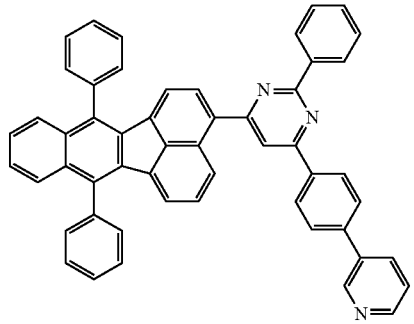
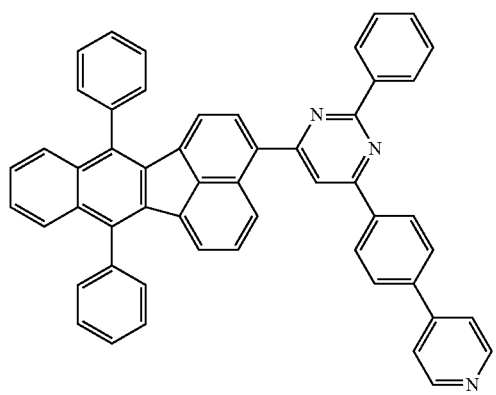
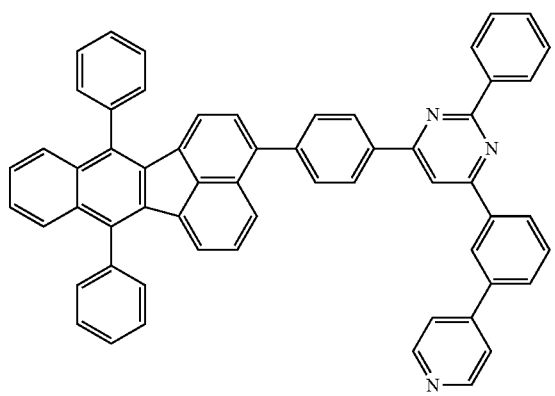

307 308
-continued
[Formula 142]
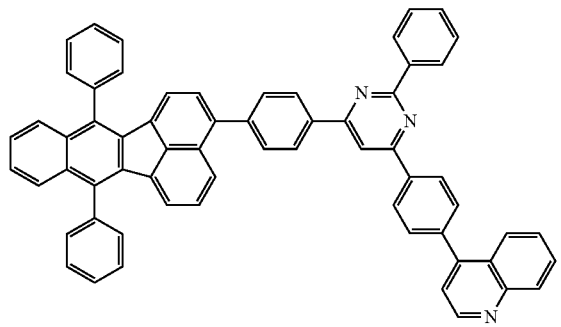 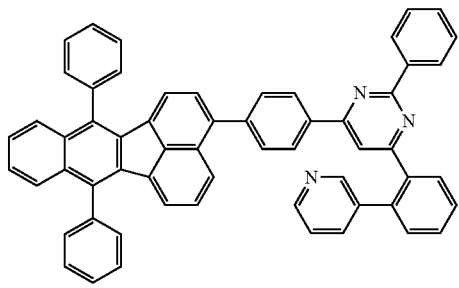
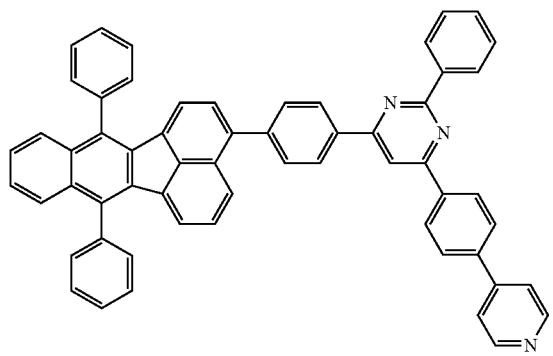 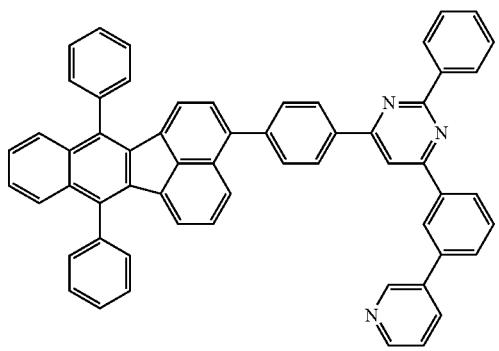
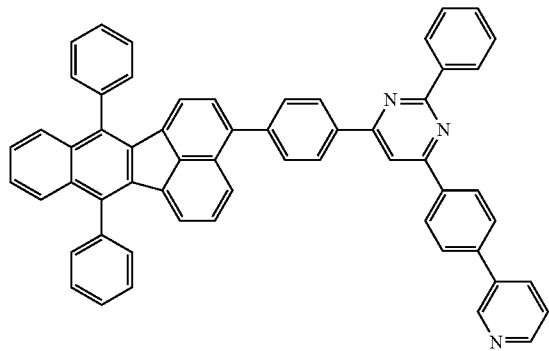
[Formula 143]
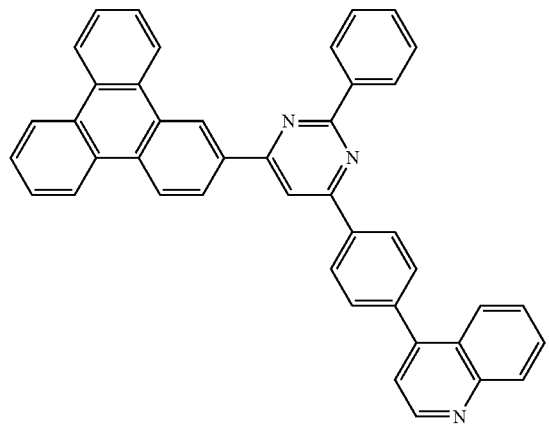 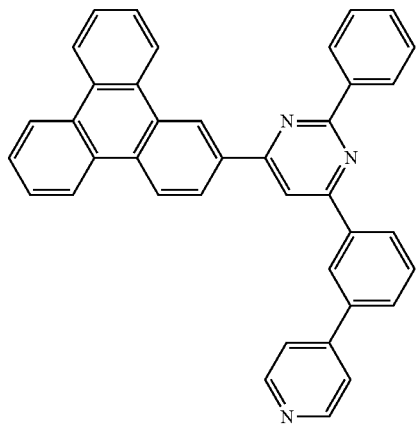

309
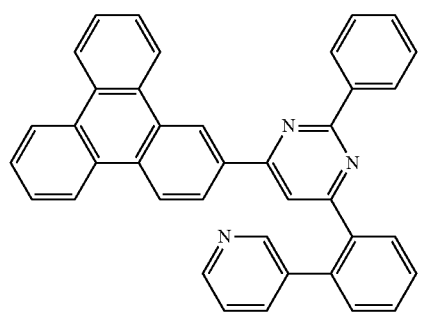
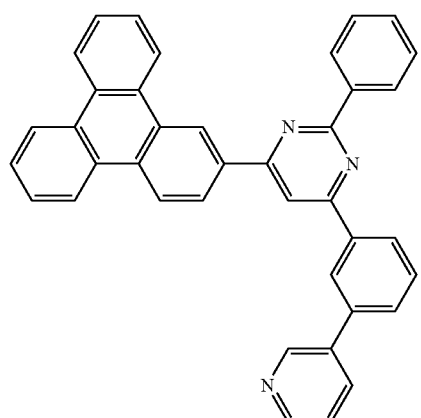
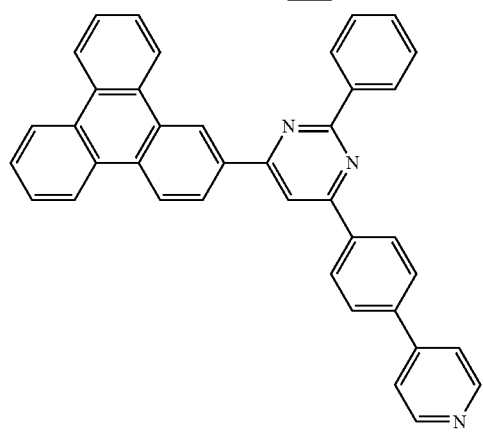
[Formula 144]
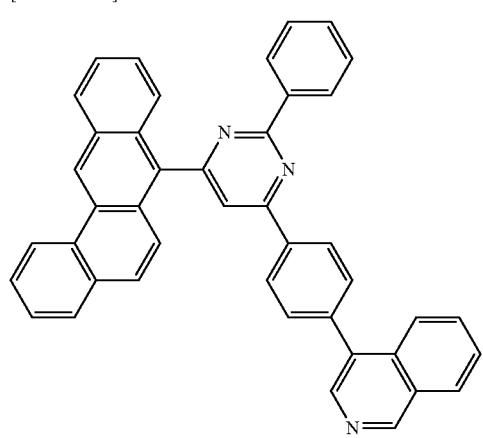
310
-continued
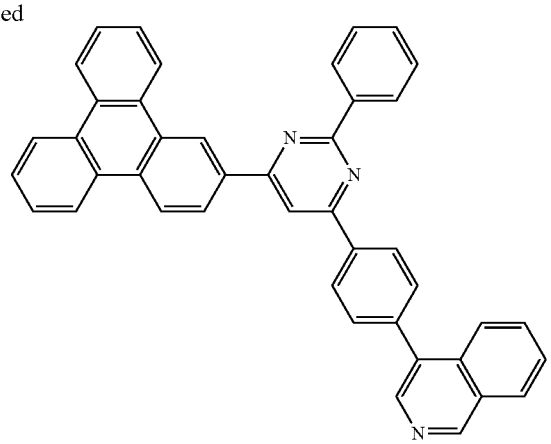
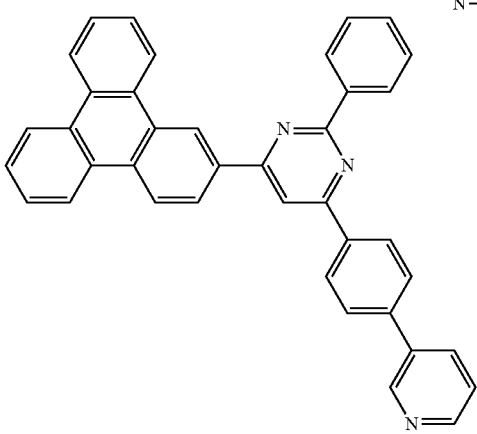
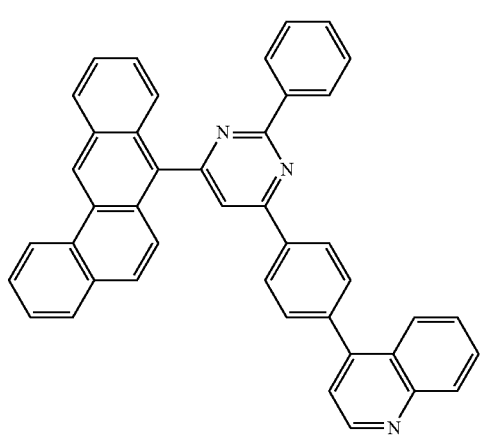

-continued
311
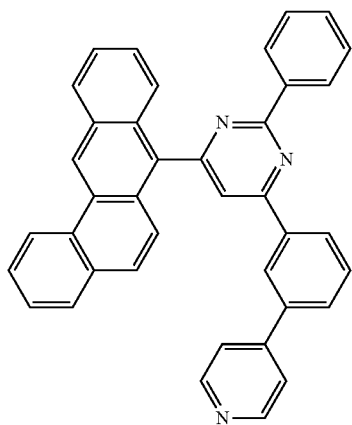
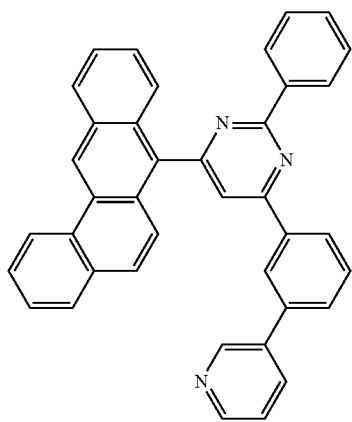
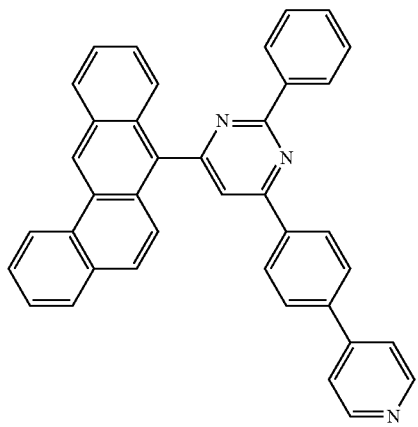
312
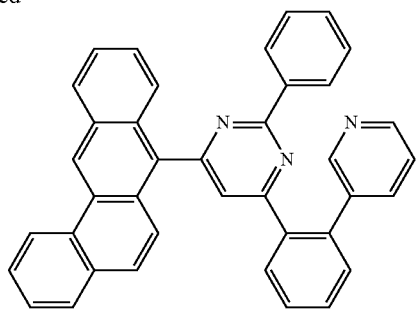
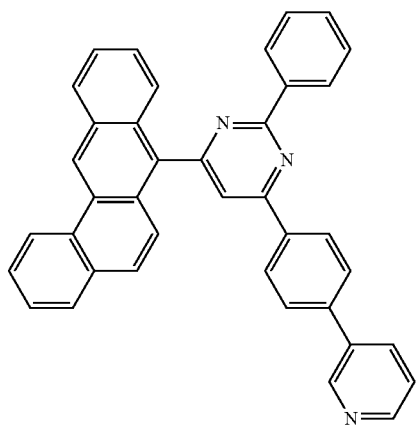
[Formula 145]
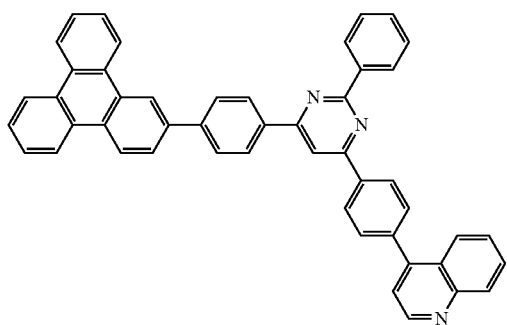
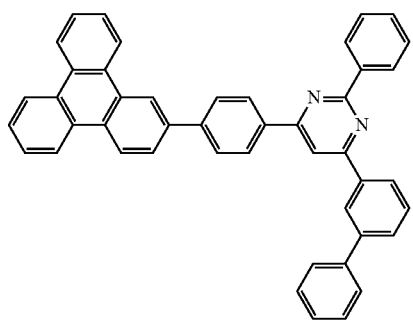

-continued
313
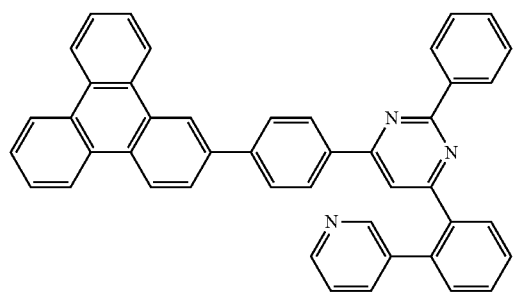
314
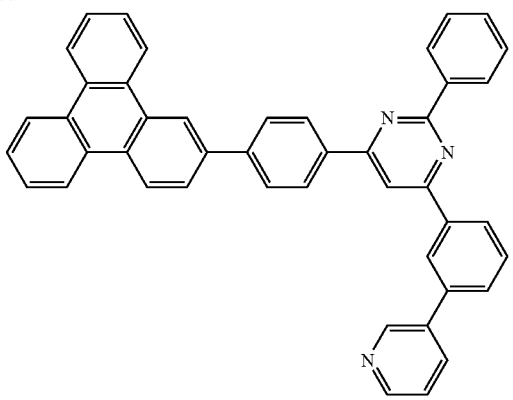
[Formula 146]
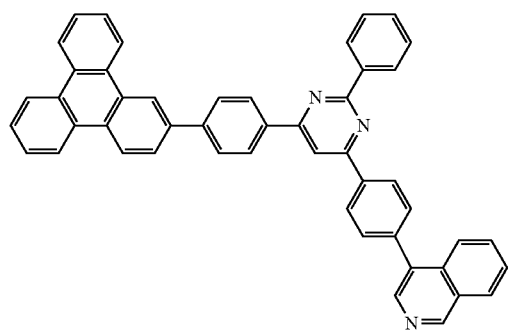
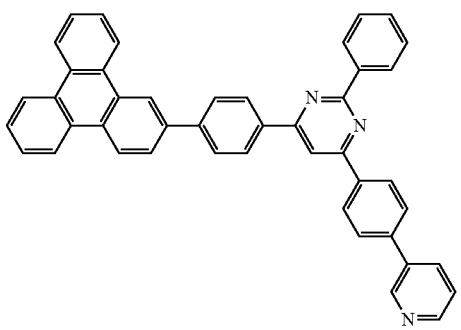
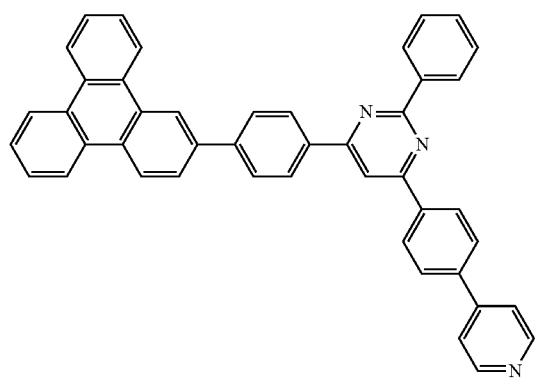
[Formula 147]
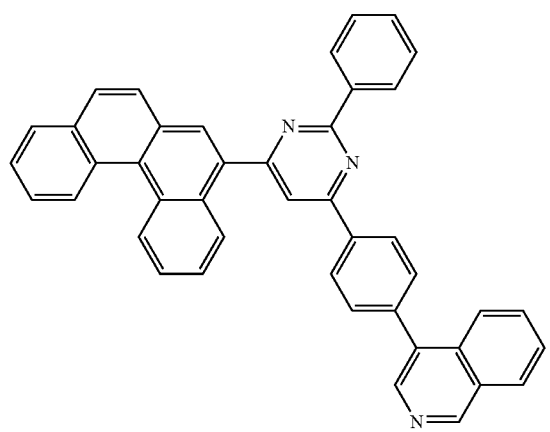
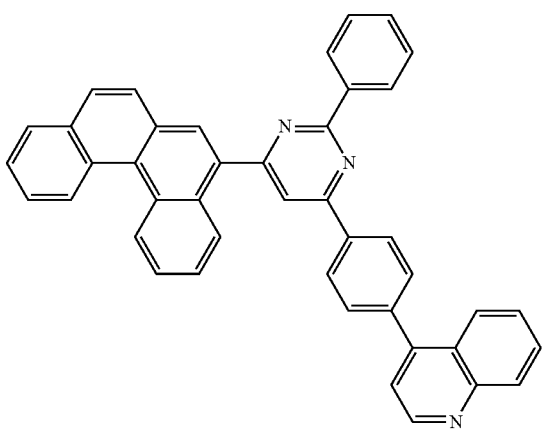

315
316
-continued
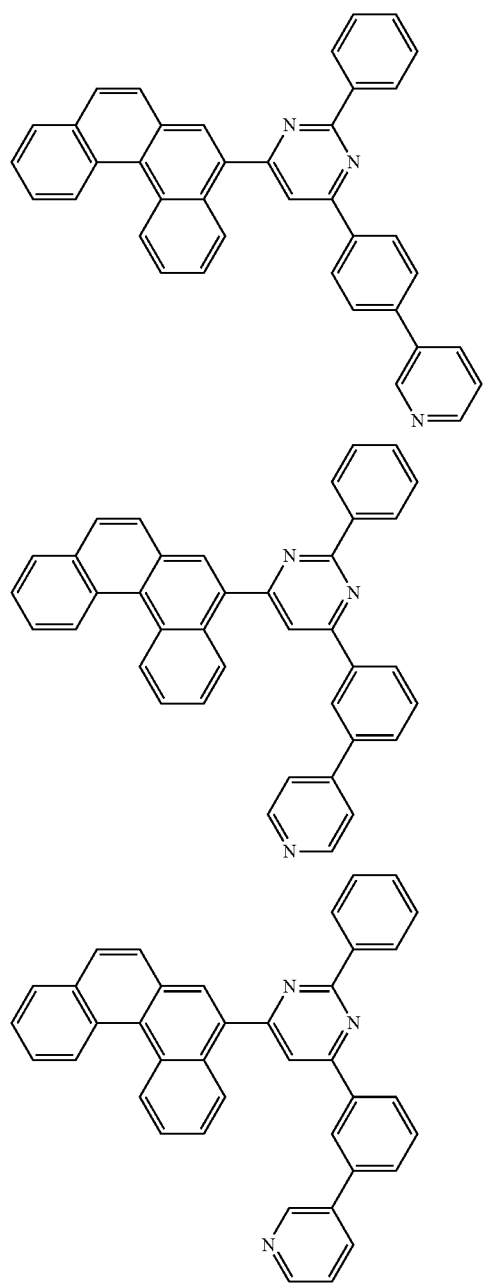
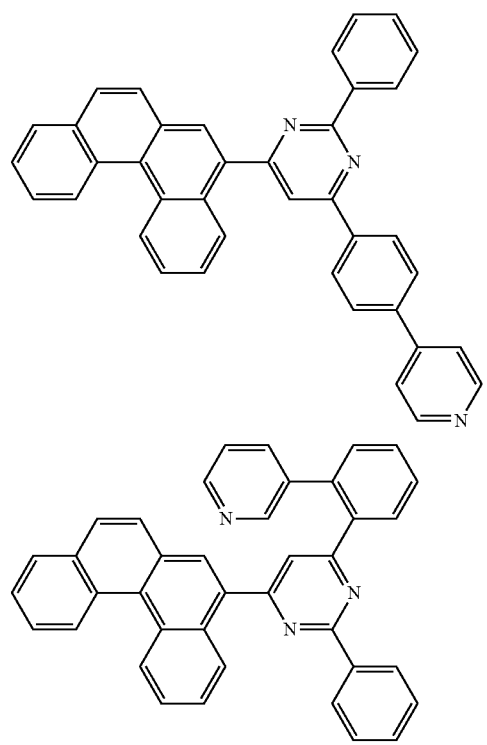
[Formula 148]
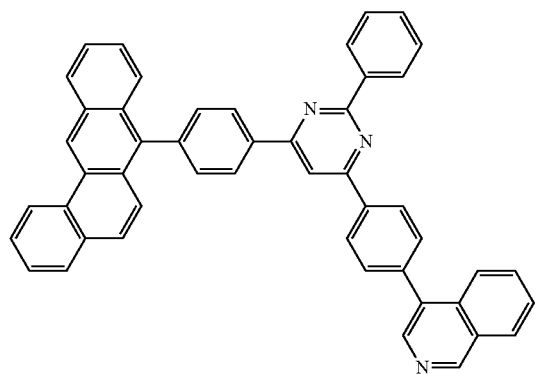
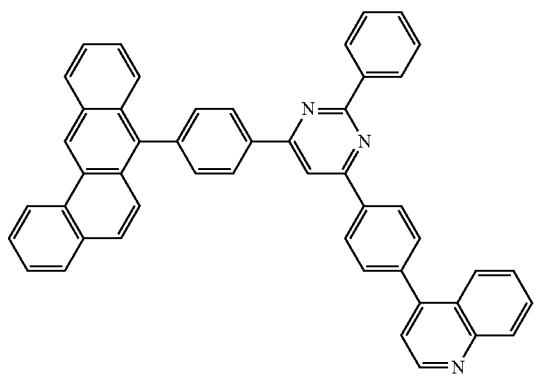

-continued
317
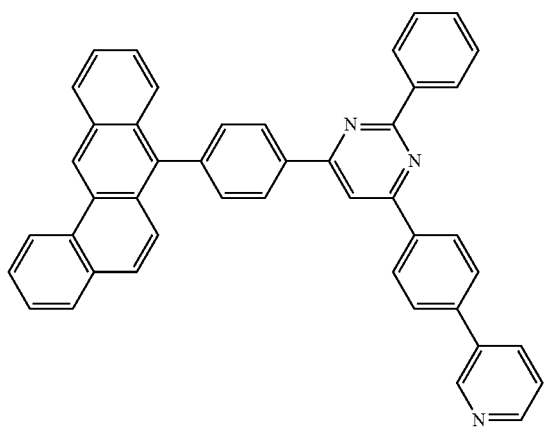
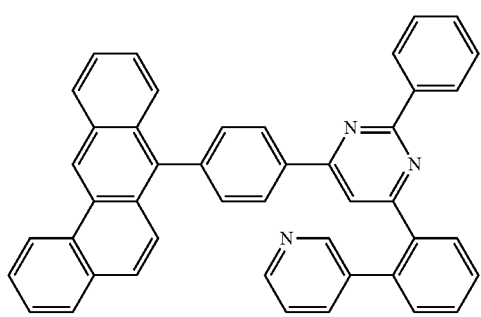
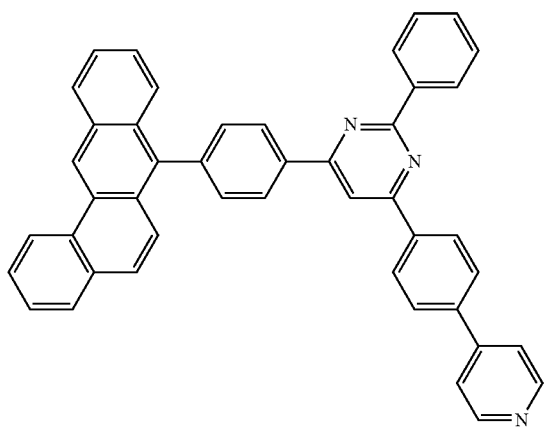
318
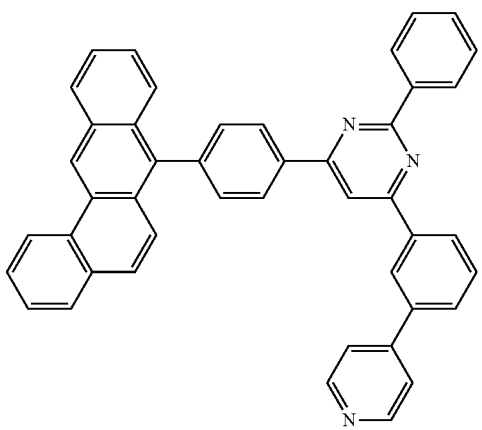
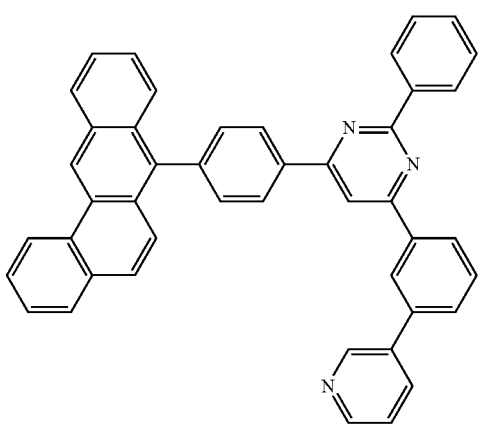
[Formula 149]
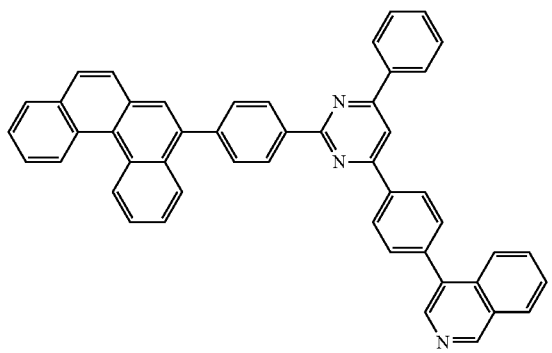
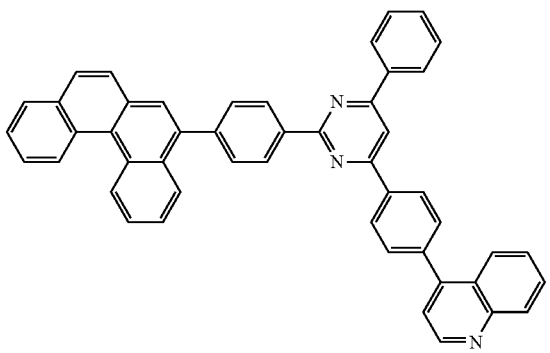

-continued
319
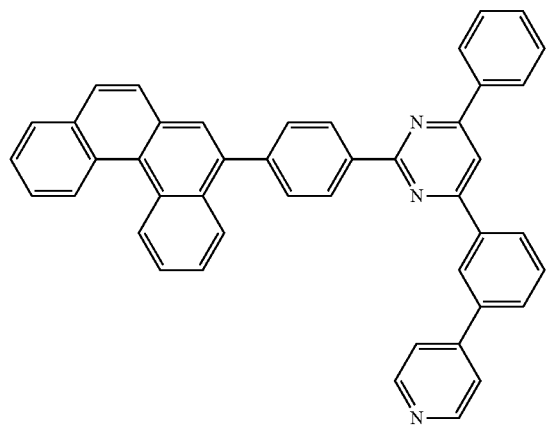
320
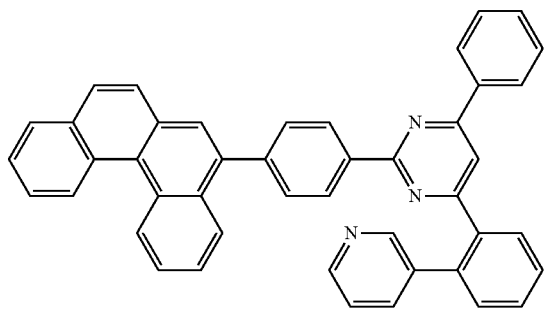
[Formula 150]
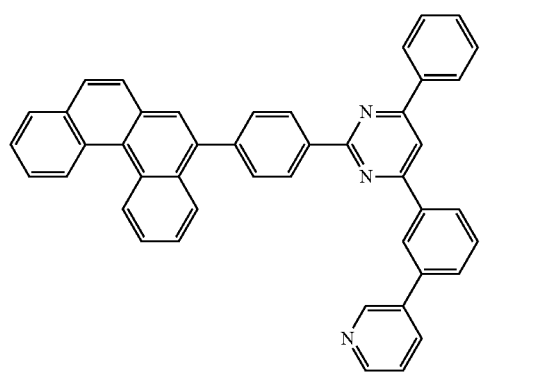
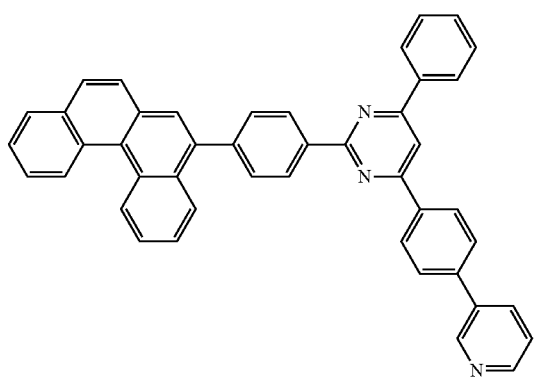
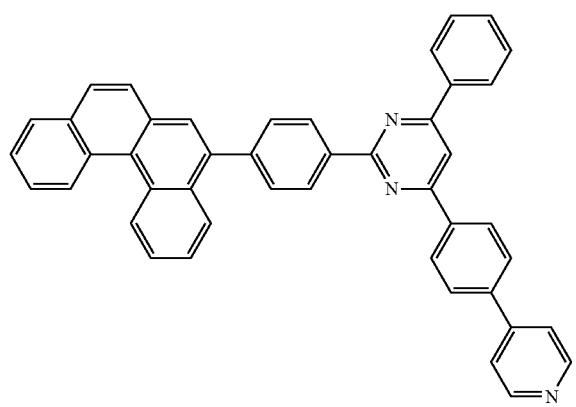
[Formula 151]
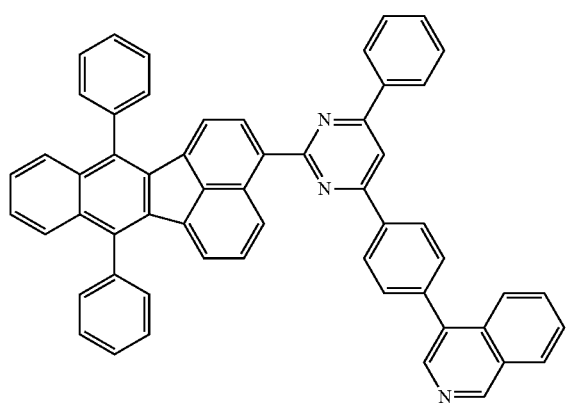
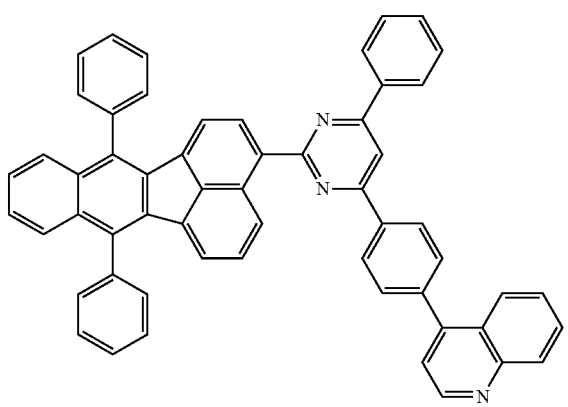

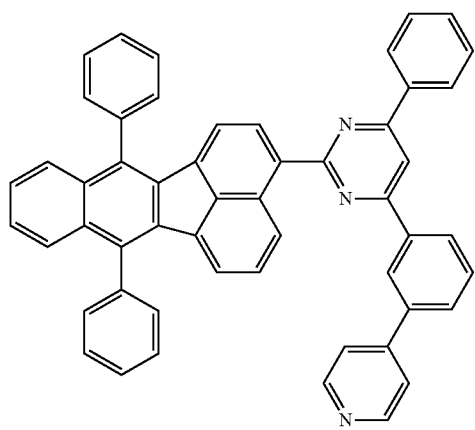
[Formula 152]
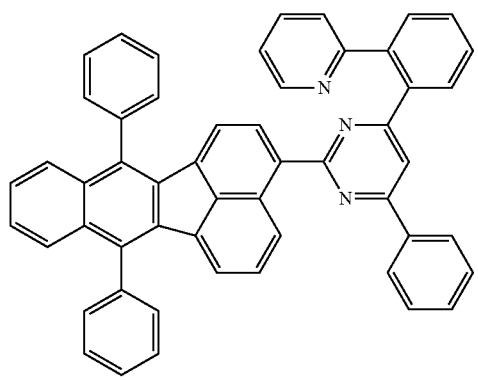
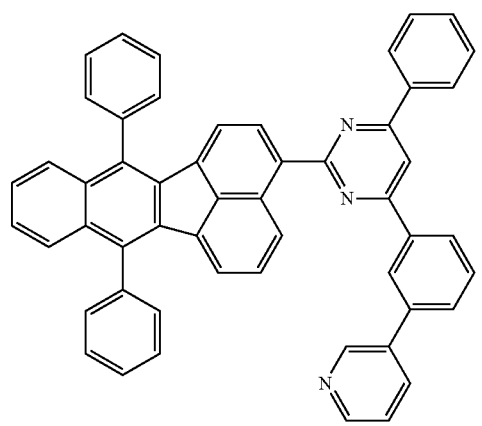
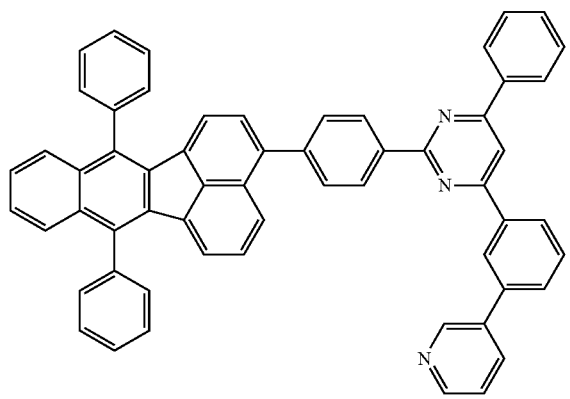
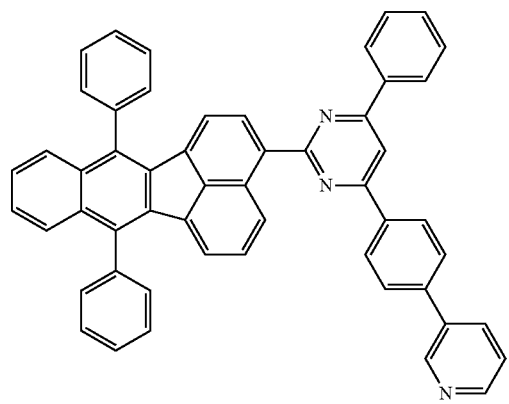
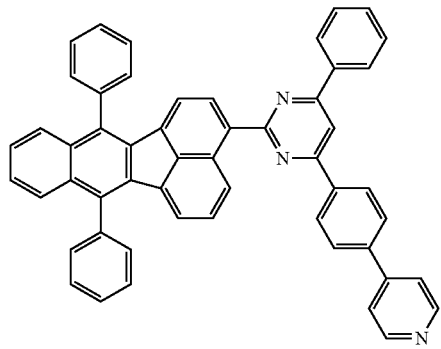
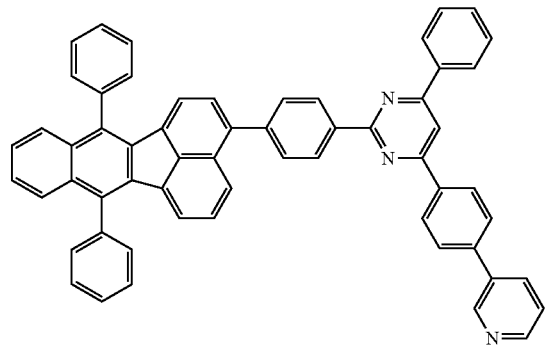

[Formula 153]
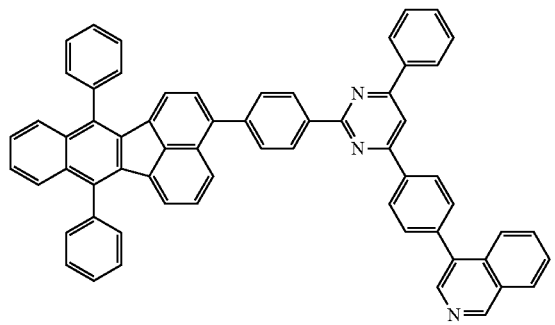
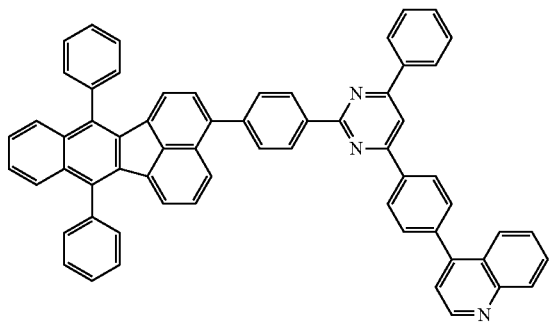
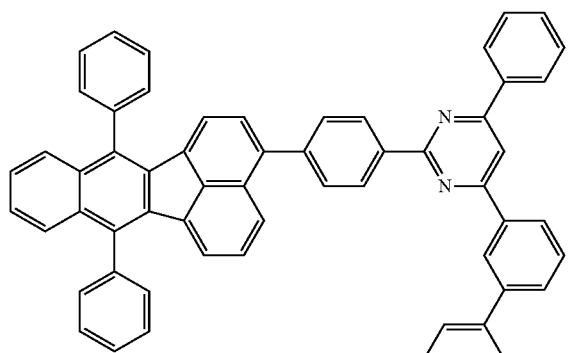
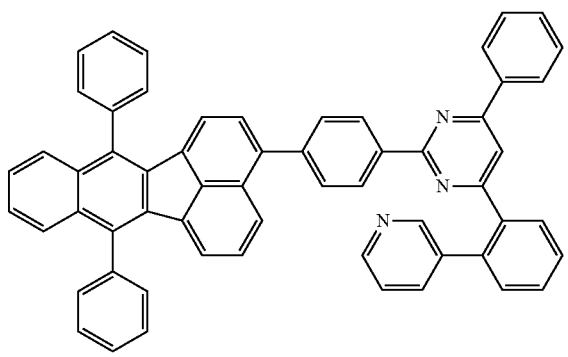
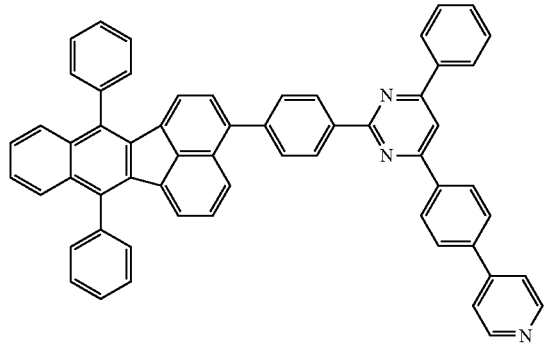
[Formula 154]
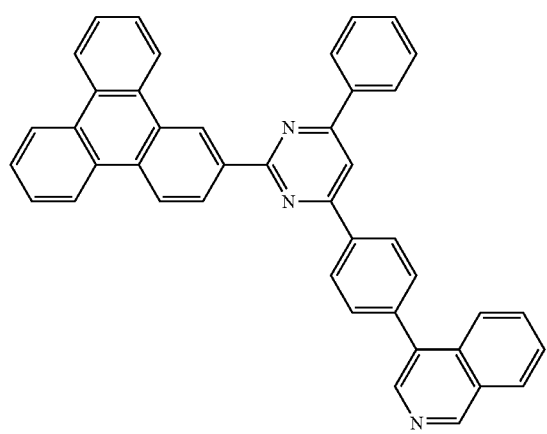
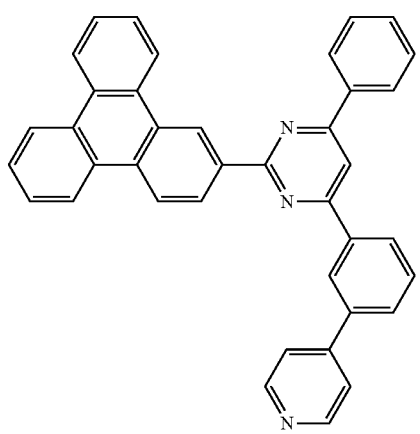

-continued
325
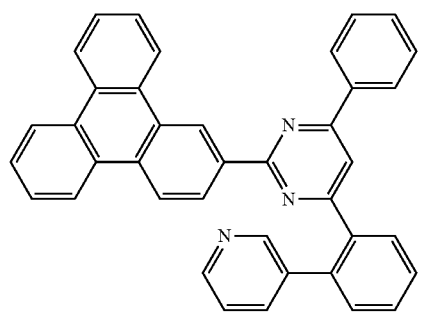
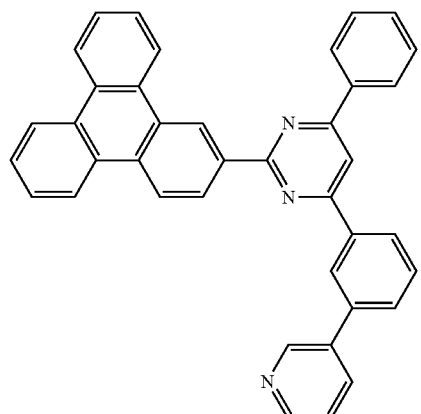
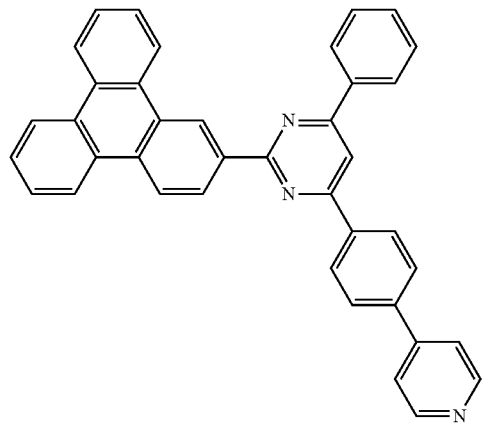
[Formula 155]
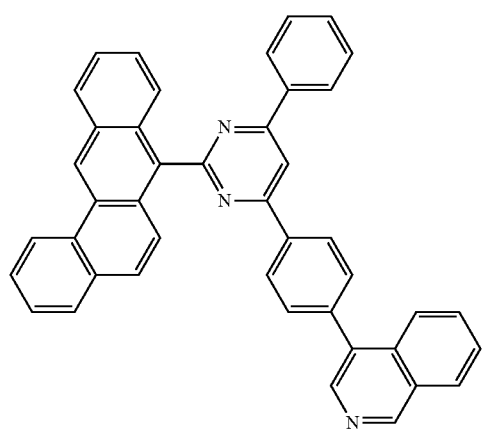
326
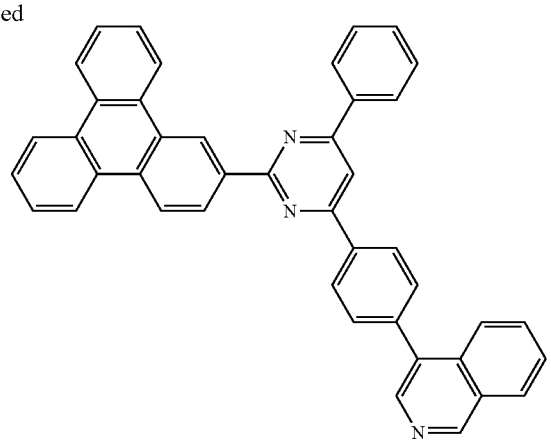
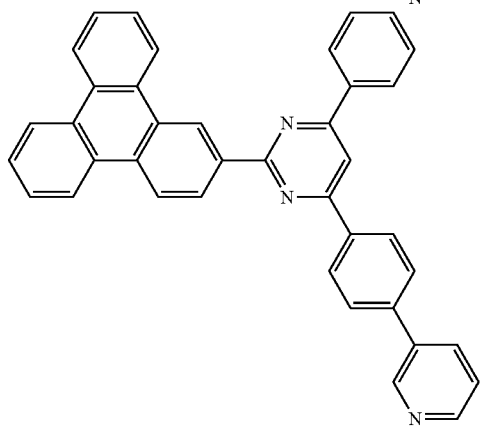
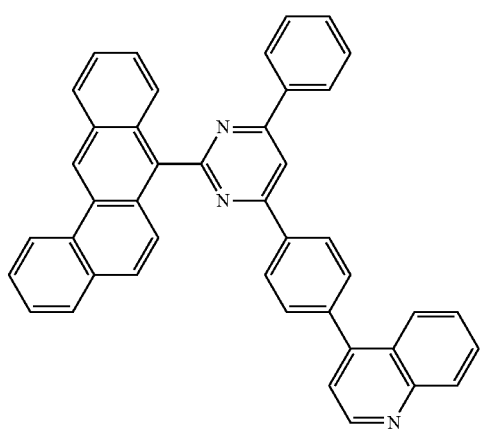

-continued
327
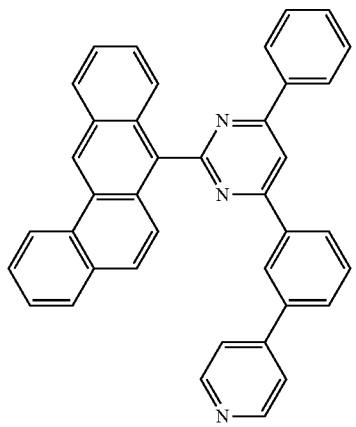
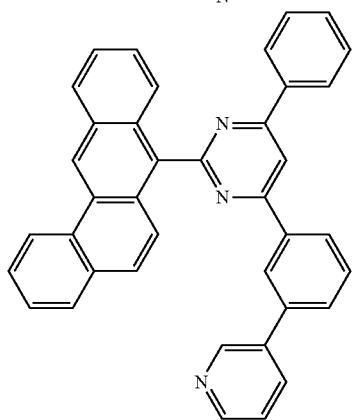
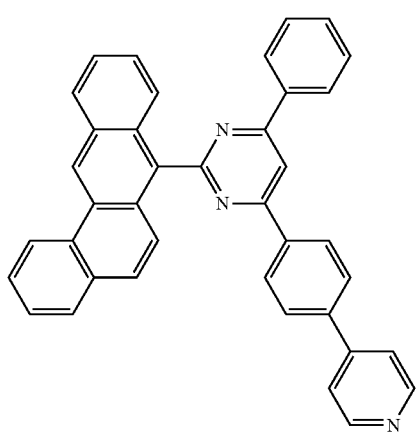
328
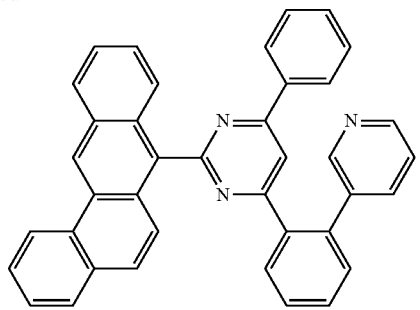
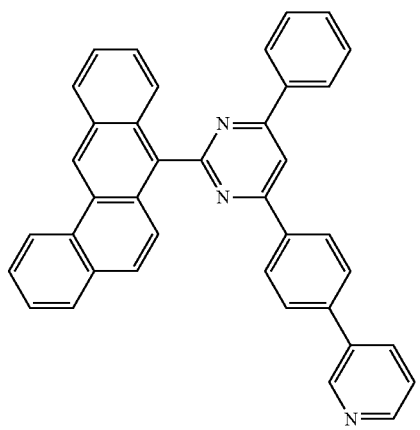
[Formula 156]
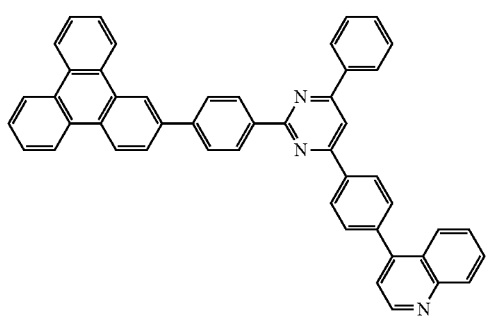
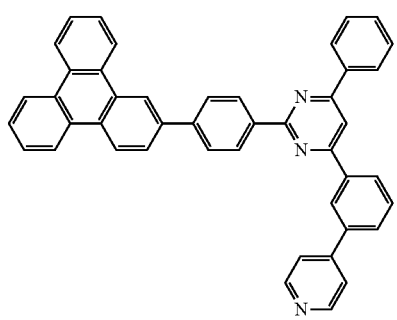

329 330
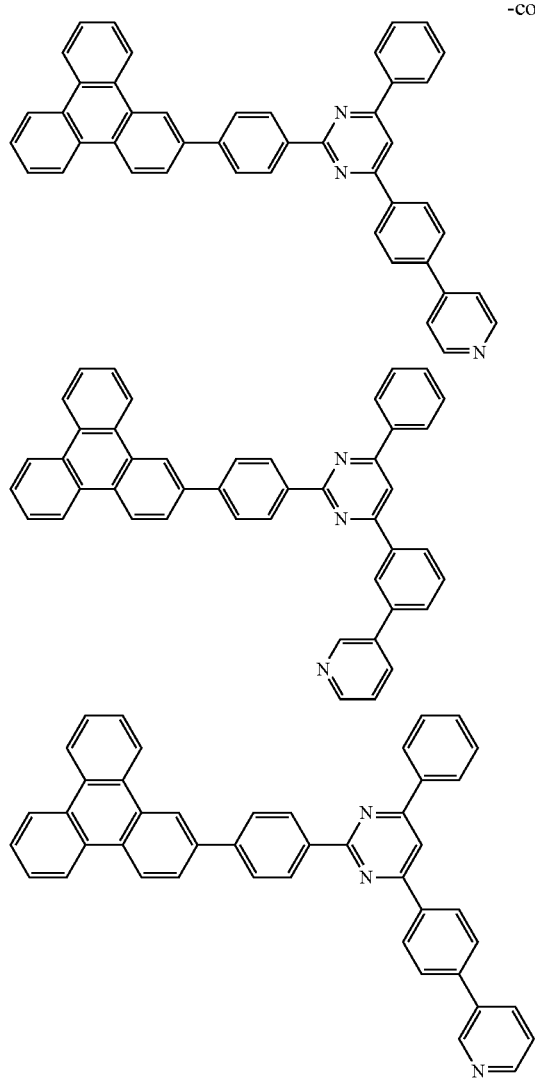
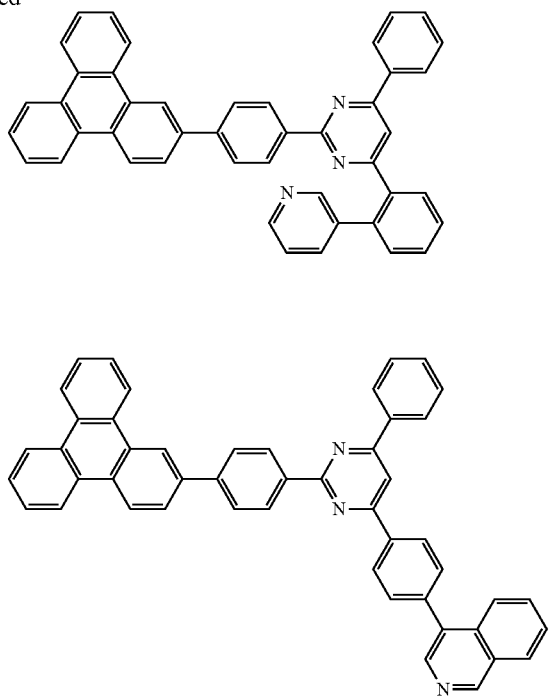
[Formula 157]
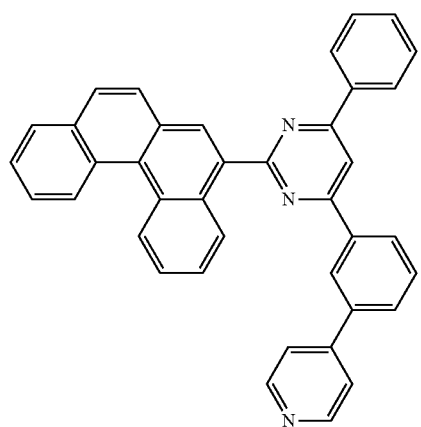
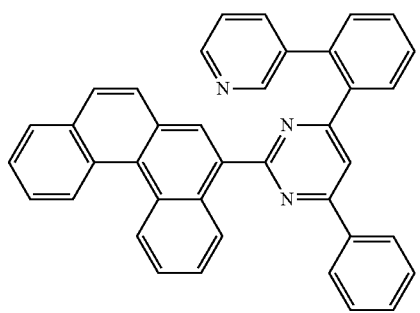

331 332
-continued
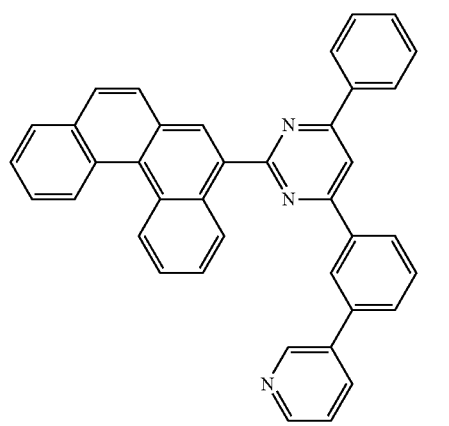
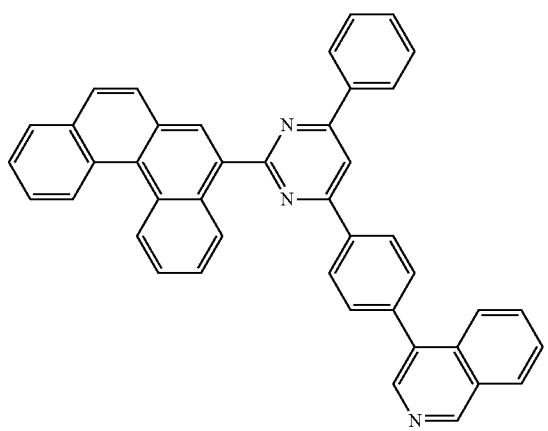
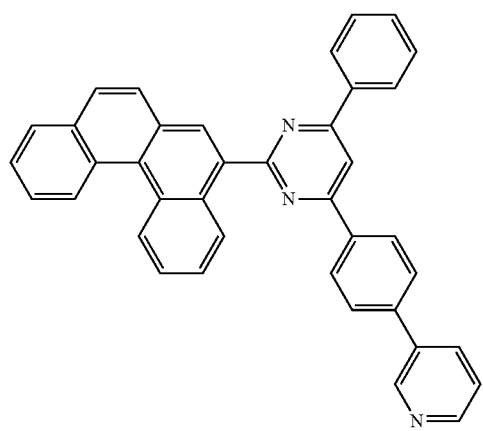
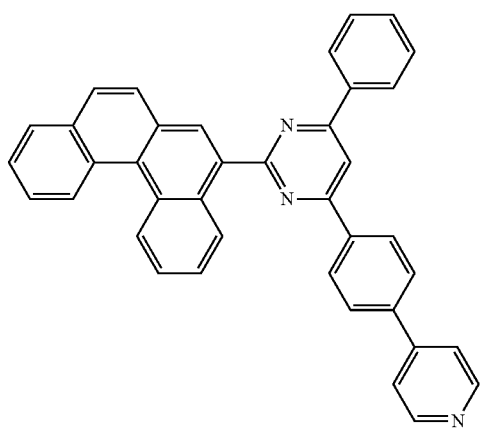
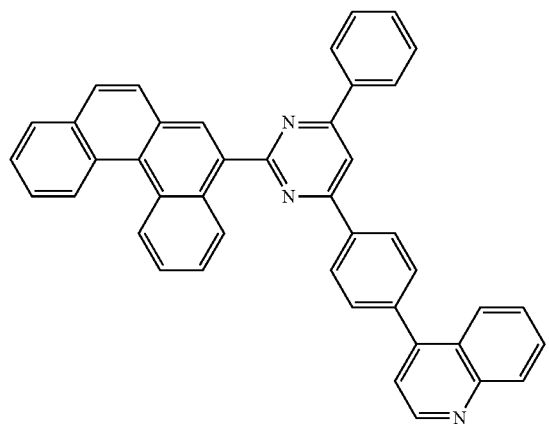
[Formula 158]
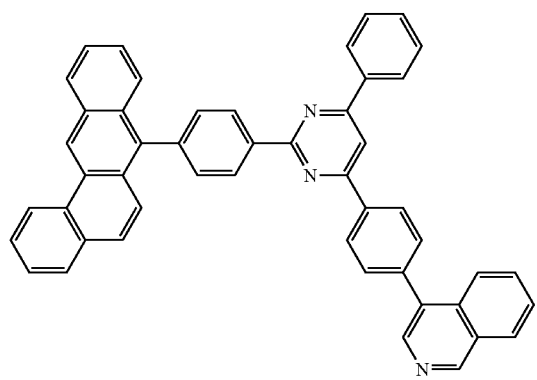
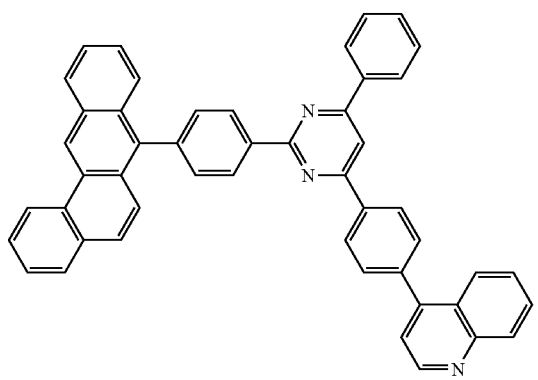

-continued
333
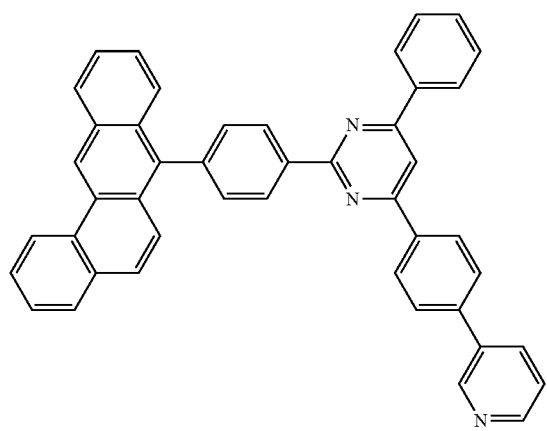
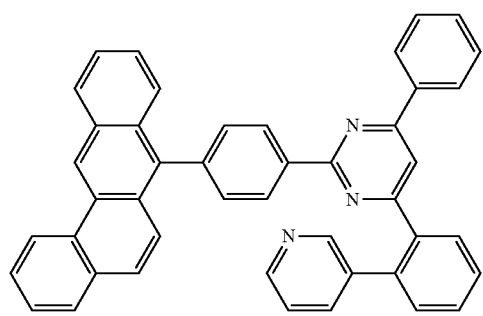
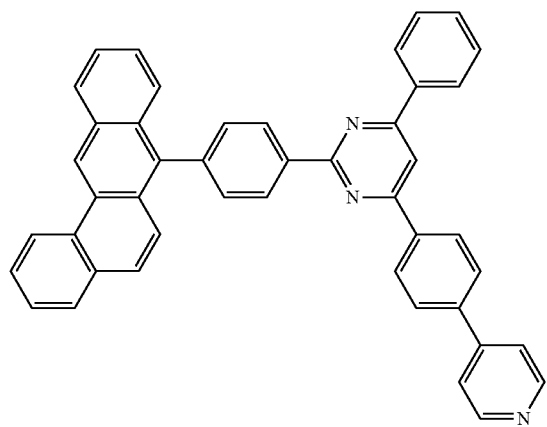
334
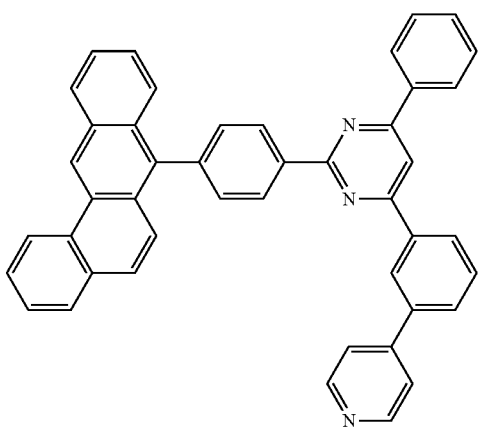
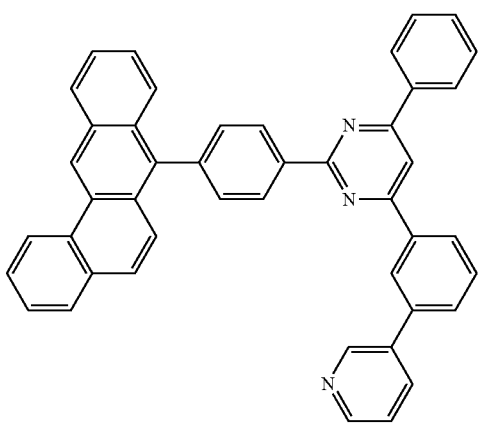
[Formula 159]
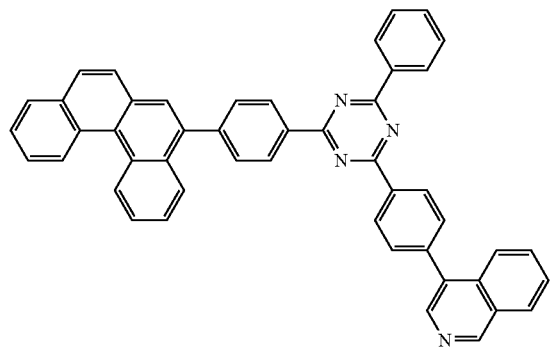
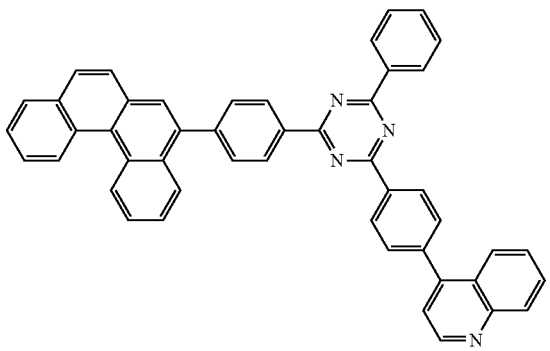

335
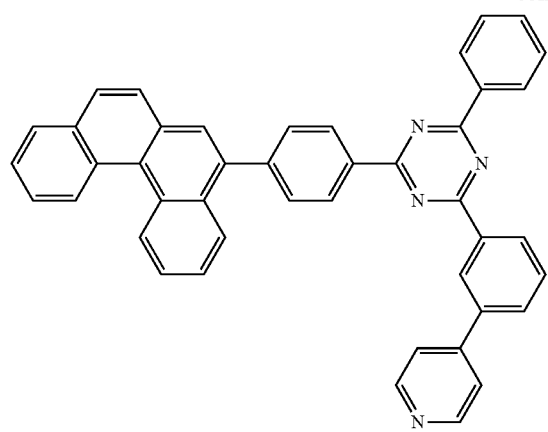
336
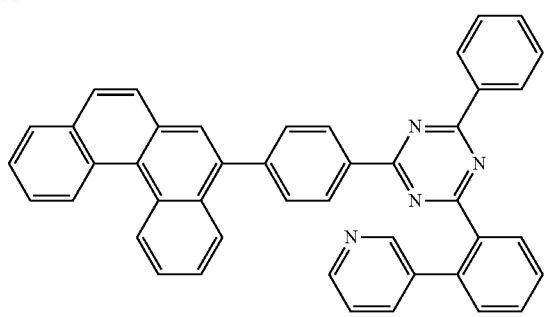
[Formula 160]
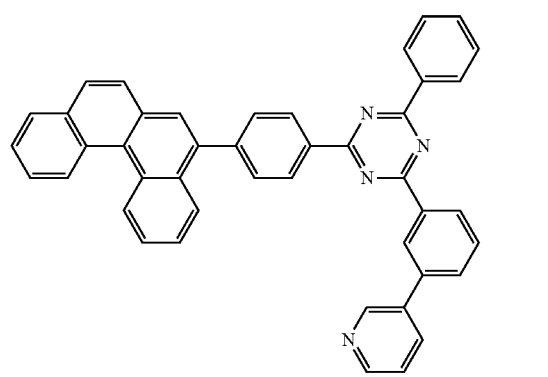
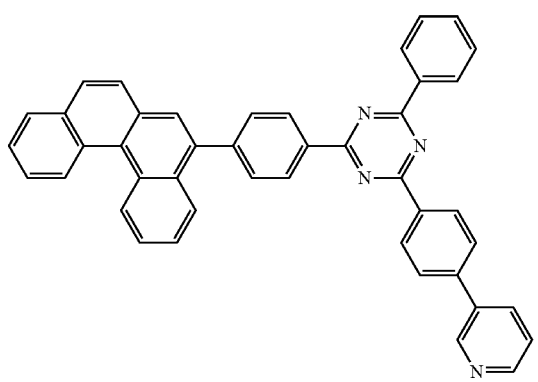
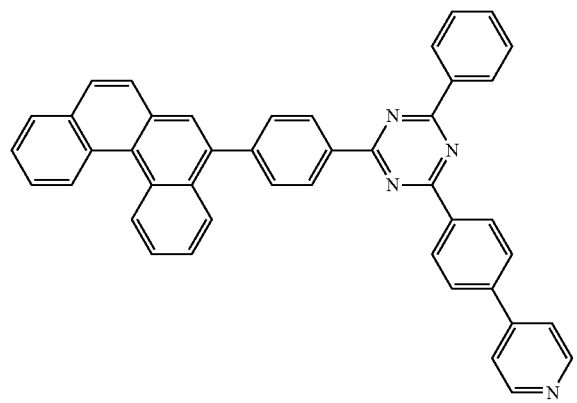
[Formula 161]
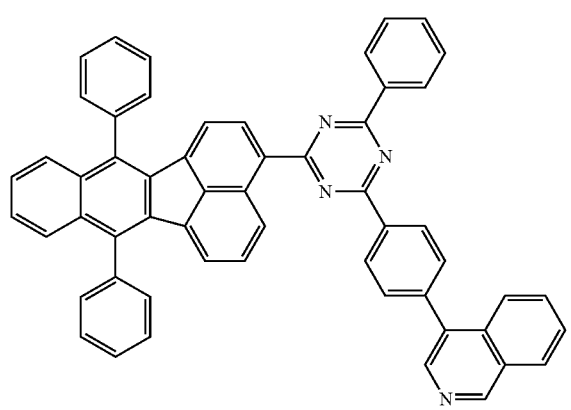
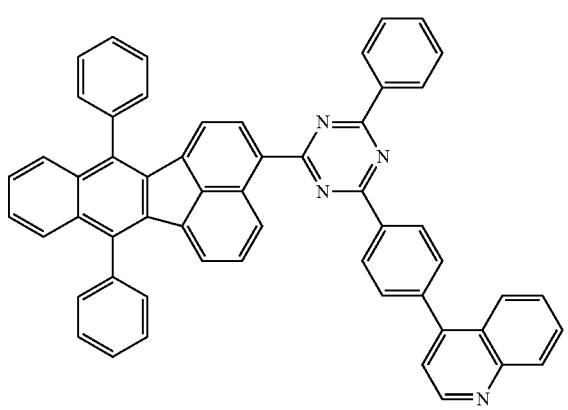

-continued
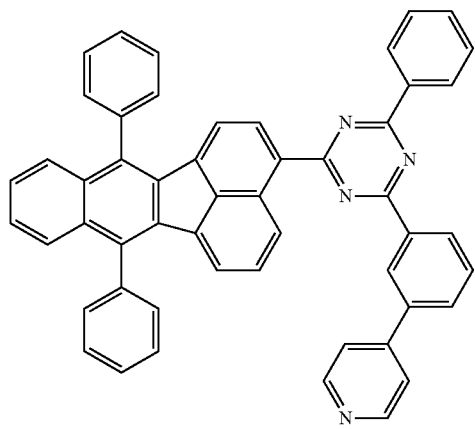
[Formula 162]
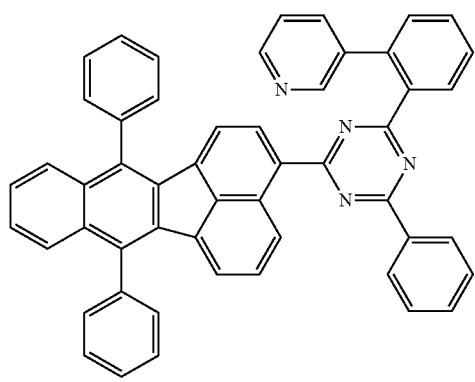
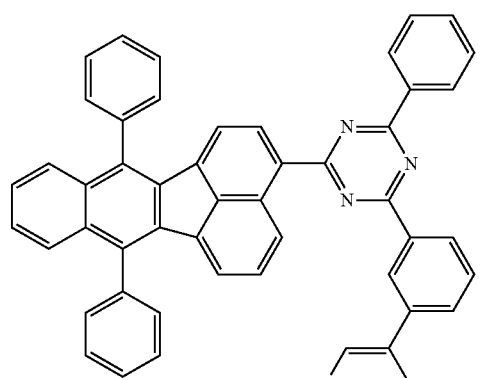
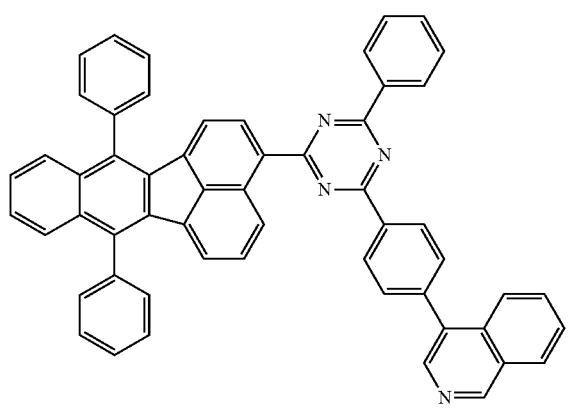
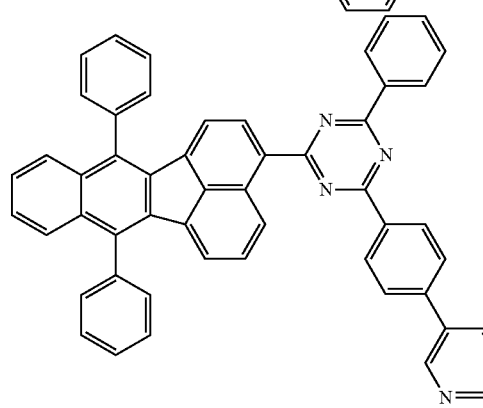
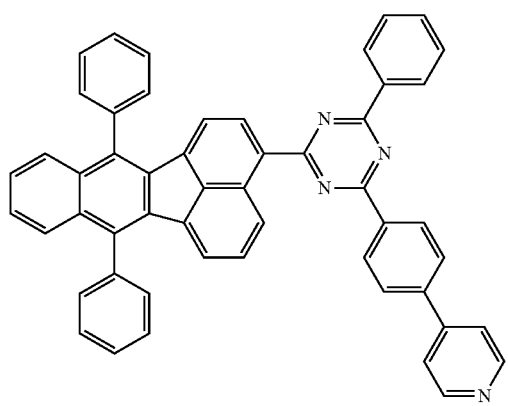
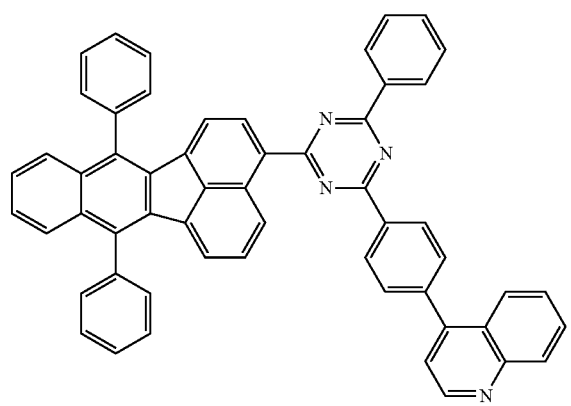

-continued
[Formula 163]
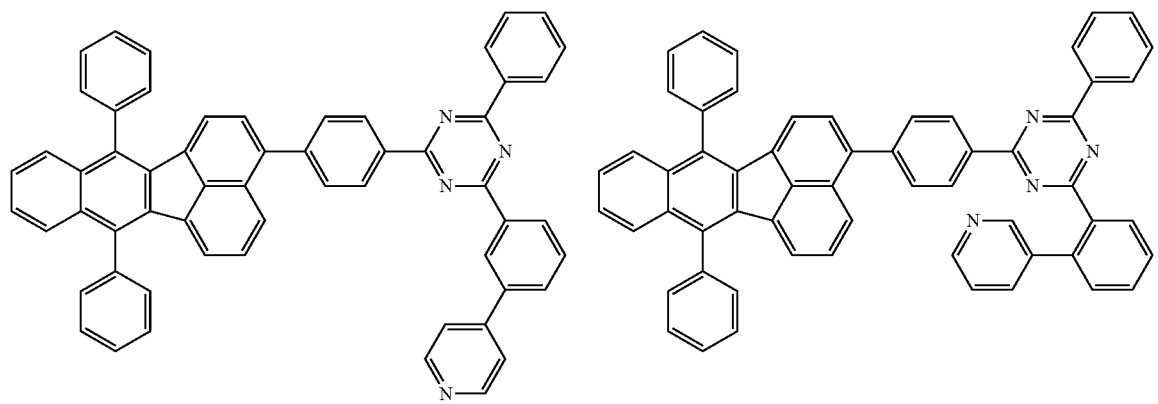
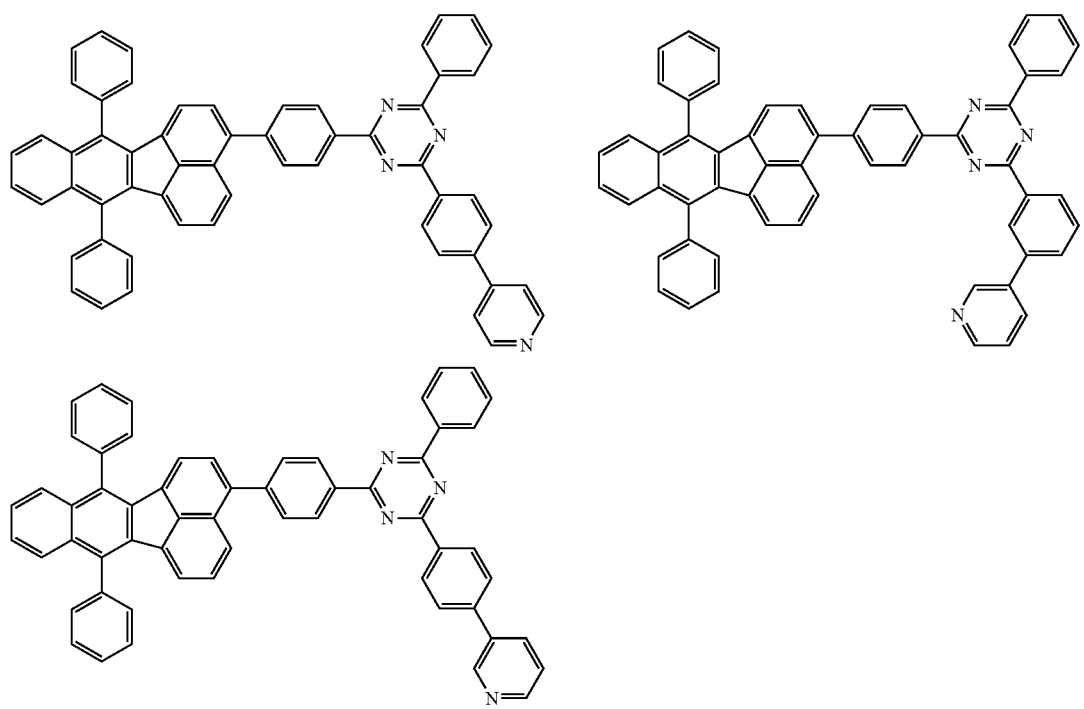
[Formula 164]
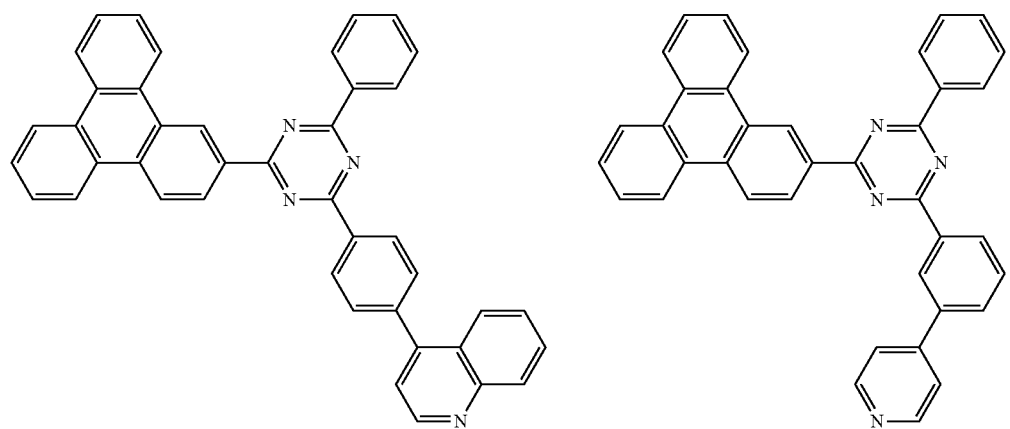

-continued
341
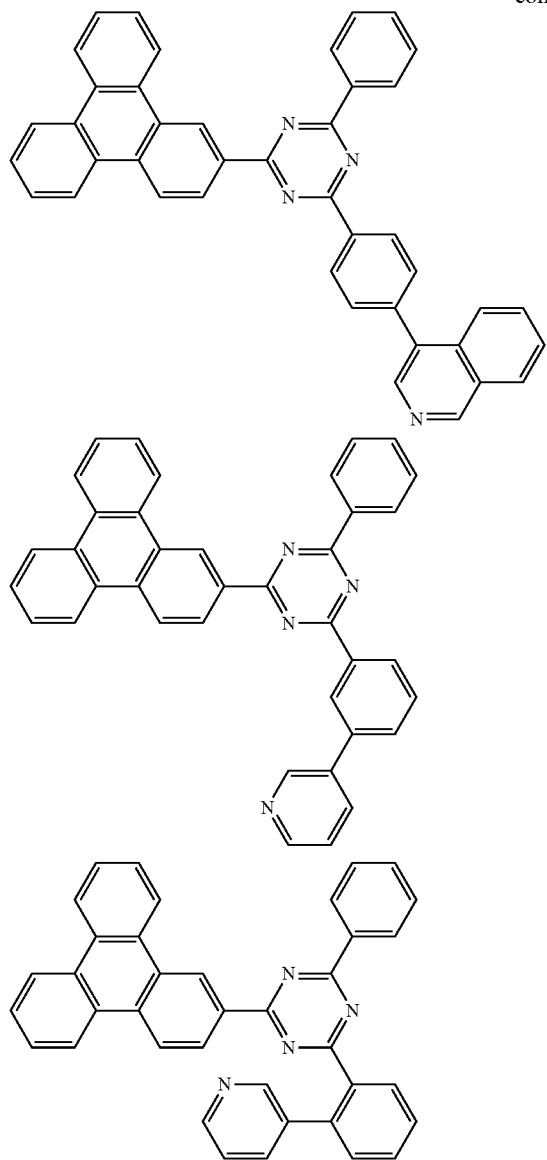
342
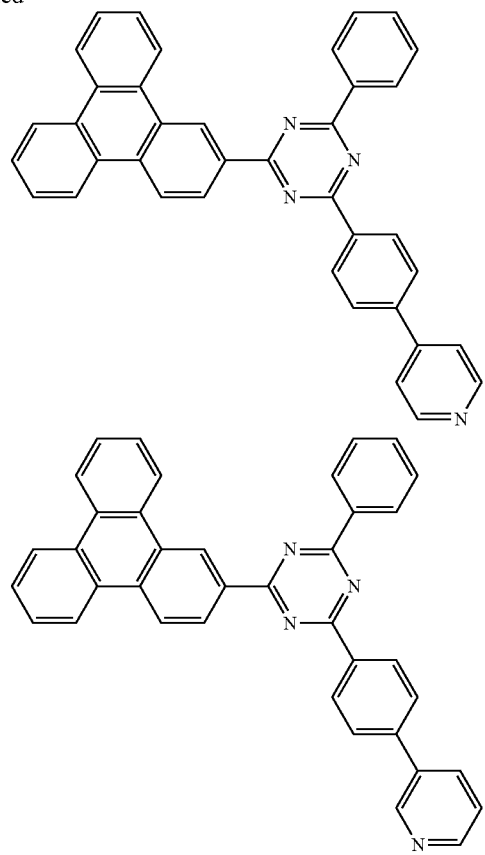
[Formula 165]
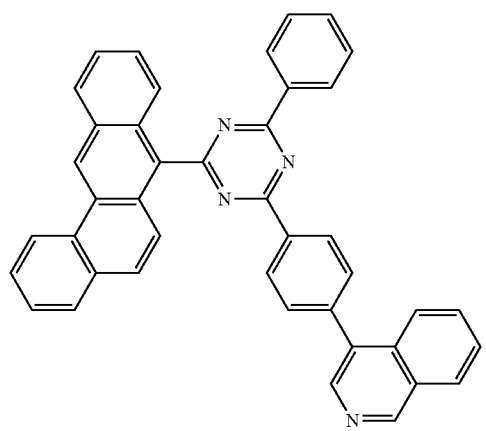
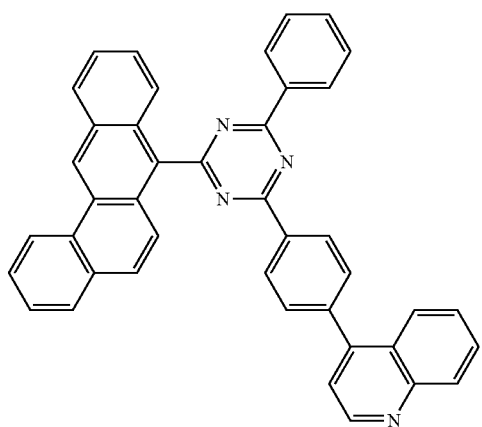

-continued
343
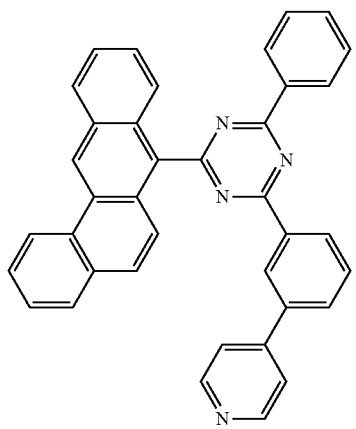
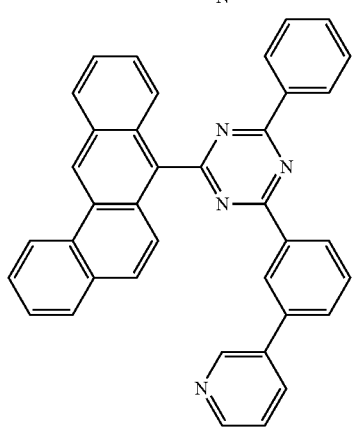
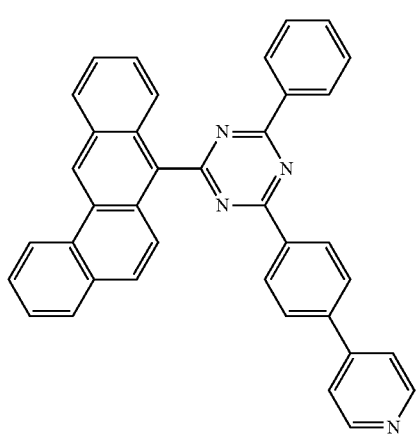
344
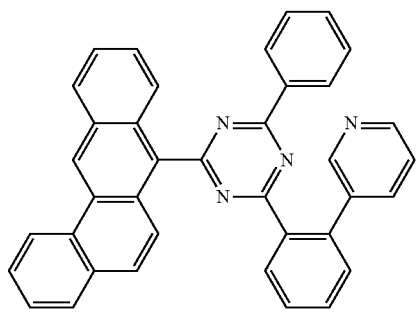
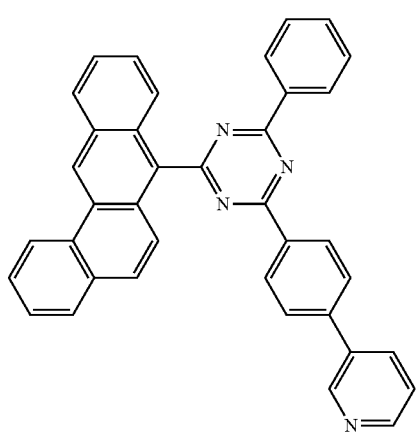
[Formula 166]
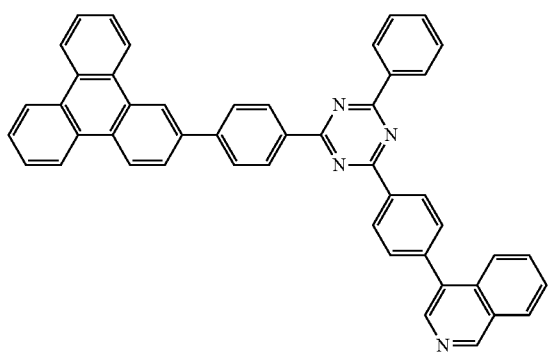
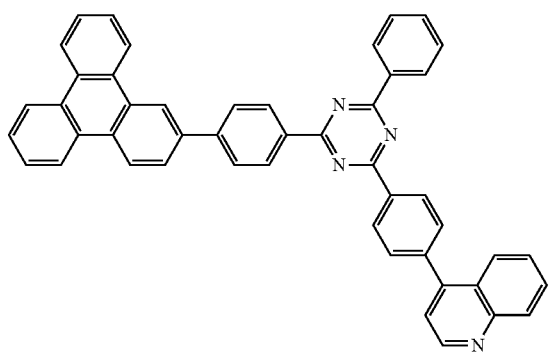

345
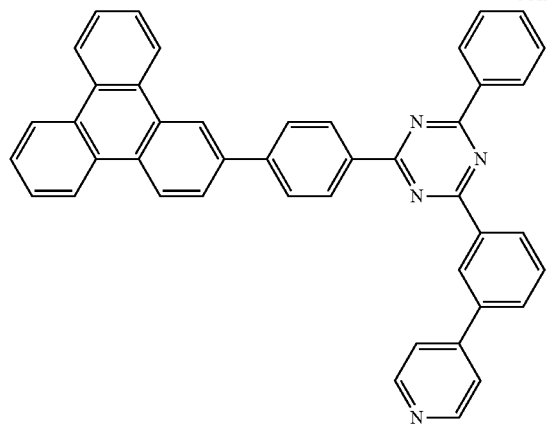
346
-continued
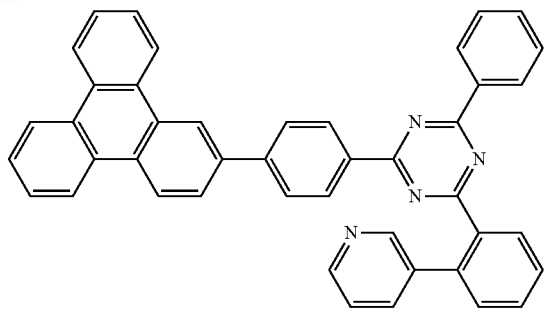
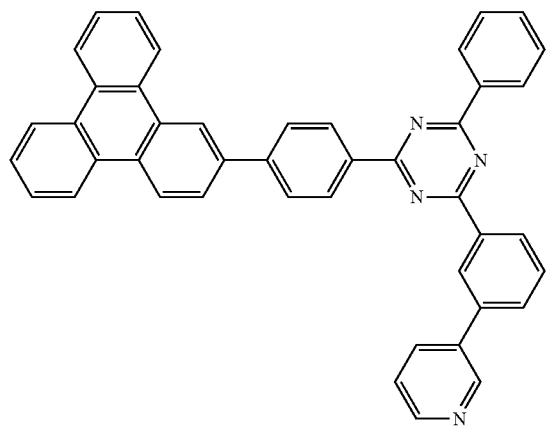
[Formula 167]
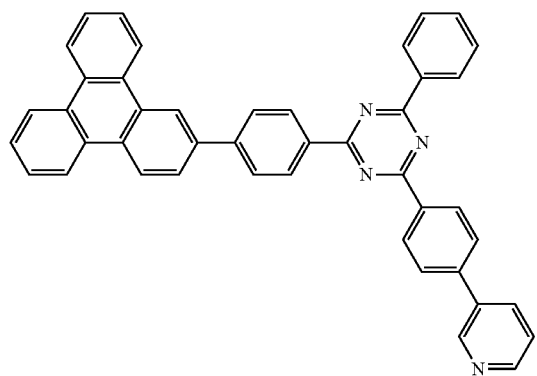
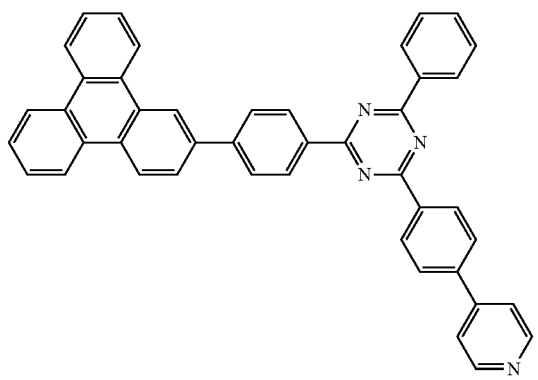

[Formula 168]
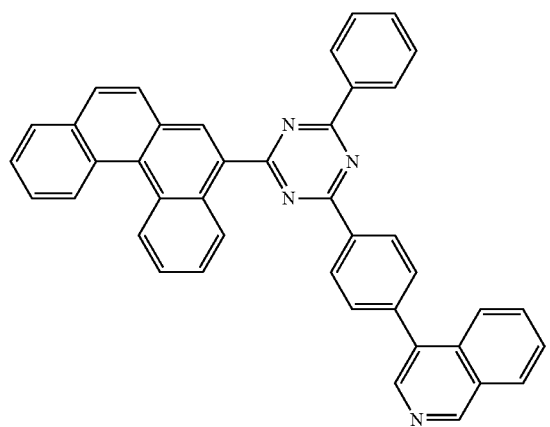 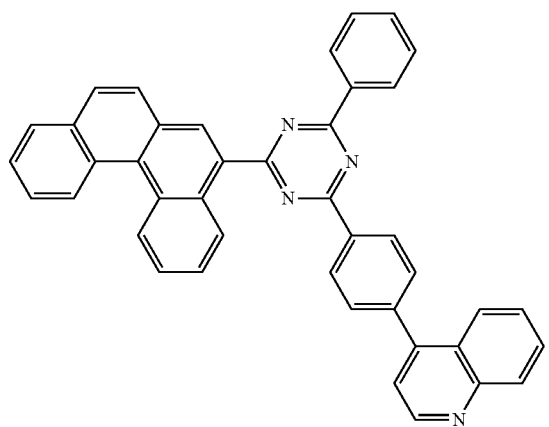
[Formula 169]
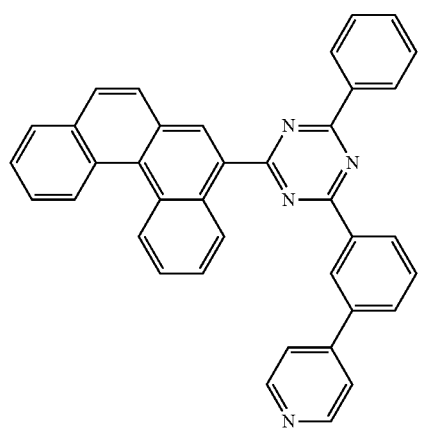 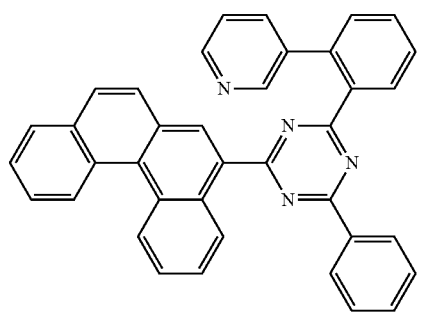
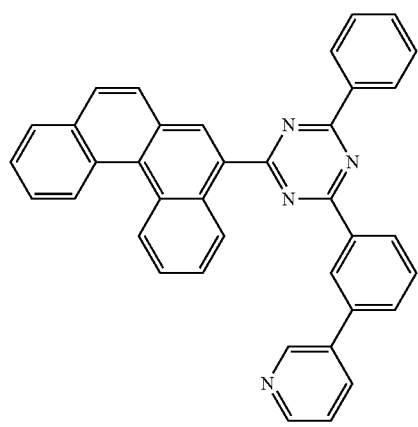 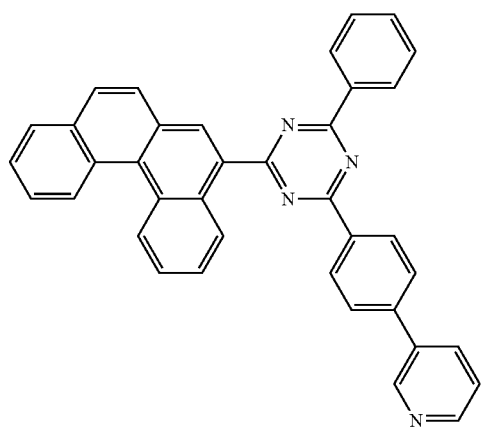

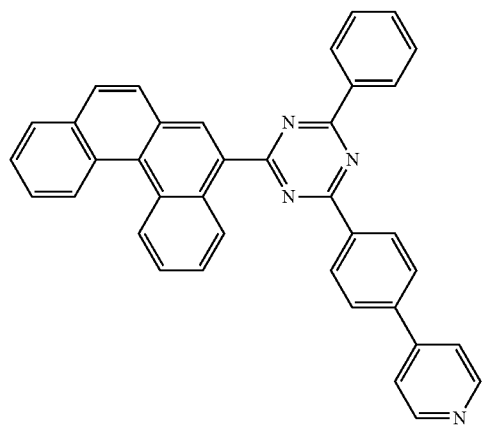
[Formula 170]
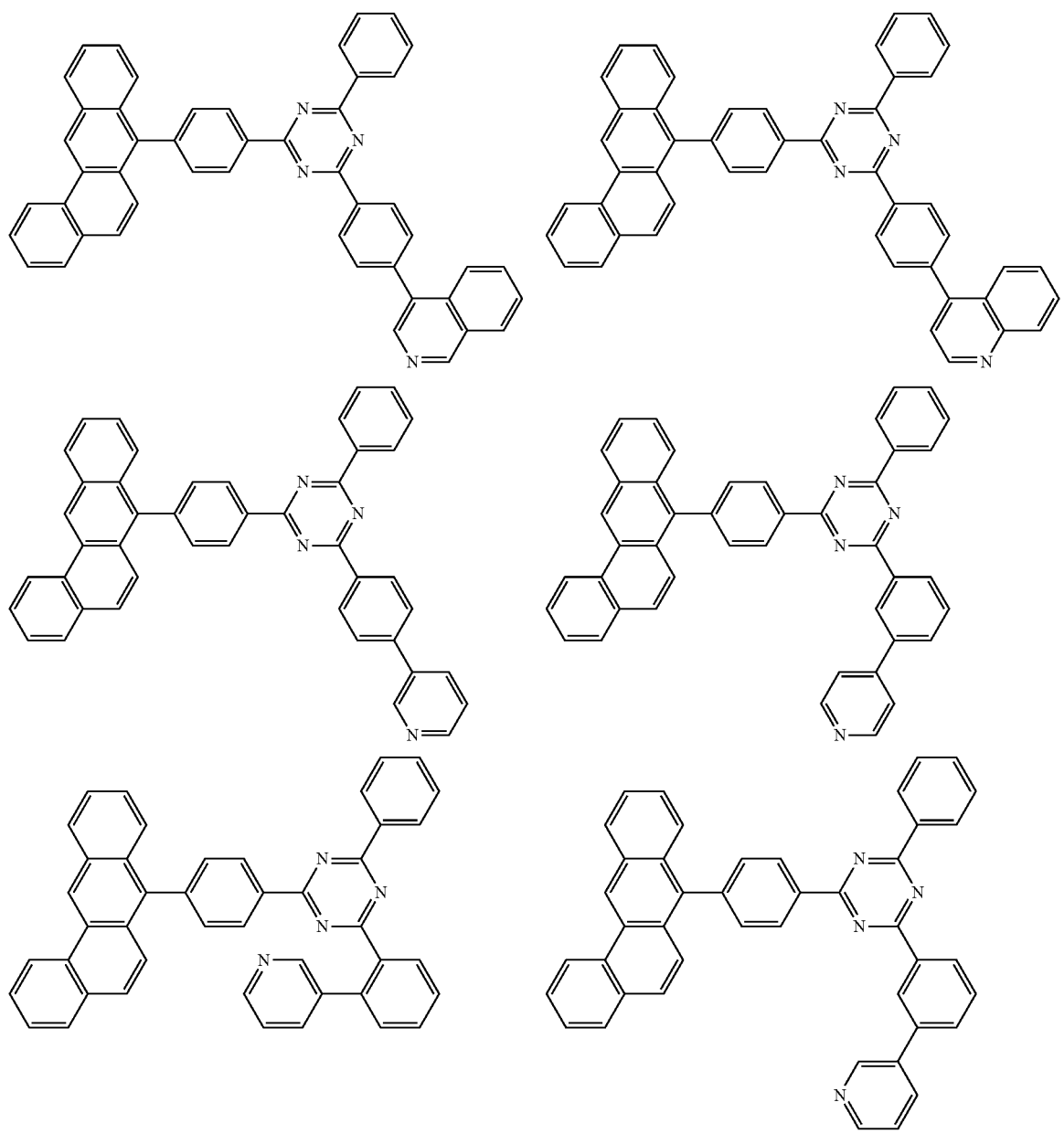

-continued
351
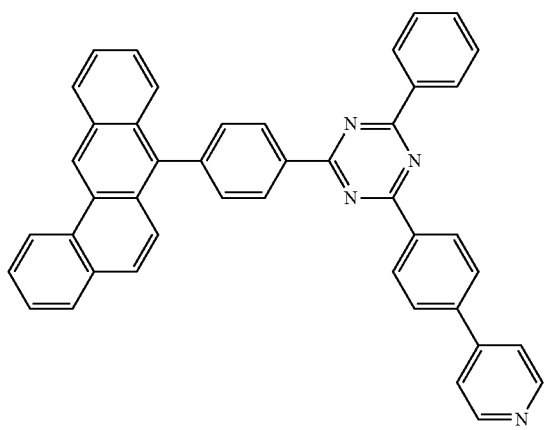
[Formula 171]
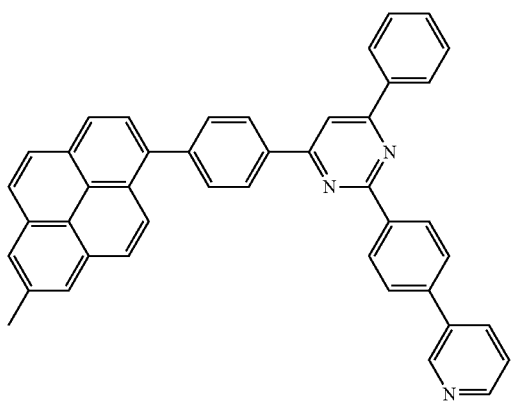
352
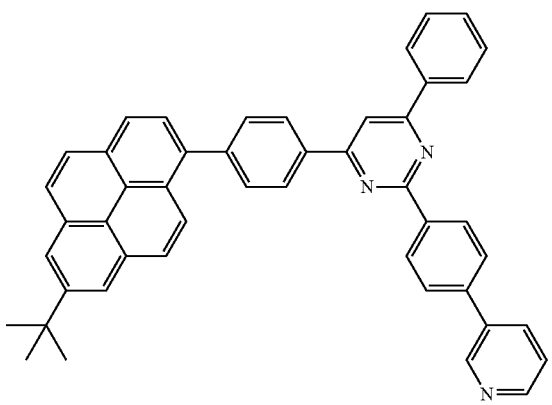
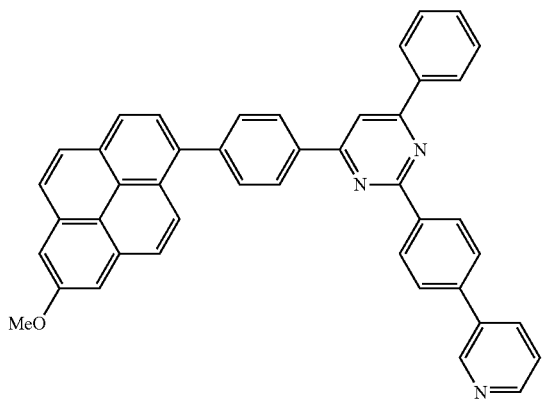
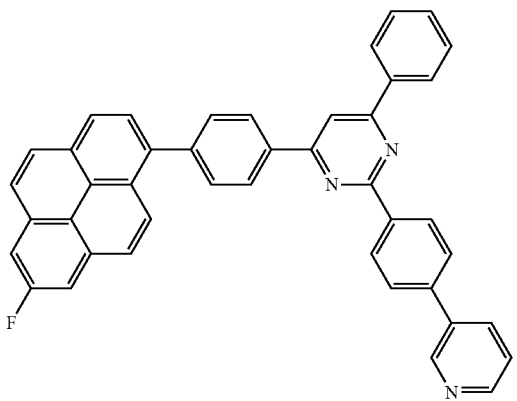
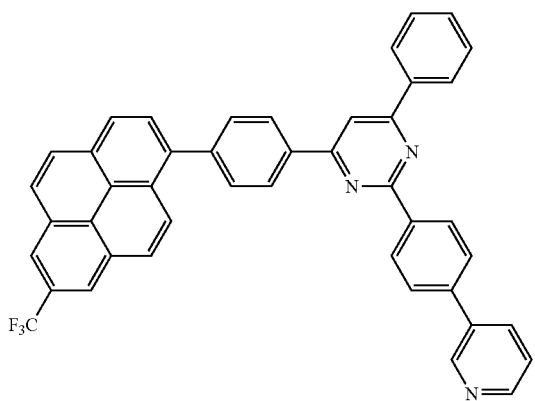
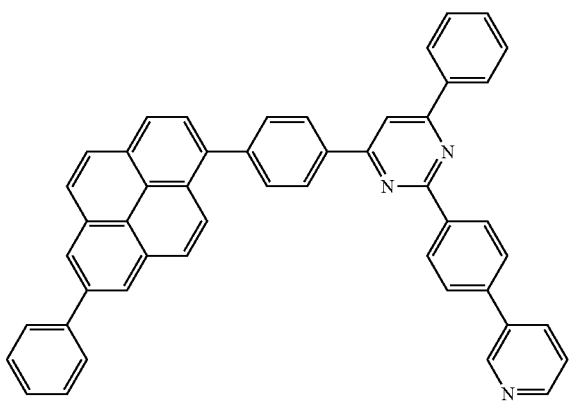

353
354
-continued
[Formula 172]
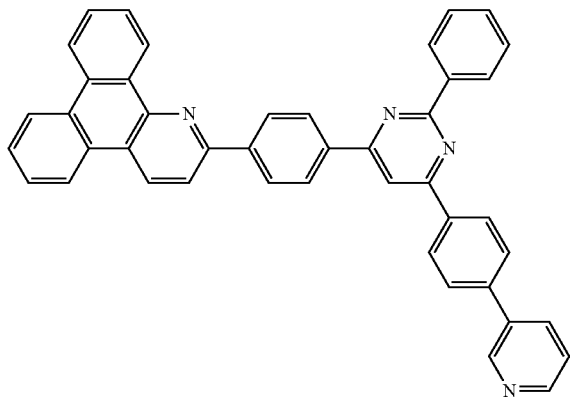
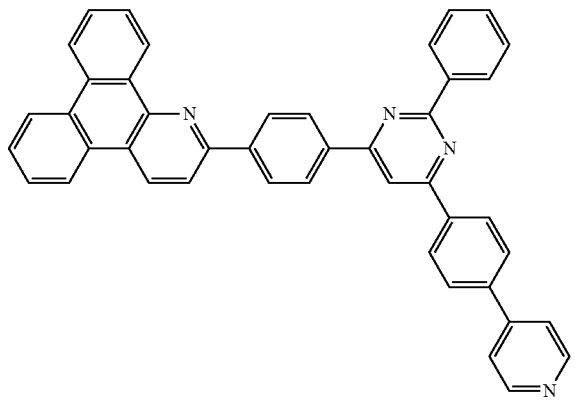
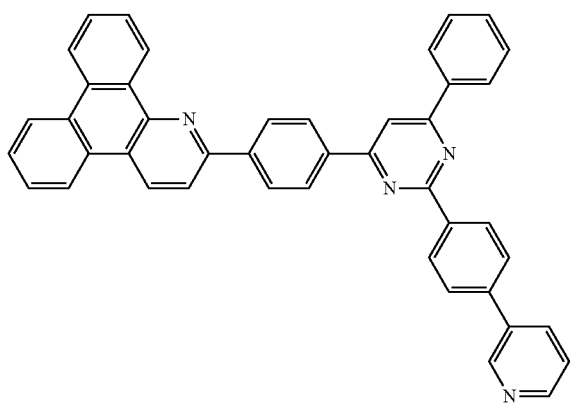
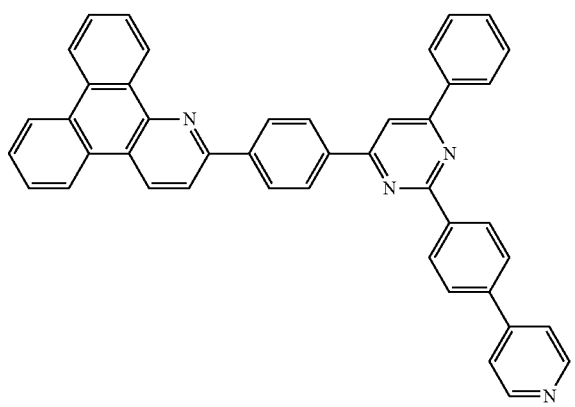
[Formula 173]
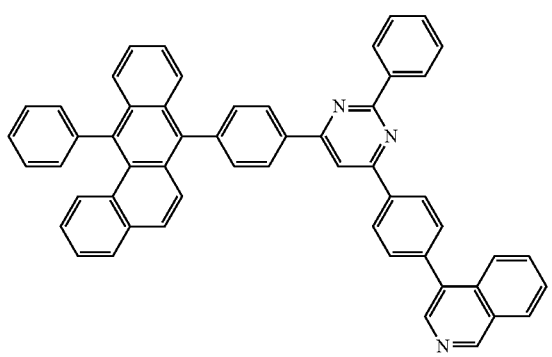
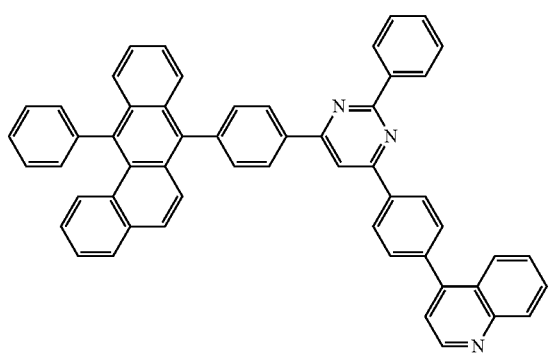
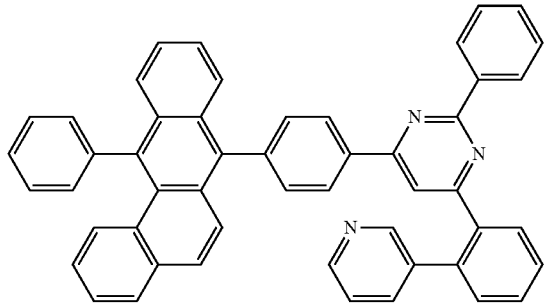
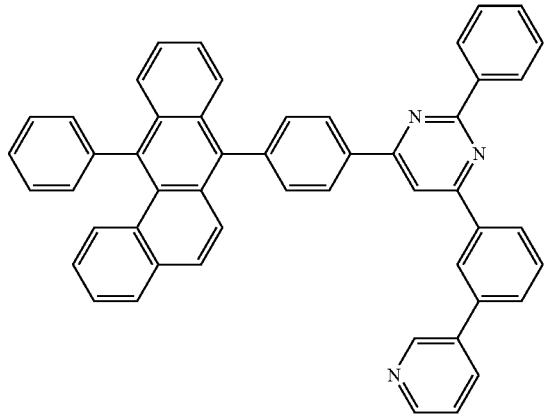

-continued
355 356
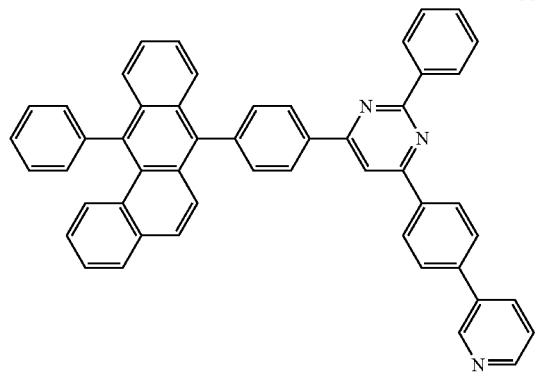
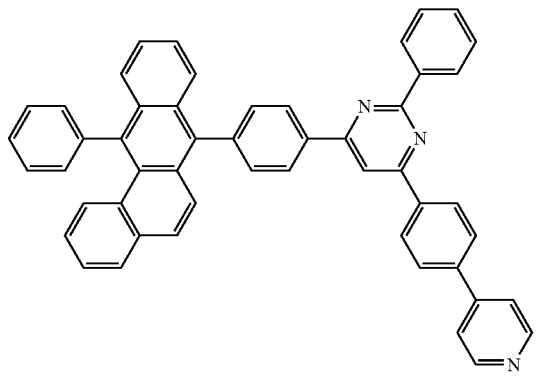
[Formula 174]
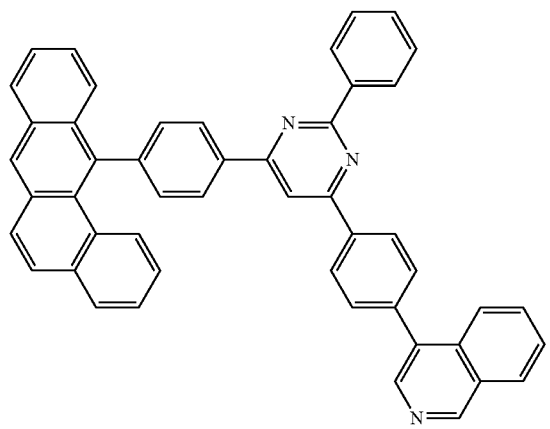
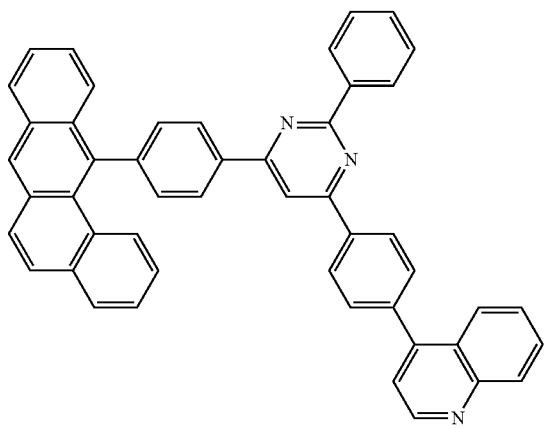
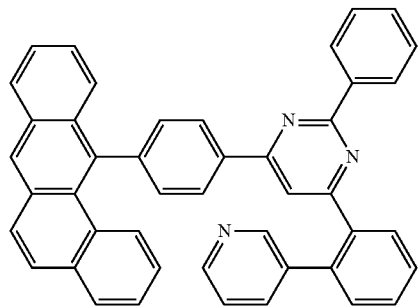
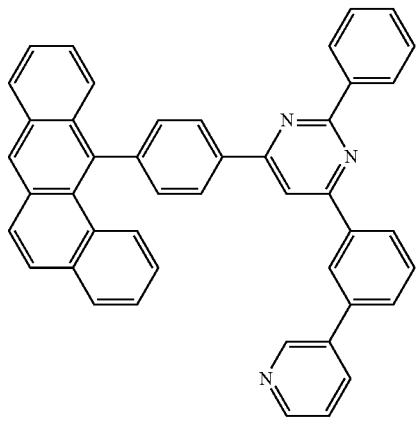
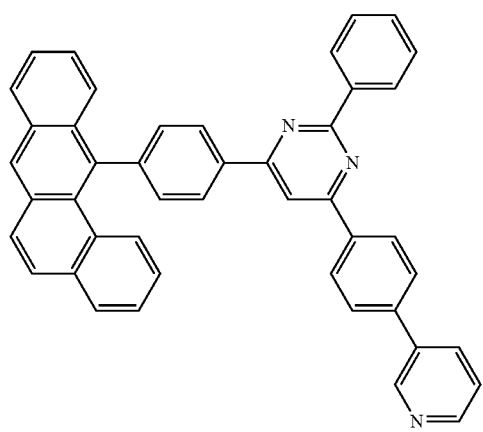
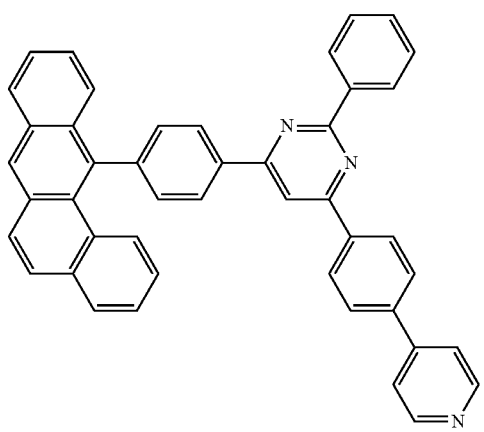

[Formula 175]
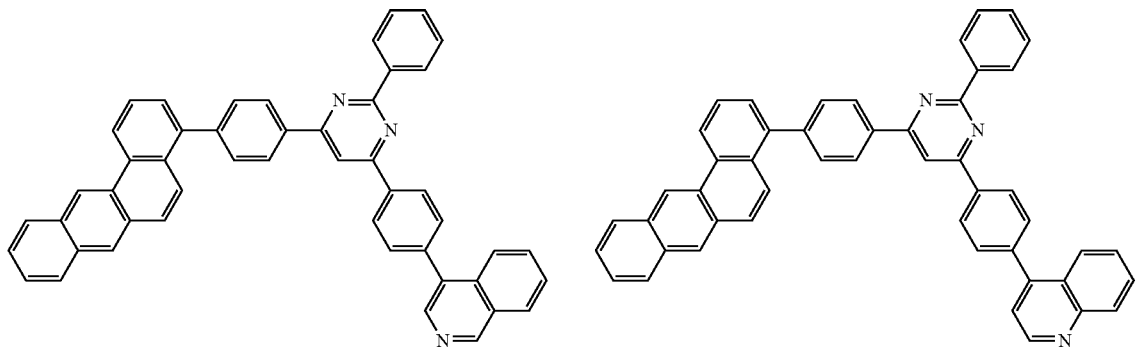
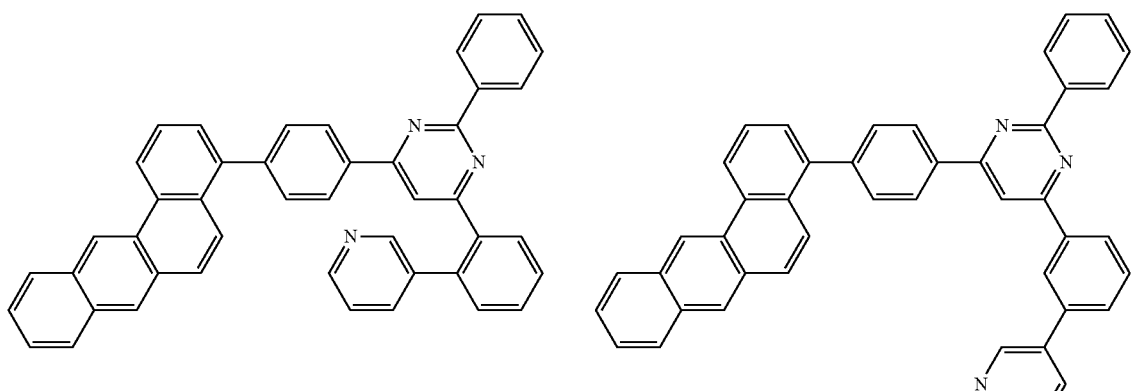
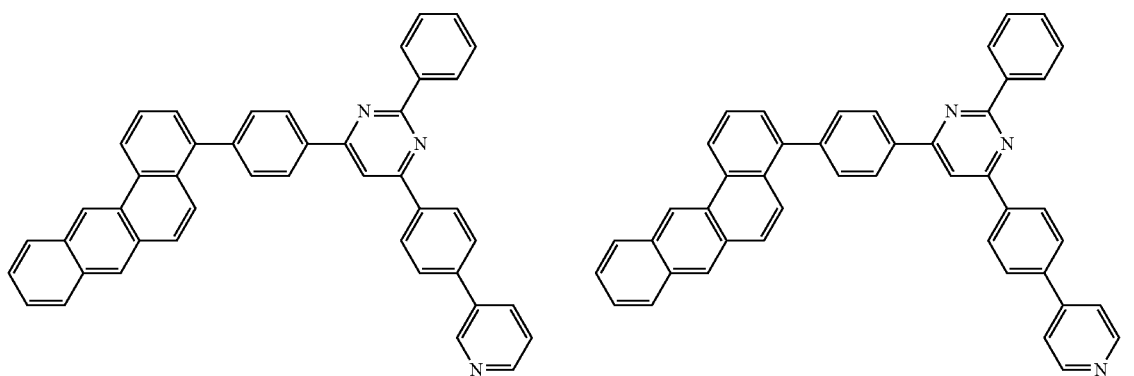
[Formula 176]
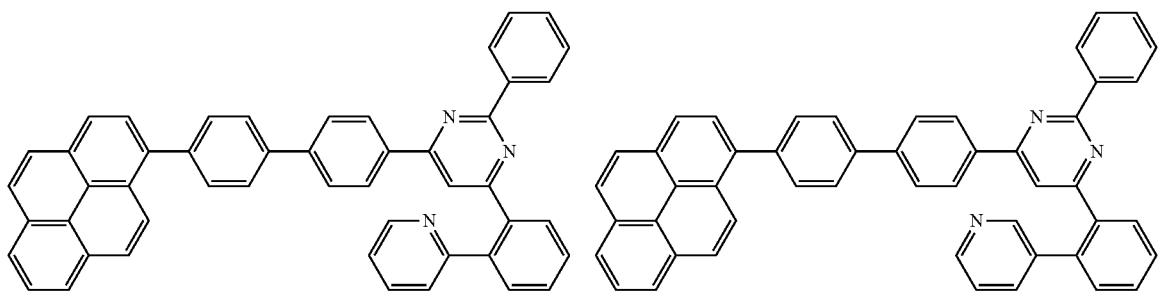

359
-continued
360
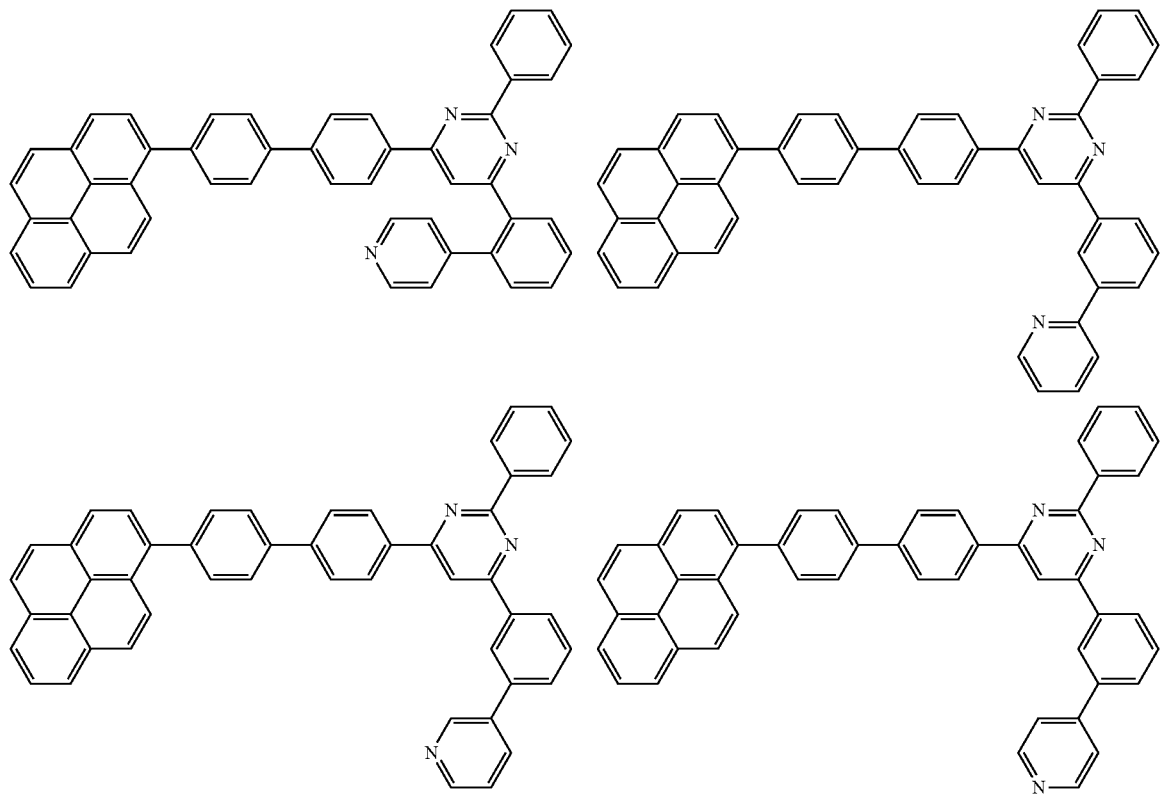
[Formula 177]
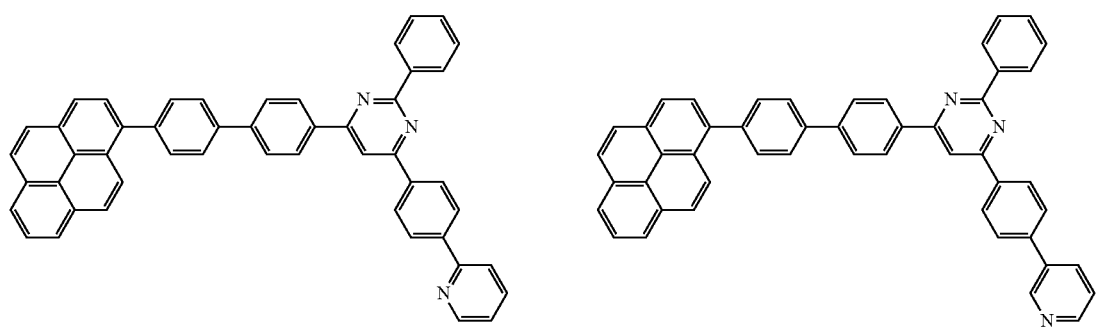
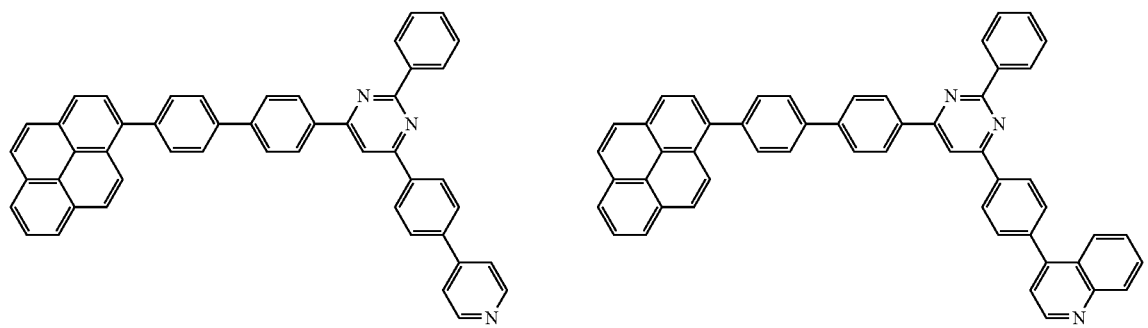

-continued
361
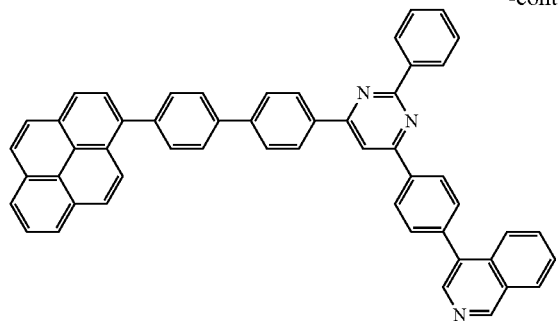
362
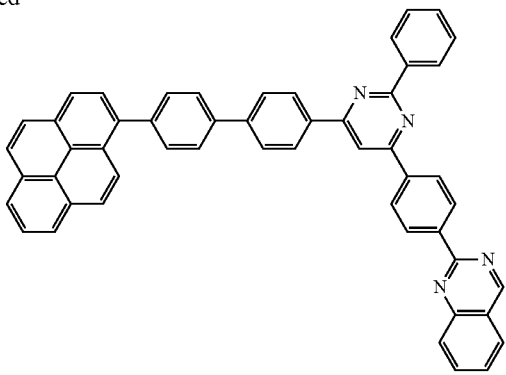
[Formula 178]
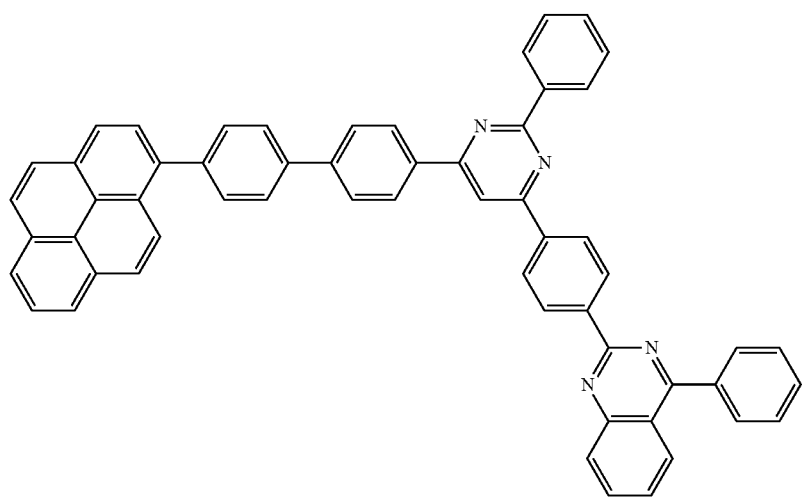
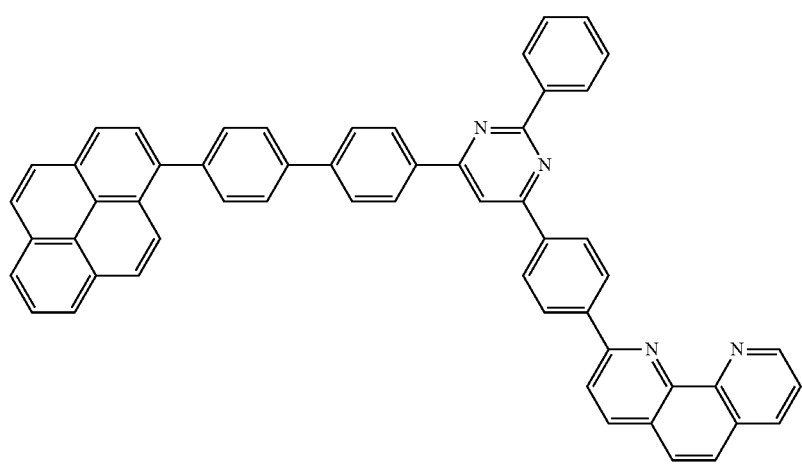

-continued
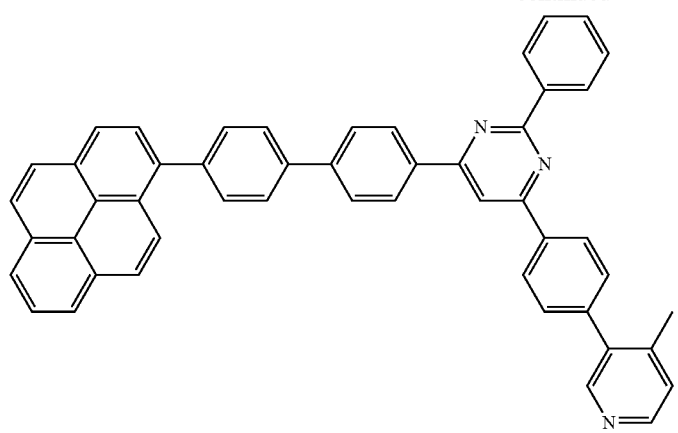
[Formula 179]
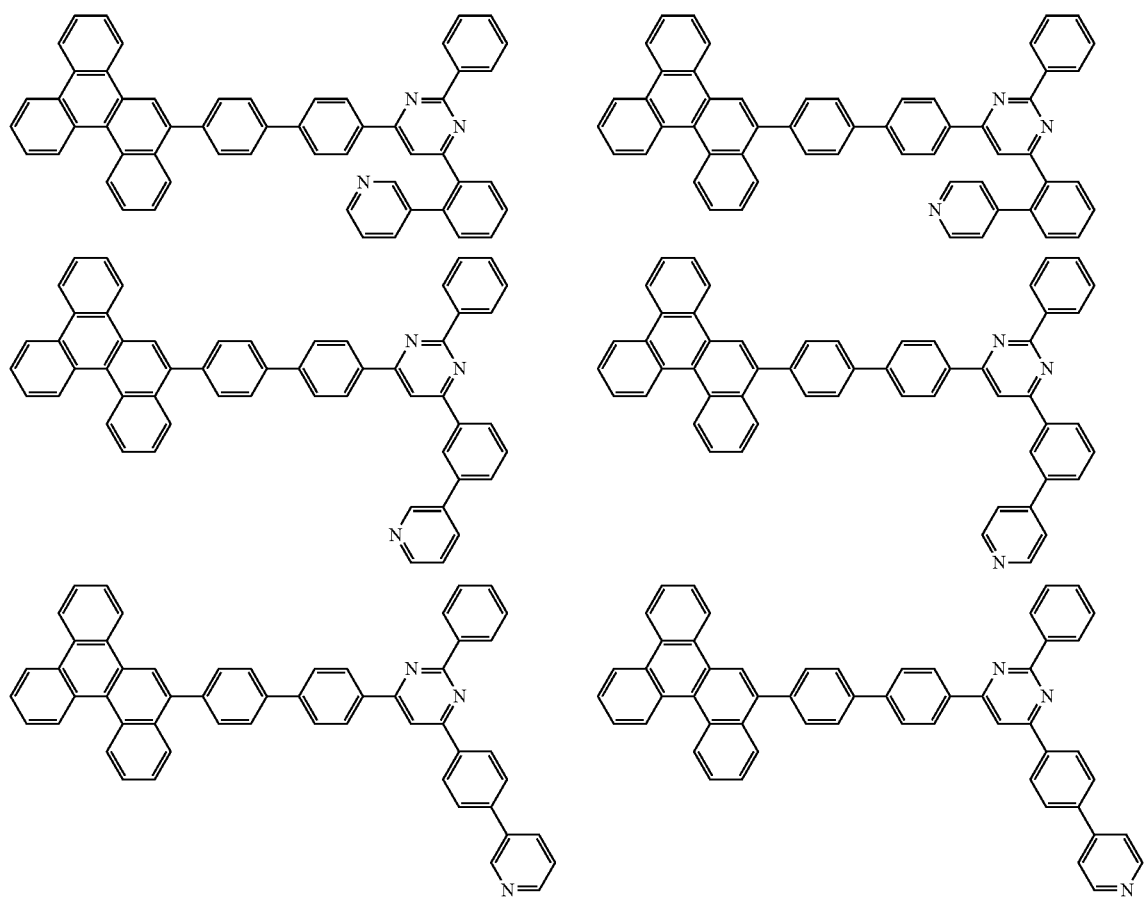
[Formula 180]
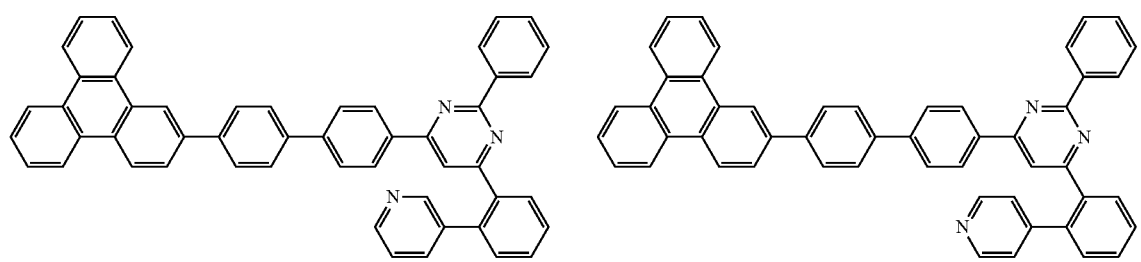

-continued
365 366
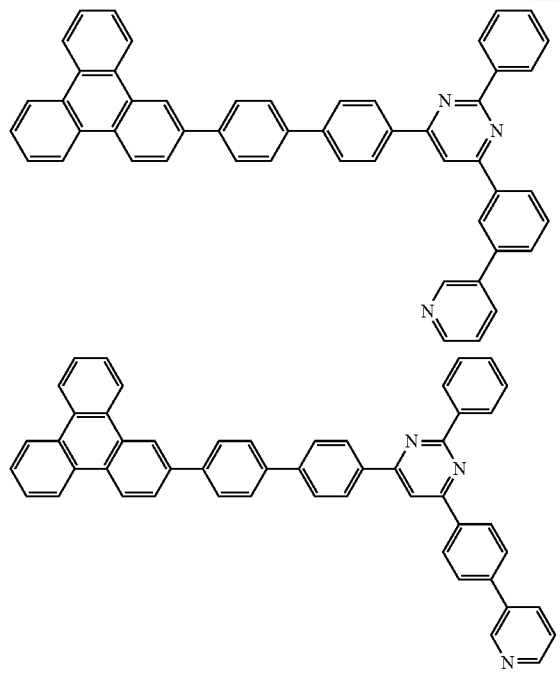 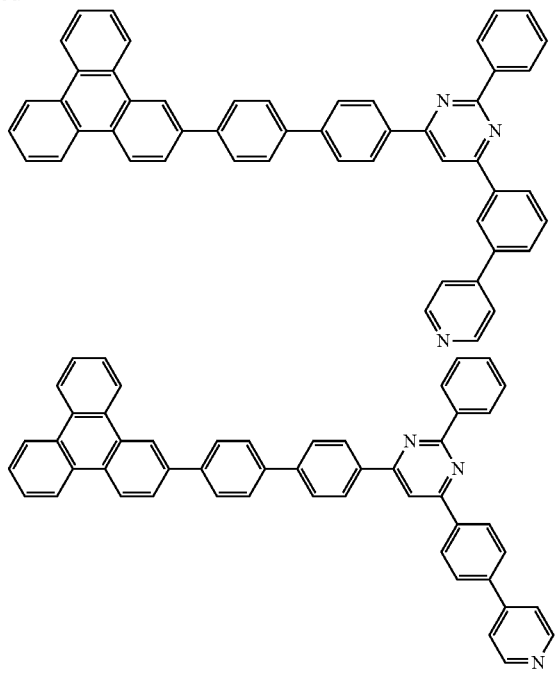
[Formula 181]
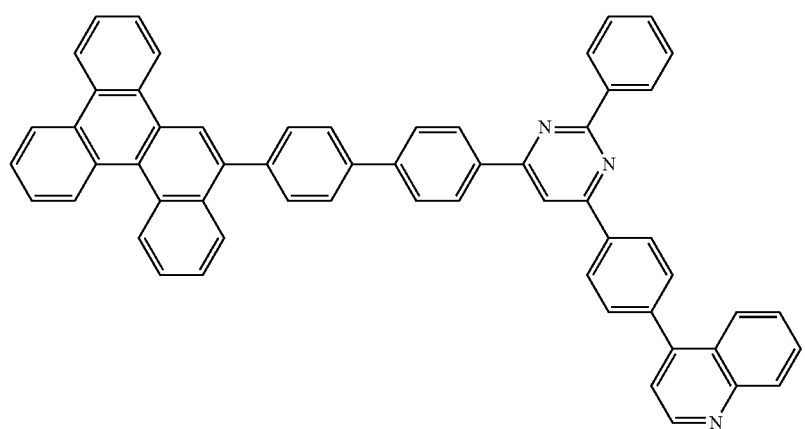
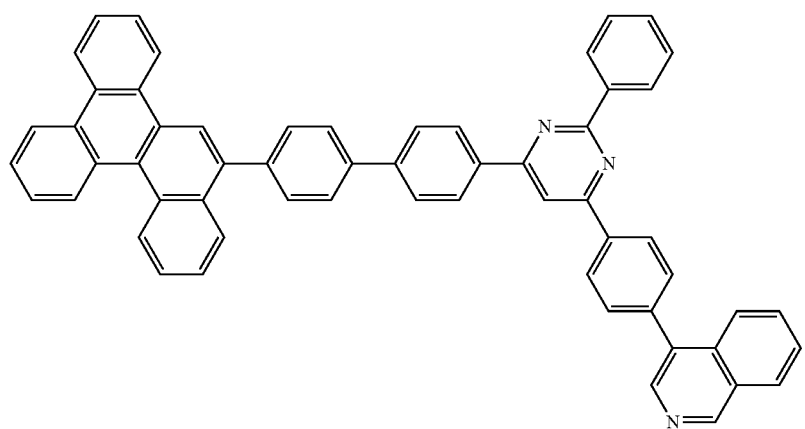

-continued
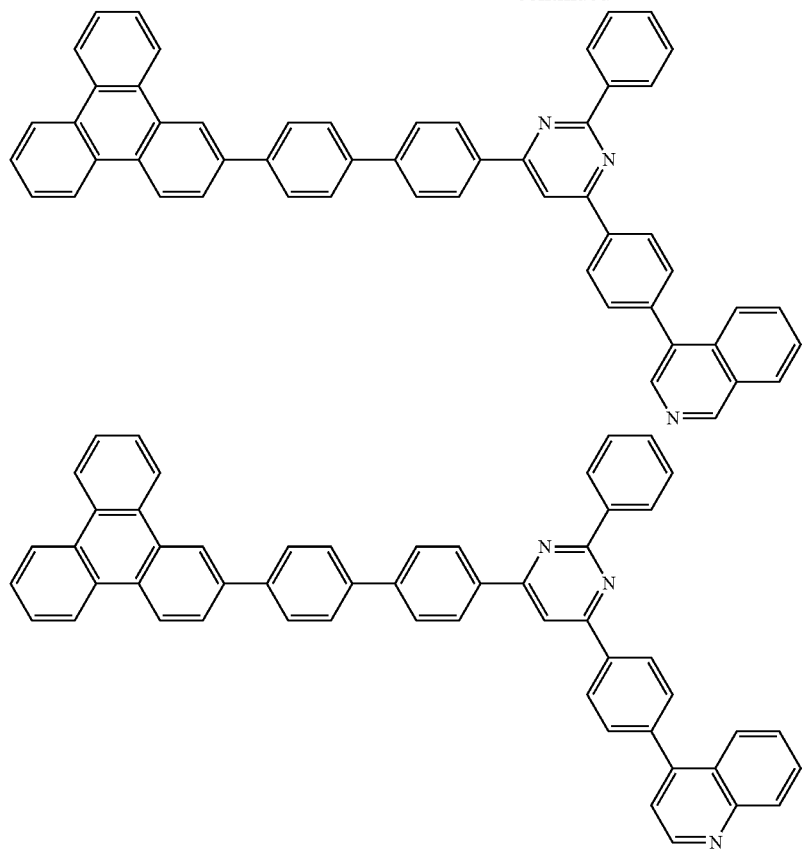
[Formula 182]
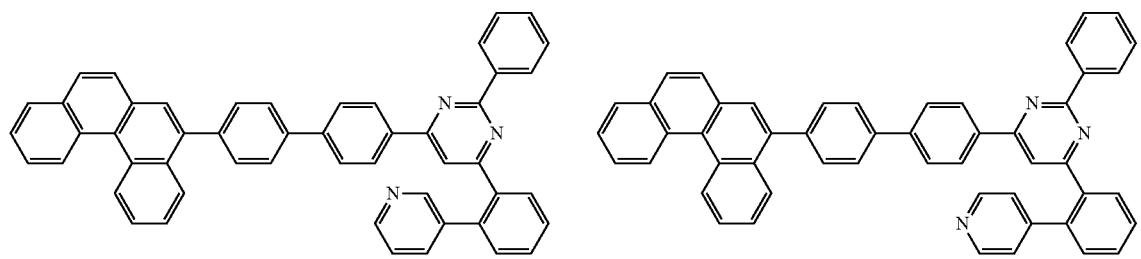
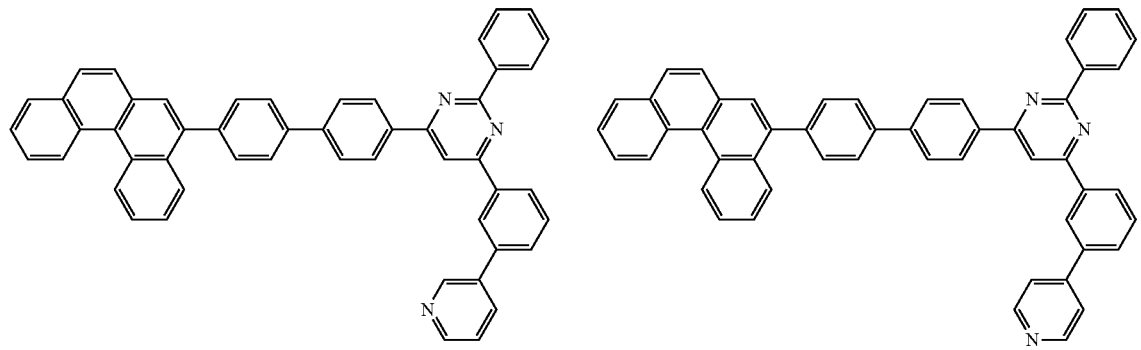

369                                370
-continued
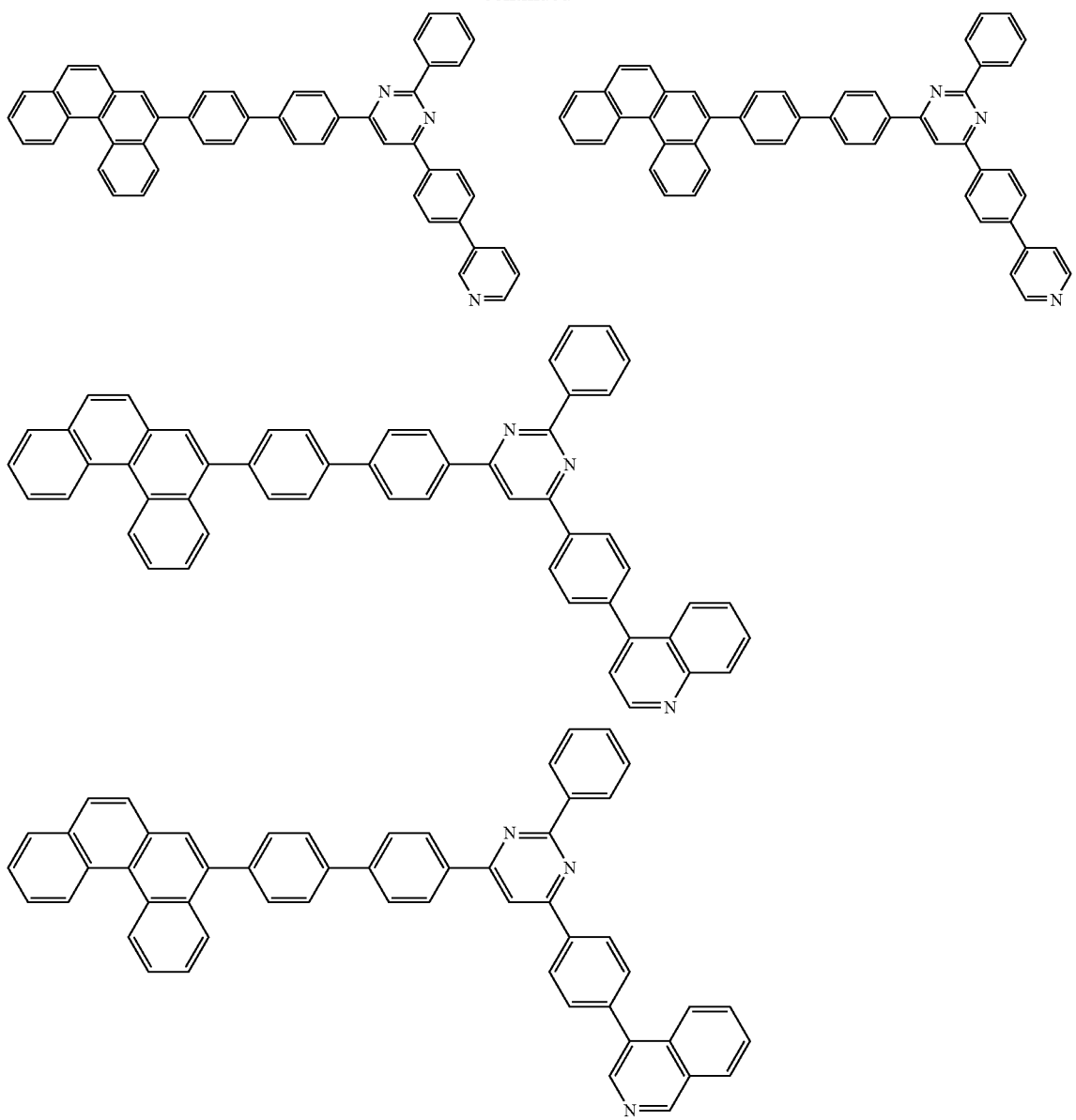
[Formula 183]
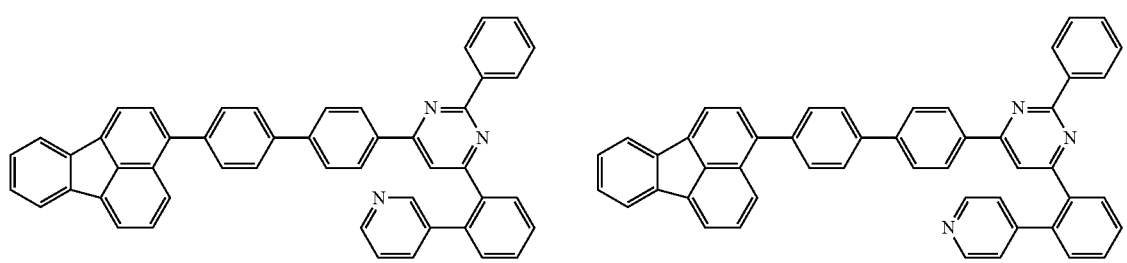

-continued
| 371 | 372 |
|---|---|
| 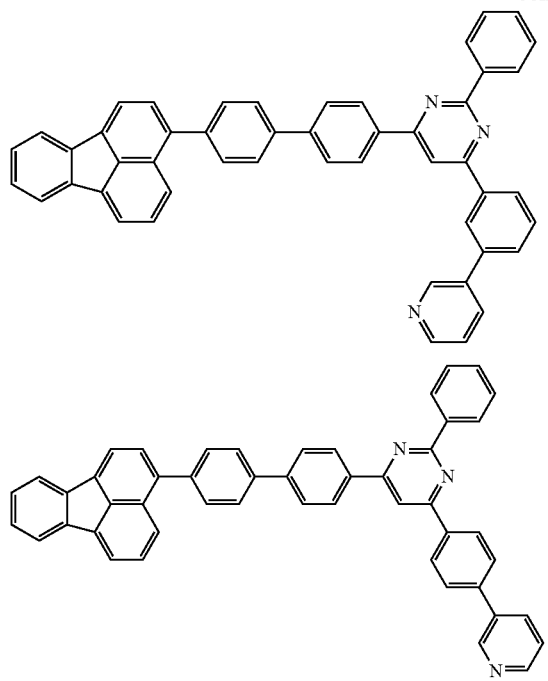 | 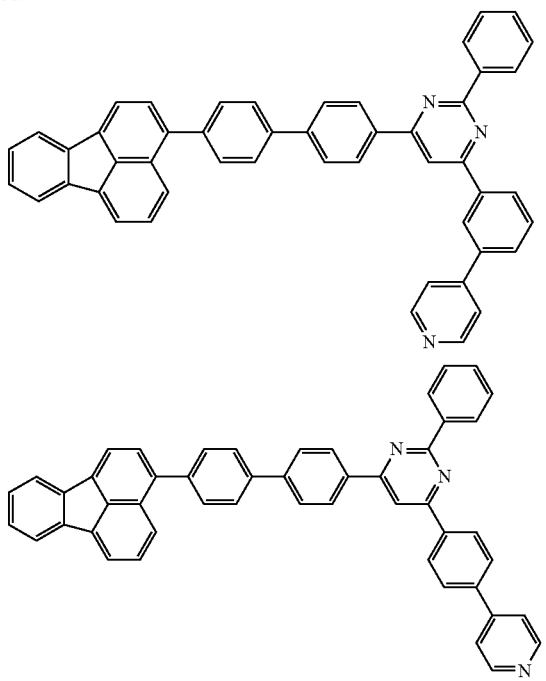 |
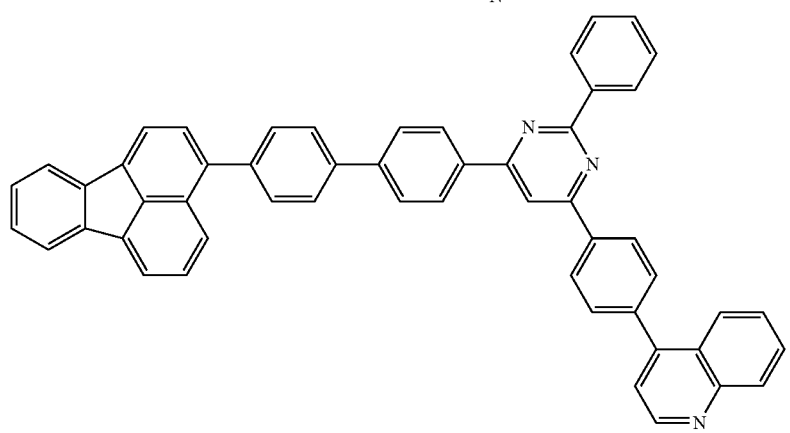
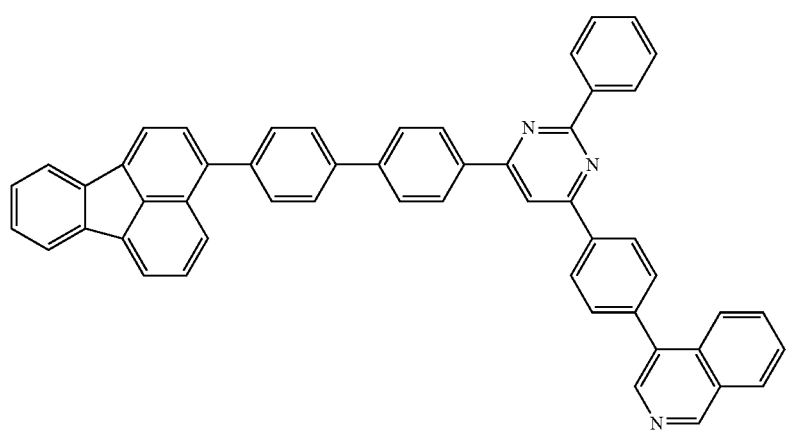

[Formula 184]
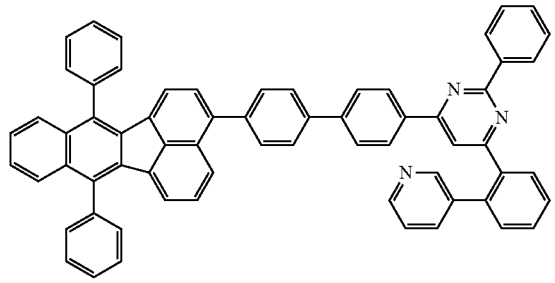
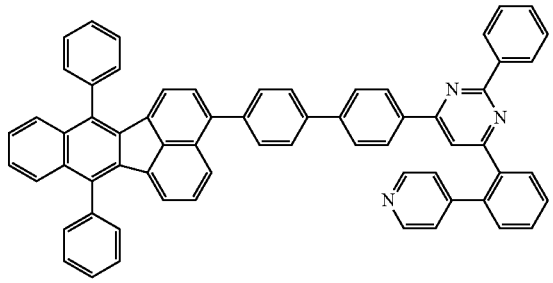
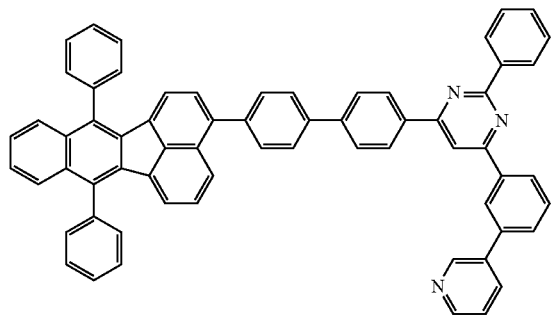
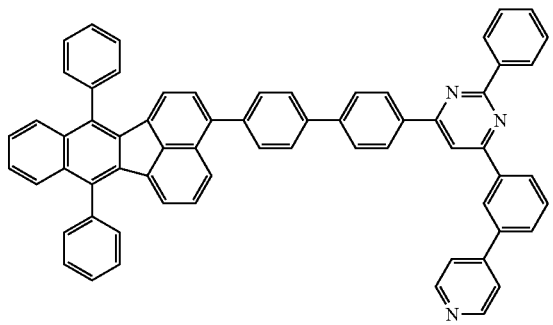
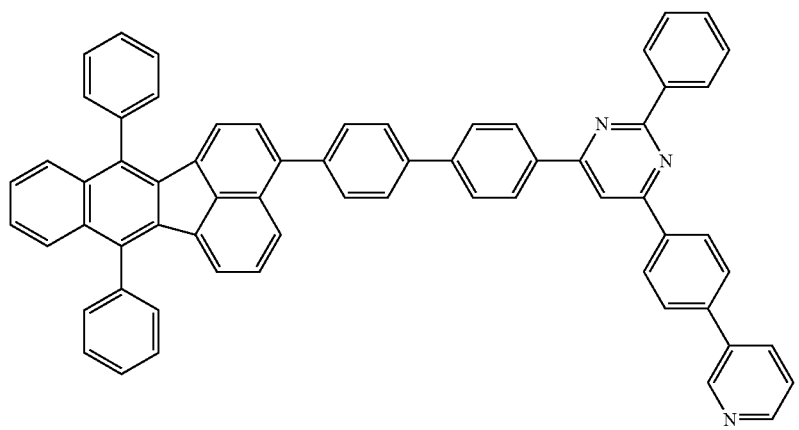
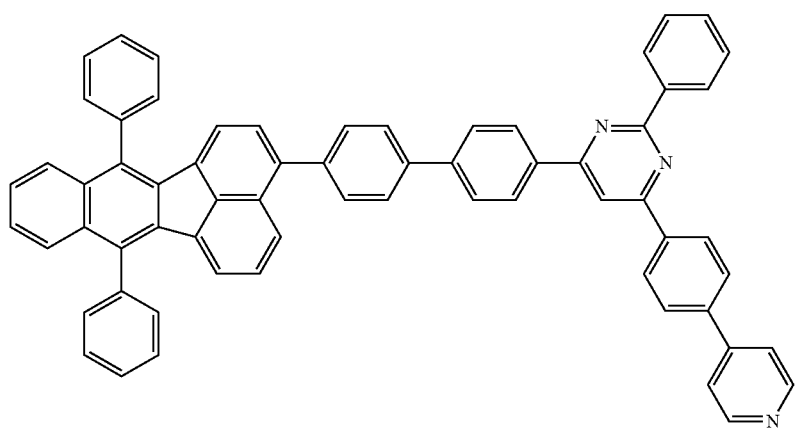

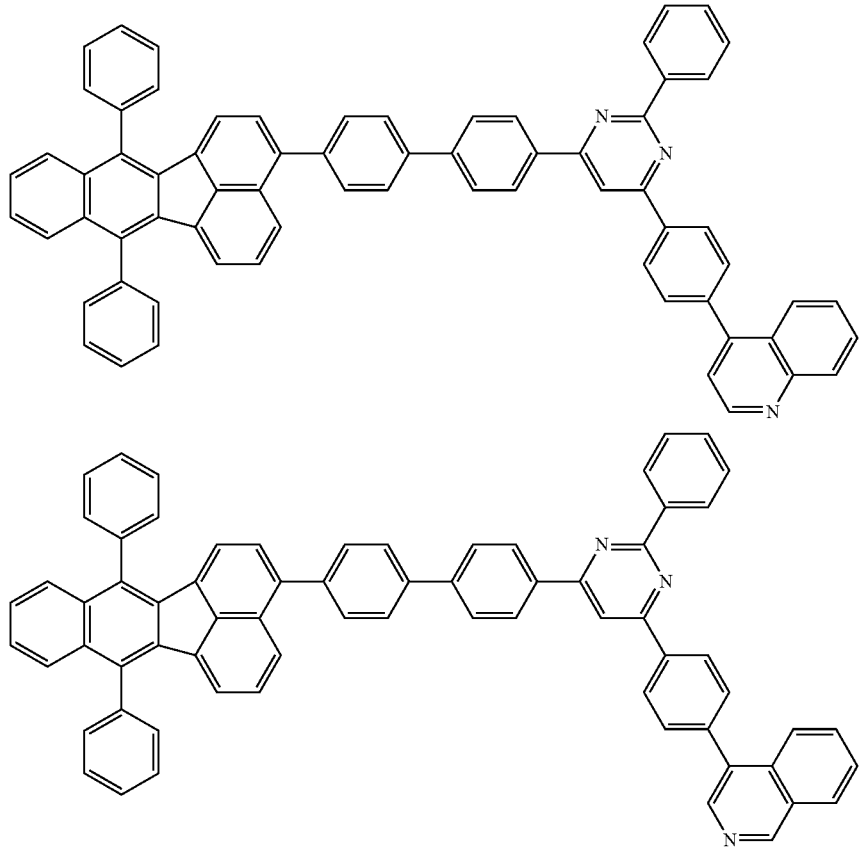
[Formula 185]
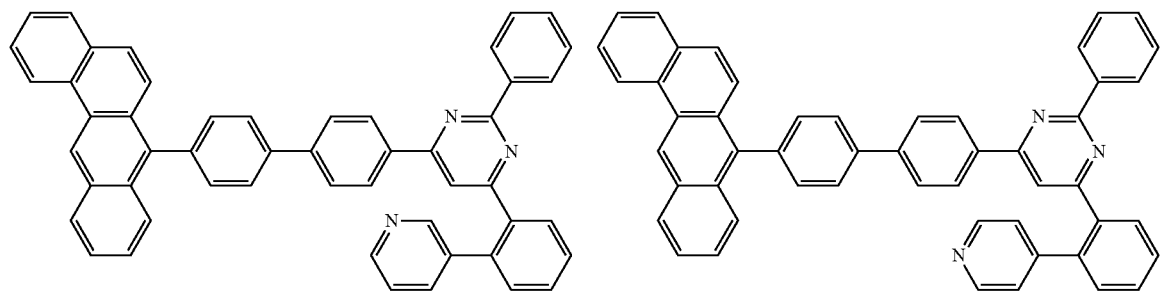
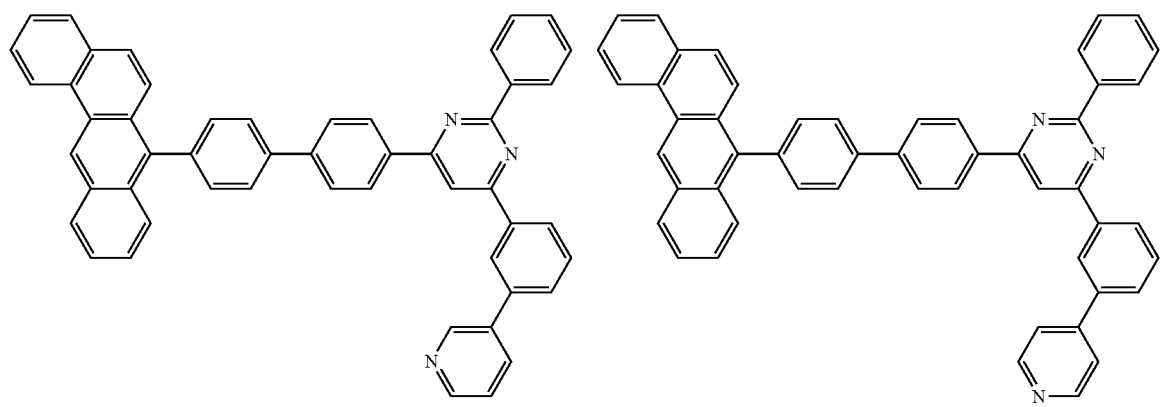

-continued
| 377 | 378 |
|---|---|
| 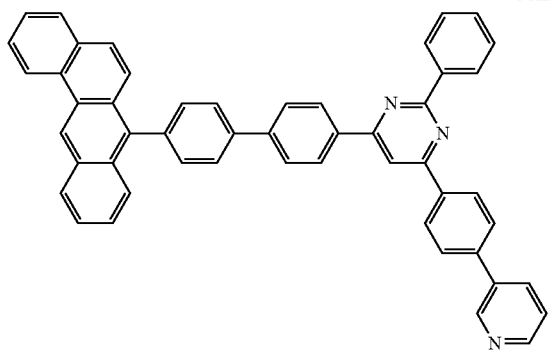 | 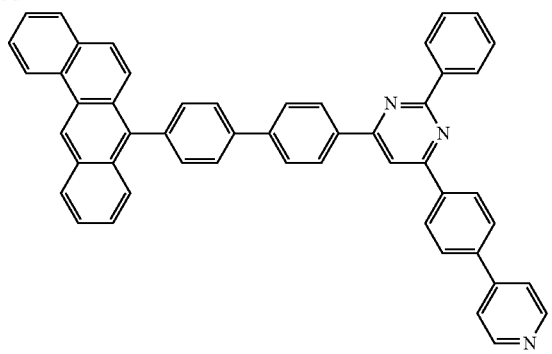 |
| 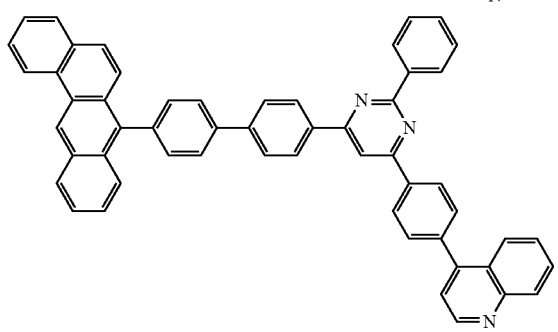 | 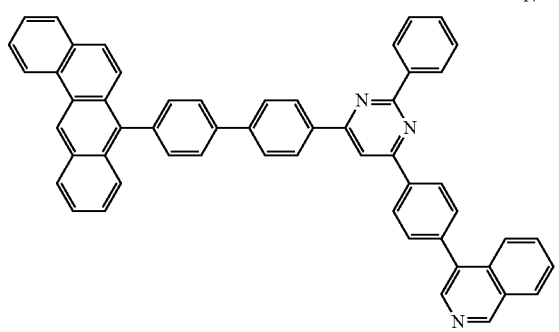 |
[Formula 186]
| 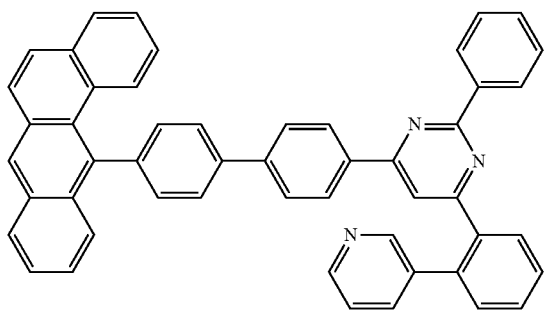 | 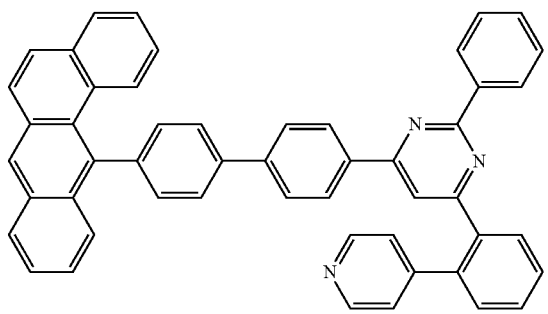 |
|---|---|
| 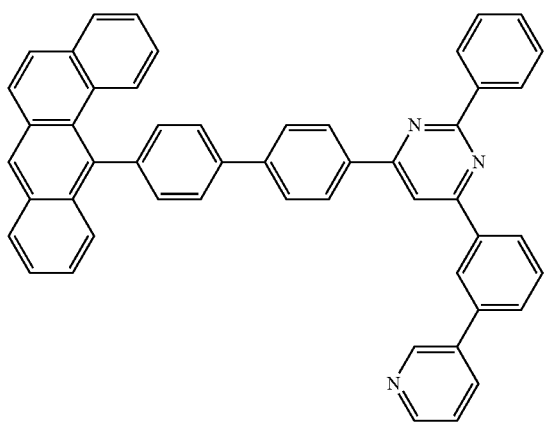 | 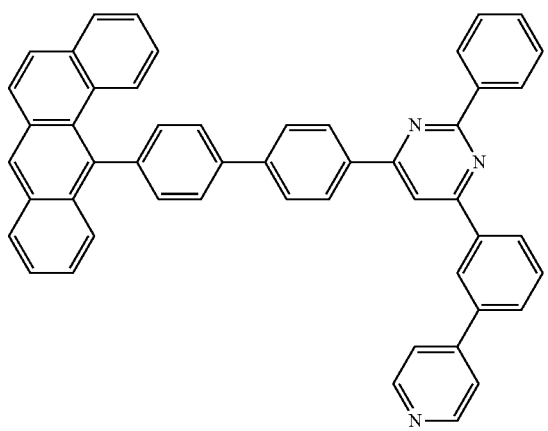 |

-continued
379 380
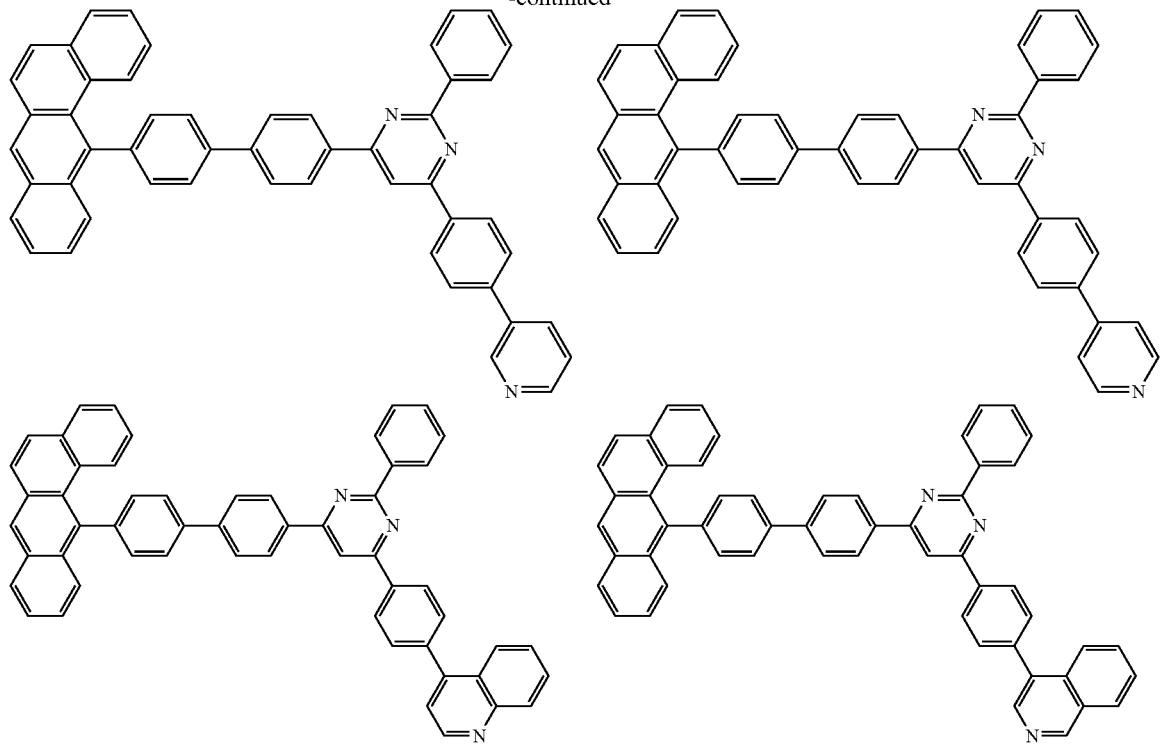
[Formula 187]
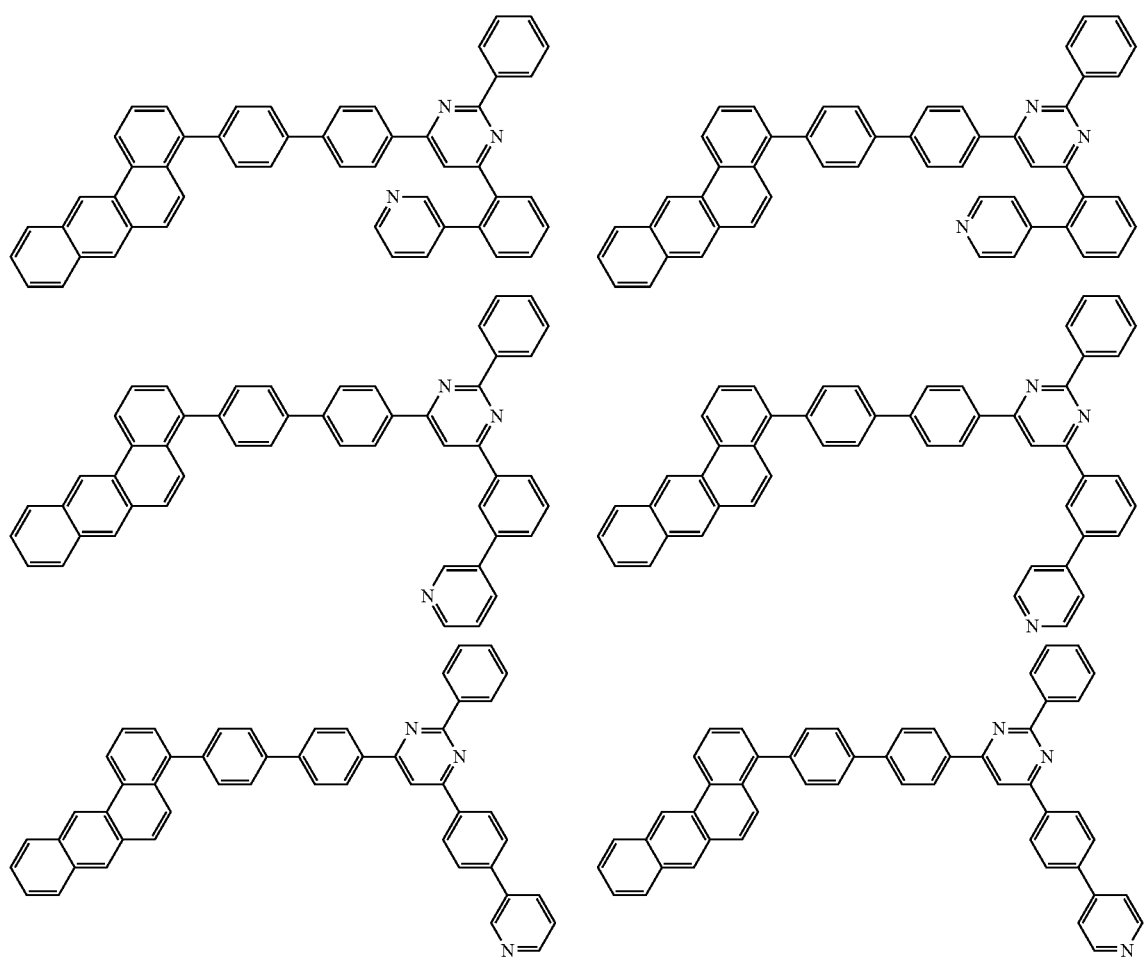

-continued
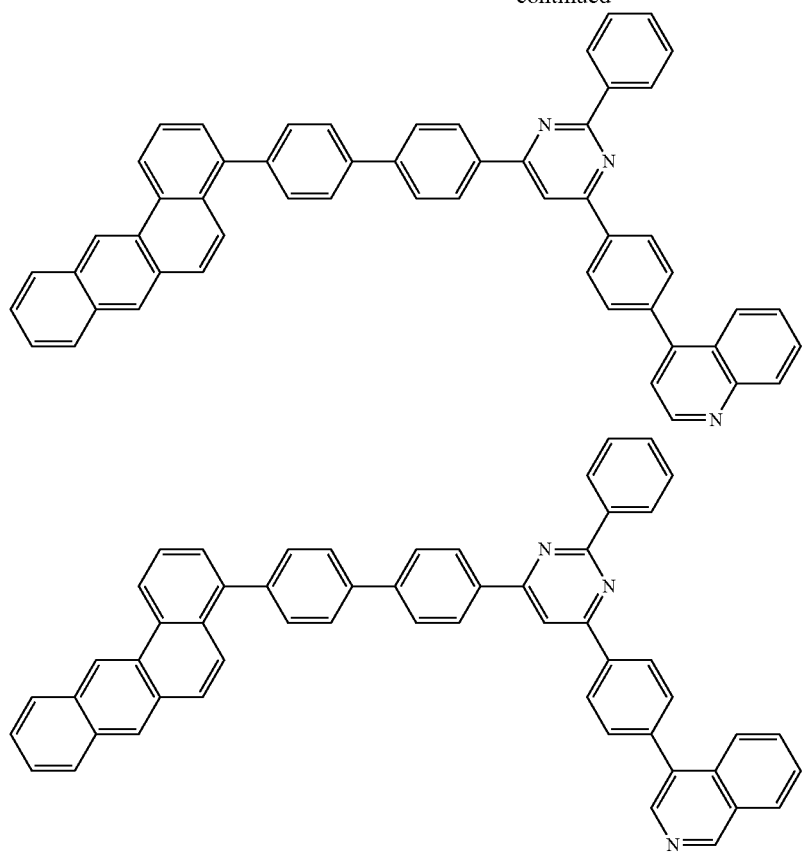
[Formula 188]
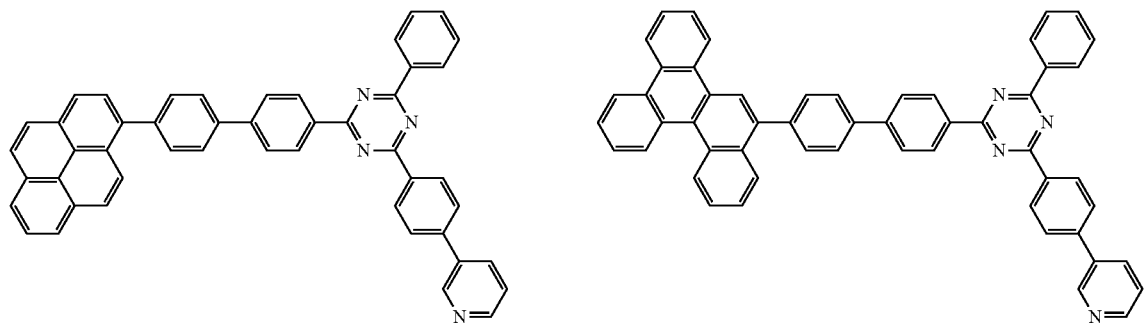
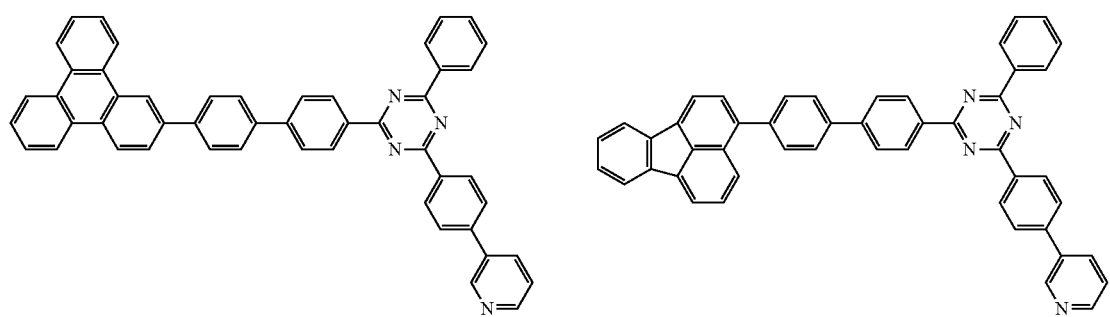

383
384
-continued
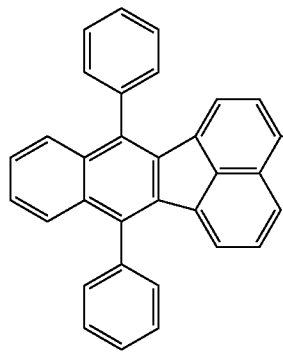
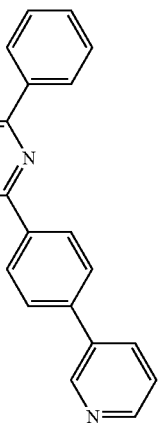
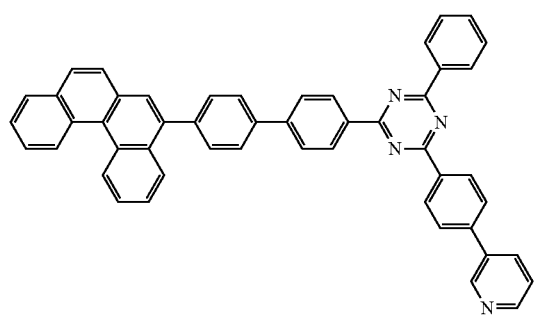
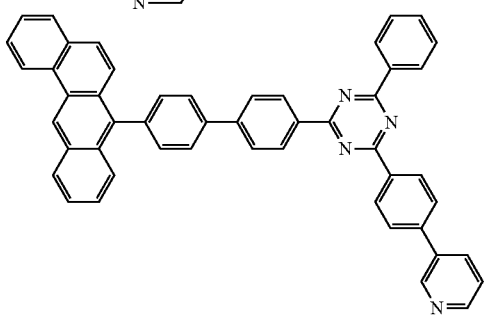
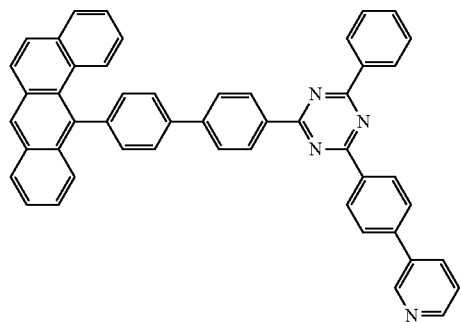
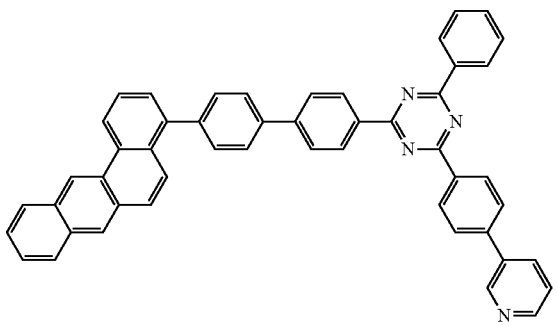
[Formula 189]
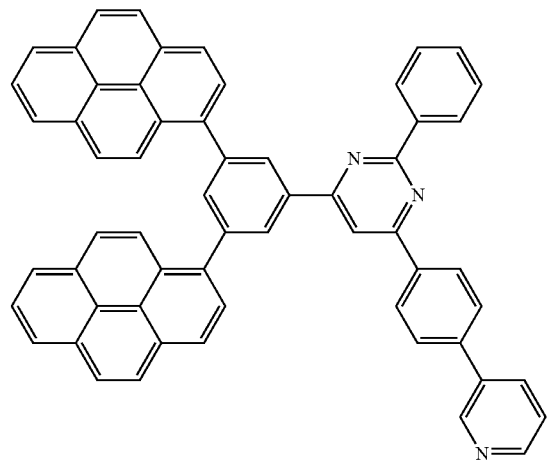
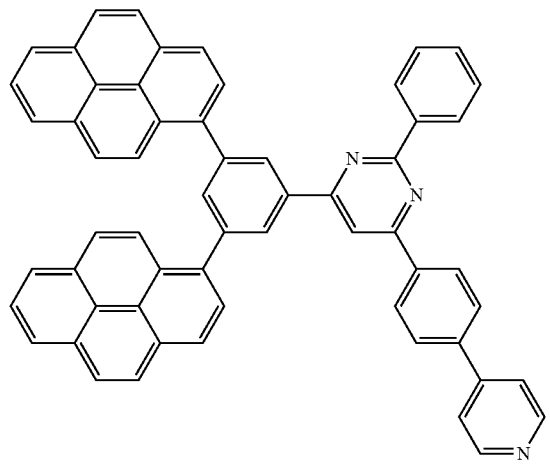

-continued
385
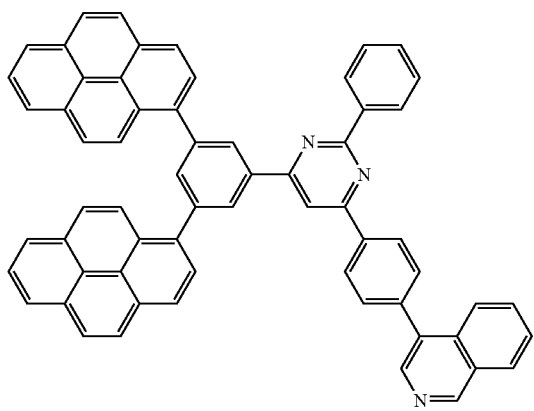
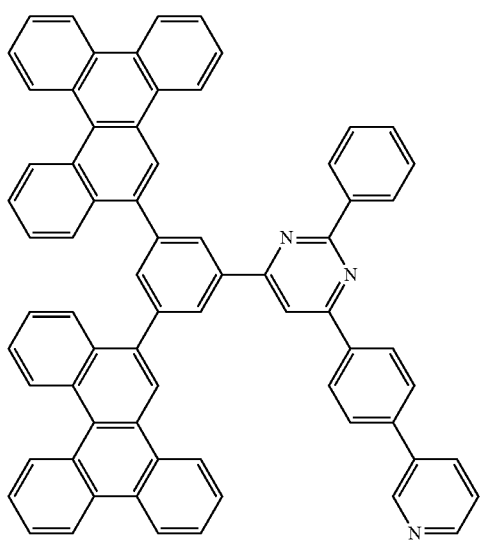
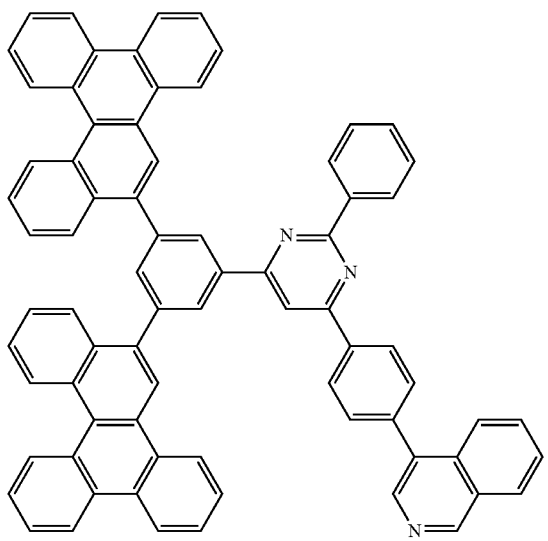
386
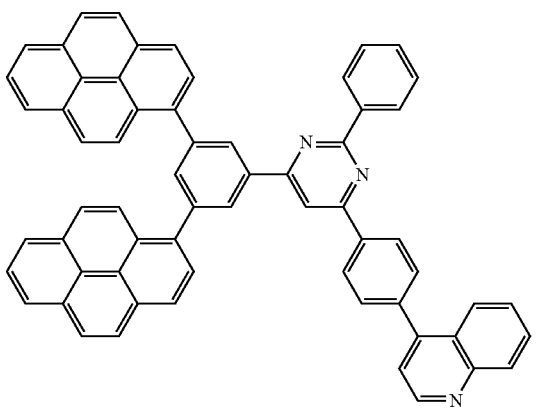
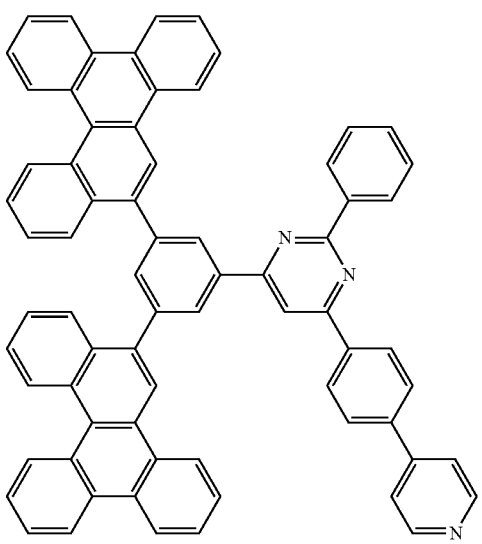
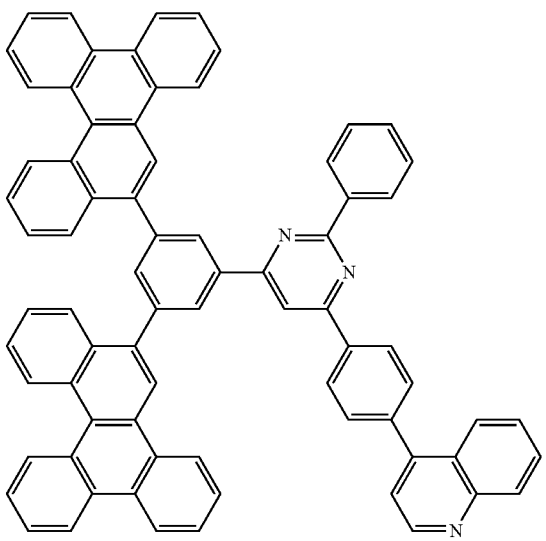

[Formula 190]
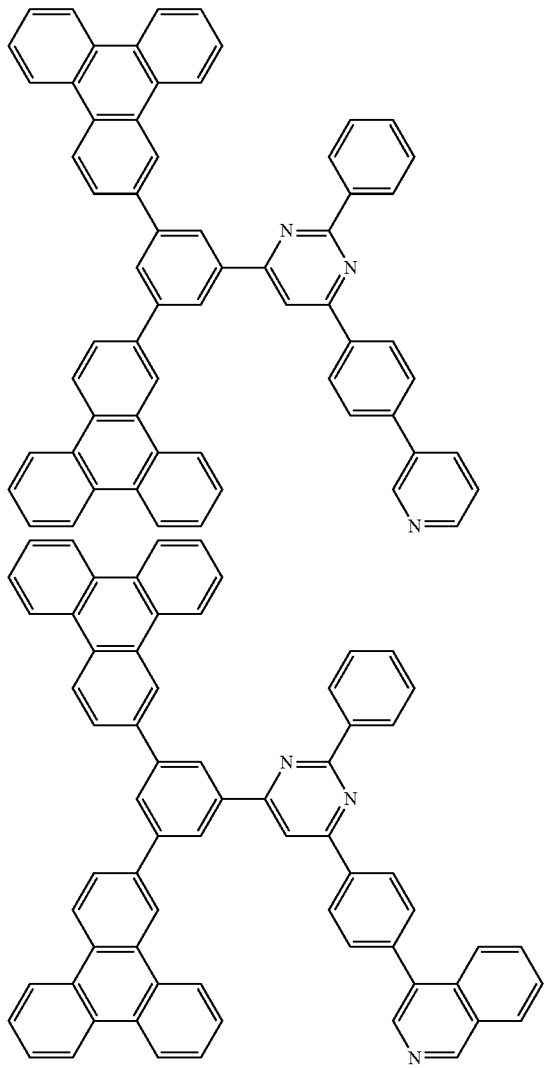
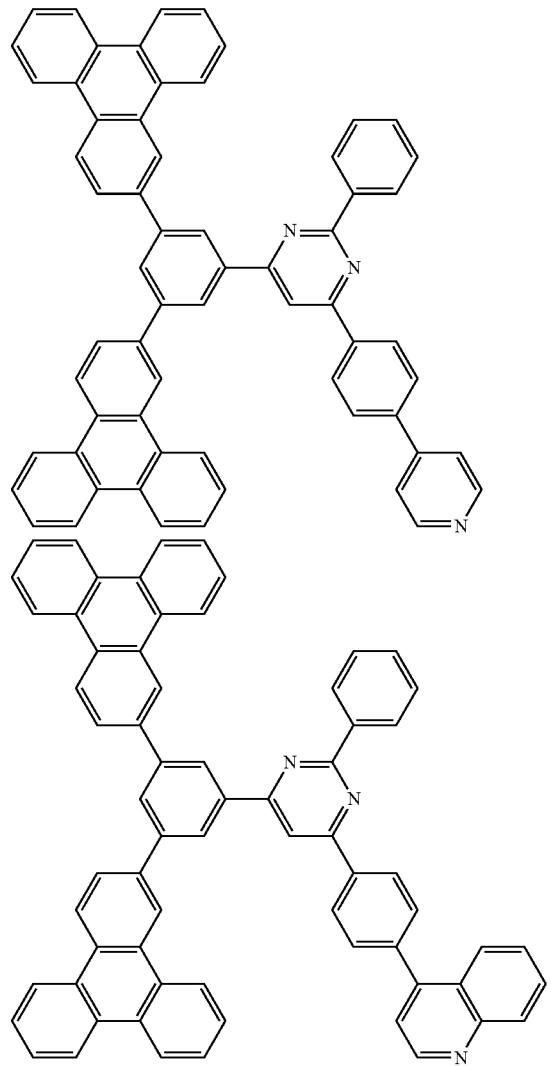
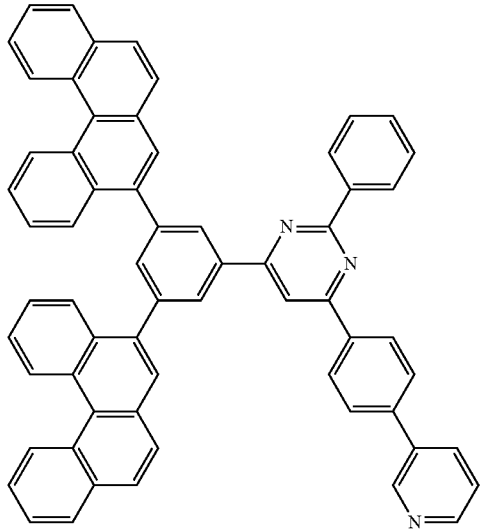
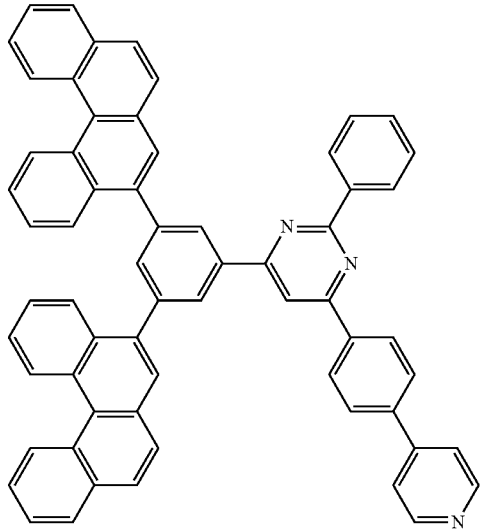

389
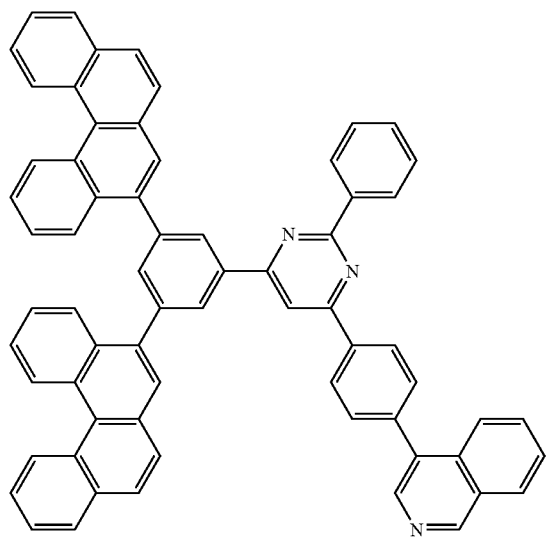
390
-continued
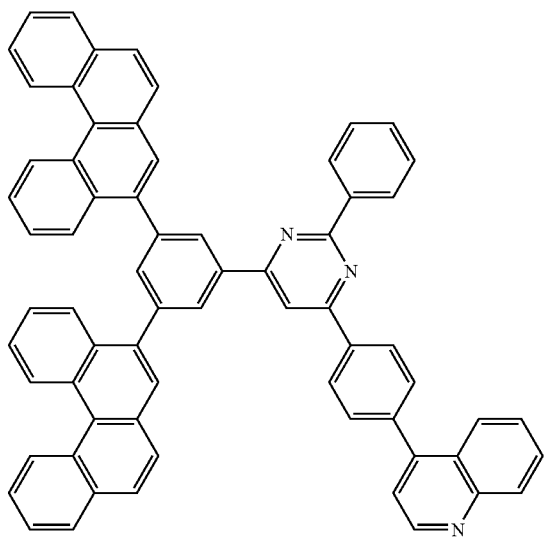
[Formula 191]
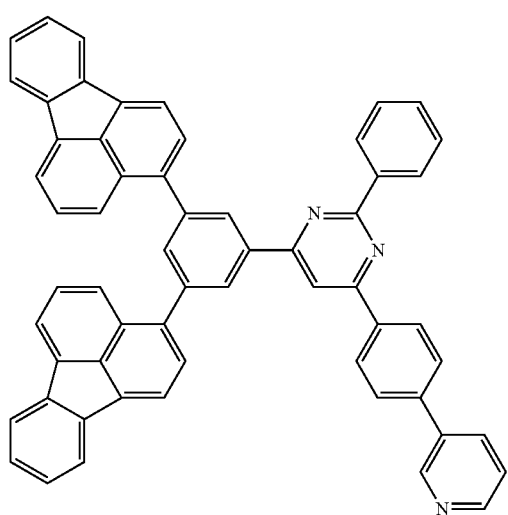
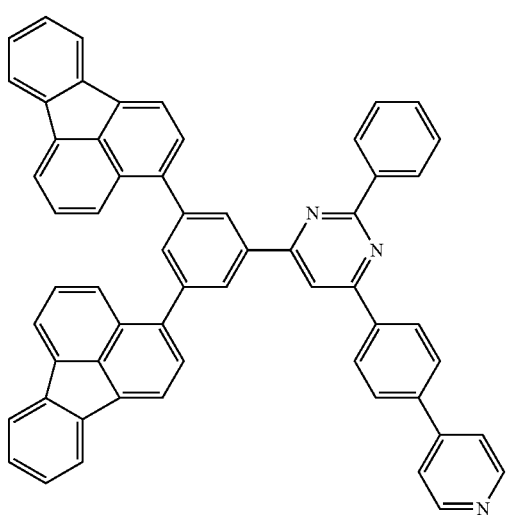
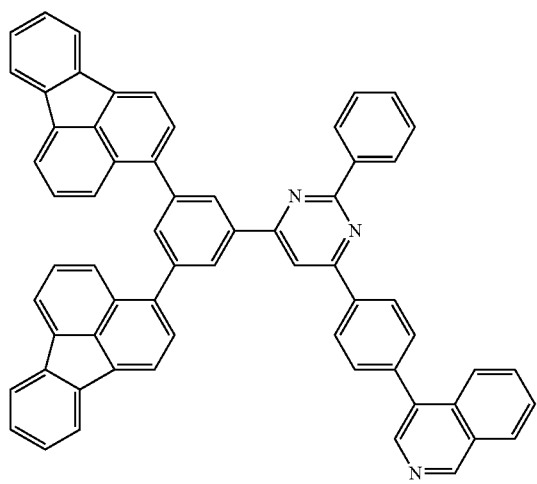
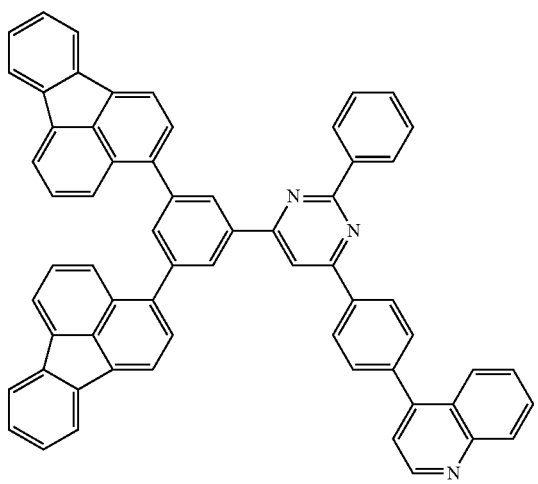

391
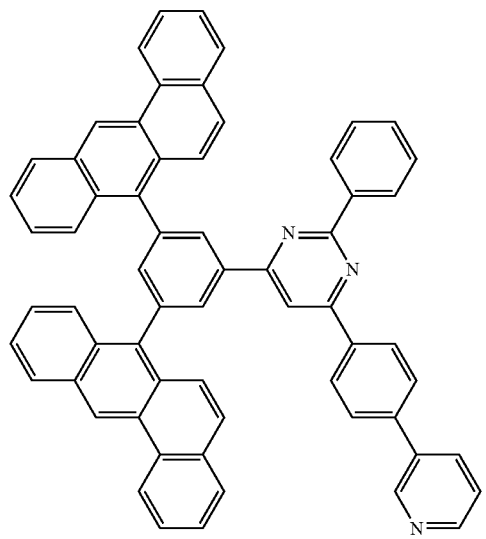
392
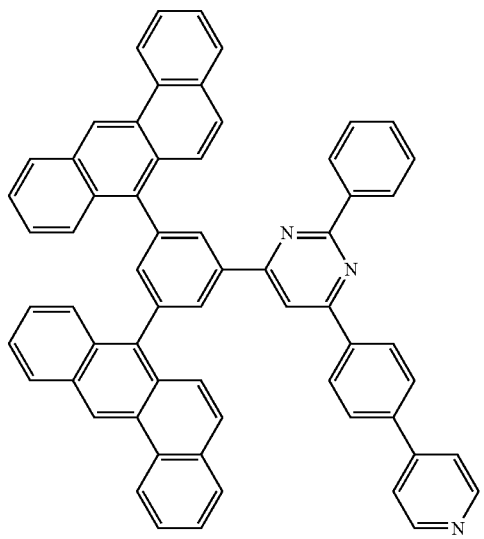
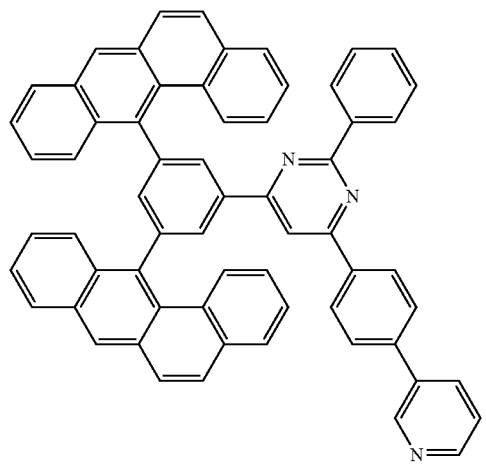
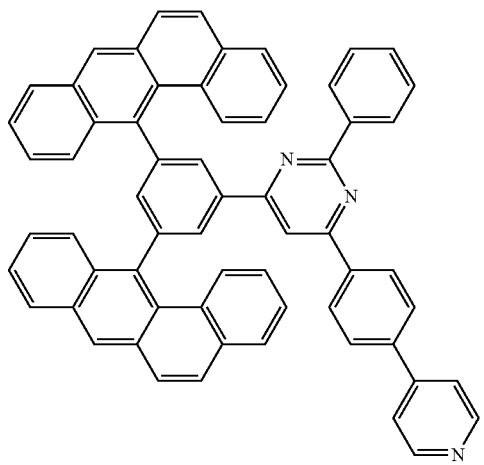
[Formula 192]
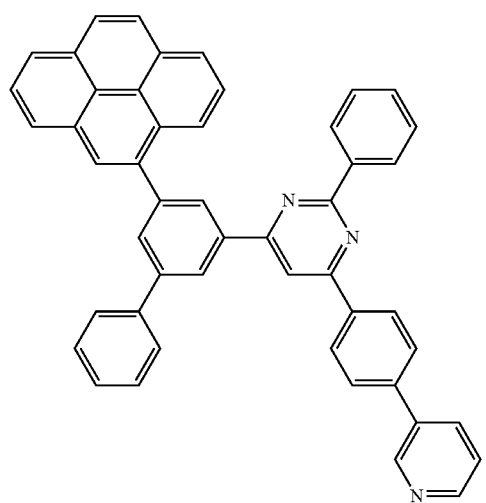
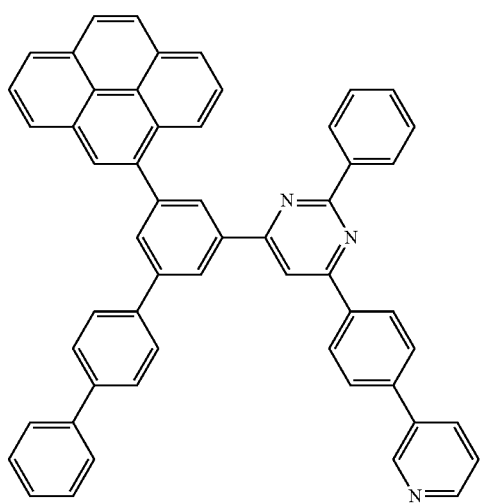

-continued
393
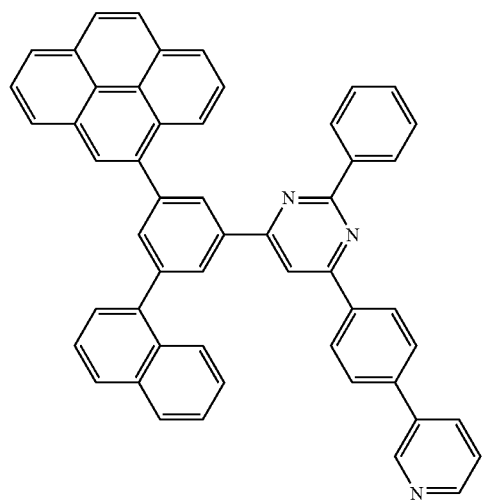
394
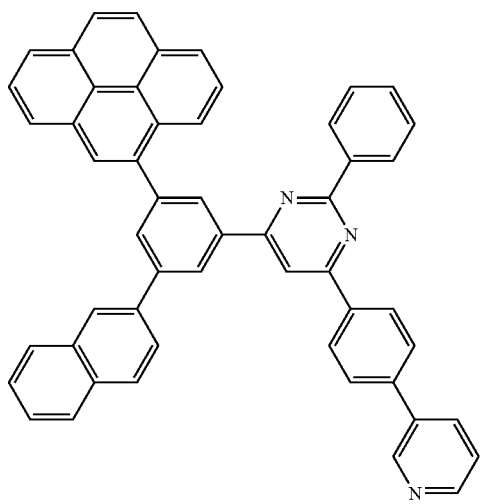
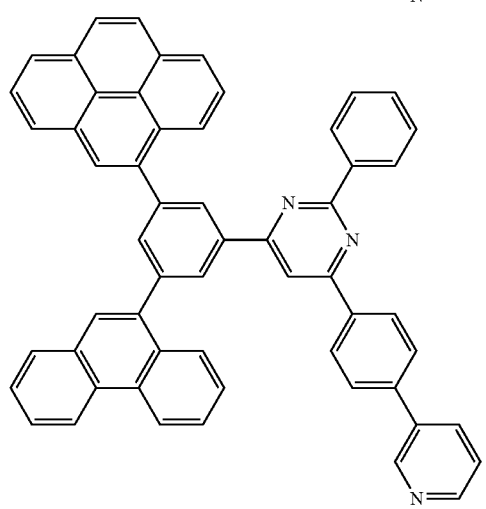
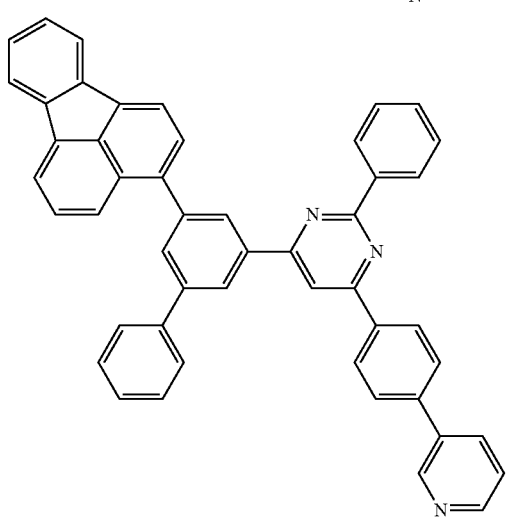
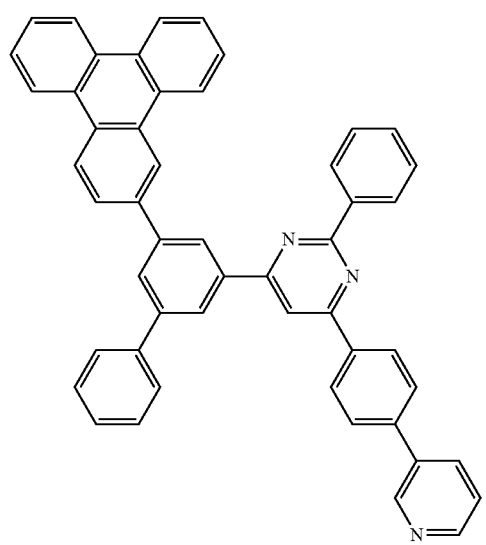

-continued
[Formula 193]
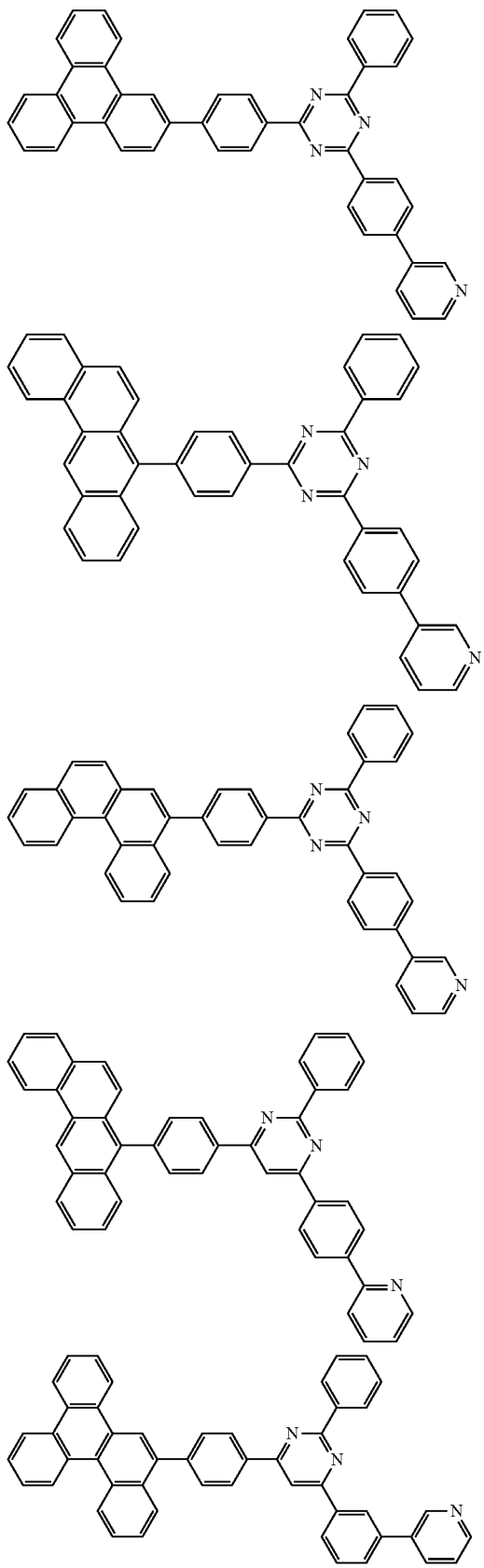
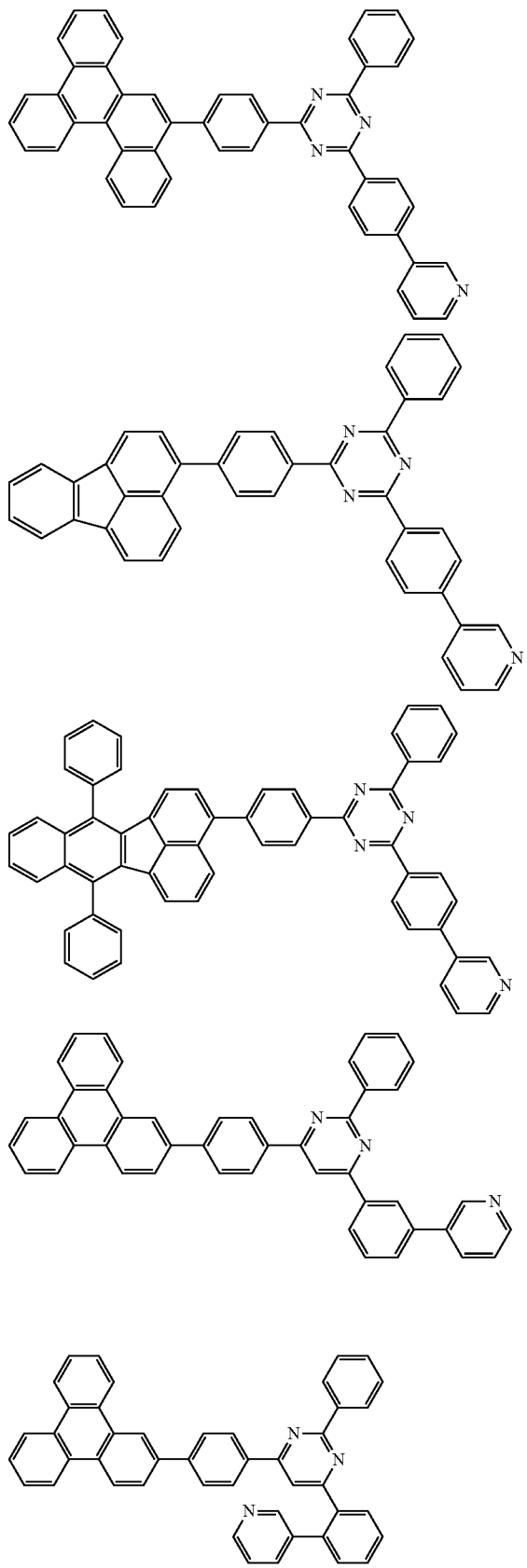

-continued
397
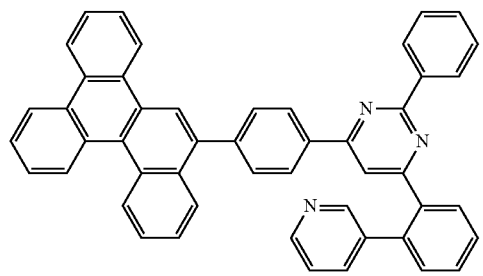
398
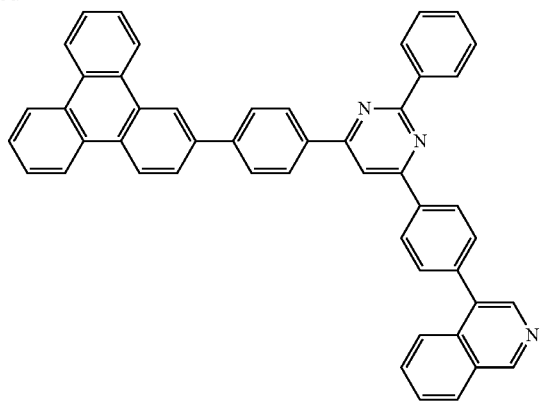
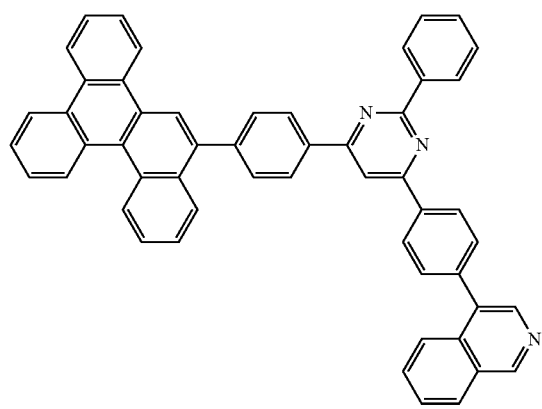
[Formula 194]
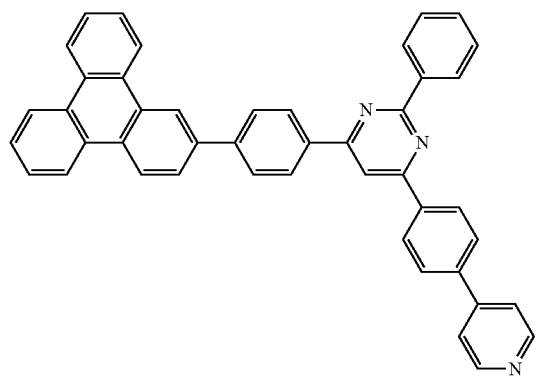
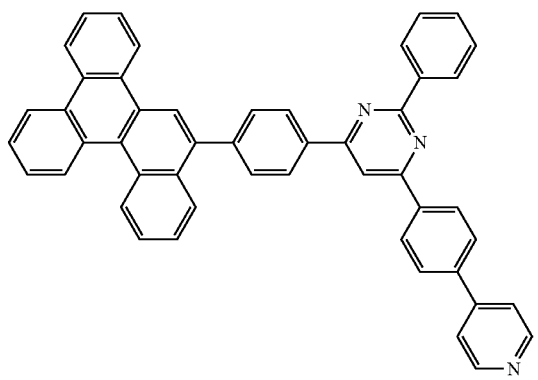
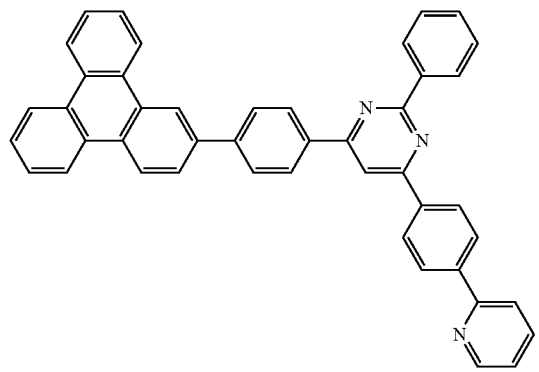

399
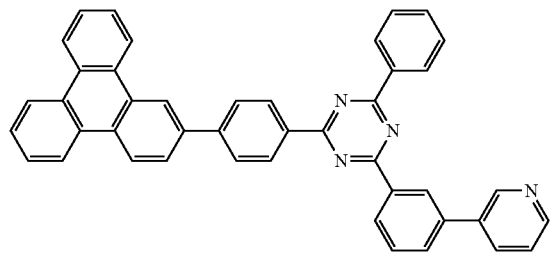
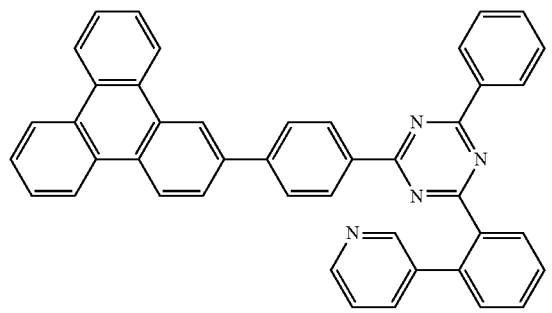
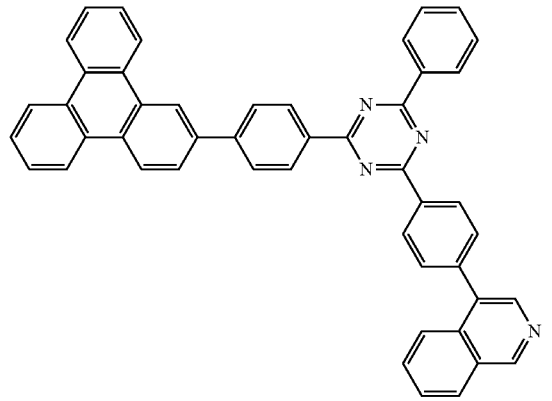
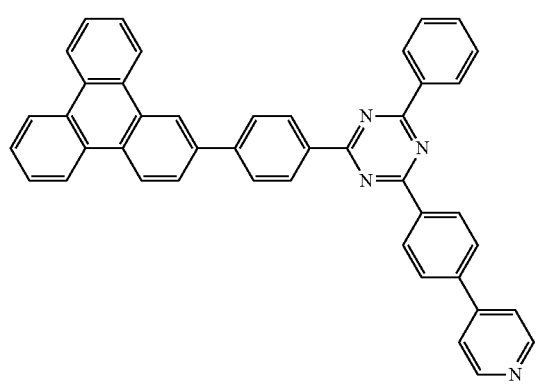
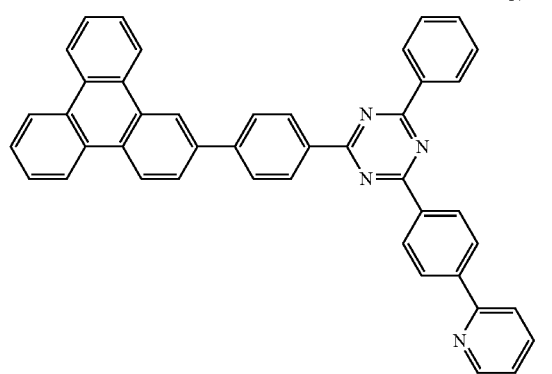
400
-continued
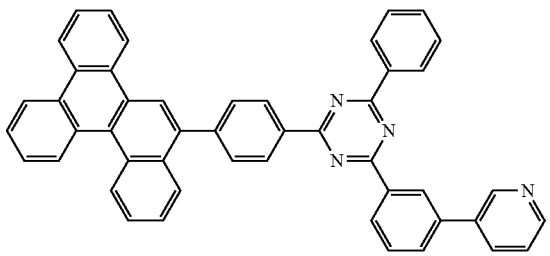
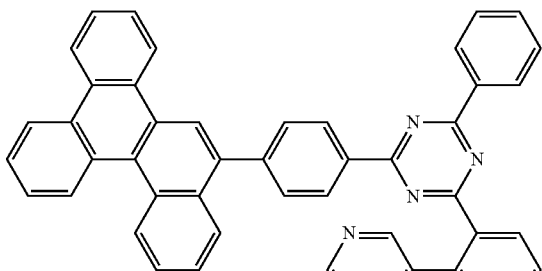
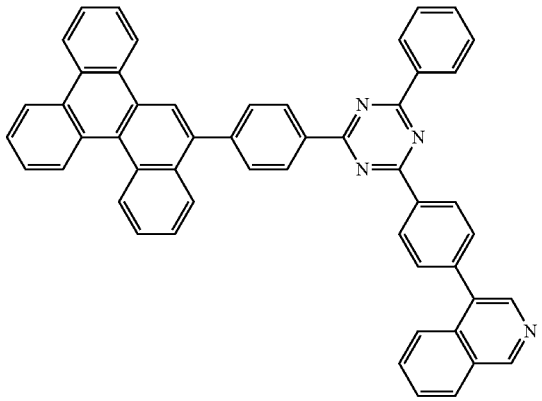
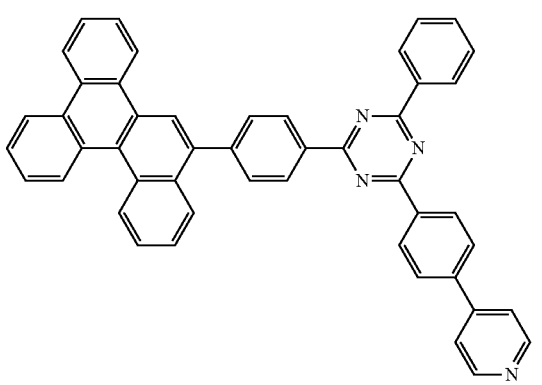
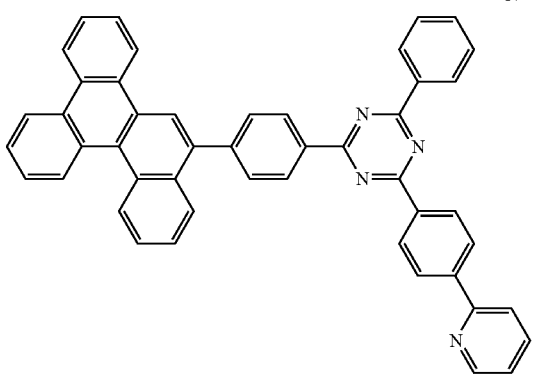

-continued
[Formula 195]
401
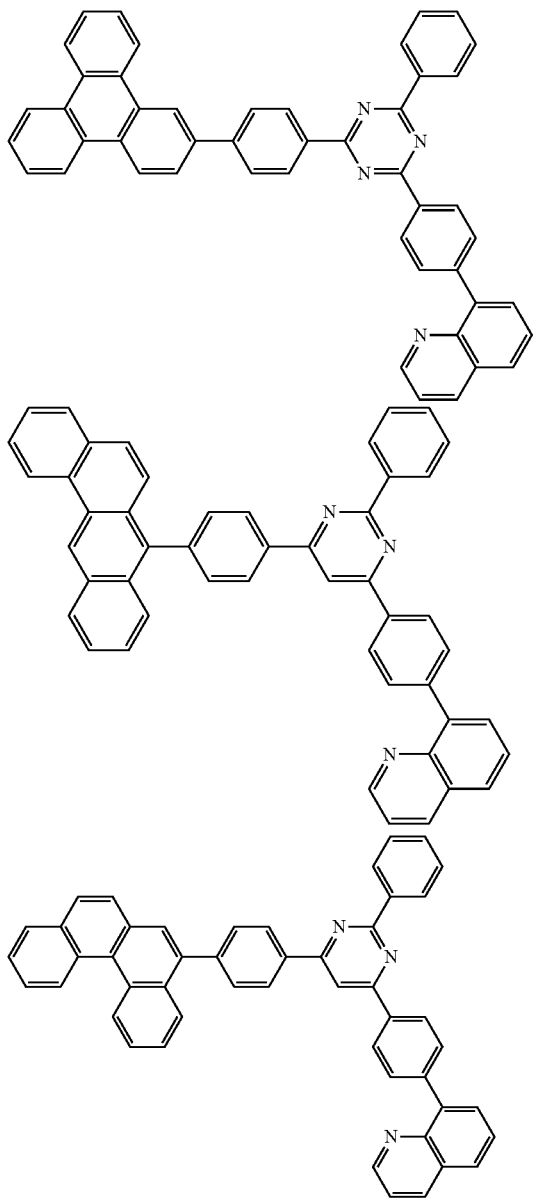
402
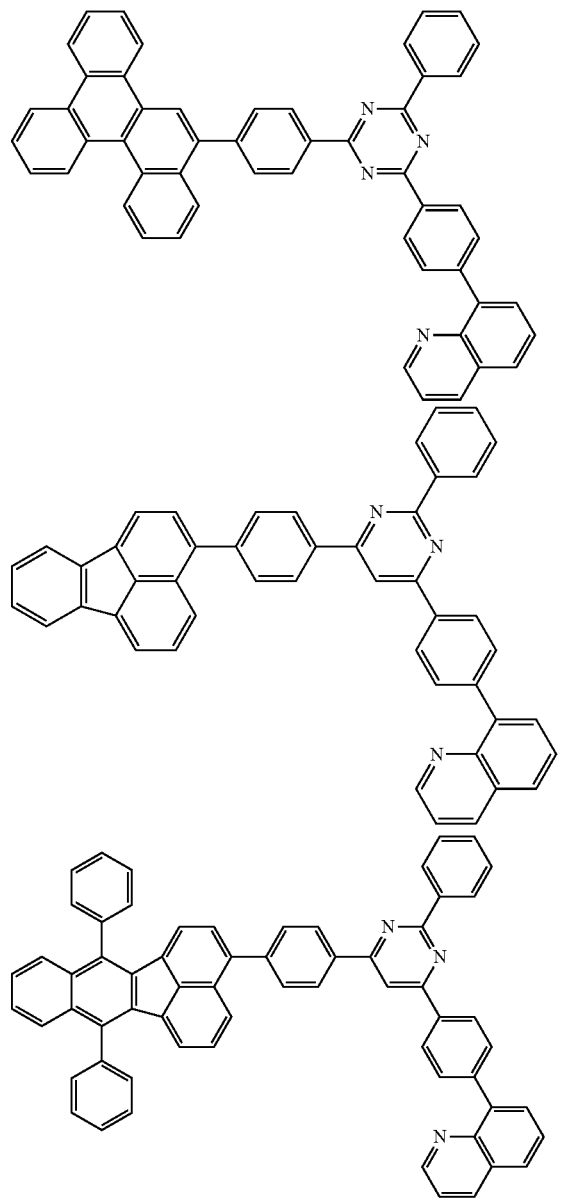
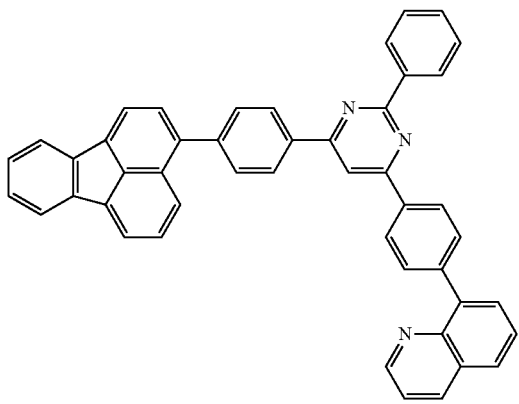
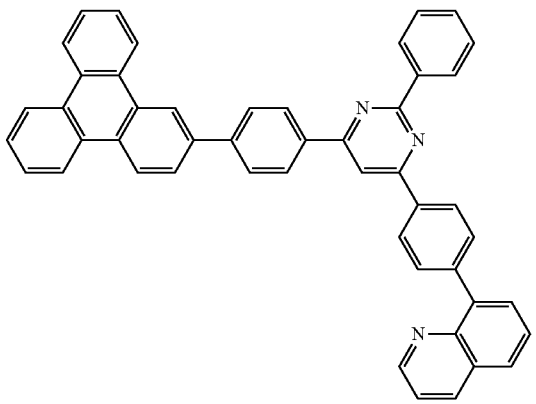

-continued
403
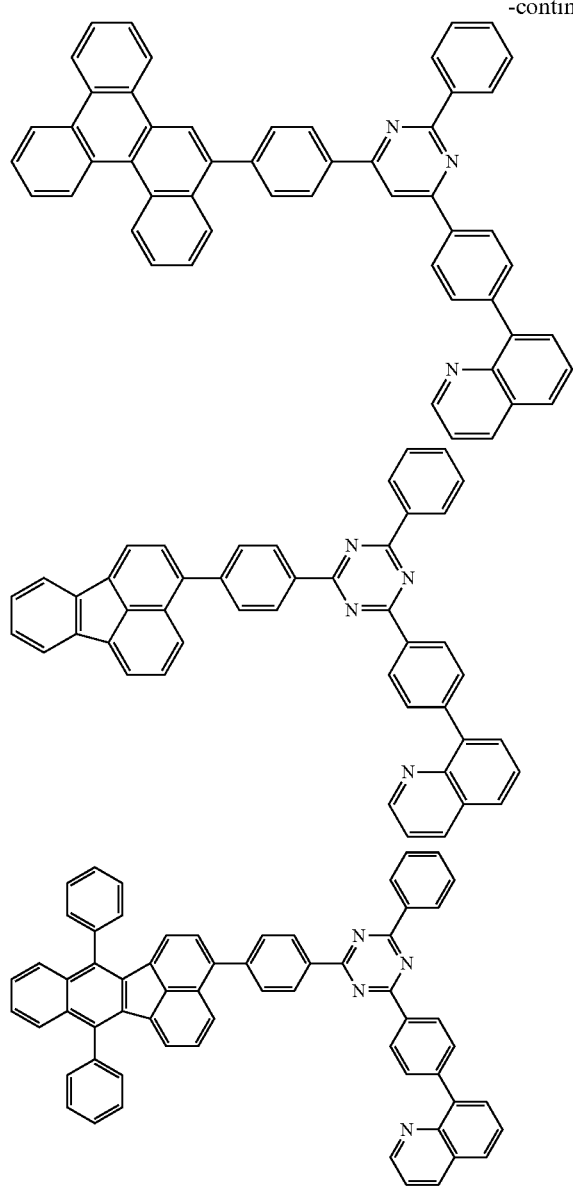
404
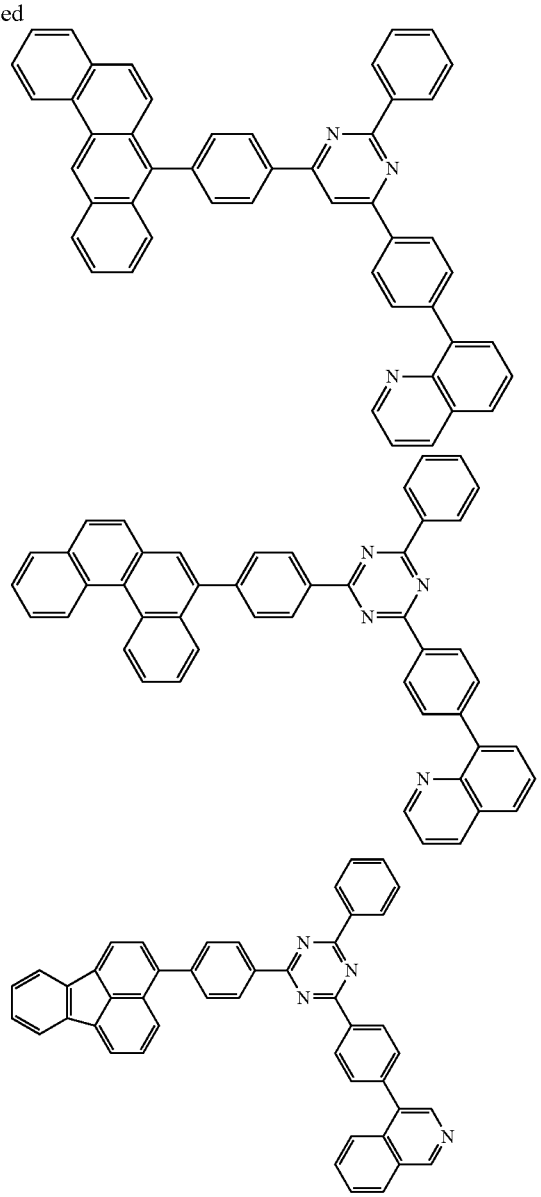
[Formula 196]
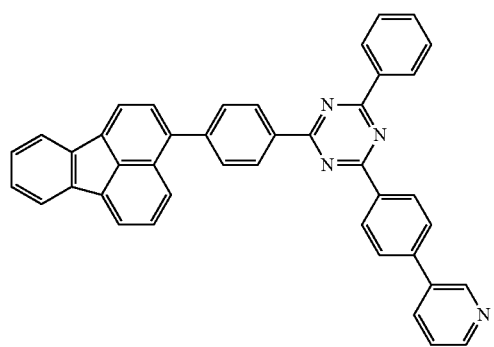
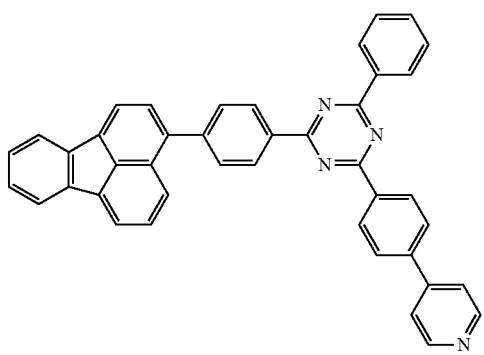

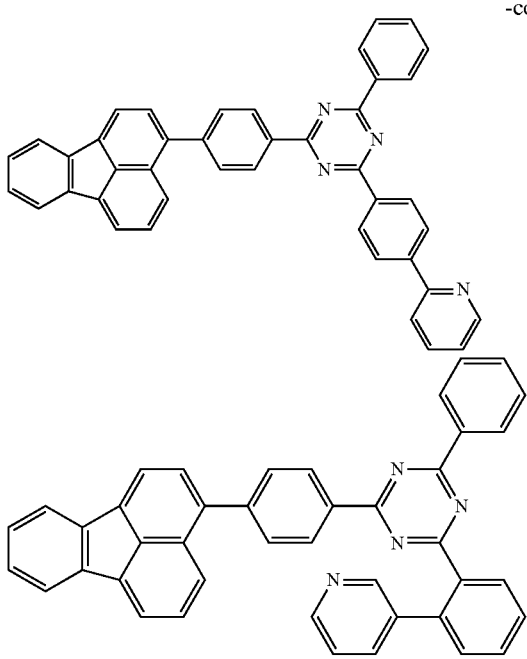
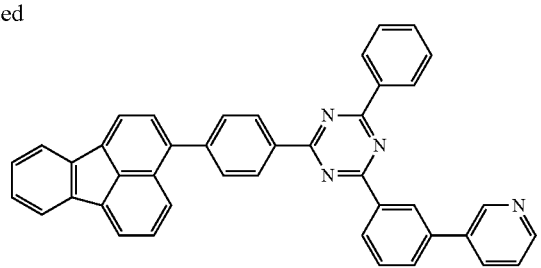

Organic-EL-Device Material

The compound according to the exemplary embodiment is usable as an organic-EL-device material. In this case, the compound according to the exemplary embodiment may be used alone as the organic-EL-device material, or alternatively, a mixture of the compound according to the exemplary embodiment and other material(s) may be used as the organic-EL-device material.

Organic EL Device

Arrangement(s) of Organic EL Device

An arrangement of an organic EL device according to the exemplary embodiment will be described.

The organic EL device includes an anode, a cathode and an organic layer. The organic layer includes at least one layer formed of an organic compound. The organic layer may further include an inorganic compound. In the organic EL device in the exemplary embodiment, at least one layer of the organic layer includes the compound according to the exemplary embodiment.

The FIGURE schematically shows an exemplary arrangement of the organic EL device according to the exemplary embodiment.

An organic EL device 1 includes a light-transmissive substrate 2, an anode 3, a cathode 4 and an organic layer 10 disposed between the anode 3 and the cathode 4.

The organic layer 10 includes an emitting layer 7, a hole injecting layer 5 interposed between the anode 3 and the emitting layer 7, a hole transporting layer 6 interposed between the hole injecting layer 5 and the emitting layer 7, and an electron transporting zone 11 interposed between the emitting layer 7 and the cathode 4.

The electron transporting zone 11 contains the compound according to the exemplary embodiment. The electron transporting zone 11 includes an electron transporting layer 8 and an electron injecting layer 9. In the exemplary embodiment, the electron transporting layer 8 contains the compound according to the exemplary embodiment. The electron transporting layer 8 is preferably in contact with the emitting layer 7.

It is preferable that the electron transporting zone 11 contains at least one of the electron-donating dopant and the organic metal complex. The electron transporting layer 8 preferably contains the compound according to the exemplary embodiment and at least one of the electron-donating dopant and the organic metal complex. Hereinafter, the electron-donating dopant and the organic metal complex are occasionally referred to as "the electron-donating dopant and the like."

The electron-donating dopant and the like contained in the electron transporting zone 11 are preferably at least one selected from the group consisting of an alkali metal, an alkali metal compound, an alkaline earth metal, an alkaline earth metal compound, a rare earth metal, a rare earth metal compound, an organic metal complex containing an alkali metal, an organic metal complex containing an alkaline earth metal, and an organic metal complex containing a rare earth metal.

The electron-donating dopant may be at least one selected from an alkali metal, an alkali metal compound, an alkaline-earth metal, an alkaline-earth metal compound, a rare-earth metal, a rare-earth metal compound and the like.

Examples of the alkali metal include lithium (Li) (work function: 2.93 eV), sodium (Na) (work function: 2.36 eV), potassium (K) (work function: 2.28 eV), rubidium (Rb) (work function: 2.16 eV), and cesium (Cs) (work function: 1.95 eV). The alkali metal having the work function of 2.9 eV or less is preferable. Among the alkali metal, at least one of K, Rb and Cs is preferable, Rb or Cs is more preferable, and Cs is further preferable.

Examples of the alkaline earth metal include calcium (Ca) (work function: 2.9 eV), strontium (Sr) (work function: from 2.0 to 2.5 eV), and barium (Ba) (work function: 2.52 eV). The alkaline earth metal having the work function of 2.9 eV or less is preferable.

Examples of the rare earth metal include scandium (Sc), yttrium (Y), cerium (Ce), terbium (Tb) and ytterbium (Yb). The rare earth metal having the work function of 2.9 eV or less is preferable.

Among the alkali metal, the alkaline earth metal and the rare earth metal, since the above preferred metals have particularly high reducibility, addition of a relatively small amount of the metals to an electron injecting zone enables to improve a luminance intensity of the organic EL device and prolong a lifetime of the organic EL device.

Examples of the alkali metal compound include an alkali oxide and an alkali halide. Examples of the alkali oxide include lithium oxide ($Li_2O$), cesium oxide ($Cs_2O$), and potassium oxide ($K_2O$). Examples of the alkali halide include lithium fluoride (LiF), sodium fluoride (NaF), cesium fluoride (CsF), and potassium fluoride (KF). The alkali metal compound is preferably at least one of lithium fluoride (LiF), lithium oxide ($Li_2O$), and sodium fluoride (NaF).

Examples of the alkaline earth metal compounds include barium oxide (BaO), strontium oxide (SrO), and calcium oxide (CaO). Moreover, the examples of the alkaline earth metal compound include barium strontium oxide ($Ba_xSr_{1-x}O$) ($0<x<1$), which is a mixture of BaO and SrO, and barium calcium oxide ($Ba_xCa_{1-x}O$) ($0<x<1$), which is a mixture of BaO and CaO. The alkaline earth metal compound is preferably at least one of BaO, SrO and CaO.

Examples of the rare earth metal compound include ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$). The rare earth metal compound is preferably at least one of $YbF_3$, $ScF_3$ and $TbF_3$.

The organic metal complex is not particularly limited, as long as the organic metal complex contains at least one of an alkali metal ion, alkaline earth metal ion and rare earth metal ion as a metal ion.

A ligand of the organic metal complex is not particularly limited. Examples of the ligand of the organic metal complex include quinolinol, benzoquinolinol, acridinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzimidazole, hydroxybenzo triazole, hydroxy fluborane, bipyridyl, phenanthroline, phthalocyanine, porphyrin, cyclopentadiene, β-diketones, azomethines, and derivatives thereof.

The electron-donating dopant and the organic metal complex contained in the electron transporting zone 11 are preferably at least one selected from the group consisting of lithium, a lithium compound, and an organic metal complex containing lithium. More preferably, the electron transporting zone 11 contains 8-quinolinolato lithium.

When the compound according to the exemplary embodiment, the electron-donating dopant and the like are contained in the electron transporting layer 8, respective amounts of the compound according to the exemplary embodiment, the electron-donating dopant and the like are added preferably at a ratio (the compound according to the exemplary embodiment: the electron-donating dopant, the organic metal complex and the like being 100:1 to 1:100, more preferably 5:1 to 1:5, further preferably 2:1 to 1:2.

Film Thickness of Electron Transporting Layer

A film thickness of the electron transporting layer 8 is not particularly limited, but is preferably in a typical range of 0.1 nm to 1 μm.

The electron transporting zone 11 of the organic EL device 1 according to the exemplary embodiment may further include a second electron transporting layer in addition to the electron transporting layer 8. The electron transporting layer 8 is preferably interposed between the emitting layer 7 and the second electron transporting layer.

The second electron transporting layer is a layer containing a highly electron-transporting substance. For the second electron transporting layer, at least one of 1) a metal complex such as an aluminum complex, beryllium complex and zinc complex, 2) heteroaromatic compound such as an imidazole derivative, benzimidazole derivative, azine derivative, carbazole derivative, and phenanthroline derivative, and 3) a high-molecule compound are usable. Specifically, as a low-molecule organic compound, a metal complex such as Alq, tris(4-methyl-8-quinolinolato)aluminum (abbreviation: $Almq_3$), bis(10-hydroxybenzo[h]quinolinato) beryllium (abbreviation: $BeBq_2$), BAlq, Znq, ZnPBO and ZnBTZ is usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) are usable. In the above second electron transporting layer, a benzimidazole compound is suitably usable. Moreover, a high-molecule compound is also usable for the second electron transporting layer. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy) and the like are usable.

The above-described substances mostly have an electron mobility of $10^{-6}$ cm$^2$/(V·s) or more. However, any substance having an electron transporting performance higher than a hole transporting performance may be used for the second electron transporting layer in addition to the above substances. Moreover, two or more layers containing the above substances may be laminated in addition to the electron transporting layer 8 (first electron transporting layer) and the second electron transporting layer. Further, the electron transporting layer 8 may contain the compound usable for the second electron transporting layer.

Next, other components of the organic EL device 1 will be described.

Substrate

The substrate 2 is used as a support for the organic EL device 1. For instance, glass, quartz, plastics and the like are usable as the substrate 2. A flexible substrate is also usable. The flexible substrate means a bendable substrate and is exemplified by plastic substrates formed of polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal having a large work function (specifically, 4.0 eV or more), alloy, an electrically conductive compound and a mixture thereof are preferably usable as the anode 3 formed on the substrate 2. Specific examples of the material for the anode include indium tin oxide (ITO), indium tin oxide containing silicon or silicon oxide, indium zinc oxide, tungsten oxide, indium oxide containing zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), nitrides of a metal material (e.g., titanium nitride) and the like are usable.

The above materials are typically formed into a film by sputtering. For instance, a target of the indium zinc oxide which is prepared by adding zinc oxide in a range from 1 mass % to 10 mass % relative to indium oxide is used for forming a film by sputtering. Moreover, for instance, as for the indium oxide containing tungsten oxide and zinc oxide, a target thereof prepared by adding tungsten oxide in a range from 0.5 mass % to 5 mass % and zinc oxide in a range from 0.1 mass % to 1 mass % relative to indium oxide is usable for forming a film by sputtering. In addition, vapor deposition, coating, ink jet printing, spin coating and the like may be used for forming a film.

Among the organic layers formed on the anode 3, since the hole injecting layer 5 formed adjacent to the anode 3 is formed of a composite material in which holes are easily injectable irrespective of the work function of the anode 3, other materials usable as an electrode material (e.g., a metal, alloy, electrically conductive compound, mixture thereof, and elements belonging to Group 1 or 2 in the periodic table of the elements) are also usable for the anode 3.

A material having a small work function such as elements belonging to Groups 1 and 2 in the periodic table of the elements, specifically, an alkali metal such as lithium (Li) and cesium (Cs), an alkaline earth metal such as magnesium (Mg), calcium (Ca) and strontium (Sr), alloys (e.g., MgAg and AlLi) including the alkali metal or the alkaline earth metal, a rare earth metal such as europium (Eu) and ytterbium (Yb), alloys including the rare earth metal are also usable for the anode 3. When the cathode 3 is formed of the alkali metal, alkaline earth metal and alloys thereof, vapor deposition and sputtering are usable. Further, when the anode 3 is formed of silver paste and the like, coating, ink jet printing and the like are usable.

Hole Injecting Layer

The hole injecting layer 5 is a layer containing a highly hole-injectable substance. Examples of the highly hole-injectable substance include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

In addition, the examples of the highly hole-injectable substance further include: an aromatic amine compound that is a low-molecule compound such as 4,4',4''-tris(N,N-diphenylamino)triphenylamine (abbreviation: TDATA), 4,4',4''-tris[N-(3-methylphenyl)-N-phenyl amino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris [N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1).

Moreover, a high-molecule compound (e.g., an oligomer, dendrimer and polymer) is also usable as the highly hole-injectable substance. Examples of the high-molecule compound include poly(N-vinylcarbazole) (abbreviation: PVK), poly(4-vinyltriphenylamine) (abbreviation: PVTPA), poly [N-(4-{N'-[4-(4-diphenylamino)phenyl]phenyl-N'-phenylamino}phenyl) methacrylamido] (abbreviation: PTPDMA), and poly[N,N'-bis(4-butylphenyl)-N,N'-bis(phenyl) benzidine] (abbreviation: Poly-TPD). Moreover, the examples of the high-molecule compound include a high-molecule compound added with an acid such as poly(3,4-ethylene dioxythiophene)/poly(styrene sulfonic acid) (PEDOT/PSS), and polyaniline/poly(styrene sulfonic acid) (PAni/PSS). An electron accepting compound may be used for the hole injecting layer. The electron accepting compound is exemplified by dipyrazino[2,3-f:20,30-h]quinoxaline-2,3,6,7,10,11-hexacarbonitrile (HAT-CN).

Hole Transporting Layer

The hole transporting layer 6 is a layer containing a highly hole-transporting substance. An aromatic amine compound, carbazole derivative, anthracene derivative and the like are usable for the hole transporting layer 6. Specifically, for instance, an aromatic amine compound is usable for the hole transporting layer. Examples of the aromatic amine compound include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/(V·s) or more.

The hole transporting layer 6 is a layer containing a highly hole-transporting substance. An aromatic amine compound, carbazole derivative, anthracene derivative and the like are usable for the hole transporting layer 6. Specifically, for instance, an aromatic amine compound is usable for the hole transporting layer. Examples of the aromatic amine compound include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/(V·s) or more.

However, any substance having a hole transporting performance higher than an electron transporting performance may be used in addition to the above substances. A layer including the highly hole-transporting substance may be provided in the form of a single layer or a laminate of two or more layers.

When the hole transporting layer includes two or more layers, one of the layers with a larger energy gap is preferably provided closer to the emitting layer 7.

Emitting Layer

The emitting layer 7 is a layer containing a highly emittable substance and can be formed of various materials. For instance, a fluorescent compound emitting fluorescence and a phosphorescent compound emitting phosphorescence are usable as the highly emittable substance. The fluorescent compound is a compound capable of emitting in a singlet state. The phosphorescent compound is a compound capable of emitting in a triplet state.

Examples of a blue fluorescent material usable for the emitting layer 7 include a pyrene derivative, styrylamine derivative, chrysene derivative, fluoranthene derivative, fluorene derivative, diamine derivative, and triarylamine derivative. Specific examples of the blue fluorescent material include N,N'-bis[4-(9H-carbazole-9-yl)phenyl]-N,N'-diphenylstilbene-4,4'-diamine (abbreviation: YGA2S), 4-(9H-carbazole-9-yl)-4'-(10-phenyl-9-anthryl)triphenylamine (abbreviation: YGAPA), and 4-(10-phenyl-9-anthryl)-4'-(9-phenyl-9H-carbazole-3-yl)triphenylamine (abbreviation: PCBAPA).

A green fluorescent material usable for the emitting layer 7 is exemplified by an aromatic amine derivative. Specific examples of the green fluorescent material include N-(9,10-diphenyl-2-anthryl)-N,9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylene diamine (abbreviation: 2DPABPhA), N-[9,10-bis(1,1'-biphenyl-2-yl)]-N-[4-(9H-carbazole-9-yl)phenyl]-N-phenylanthracene-2-amine (abbreviation: 2YGABPhA), and N,N,9-triphenylanthracene-9-amine (abbreviation: DPhAPhA).

A red fluorescent material usable for the emitting layer 7 is exemplified by a tetracene derivative and a diamine derivative. Specific examples of the red fluorescent material include N,N,N',N'-tetrakis(4-methylphenyl)tetracene-5,11-diamine (abbreviation: p-mPhTD), and 7,14-diphenyl-N,N,N',N'-tetrakis(4-methylphenyl)acenaphtho[1,2-a]fluoranthene-3,10-diamine (abbreviation: p-mPhAFD).

A blue phosphorescent material usable for the emitting layer 7 is exemplified by a metal complex such as an iridium complex, osmium complex, and platinum complex. Specific examples of the blue phosphorescent material include bis[2-(4',6'-difluorophenyl)pyridinato-N,C2']iridium(III)tetrakis(1-pyrazolyl)borate (abbreviation: FIr6), bis[2-(4',6'-difluorophenyl)pyridinato-N,C2']iridium(III)picolinate (abbreviation: FIrpic), bis[2-(3',5'bistrifluoromethylphenyl)pyridinato-N,C2']iridium(III)picolinate (abbreviation: Ir(CF3ppy)$_2$(pic)), and bis[2-(4',6'-difluorophenyl)pyridinato-N,C2']iridium(III)acetylacetonato (abbreviation: FIracac).

A green phosphorescent material usable for the emitting layer 7 is exemplified by an iridium complex. Examples of the green phosphorescent material further include tris(2-phenylpyridinato-N,C2')iridium(III) (abbreviation: Ir(ppy)$_3$), bis(2-phenylpyridinato-N,C2')iridium(III)acetylacetonato (abbreviation: Ir(ppy)$_2$(acac)), bis(1,2-diphenyl-1H-benzimidazolato)iridium(III)acetylacetonato (abbreviation: Ir(pbi)$_2$(acac)), and bis(benzo[h]quinolinato)iridium(III) acetylacetonato (abbreviation: Ir(bzq)$_2$(acac)).

A red phosphorescent material usable for the emitting layer 7 is exemplified by a metal complex such as an iridium complex, platinum complex, terbium complex and europium complex. Specifically, the red phosphorescent material is exemplified by an organic metal complex such as bis[2-(2'-benzo[4,5-α]thienyl)pyridinato-N,C3']iridium(III)acetylacetonato (abbreviation: Ir(btp)$_2$(acac)), bis(1-phenylisoquinolinato-N,C2')iridium(III)acetylacetonato (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), and 2,3,7,8,12,13,17,18-octaethyl-21H,23H-porphyrinplatinum(II) (abbreviation: PtOEP).

Since a rare earth metal complex such as tris(acetylacetonato)(monophenanthroline)terbium(III) (abbreviation: Tb(acac)$_3$(Phen)), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium (III) (abbreviation: Eu(TTA)$_3$(Phen)) produces emission from a rare earth metal ion (electron transition between different multiplicities), the rare earth metal complex is usable as the phosphorescent compound.

The emitting layer 7 may be provided by dispersing the above-described highly emittable substance (which is occasionally referred to as a guest material, emitter, luminescent material or dopant material) in another substance (which is occasionally referred to as a host material or matrix material). As the substance for dispersing the highly emittable substance, various compounds are usable, among which a substance having a Lowest Unoccupied Molecular Orbital level (LUMO level) higher than that of the highly emittable substance and a Highest Occupied Molecular Orbital (HOMO level) lower than that of the highly emittable substance is preferable.

Examples of the host material include 1) a metal complex such as an aluminum complex, beryllium complex or zinc complex, 2) a heterocyclic compound such as an oxadiazole derivative, benzimidazole derivative or phenanthroline derivative, 3) a fused aromatic compound such as a carbazole derivative, anthracene derivative, phenanthrene derivative, pyrene derivative or chrysene derivative, and 4) an aromatic amine compound such as a triarylamine derivative or a fused polycyclic amine derivative. Moreover, a plurality of kinds of the substances (the host material) for dispersing the highly emittable substance (the guest material) are usable.

Examples of the metal complex as the host material include tris(8-quinolinolato)aluminum(III) (abbreviation: Alq), tris(4-methyl-8-quinolinolato)aluminum(III)(abbreviation: Almq$_3$), bis(10-hydroxybenzo[h]quinolinato)beryllium (II)(abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ).

Examples of the heterocyclic compound as the host material include 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen) and bathocuproine (abbreviation: BCP)

Examples of the fused atomatic compound as the host material include 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), 9,10-diphenylanthracene (abbreviation: DPAnth), and 6,12-dimethoxy-5,11-diphenylchrysene.

Examples of the aromatic amine compound as the host material include N,N-diphenyl-9-[4-(10-phenyl-9-anthryl)phenyl]-9H-carbazole-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazole-3-amine (abbreviation: PCAPA), N,9-diphenyl-N-{4-[4-(10-phenyl-9-anthryl)phenyl]phenyl}-9H-carbazole-3-amine (abbreviation: PCAPBA), N-(9,10-diphenyl-2-anthryl)-N,9-diphenyl-9H-carbazole-3-amine (abbreviation: 2PCAPA), NPB (or α-NPD), TPD, DFLD-PBi, and BSPB.

Electron Injecting Layer

The electron injecting layer 9 is a layer containing a highly electron-injectable substance. Examples of a material for the electron injecting layer 9 include an alkali metal, alkaline earth metal and a compound thereof, examples of which include lithium (Li), cesium (Cs), calcium (Ca), lithium fluoride (LiF), cesium fluoride (CsF), calcium fluoride ($CaF_2$), and lithium oxide (LiOx). In addition, a substance containing an alkali metal, alkaline earth metal and a compound thereof in the electron-transporting substance, specifically, a substance containing magnesium (Mg) in Alq may be used. In this case, electrons can be more efficiently injected from the cathode 4.

Alternatively, a composite material provided by mixing an organic compound with an electron donor may be used for the electron injecting layer 9. The composite material exhibits excellent electron injecting performance and electron transporting performance since the electron donor generates electron in the organic compound. In this arrangement, the organic compound is preferably a material exhibiting an excellent transforming performance of the generated electrons. Specifically, for instance, the above-described substance for the electron transporting layer 8 (e.g., the metal complex and heteroaromatic compound) is usable. The electron donor may be any substance exhibiting an electron donating performance to the organic compound.

Specifically, an alkali metal, an alkaline earth metal or a rare earth metal is preferable, examples of which include lithium, cesium, magnesium, calcium, erbium and ytterbium. Moreover, an alkali metal oxide and alkaline earth metal oxide are preferably used, examples of which include lithium oxide, calcium oxide, and barium oxide. Further, Lewis base such as magnesium oxide is also usable. Furthermore, tetrathiafulvalene (abbreviation: TTF) is also usable.

Cathode

Metal, alloy, an electrically conductive compound, a mixture thereof and the like, which have a small work function (specifically, 3.8 eV or less), are preferably usable as a material for the cathode 4. Examples of the material for the cathode include elements belonging to Groups 1 and 2 in the periodic table of the elements, specifically, the alkali metal such as lithium (Li) and cesium (Cs), the alkaline earth metal such as magnesium (Mg), calcium (Ca) and strontium (Sr), alloys (e.g., MgAg and AlLi) including the alkali metal or the alkaline earth metal, the rare earth metal such as europium (Eu) and ytterbium (Yb), and alloys including the rare earth metal.

When the cathode 4 is formed of the alkali metal, alkaline earth metal and alloy thereof, vapor deposition and sputtering are usable. Further, when the cathode 4 is formed of silver paste and the like, coating, ink jet printing and the like are usable.

By providing the electron injecting layer 9, various conductive materials such as Al, Ag, ITO, graphene, and indium tin oxide containing silicon or silicon oxide are usable for forming the cathode 4 irrespective of the magnitude of the work function. The conductive materials can be formed into a film by sputtering, ink jet printing, spin coating and the like.

Layer Formation Method(s)

A method for forming each layer of the organic EL device in the exemplary embodiment is not limited except for the above particular description. Known methods of dry film-forming and wet film-forming are applicable. Examples of the dry film-forming include vacuum deposition, sputtering, plasma deposition method and ion plating. Examples of the wet film-forming include spin coating, dipping, flow coating and ink-jet.

Film Thickness

A film thickness of each of the organic layers in the organic EL device 1 according to the exemplary embodiment is not limited except for the above particular description. The film thickness is generally preferably in the range from several nanometers to 1 µm, since too small thickness possibly causes defects such as a pin hole while too large thickness requires high voltage to be applied and lowers efficiency.

In the exemplary embodiment, the number of carbon atoms forming a ring (also referred to as ring carbon atoms) means the number of carbon atoms included in atoms forming the ring itself of a compound in which the atoms are bonded to form the ring (e.g., a monocyclic compound, a fused ring compound, a cross-linked compound, a carbocyclic compound, and a heterocyclic compound). When the ring is substituted by a substituent, the "ring carbon atoms" do not include carbon(s) contained in the substituent. Unless specifically described, the same applies to the "ring carbon atoms" described later. For instance, a benzene ring has 6 ring carbon atoms, a naphthalene ring has 10 ring carbon atoms, a pyridinyl group has 5 ring carbon atoms, and a furanyl group has 4 ring carbon atoms. When the benzene ring and/or the naphthalene ring is substituted by, for instance, an alkyl group, the number of carbon atoms of the alkyl group is not included in the number of the ring carbon atoms. When a fluorene ring is substituted by, for instance, a fluorene ring (e.g., a spirofluorene ring), the number of carbon atoms of the fluorene ring as a substituent is not counted in the number of the ring carbon atoms for the fluorene ring.

In the exemplary embodiment, the number of atoms forming a ring (also referred to as ring atoms) means the number of atoms forming the ring itself of a compound in which the atoms are bonded to form the ring (e.g., a monocyclic compound, a fused ring compound, a cross-linked compound, a carbocyclic compound, and a heterocyclic compound). Atom(s) not forming the ring (e.g., a hydrogen atom for terminating the atoms forming the ring) and atoms included in a substituent substituting the ring are not counted in the number of the ring atoms. Unless specifically described, the same applies to the "ring atoms" described later. For instance, a pyridine ring has 6 ring atoms, a quinazoline ring has 10 ring atoms, and a furan ring has 5 ring atoms. Hydrogen atoms respectively bonded to the pyridine ring and the quinazoline ring and atoms forming the substituents are not counted in the number of the ring atoms. When a fluorene ring is substituted by, for instance, a fluorene ring (e.g., a spirofluorene ring), the number of atoms of the fluorene ring as a substituent is not included in the number of the ring atoms for the fluorene ring.

Next, each of substituents described in the above formulae will be described.

Examples of the aromatic hydrocarbon group (occasionally referred to as an aryl group) having 6 to 30 ring carbon atoms in the exemplary embodiment include a phenyl group, biphenyl group, terphenyl group, naphthyl group, anthryl group, phenanthryl group, fluorenyl group, pyrenyl group, chrysenyl group, fluoranthenyl group, benzo[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aromatic hydrocarbon group in the exemplary embodiment group preferably has 6 to 20 ring carbon atoms, more preferably 6 to 14 ring carbon atoms, further preferably 6 to 12 ring carbon atoms. Among the aromatic hydrocarbon group, a phenyl group, biphenyl group, naphthyl group, phenanthryl group, terphenyl group, and fluorenyl group are particularly preferable. A carbon atom at a position 9 of each of 1-fluorenyl group, 2-fluorenyl group, 3-fluorenyl group and 4-fluorenyl group is preferably substituted by a substituted or unsubstituted alkyl group having 1 to 30 carbon atoms or a substituted or unsubstituted aromatic hydrocarbon group having 6 to 18 ring carbon atoms described later in the exemplary embodiment.

The heterocyclic group (occasionally, referred to as a heteroaryl group, heteroaromatic ring group or aromatic heterocyclic group) having 5 to 30 ring atoms in the exemplary embodiment preferably contains as a hetero atom at least one atom selected from the group consisting of nitrogen, sulfur, oxygen, silicon, selenium atom and germanium atom, and more preferably contains at least one atom selected from the group consisting of nitrogen, sulfur and oxygen.

The alkyl group having 1 to 30 carbon atoms in the exemplary embodiment may be linear, branched or cyclic. Examples of the linear or branched alkyl group are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, amyl group, isoamyl group, 1-methylpentyl group, 2-methylpentyl group, 1-pentylhexyl group, 1-butylpentyl group, 1-heptyloctyl group and 3-methylpentyl group.

The linear or branched alkyl group in the exemplary embodiment preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group and neopentyl group are particularly preferable.

Examples of the cycloalkyl group having 3 to 30 carbon atoms in the exemplary embodiment are a cyclopropyl group, cyclobutyl group, cyclopentyl group, cyclohexyl group, 4-metylcyclohexyl group, adamantyl group and norbornyl group. The cycloalkyl group preferably has 3 to 10 ring carbon atoms, more preferably 5 to 8 ring carbon atoms. Among the cycloalkyl group, a cyclopentyl group and a cyclohexyl group are particularly preferable.

A halogenated alkyl group provided by substituting the alkyl group with a halogen atom is exemplified by a halogenated alkyl group provided by substituting the alkyl group having 1 to 30 carbon atoms with one or more halogen groups. Specific examples of the halogenated alkyl group includes a fluoromethyl group, difluoromethyl group, trifluoromethyl group, fluoroethyl group, trifluoromethylmethyl group, trifluoroethyl group, and pentafluoroethyl group.

The alkenyl group having 2 to 30 carbon atoms in the exemplary embodiment may be linear, branched or cyclic. Examples of the alkenyl group are a vinyl group, propenyl group, butenyl group, oleyl group, eicosapentaenyl group, docosahexaenyl group, styryl group, 2,2-diphenylvinyl group, 1,2,2-triphenylvinyl group, 2-phenyl-2-propenyl group, cyclopentadienyl group, cyclopentenyl group, cyclohexenyl group and cyclohexadienyl group.

The alkynyl group having 2 to 30 carbon atoms in the exemplary embodiment may be linear, branched or cyclic. Examples of the alkynyl group having 2 to 30 carbon atoms are an ethynyl group, a propynyl group and a 2-phenylethynyl group.

Examples of a substituted silyl group in the exemplary embodiment include an alkylsilyl group having 3 to 30 carbon atoms and an arylsilyl group having 6 to 30 ring carbon atoms.

The alkylsilyl group having 3 to 30 carbon atoms in the exemplary embodiment is exemplified by a trialkylsilyl group having the above examples of the alkyl group having 1 to 30 carbon atoms. Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups in the trialkylsilyl group may be mutually the same or different.

Examples of the arylsilyl group having 6 to 30 ring carbon atoms in the exemplary embodiment are a dialkylarylsilyl group, alkyldiarylsilyl group and triarylsilyl group.

The dialkylarylsilyl group is exemplified by a dialkylarylsilyl group having two of the examples of the alkyl group having 1 to 30 carbon atoms and one of the examples of the aromatic hydrocarbon group having 6 to 30 ring carbon atoms. The dialkylarylsilyl group preferably has 8 to 30 carbon atoms.

The alkyldiarylsilyl group is exemplified by a alkyldiarylsilyl group having one of the examples of the alkyl group having 1 to 30 carbon atoms and two of the examples of the aromatic hydrocarbon group having 6 to 30 ring carbon atoms. The dialkylarylsilyl group preferably has 13 to 30 carbon atoms.

The triarylsilyl group is exemplified by a triarylsilyl group having three of the examples of the aromatic hydrocarbon group having 6 to 30 ring carbon atoms. The triarylsilyl group preferably has 18 to 30 carbon atoms.

The alkoxy group having 1 to 30 carbon atoms in the exemplary embodiment is represented by $-OZ_1$. $Z_1$ is exemplified by the above alkyl group having 1 to 30 carbon atoms. Examples of the alkoxy group are a methoxy group, ethoxy group, propoxy group, butoxy group, pentyloxy group and hexyloxy group. The alkoxy group preferably has 1 to 20 carbon atoms.

A halogenated alkoxy group provided by substituting the alkoxy group with a halogen atom is exemplified by a halogenated alkoxy group provided by substituting the alkoxy group having 1 to 30 carbon atoms with one or more fluorine groups.

The aryloxy group having 6 to 30 ring carbon atoms in the exemplary embodiment is represented by $-OZ_2$. $Z_2$ is exemplified by the above aromatic hydrocarbon group having 6 to 30 ring carbon atoms. The aryloxy group preferably has 6 to 20 ring carbon atoms. The aryloxy group is exemplified by a phenoxy group.

The alkylthio group having 1 to 30 carbon atoms is represented by $-SR_V$. $R_V$ is exemplified by the alkyl group having 1 to 30 carbon atoms. The alkylthio group preferably has 1 to 20 carbon atoms.

The arylthio group having 6 to 30 ring carbon atoms is represented by —SR$_W$. R$_W$ is exemplified by the above aromatic hydrocarbon group having 6 to 30 ring carbon atoms. The arylthio group preferably has 6 to 20 ring carbon atoms.

Examples of the halogen atom are a fluorine atom, a chlorine atom, a bromine atom and an iodine atom, among which a fluorine atom is preferable.

An aldehyde group, carbonyl group, ester group, carbamoyl group, and amino group may be substituted by aliphatic hydrocarbon, alicyclic hydrocarbon, aromatic hydrocarbon, or hetero ring. The aliphatic hydrocarbon, alicyclic hydrocarbon, aromatic hydrocarbon, and hetero ring may further have a substituent.

A siloxanyl group is a silicon compound group with an ether bond and exemplified by trimethylsiloxanyl group.

In the exemplary embodiment, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a hetero ring including a saturated ring, unsaturated ring, or aromatic ring.

In the exemplary embodiment, a hydrogen atom includes isotope having different numbers of neutrons, specifically, protium, deuterium and tritium.

Herein, examples of the substituent meant by "substituted or unsubstituted" include an aralkyl group, alkylamino group, arylamino group, hydroxyl group, nitro group, and carboxy group in addition to the above-described aromatic hydrocarbon group, heterocyclic group, alkyl group (linear or branched alkyl group, cycloalkyl group, haloalkyl group), alkenyl group, alkynyl group, alkylsilyl group, arylsilyl group, alkoxy group, aryloxy group, alkylthio group, arylthio group, halogen atom, and cyano group.

Among the above substituents, the aromatic hydrocarbon group, heterocyclic group, alkyl group, halogen atom, alkylsilyl group, arylsilyl group and cyano group are preferable and the specific preferable substituents described in each of the substituents are further preferable.

The substituents may further be substituted by an aralkyl group, alkylamino group, arylamino group, hydroxyl group, nitro group, and carboxy group in addition to the above-described aromatic hydrocarbon group, heterocyclic group, alkyl group, alkenyl group, alkynyl group, alkylsilyl group, arylsilyl group, alkoxy group, aryloxy group, alkylthio group, arylthio group, halogen atom, and cyano group. In addition, plural ones of these substituents may be mutually bonded to form a ring.

The aralkyl group is preferably an aralkyl group having 6 to 30 ring carbon atoms and is represented by —Z$_3$-Z$_4$. Z$_3$ is exemplified by an alkylene group derived from the above alkyl group having 1 to 30 carbon atoms. Z$_4$ is exemplified by the examples of the aromatic hydrocarbon group having 6 to 30 ring carbon atoms. This aralkyl group is preferably an aralkyl group having 7 to 30 carbon atoms, in which an aromatic hydrocarbon moiety has 6 to 30 carbon atoms, preferably 6 to 20 carbon atoms, more preferably 6 to 12 carbon atoms and an alkyl moiety has 1 to 30 carbon atoms, preferably 1 to 20 carbon atoms, more preferably 1 to 10 carbon atoms, further preferably 1 to 6 carbon atoms. Examples of the aralkyl group include a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

The alkylamino group having 2 to 30 carbon atoms is represented by —NHR$_V$ or —N(R$_V$)$_2$. R$_V$ is exemplified by the alkyl group having 1 to 30 carbon atoms.

The arylamino group having 6 to 60 ring carbon atoms is represented by —NHR$_W$ or —N(R$_W$)$_2$. R$_W$ is exemplified by the above aromatic hydrocarbon group having 6 to 30 ring carbon atoms.

"Unsubstituted" in "substituted or unsubstituted" means that a group is not substituted by the above-described substituents but bonded with a hydrogen atom.

In the exemplary embodiment, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. Herein, "YY" is larger than "XX." "XX" and "YY" each mean an integer of 1 or more.

In the exemplary embodiment, "XX to YY atoms" in the description of "substituted or unsubstituted ZZ group having XX to YY atoms" represent atoms of an unsubstituted ZZ group and does not include atoms of a substituent(s) of the substituted ZZ group. Herein, "YY" is larger than "XX." "XX" and "YY" each mean an integer of 1 or more.

In the exemplary embodiment, when the substituents are bonded to each other to form a cyclic structure, the cyclic structure is a saturated ring, an unsaturated ring, an aromatic hydrocarbon ring or a hetero ring. Moreover, in the exemplary embodiment, examples of the aromatic hydrocarbon ring and the hetero ring include a cyclic structure from which the above monovalent group is derived.

In the exemplary embodiment, examples of the aromatic hydrocarbon group and the heterocyclic group in the linking group include a divalent or multivalent group obtained by eliminating one or more atoms from the above monovalent groups. Examples of the "substituted or unsubstituted, linear or branched hydrocarbon group having a carbon-carbon double bond and 2 to 30 carbon atoms" in the linking group include a divalent or multivalent group obtained by eliminating one or more atoms from the above alkenyl group. Examples of the "substituted or unsubstituted, linear or branched hydrocarbon group having a carbon-carbon triple bond and 2 to 30 carbon atoms" in the linking group include a divalent or multivalent group obtained by eliminating one or more atoms from the above alkynyl group.

With use of the compound according to the exemplary embodiment, the drive voltage of the organic EL device is reducible and the luminous efficiency is improvable.

Electronic Device

The organic EL device 1 according to one of the above exemplary embodiments is usable in an electronic device such as a display unit and a light-emitting unit. Examples of the display unit include display components such as en organic EL panel module, TV, mobile phone, tablet, and personal computer. Examples of the light-emitting unit include an illuminator and a vehicle light.

Modification of Embodiments

It should be noted that the invention is not limited to the above exemplary embodiments but may include any modification and improvement as long as such modification and improvement are compatible with the invention.

An arrangement of the organic EL device of the invention is not particularly limited to the arrangement described in the above exemplary embodiment.

For instance, a blocking layer may be provided adjacent to an anode-side or a cathode-side of the emitting layer. The blocking layer is preferably provided in contact with the emitting layer to at least block holes, electrons or excitons.

For instance, when the blocking layer is provided in contact with the cathode-side of the emitting layer, the blocking layer permits transport of electrons, but blocks holes from reaching a layer provided near the cathode (e.g., the electron transporting layer) beyond the blocking layer. When the organic EL device includes the electron transporting layer, the blocking layer is preferably interposed between the emitting layer and the electron transporting layer.

When the blocking layer is provided in contact with the anode-side of the emitting layer, the blocking layer permits transport of holes, but blocks electrons from reaching a layer provided near the anode (e.g., the hole transporting layer) beyond the blocking layer. When the organic EL device includes the hole transporting layer, the blocking layer is preferably interposed between the emitting layer and the hole transporting layer.

Further, the blocking layer may be provided in contact with the emitting layer to prevent an excitation energy from leaking from the emitting layer into neighboring layers. The blocking layer blocks excitons generated in the emitting layer from moving into a layer provided near the electrode (e.g., the electron transporting layer and the hole transporting layer) beyond the blocking layer.

The emitting layer is preferably in contact with the blocking layer.

Further, specific arrangements and configurations for practicing the invention may be altered to other arrangements and configurations compatible with the invention.

The compound according to the exemplary embodiment may be contained in the electron injecting layer 9, or may be contained in both of the electron transporting layer 8 and the electron injecting layer 9. The compound according to the exemplary embodiment may be contained in other organic layers.

EXAMPLES

Examples of the invention will be described below. However, the invention is not limited to Examples.

Synthesis Example 1

A synthesis scheme of a compound (1) is shown below.

[Formula 197]

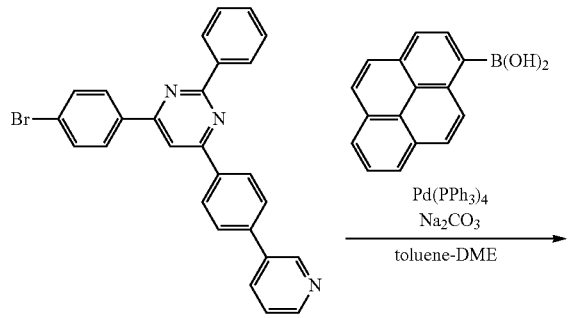

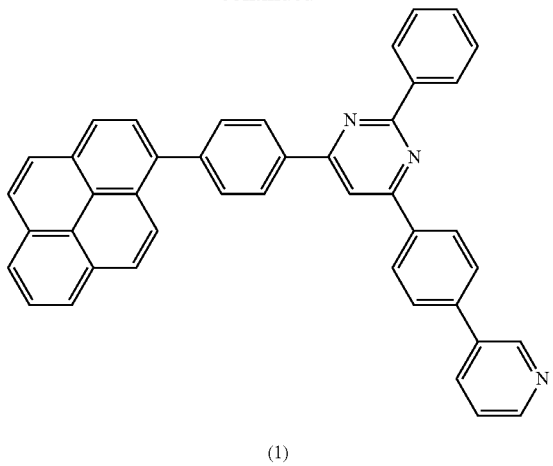

(1)

Under an argon gas atmosphere, 4-(4-bromophenyl)-2-phenyl-6-(4-(pyridine-3-yl)phenyl)pyridine (15.0 g, 32.3 mmol), pyrene-1-boronic acid (9.54 g, 38.8 mmol), tetrakis (triphenylphosphine)palladium(0) (0.747 g, 0.646 mmol), an aqueous solution of sodium carbonate (2M, 32.3 mL, 64.6 mmol), toluene (323 mL) and dimethylether (108 mL) were added into a reactor and stirred at 85 degrees C. for 10 hours. After the reaction, the reaction solution was cooled down to room temperature. The deposited crystals were separated by filtration. The crystals obtained by filtration were refined by silica-gel column chromatography. The refined crystals were washed with methanol to obtain a compound (1) (9.90 g, 16.9 mmol). As a result of mass analysis of the compound, m/e was equal to 585, whereby the obtained compound was identified to be the compound (1) (Exact mass: 585.22). A yield of the compound (1) was 52%. It should be noted that DME in the reaction scheme is an abbreviation of dimethylether.

Synthesis Example 2

A synthesis scheme of a compound (2) is shown below.

[Formula 198]

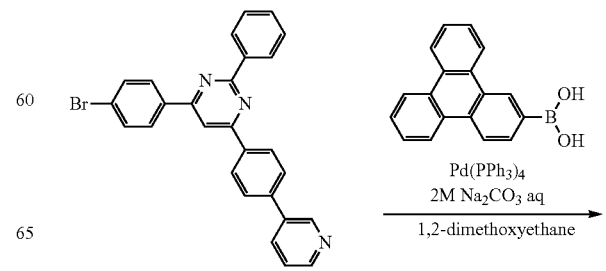

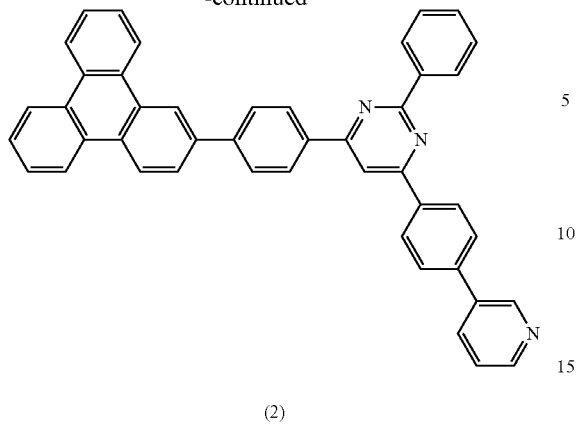

(2)

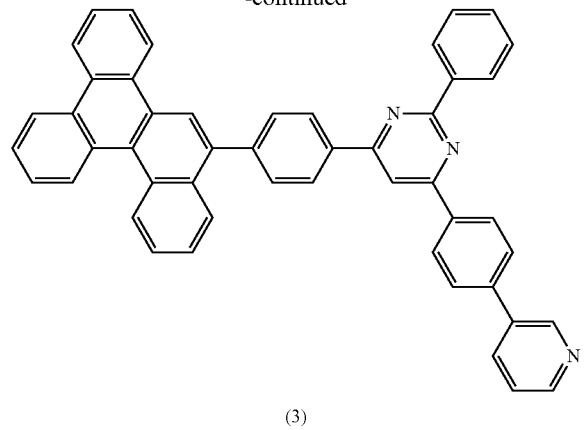

(3)

Under an argon gas atmosphere, 4-(4-bromophenyl)-2-phenyl-6-(4-(pyridine-3-yl)phenyl)pyridine (3.25 g, 7.00 mmol), triphenylene-2-boronic acid (1.91 g, 7.00 mmol), tetraki(triphenylphosphine)palladium(0) (0.140 g, 0.162 mmol), an aqueous solution of sodium carbonate (2M, 10.5 mL, 21.0 mmol), and 1,2-dimethoxyethane (35 mL) were added into a reactor and stirred at 85 degrees C. for three hours. After the reaction, the reaction solution was cooled down to room temperature. The deposited crystals were separated by filtration. The crystals obtained by filtration were recrystallized with toluene to obtain a compound (2) (3.13 g, 5.12 mmol). As a result of mass analysis of this compound, m/e was equal to 611, whereby the obtained compound was identified to be the compound (2) (Exact mass: 611.24). A yield of the compound (2) was 73%.

Synthesis Example 3

A synthesis scheme of a compound (3) is shown below.

[Formula 199]

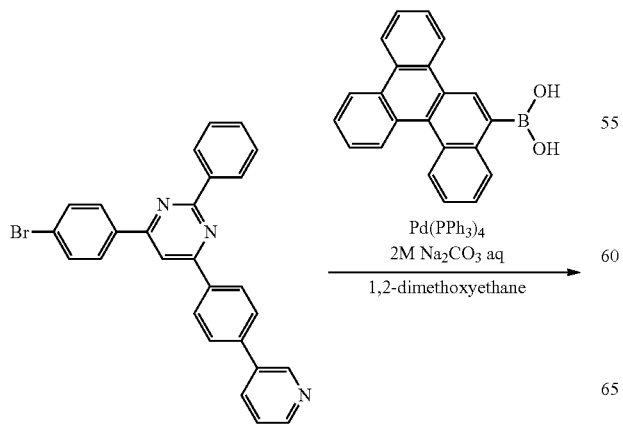

Synthesis Example 3 was conducted in the same manner as Synthesis Example 2 except for using benzo[g]chrysene-10-boronic acid in place of triphenylene-2-boronic acid in the synthesis of the compound (2) in Synthesis Example 2, so that a compound (3) was obtained. As a result of mass analysis of this compound, m/e was equal to 661, whereby the obtained compound was identified to be the compound (3) (Exact mass: 611.25). A yield of the compound (3) was 60%.

Synthesis Example 4

A synthesis scheme of a compound (4) is shown below.

[Formula 200]

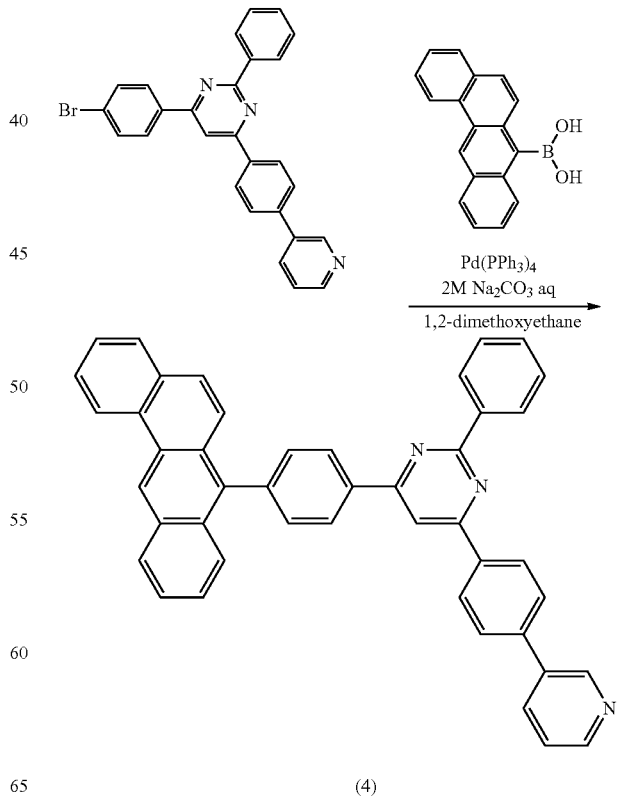

(4)

Synthesis Example 4 was conducted in the same manner as Synthesis Example 2 except for using benzo[a]anthracene-7-boronic acid in place of triphenylene-2-boronic acid in the synthesis of the compound (2) in Synthesis Example 2, so that a compound (4) was obtained. As a result of mass analysis of this compound, m/e was equal to 611, whereby the obtained compound was identified to be the compound (4) (Exact mass: 611.24). A yield of the compound (4) was 56%.

Synthesis Example 5

A synthesis scheme of a compound (5) is shown below.

[Formula 201]

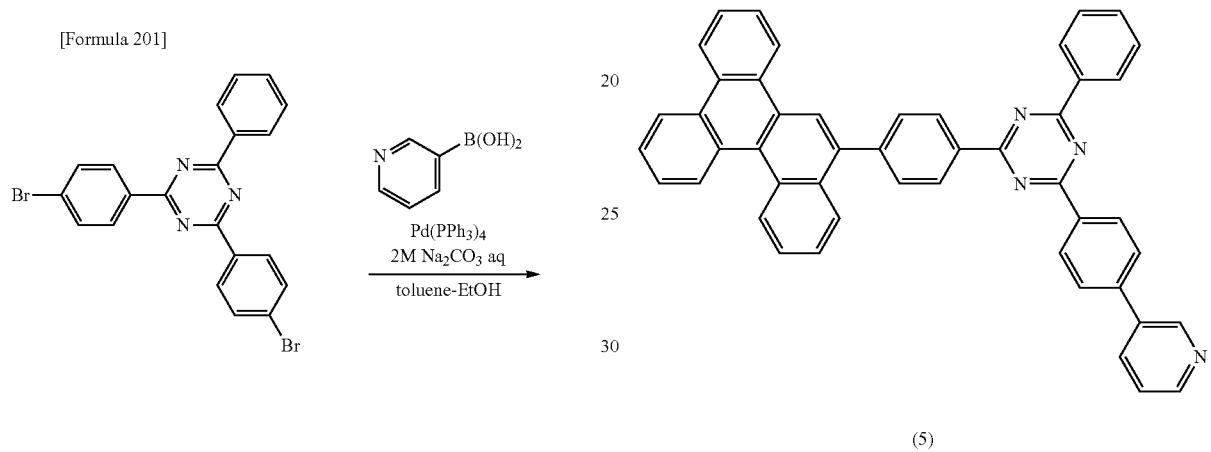

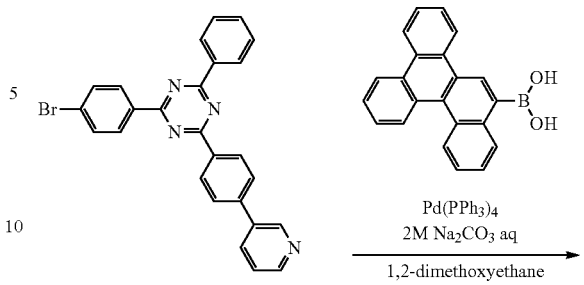

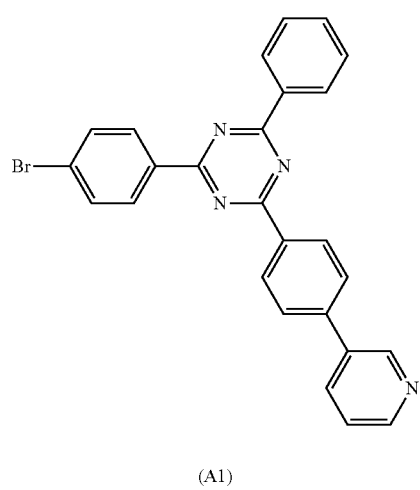

(5-1) Synthesis of Intermediate (A1)

Under an argon gas atmosphere, toluene (1500 mL) and ethanol (500 mL) were added into a mixture of 2,4-bis(4-bromophenyl)-6-phenyl-1,3,5-triazine (128 g, 275 mmol), 3-pyridyl boronic acid (33.8 g, 275 mmol), tetrakis(triphenylphosphine)palladium(0) (6.36 g, 5.50 mmol), and an aqueous solution of 2M sodium carbonate (43.8 g, 413 mmol) and stirred at 85 degrees C. for eight hours. After the reaction, the reaction solution was cooled down to room temperature. The deposited crystals were separated by filtration. Subsequently, the crystals separated by filtration were refined by silica-gel column chromatography to obtain an intermediate (A1) (51.2 g, 110 mmol). A yield of the intermediate (A1) was 40%.

(5-2) Synthesis of Compound (5)

Synthesis of the compound (5) was conducted in the same manner as Synthesis Example 2 except for using benzo[g]chrysene-10-boronic acid in place of triphenylene-2-boronic acid and using the intermediate (A1) in place of 4-(4-bromophenyl)-2-phenyl-6-(4-(pyridine-3-yl)phenyl)pyridine in the synthesis of the compound (2) in Synthesis Example 2. As a result of mass analysis of this compound, m/e was equal to 662, whereby the obtained compound was identified to be the compound (5) (Exact mass: 662.25). A yield of the compound (5) was 75%.

Synthesis Example 6
A synthesis scheme of a compound (6) is shown below.
[Formula 202]
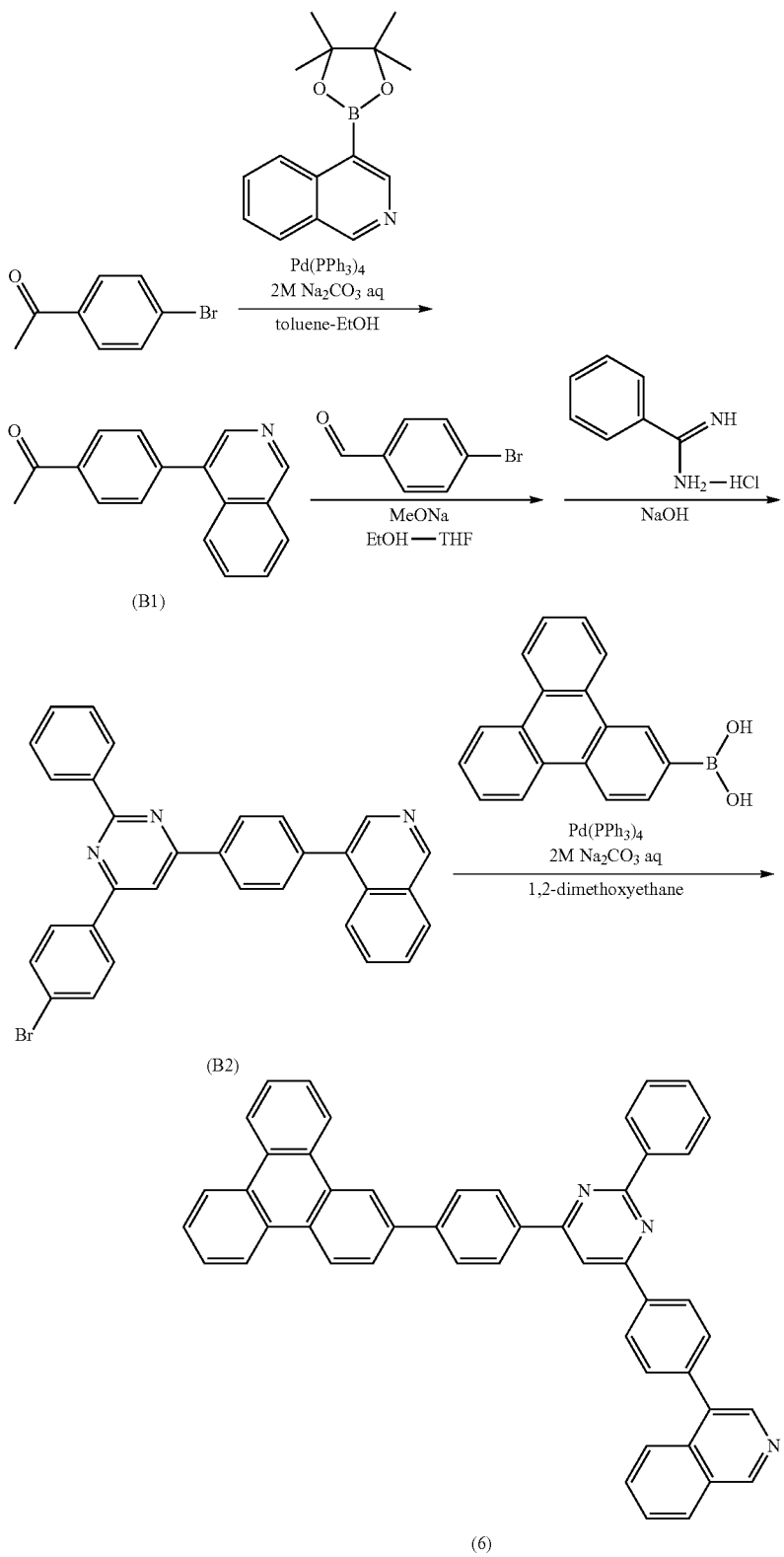

(6-1) Synthesis of Intermediate (B1)

Under an argon gas atmosphere, into a mixture of 4-bromoacetophenone (25.0 g, 126 mmol), 4-(4,4,5,5-tetramethyl-1,3,2-dioxaborolane-2-yl)isoquinoline (32.0 g, 126 mmol), tetrakis(triphenylphosphine)palladium(0) (2.90 g, 2.51 mmol), and an aqueous solution of 2M sodium carbonate (126 mL, 251 mol), toluene (416 mL) and ethanol (154 mL) were added and the obtained mixture was stirred at 75 degrees C. for 39 hours. After the reaction, the reaction solution was cooled down to room temperature, to which toluene (200 mL) and water (200 mL) were added. After the reaction solution is separated, the obtained organic layer was concentrated under reduced pressure. A mixture obtained by concentration under reduce pressure was dissolved in toluene. The obtained toluene solution of the mixture was subjected to silica-gel short column chromatography. A solution obtained by silica-gel short column chromatography was concentrated under reduced pressure to obtain an intermediate (B1) (23.7 g, 95.8 mmol). A yield of the intermediate (B1) was 76%.

(6-2) Synthesis of Intermediate (B2)

Under an argon gas atmosphere, into a mixture of 4-bromobenzaldehyde (17.2 g, 93.0 mmol), the intermediate (B1) (23.0 g, 93.0 mmol), ethanol (400 mL), and tetrahydrofuran (200 mL), a methanol solution of sodium methoxide (28%, 7.2 mL) was dropped and the obtained mixture was stirred at room temperature for two hours. To a reaction solution after the stirring, benzamidine hydrochloride (14.6 g, 3.0 mmol) and sodium hydroxide (4.46 g, 112 mmol) were added and the obtained mixture was stirred at 72 degrees C. for 17 hours. After the reaction, the reaction solution was cooled down to room temperature, to which water (400 mL) was added to separate precipitate by filtration. The precipitate was washed with water and methanol. After the washing, the obtained mixture was dissolved in toluene by heating. The obtained toluene solution of the mixture was subjected to silica-gel short column chromatography. A solution obtained by silica-gel short column chromatography was concentrated under reduced pressure to precipitate crystals, so that an intermediate (B2) (19.0 g, 37.2 mmol) was obtained. A yield of the intermediate (B2) was 40%.

(6-3) Synthesis of Compound (6)

Synthesis of the compound (6) was conducted in the same manner as Synthesis Example 2 except for using the intermediate (B2) in place of 4-(4-bromophenyl)-2-phenyl-6-(4-(pyridine-3-yl)phenyl)pyridine in the synthesis of the compound (2) in Synthesis Example 2, so that the compound (7) was obtained. As a result of mass analysis of this compound, m/e was equal to 662, whereby the obtained compound was identified to be the compound (6) (Exact mass: 662.25). A yield of the compound (6) was 70%.

Synthesis Example 7

A synthesis scheme of a compound (7) is shown below.

[Formula 203]

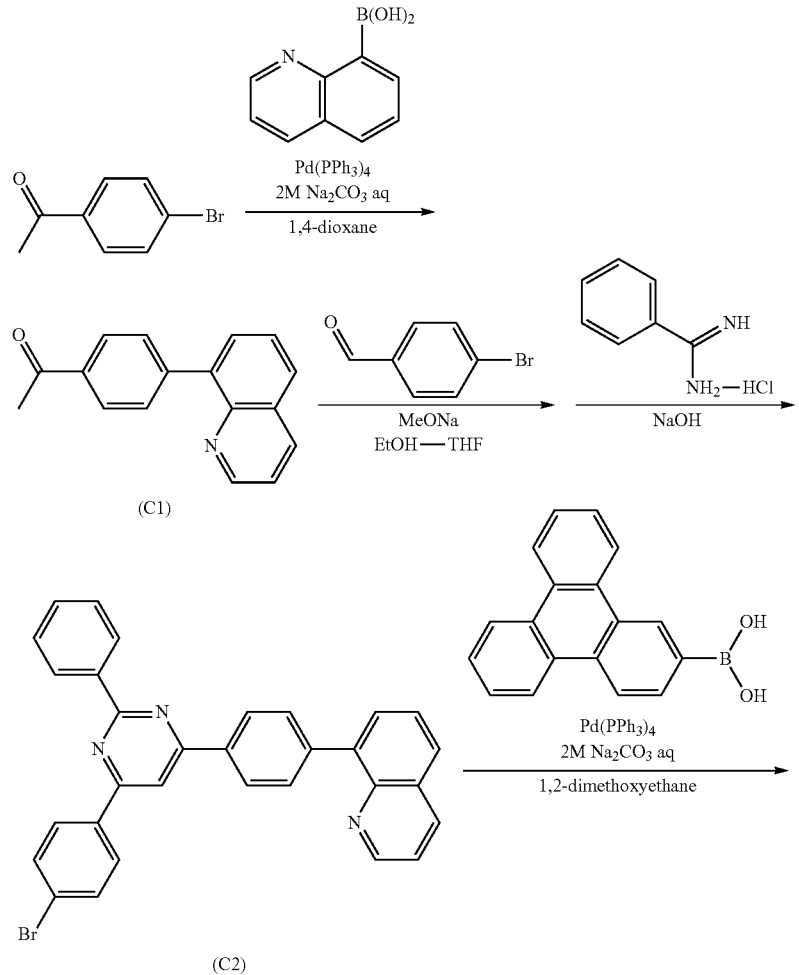

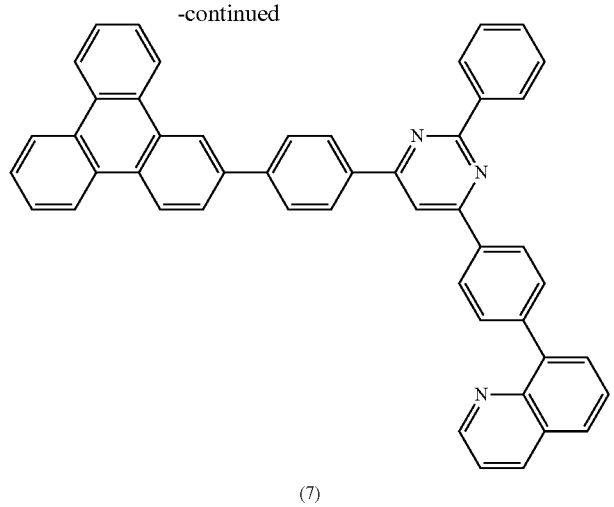

(7)

(7-1) Synthesis of Intermediate (C1)

Under an argon gas atmosphere, into a mixture of 4-bromoacetophenone (27.9 g, 140 mmol), quinoline-8-boronic acid (24.2 g, 140 mmol), tetrakis(triphenylphosphine)palladium(0) (3.20 g, 2.80 mmol), and an aqueous solution of 2M sodium carbonate (140 mL, 280 mol), dioxane (520 mL) was added and the obtained mixture was stirred at 85 degrees C. for 58 hours. After the reaction, the reaction solution was cooled down to room temperature, to which toluene (300 mL) and water (300 mL) were added to separate the reaction solution. Subsequently, the obtained organic layer was concentrated under reduced pressure. A mixture obtained by concentration under reduce pressure was dissolved in toluene. The obtained toluene solution of the mixture was subjected to silica-gel short column chromatography. A solution obtained by silica-gel short column chromatography was concentrated under reduced pressure to precipitate crystals, so that an intermediate (C1) (27.4 g, 109 mmol) was obtained. A yield of the intermediate (C1) was 78%.

(7-2) Synthesis of Intermediate (C2)

Under an argon gas atmosphere, into a mixture of 4-bromobenzaldehyde (20.5 g, 111 mmol), the intermediate (C1) (27.4 g, 111 mmol), ethanol (410 mL), and tetrahydrofuran (270 mL), a methanol solution of sodium methoxide (28%, 9 mL) was dropped and the obtained mixture was stirred at room temperature. To a reaction solution after the stirring, benzamidine hydrochloride (17.4 g, 111 mmol) and sodium hydroxide (5.30 g, 130 mmol) were added and the obtained mixture was stirred at 70 degrees C. for 23 hours. After the reaction, the reaction solution was cooled down to room temperature, to which water (280 mL) was added to separate precipitate by filtration. The precipitate was washed with water and methanol. After the washing, the obtained mixture was dissolved in toluene by heating. The obtained toluene solution of the mixture was subjected to silica-gel short column chromatography. A solution obtained by silica-gel short column chromatography was concentrated under reduced pressure to precipitate crystals, so that an intermediate (C2) (15.4 g, 30.0 mmol) was obtained. A yield of the intermediate (C2) was 27%.

(7-3) Synthesis of Compound (7)

Synthesis of the compound (7) was conducted in the same manner as Synthesis Example 2 except for using the intermediate (C2) in place of 4-(4-bromophenyl)-2-phenyl-6-(4-(pyridine-3-yl)phenyl)pyridine in the synthesis of the compound (2) in Synthesis Example 2, so that the compound (7) was obtained. As a result of mass analysis of this compound, m/e was equal to 662, whereby the obtained compound was identified to be the compound (7) (Exact mass: 662.25). A yield of the compound (7) was 70%.

Synthesis Example 8

A synthesis scheme of a compound (8) is shown below.

[Formula 204]

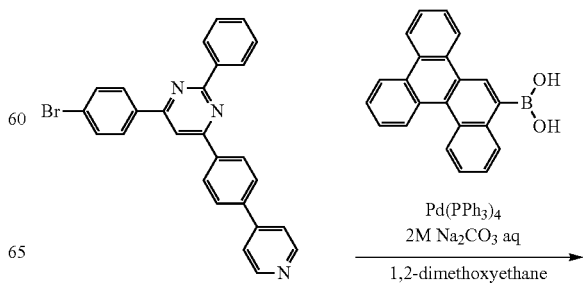

-continued

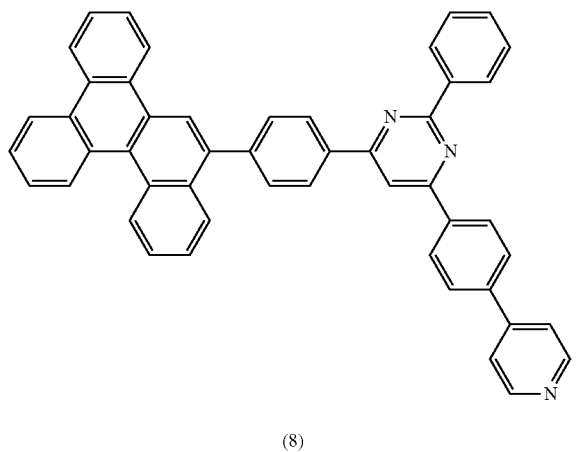

(8)

Synthesis of the compound (8) was conducted in the same manner as Synthesis Example 2 except for using benzo[g]chrysene-10-boronic acid in place of triphenylene-2-boronic acid and using 4-(4-bromophenyl)-2-phenyl-6-(4-(pyridine-2-yl)phenyl)pyridine in place of 4-(4-bromophenyl)-4-phenyl-6-(4-(pyridine-3-yl)phenyl)pyridine in the synthesis of the compound (2) in Synthesis Example 2, so that the compound (9) was obtained. As a result of mass analysis of this compound, m/e was equal to 662, whereby the obtained compound was identified to be the compound (8) (Exact mass: 662.25). A yield of the compound (8) was 70%.

Synthesis Example 9

A synthesis scheme of a compound (9) is shown below.

[Formula 205]

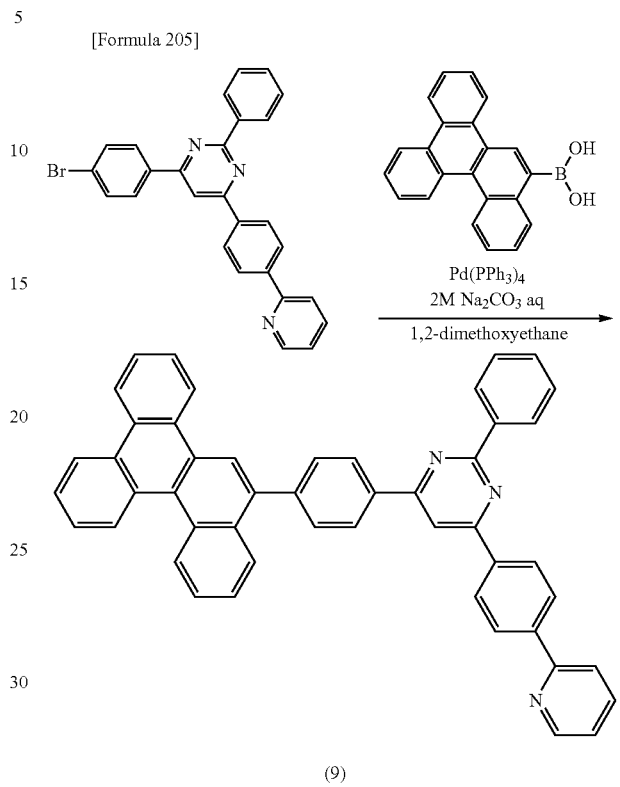

(9)

Synthesis of the compound (9) was conducted in the same manner as Synthesis Example 2 except for using benzo[g]chrysene-10-boronic acid in place of triphenylene-2-boronic acid and using 4-(4-bromophenyl)-2-phenyl-6-(4-(pyridine-2-yl)phenyl)pyridine in place of 4-(4-bromophenyl)-2-phenyl-6-(4-(pyridine-3-yl)phenyl)pyridine in the synthesis of the compound (2) in Synthesis Example 2, so that the compound (9) was obtained. As a result of mass analysis of this compound, m/e was equal to 662, whereby the obtained compound was identified to be the compound (9) (Exact mass: 662.25). A yield of the compound (9) was 53%.

Synthesis Example 10

A synthesis scheme of a compound (10) is shown below.

[Formula 206]

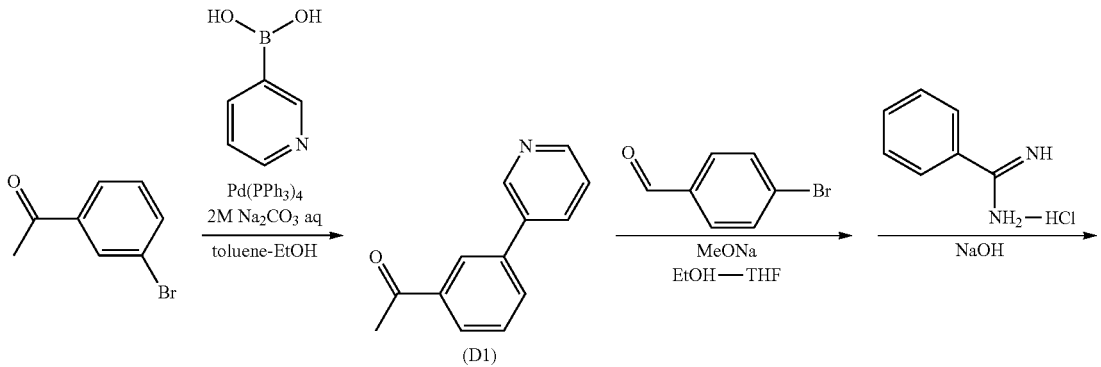

(D1)

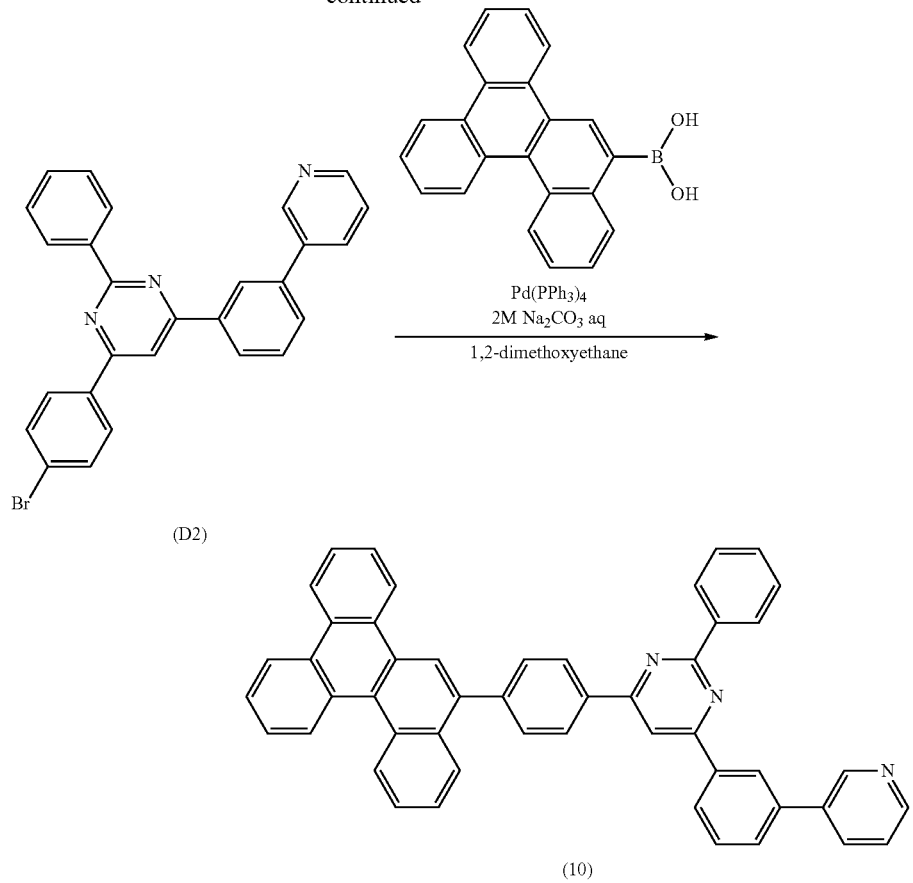

(10-1) Synthesis of Intermediate (D1)

Synthesis of an intermediate (D1) was conducted in the same manner as synthesis of the intermediate (C1) in Synthesis Example (7-1) except for using 3-bromoacetophenone in place of 4-bromoacetophenone and using 3-pyridine boronic acid in place of quinoline-8-boronic acid, so that the intermediate (D1) was obtained. A yield of the intermediate (D1) was 70%.

(10-2) Synthesis of Intermediate (D2)

Synthesis of an intermediate (D2) was conducted in the same manner as synthesis of the intermediate (C2) in Synthesis Example (7-2) except for using the intermediate (D1) in place of the intermediate (C1), so that the intermediate (D2) was obtained. A yield of the intermediate (D2) was 31%.

(10-3) Synthesis of Compound (10)

Synthesis of the compound (10) was conducted in the same manner as Synthesis Example 2 except for using benzo[g]chrysene-10-boronic acid in place of triphenylene-2-boronic acid and using the intermediate (D2) in place of 4-(4-bromophenyl)-2-phenyl-6-(4-(pyridine-3-yl)phenyl) pyridine in the synthesis of the compound (2) in Synthesis Example 2, so that the compound (10) was obtained. As a result of mass analysis of this compound, m/e was equal to 661, whereby the obtained compound was identified to be the compound (10) (Exact mass: 611.25). A yield of the compound (10) was 56%.

Synthesis Example 11

A synthesis scheme of a compound (11) is shown below.

[Formula 207]

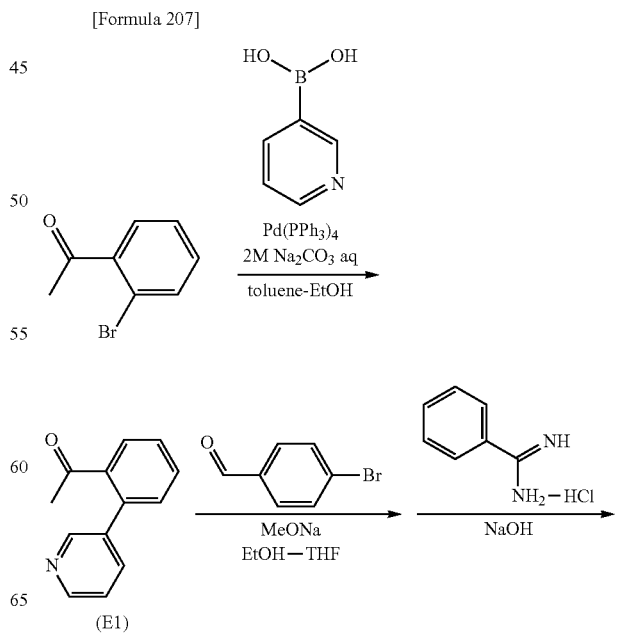

-continued

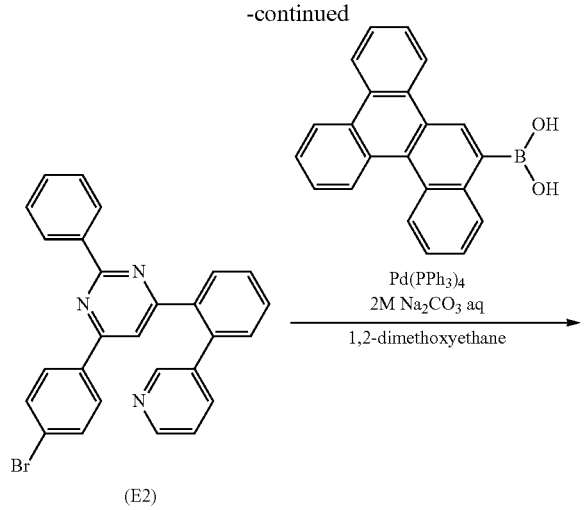

(E2)

(11)

Synthesis Example 12

A synthesis scheme of a compound (12) is shown below.

[Formula 208]

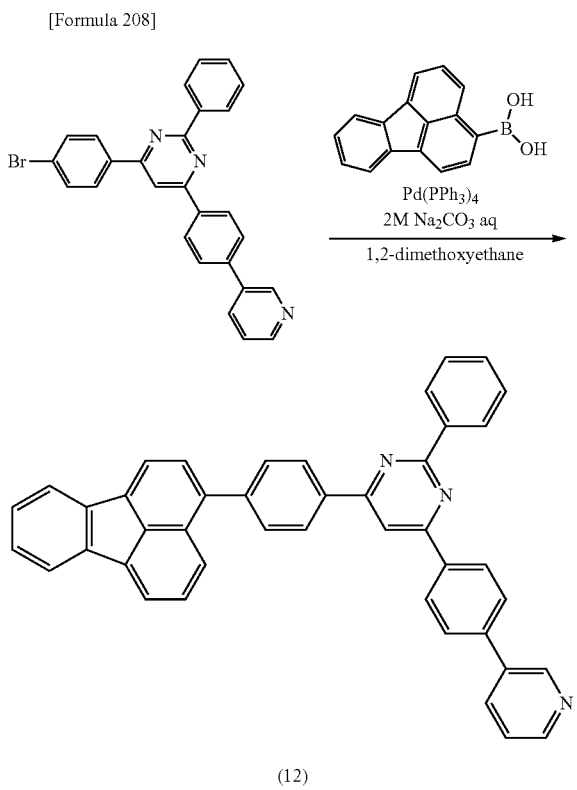

(12)

(11-1) Synthesis of Intermediate (E1)

Synthesis of an intermediate (E1) was conducted in the same manner as synthesis of the intermediate (C1) in Synthesis Example (7-1) except for using 2-bromoacetophenone in place of 4-bromoacetophenone and using 3-pyridine boronic acid in place of quinoline-8-boronic acid, so that the intermediate (E1) was obtained. A yield of the intermediate (E1) was 71%.

(11-2) Synthesis of Intermediate (E2)

Synthesis of an intermediate (E2) was conducted in the same manner as synthesis of the intermediate (C2) in Synthesis Example (7-2) except for using the intermediate (E1) in place of the intermediate (C1), so that the intermediate (E2) was obtained. A yield of the intermediate (E2) was 27%.

(11-3) Synthesis of Compound (11)

Synthesis of the compound (11) was conducted in the same manner as Synthesis Example 2 except for using benzo[g]chrysene-10-boronic acid in place of triphenylene-2-boronic acid and using the intermediate (E2) in place of 4-(4-bromophenyl)-2-phenyl-6-(4-(pyridine-3-yl)phenyl) pyridine in the synthesis of the compound (2) in Synthesis Example 2, so that the compound (11) was obtained. As a result of mass analysis of this compound, m/e was equal to 661, whereby the obtained compound was identified to be the compound (11) (Exact mass: 611.25). A yield of the compound (11) was 57%.

Synthesis Example 12 was conducted in the same manner as Synthesis Example 2 except for using fluoranthene-3-boronic acid in place of triphenylene-2-boronic acid in the synthesis of the compound (2) in Synthesis Example 2, so that the compound (12) was obtained. As a result of mass analysis of the compound, m/e was equal to 585, whereby the obtained compound was identified to be the compound (12) (Exact mass: 585.22). A yield of the compound (12) was 61%.

Manufacturing of Organic EL Device

Compounds used for manufacturing the organic EL device will be shown below.

[Formula 209]

HI-1

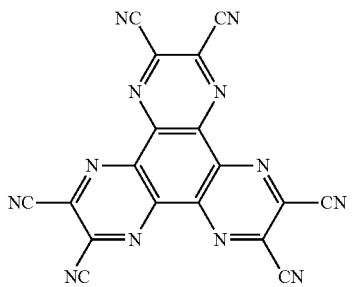

-continued

HT-1

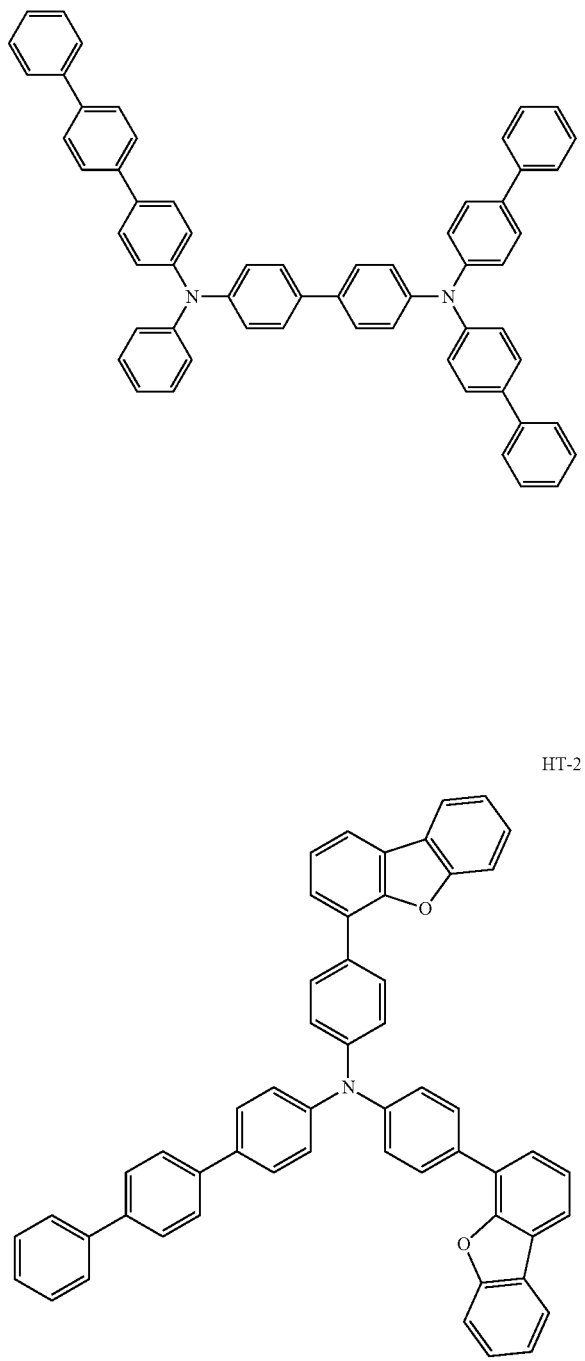

[Formula 210]

HT-2

BH-1

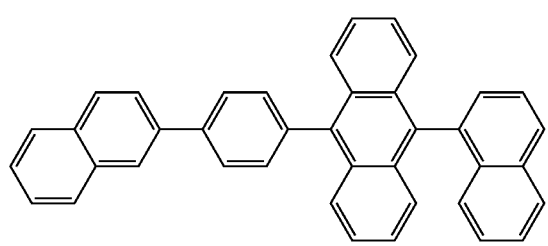

-continued

BD-1

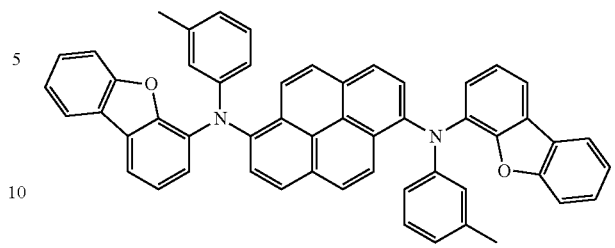

[Formula 211]

E-1

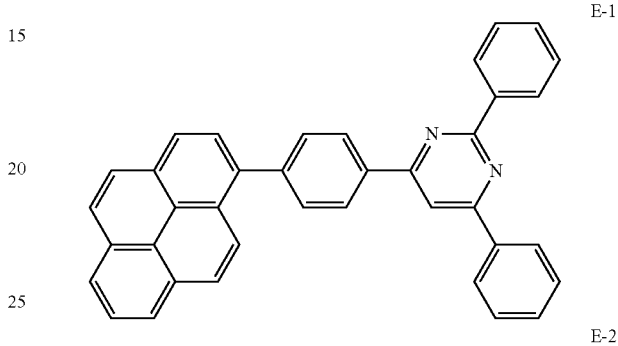

E-2

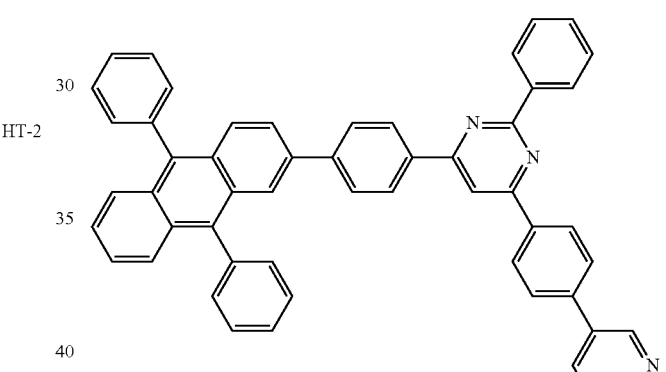

Example 1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was set to be 130-nm thick.

After the glass substrate having the transparent electrode line was cleaned, the glass substrate was mounted on a substrate holder of a vacuum evaporation apparatus. Initially, a compound HI-1 (the electron accepting compound) was deposited on a surface of the glass substrate where the transparent electrode line was provided in a manner to cover the transparent electrode, thereby forming a 5-nm thick HI-1 film of the compound HI-1 to form a hole injecting layer.

Next, on the hole injecting layer, a compound HT-1 was deposited as a first hole transporting material to form a 80-nm thick HT-1 film, thereby providing a first hole transporting layer.

Next, on the first hole transporting layer, a compound HT-2 was deposited to form a 10-nm thick HT-2 film, thereby providing a second hole transporting layer.

Further, a compound BH-1 and a compound BD-1 were co-deposited on the HT-2 film at a mass ratio of the compound BH-1: the compound BD-1 being 24:1 to form a 25-nm thick emitting layer.

Subsequent to the formation of the emitting layer, the compound (1) and 8-quinolinolato lithium (Liq) were co-deposited at a mass ratio of 50:50 to form a 25-nm thick electron transporting layer.

Liq was deposited on the electron transporting layer to form a 1-nm thick electron injecting layer.

A metal Al was deposited on the electron injecting layer to form an 80-nm thick metal cathode.

Thus, the organic EL device of Example 1 was manufactured.

A device arrangement of the organic EL device of Example 1 is roughly shown as follows.

ITO(130)/HI-1(5)/HT-1(80)/HT-2(10)/BH-1:BD-1(25, 4%)/Compound (1):Liq (25, 50%)/Liq(1)/Al(80)

Numerals in parentheses represent a film thickness (unit: nm). The numerals represented by percentage in the same parentheses indicate a concentration (mass %) of the compound BD-1 in the emitting layer or a concentration (mass %) of Liq in the electron transporting layer.

Example 2

An organic EL device of Example 2 was manufactured in the same manner as the organic EL device of Example 1 except for using the compound (2) in place of the compound (1).

A device arrangement of the organic EL device of Example 2 is roughly shown as follows.

ITO(130)/HI-1(5)/HT-1(80)/HT-2(10)/BH-1:BD-1(25, 4%)/Compound (2):Liq (25, 50%)/Liq(1)/Al(80)

Example 3

An organic EL device of Example 3 was manufactured in the same manner as the organic EL device of Example 1 except for using the compound (3) in place of the compound (1).

A device arrangement of the organic EL device of Example 3 is roughly shown as follows.

ITO(130)/HI-1(5)/HT-1(80)/HT-2(10)/BH-1:BD-1(25, 4%)/Compound (3):Liq (25, 50%)/Liq(1)/Al(80)

Example 4

An organic EL device of Example 4 was manufactured in the same manner as the organic EL device of Example 1 except for using the compound (4) in place of the compound (1).

A device arrangement of the organic EL device of Example 4 is roughly shown as follows.

ITO(130)/HI-1(5)/HT-1(80)/HT-2(10)/BH-1:BD-1(25, 4%)/Compound (4):Liq (25, 50%)/Liq(1)/Al(80)

Example 5

An organic EL device of Example 5 was manufactured in the same manner as the organic EL device of Example 1 except for using the compound (5) in place of the compound (1).

A device arrangement of the organic EL device of Example 5 is roughly shown as follows.

ITO(130)/HI-1(5)/HT-1(80)/HT-2(10)/BH-1:BD-1(25, 4%)/Compound (5):Liq (25, 50%)/Liq(1)/Al(80)

Example 6

An organic EL device of Example 6 was manufactured in the same manner as the organic EL device of Example 1 except for using the compound (6) in place of the compound (1).

A device arrangement of the organic EL device of Example 6 is roughly shown as follows.

ITO(130)/HI-1(5)/HT-1(80)/HT-2(10)/BH-1:BD-1(25, 4%)/Compound (6):Liq (25, 50%)/Liq(1)/Al(80)

Example 7

An organic EL device of Example 7 was manufactured in the same manner as the organic EL device of Example 1 except for using the compound (7) in place of the compound (1).

A device arrangement of the organic EL device of Example 7 is roughly shown as follows.

ITO(130)/HI-1(5)/HT-1(80)/HT-2(10)/BH-1:BD-1(25, 4%)/Compound (7):Liq (25, 50%)/Liq(1)/Al(80)

Example 8

An organic EL device of Example 8 was manufactured in the same manner as the organic EL device of Example 1 except for using the compound (8) in place of the compound (1).

A device arrangement of the organic EL device of Example 8 is roughly shown as follows.

ITO(130)/HI-1(5)/HT-1(80)/HT-2(10)/BH-1:BD-1(25, 4%)/Compound (8):Liq (25, 50%)/Liq(1)/Al(80)

Example 9

An organic EL device of Example 9 was manufactured in the same manner as the organic EL device of Example 1 except for using the compound (9) in place of the compound (1).

A device arrangement of the organic EL device of Example 9 is roughly shown as follows.

ITO(130)/HI-1(5)/HT-1(80)/HT-2(10)/BH-1:BD-1(25, 4%)/Compound (9):Liq (25, 50%)/Liq(1)/Al(80)

Example 10

An organic EL device of Example 10 was manufactured in the same manner as the organic EL device of Example 1 except for using the compound (10) in place of the compound (1).

A device arrangement of the organic EL device of Example 10 is roughly shown as follows.

ITO(130)/HI-1(5)/HT-1(80)/HT-2(10)/BH-1:BD-1(25, 4%)/Compound (10):Liq (25, 50%)/Liq(1)/Al(80)

Example 11

An organic EL device of Example 11 was manufactured in the same manner as the organic EL device of Example 1 except for using the compound (11) in place of the compound (1).

A device arrangement of the organic EL device of Example 11 is roughly shown as follows.

ITO(130)/HI-1(5)/HT-1(80)/HT-2(10)/BH-1:BD-1(25, 4%)/Compound (11):Liq (25, 50%)/Liq(1)/Al(80)

Example 12

An organic EL device of Example 12 was manufactured in the same manner as the organic EL device of Example 1 except for using the compound (12) in place of the compound (1).

A device arrangement of the organic EL device of Example 12 is roughly shown as follows.

ITO(130)/HI-1(5)/HT-1(80)/HT-2(10)/BH-1:BD-1(25, 4%)/Compound (12):Liq (25, 50%)/Liq(1)/Al(80)

Comparative Example 1

An organic EL device of Comparative Example 1 was manufactured in the same manner as the organic EL device of Example 1 except for using the compound E-1 in place of the compound (1).

A device arrangement of the organic EL device of Comparative Example 1 is roughly shown as follows.

ITO(130)/HI-1(5)/HT-1(80)/HT-2(10)/BH-1:BD-1(25, 4%)/E-1:Liq(25, 50%)/Liq(1)/Al(80)

Comparative Example 2

An organic EL device of Comparative Example 2 was manufactured in the same manner as the organic EL device of Example 1 except for using the compound E-2 in place of the compound (1).

A device arrangement of the organic EL device of Comparative Example 2 is roughly shown as follows.

ITO(130)/HI-1(5)/HT-1(80)/HT-2(10)/BH-1:BD-1(25, 4%)/E-2:Liq(25, 50%)/Liq(1)/Al(80)

The manufactured organic EL devices were measured according to the following method and evaluated with respect to performance. The results are shown in Table 1.
(1) Drive Voltage Voltage was applied between the anode (ITO transparent electrode) and the metal cathode (metal Al) such that a current density was 10 mA/cm², where the voltage (unit: V) was measured.
(2) External Quantum Efficiency Voltage was applied on each of the organic EL devices such that a current density was 10 mA/cm², where spectral radiance spectra were measured by a spectroradiometer (CS-1000 manufactured by Konica Minolta, Inc.). The external quantum efficiency (at 10 mA/cm², unit: %) was calculated from the obtained spectral radiance spectra, assuming that the spectra were provided under a Lambertian radiation.

The maximum external quantum efficiency (EQE max.) was calculated from the external quantum efficiency (at 10 mA/cm²) using a ratio between the maximum luminance efficiency and a luminance efficiency at 10 mA/cm².

TABLE 1

| | Electron Transporting Layer | Voltage (V) (at 10 mA/cm²) | EQE max. (%) |
|---|---|---|---|
| Example 1 | Compound (1) | 3.6 | 8.7 |
| Example 2 | Compound (2) | 3.7 | 9.1 |
| Example 3 | Compound (3) | 3.5 | 9.1 |
| Example 4 | Compound (4) | 3.6 | 8.5 |
| Example 5 | Compound (5) | 3.6 | 9.0 |

TABLE 1-continued

| | Electron Transporting Layer | Voltage (V) (at 10 mA/cm²) | EQE max. (%) |
|---|---|---|---|
| Example 6 | Compound (6) | 3.7 | 9.0 |
| Example 7 | Compound (7) | 3.6 | 8.7 |
| Example 8 | Compound (8) | 3.7 | 8.5 |
| Example 9 | Compound (9) | 3.5 | 8.9 |
| Example 10 | Compound (10) | 3.5 | 9.0 |
| Example 11 | Compound (11) | 3.6 | 9.0 |
| Example 12 | Compound (12) | 3.6 | 8.8 |
| Comparative Ex. 1 | Compound E-1 | 5.7 | 6.4 |
| Comparative Ex. 2 | Compound E-2 | 3.7 | 8.0 |

It is understood from the above that voltage reduction and efficiency improvement of the organic EL device are attainable by using the compound of the invention.

By comparison between Examples 1 to 12 with the compounds (1) to (12) and Comparative Example 1 with the compound E-1, it has been found that the organic EL device is driven at a low voltage with a high efficiency with use of the compound having a nitrogen-containing hetero ring at a terminal of a molecular structure.

By comparison between Examples 1 to 12 with the compounds (1) to (12) and Comparative Example 2 with the compound E-2, it has been found that the organic EL device is driven at a lower voltage with a higher efficiency with use of the compound having the fused ring structure in which 4 or more rings are fused and the number of the ring atoms is 22 or less in a molecule than with use of a compound having a fused ring structure in which 3 or less rings are fused in a molecule.

Although some of the exemplary embodiments and/or Examples of the invention are described in detail as described above, those skilled in the art easily add many modifications to the above exemplary embodiments and/or Examples without substantially departing from the novel teaching and the advantages of the invention. Accordingly, the many modifications are encompasses in the scope of the invention.

The invention claimed is:
1. A compound represented by a formula (1) below,

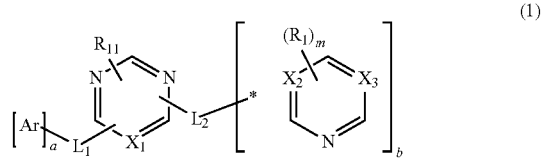

(1)

where:
Ar is an aromatic hydrocarbon group derived from any ring selected from the group consisting of rings represented by formulae (11a) to (11e) and optionally has a substituent,

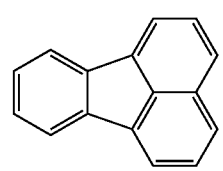

(11a)

(11b)
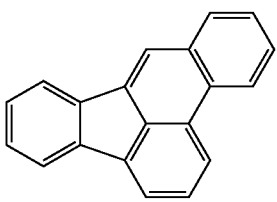

(11c)
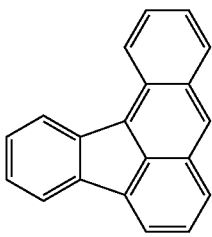

(11d)
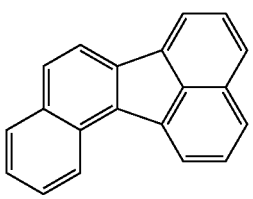

(11e)
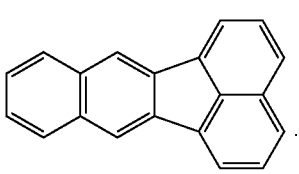

a is 1 or 2;
a plurality of Ar are optionally the same or different;
$R_{11}$ is a substituted or unsubstituted phenyl group, a substituted or unsubstituted biphenyl group, a substituted or unsubstituted terphenyl group, a substituted or unsubstituted phenanthryl group, a substituted or unsubstituted fluorenyl group, a substituted or unsubstituted pyrenyl group, a substituted or unsubstituted chrysenyl group, a substituted or unsubstituted fluoranthenyl group, a substituted or unsubstituted benzo[a]anthryl group, a substituted or unsubstituted benzo[c]phenanthryl group, a substituted or unsubstituted triphenylenyl group, a substituted or unsubstituted benzo[k]fluoranthenyl group, a substituted or unsubstituted benzo[g]chrysenyl group, a substituted or unsubstituted benzo[b]triphenylenyl group, a substituted or unsubstituted picenyl group, or a substituted or unsubstituted perylenyl group
when $R_{11}$ has a substituent, the substituent is not a heterocyclic group;
$X_1$ represents a nitrogen atom or a carbon atom bonded with $R_{12}$ ($CR_{12}$);
$R_{12}$ represents a hydrogen atom or a substituent;
$L_1$ represents a linking group;
$L_1$ as the linking group is selected from the group consisting of a substituted or unsubstituted aromatic hydrocarbon group having 6 to 12 ring carbon atoms, a substituted or unsubstituted heterocyclic group having 5 to 30 ring atoms, a substituted or unsubstituted and linear or branched hydrocarbon group having a carbon-carbon double bond and 2 to 30 carbon atoms, and a substituted or unsubstituted and linear or branched hydrocarbon group having a carbon-carbon triple bond and 2 to 30 carbon atoms;
$X_2$ and $X_3$ each independently represent a nitrogen atom or a carbon atom bonded with $R_2$ ($CR_2$);
$R_1$ and $R_2$ each independently represent a hydrogen atom or a substituent;
$R_1$ as the substituent and $R_2$ as the substituent are each independently selected from the group consisting of a substituted or unsubstituted alkyl group having 1 to 30 carbon atoms, a substituted or unsubstituted halogenated alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aromatic hydrocarbon group having 6 to 14 ring carbon atoms, a substituted or unsubstituted alkoxy group having 1 to 30 carbon atoms, a substituted or unsubstituted aryloxy group having 6 to 14 ring carbon atoms, a substituted or unsubstituted alkylthio group having 1 to 30 carbon atoms, a substituted or unsubstituted arylthio group having 6 to 14 ring carbon atoms, a substituted or unsubstituted silyl group, a nitro group, a cyano group, and a halogen atom;
$R_{12}$ as the substituent is selected from the group consisting of a substituted or unsubstituted alkyl group having 1 to 30 carbon atoms, a substituted or unsubstituted halogenated alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aromatic hydrocarbon group having 6 to 14 ring carbon atoms, a substituted or unsubstituted alkoxy group having 1 to 30 carbon atoms, a substituted or unsubstituted aryloxy group having 6 to 14 ring carbon atoms, a substituted or unsubstituted alkylthio group having 1 to 30 carbon atoms, a substituted or unsubstituted arylthio group having 6 to 14 ring carbon atoms, a substituted or unsubstituted silyl group, a nitro group, a cyano group, and a halogen atom;
when $R_{12}$ is the substituted or unsubstituted aromatic hydrocarbon group having 6 to 14 ring carbon atoms, $R_{12}$ is a substituted or unsubstituted phenyl group, a substituted or unsubstituted biphenyl group, a substituted or unsubstituted phenanthryl group, or a substituted or unsubstituted fluorenyl group,
when $R_{12}$ is an aromatic hydrocarbon group having a substituent and 6 to 14 ring carbon atoms, the substituent is not a heterocyclic group;
m is an integer of 2 or more;
a plurality of $R_1$ are optionally the same or different;
a plurality of $R_2$ are optionally the same or different;
$R_1$ and $R_2$ are optionally bonded to each other to form a ring structure;
$L_2$ is a linking group and $L_2$ as the linking group is selected from the group consisting of a substituted or unsubstituted aromatic hydrocarbon group having 6 to 30 ring carbon atoms;
b is an integer of 1 to 5;
a structure parenthesized by b is optionally the same or different, and
* indicates a bonding site to $L_2$ in the structure parenthesized by b.

2. The compound according to claim 1, wherein a is 1.
3. The compound according to claim 1, wherein b is 1.

4. The compound according to claim 1, wherein
L₁ as the linking group is a substituted or unsubstituted aromatic hydrocarbon group having 6 to 12 ring carbon atoms.
5. The compound according to claim 1, wherein
L₁ is selected from the group consisting of a substituted or unsubstituted phenylene group, a substituted or unsubstituted naphthalenediyl group, and a substituted or unsubstituted biphenyldiyl group.
6. The compound according to claim 1, wherein
L₁ is a substituted or unsubstituted phenylene group.
7. The compound according to claim 1, wherein
L₂ is selected from the group consisting of a substituted or unsubstituted phenylene group, a substituted or unsubstituted naphthalenediyl group, and a substituted or unsubstituted biphenyldiyl group.
8. The compound according to claim 1, wherein
L₂ is a substituted or unsubstituted phenylene group.
9. The compound according to claim 1, wherein
R₁ and R₂ each independently represent a hydrogen atom or a substituted or unsubstituted aromatic hydrocarbon group having 6 to 14 ring carbon atoms.
10. The compound according to claim 1, wherein
R₁ and R₂ are each a hydrogen atom.
11. The compound according to claim 1, wherein
at least one of X₂ and X₃ is a carbon atom bonded with R₂ (CR₂).
12. The compound according to claim 1, wherein
X₂ and X₃ are each a carbon atom bonded with R₂ (CR₂).
13. The compound according to claim 12, wherein
X₂ and X₃ are each a carbon atom bonded with R₂ (CR₂), and R₁ and R₂ are each a hydrogen atom.
14. The compound according to claim 1, wherein
in the compound represented by the formula (1), a structure represented by a formula (1b) is represented by a formula (1b-1) or a formula (1b-2),

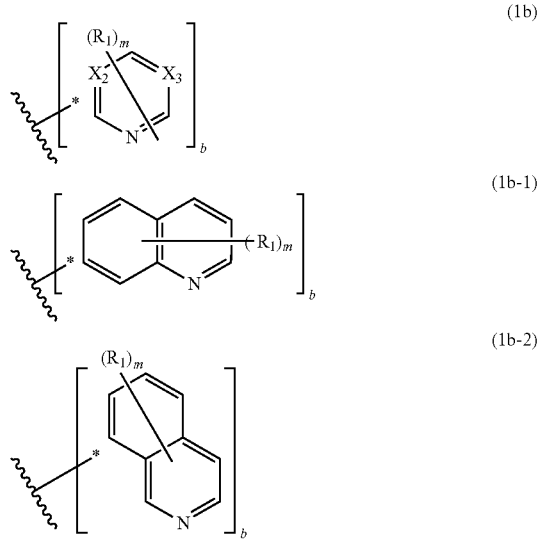

in the formula (1b-1) and the formula (1b-2),
R₁, *, m and b respectively represent the same as R₁, *, m and b in the formula (1), and
a plurality of R₁ are optionally bonded to each other to form a ring structure.

15. The compound according to claim 14, wherein
R₁ is a hydrogen atom in the formula (1b-1) and the formula (1b-2).
16. An organic-electroluminescence-device material comprising the compound according to claim 1.
17. An organic electroluminescence device, comprising:
an anode;
a cathode; and
one or more organic layers comprising an emitting layer, wherein
at least one of the organic layers comprises the compound according to claim 1.
18. An organic electroluminescence device, comprising:
an anode;
a cathode; and
an organic layer comprising an emitting layer and an electron transporting zone, wherein
the emitting layer is interposed between the anode and the cathode,
the electron transporting zone is interposed between the emitting layer and the cathode, and
the electron transporting zone comprises the compound according to claim 1.
19. The organic electroluminescence device according to claim 18, wherein the electron transporting zone further comprises at least one of an electron-donating dopant and an organic metal complex.
20. The organic electroluminescence device according to claim 19, wherein the electron-donating dopant and the organic metal complex are each at least one selected from the group consisting of an alkali metal, an alkali metal compound, an alkaline earth metal, an alkaline earth metal compound, a rare earth metal, a rare earth metal compound, an organic metal complex comprising an alkali metal, an organic metal complex comprising an alkaline earth metal, and an organic metal complex comprising a rare earth metal.
21. The organic electroluminescence device according to claim 19, wherein the electron-donating dopant and the organic metal complex are each at least one selected from the group consisting of lithium, a lithium compound, and an organic metal complex comprising lithium.
22. The organic electroluminescence device according to claim 18, wherein the electron transporting zone further comprises 8-quinolinolato lithium.
23. The organic electroluminescence device according to claim 17, further comprising a hole transporting layer interposed between the anode and the emitting layer.
24. An electronic device comprising the organic electroluminescence device according to claim 17.
25. The compound according to claim 1, wherein
a is 1,
b is 1,
L₁ as the linking group is a substituted or unsubstituted aromatic hydrocarbon group having 6 to 12 ring carbon atoms,
L₂ is selected from the group consisting of a substituted or unsubstituted phenylene group, a substituted or unsubstituted naphthalenediyl group, and a substituted or unsubstituted biphenyldiyl group, and
R₁ and R₂ each independently represent a hydrogen atom or a substituted or unsubstituted aromatic hydrocarbon group having 6 to 14 ring carbon atoms.
26. The compound according to claim 1, wherein Ar has no substituent.

* * * * *